United States Patent
Jeon et al.

(10) Patent No.: US 10,581,000 B2
(45) Date of Patent: Mar. 3, 2020

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Soonok Jeon, Seoul (KR); Sangmo Kim, Hwaseong-si (KR); Joonghyuk Kim, Seoul (KR); Youngseok Park, Yongin-si (KR); Youngmok Son, Hwaseong-si (KR); Yeonsook Chung, Seoul (KR); Yongsik Jung, Yongin-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 588 days.

(21) Appl. No.: 14/859,815

(22) Filed: Sep. 21, 2015

(65) Prior Publication Data
US 2016/0190482 A1    Jun. 30, 2016

(30) Foreign Application Priority Data
Dec. 30, 2014    (KR) .................. 10-2014-0194316

(51) Int. Cl.
| | | |
|---|---|---|
| H01L 51/00 | (2006.01) | |
| C07D 409/14 | (2006.01) | |
| C09K 11/02 | (2006.01) | |
| C09K 11/06 | (2006.01) | |
| H01L 51/50 | (2006.01) | |

(52) U.S. Cl.
CPC ........ *H01L 51/0074* (2013.01); *C07D 409/14* (2013.01); *C09K 11/025* (2013.01);
(Continued)

(58) Field of Classification Search
CPC .... C07D 409/14; C09K 11/025; C09K 11/06; H01L 51/0072; H01L 51/0074;
(Continued)

(56) References Cited

U.S. PATENT DOCUMENTS

| | | | |
|---|---|---|---|
| 4,983,568 A * | 1/1991 | Ikeda | .............. B41M 5/3375 |
| | | | 503/208 |
| 5,077,142 A | 12/1991 | Sakon et al. | |

(Continued)

FOREIGN PATENT DOCUMENTS

| | | | |
|---|---|---|---|
| CN | 1502636 A | * | 6/2004 |
| JP | 5214334 A | | 8/1993 |

(Continued)

OTHER PUBLICATIONS

Wang et al., Organic Letters, (2014), 16(17), pp. 4574-4577.*
(Continued)

*Primary Examiner* — Dawn L Garrett
(74) *Attorney, Agent, or Firm* — Cantor Colburn LLP

(57) ABSTRACT

A condensed cyclic compound represented by Formula 1:

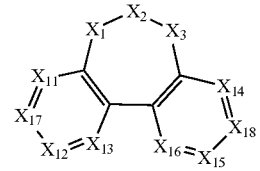

Formula 1 wherein in Formula 1, groups $X_1$ to $X_3$ and $X_{11}$ to $X_{18}$ are the same as described in the specification.

20 Claims, 2 Drawing Sheets

(52) U.S. Cl.
CPC ............ *C09K 11/06* (2013.01); *H01L 51/008* (2013.01); *H01L 51/009* (2013.01); *H01L 51/0072* (2013.01); *H01L 51/0085* (2013.01); *H01L 51/5016* (2013.01)

(58) Field of Classification Search
CPC . H01L 51/008; H01L 51/0085; H01L 51/009; H01L 51/5016; H05B 33/20
See application file for complete search history.

(56) References Cited

U.S. PATENT DOCUMENTS

| | | | |
|---|---|---|---|
| 6,303,238 B1 * | 10/2001 | Thompson | C07D 487/22 252/301.16 |
| 9,793,496 B2 * | 10/2017 | Shin | H01L 51/0072 |
| 2004/0067388 A1 | 4/2004 | Suzuki | |
| 2012/0065338 A1 | 3/2012 | Towns et al. | |

FOREIGN PATENT DOCUMENTS

| | | | |
|---|---|---|---|
| KR | 101346467 B1 | | 12/2013 |
| KR | 10-2015-0021861 | * | 3/2015 |
| WO | 2013124029 A3 | | 8/2013 |

OTHER PUBLICATIONS

Hammam et al., Z. Naturforsch. 55b, 417-424 (2000).*
Zheng et al., Chem. Res. Chinese U., (2007), 23(6), pp. 720-725.*
Machine translation for CN 1502636 A (publication date: Jun. 2004).*
Hammam et al., Z. Naturforsch. 55b, 417-424, (2000). (Year: 2000).*

* cited by examiner

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0194316, filed on Dec. 30, 2014, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices (OLEDs) are self-emission devices that have wide viewing angles, high contrast ratios, and short response times. In addition, OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons, which then change from an excited state to a ground state, generating light.

Various types of organic light emitting devices are known. However, there still remains a need in OLEDs having low driving voltage, high efficiency, high brightness, and long lifespan.

SUMMARY

Provided are novel condensed cyclic compounds and organic light-emitting devices including the same.

Additional aspects will be set forth in part in the description which follows and, in part, will be apparent from the description, or may be learned by practice of the presented exemplary embodiments.

According to an aspect of an exemplary embodiment, a condensed cyclic compound represented by Formula 1 is provided:

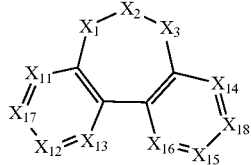

Formula 1 wherein in Formula 1, $X_1$ may be selected from O, S, S(=O)$_2$, N-(L$_1$)$_{a1}$-(R$_1$), C(R$_4$)(R$_5$), and Si(R$_4$)(R$_5$), $X_2$ may be selected from O, S, S(=O)$_2$, N-(L$_2$)$_{a2}$-(R$_2$), C(R$_6$)(R$_7$), and Si(R$_6$)(R$_7$), $X_3$ may be selected from O, S, S(=O)$_2$, N-(L$_3$)$_{a3}$-(R$_3$), C(R$_8$)(R$_9$) and Si(R$_8$)(R$_9$), $X_{11}$ may be N or C-(L$_{11}$)$_{a11}$-(R$_{11}$),
$X_{12}$ may be N or C-(L$_{12}$)$_{a12}$-(R$_{12}$),
$X_{13}$ may be N or C-(L$_{13}$)$_{a13}$-(R$_{13}$),
$X_{14}$ may be N or C-(L$_{14}$)$_{a14}$-(R$_{14}$),
$X_{15}$ may be N or C-(L$_{15}$)$_{a15}$-(R$_{15}$), and
$X_{16}$ may be N or C-(L$_{16}$)$_{a16}$-(R$_{16}$), provided that i) $X_{11}$ to $X_{18}$ are not all N, ii) $X_{11}$ to $X_{18}$ are not all CH, iii) at least one selected from $X_{17}$ and $X_{18}$ is CH, and iv) at least one selected from $X_{11}$ to $X_{16}$ is neither N nor CH, $L_1$ to $L_3$ and $L_{11}$ to $L_{18}$ may be each independently selected from —O—, —S—, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a3 and a11 to a18 may be each independently an integer selected from 0 to 3, $R_1$ to $R_9$ and $R_{11}$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$), and at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to an aspect of an exemplary embodiment, an organic light-emitting device includes:
    a first electrode;
    a second electrode; and
    an organic layer between the first electrode and the second electrode,
    wherein the organic layer includes an emission layer and at least one condensed cyclic compound represented by Formula 1.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
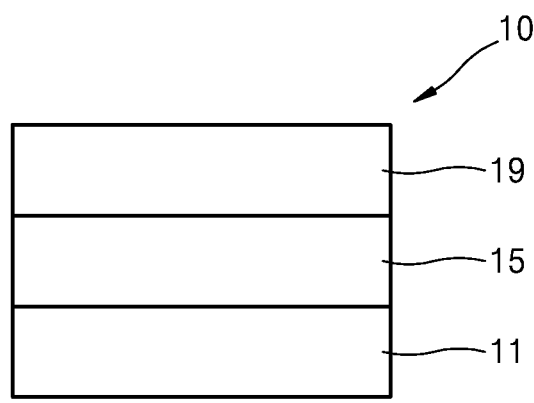
FIG. 1 is a schematic view of an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or includes any and all combinations of one or more of the associated listed items. Expressions such as at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/ or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an aspect, a condensed cyclic compound represented by Formula 1 is provided:

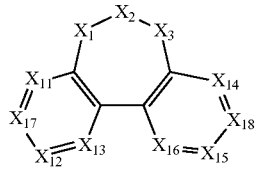

Formula 1 wherein in Formula 1,
$X_1$ may be selected from O, S, S($=$O)$_2$, N-(L$_1$)$_{a1}$-(R$_1$), C(R$_4$)(R$_5$), and Si(R$_4$)(R$_5$), $X_2$ may be selected from O, S, S($=$O)$_2$, N-(L$_2$)$_{a2}$-(R$_2$), C(R$_6$)(R$_7$), and Si(R$_6$)(R$_7$), $X_3$ may be selected from O, S, S($=$O)$_2$, N-(L$_3$)$_{a3}$-(R$_3$), C(R$_8$)(R$_9$), and Si(R$_8$)(R$_9$), $X_{11}$ may be N or C-(L$_{11}$)$_{a11}$-(R$_{11}$),
$X_{12}$ may be N or C-(L$_{12}$)$_{a12}$-(R$_{12}$),
$X_{13}$ may be N or C-(L$_{13}$)$_{a13}$-(R$_{13}$),
$X_{14}$ may be N or C-(L$_{14}$)$_{a14}$-(R$_{14}$),
$X_{15}$ may be N or C-(L$_{15}$)$_{a15}$-(R$_{15}$), and
$X_{16}$ may be N or C-(L$_{16}$)$_{a16}$-(R$_{16}$), provided that i) $X_{11}$ to $X_{18}$ are not N, ii) $X_{11}$ to $X_{18}$ are not all CH, iii) at least one selected from $X_{17}$ and $X_{18}$ is CH, and iv) at least one selected from $X_{11}$ to $X_{16}$ is neither N nor CH.

For example, in Formula 1,
$X_1$ may be C(R$_4$)(R$_5$);
$X_2$ may be C(R$_6$)(R$_7$); or
$X_3$ may be C(R$_8$)(R$_9$).

In some embodiments, $X_1$ and $X_3$ in Formula 1 may be identical, but are not limited thereto.

In an embodiment, in Formula 1,
$X_1$ may be C(R$_4$)(R$_5$), $X_2$ may be selected from O, S, S($=$O)$_2$, and N-(L$_2$)$_{a2}$-(R$_2$), and $X_3$ may be C(R$_8$)(R$_9$); or
$X_1$ may be O or S, $X_2$ may be C(R$_6$)(R$_7$), and $X_3$ may be O or S.

In some embodiments, at least one selected from $X_{11}$ to $X_{16}$ in Formula 1 may be N.

In some embodiments, in Formula 1, $X_{12}$ may be C-(L$_{12}$)$_{a12}$-(R$_{12}$), $X_{15}$ may be C-(L$_{15}$)$_{a15}$-(R$_{15}$), each of R$_{12}$ and R$_{15}$ may not be a hydrogen, and $X_{11}$, $X_{13}$, $X_{14}$, $X_{16}$, $X_{17}$, and $X_{18}$ may be CH.

In some embodiments, in Formula 1, $X_{12}$ may be C-(L$_{12}$)$_{a12}$-(R$_{12}$), $X_{18}$ may be C-(L$_{18}$)$_{a18}$-(R$_{18}$), each of R$_{12}$ and R$_{18}$ may not be a hydrogen, and $X_{11}$, $X_{12}$, $X_{13}$, $X_{14}$, $X_{16}$ and $X_{17}$ may be CH.

$L_1$ to $L_3$ and $L_{11}$ to $L_{18}$ in Formula 1 may be each independently selected from —O—, —S—, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ to $L_3$ and $L_{11}$ to $L_{18}$ in Formula 1 may be each independently selected from a cyclopentylene group, a cyclohexylene group, a cyclopentenylene group, a cyclohexenylene group, a cycloheptenylene group, a phenylene group, a naphthylene group, a fluorenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a quinoxalinylene group, a quinazolinylene group, a carbazolylene group, an acridinylene group, a phenanthrolinylene group, a phenazinylene group, a benzoxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, an imidazopyrimidinylene group, and an imidazopyridinylene group; and a cyclopentylene group, a cyclohexylene group, a cyclopentenylene group, a cyclohexenylene group, a cycloheptenylene group, a phenylene group, a naphthylene group, a fluorenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a quinoxalinylene group, a quinazolinylene group, a carbazolylene group, an acridinylene group, a phenanthrolinylene group, a phenazinylene group, a benzoxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, an imidazopyrimidinylene group and an imidazopyridinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a naphthyl group, a fluorenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a quinoxalinyl group, a quinazolinyl group, a carbazolyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, an imidazopyridinyl group, and —Si($Q_{33}$)($Q_{34}$)($Q_{33}$), wherein $Q_{33}$ to $Q_{35}$ are each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group, but they are not limited thereto.

In an embodiment, $L_1$ to $L_3$ and $L_{11}$ to $L_{18}$ in Formula 1 may be each independently selected from a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —Si($Q_{33}$)($Q_{34}$)($Q_{35}$), wherein $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group.

In some embodiments, $L_1$ to $L_3$ and $L_{11}$ to $L_{18}$ in Formula 1 may be each independently selected from a phenylene group, a naphthylene group, a pyridinylene group, a fluorenylene group, a carbazolylene group, a dibenzofuranylene group, and a dibenzothiophenylene group;

a phenylene group, a naphthylene group, a pyridinylene group, a fluorenylene group, a carbazolylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —Si($Q_{33}$)($Q_{34}$)($Q_{35}$), wherein $C_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group.

a1 to a3 and a11 to a18 in Formula 1 may be each independently an integer selected from 0 to 3.

a1 in Formula 1 indicates the number of groups $L_1$, and when a1 is 0, *-$(L_1)_{a1}$-*' indicates a single bond. When a1 is 2 or more, 2 or more groups $L_1$ may be identical or different. a2, a3 and a11 to a18 may be understood by referring to the description presented in connection with a1 and the structure of Formula 1.

In an embodiment, a1 to a3 and a11 to a18 may be each independently 0, 1, or 2.

In some embodiments, a1 to a3 and a11 to a18 may be each independently 0 or 1, but they are not limited thereto.

$R_1$ to $R_9$ and $R_{11}$ to $R_{18}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

For example, $R_1$ to $R_3$ in Formula 1 may be each independently selected from
a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and
a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —Si($Q_{33}$)($Q_{34}$)($Q_{35}$),
wherein $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group.

In some embodiments, $R_4$ to $R_9$ in Formula 1 may be each independently selected from
a hydrogen, a deuterium, a $C_1$-$C_{10}$ alkyl group, a $C_1$-$C_{10}$ alkoxy group, a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and
a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —Si($Q_{33}$)($Q_{34}$)($Q_{35}$),
wherein $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group.

In some embodiments, $R_{11}$ to $R_{18}$ in Formula 1 may be each independently selected from
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, and a naphthyl group;
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group substituted with a $C_1$-$C_{20}$ alkyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazoyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{33}$); and —Si($Q_3$)($Q_4$)($Q_3$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In an embodiment, in Formula 1, $R_1$ to $R_3$ may be each independently selected from groups represented by Formulae 4-1 to 4-51, 5-1 to 5-6, and 6-1 to 6-10, $R_{11}$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

groups represented by Formulae 4-1 to 4-51, 5-1 to 5-6, and 6-1 to 6-10; and

—Si($Q_3$)($Q_4$)($Q_5$), wherein $Q_3$ to $Q_5$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

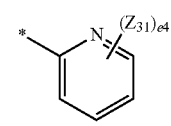

Formula 4-1

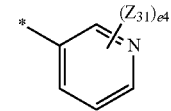

Formula 4-2

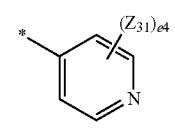

Formula 4-3

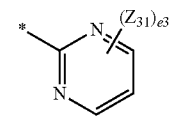

Formula 4-4

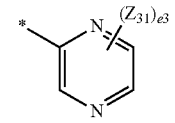

Formula 4-5

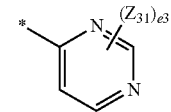

Formula 4-6

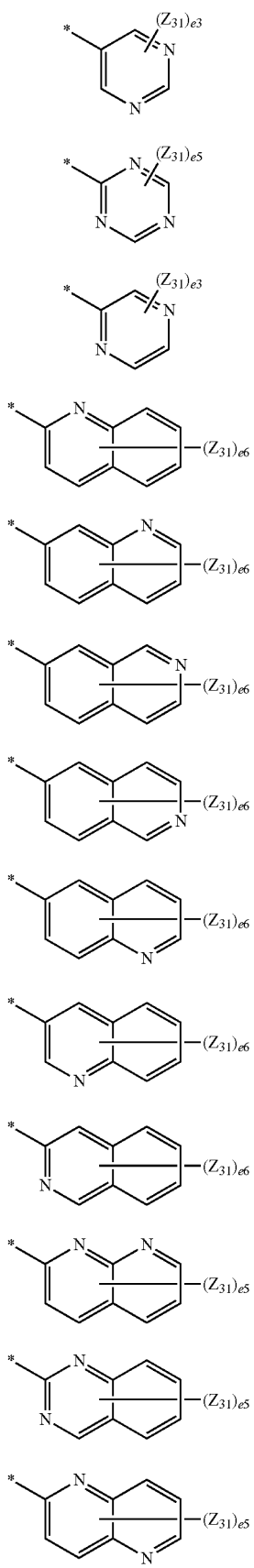

-continued
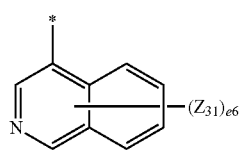
Formula 4-31
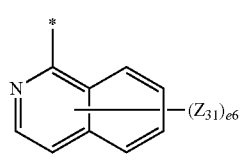
Formula 4-32
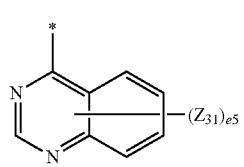
Formula 4-33
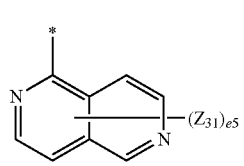
Formula 4-34
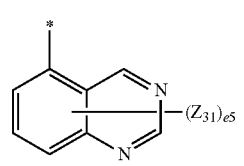
Formula 4-35
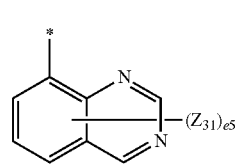
Formula 4-36
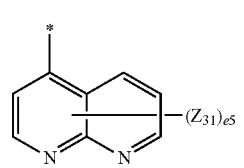
Formula 4-37
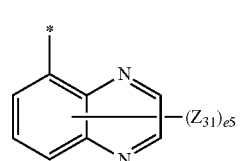
Formula 4-38
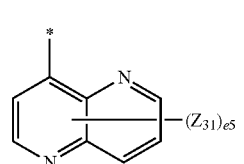
Formula 4-39
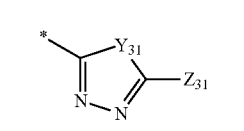
Formula 4-40
-continued
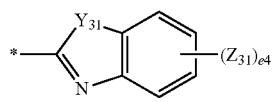
Formula 4-41
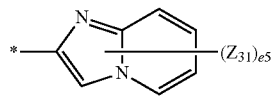
Formula 4-42
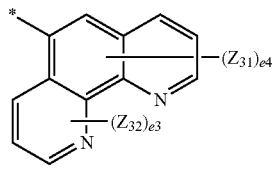
Formula 4-43
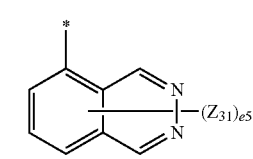
Formula 4-44
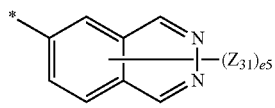
Formula 4-45
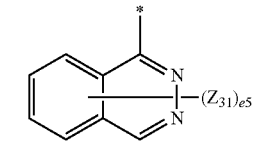
Formula 4-46
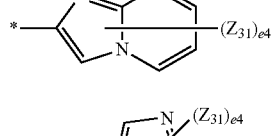
Formula 4-47
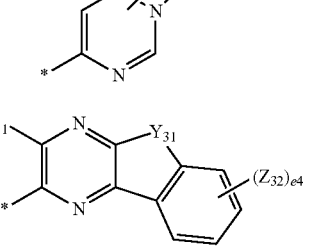
Formula 4-48
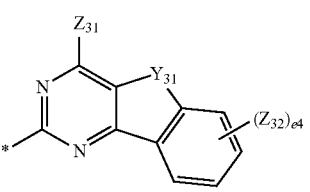
Formula 4-49
Formula 4-50

-continued
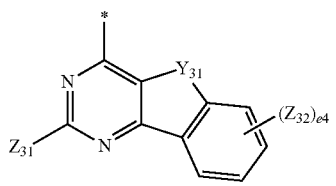
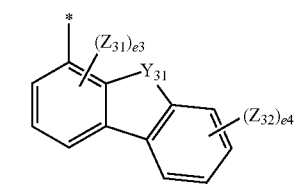
Formula 4-51
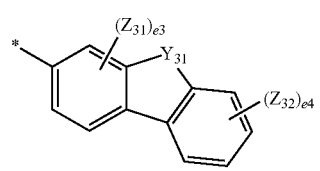
Formula 5-1
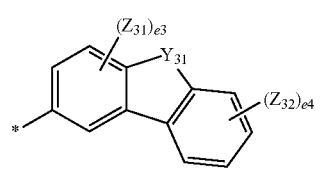
Formula 5-2
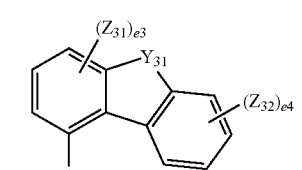
Formula 5-3
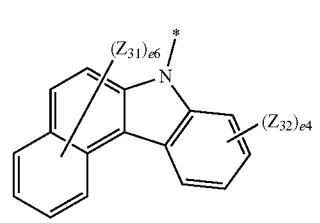
Formula 5-4
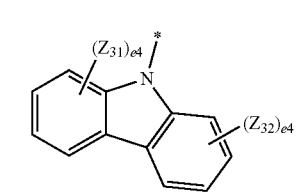
Formula 5-5
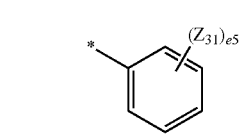
Formula 5-6
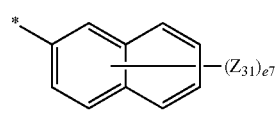
Formula 6-1
Formula 6-2
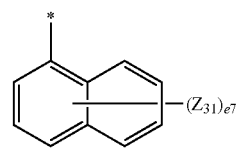
Formula 6-3
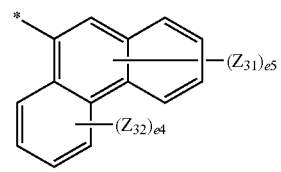
Formula 6-4
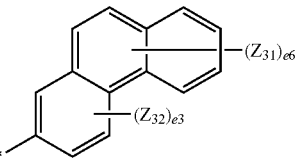
Formula 6-5
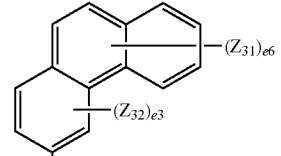
Formula 6-6
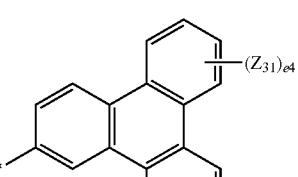
Formula 6-7
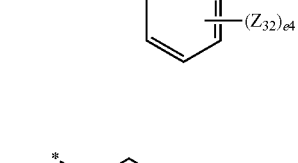
Formula 6-8
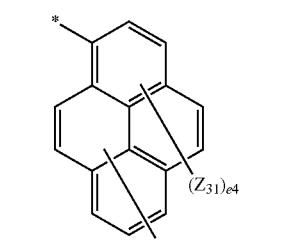
Formula 6-9
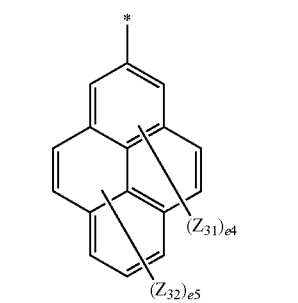

Formula 6-10

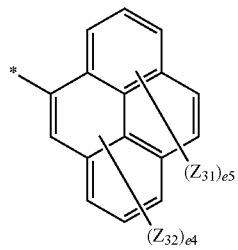

wherein in Formulae 4-1 to 4-51, 5-1 to 5-6, and 6-1 to 6-10, $Y_{31}$ may be selected from O, S, $C(Z_{33})(Z_{34})$, $N(Z_{35})$, and $Si(Z_{36})(Z_{37})$, $Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group substituted with a $C_1$-$C_{20}$ alkyl group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —$Si(Q_{33})(Q_{34})(Q_{35})$, wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, e2 may be 1 or 2,
e3 may be an integer selected from 1 to 3,
e4 may be an integer selected from 1 to 4,
e5 may be an integer selected from 1 to 5,
e6 may be an integer selected from 1 to 6,
e7 may be an integer selected from 1 to 7, and
* indicates a binding site to a neighboring atom.

In an embodiment, $R_{11}$ to $R_{18}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

groups represented by Formulae 4-1(1) to 4-8(1), 4-1(2) to 4-8(2), 4-1(3) to 4-8(3), 5-1(1) to 5-4(1), 5-1(2) to 5-4(2), 5-1(3) to 5-4(3), 5-1(4) to 5-4(4), 5-6(1) to 5-6(3), and 6-1(1) to 6-1(8); and —$Si(Q_3)(Q_4)(Q_5)$, wherein $Q_3$ to $Q_5$ may be each independently selected from a hydrogen, a $C_1$-$C_{20}$ alkyl group, a $C_1$-$C_{20}$ alkoxy group, a phenyl group, and a naphthyl group, but they are not limited thereto:

Formula 4-1(1)

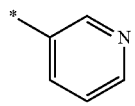

Formula 4-2(1)

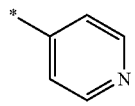

Formula 4-3(1)

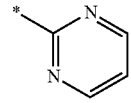

Formula 4-4(1)

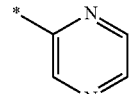

Formula 4-5(1)

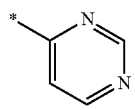

Formula 4-6(1)

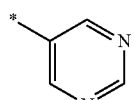

Formula 4-7(1)

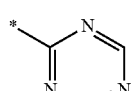

Formula 4-8(1)

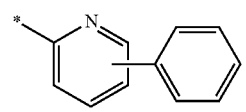

Formula 4-1(2)

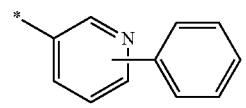

Formula 4-2(2)

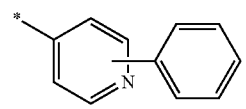

Formula 4-3(2)

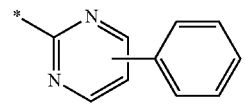

Formula 4-4(2)

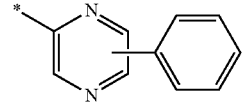

Formula 4-5(2)

Formula 4-6(2)
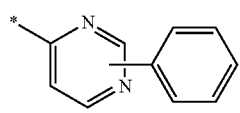
Formula 4-7(2)
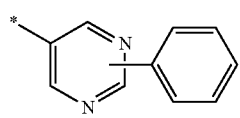
Formula 4-8(2)
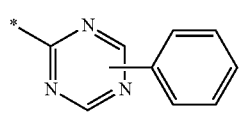
Formula 4-1(3)
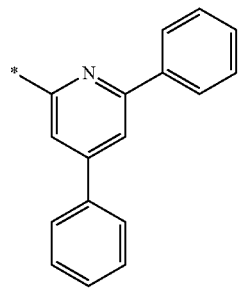
Formula 4-2(3)
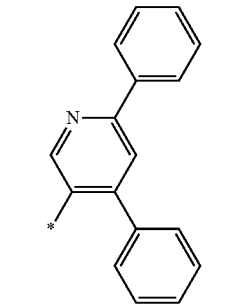
Formula 4-3(3)
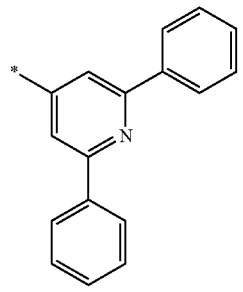
Formula 4-4(3)
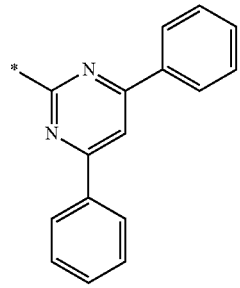
Formula 4-5(3)
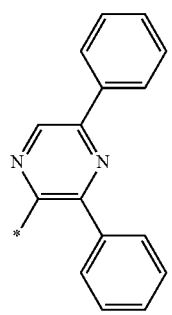
Formula 4-6(3)

Formula 4-7(3)
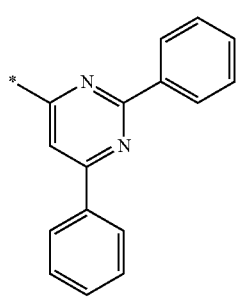
Formula 4-8(3)
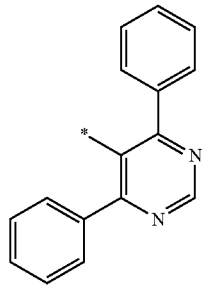
Formula 5-1(1)
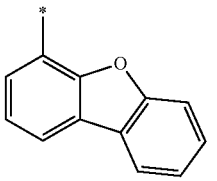
Formula 5-2(1)
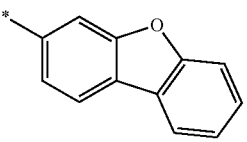

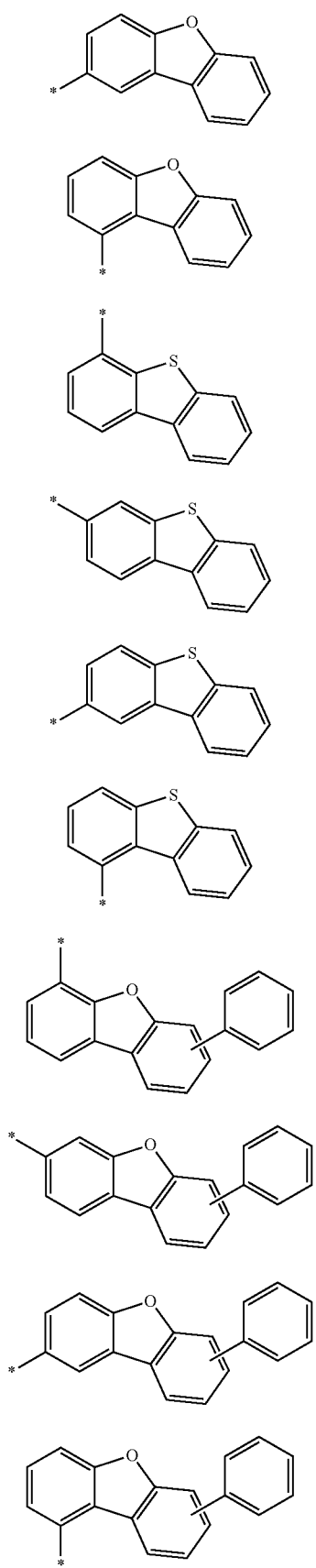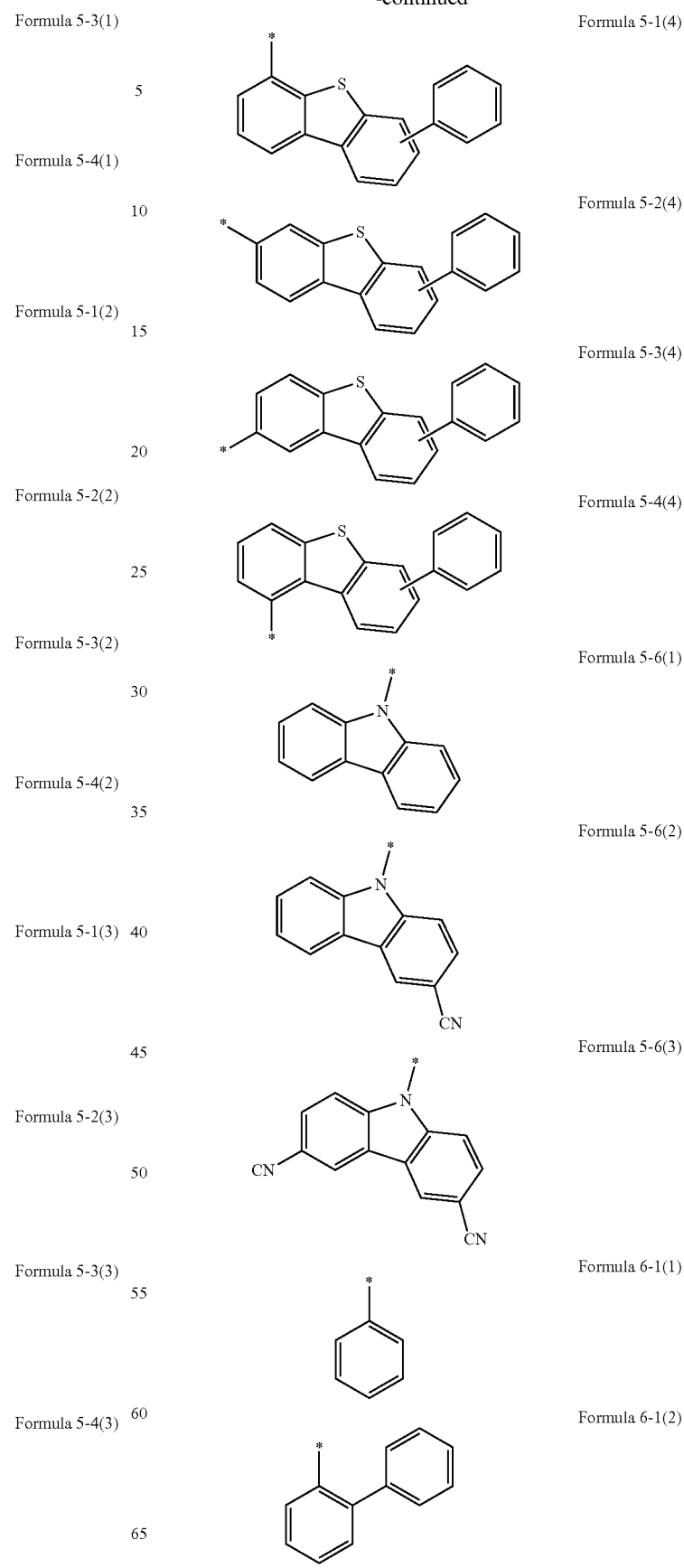

Formula 6-1(3)

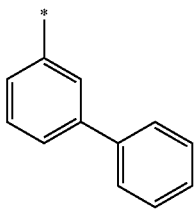

Formula 6-1(4)

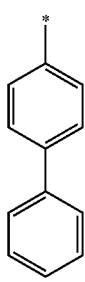

Formula 6-1(5)

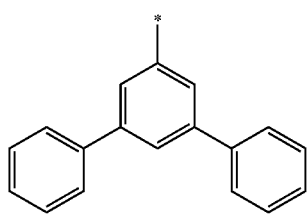

Formula 6-1(6)

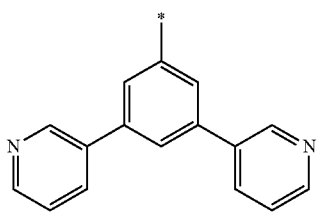

Formula 6-1(7)

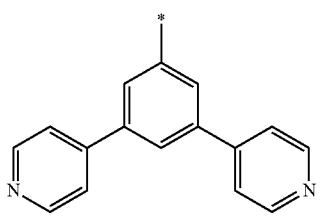

Formula 6-1(8)

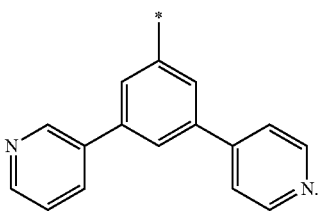

In some embodiments, in Formula 1, $X_{11}$ may be C-$(L_{11})_{a11}$-$(R_{11})$, $X_{12}$ may be C-$(L_{12})_{a12}$-$(R_{12})$, $X_{13}$ may be C-$(L_{13})_{a3}$-$(R_{13})$, $X_{14}$ may be C-$(L_{14})_{a14}$-$(R_{14})$, $X_{15}$ may be C-$(L_{15})_{a15}$-$(R_{15})$, $X_{16}$ may be C-$(L_{16})_{a16}$-$(R_{16})$, $X_{17}$ may be CH, and $X_{18}$ may be C-$(L_{18})_{a18}$-$(R_{18})$, and $R_{18}$ and at least one selected from $R_{11}$ to $R_{16}$ (for example, $R_{12}$ and $R_{18}$) may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{20}$ aryl group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

In some embodiments, $X_{11}$ may be C-$(L_{11})_{a11}$-$(R_{11})$, $X_{12}$ may be C-$(L_{12})_{a12}$-$(R_{12})$, $X_{13}$ may be C-$(L_{13})_{a13}$-$(R_{13})$, $X_{14}$ may be C-$(L_{14})_{a14}$-$(R_{14})$, $X_{15}$ may be C-$(L_{15})_{a15}$-$(R_{15})$, $X_{16}$ may be C-$(L_{16})_{a16}$-$(R_{16})$, $X_{17}$ may be CH, and $X_{18}$ may be CH, and at least one selected from $R_{11}$ to $R_{16}$ (for example, $R_{12}$ and $R_{15}$) may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{20}$ aryl group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

In some embodiments, at least one selected from $R_{11}$ to $R_{16}$ in Formula 1 may be selected from a $C_6$-$C_{20}$ aryl group, a $C_1$-$C_{20}$ heteroaryl group, a monovalent non-aromatic condensed polycyclic group, and a monovalent non-aromatic condensed heteropolycyclic group, each substituted with at least one selected from at least one cyano group.

In some embodiments, in Formula 1, $X_{11}$ may be C-$(L_{11})_{a11}$-$(R_{11})$, $X_{12}$ may be C-$(L_{12})_{a12}$-$(R_{12})$, $X_{13}$ may be C-$(L_{13})_{a13}$-$(R_{13})$, $X_{14}$ may be C-$(L_{14})_{a14}$-$(R_{14})$, $X_{15}$ may be C-$(L_{15})_{a15}$-$(R_{15})$, $X_{16}$ may be C-$(L_{16})_{a16}$-$(R_{16})$, $X_{17}$ may be CH, $X_{18}$ may be C-$(L_8)_{a18}$-$(R_{18})$, and at least one selected from $R_{11}$ to $R_{16}$ and $R_{18}$ (for example, at least two selected from $R_{11}$ to $R_{16}$ and $R_{18}$) may be selected from groups represented by Formulae 4-1 to 4-51, 5-1 to 5-6, and 6-1 to 6-10 (for example, groups represented by Formulae 4-1(1) to 4-8(1), 4-1(2) to 4-8(2), 4-1(3) to 4-8(3), 5-1(1) to 5-4(1), 5-1(2) to 5-4(2), 5-1(3) to 5-4(3), 5-1(4) to 5-4(4), 5-6(1) to 5-6(3), and 6-1(1) to 6-1(8)), but they are not limited thereto.

In some embodiments, in Formula 1, $X_{11}$ may be C-$(L_{11})_{a11}$-$(R_{11})$, $X_{12}$ may be C-$(L_{12})_{a12}$-$(R_{12})$, $X_{13}$ may be C-$(L_{13})_{a13}$-$(R_{13})$, $X_{14}$ may be C-$(L_{14})_{a14}$-$(R_{14})$, $X_{15}$ may be C-$(L_{15})_{a15}$-$(R_{15})$, $X_{16}$ may be C-$(L_{16})_{a16}$-$(R_{16})$, $X_{17}$ and $X_{18}$ may be CH, and at least one selected from $R_{11}$ to $R_{16}$ (for example, at least two selected from $R_{11}$ to $R_{16}$) may be selected from groups represented by Formulae 4-1 to 4-51, 5-1 to 5-6, and 6-1 to 6-10 (for example, groups represented by Formulae 4-1(1) to 4-8(1), 4-1(2) to 4-8(2), 4-1(3) to 4-8(3), 5-1(1) to 5-4(1), 5-1(2) to 5-4(2), 5-1(3) to 5-4(3), 5-1(4) to 5-4(4), 5-6(1) to 5-6(3), and 6-1(1) to 6-1(8)), but they are not limited thereto.

In an embodiment, the condensed cyclic compound represented by Formula 1 may be represented by one of Formulae 1A and 1B:

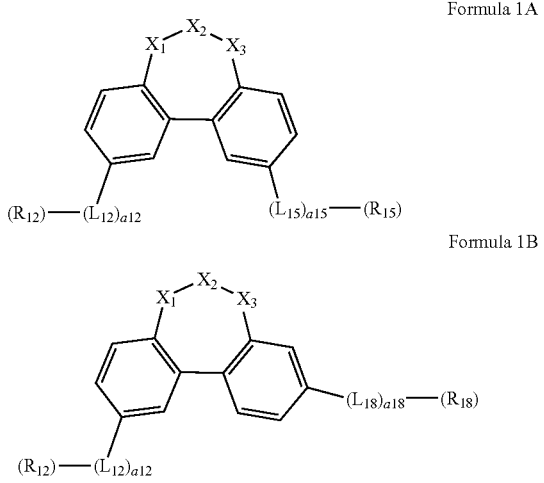

Formula 1A

Formula 1B wherein in Formulae 1A and 1B, $X_1$, $X_2$, $X_3$, $L_{12}$, $L_{15}$, $L_{18}$, a12, a15, a18, $R_{12}$, $R_{15}$, and $R_{18}$ are the same as defined throughout the specification, provided that each of $R_{12}$, $R_{15}$, and $R_{18}$ in Formulae 1A and 1B is not a hydrogen.

For example, in Formulae 1A and 1B, $X_1$ may be $C(R_4)(R_5)$, $X_2$ may be selected from O, S, $S(=O)_2$, and $N-(L_2)_{a2}-(R_2)$, and $X_3$ may be $C(R_8)(R_9)$, or $X_1$ may be O or S, $X_2$ may be $C(R_6)(R_7)$, and $X_3$ may be O or S, $L_{12}$, $L_{15}$, and $L_{18}$ may be each independently selected from a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —$Si(Q_{33})(Q_{34})(Q_{35})$, a12, a15, and a18 may be each independently 0 or 1, $R_2$ may be selected from groups represented by Formulae 4-1 to 4-51, 5-1 to 5-6, and 6-1 to 6-10, $R_4$ to $R_9$ may be each independently selected from a hydrogen, a deuterium, a $C_1$-$C_{10}$ alkyl group, a $C_1$-$C_{10}$ alkoxy group, a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —$Si(Q_{33})(Q_{34})(Q_{35})$, and $R_{12}$, $R_{15}$, and $R_{18}$ may be each independently selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

groups represented by Formulae 4-1 to 4-51, 5-1 to 5-6, and 6-1 to 6-10; and

—$Si(Q_3)(Q_4)(Q_5)$, wherein $Q_3$ to $Q_5$ and $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group, but they are not limited thereto.

In some embodiments, in Formulae 1A and 1B, $X_1$ may be $C(R_4)(R_5)$, $X_2$ may be selected from O, S, $S(=O)_2$, and $N-(L_2)_{a2}-(R_2)$, and $X_3$ may be $C(R_8)(R_9)$, or $X_1$ may be O or S, $X_2$ may be $C(R_6)(R_7)$, and $X_3$ may be O or S, $L_{12}$, $L_{15}$, and $L_{18}$ may be each independently selected from a phenylene group, a naphthylene group, a pyridinylene group, a fluorenylene group, a carbazolylene group, a dibenzofuranylene group, and a dibenzothiophenylene group; and a phenylene group, a naphthylene group, a pyridinylene group, a fluorenylene group, a carbazolylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —Si($Q_{33}$)($Q_{34}$)($Q_{35}$), a12, a15, and a18 may be each independently 0 or 1, $R_2$, $R_{12}$, $R_{15}$, and $R_{18}$ may be each independently groups represented by Formulae 4-1 to 4-51, 5-1 to 5-6, and 6-1 to 6-10 (for example, groups represented by Formulae 4-1(1) to 4-8(1), 4-1(2) to 4-8(2), 4-1(3) to 4-8(3), 5-1(1) to 5-4(1), 5-1(2) to 5-4(2), 5-1(3) to 5-4(3), 5-1(4) to 5-4(4), 5-6(1) to 5-6(3), and 6-1(1) to 6-1(8)), and $R_4$ to $R_9$ may be each independently selected from a hydrogen, a deuterium, a $C_1$-$C_{10}$ alkyl group, a $C_1$-$C_{10}$ alkoxy group, a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —Si($Q_{33}$)($Q_{34}$)($Q_{35}$), wherein $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group, but they are not limited thereto.

In some embodiments, the condensed cyclic compound represented by Formula 1 may be represented by one of Formulae 1A(1) to 1A(3) and 1B(1) to 1B(3), but the chemical structure therefor is not limited thereto:

Formula 1A(1)

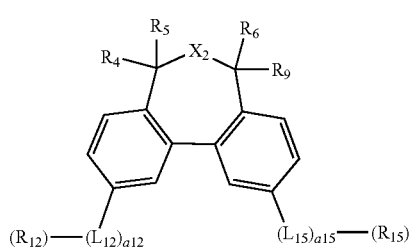

Formula 1A(2)

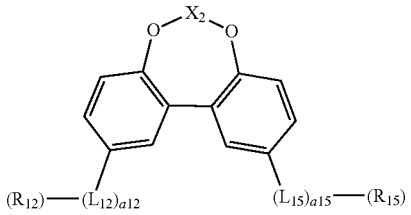

Formula 1A(3)

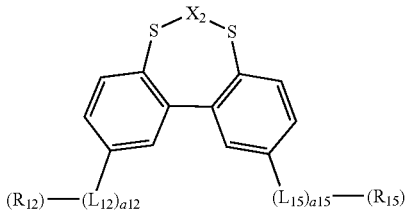

Formula 1B(1)

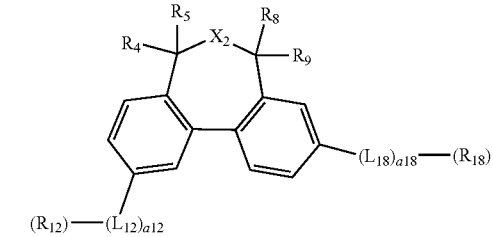

Formula 1B(2)

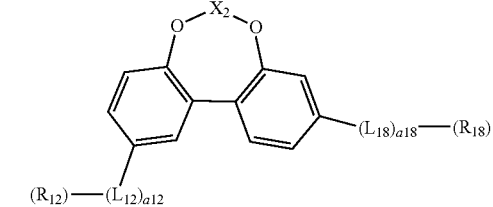

Formula 1B(3)

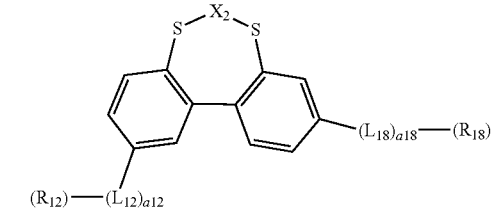

$X_2$, $L_{12}$, $L_{15}$, $L_{18}$, a12, a15, a18, $R_4$, $R_5$, $R_8$, $R_9$, $R_{12}$, $R_{15}$, and $R_{18}$ in Formulas 1A(1) to 1A(3) and 1B(1) to 1B(3) are the same as defined in the present specification, and $R_{12}$, $R_{15}$, and $R_{18}$ are not a hydrogen.

For example, in Formulae 1A(1) to 1A(3) and 1B(1) to 1B(3), $X_2$ is selected from O, S, S(=O)$_2$, N-($L_2$)$_{a2}$-($R_2$), and C($R_6$)($R_7$), $L_{12}$, $L_{15}$, and $L_{18}$ may be each independently selected from a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —Si($Q_{33}$)($Q_{34}$)($Q_{35}$), a12, a15, and a18 are each independently 0 or 1, $R_2$ is selected from groups represented by Formulae 4-1 to 4-51, 5-1 to 5-6, and 6-1 to 6-10, $R_4$ to $R_9$ may be each independently selected from a hydrogen, a deuterium, a $C_1$-$C_{10}$ alkyl group, a $C_1$-$C_{10}$ alkoxy group, a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —Si($Q_{33}$)($Q_{34}$)($Q_{35}$), $R_{12}$, $R_{15}$, and $R_{18}$ may be each independently selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

groups represented by Formulae 4-1 to 4-51, 5-1 to 5-6, and 6-1 to 6-10; and

—Si($Q_3$)($Q_4$)($Q_5$), wherein $Q_3$ to $Q_5$ and $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group, but they are not limited thereto.

In some embodiments, $X_2$ in Formulae 1A(1) and 1B(1) may be selected from O, S, S(=O)$_2$, and N-($L_2$)$_{a2}$-($R_2$), $X_2$ in Formulae 1A(2) and 1B(2) may be selected from S, N-($L_2$)$_{a2}$-($R_2$) and C($R_6$)($R_7$), $X_2$ in Formulae 1A(3) and 1B(3) may be selected from O, N-($L_2$)$_{a2}$-($R_2$) and C($R_6$)($R_7$), in Formulae 1A(1) to 1A(3), and 1B(1) to 1B(3), $L_{12}$, $L_{15}$, and $L_{18}$ may be each independently selected from a phenylene group, a naphthylene group, a pyridinylene group, a fluorenylene group, a carbazolylene group, a dibenzofuranylene group, and a dibenzothiophenylene group; and a phenylene group, a naphthylene group, a pyridinylene group, a fluorenylene group, a carbazolylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —Si($Q_{33}$)($Q_{34}$)($Q_{35}$), a12, a15, and a18 may be each independently 0 or 1, $R_2$, $R_{12}$, $R_{15}$, and $R_{18}$ may be each independently selected from groups represented by Formulae 4-1 to 4-51, 5-1 to 5-6, and 6-1 to 6-10 (for example, groups represented by Formulae 4-1(1) to 4-8(1), 4-1(2) to 4-8(2), 4-1(3) to 4-8(3), 5-1(1) to 5-4(1), 5-1(2) to 5-4(2), 5-1(3) to 5-4(3), 5-1(4) to 5-4(4), 5-6(1) to 5-6(3), and 6-1(1) to 6-1(8)), and $R_4$ to $R_9$ may be each independently selected from a hydrogen, a deuterium, a $C_1$-$C_{10}$ alkyl group, a $C_1$-$C_{10}$ alkoxy group, a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —Si$(Q_{33})(Q_{34})(Q_{35})$, wherein $Q_{33}$ to $Q_{35}$ may be each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group, but they are not limited thereto.

For example, the condensed cyclic compound represented by Formula 1 may be one of Compounds 1 to 768, but is not limited thereto:

1

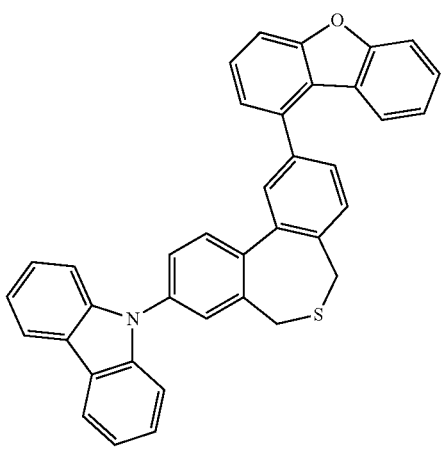

2

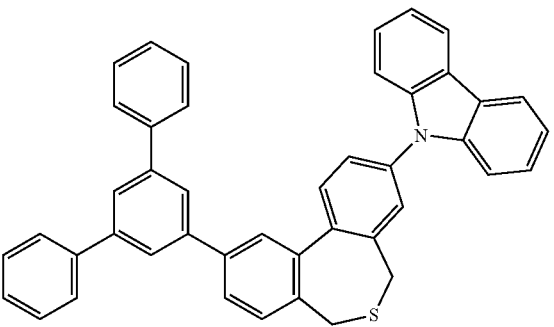

3


4

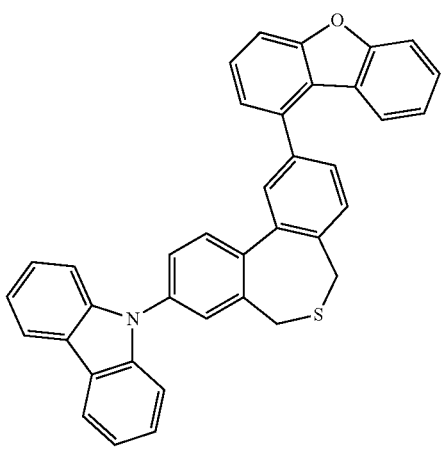

5


6

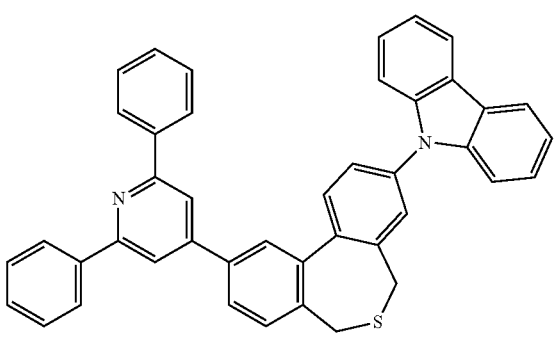

-continued
7
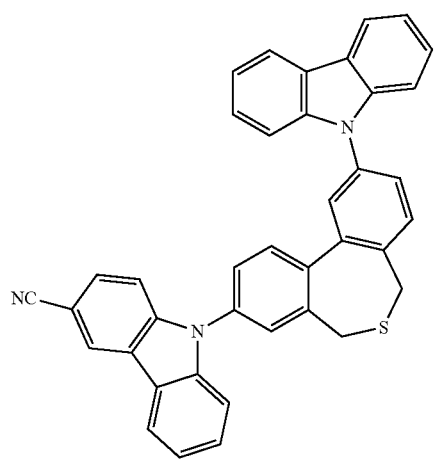
8
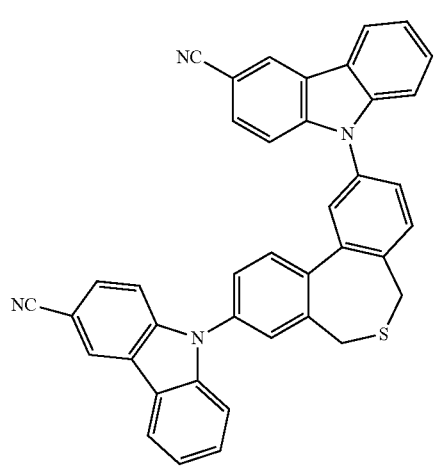
9
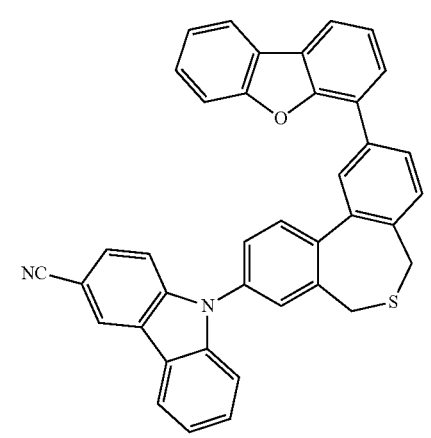
-continued
10
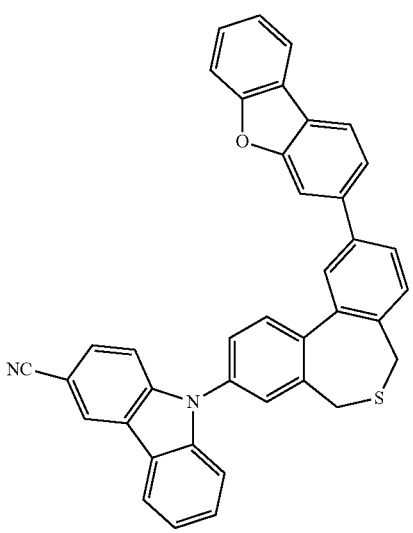
11
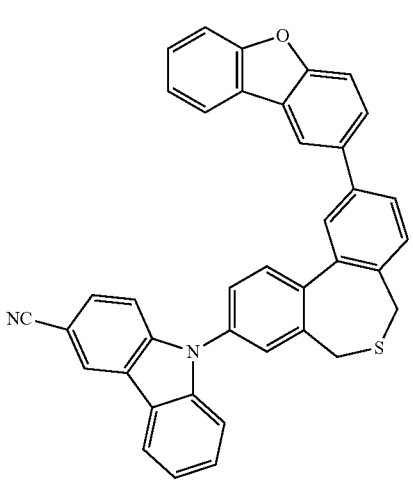
12
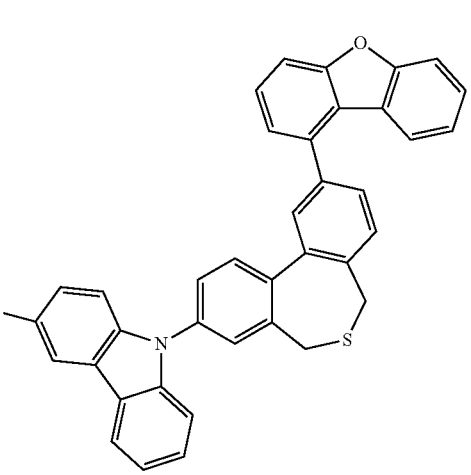

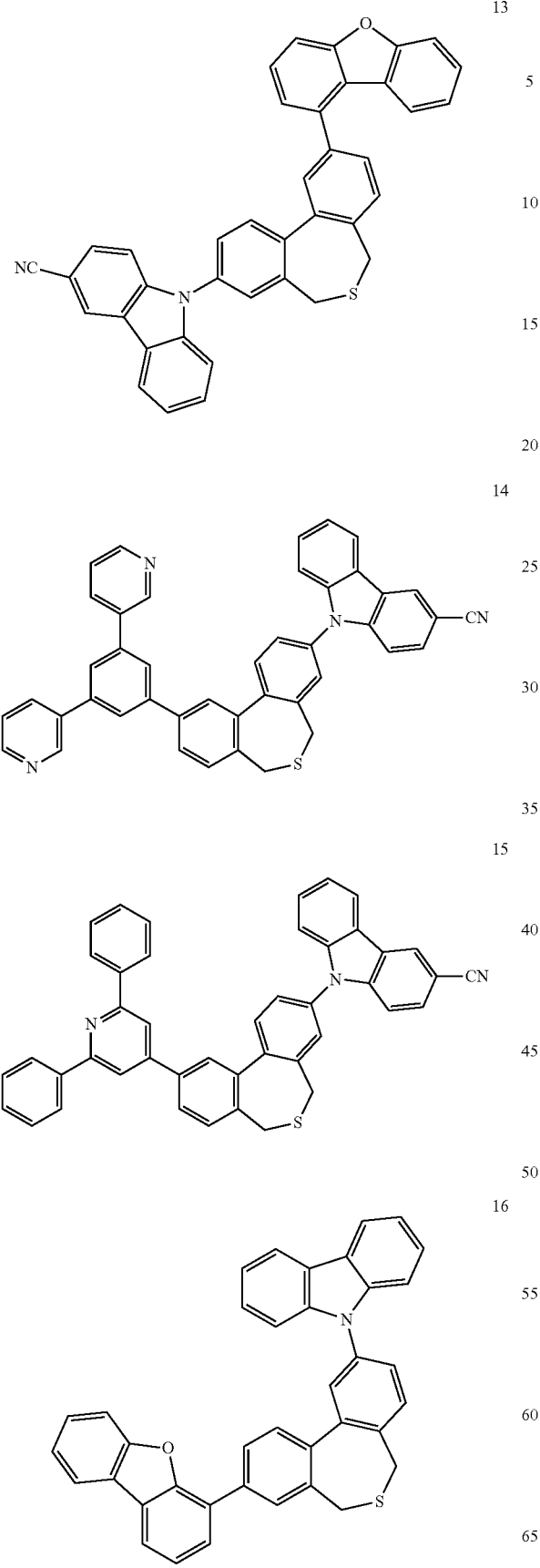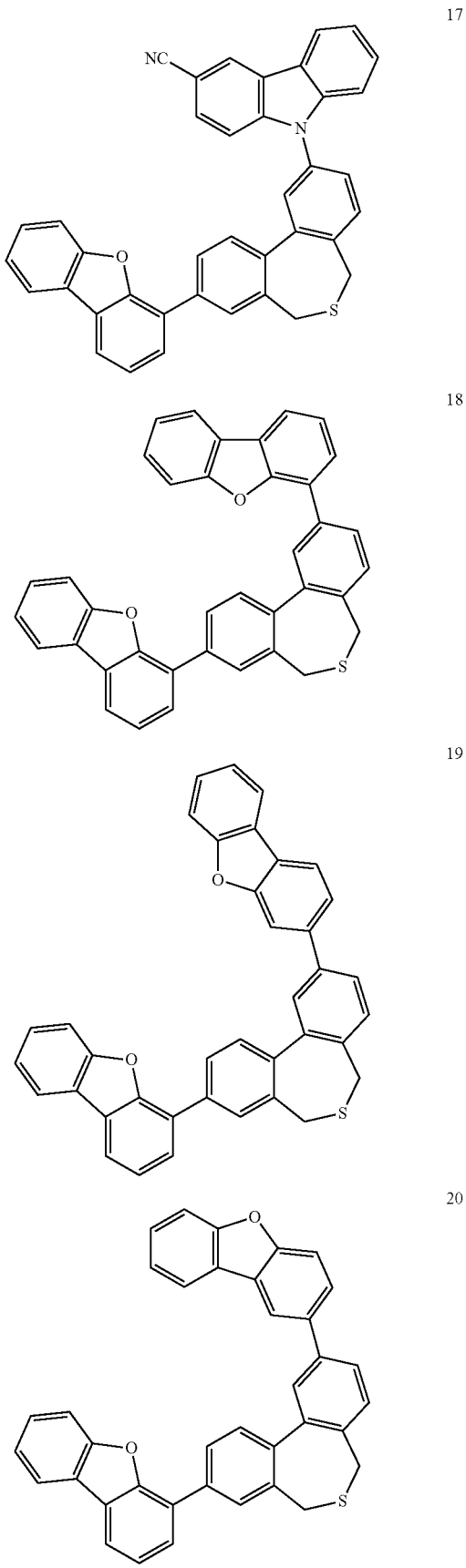

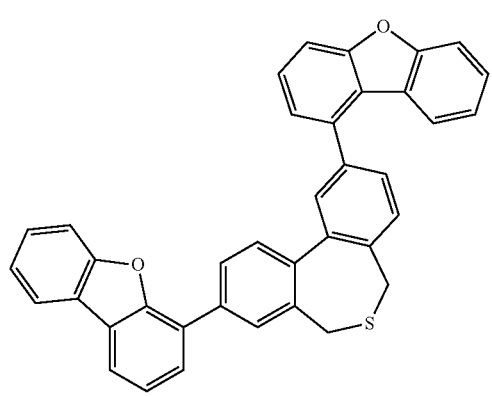
21
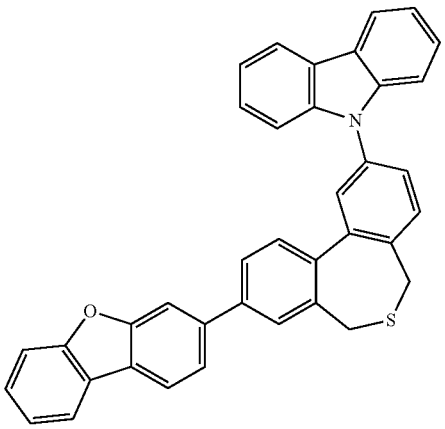
25
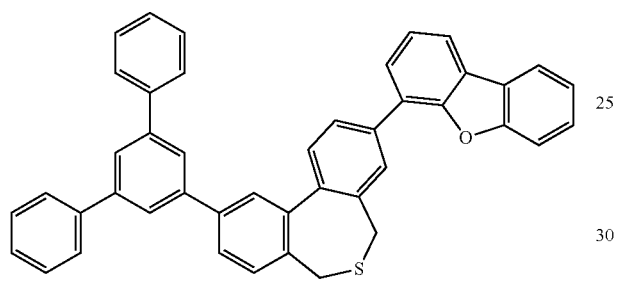
22
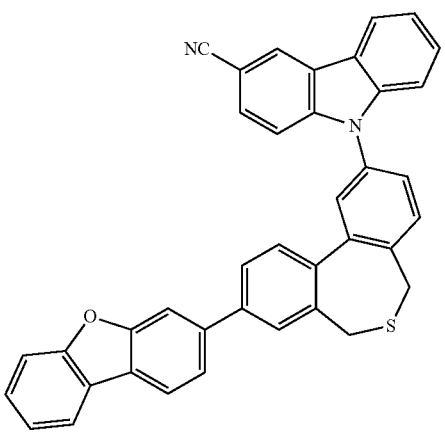
26
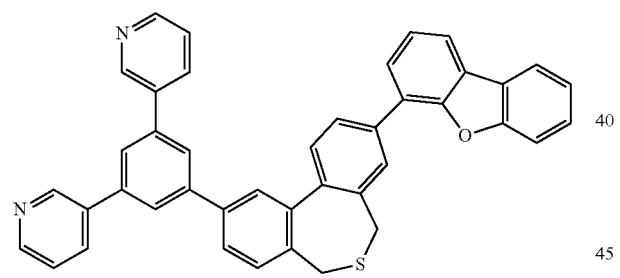
23
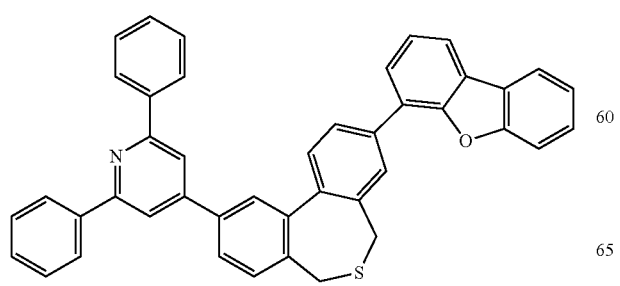
24
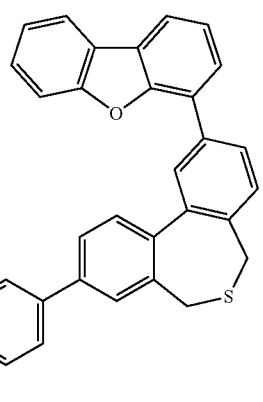
27

28
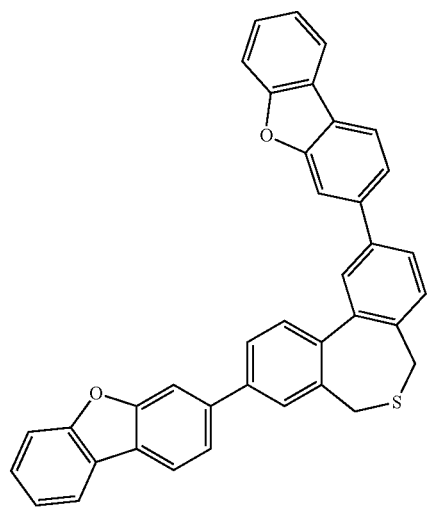
29
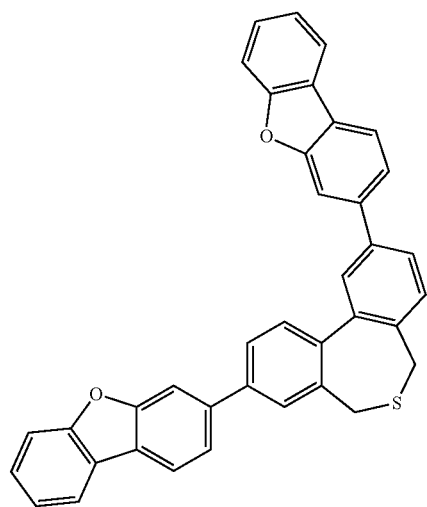
30
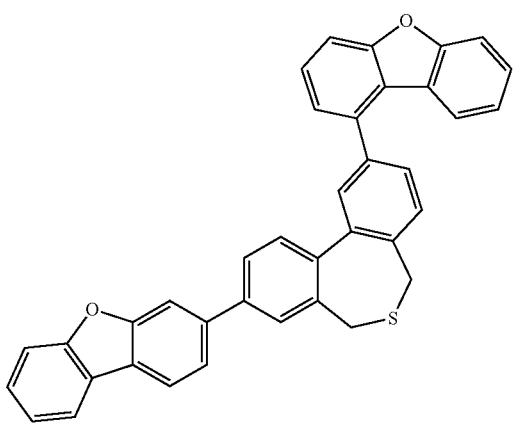
31
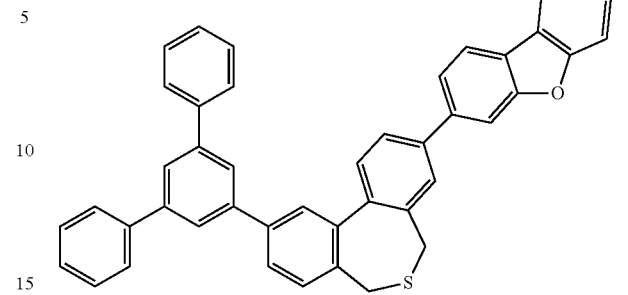
32
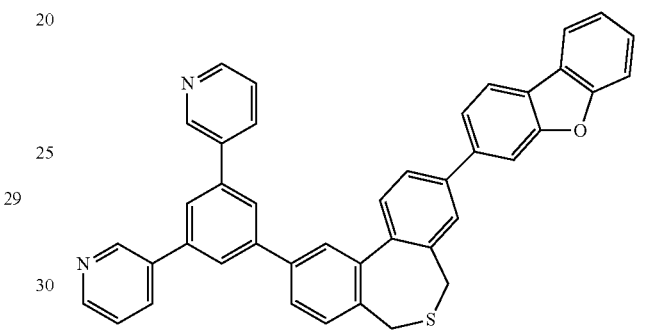
33
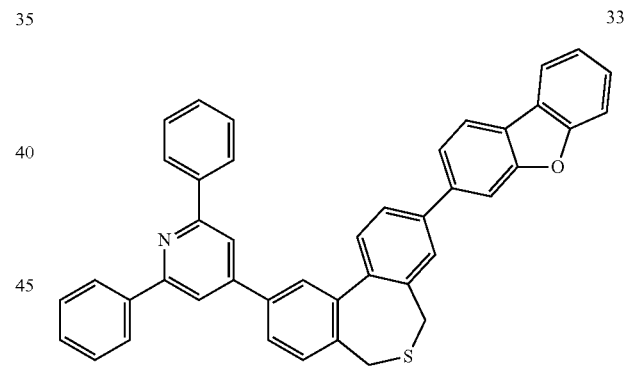
34
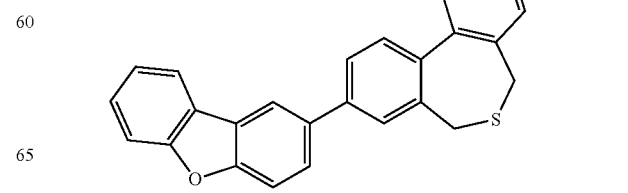

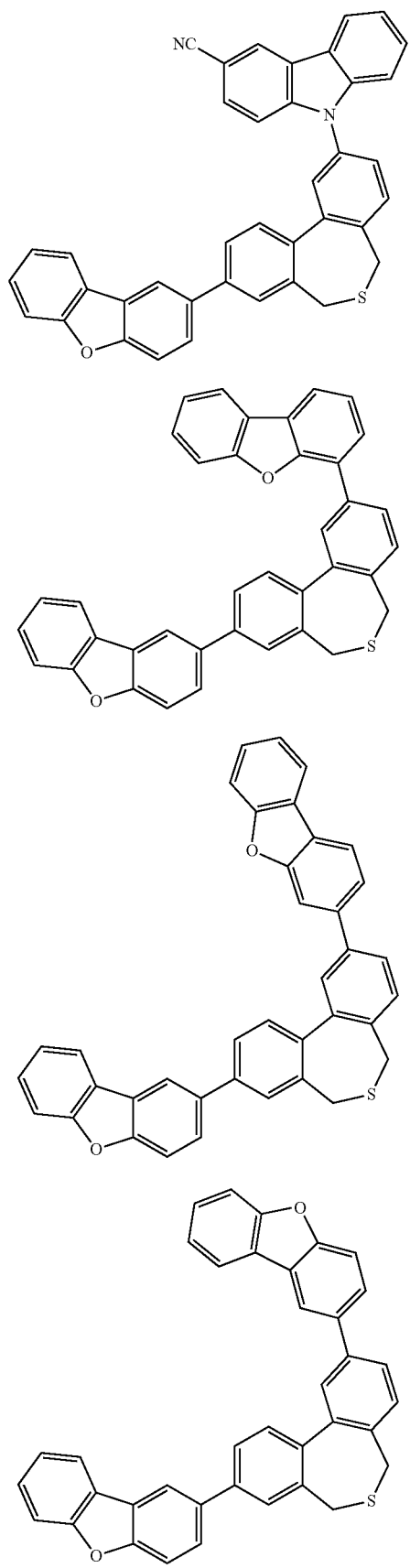
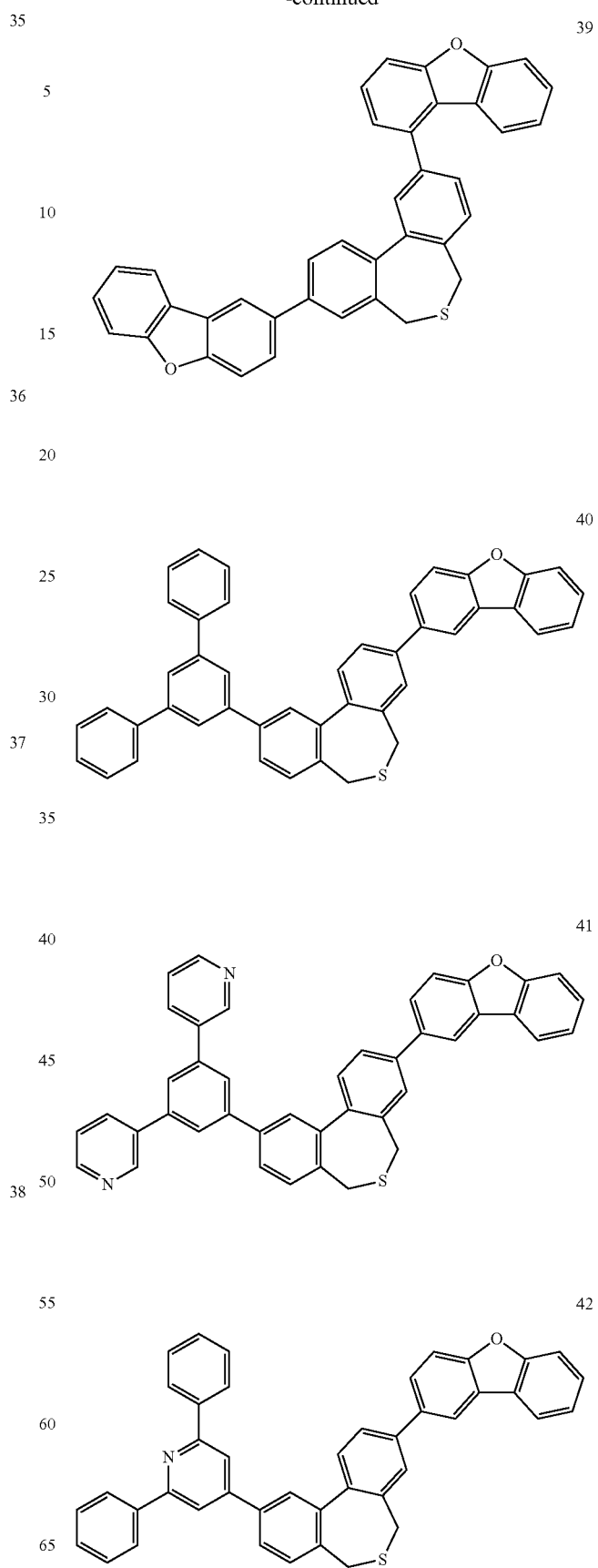

43
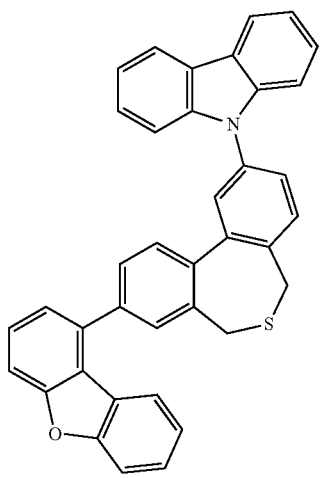
44
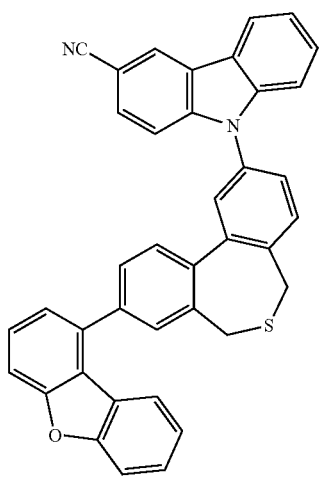
45
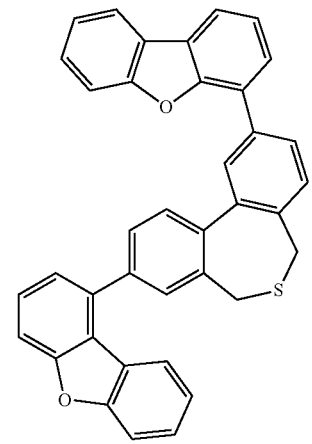
46
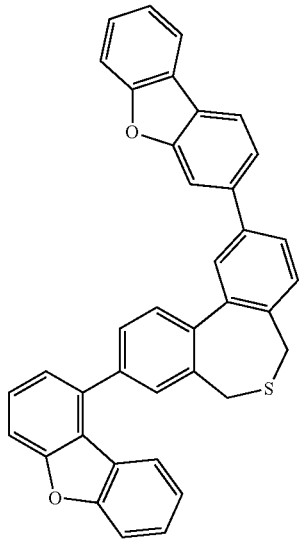
47
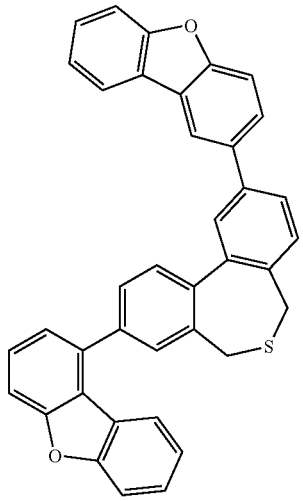
48
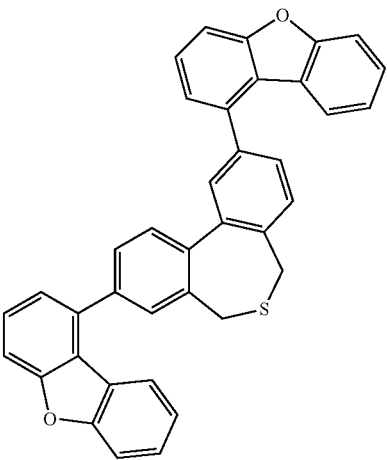

49
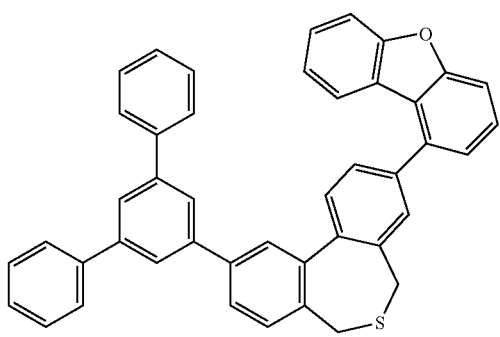
50
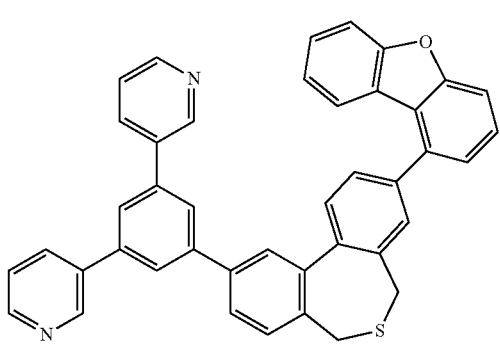
51
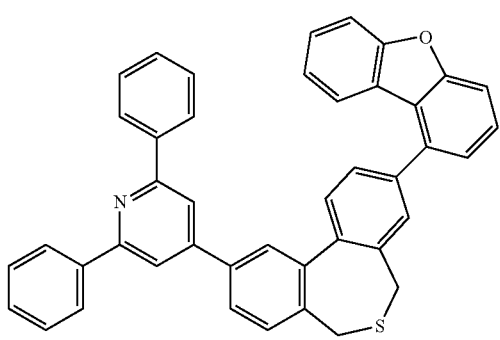
52
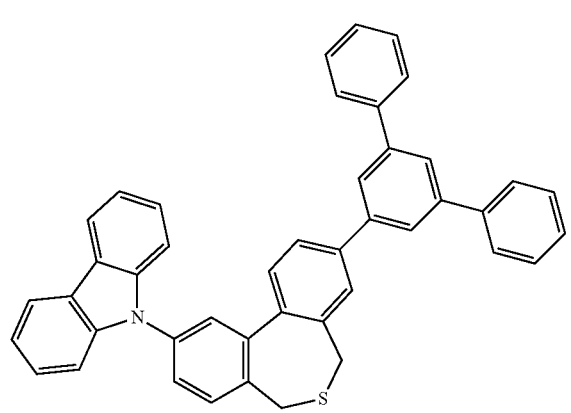
53
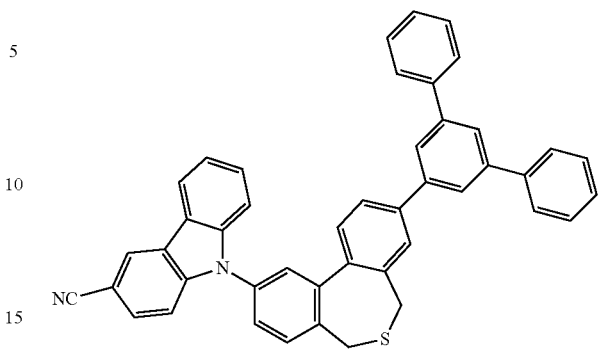
54
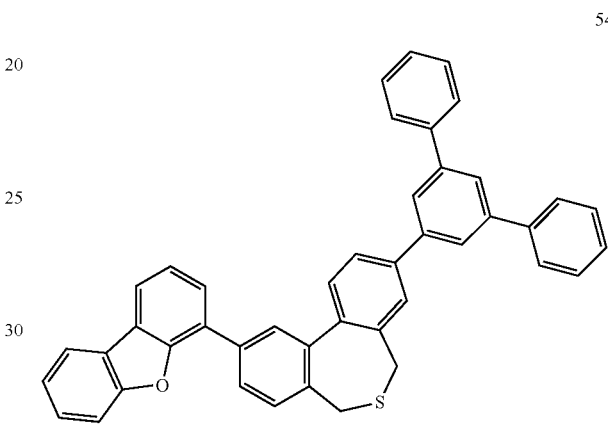
55
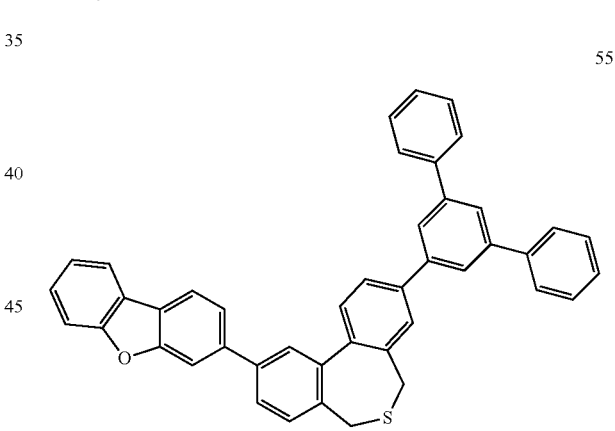
56
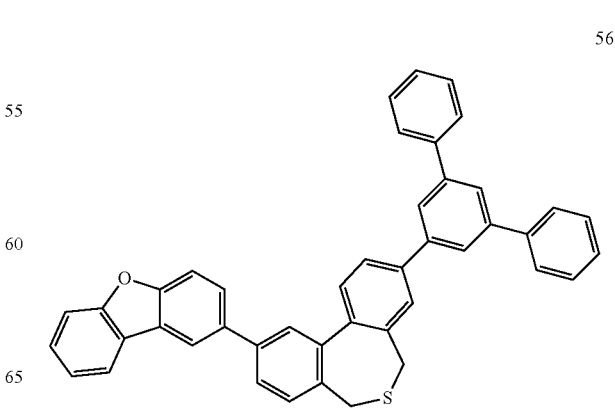

57
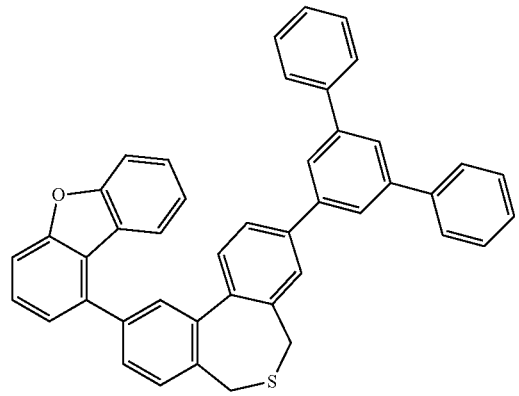
58
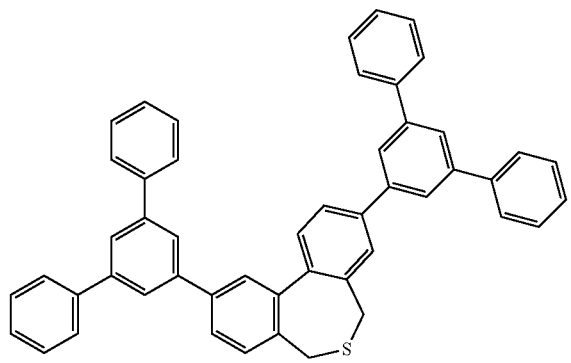
59
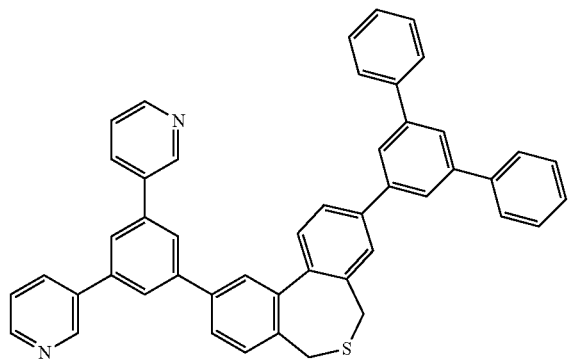
60
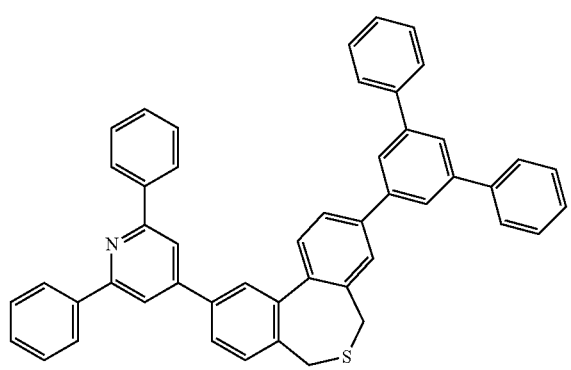
61
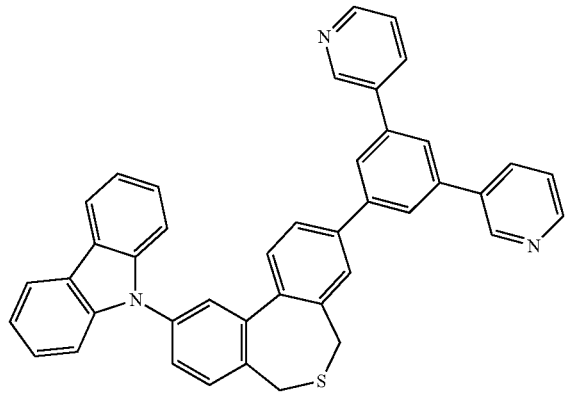
62
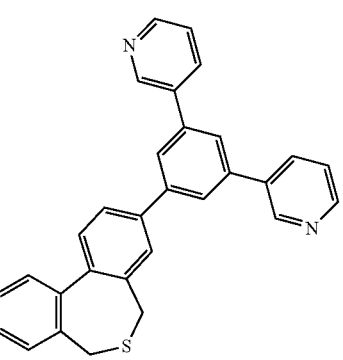
63
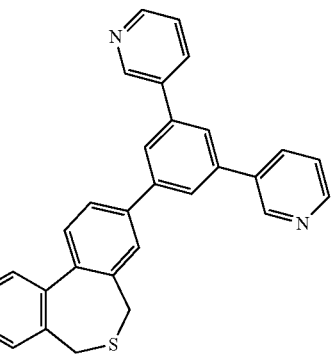
64
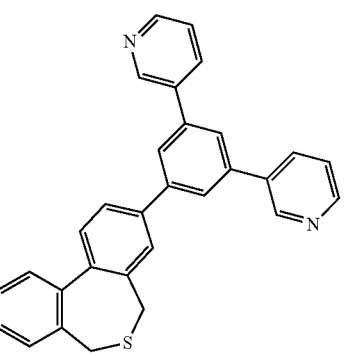

65
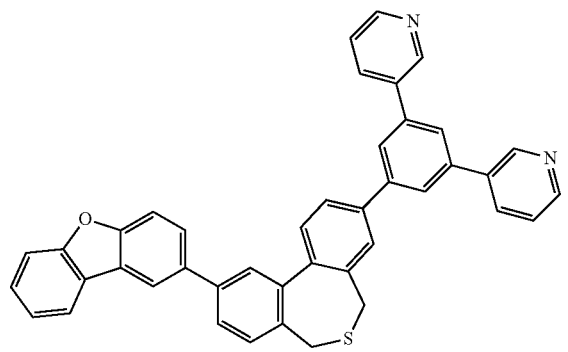
66
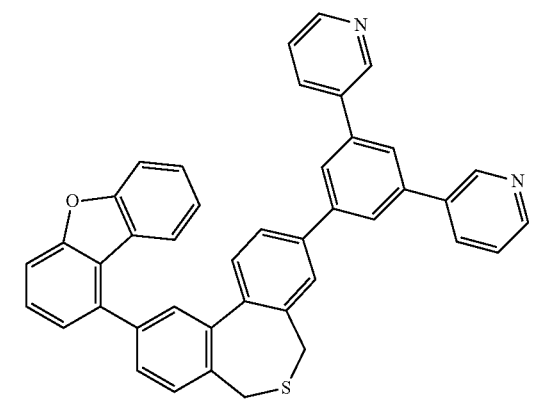
67
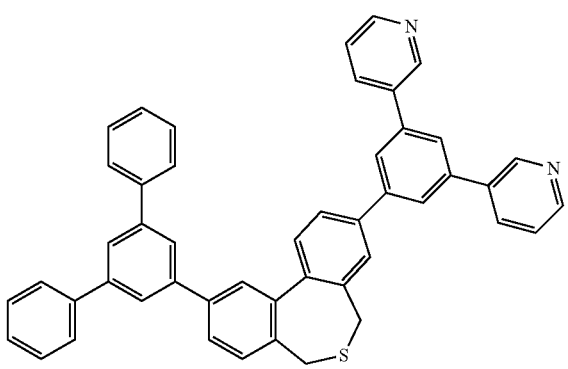
68
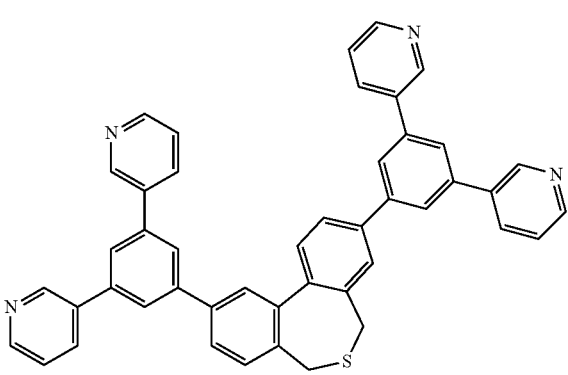
69
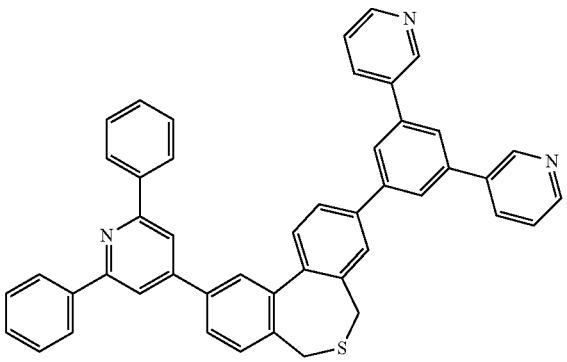
70
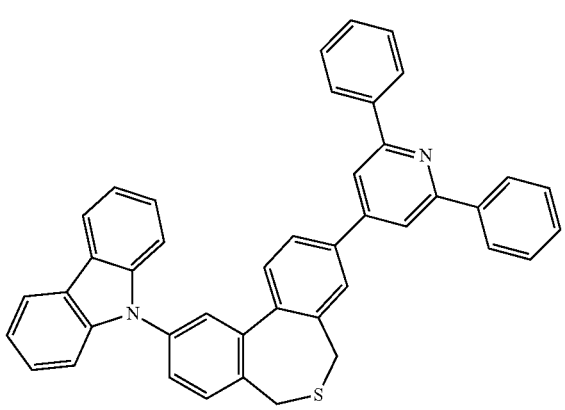
71
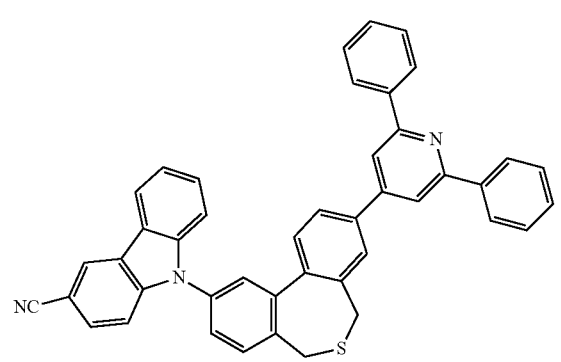
72
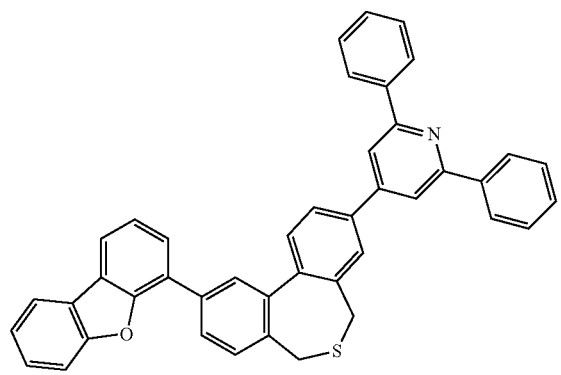

73
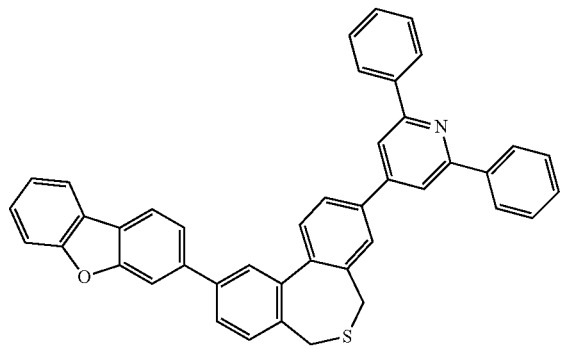
74
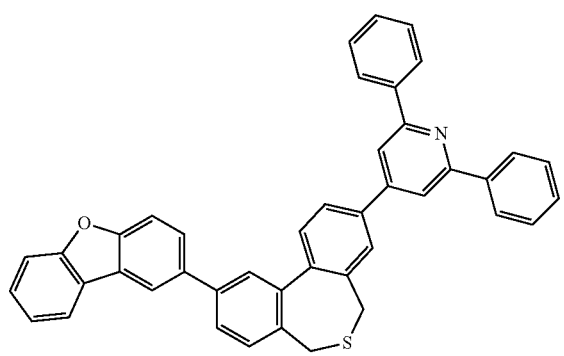
75
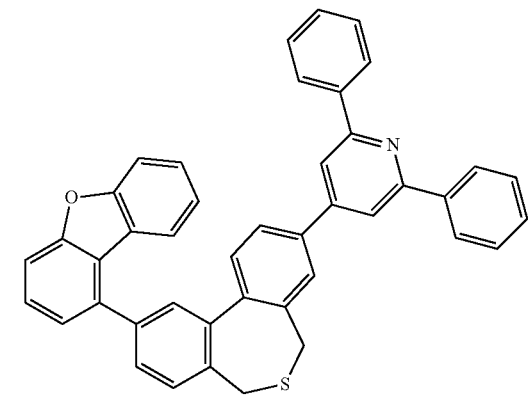
76
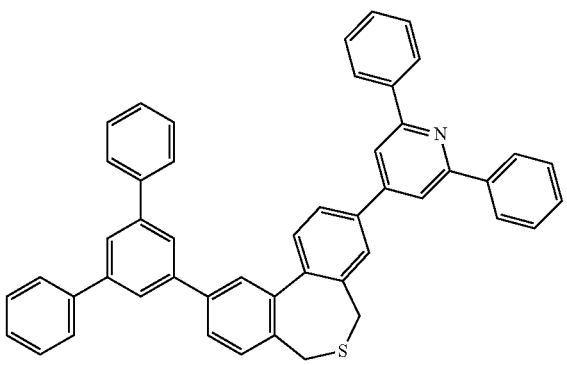
77
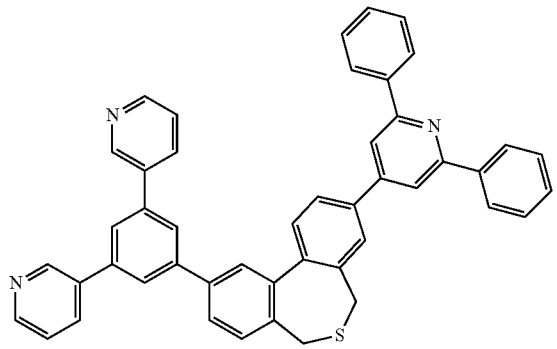
78
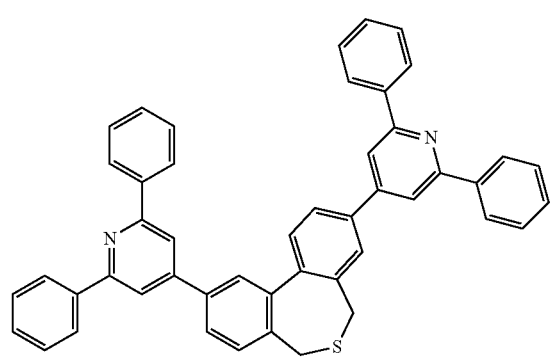
79
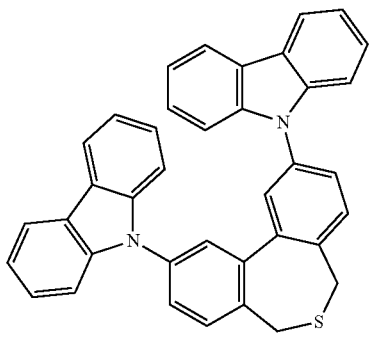
80
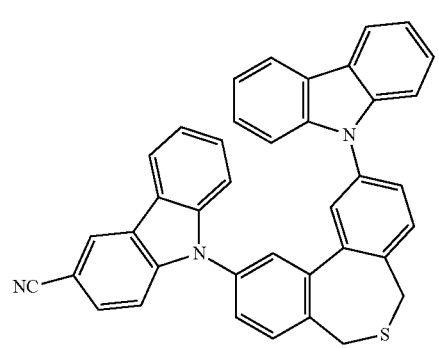

81
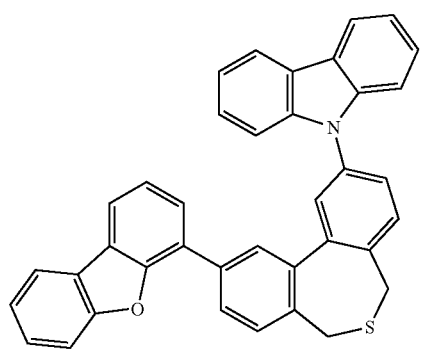
82
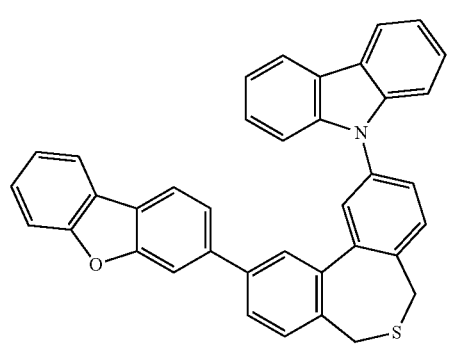
83
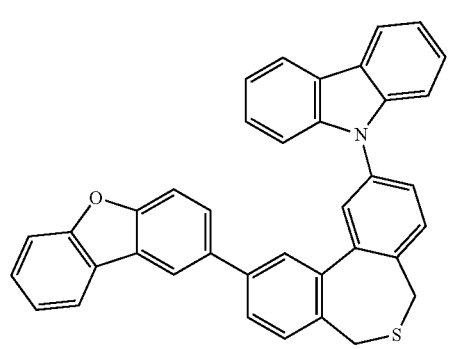
84
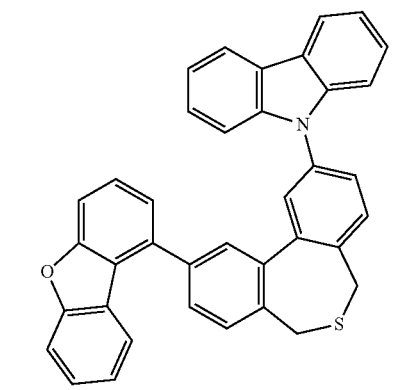
85
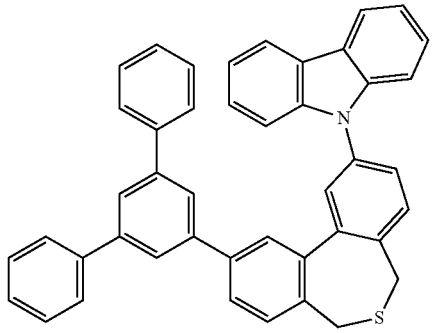
86
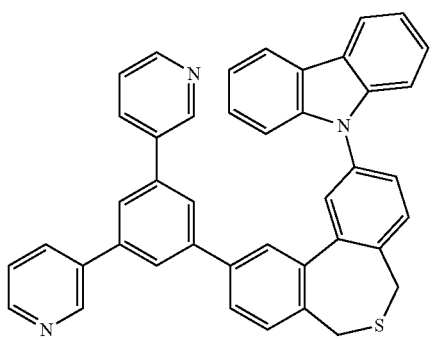
87
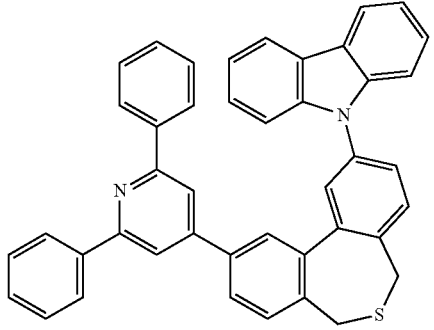
88
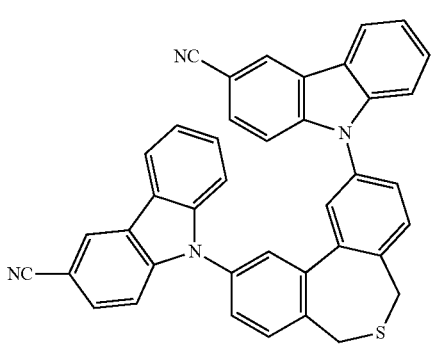

57
-continued
89
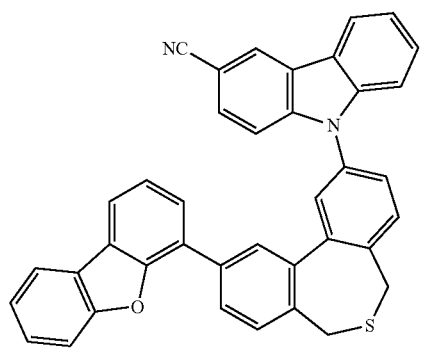
90
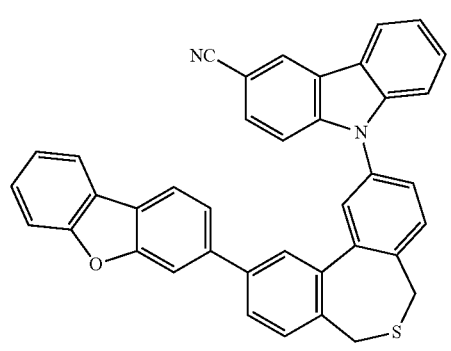
91
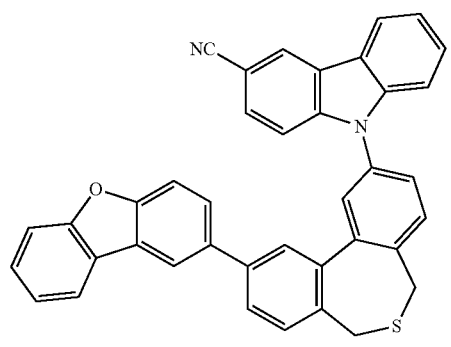
92
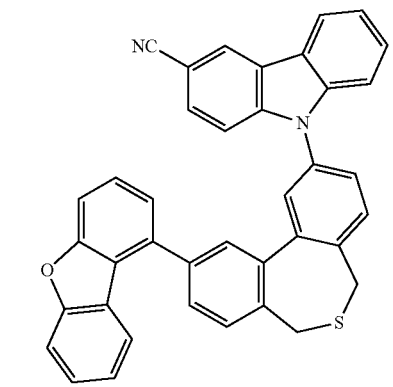
58
-continued
93
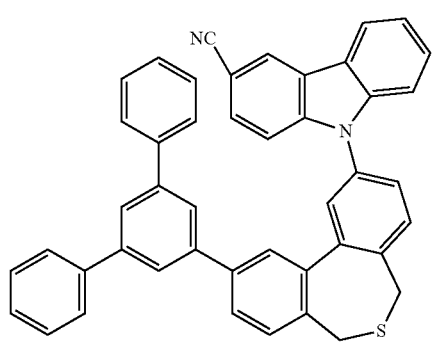
94
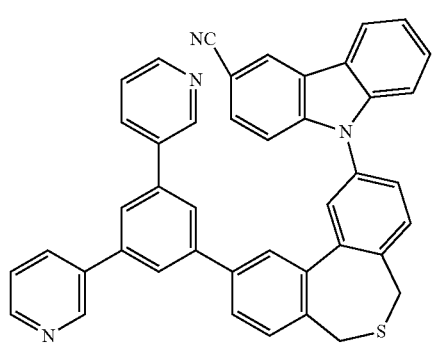
95
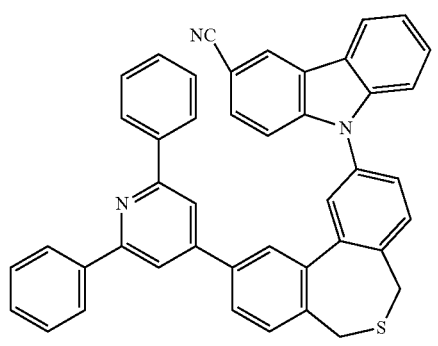
96
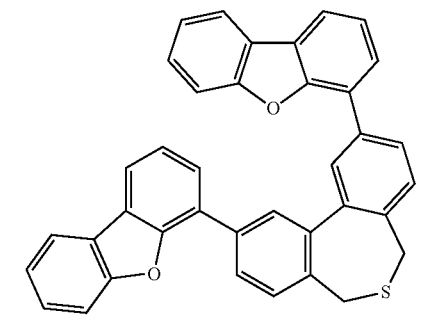

97
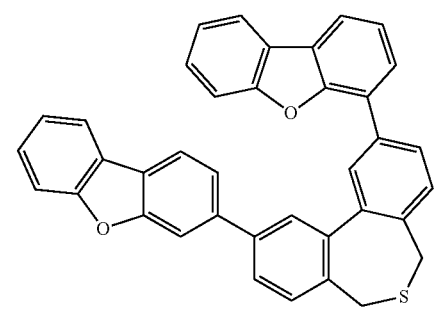
98
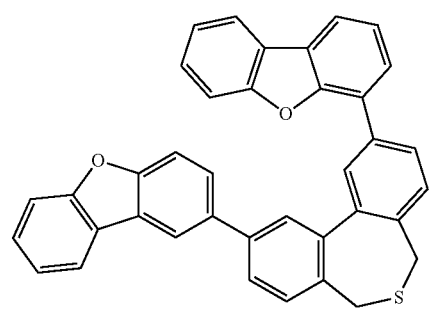
99
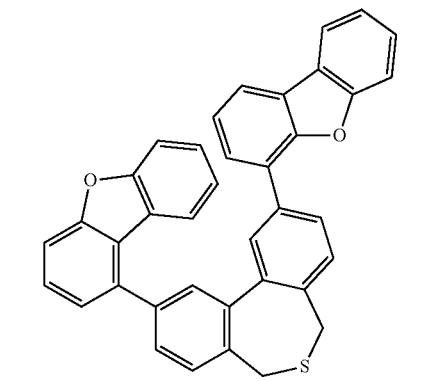
100
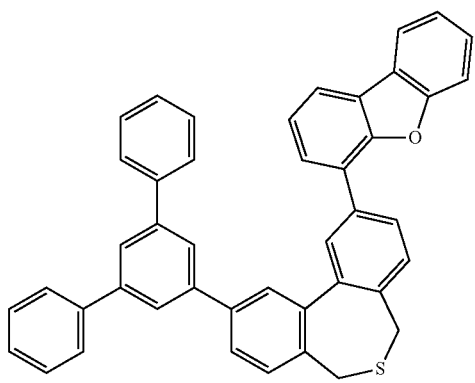
101
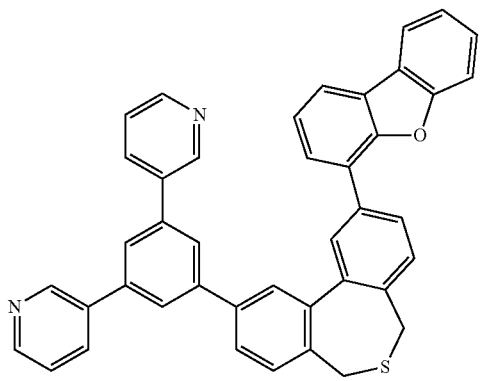
102
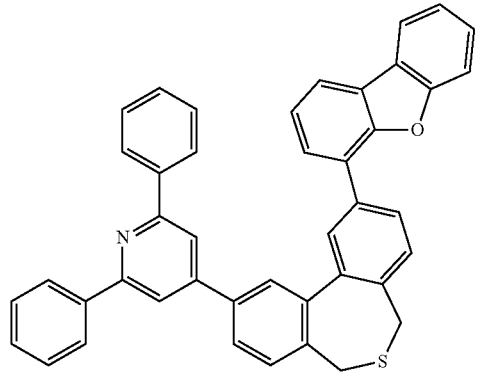
103
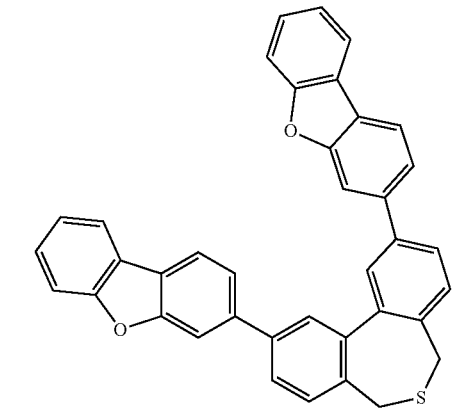
104
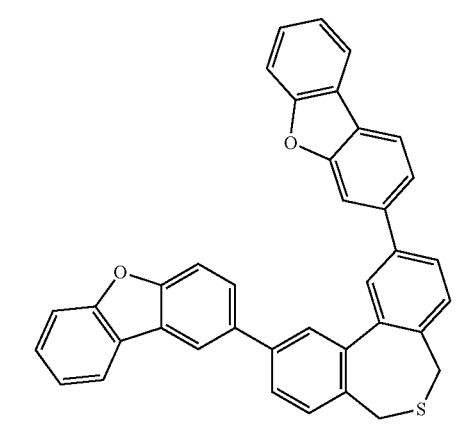

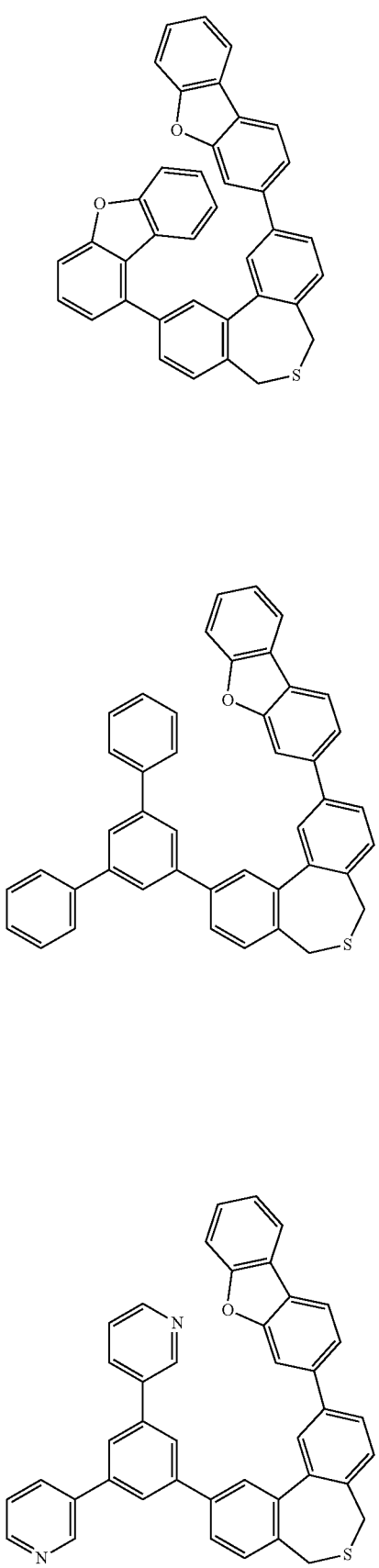
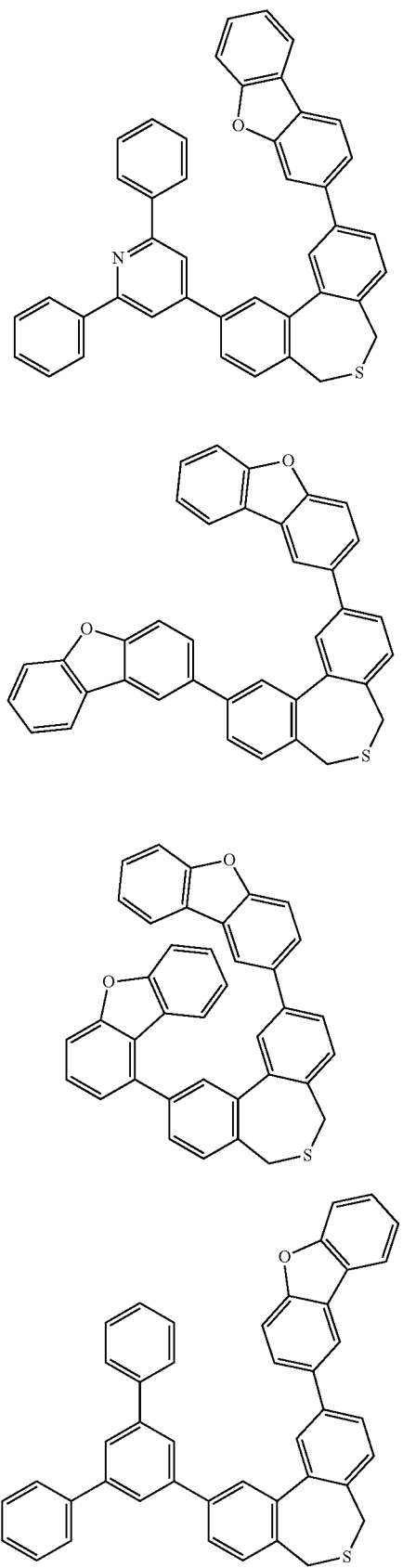

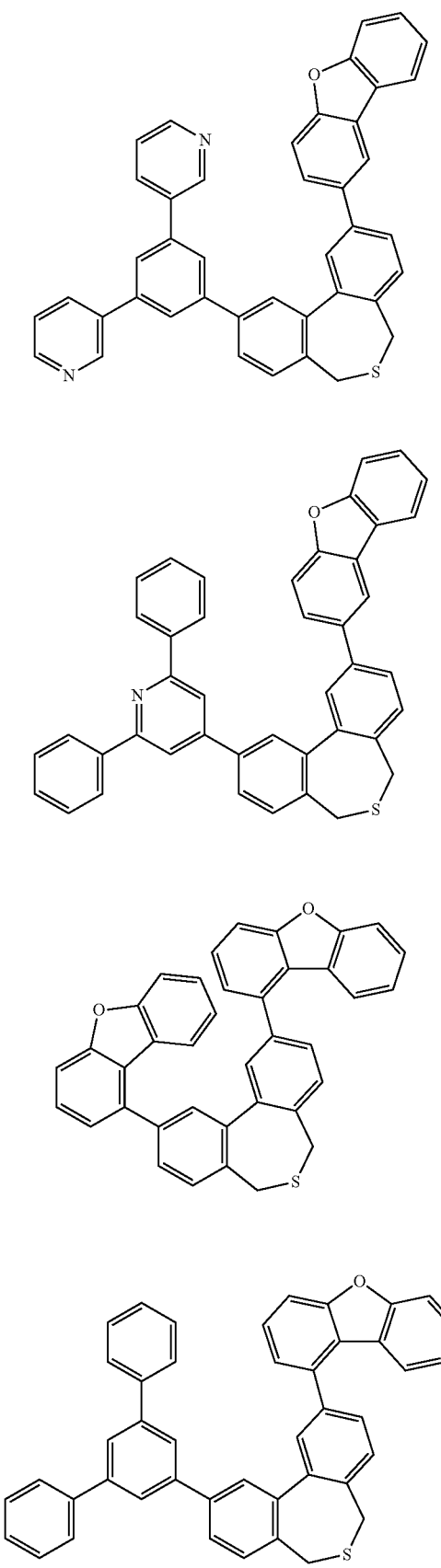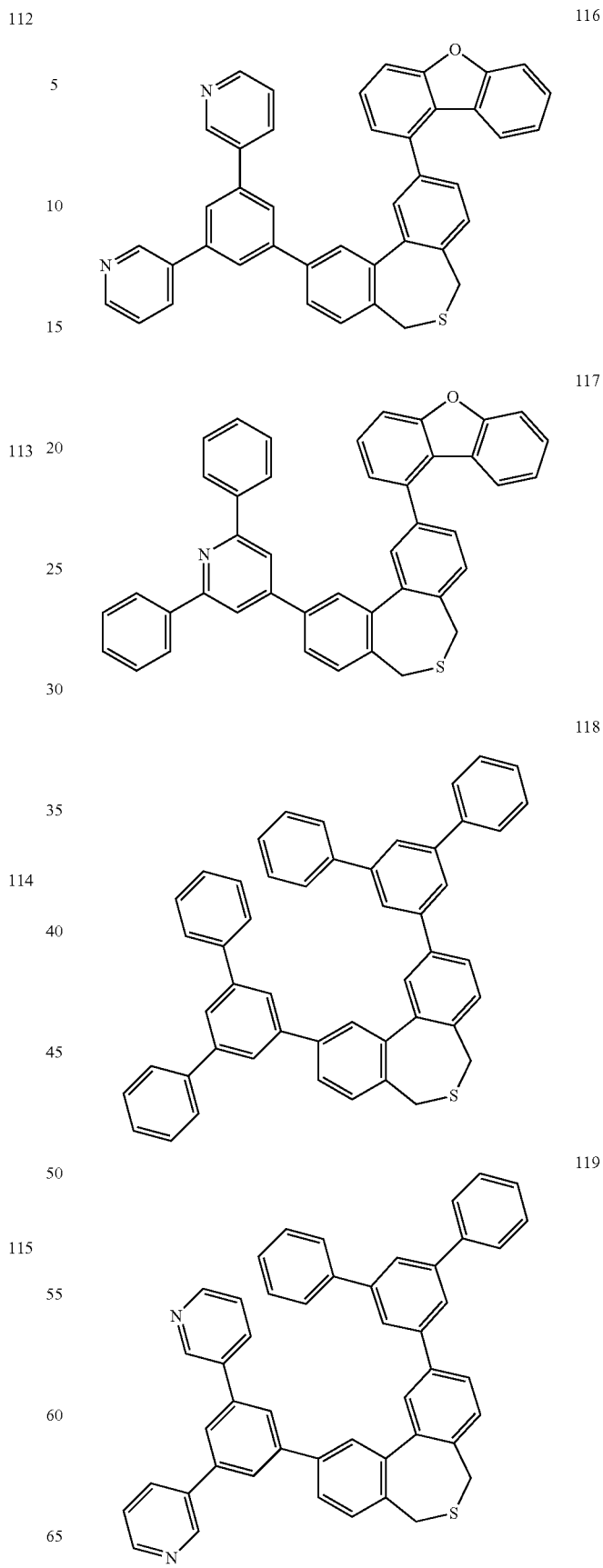

120
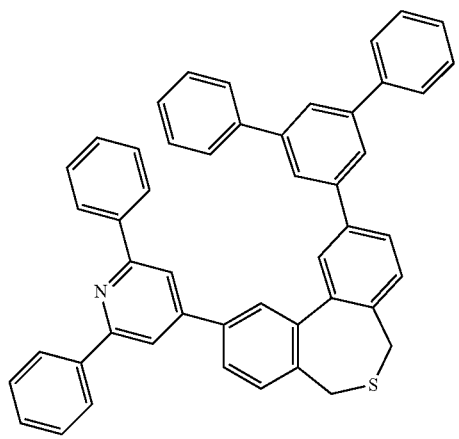
121
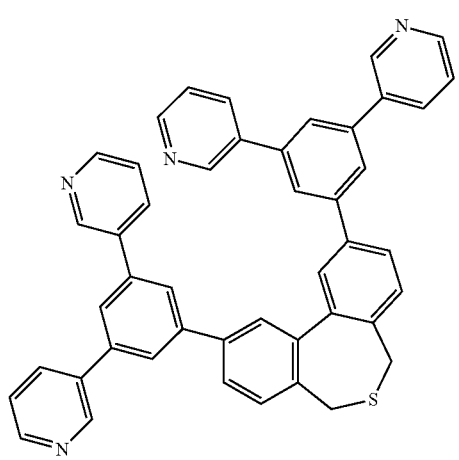
122
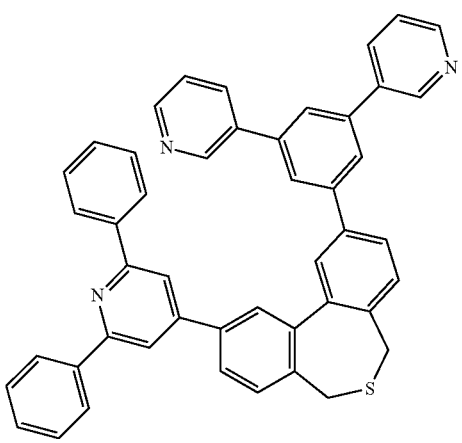
123
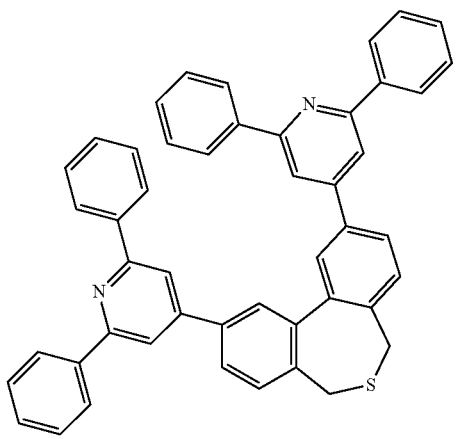
124
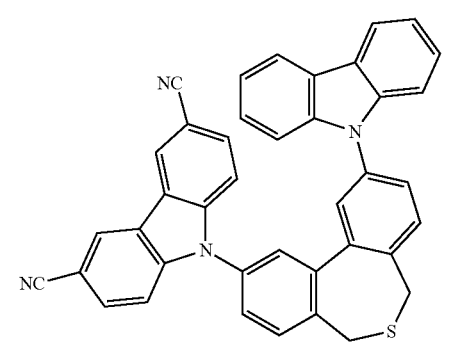
125
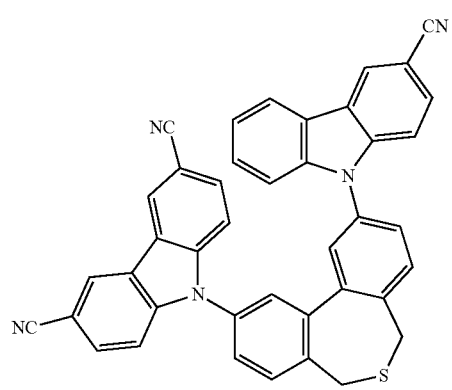
126
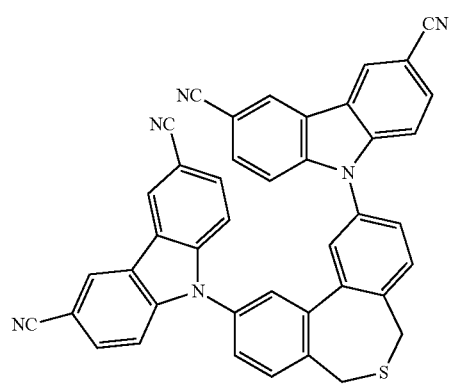

-continued
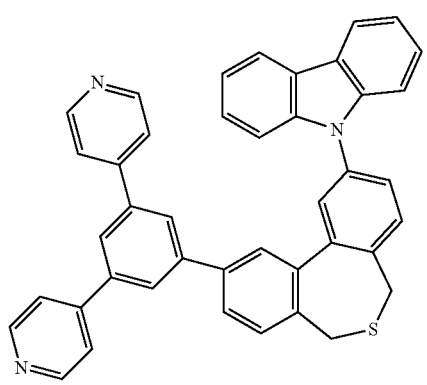
127
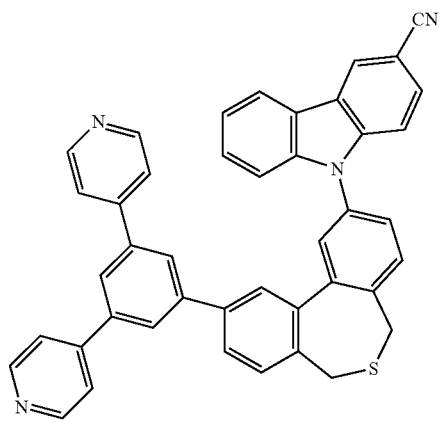
128
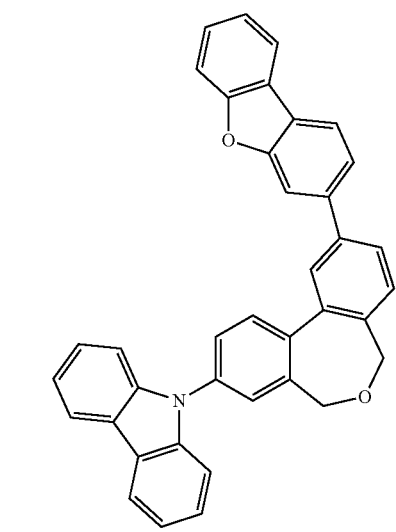
129
-continued
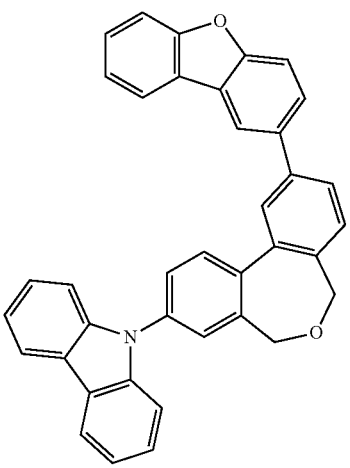
130
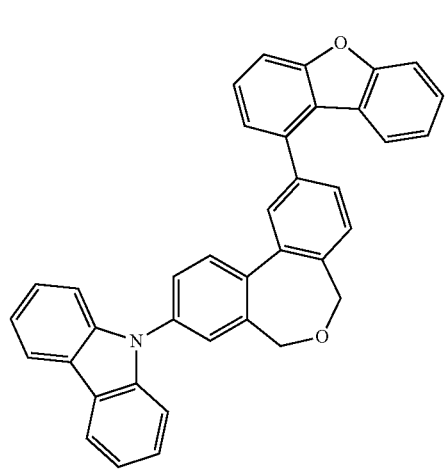
131
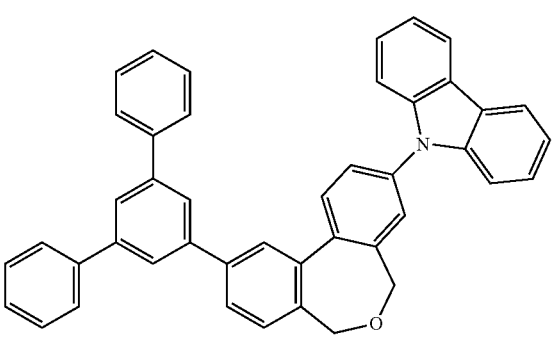
132
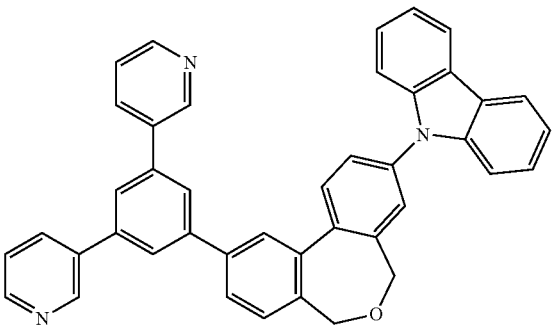
133

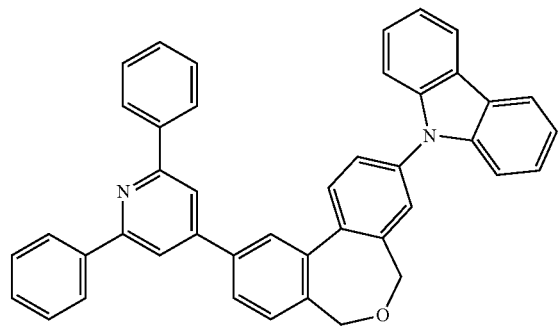
134
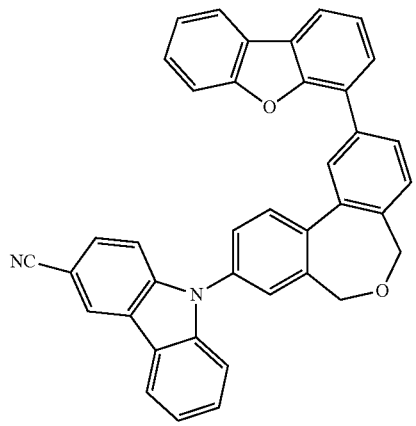
137
135
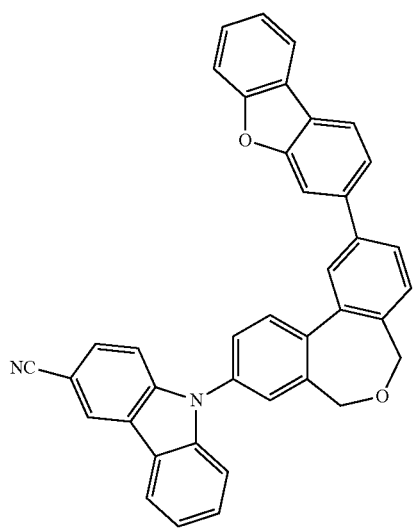
138
136
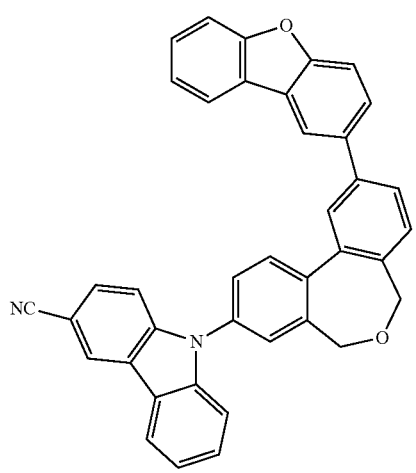
139

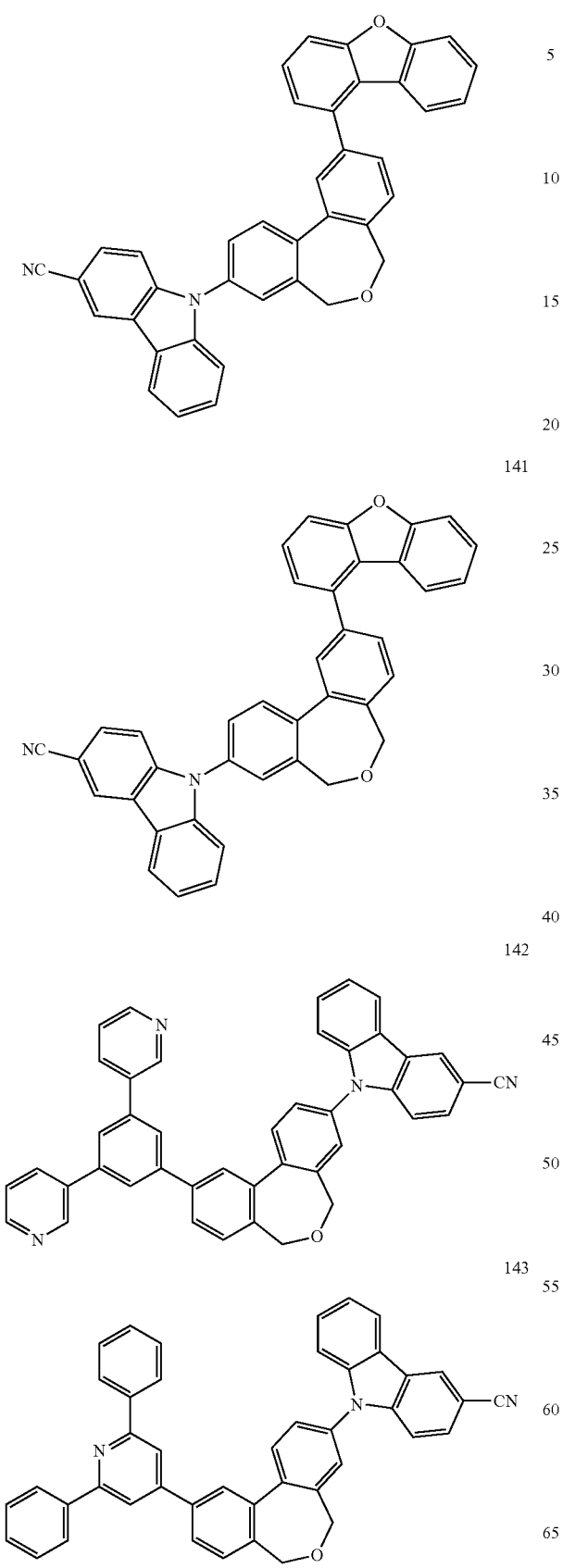
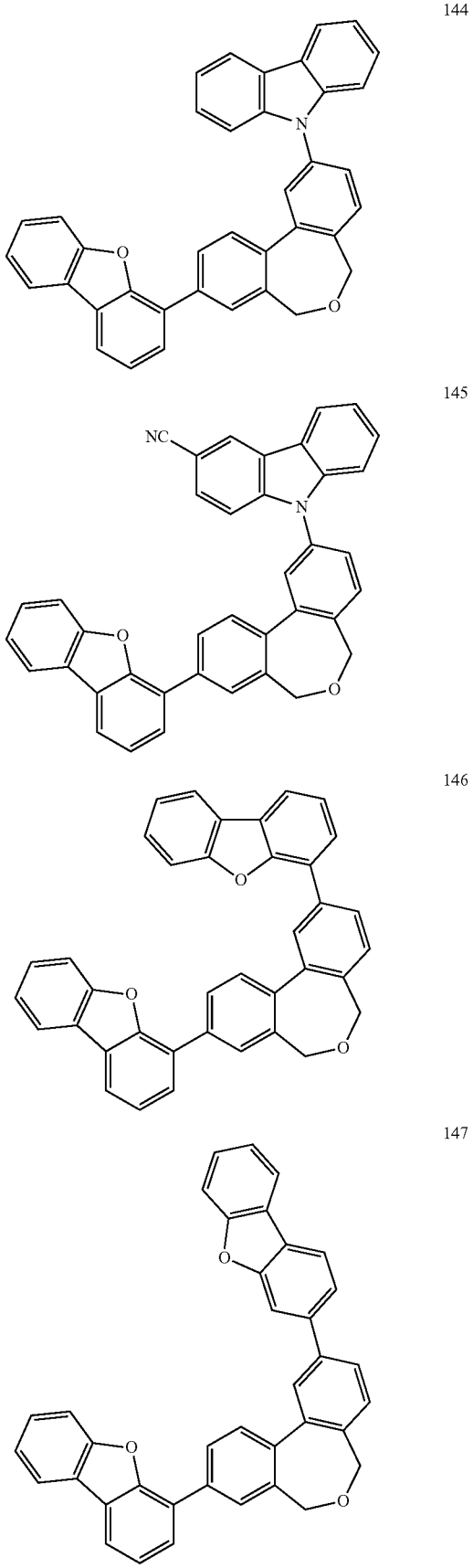

148
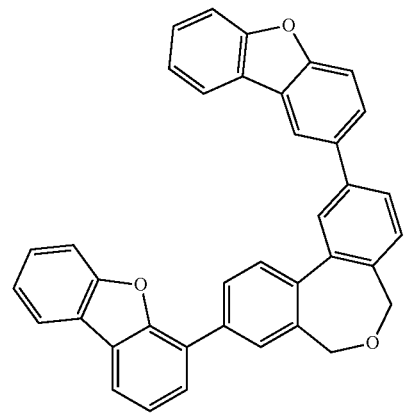
149
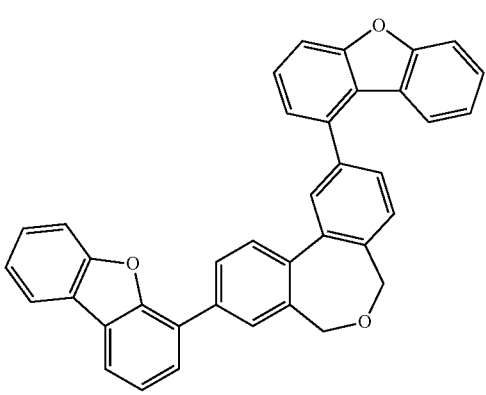
150
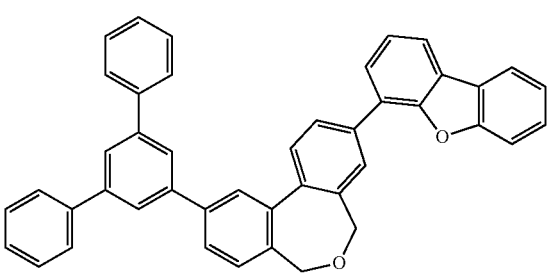
151
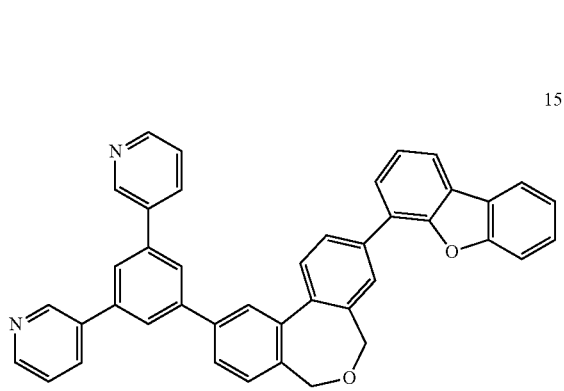
152
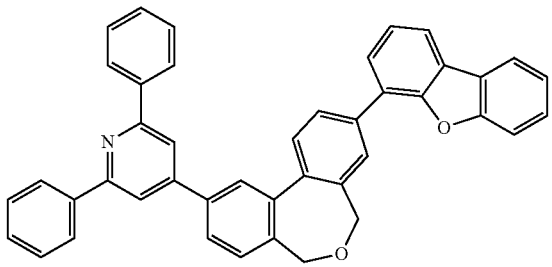
153
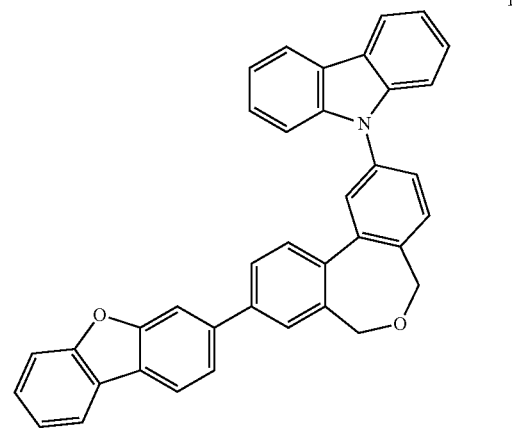
154
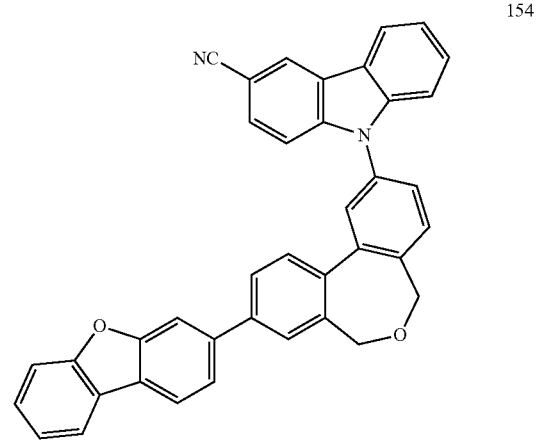
155
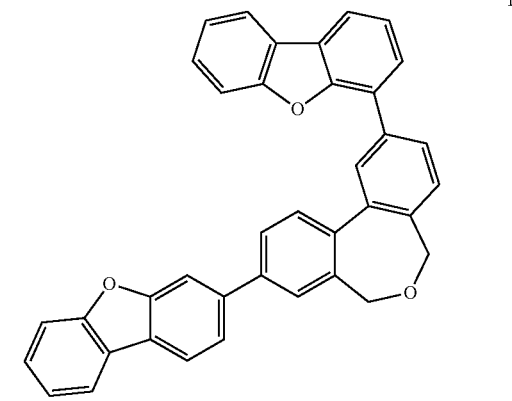

75
-continued
156
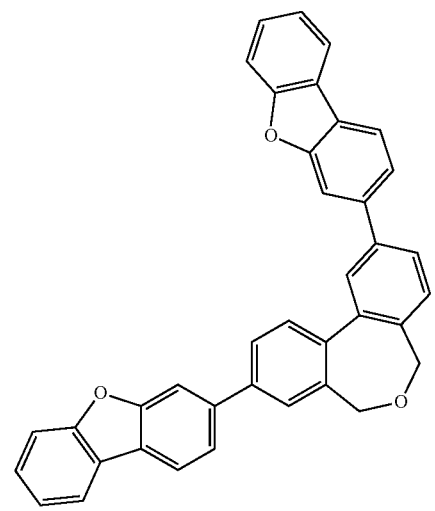
157
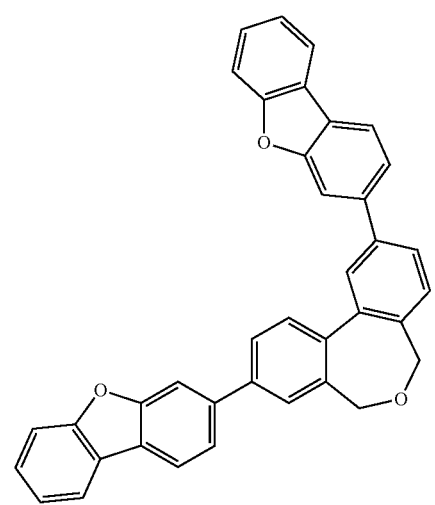
158
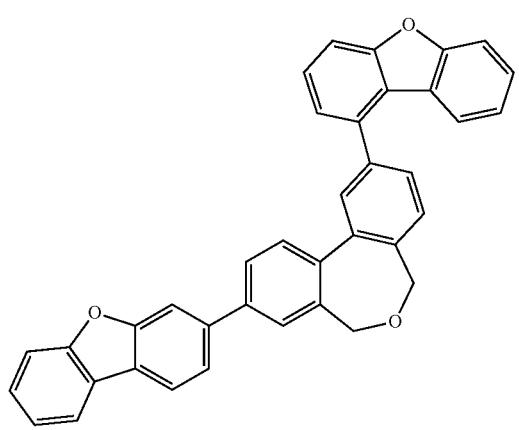
76
-continued
159
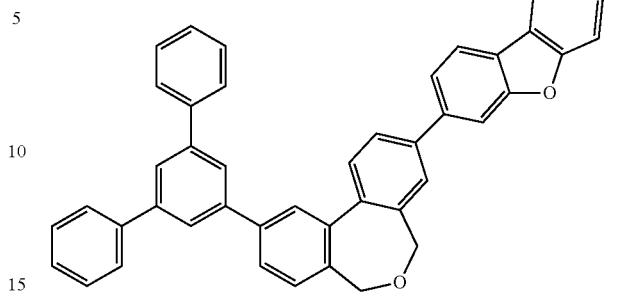
160
161
162
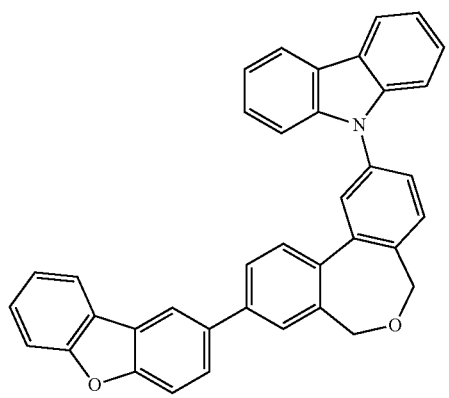

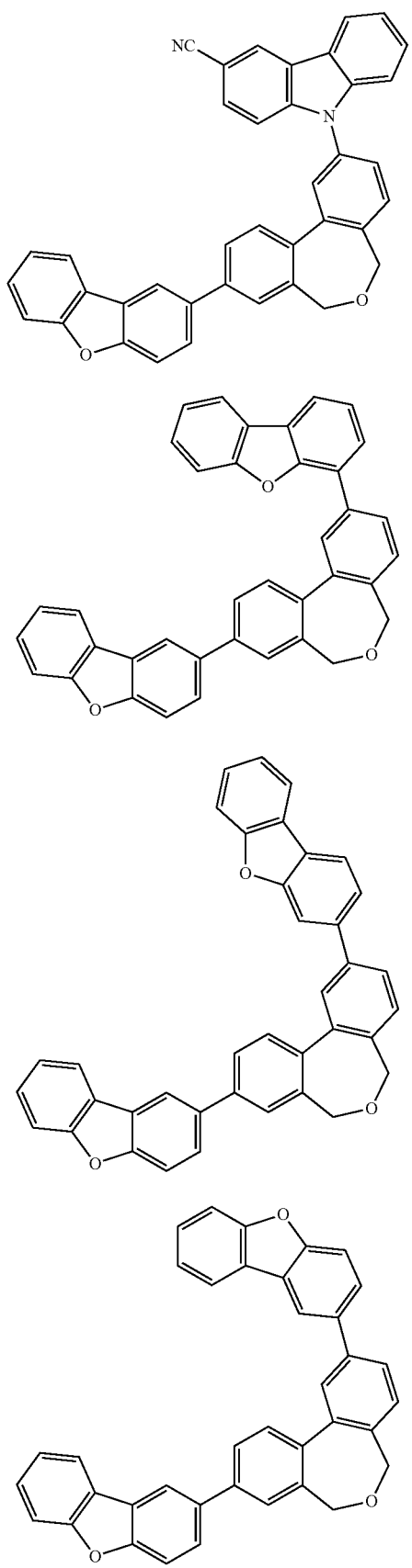
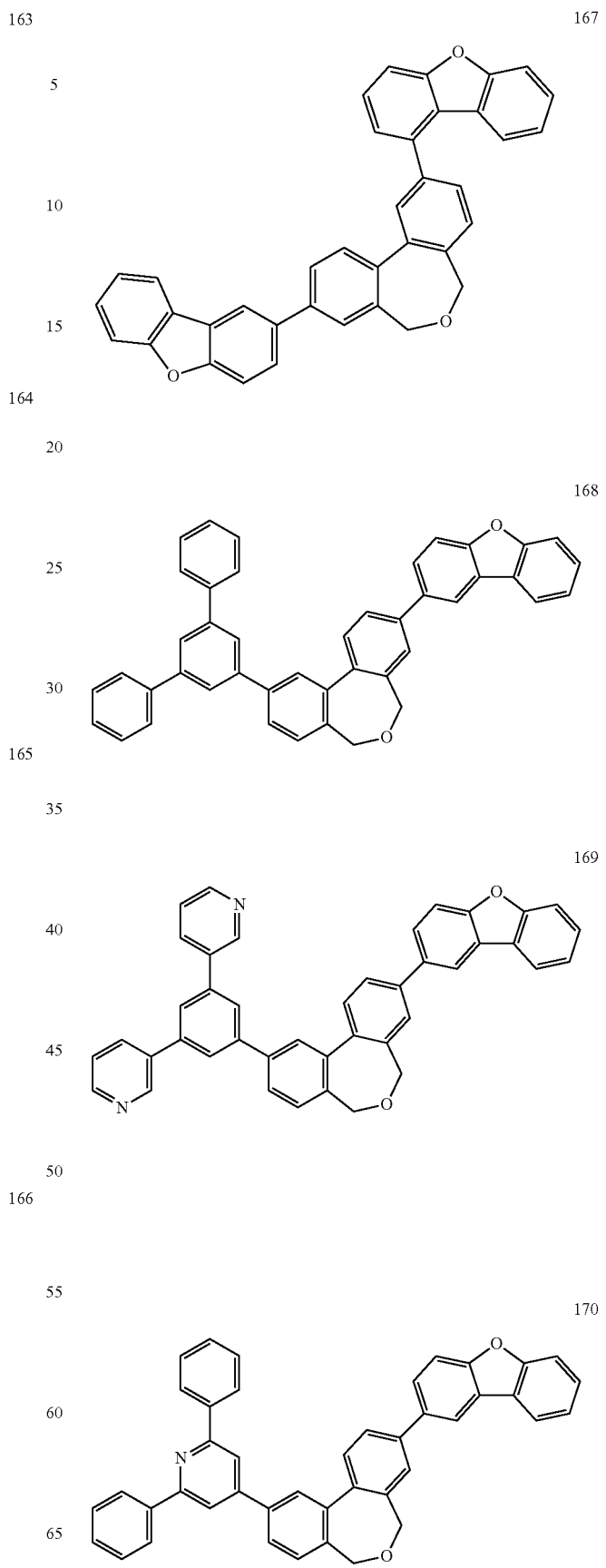

171
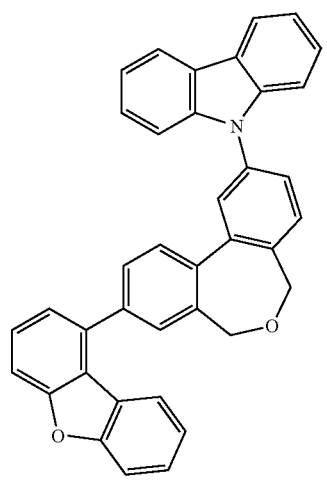
172
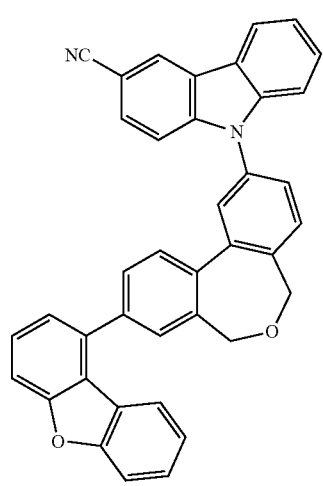
173
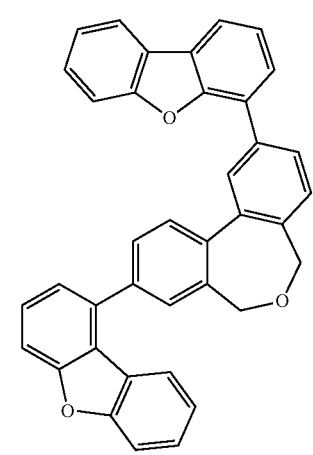
174
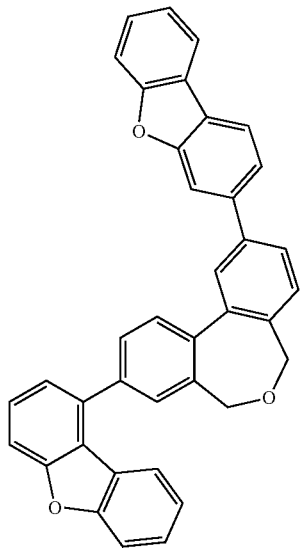
175
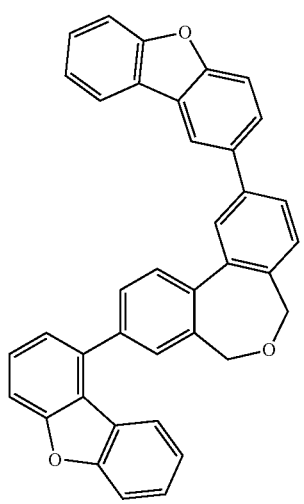
176
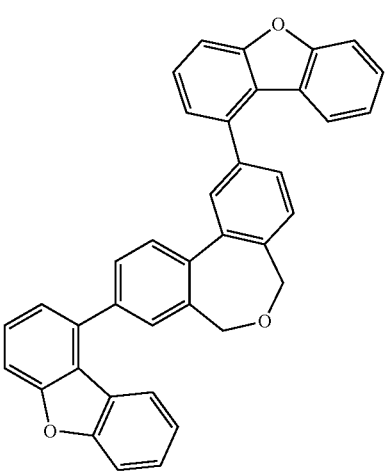

177
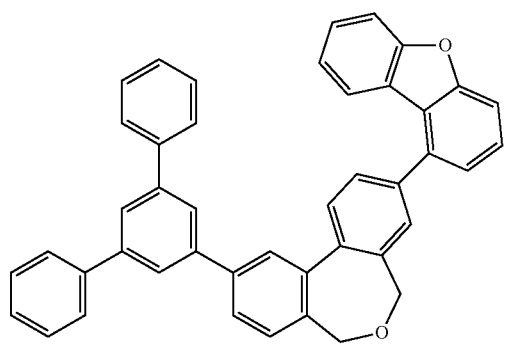
178
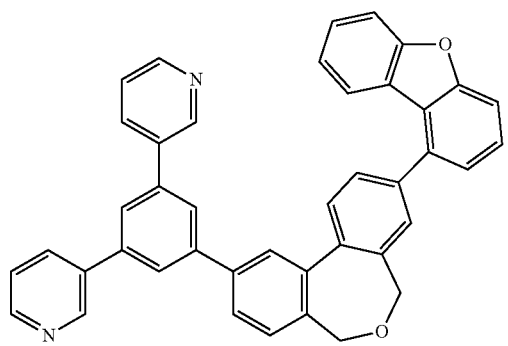
179
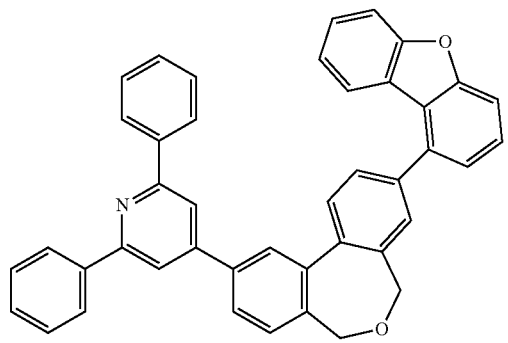
180
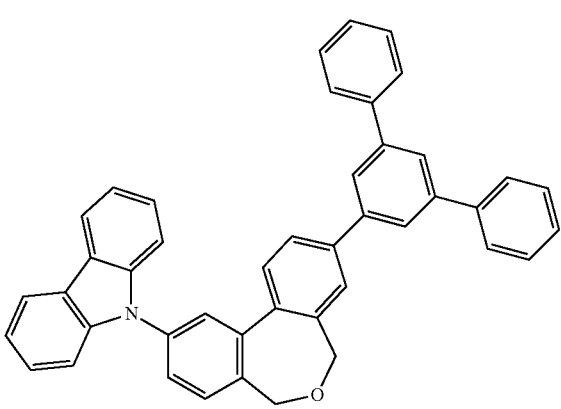
181
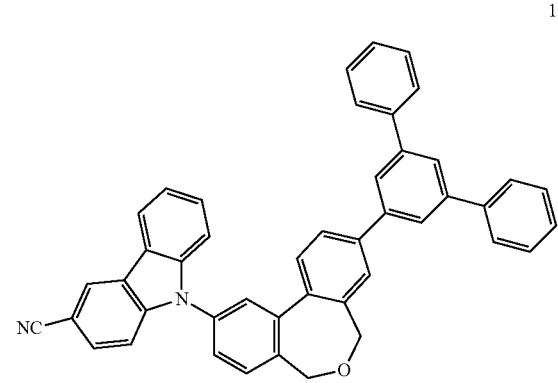
182
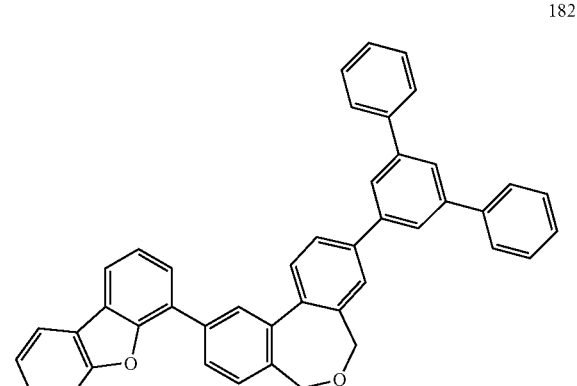
183
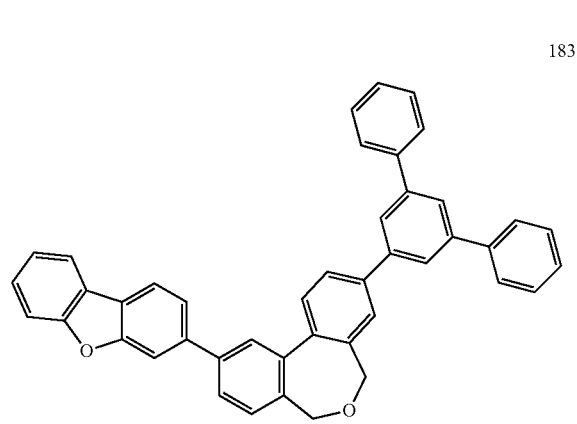
184
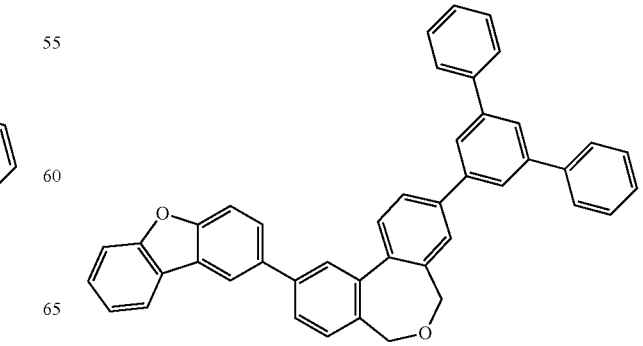

185
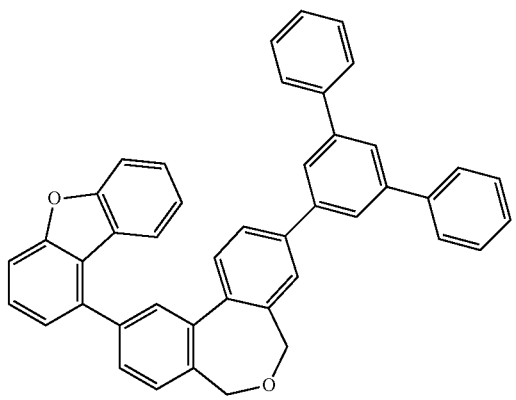
186
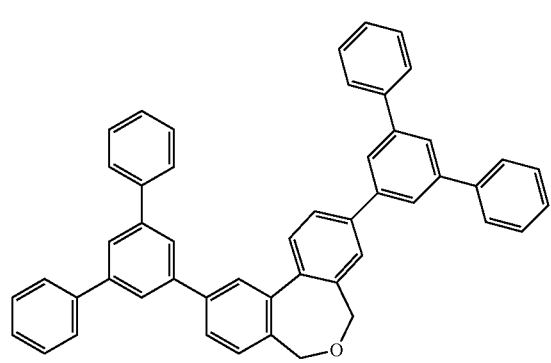
187
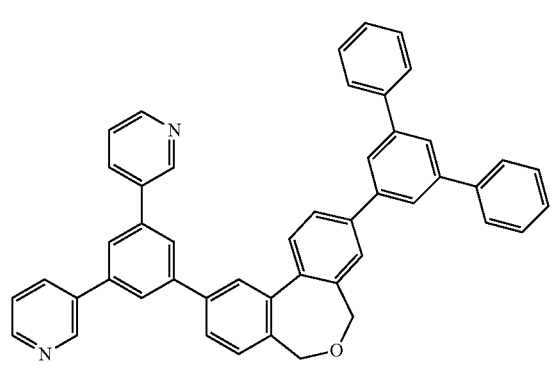
188
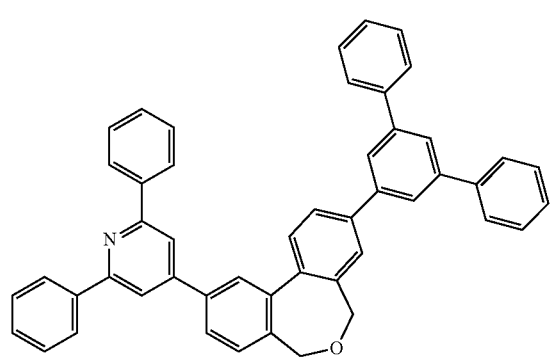
189
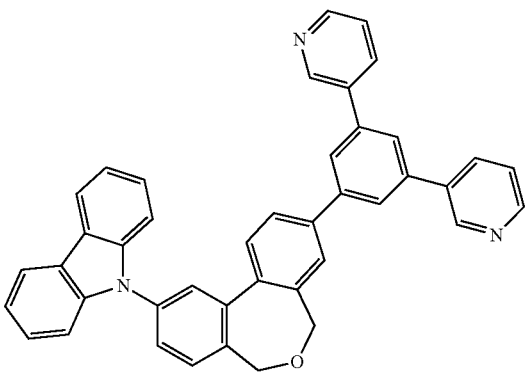
190
191
192

-continued
193
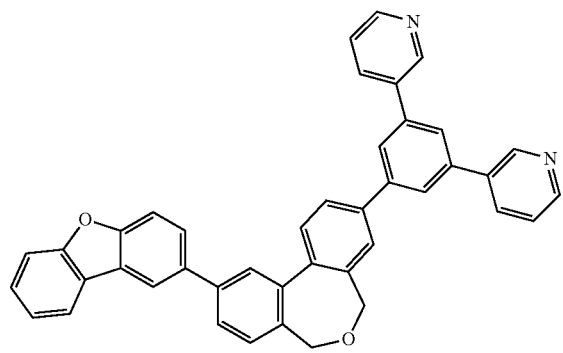
194
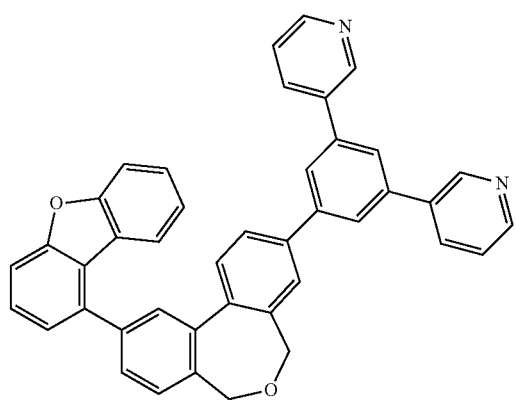
195
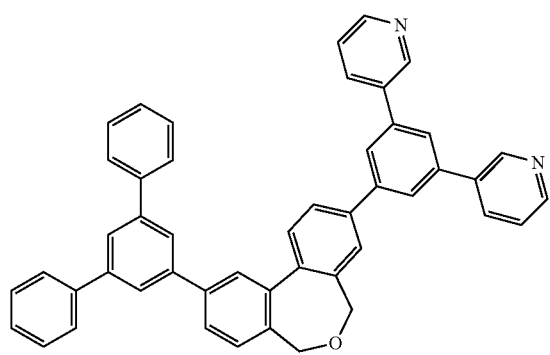
196
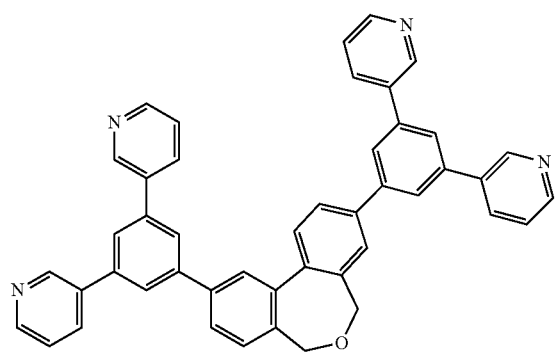
-continued
197
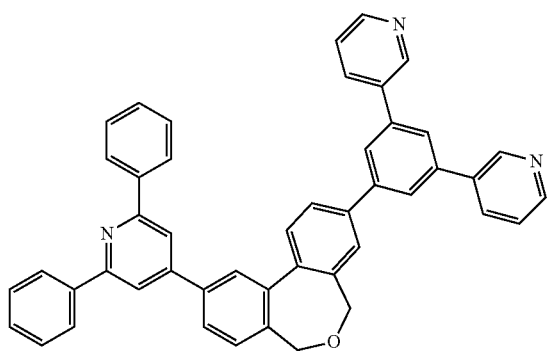
198
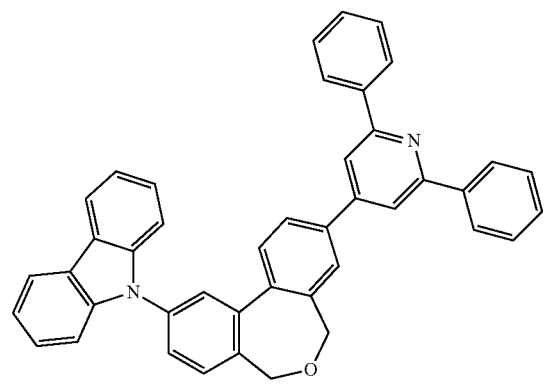
199
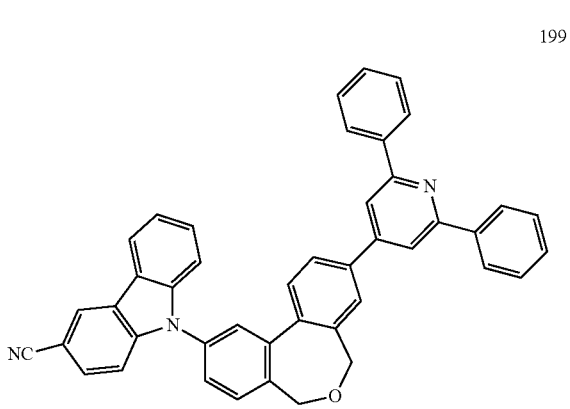
200
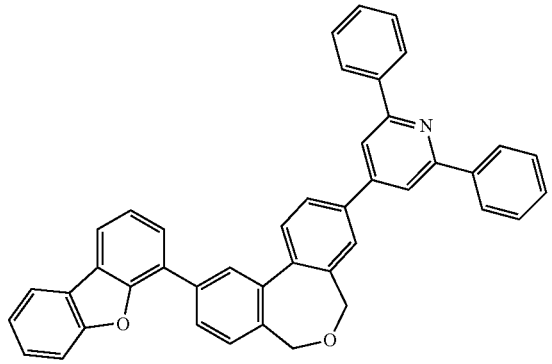

201
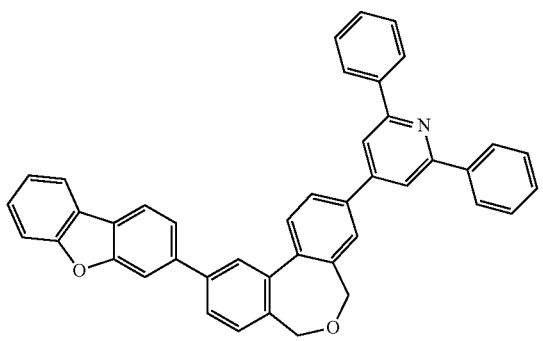
202
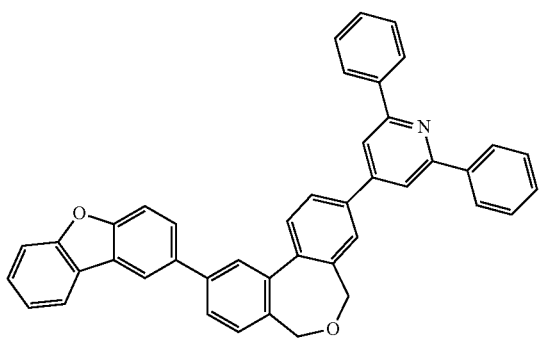
203
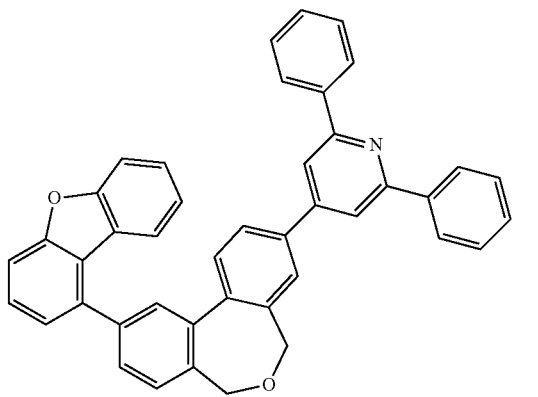
204
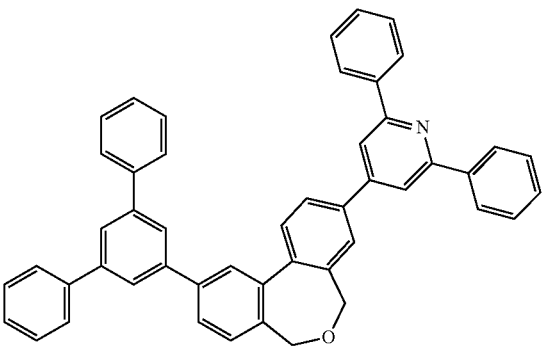
205
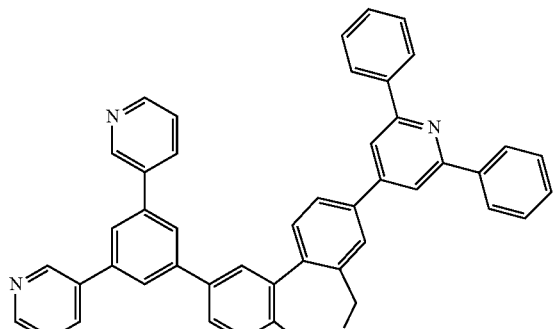
206
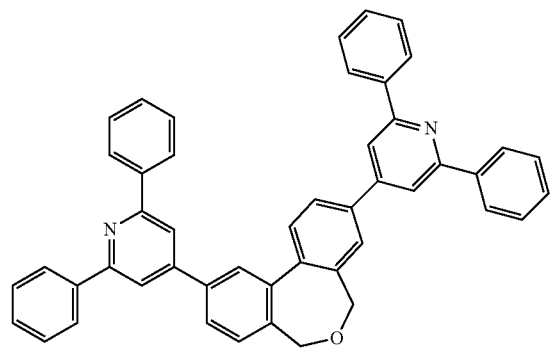
207
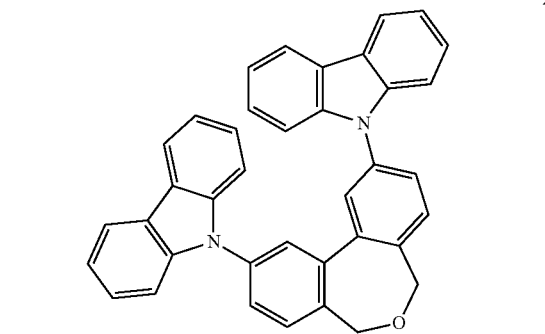
208
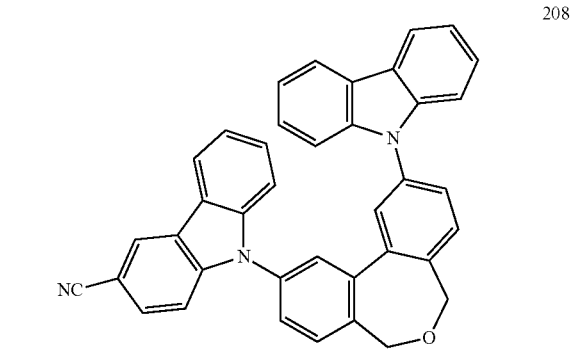

209
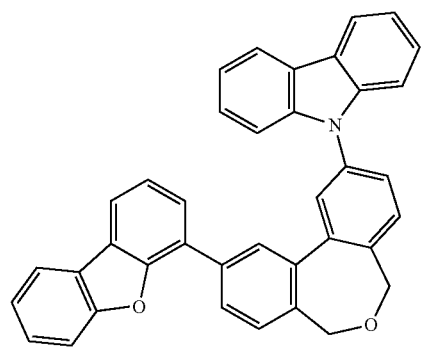
210
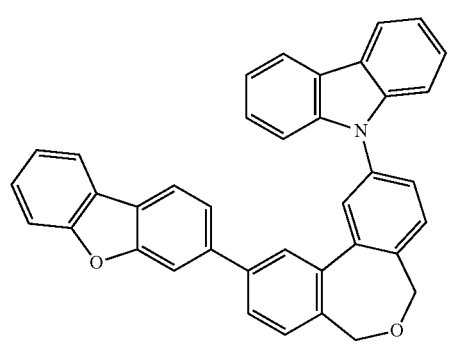
211
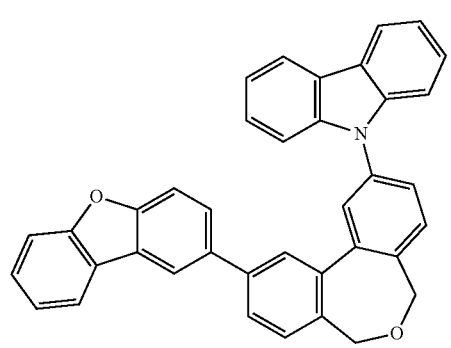
212
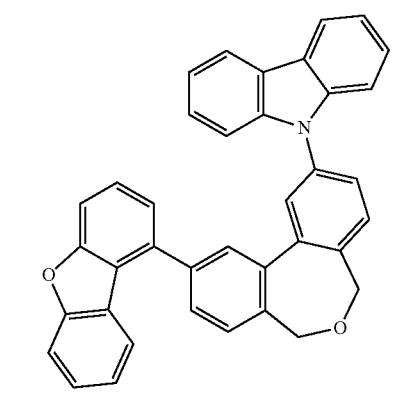
213
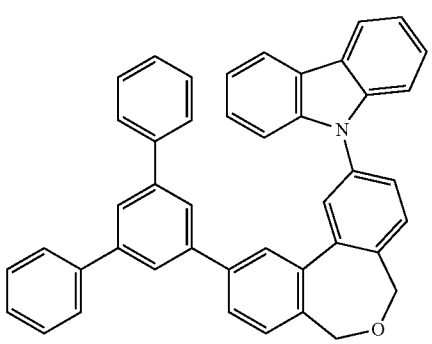
214
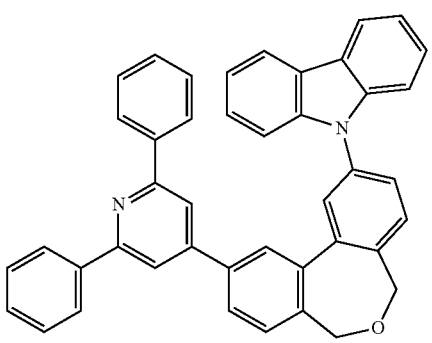
215
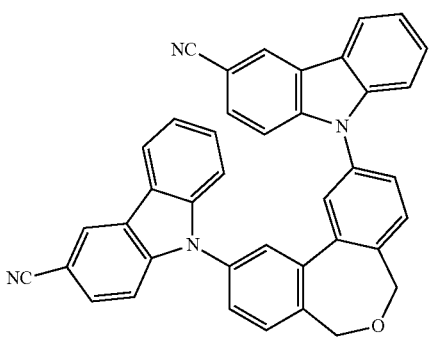
216

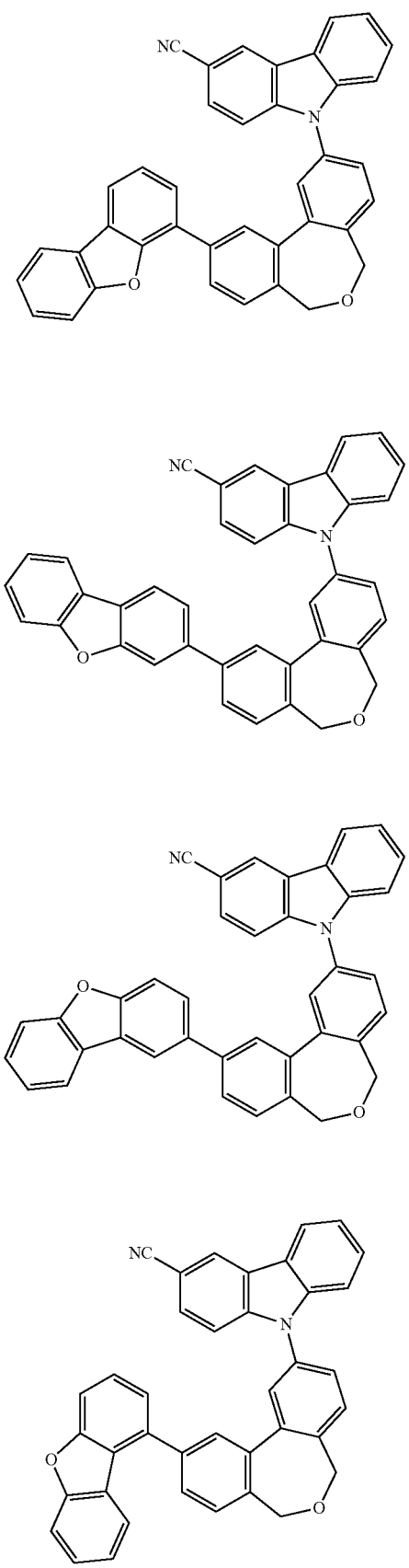
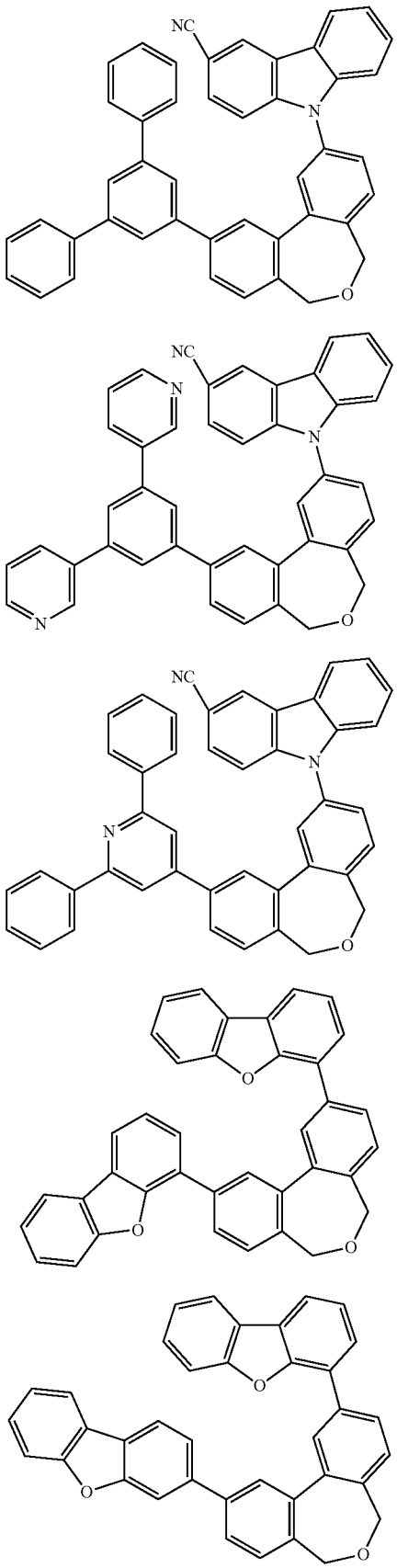

226
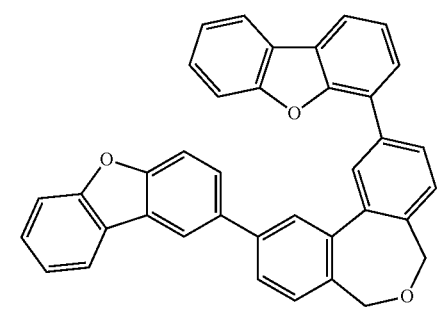
227
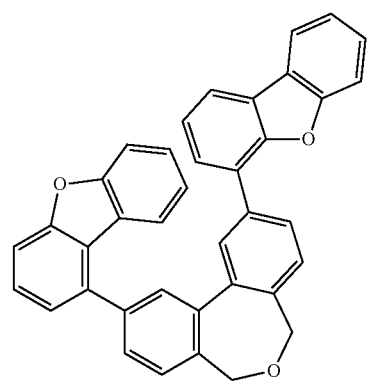
228
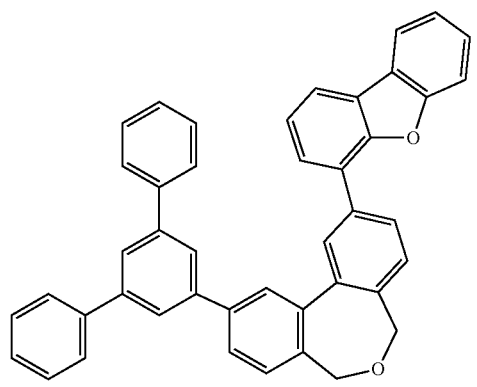
229
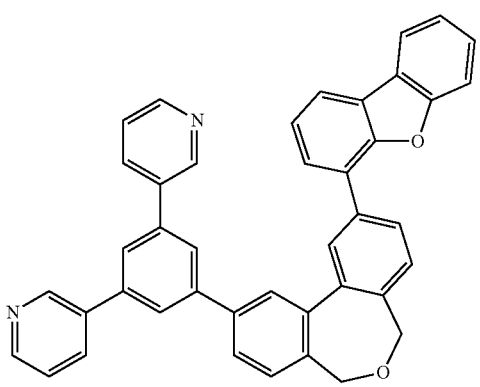
230
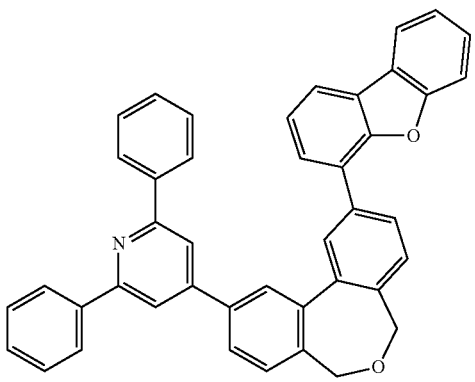
231
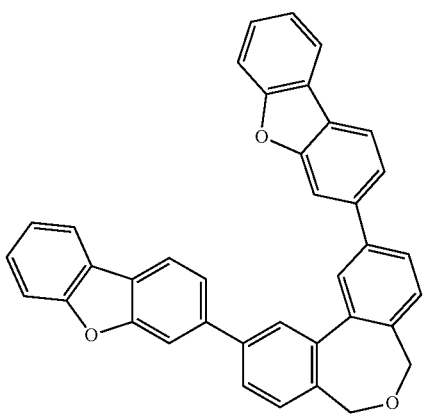
232
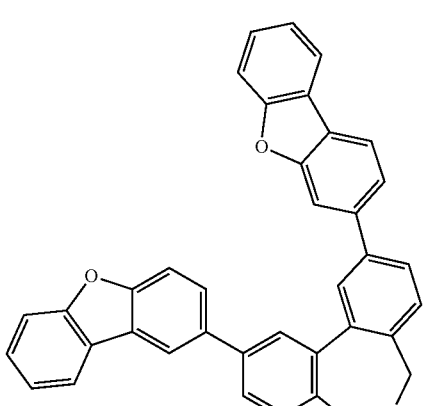
233
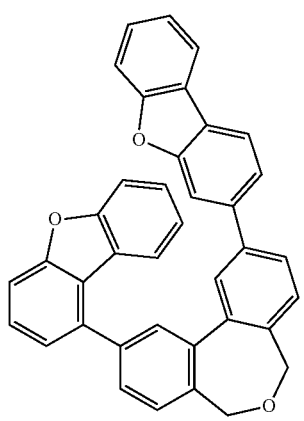

| 234 | 238 |
|---|---|
| 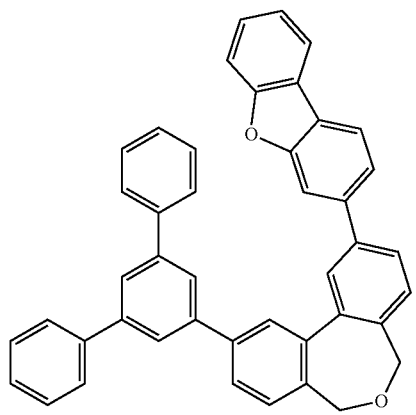 | 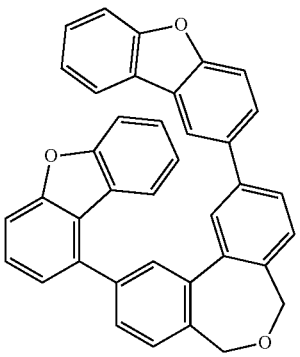 |
| 235 | 239 |
| 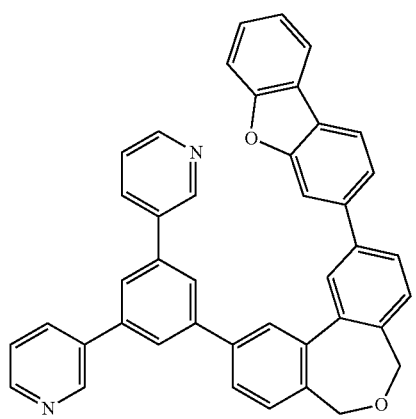 | 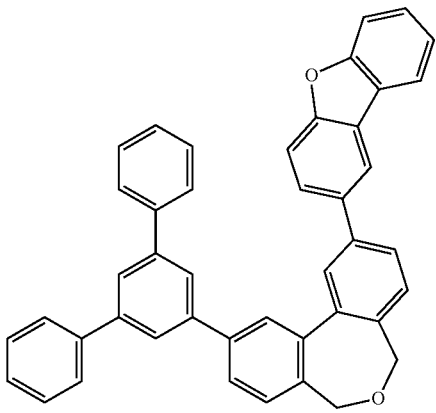 |
| 236 | 240 |
| 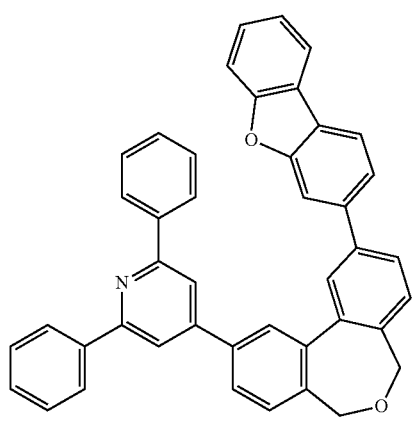 | 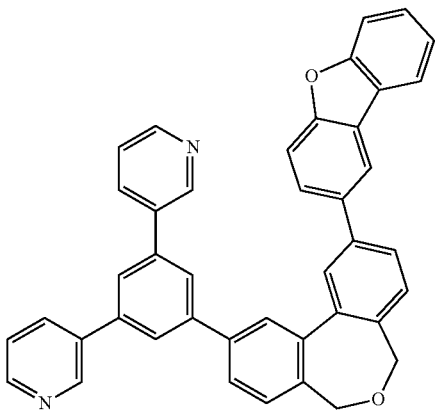 |
| 237 | 241 |
| 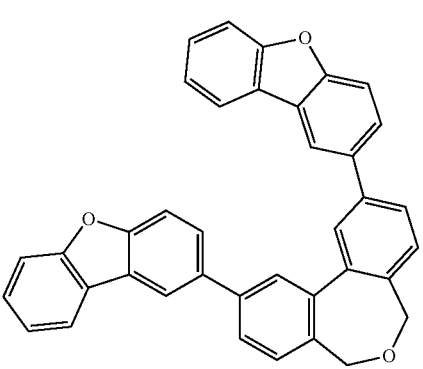 | 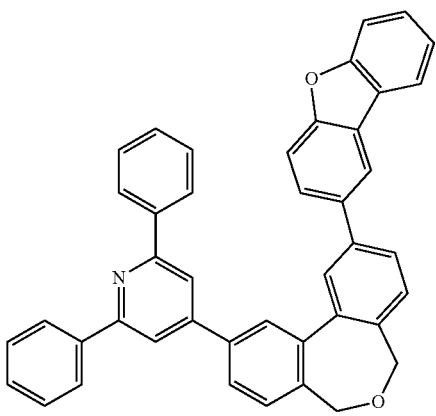 |

242
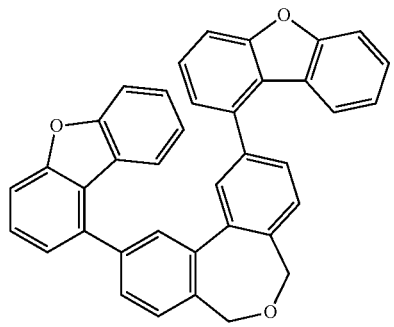
243
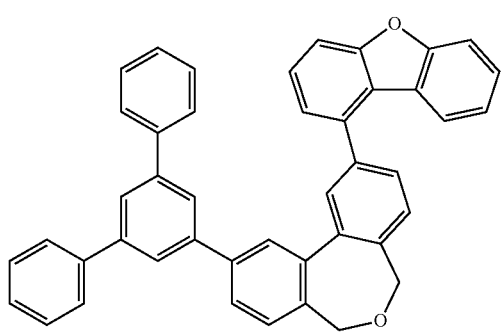
244
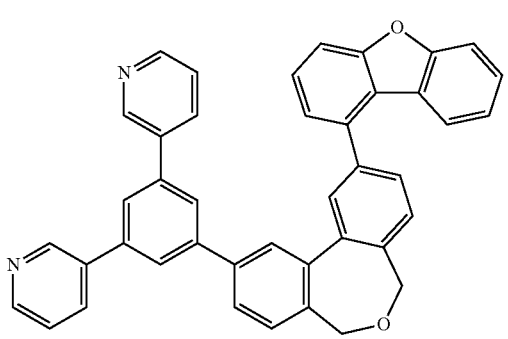
245
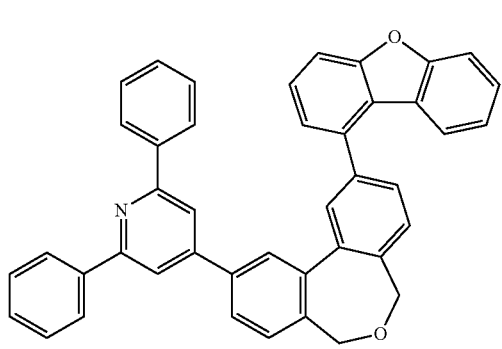
246
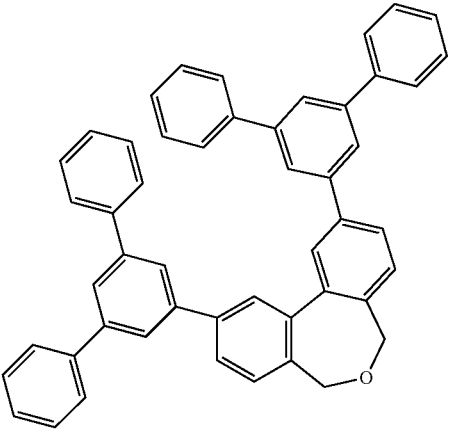
247
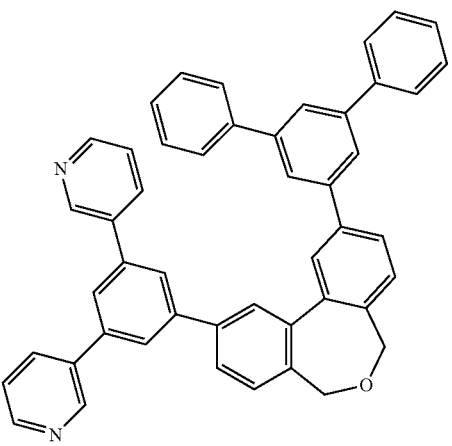
248
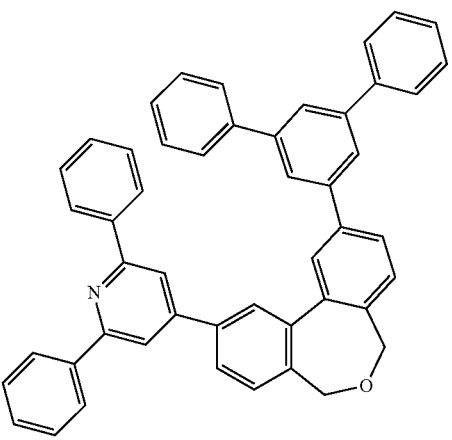

249
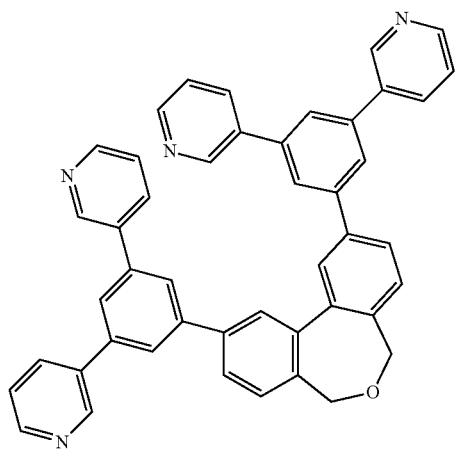
250
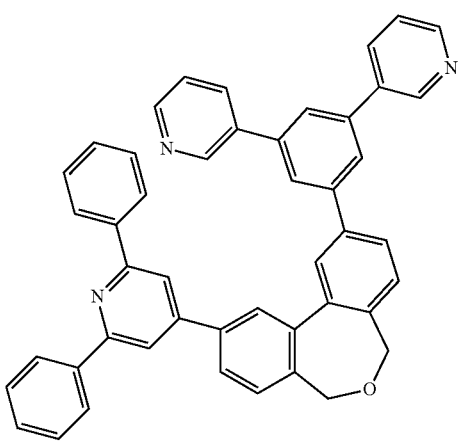
251
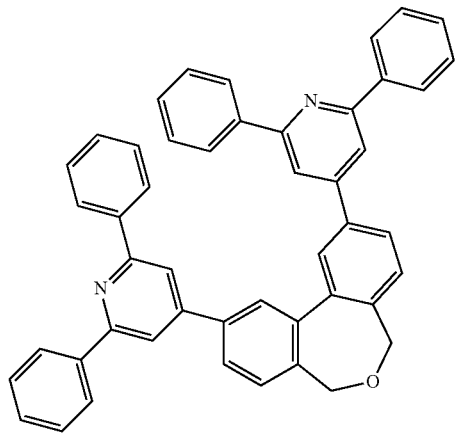
252
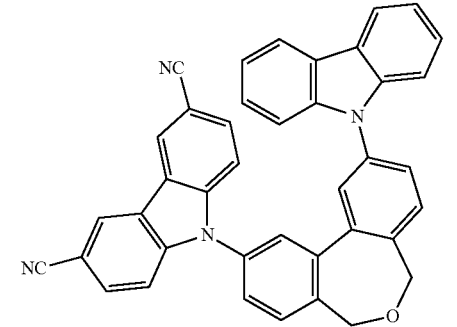
253
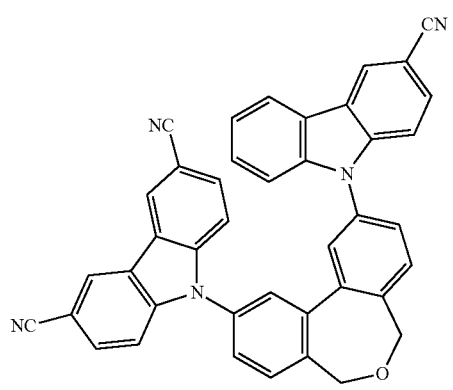
254
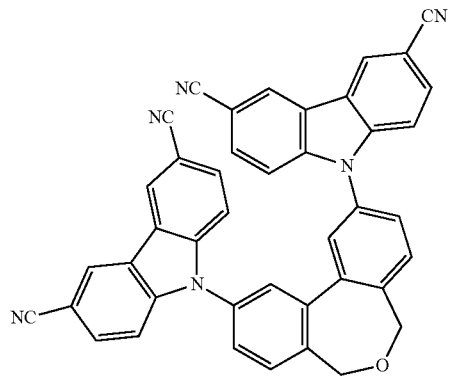
255
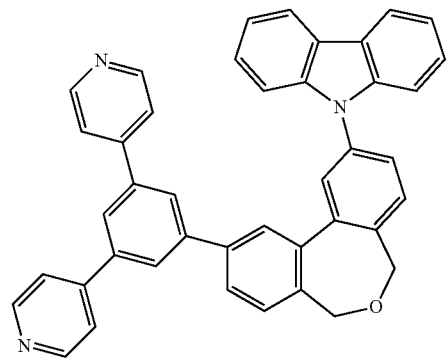
256
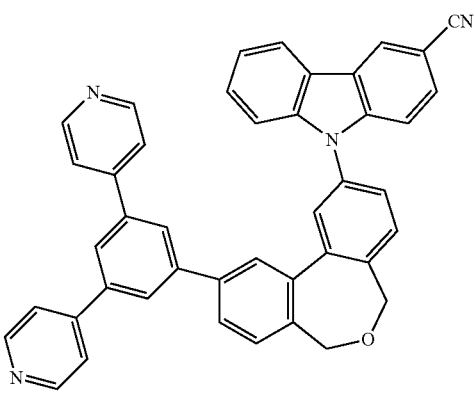

101
-continued
257
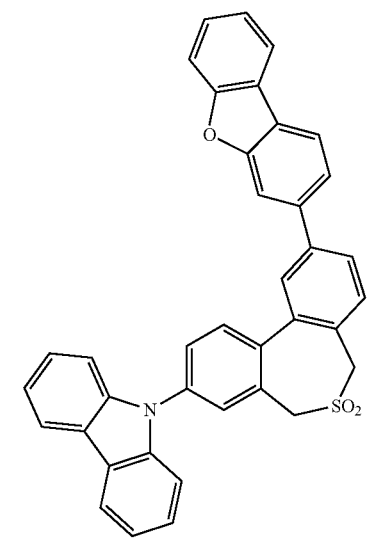
258
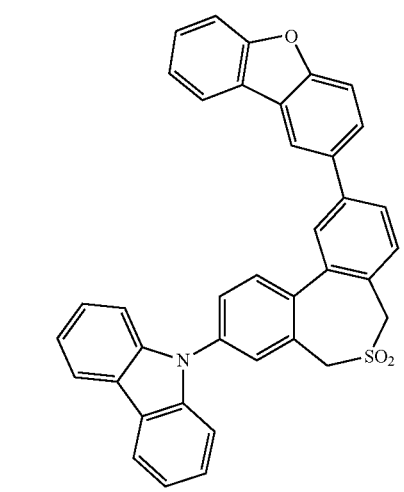
259
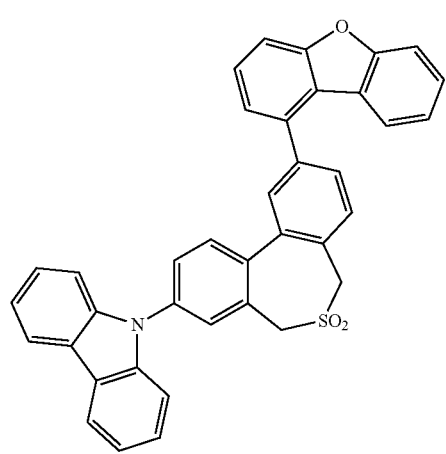
102
-continued
260
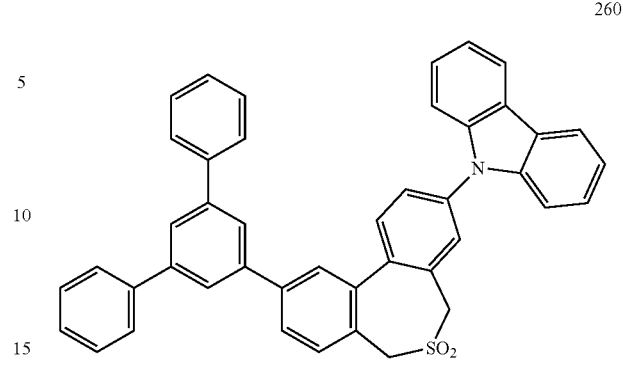
261
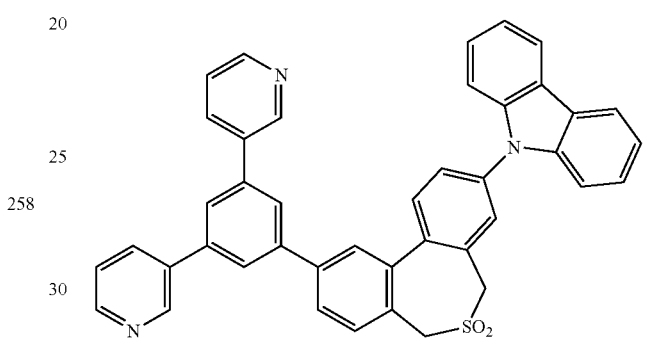
262
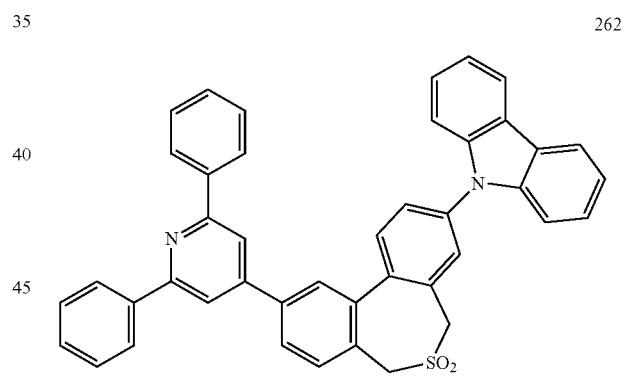
263
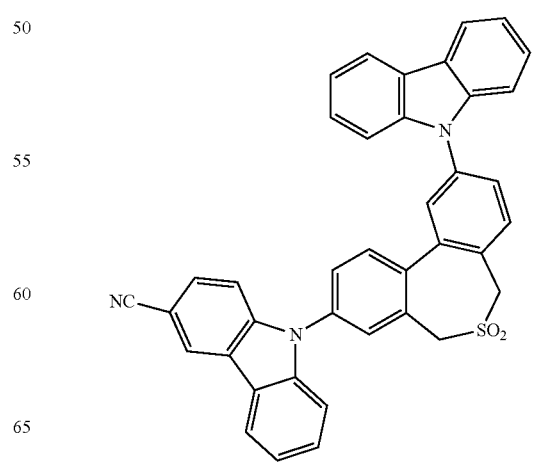

103 -continued
264
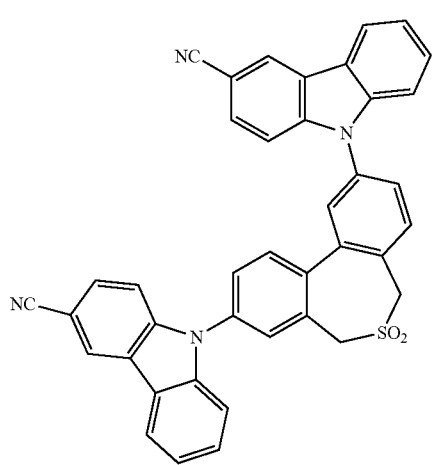
265
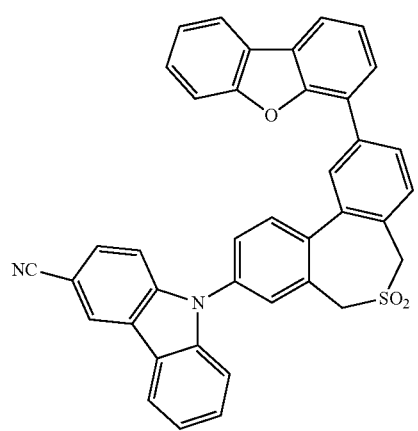
266
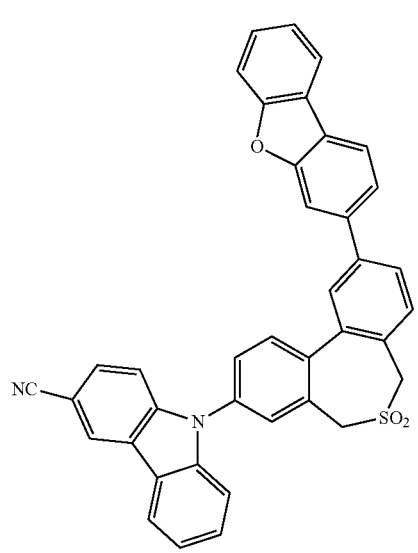
104 -continued
267
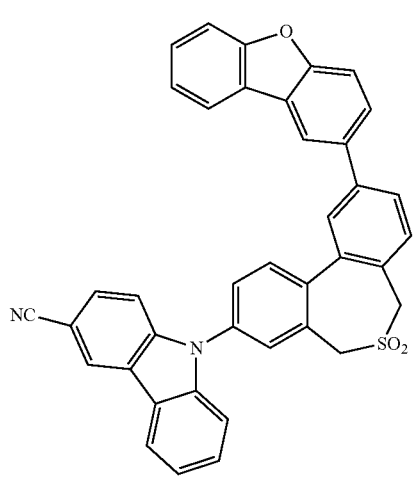
268
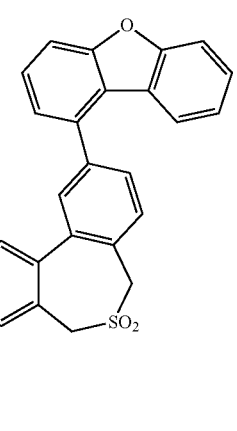
269
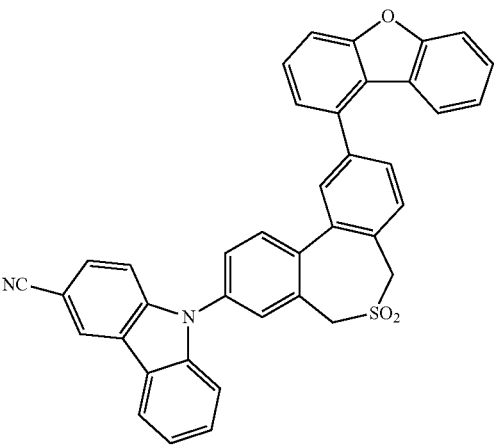

270
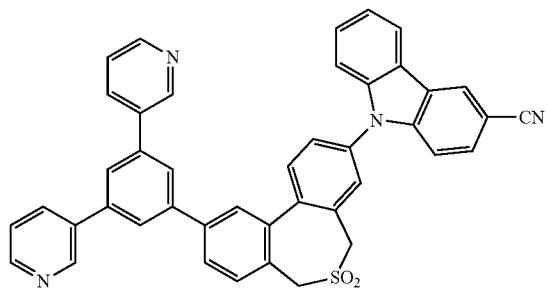
371
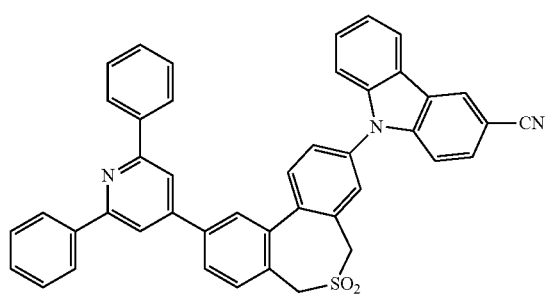
272
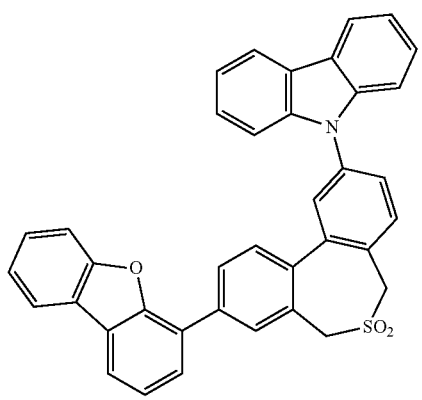
273
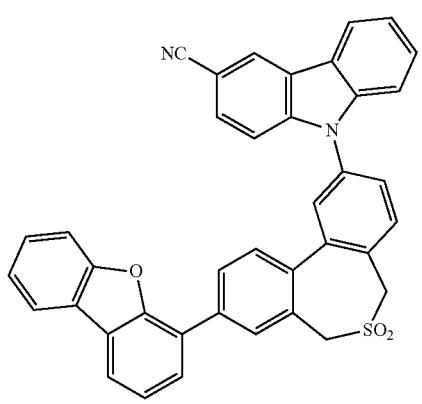
274
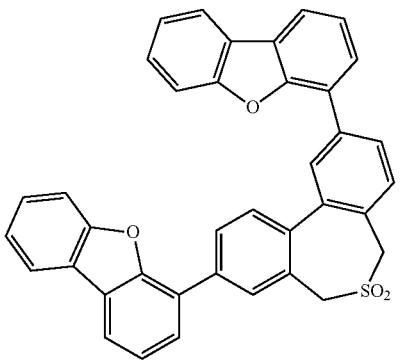
275
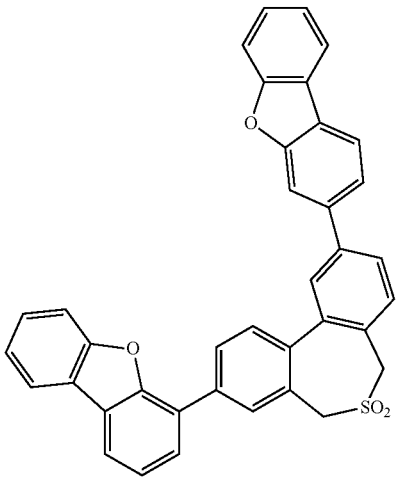
276
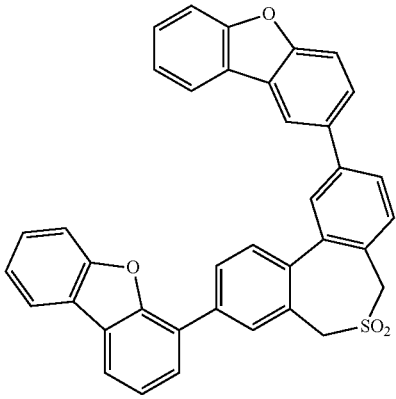
277
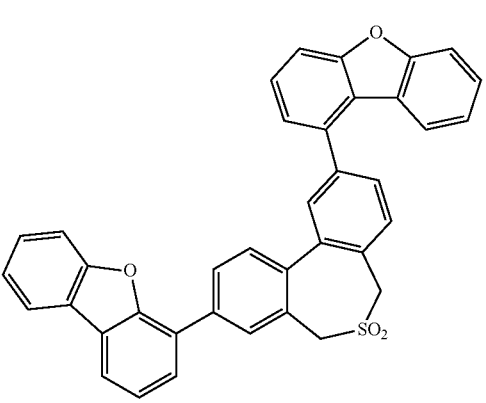

278

279
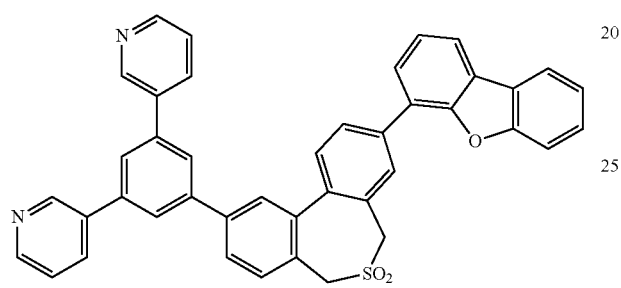
280
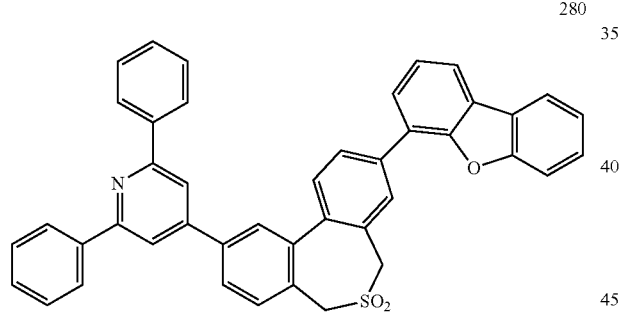
281
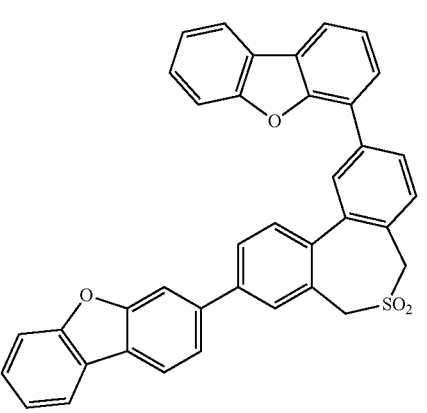
282
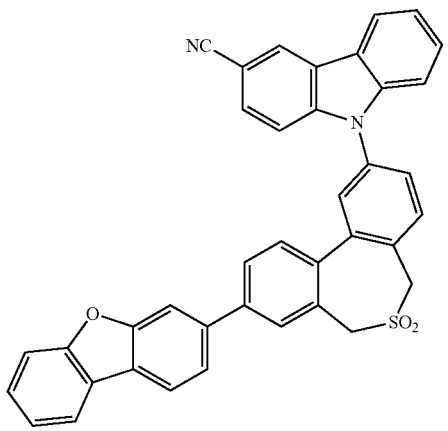
283
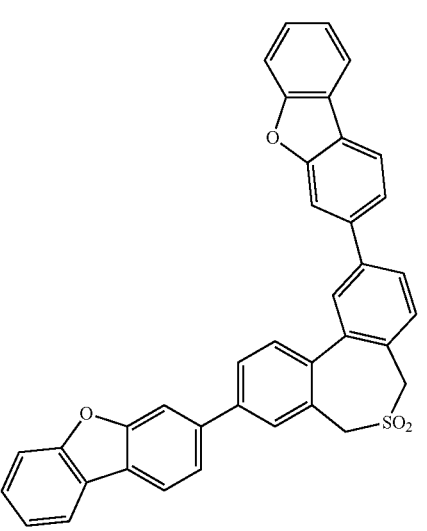
284

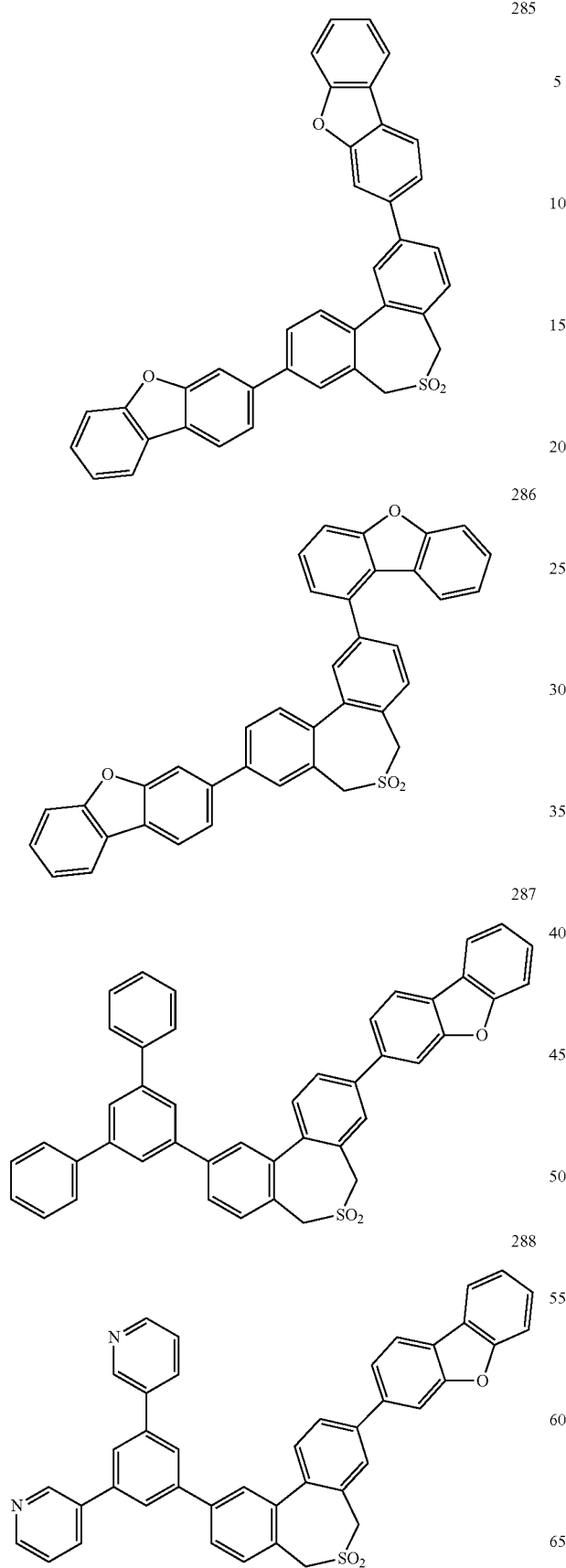
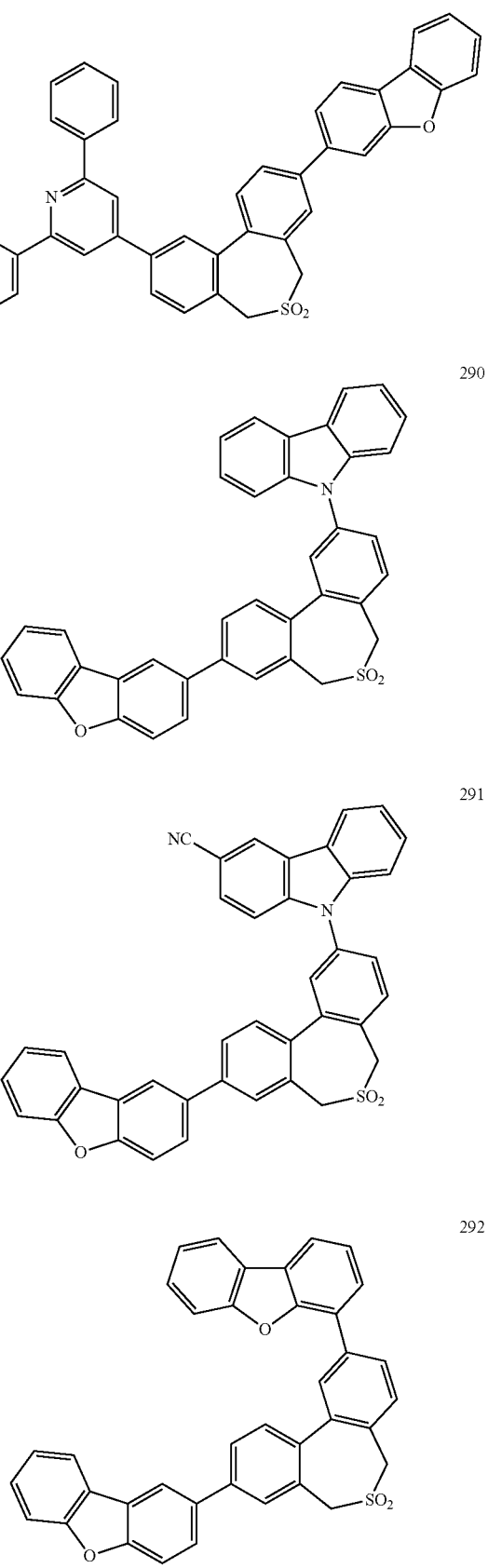

US 10,581,000 B2
111
-continued
293
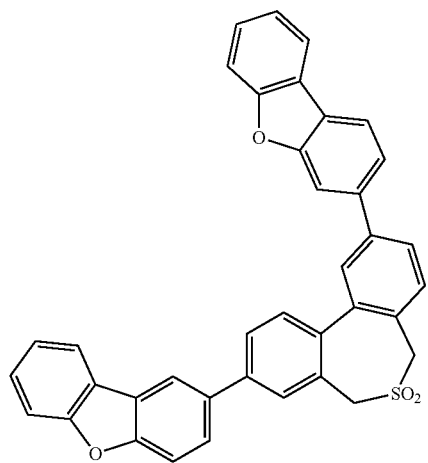
294
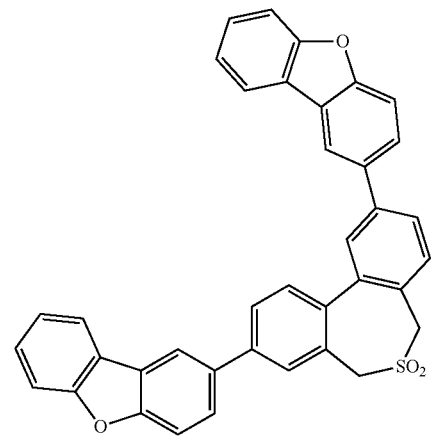
295
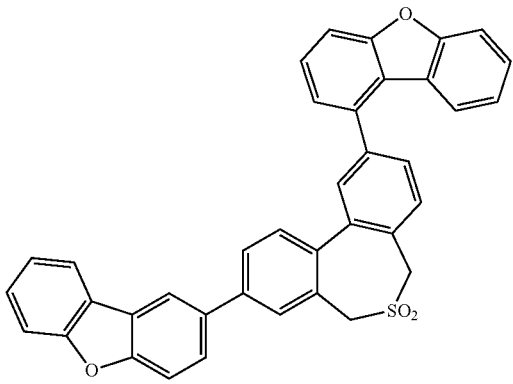
296
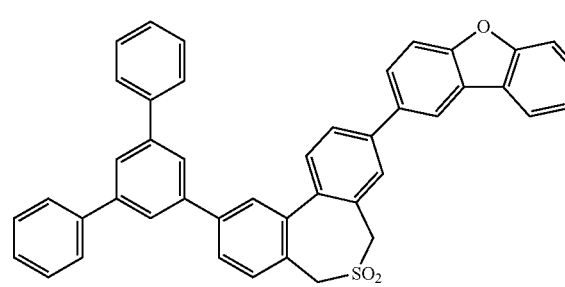
112
-continued
297
298
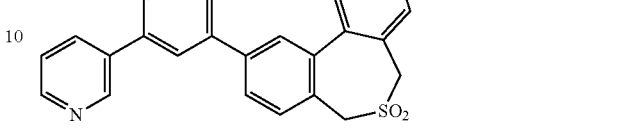
299
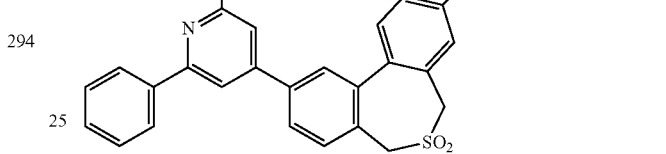
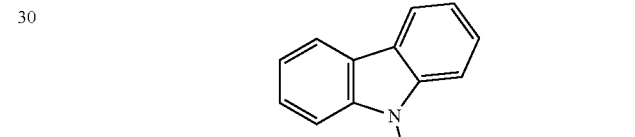
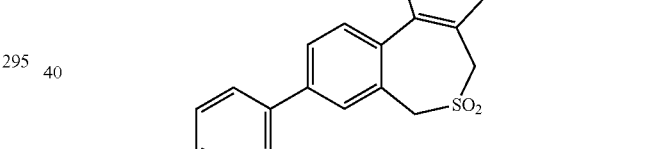
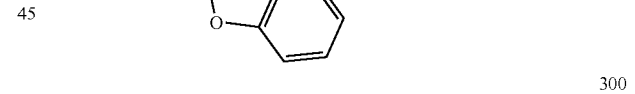
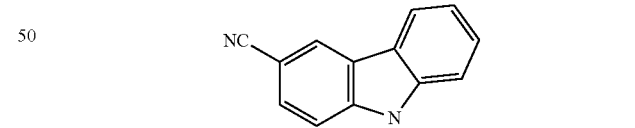

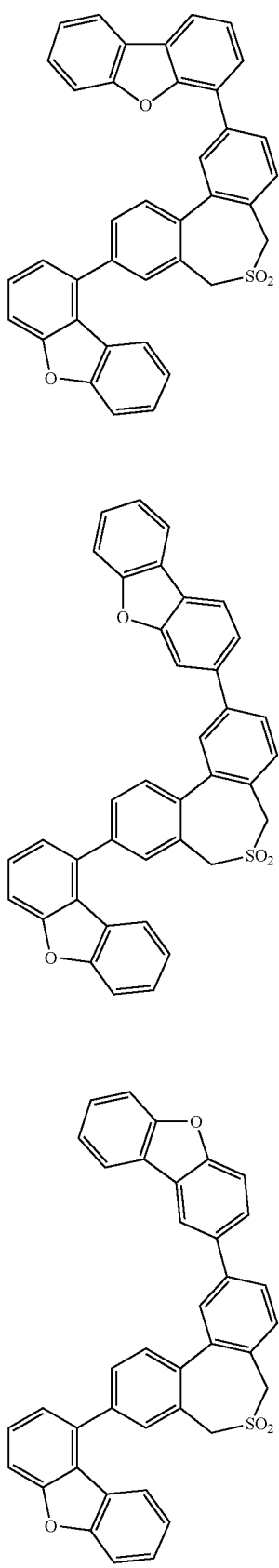
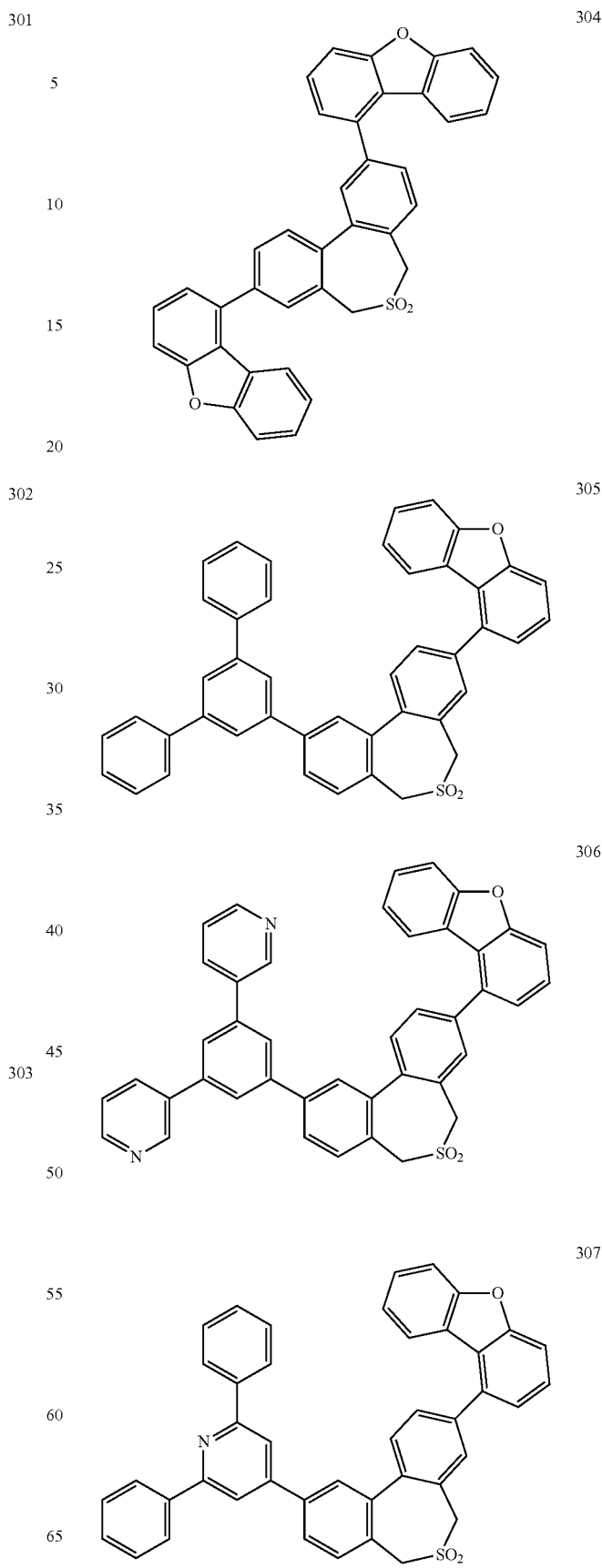

308

309

310

311

312

313

314

315

117
-continued

316

317

318

319

118
-continued

320

321

322

323

324
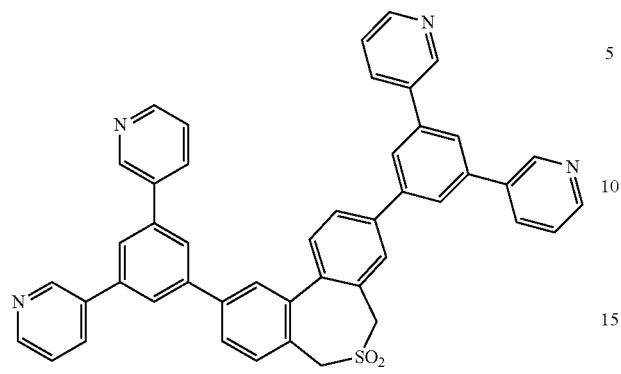
325
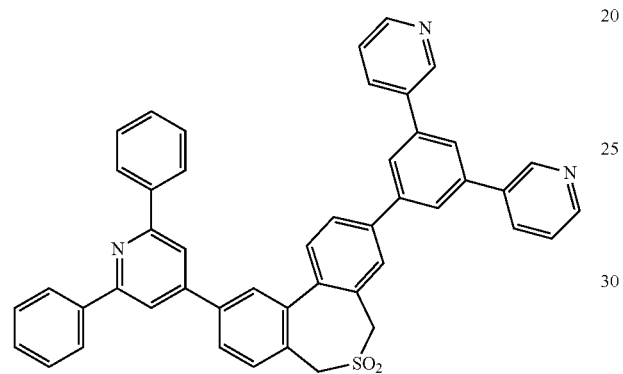
326
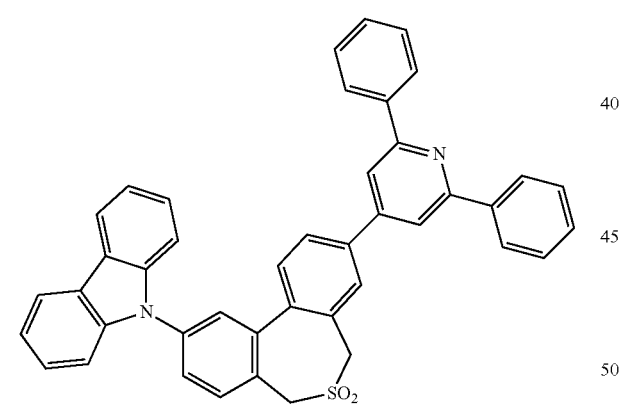
327
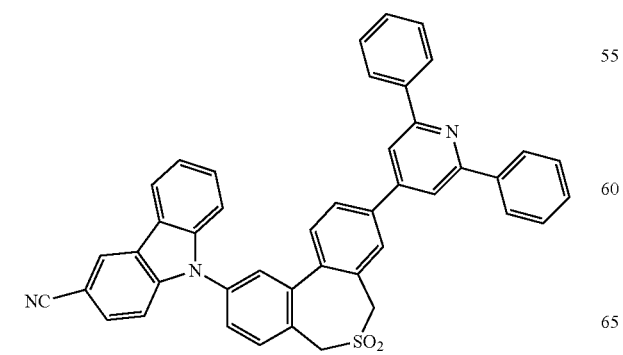
328
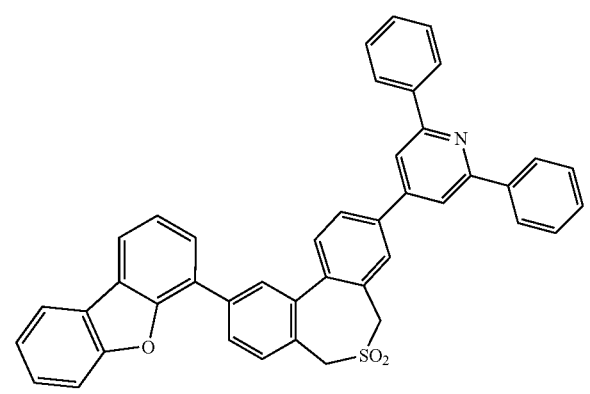
329
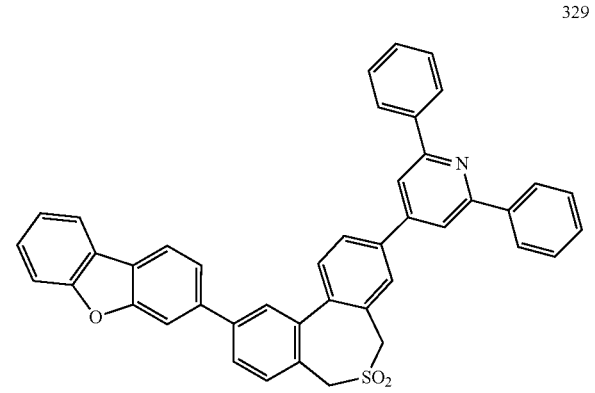
330
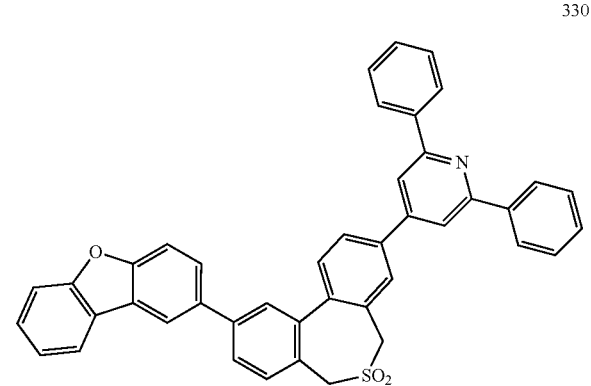
331
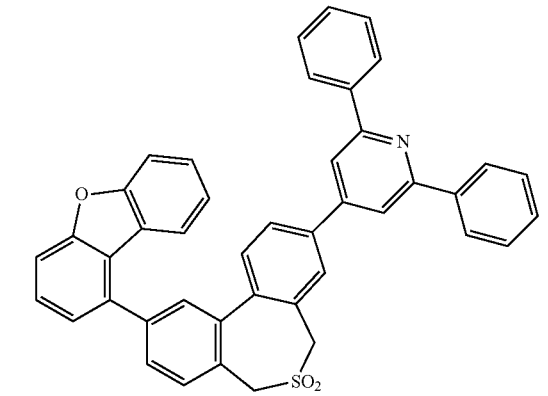

-continued
332
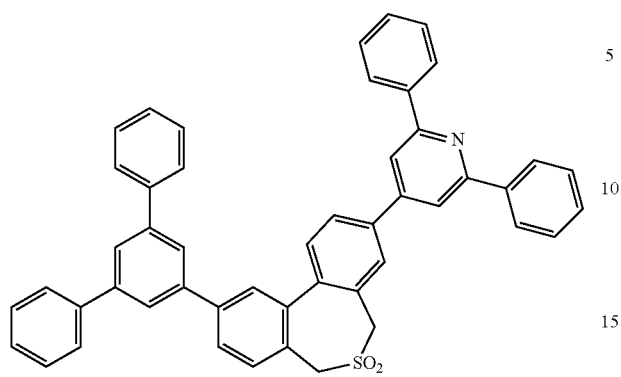
333
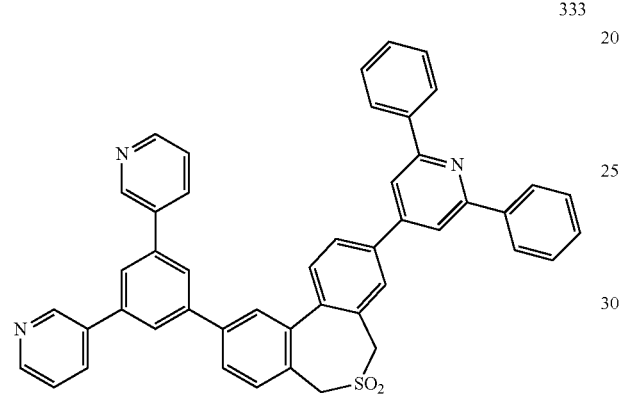
334
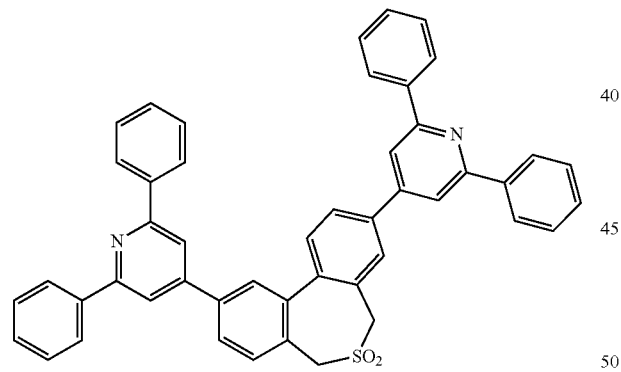
335
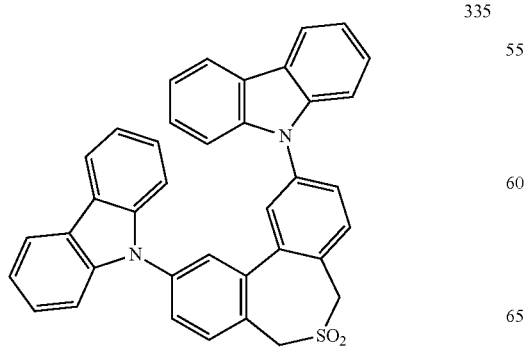
-continued
336
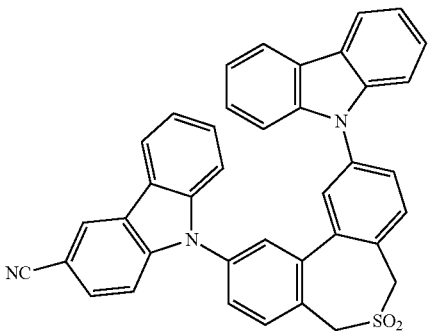
337
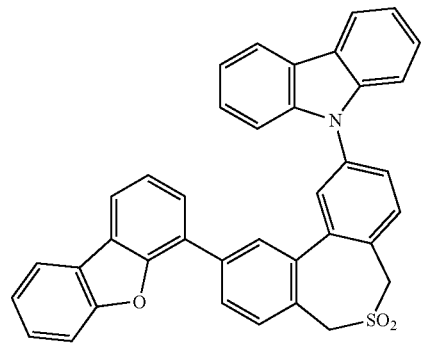
338
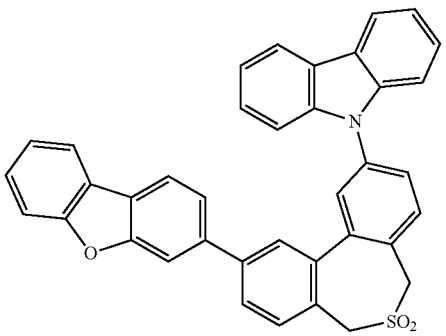
339
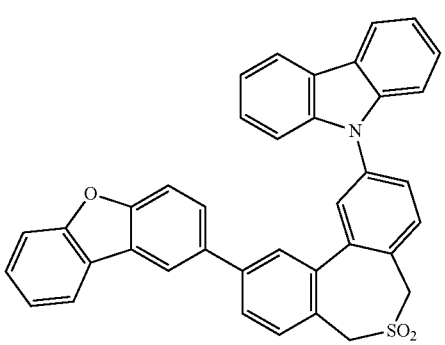

340
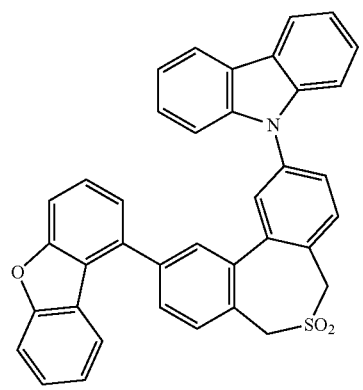
341
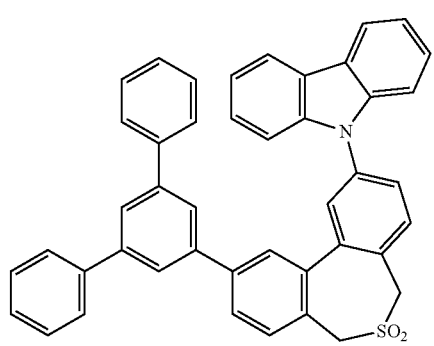
342
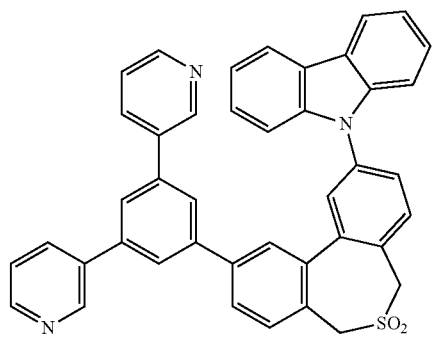
343
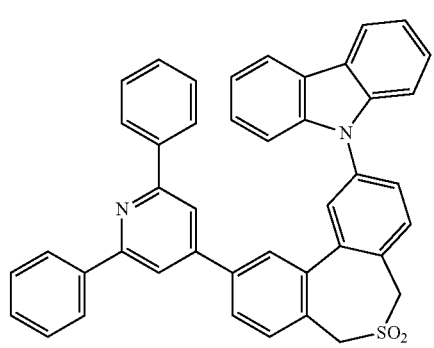
344
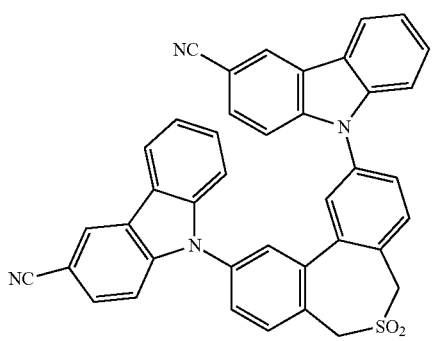
345
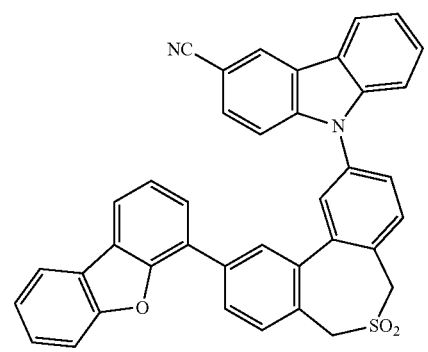
346
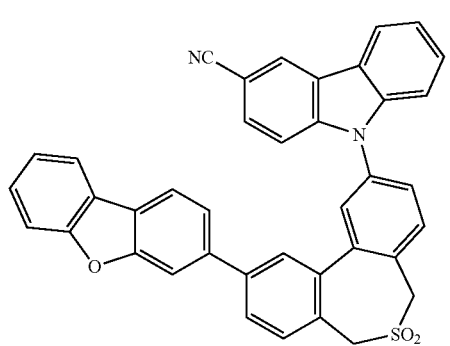
347
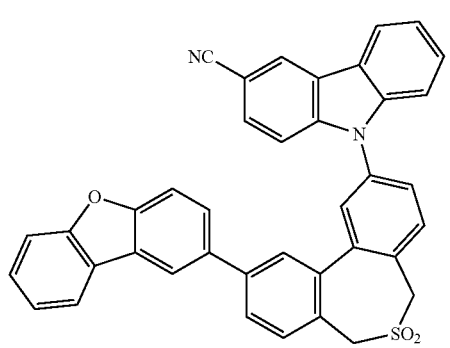

-continued
348
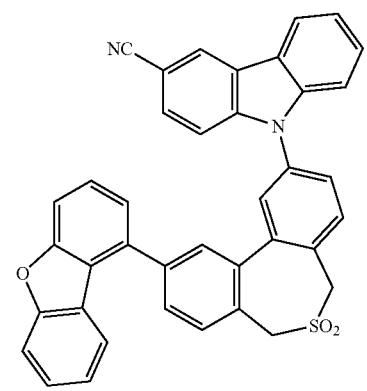
349
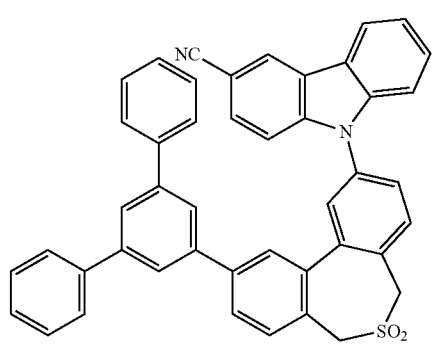
350
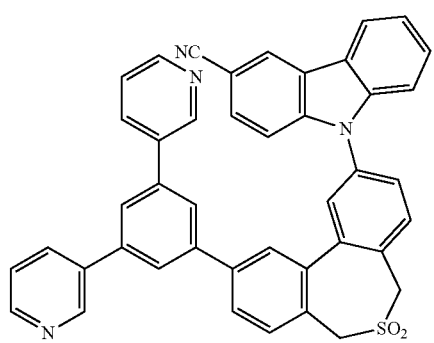
351
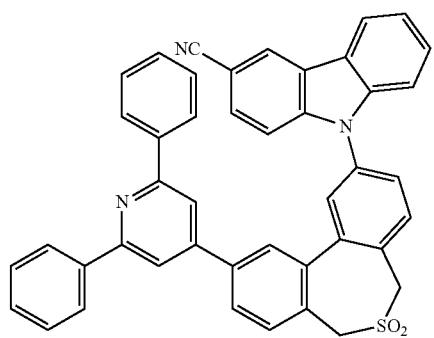
-continued
352
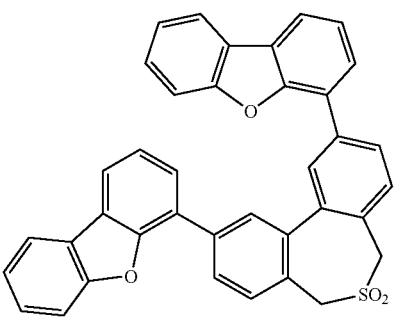
353
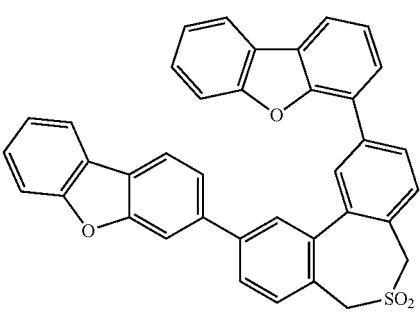
354
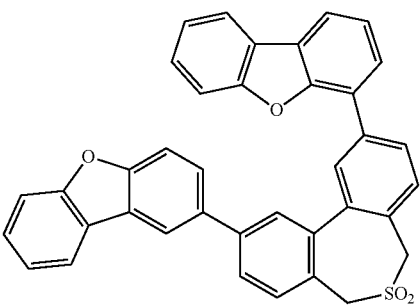
355
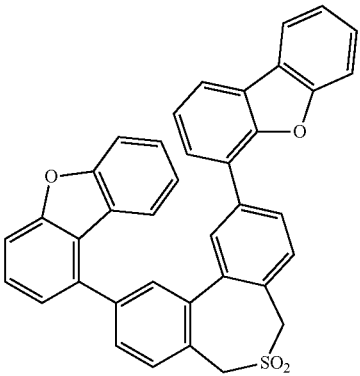

127
-continued
356
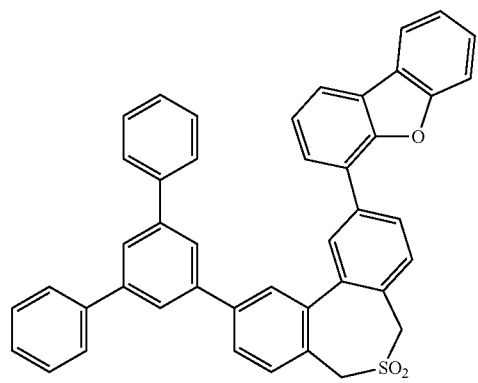
357
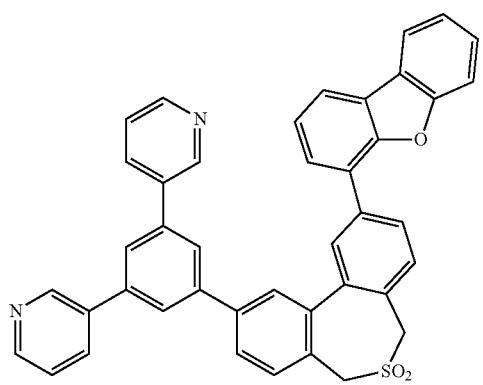
358
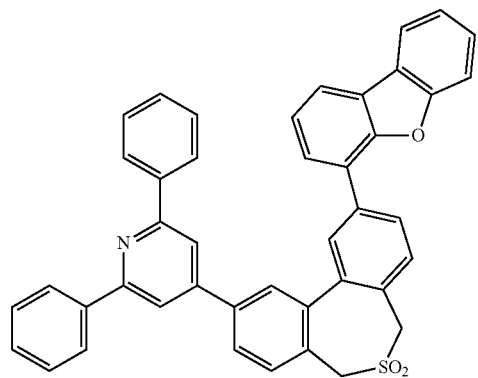
359
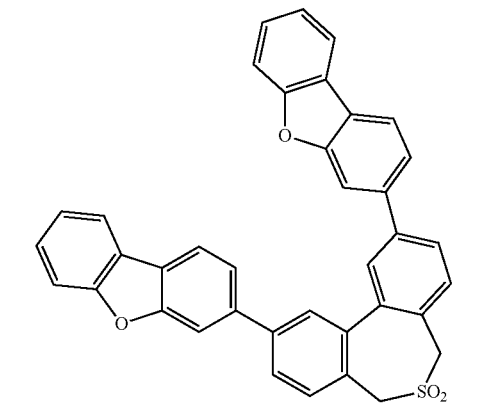
128
-continued
360
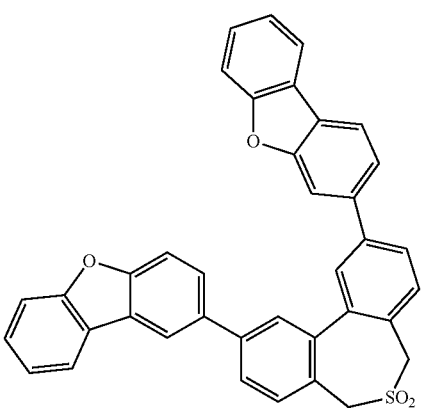
361
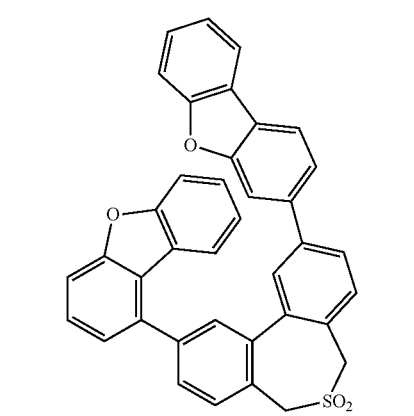
362
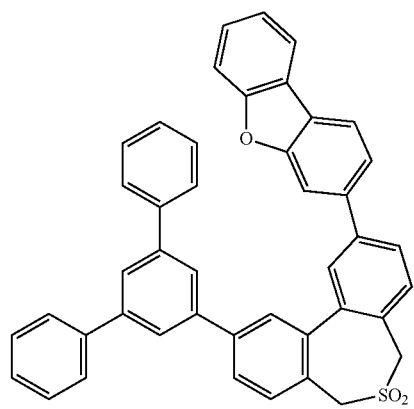
363
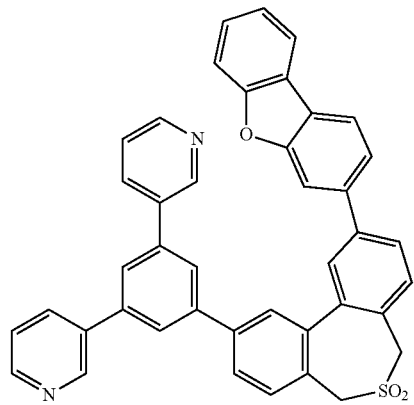

129
-continued
364
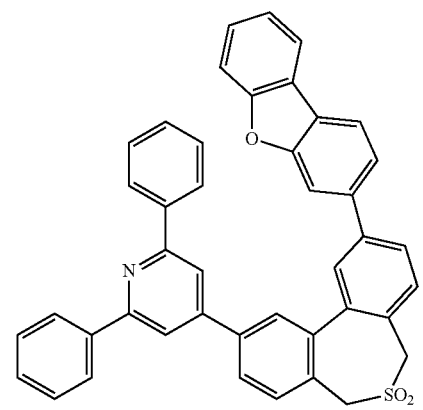
365
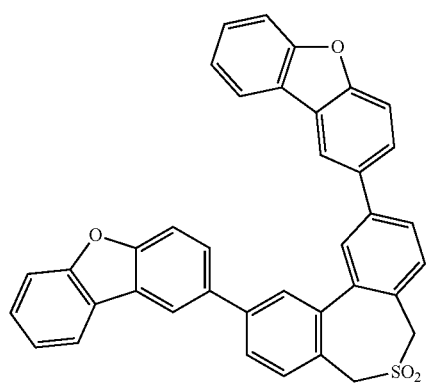
366
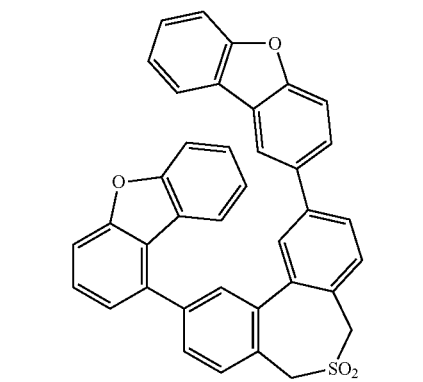
367
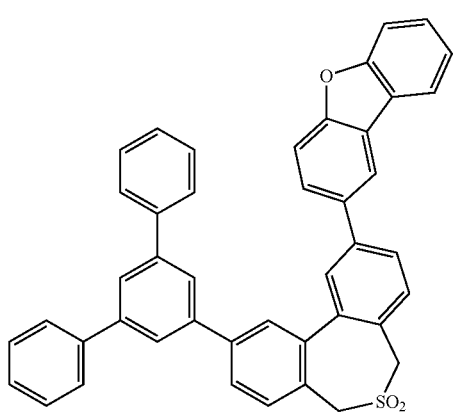
130
-continued
368
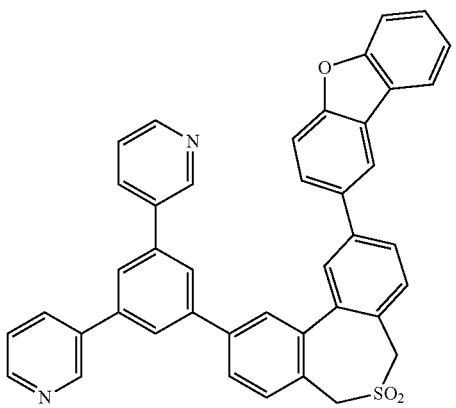
369
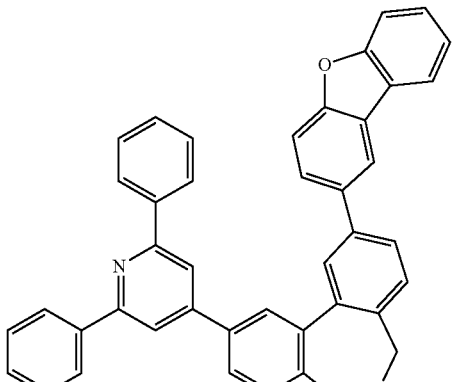
370
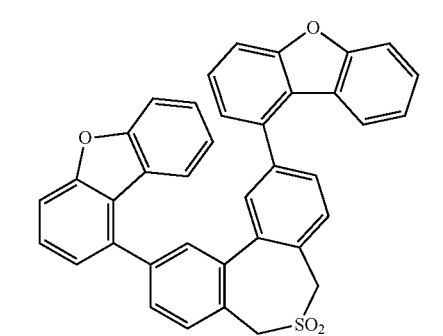
371
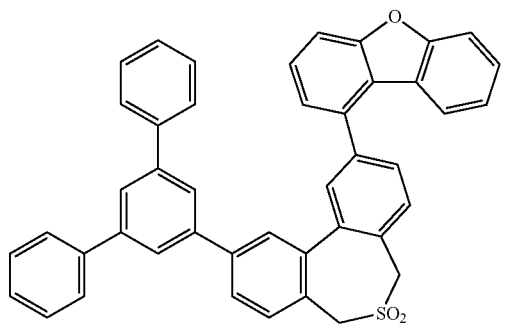

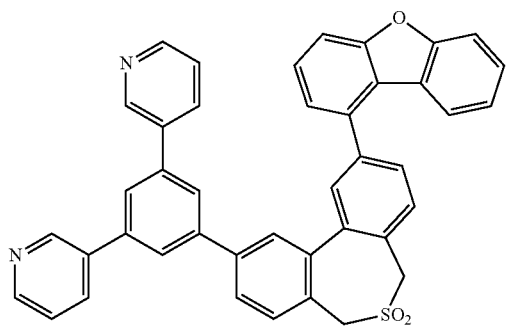
372
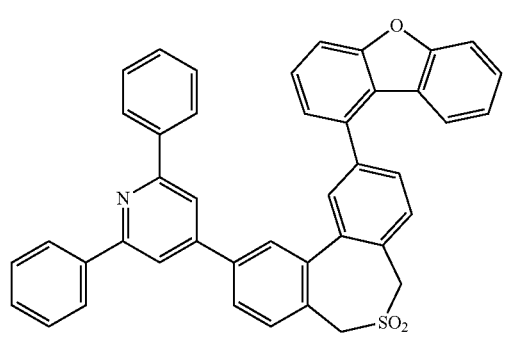
373

374
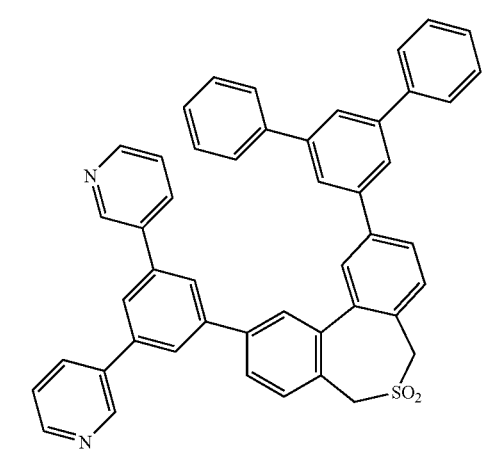
375
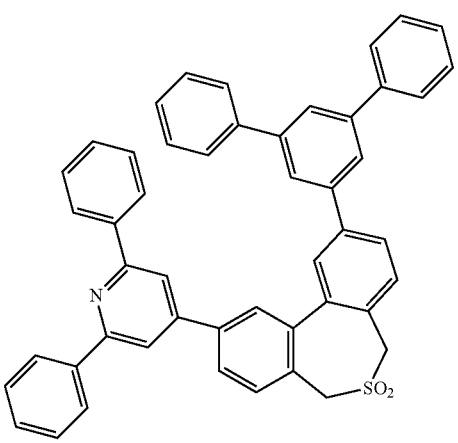
376
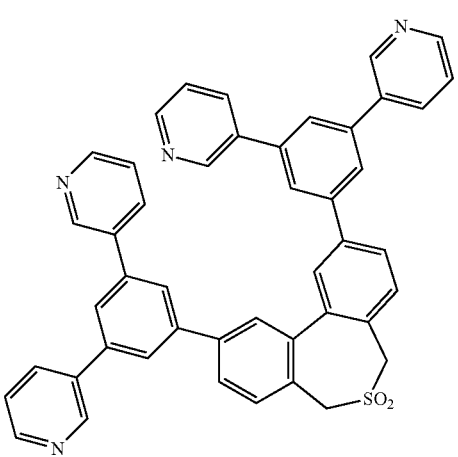
377
378

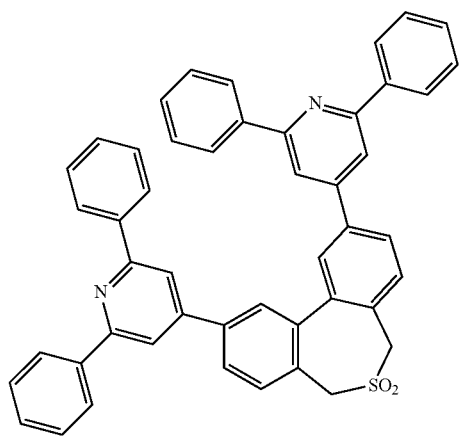
379
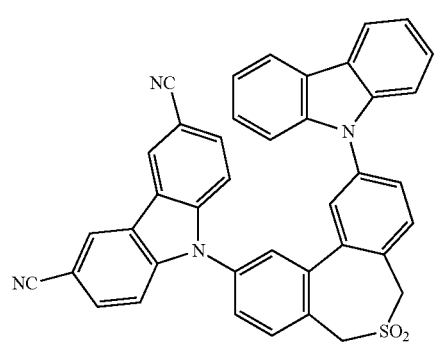
380
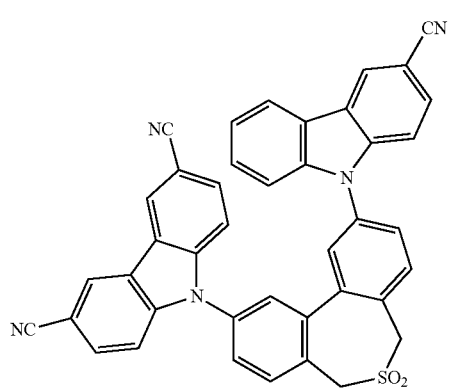
381
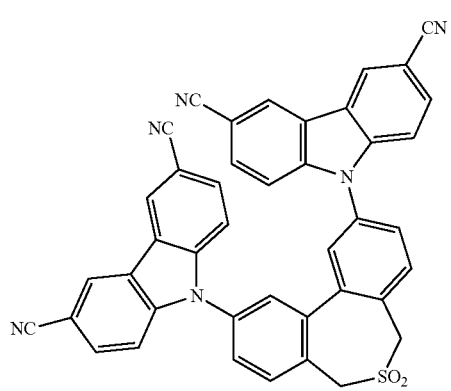
382
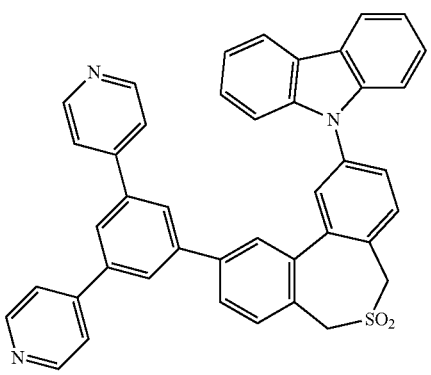
383
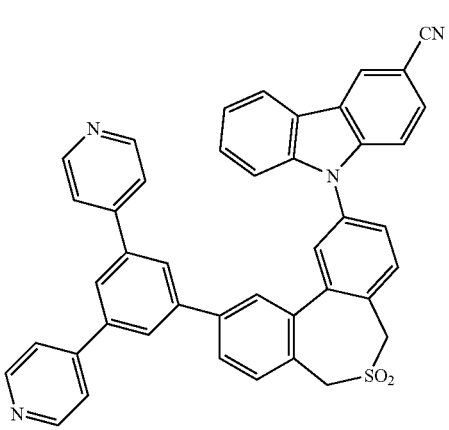
384
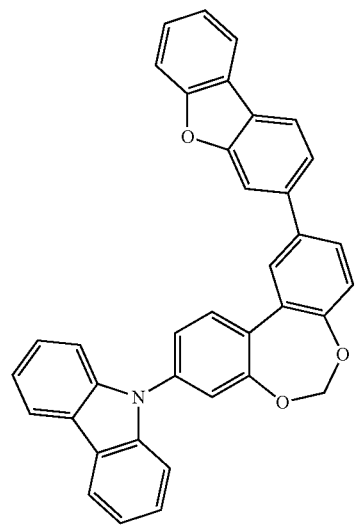
385

| 135 | 136 |
|---|---|
| -continued | -continued |
| 386 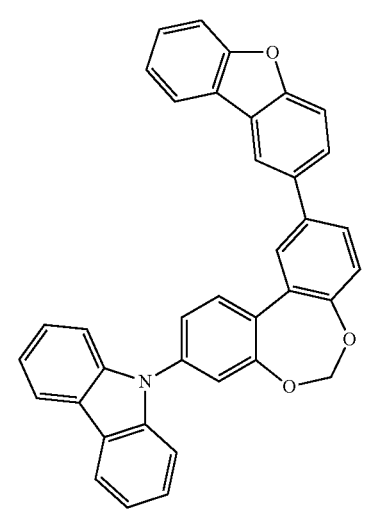 | 390 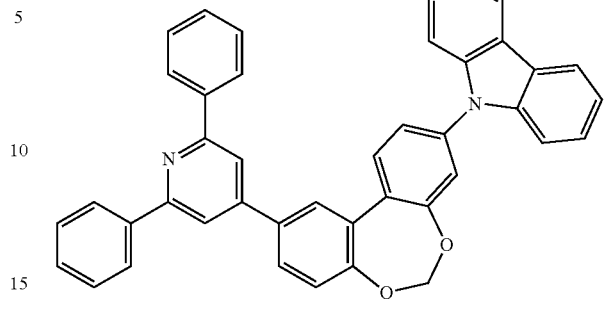 |
| 387 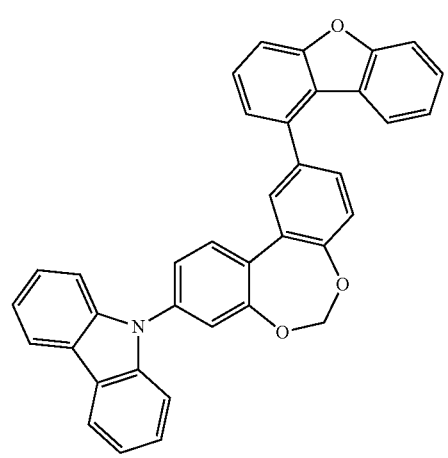 | 391 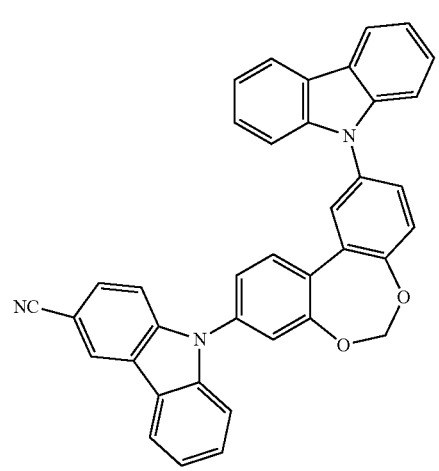 |
| 388 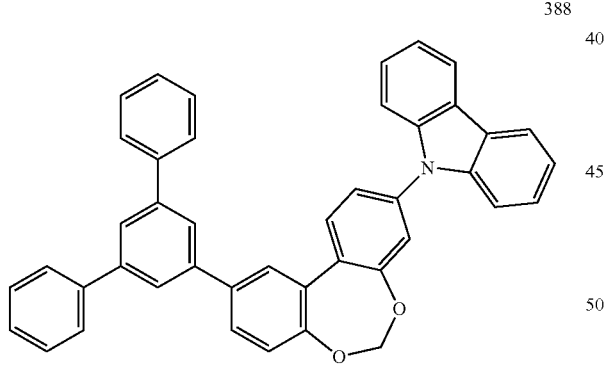 | |
| 389 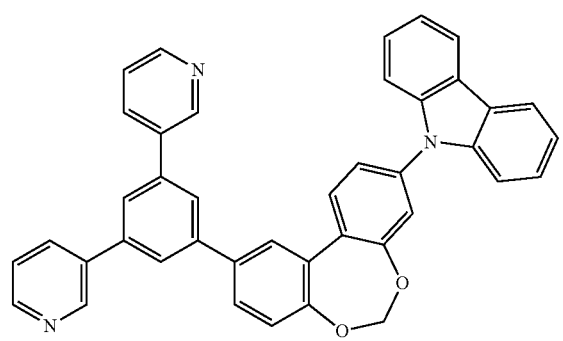 | 392 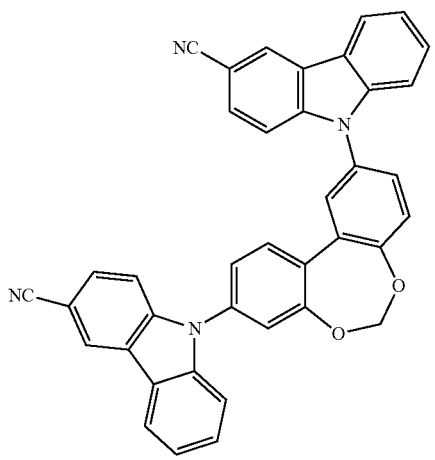 |

393
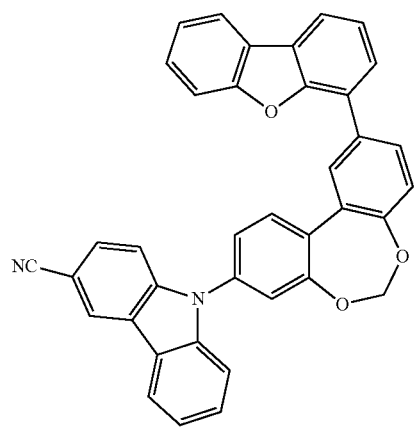
394
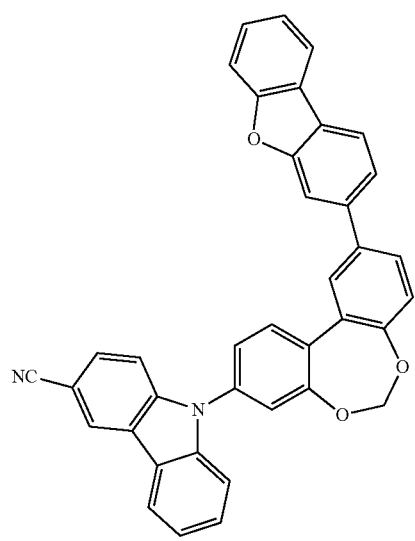
395
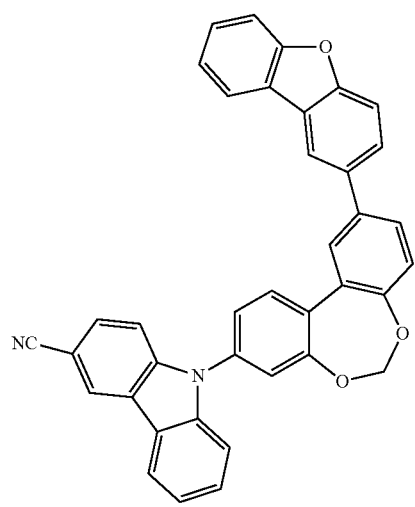
396
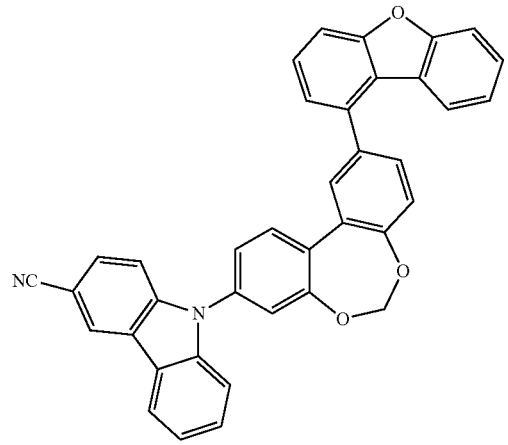
397
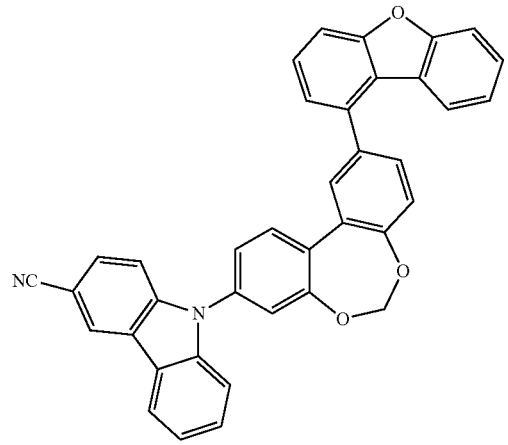
398
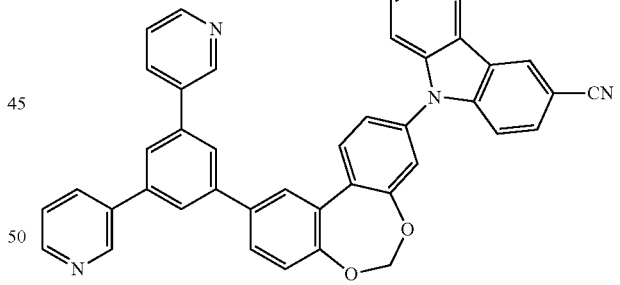
399
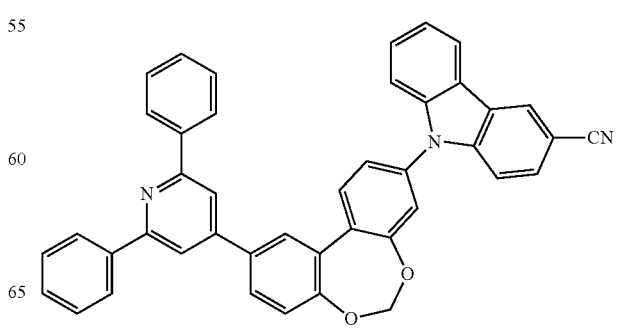

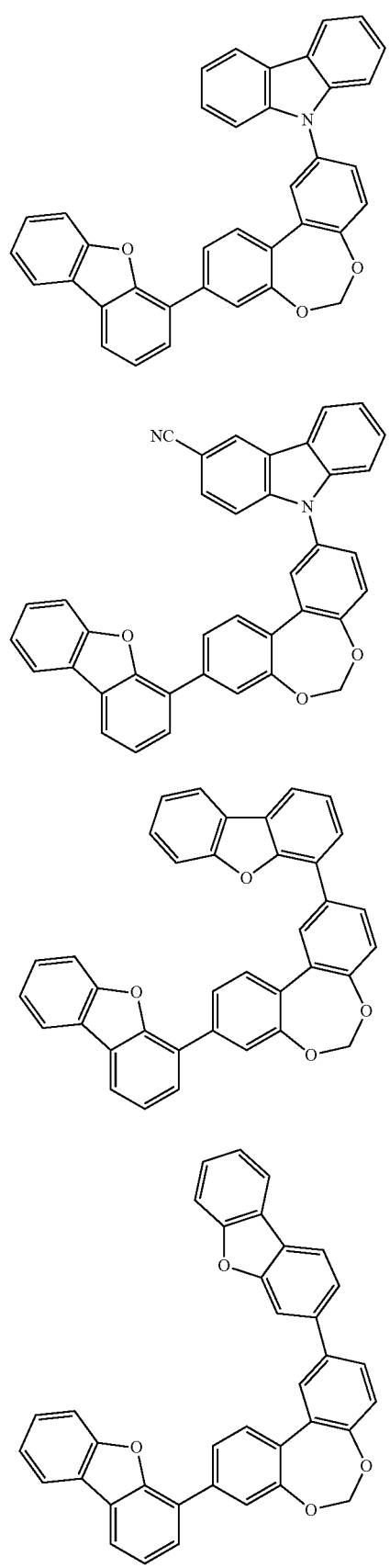
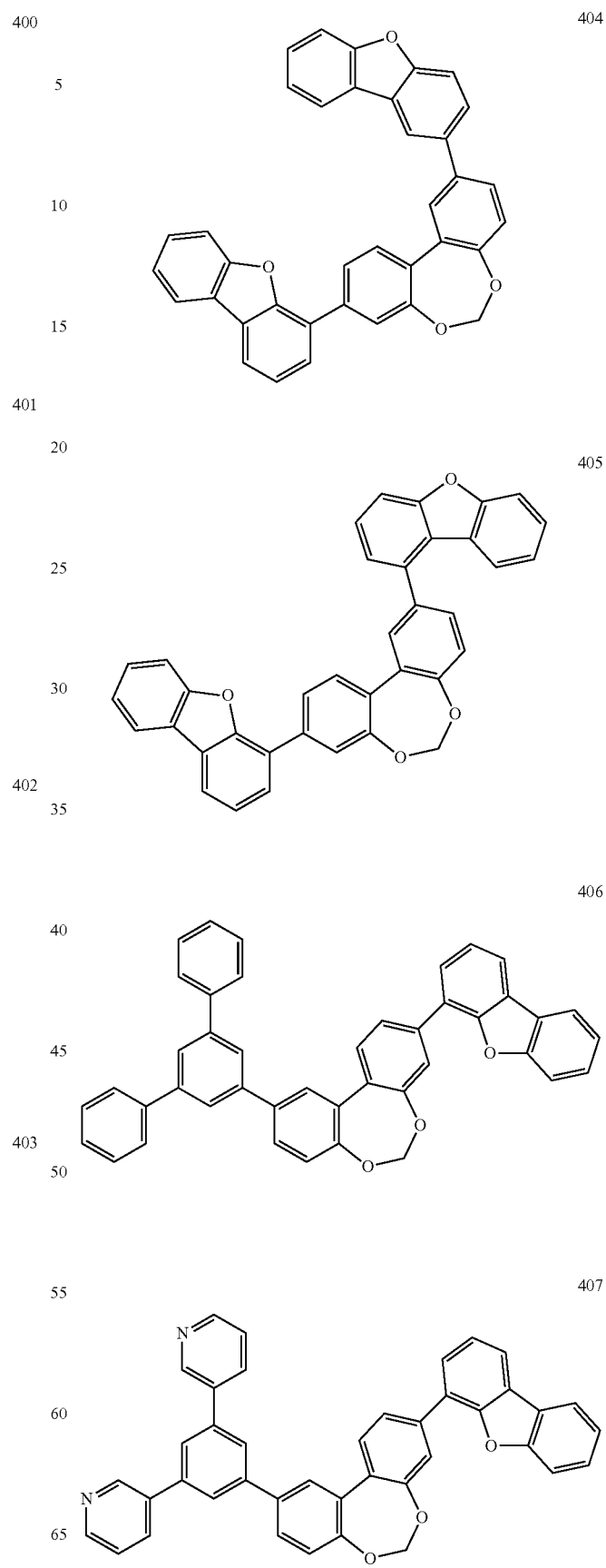

141
-continued
408
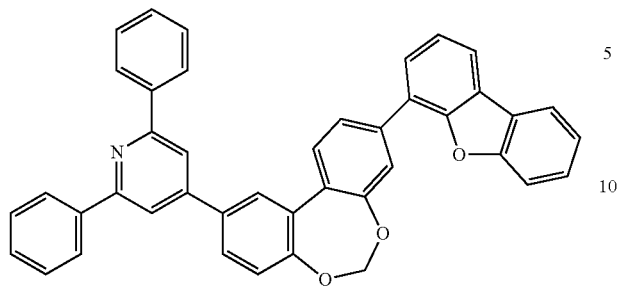
409
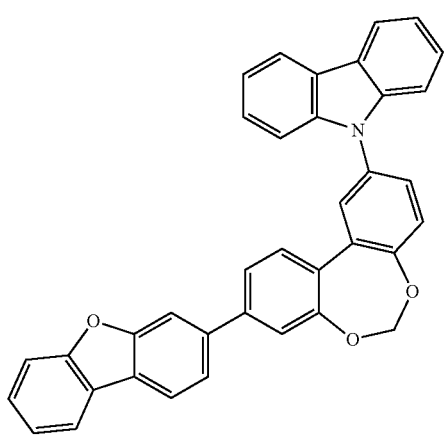
410
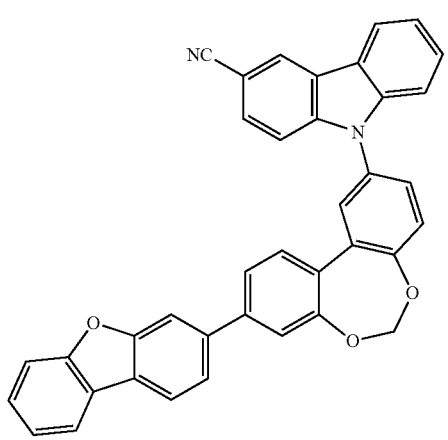
411
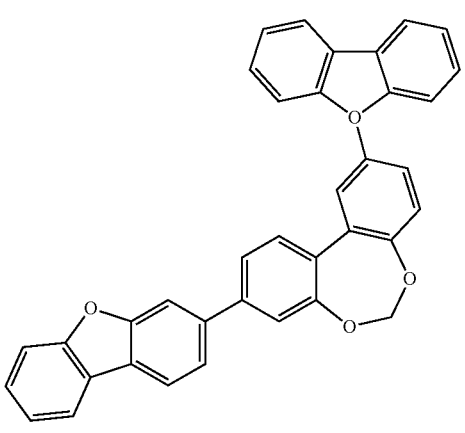
142
-continued
412
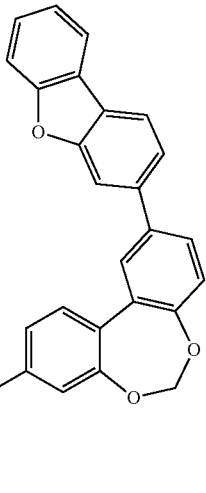
413
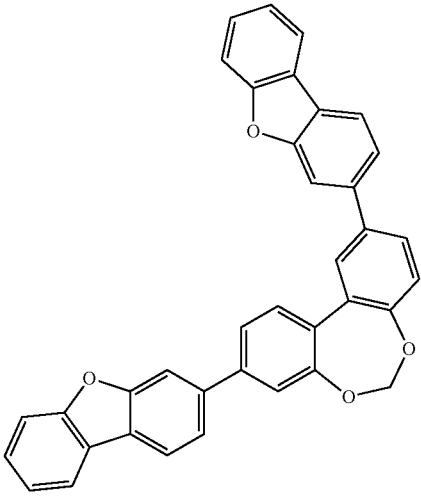
414
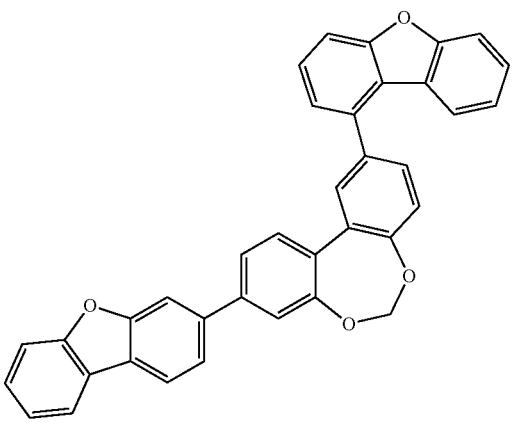

415
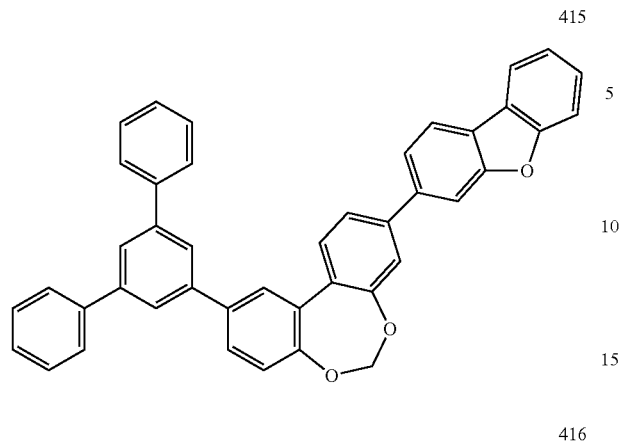
416
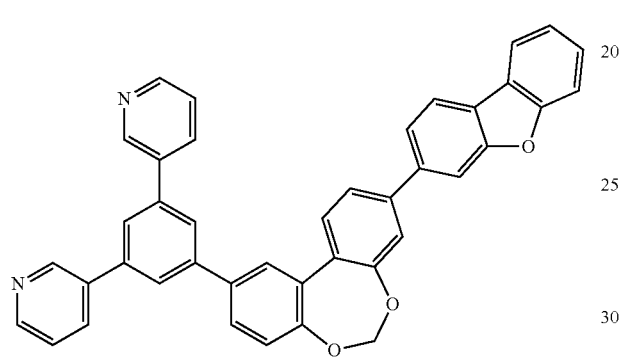
417
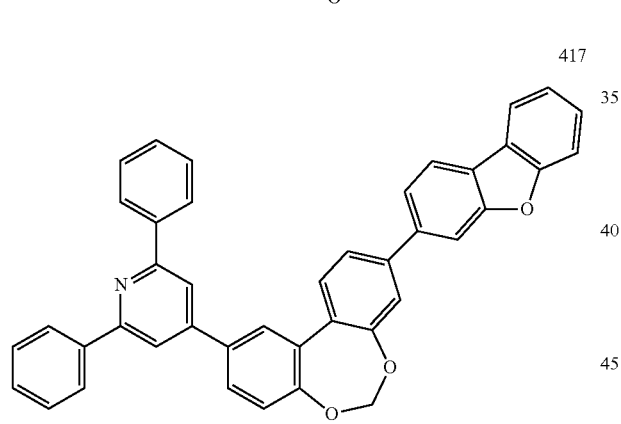
418
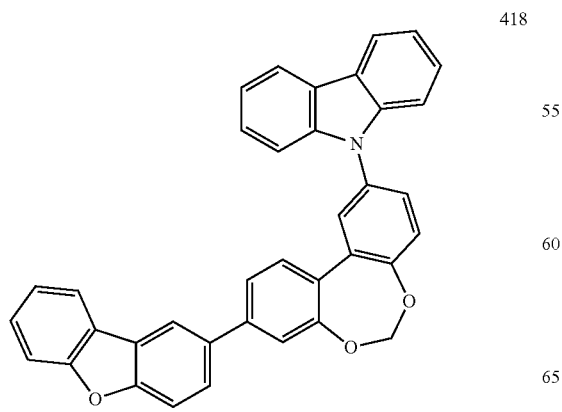
419
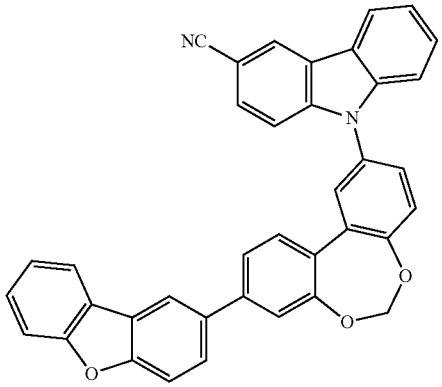
420
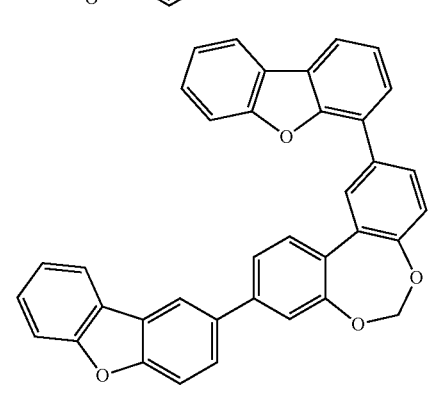
421
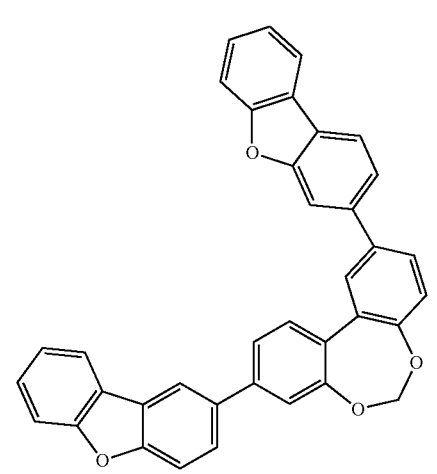
422
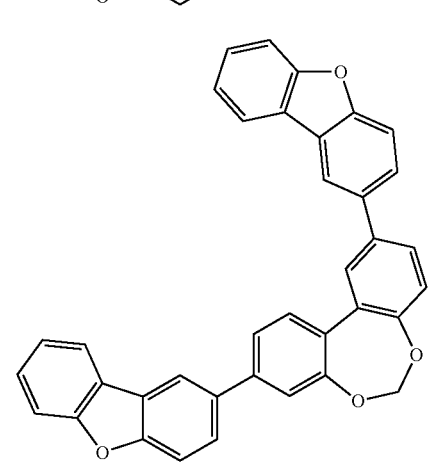

423
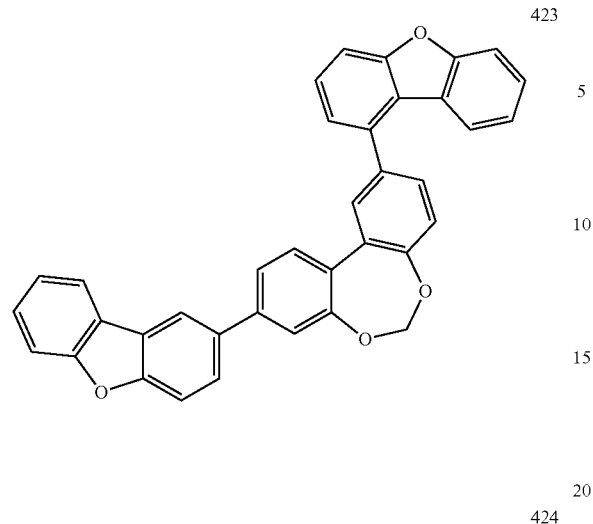
424
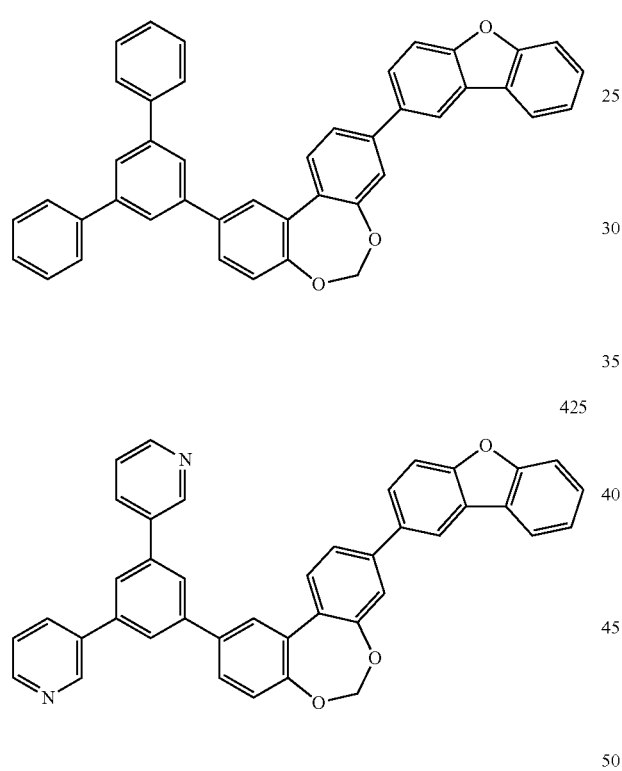
425
426
427
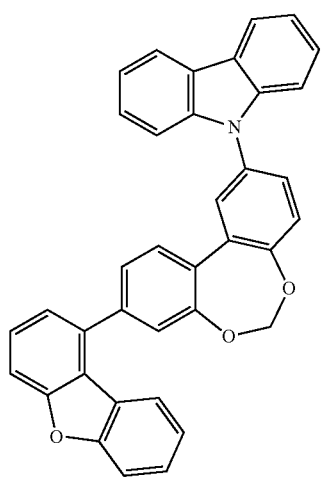
428
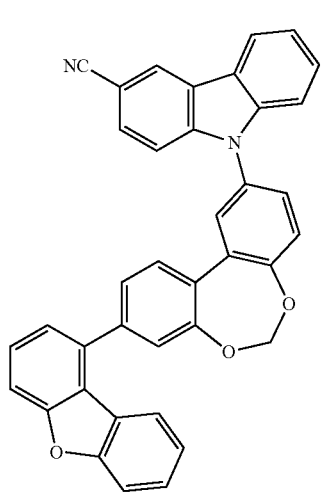
429
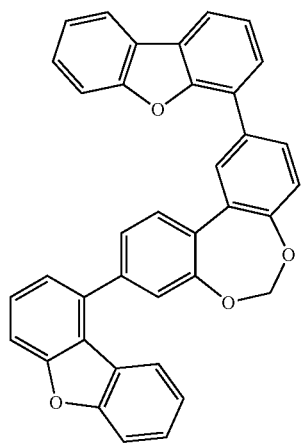

430
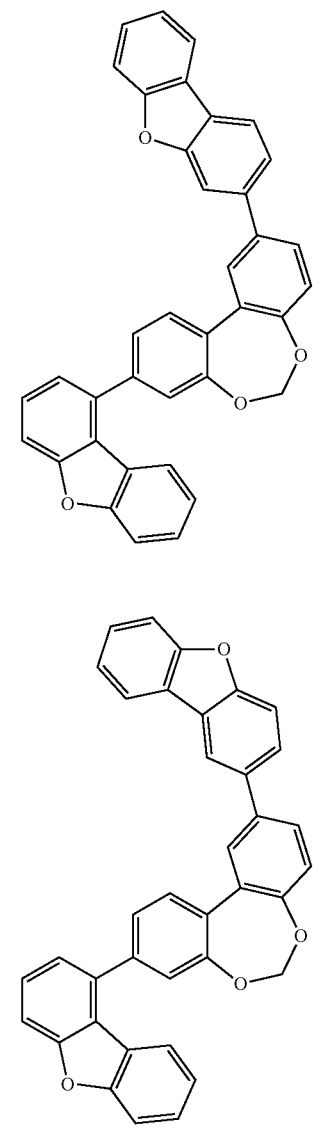
431
433
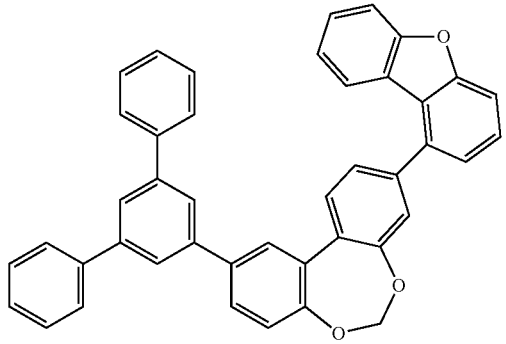
434
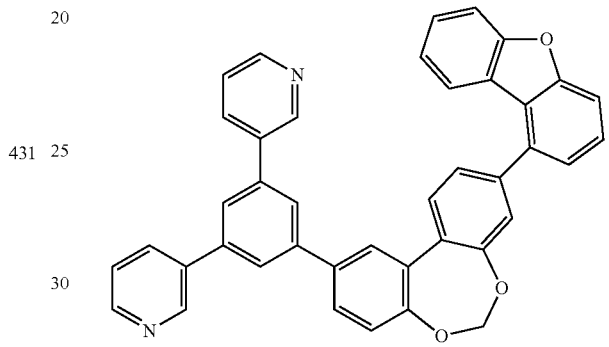
435
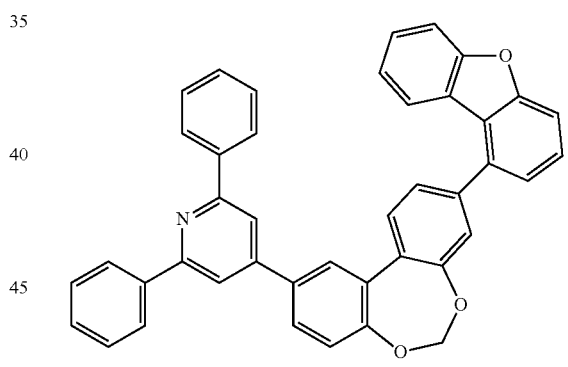
432
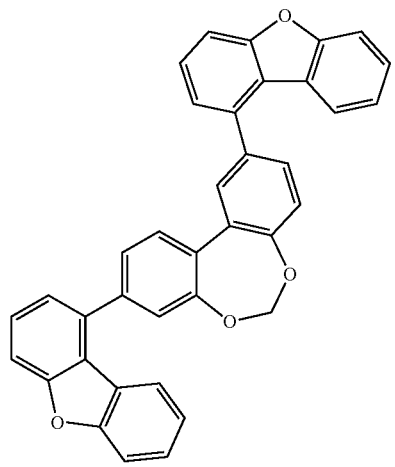
436
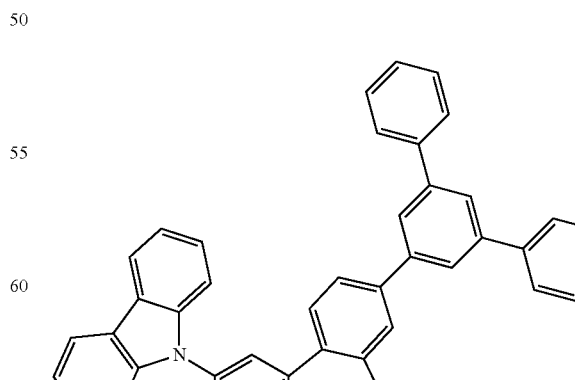

437
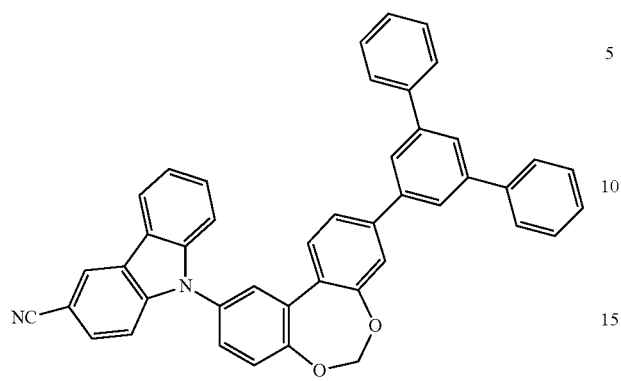
441
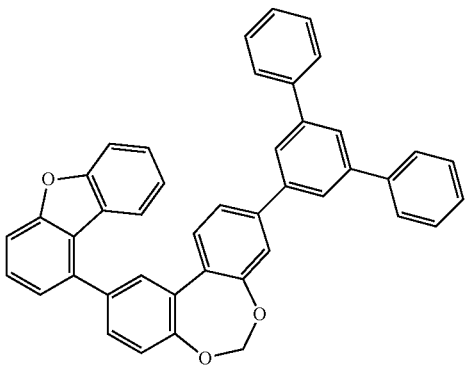
438
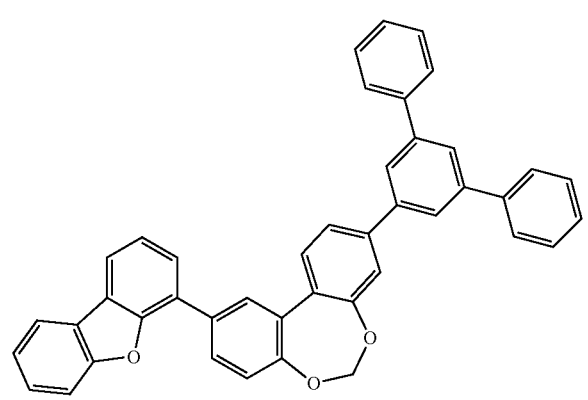
442
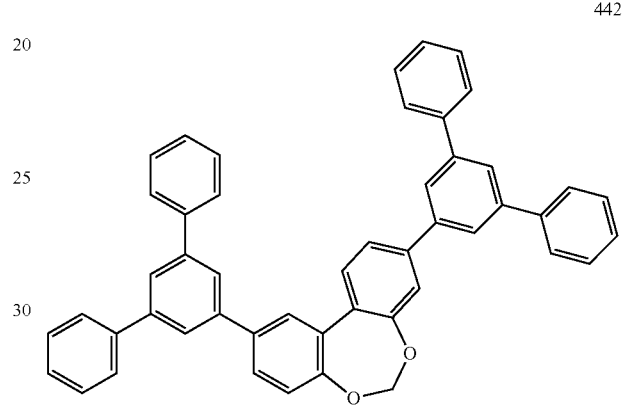
439
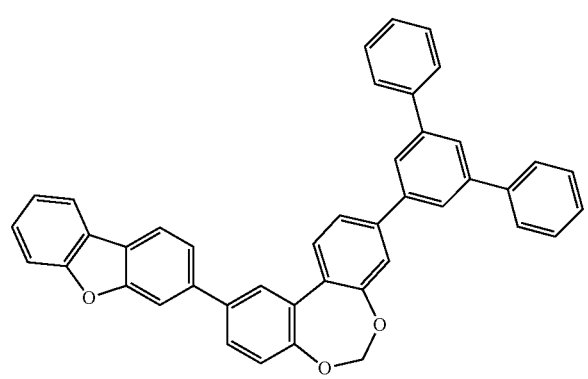
443
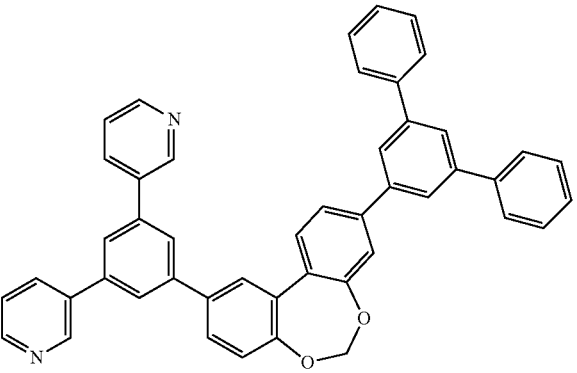
440
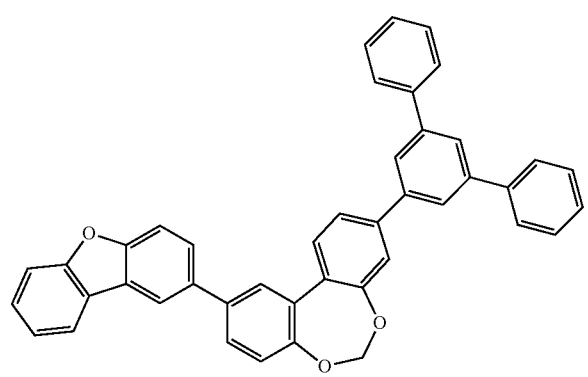
444
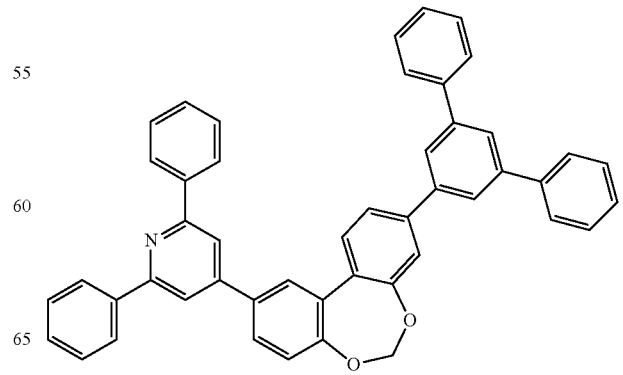

445
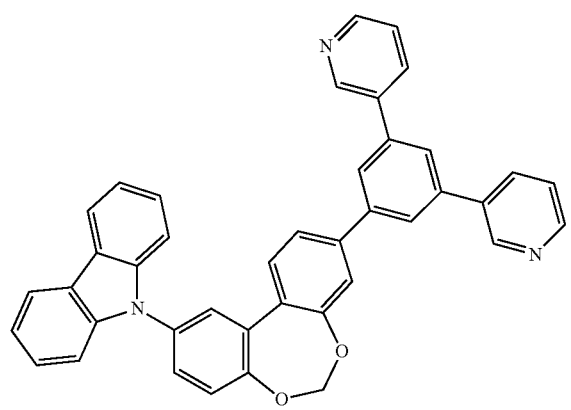
446
449
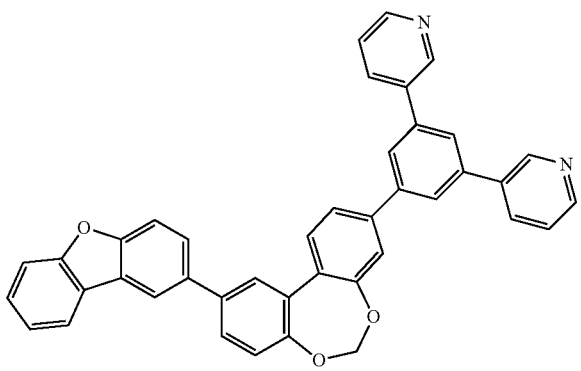
450
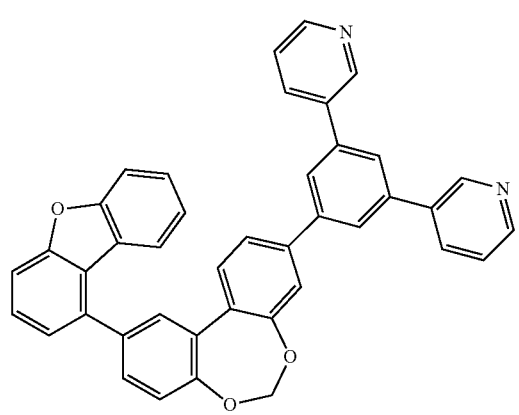
447
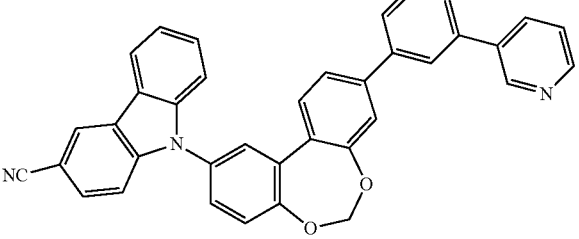
451
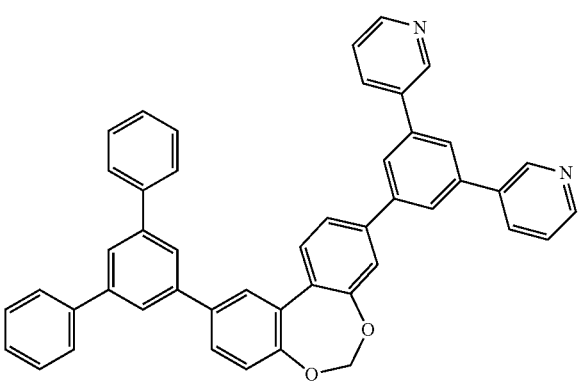
448
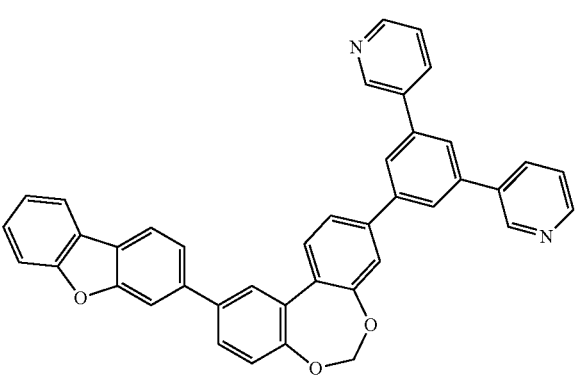
452
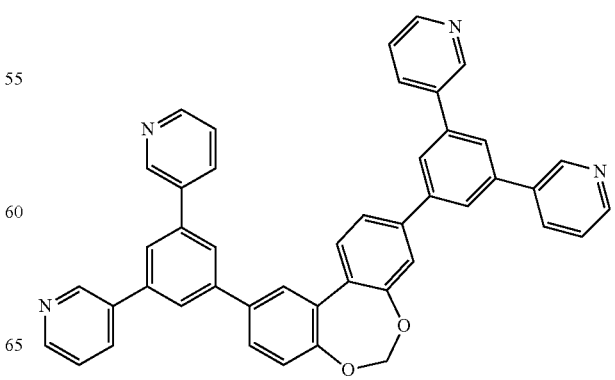

-continued
453
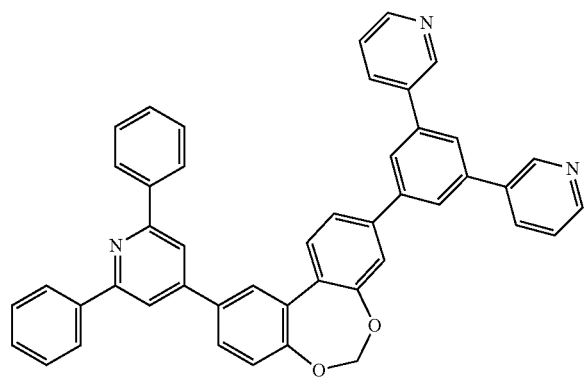
454
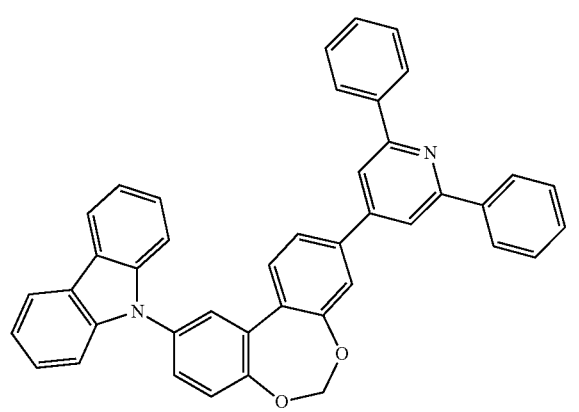
455
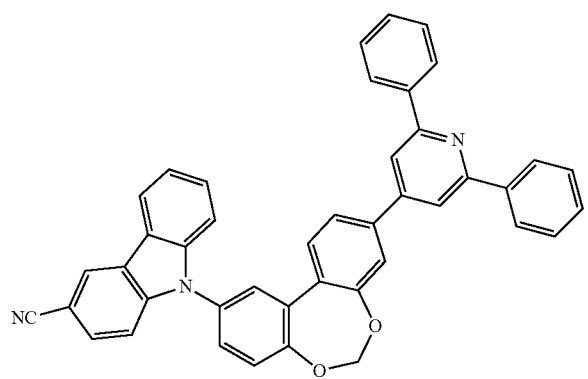
456
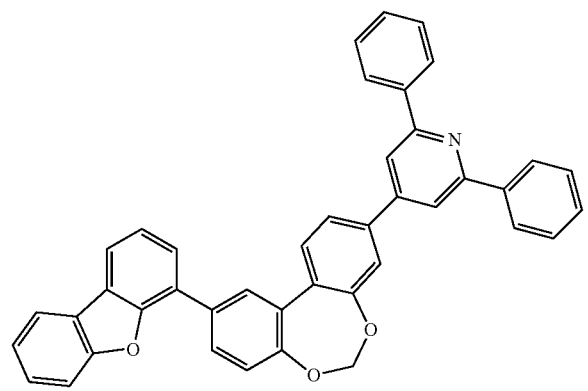
-continued
457
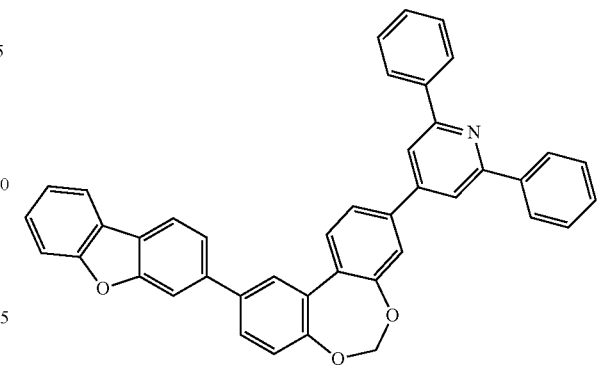
458
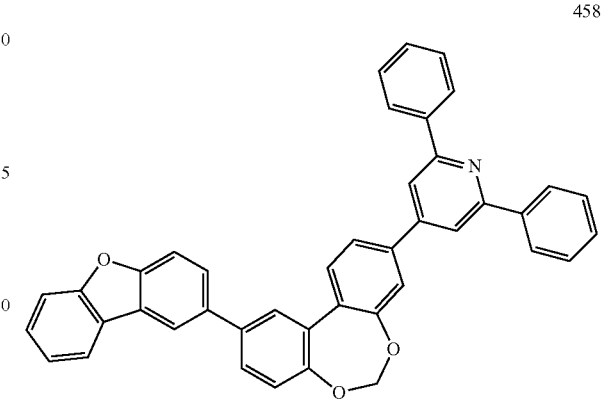
459
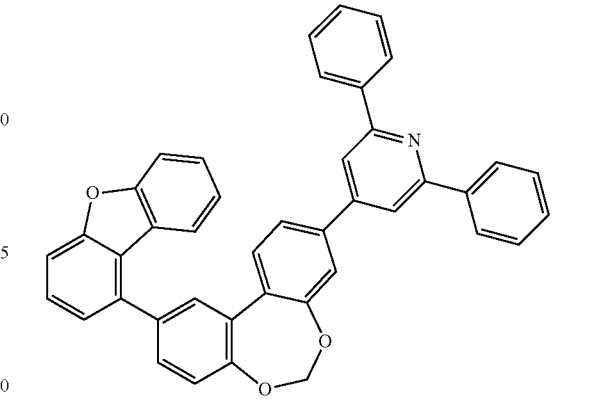
460
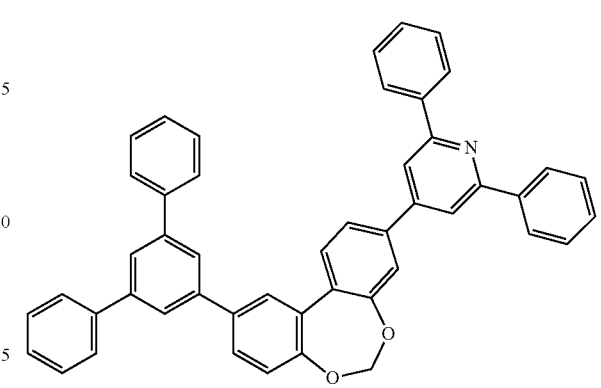

461
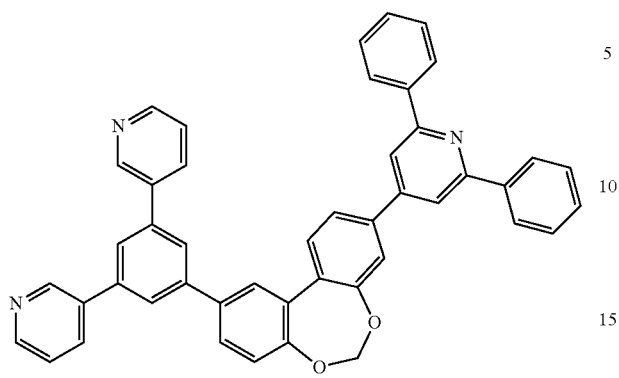
462
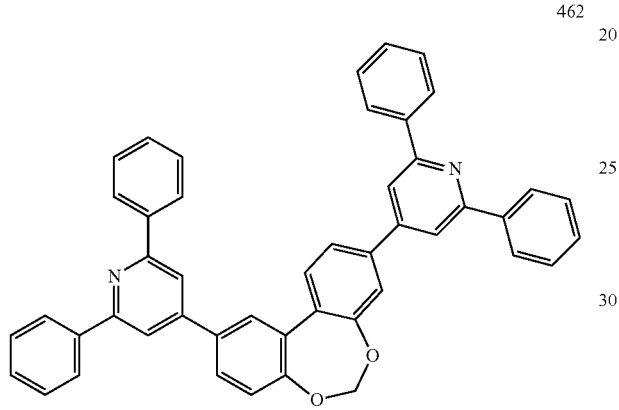
463
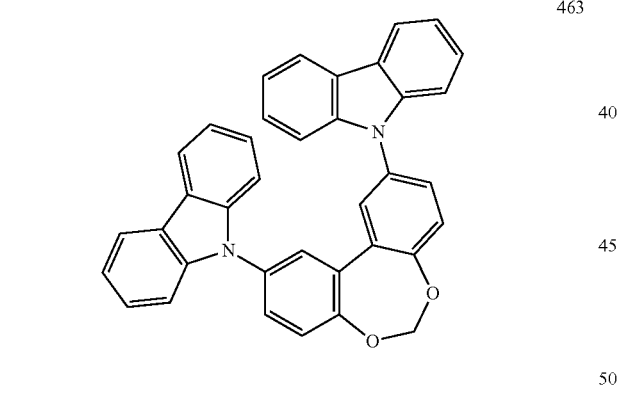
464
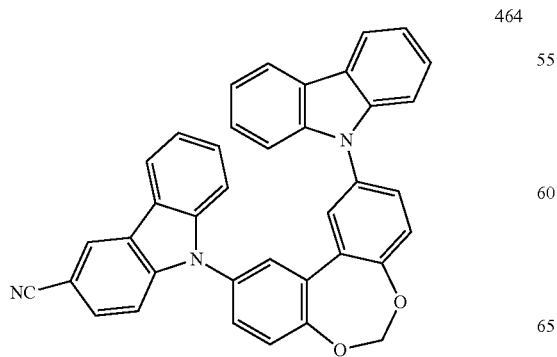
465
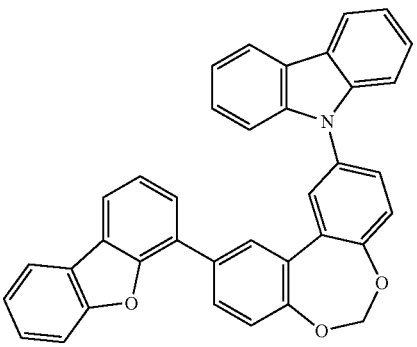
466
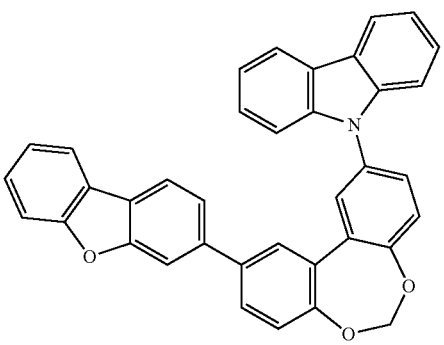
467
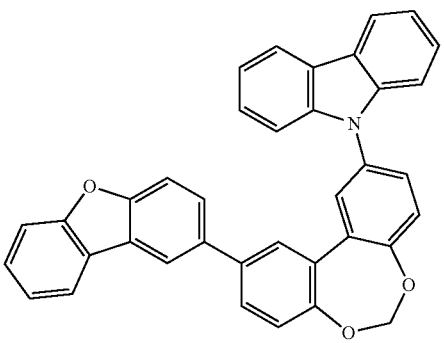
468
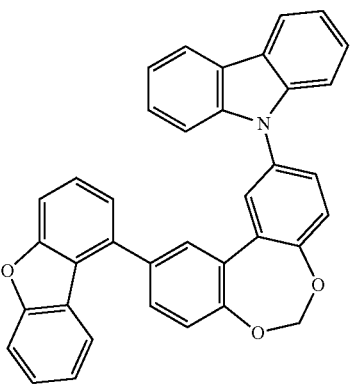

469
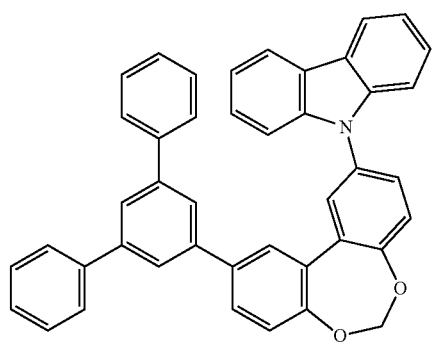
470
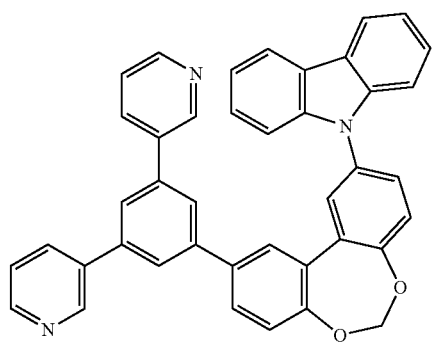
471
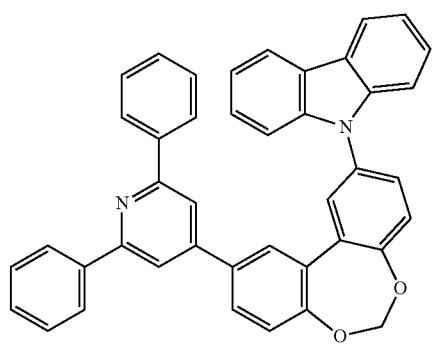
472
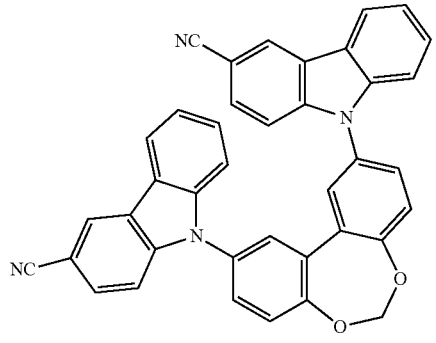
473
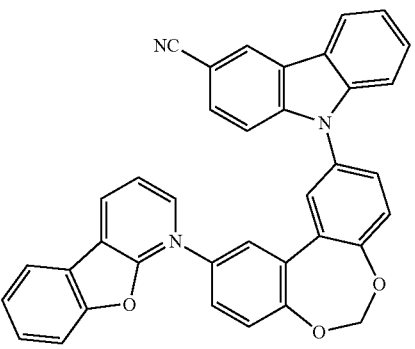
474
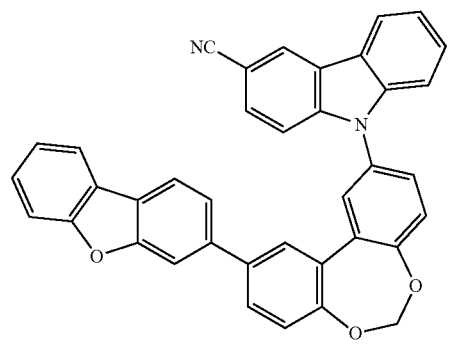
475
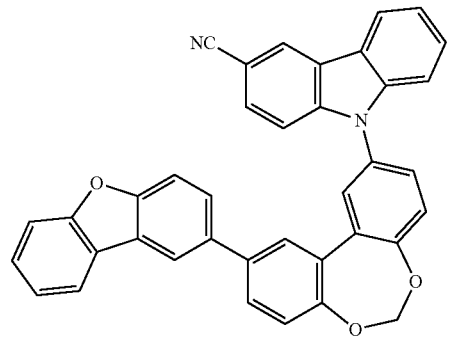
476
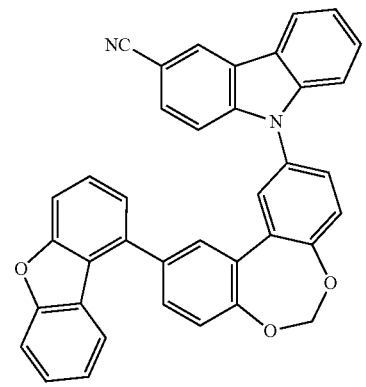

159
-continued
477
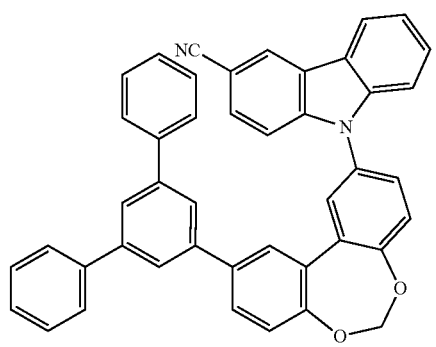
478
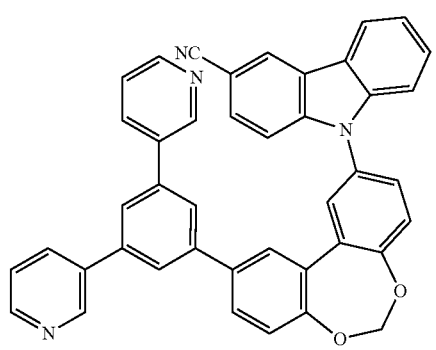
479
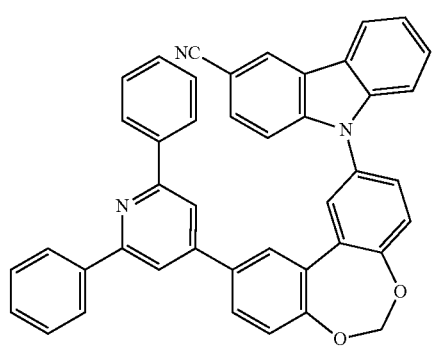
480
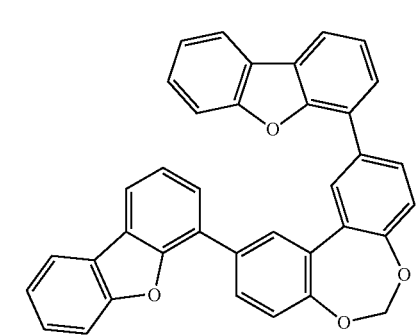
160
-continued
481
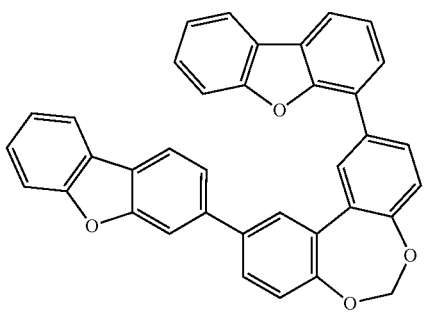
482
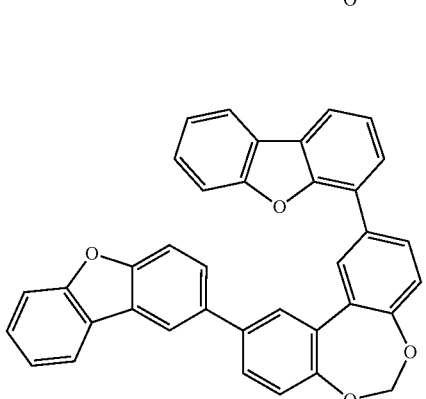
483
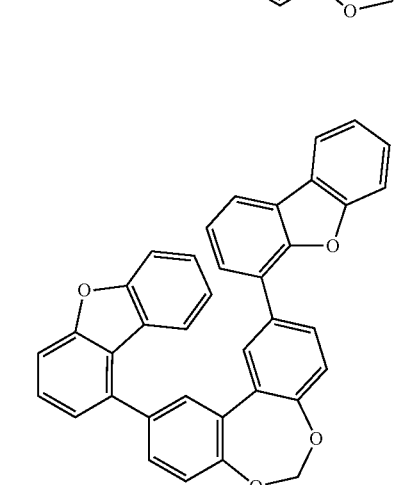
484
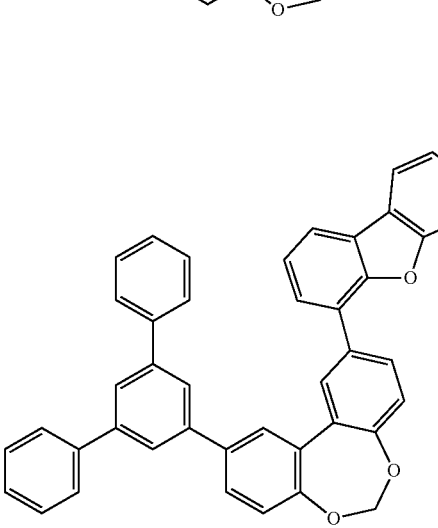

-continued
485
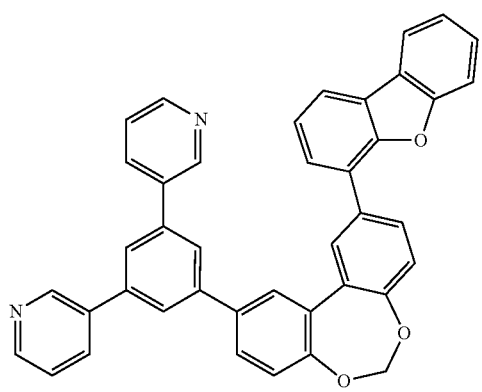
486
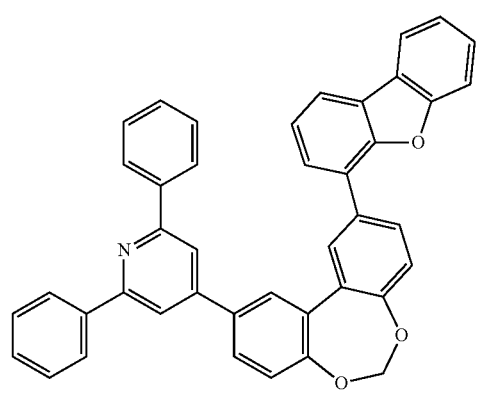
487
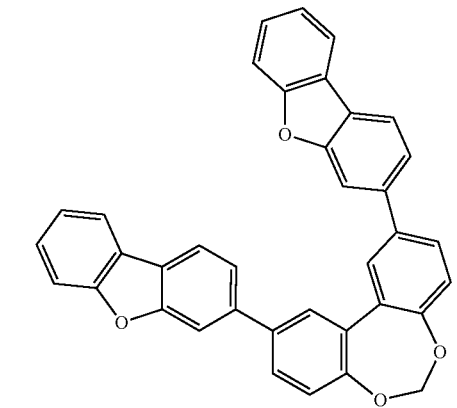
488
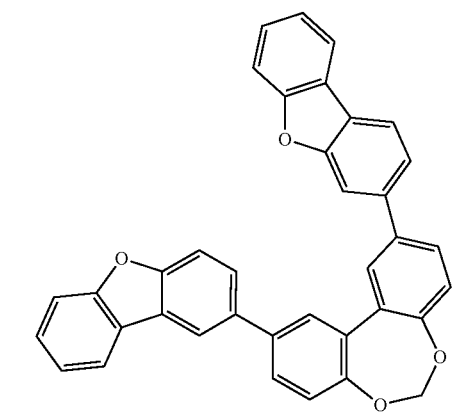
-continued
489
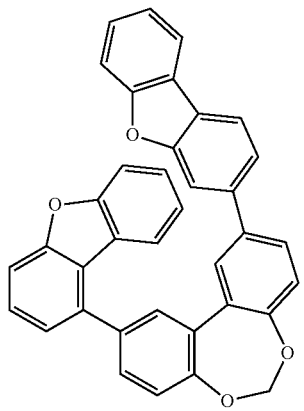
490
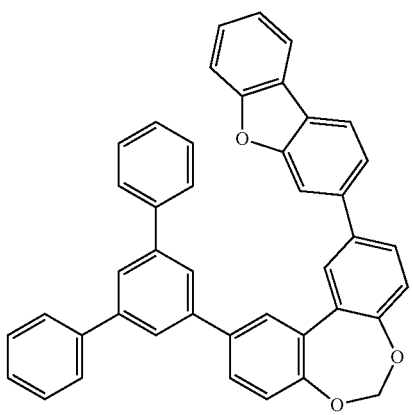
491
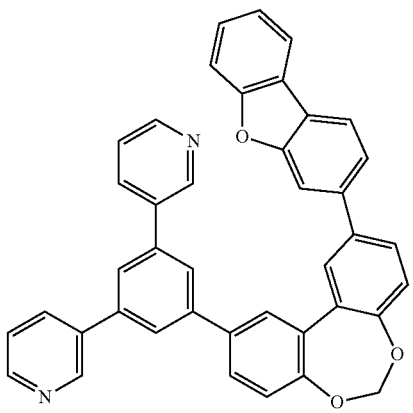
492
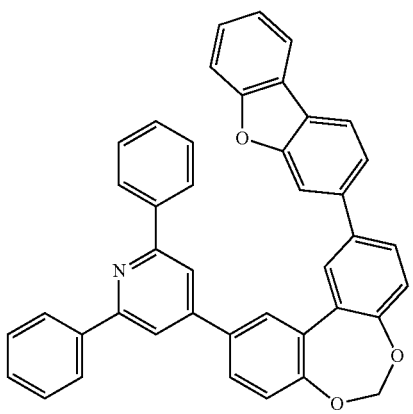

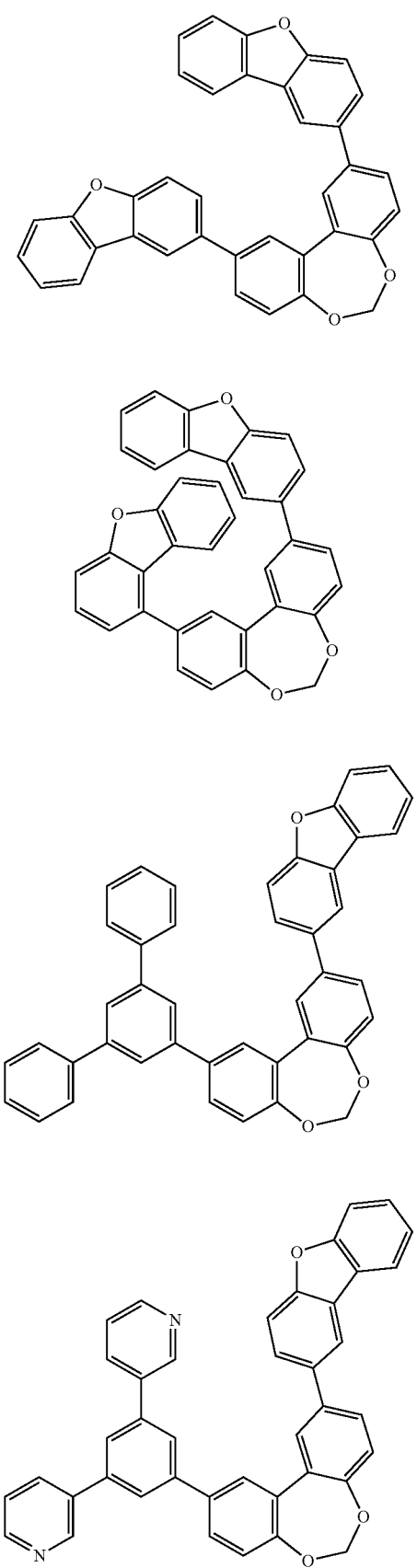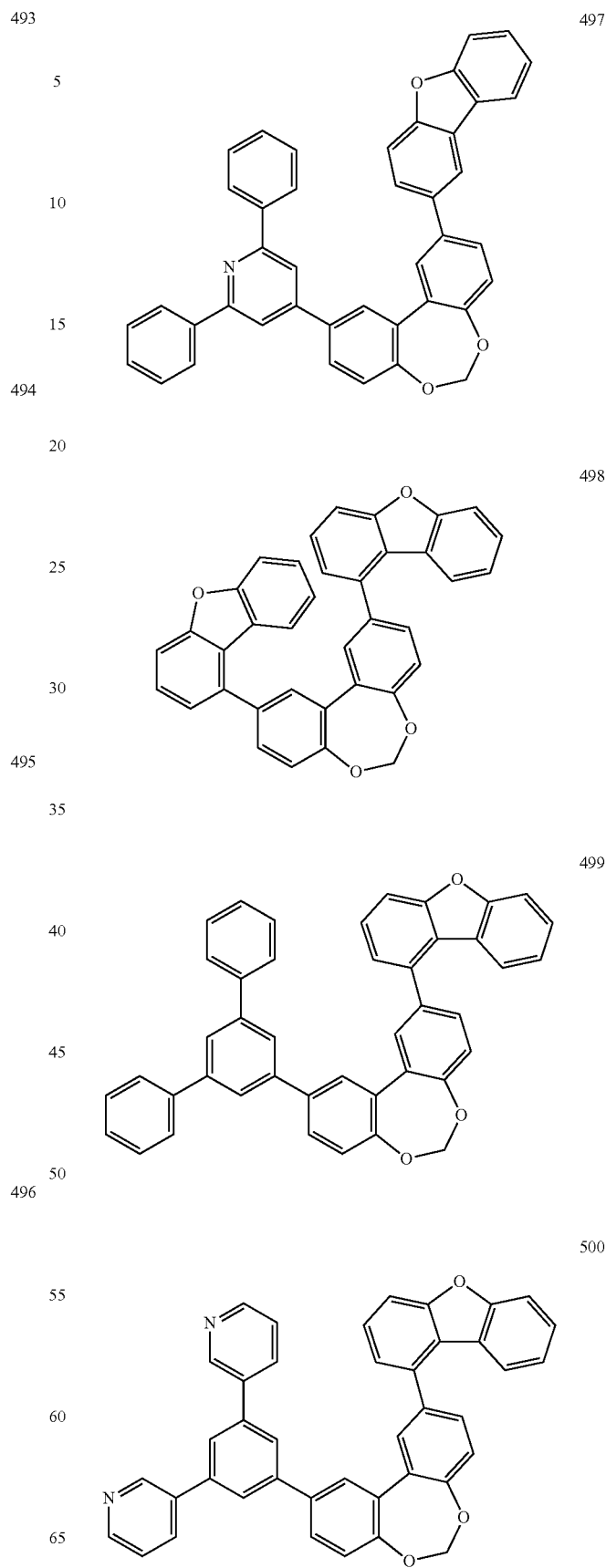

-continued
501
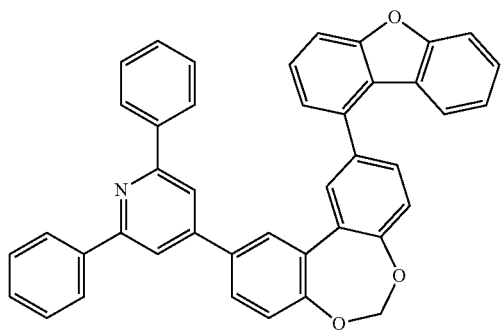
502
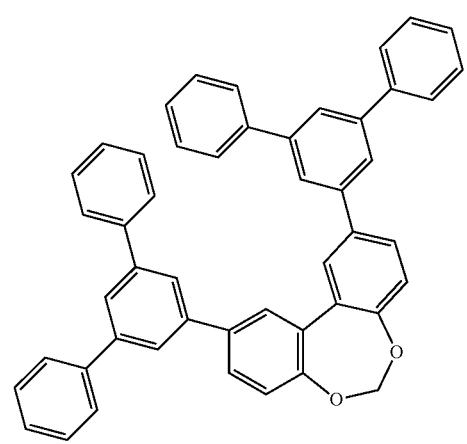
503
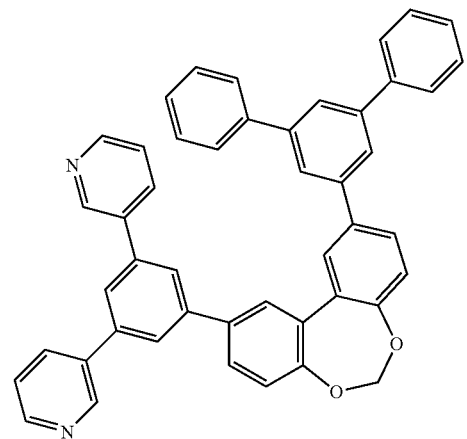
504
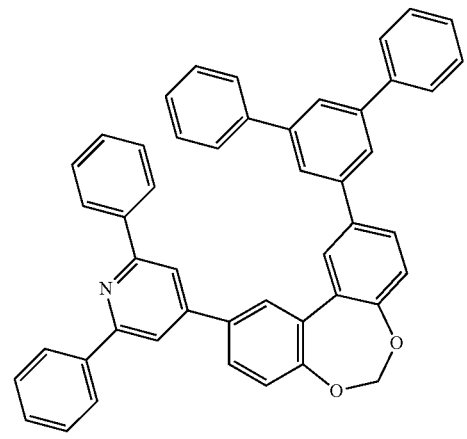
-continued
505
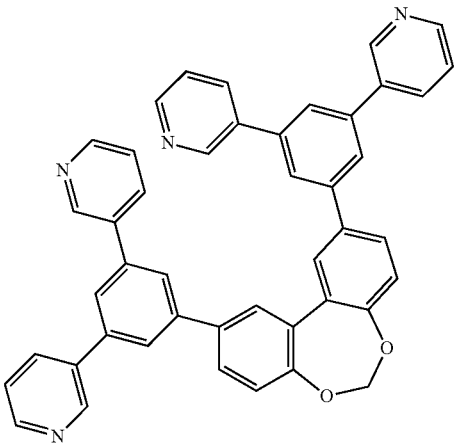
506
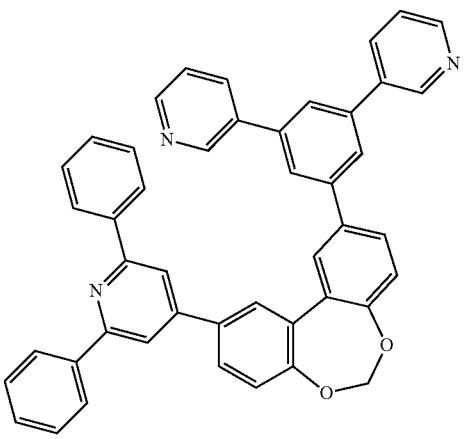
507
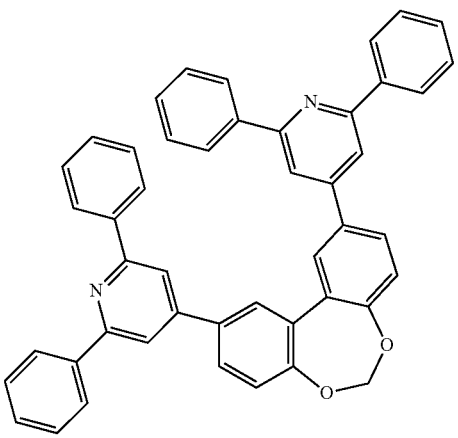
508
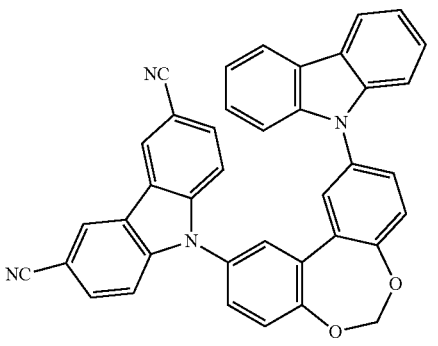

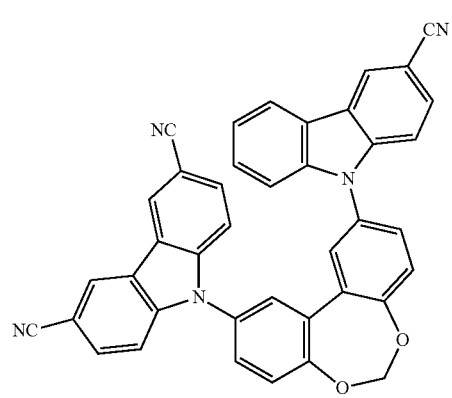
509
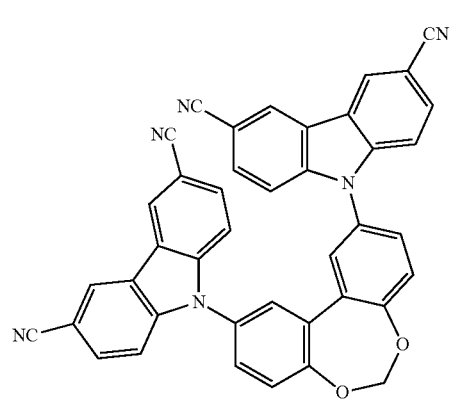
510
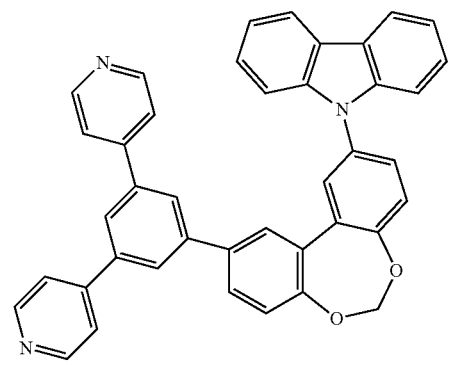
511
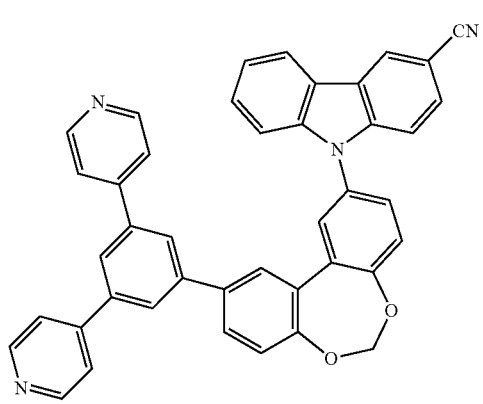
512
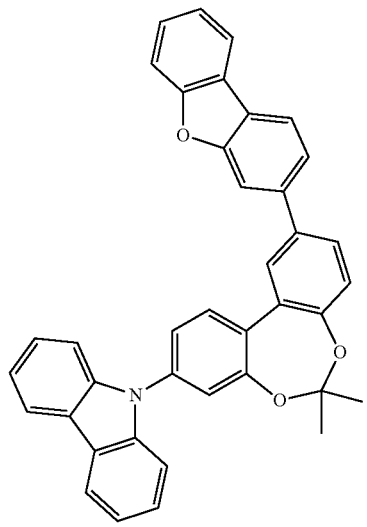
513
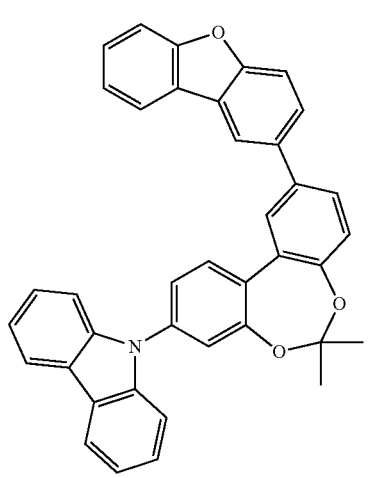
514
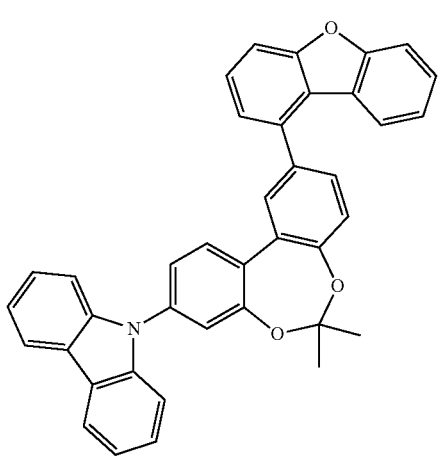
515

169
-continued
516
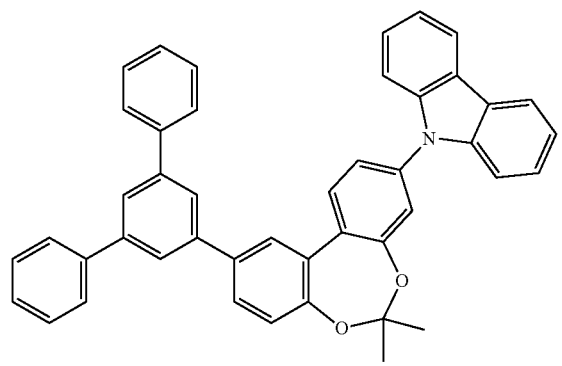
517
518
519
170
-continued
520
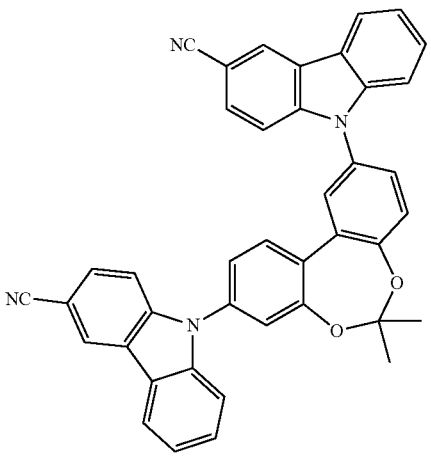
521
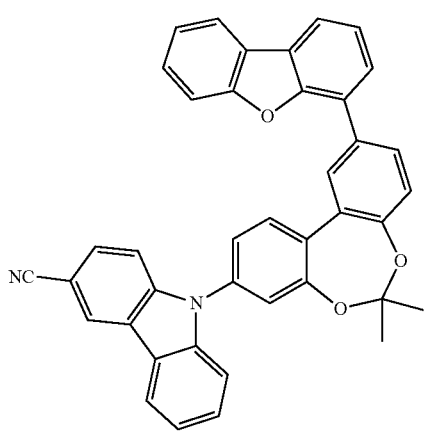
522
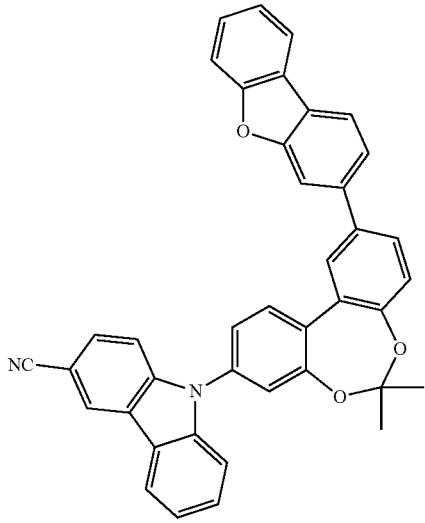

-continued
523
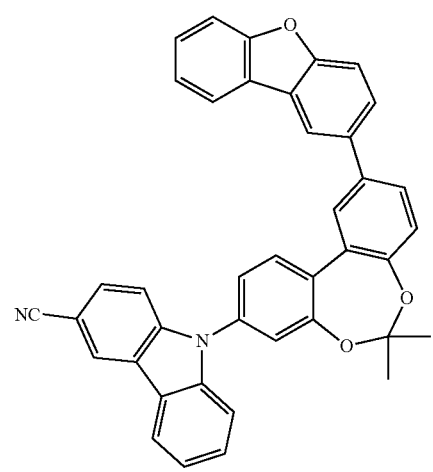
524
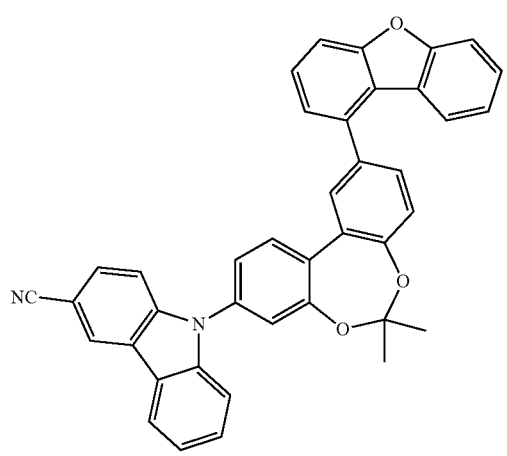
525
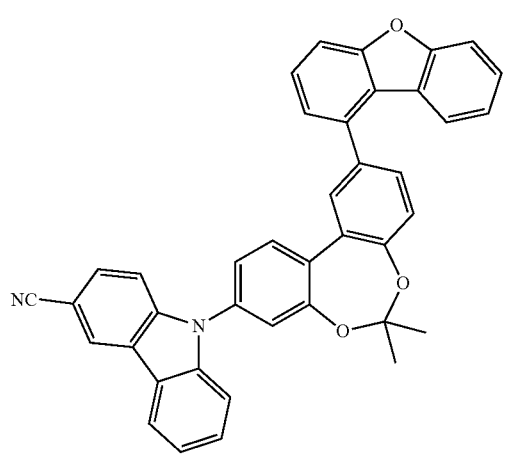
-continued
526
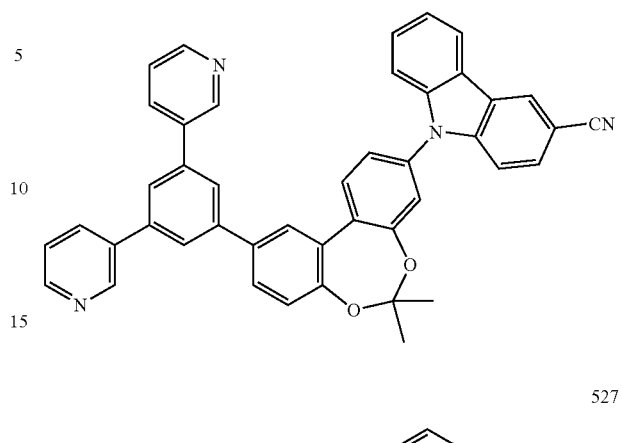
527
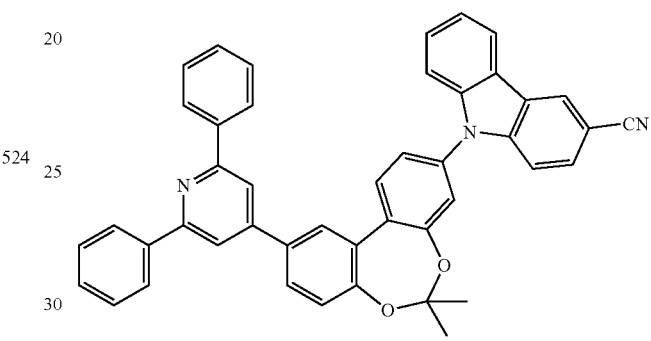
528
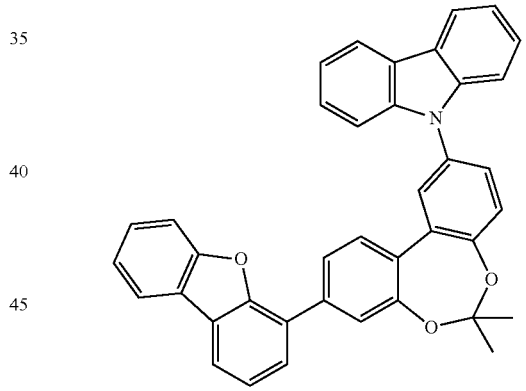
529
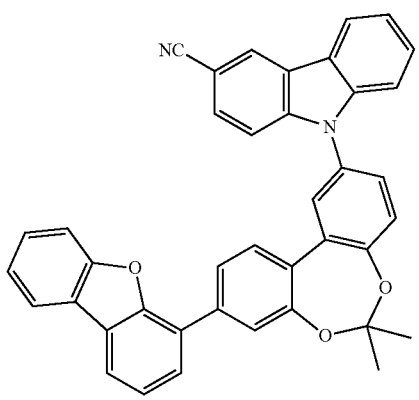

530
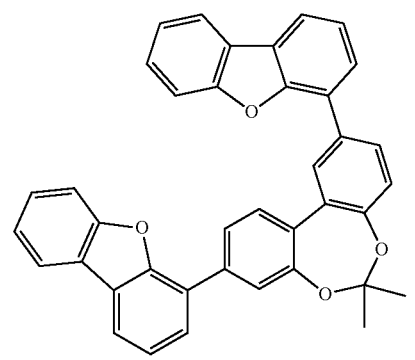
531
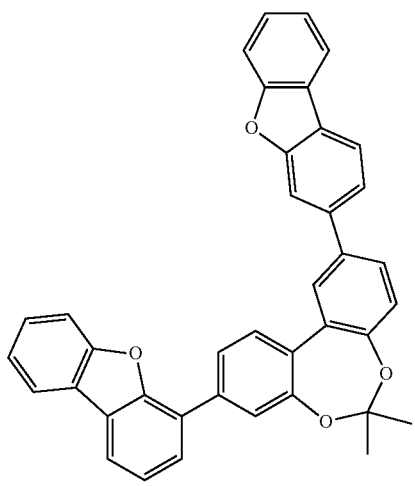
532
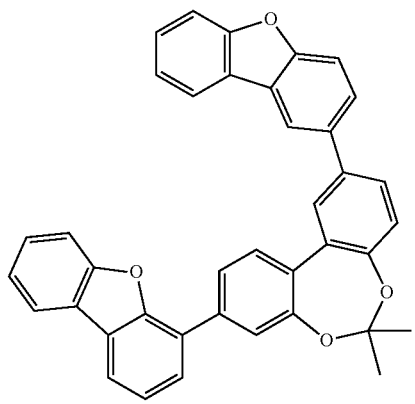
533
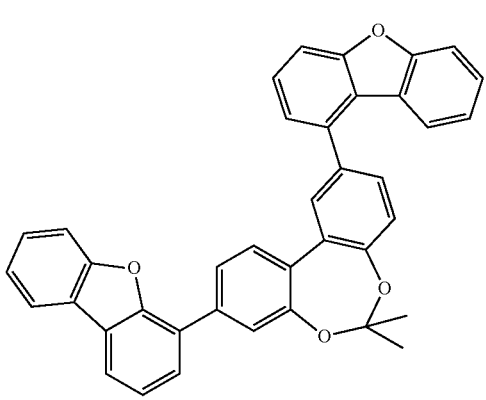
534
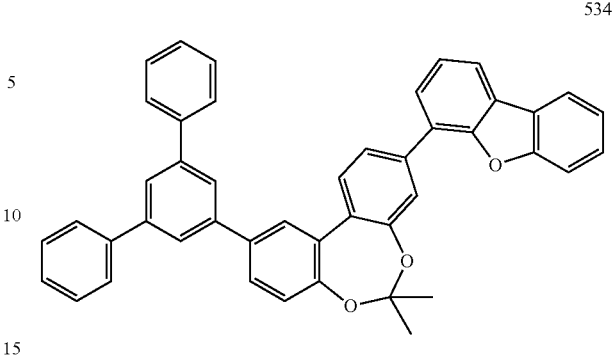
535
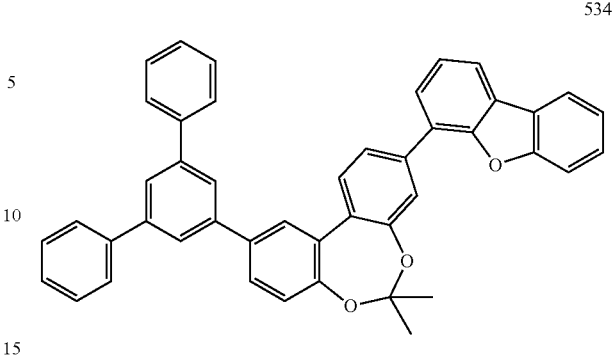
536
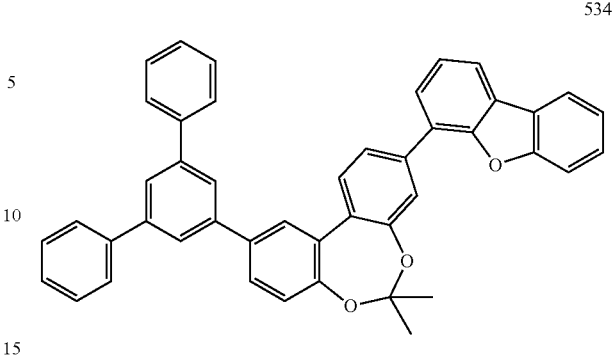
537
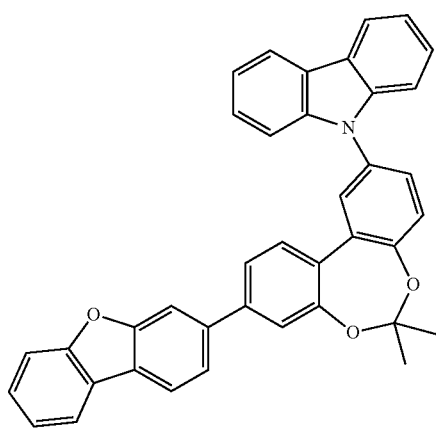

538 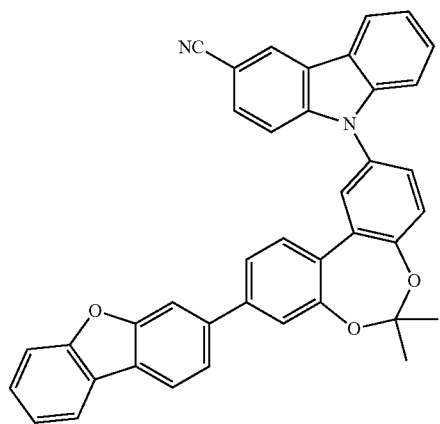
539 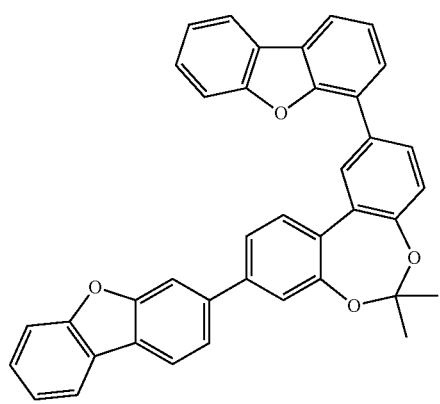
540 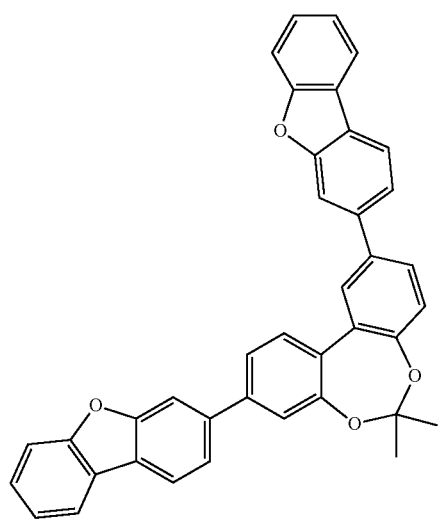
541 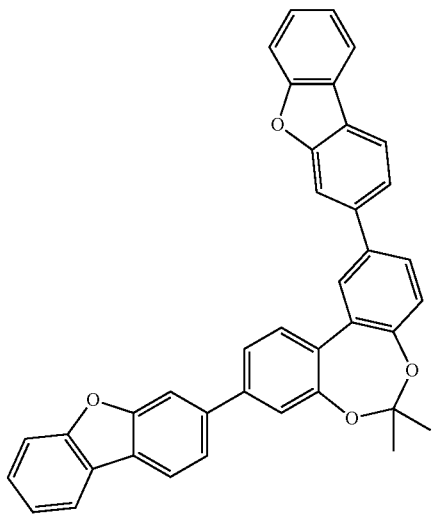
542 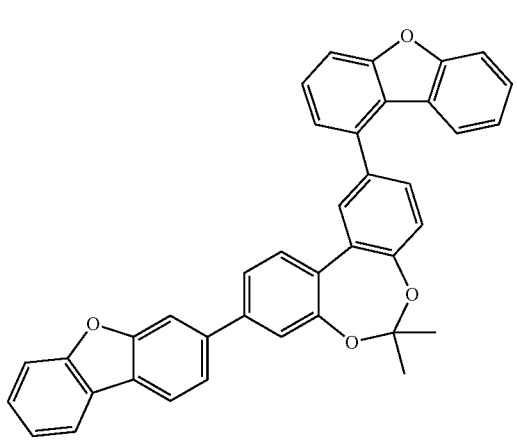
543 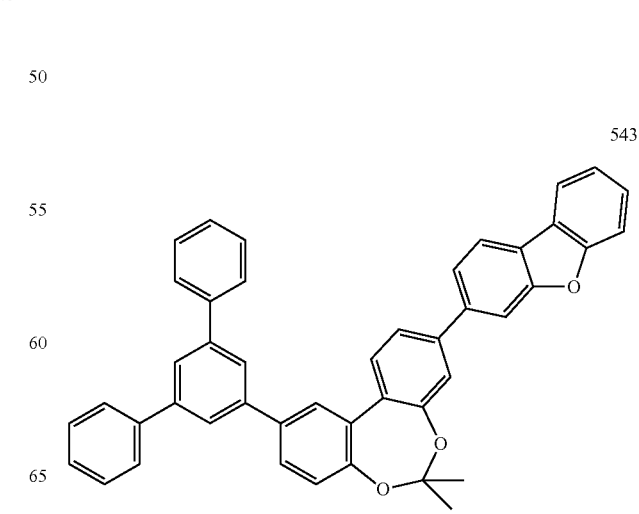

544
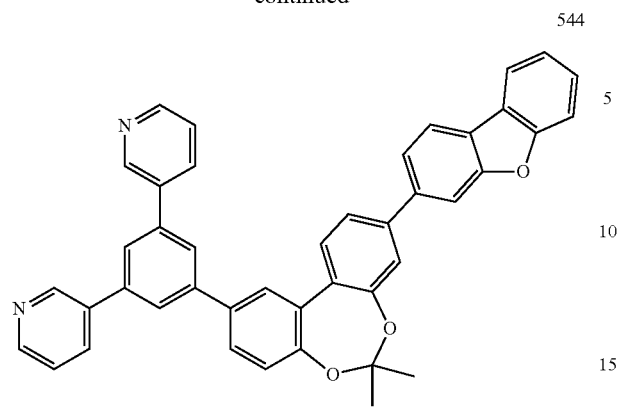
545
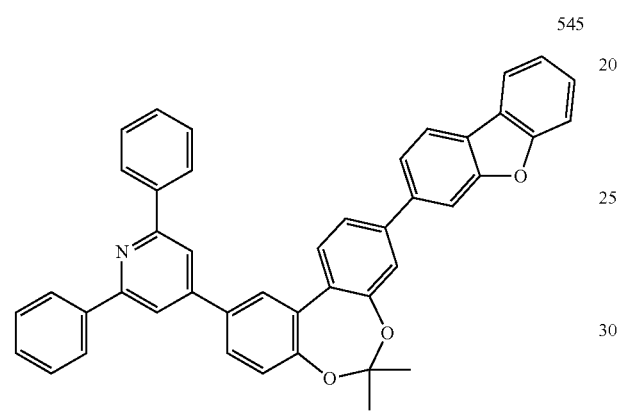
546
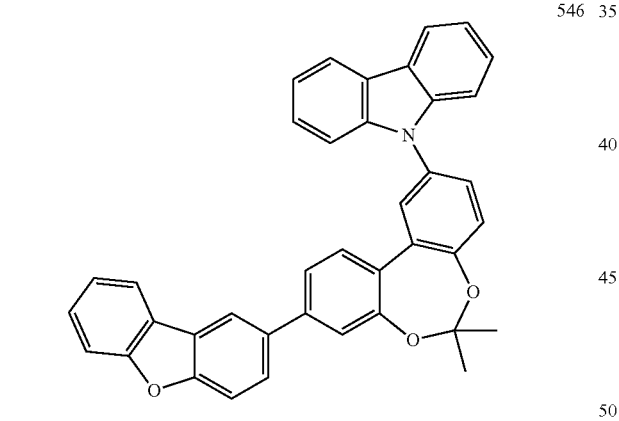
547
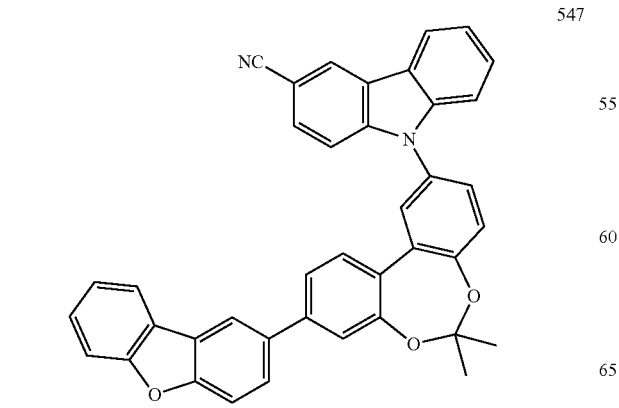
548
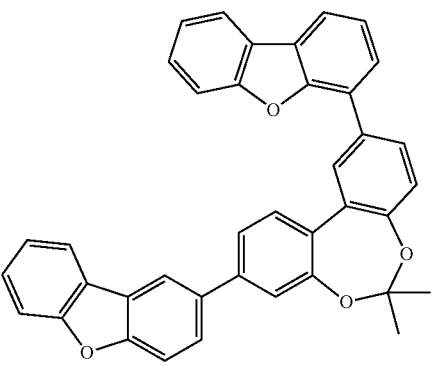
549
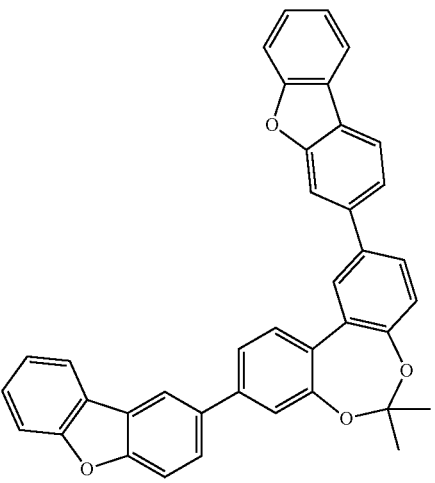
550
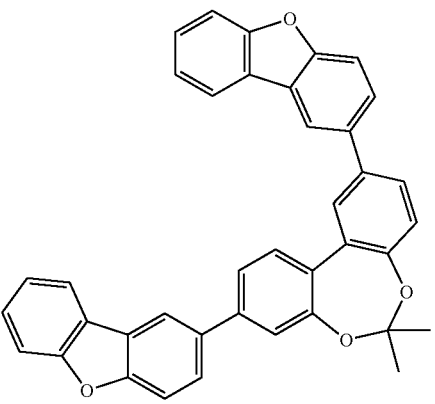
551
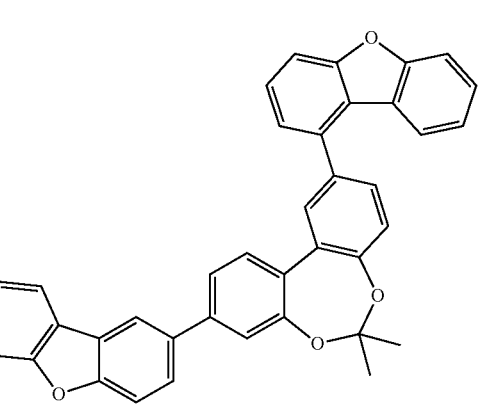

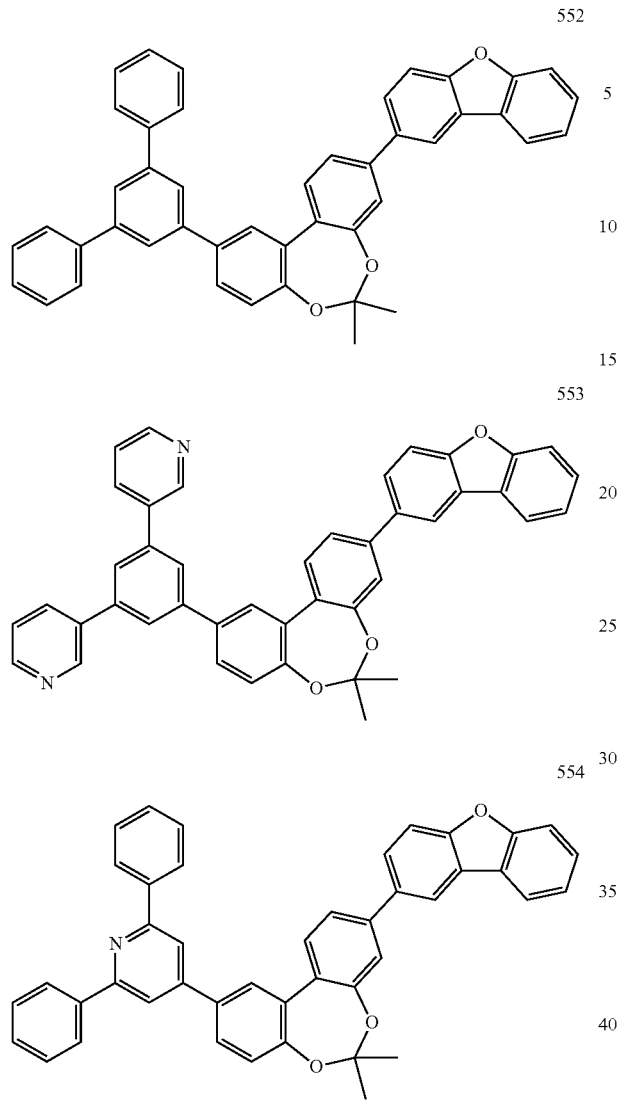
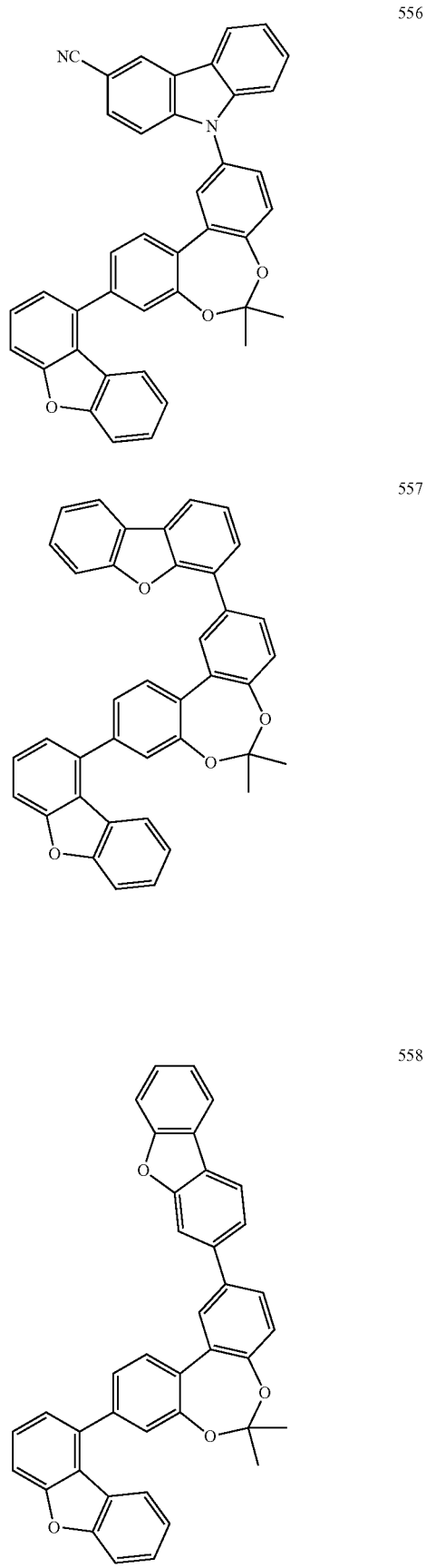

181
-continued
182
-continued
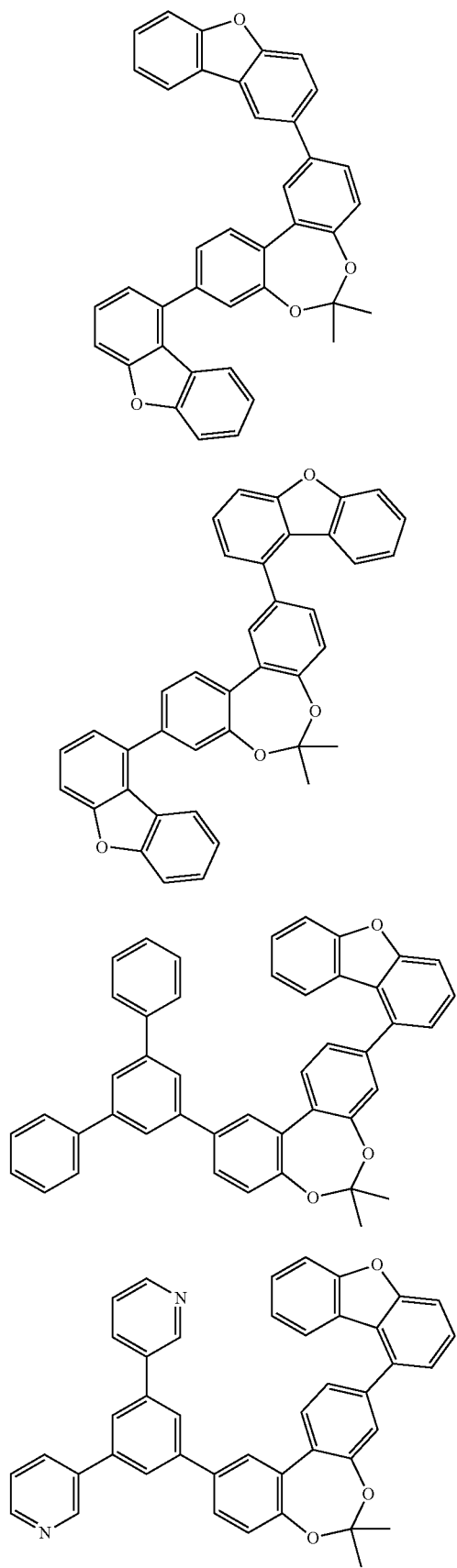
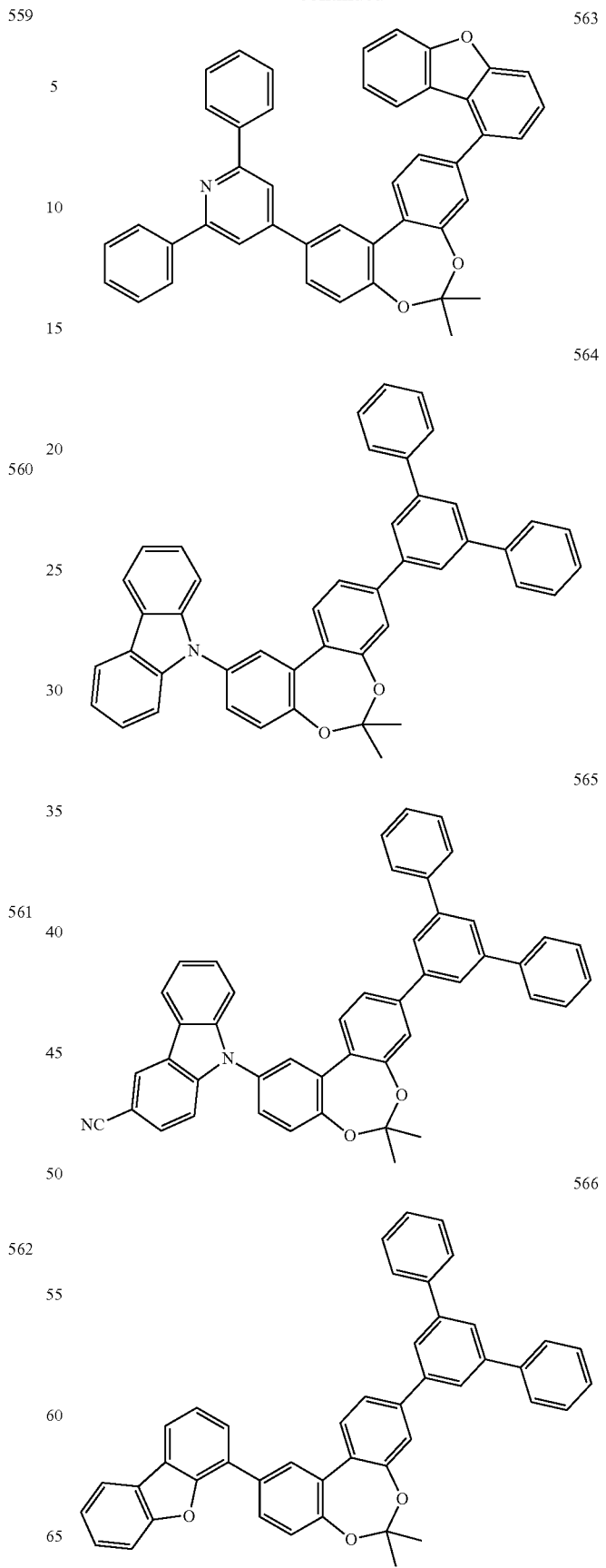

567
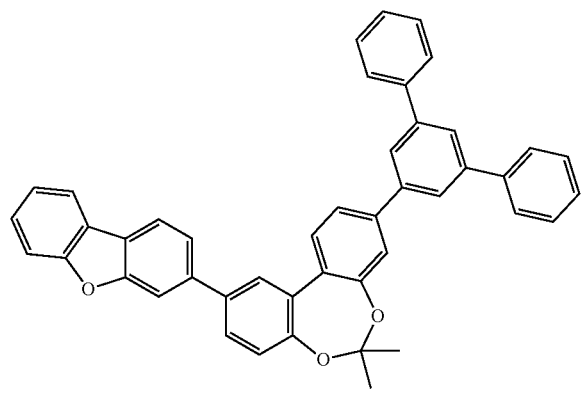
568
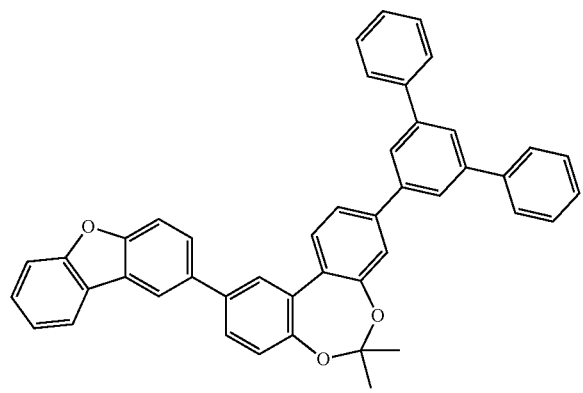
569
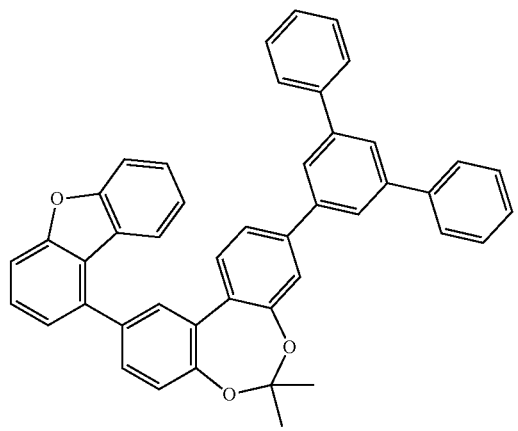
570
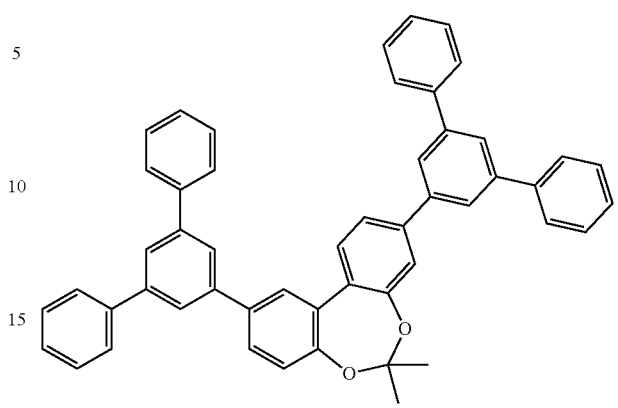
571
572
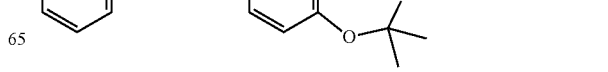

185
-continued
573
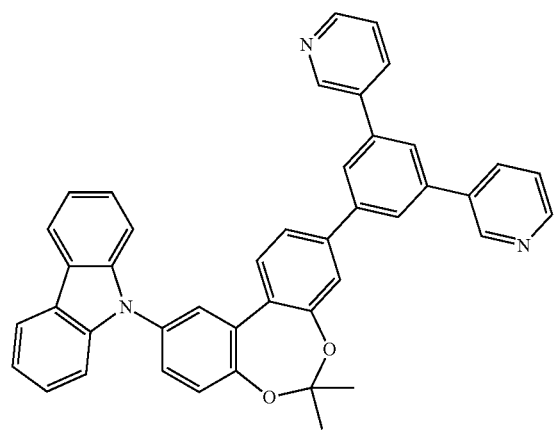
574
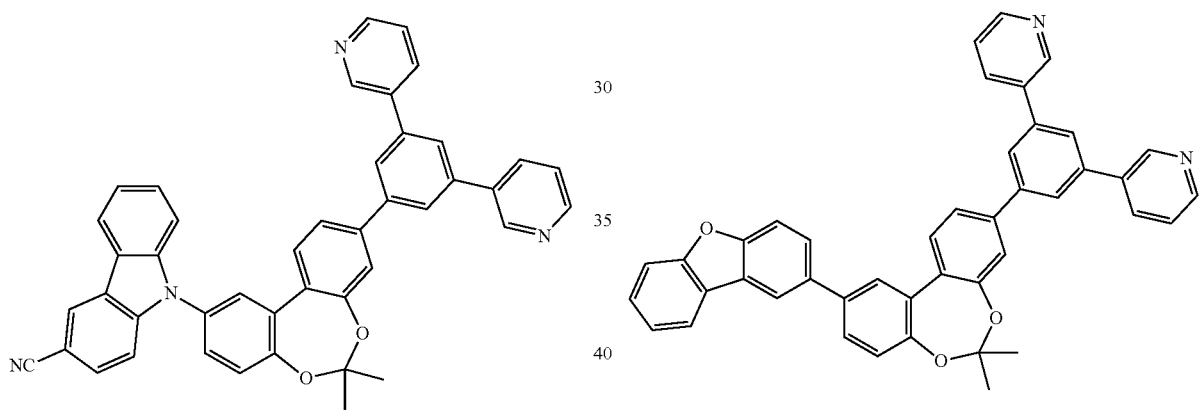
575
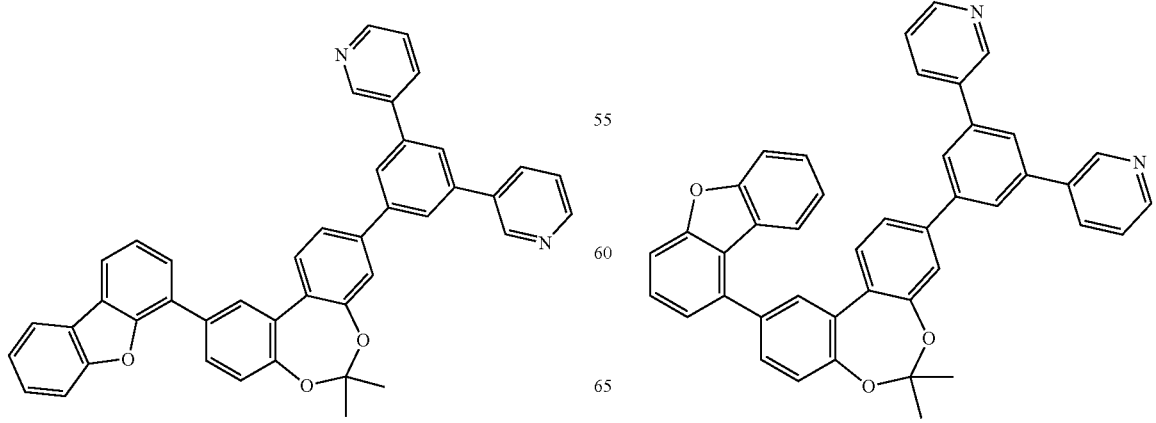
186
-continued
576
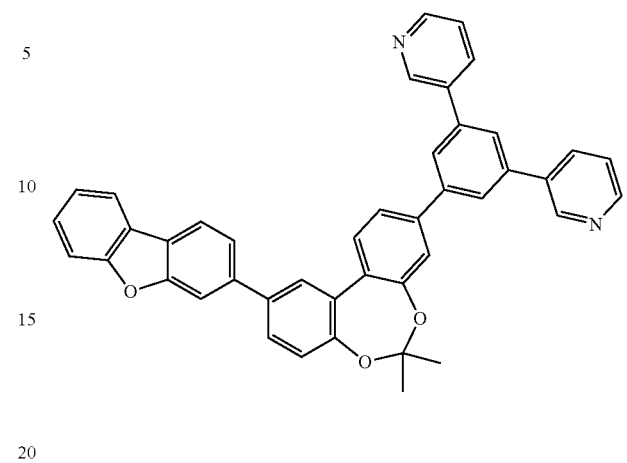
577
578

-continued
579
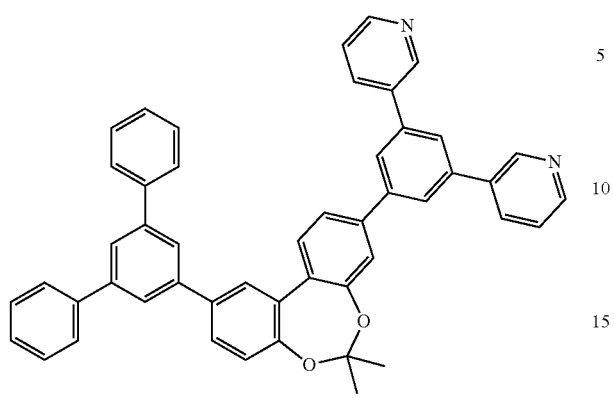
580
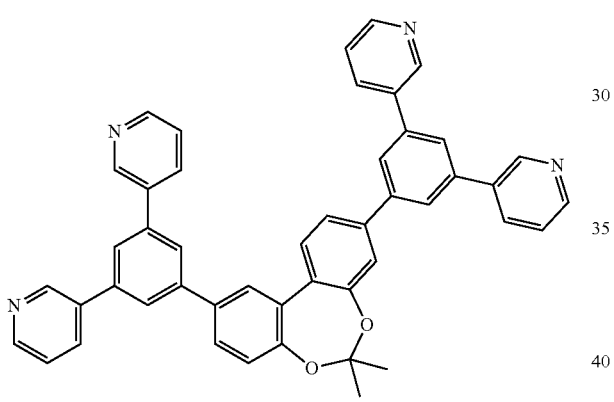
581
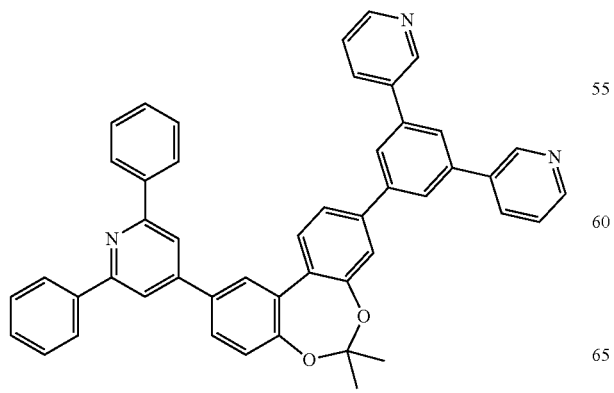
-continued
582
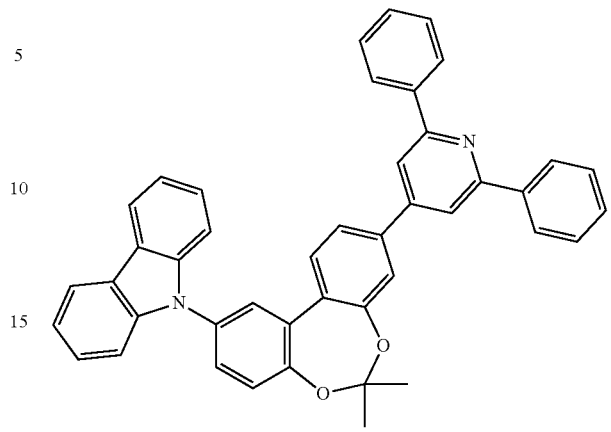
583
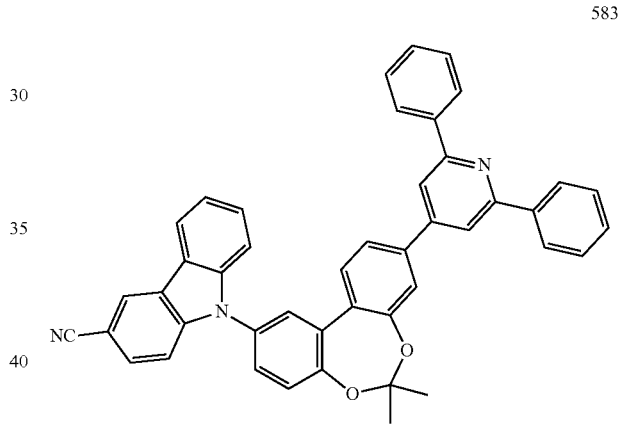
584
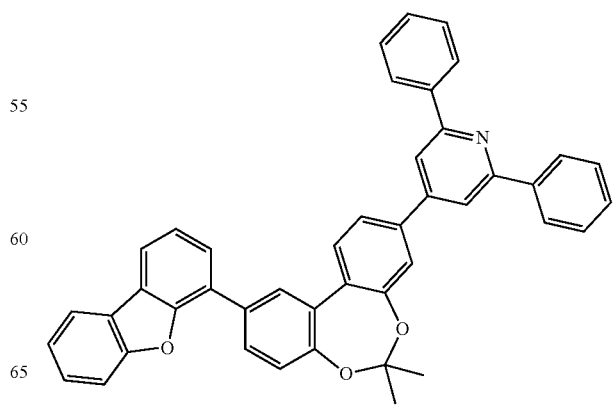

-continued
585
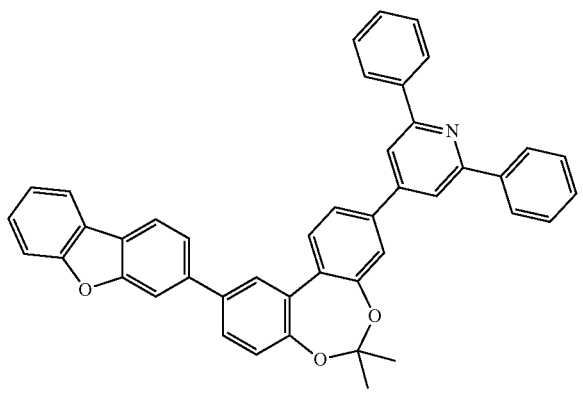
586
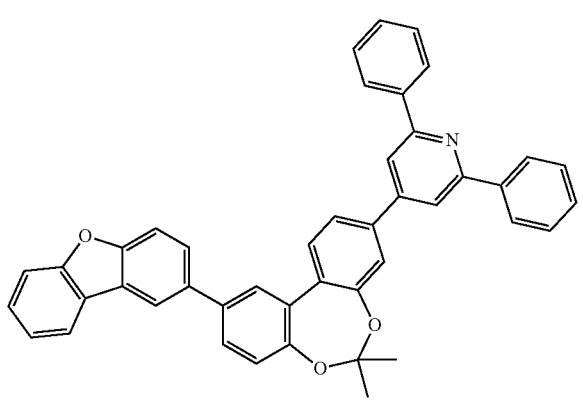
587
588
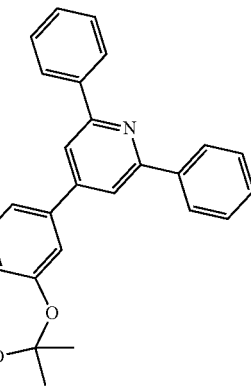
589
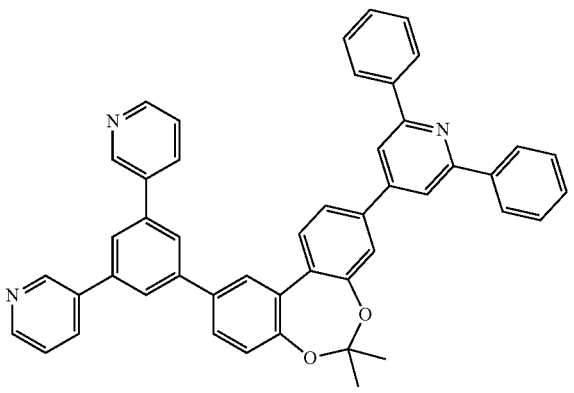
590
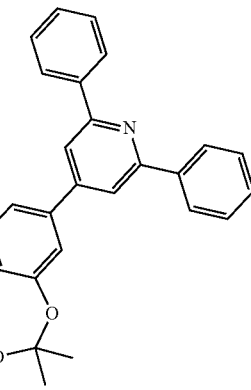
591
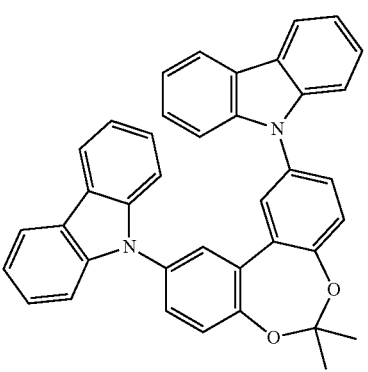

| 592 | 596 |
|---|---|
| 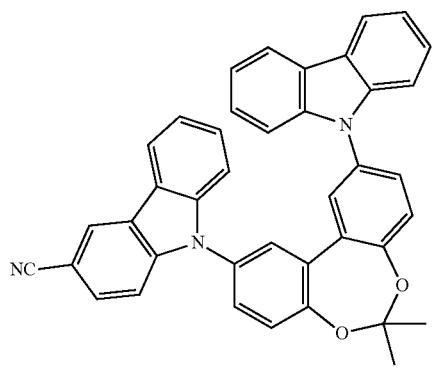 | 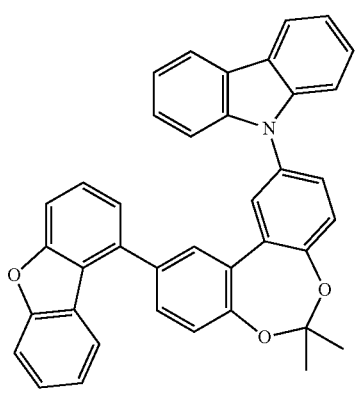 |
| 593 | 597 |
|---|---|
| 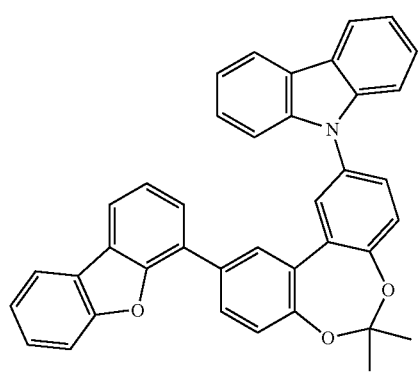 | 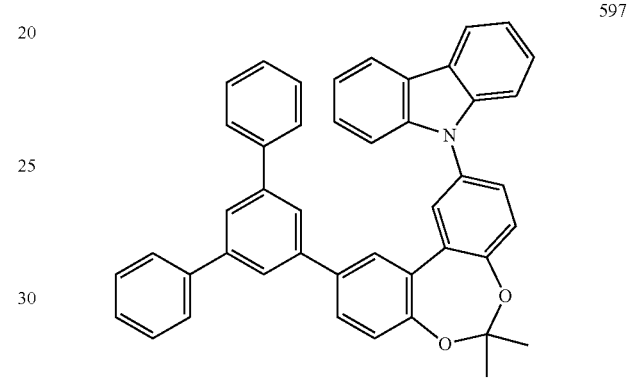 |
| 594 | 598 |
|---|---|
| 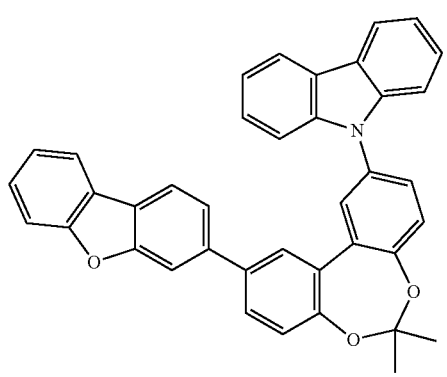 | 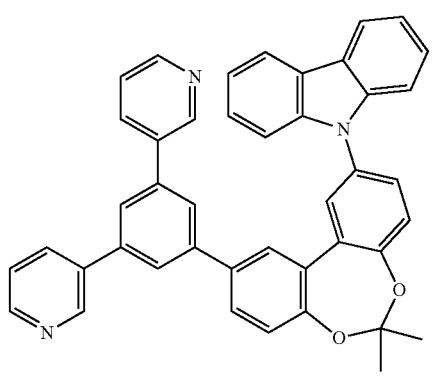 |
| 595 | 599 |
|---|---|
| 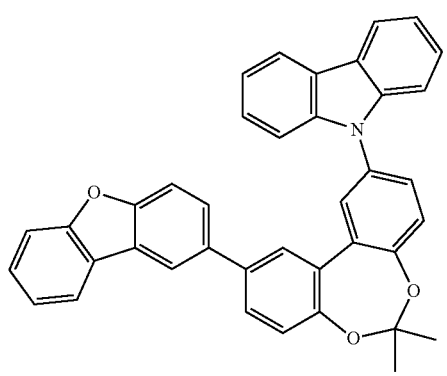 | 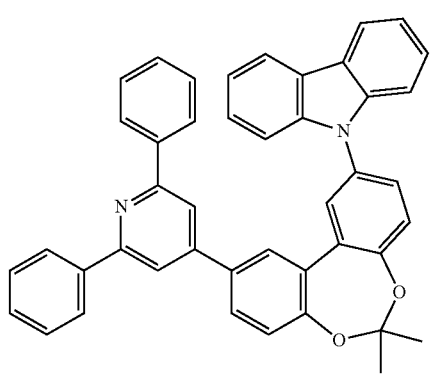 |

600
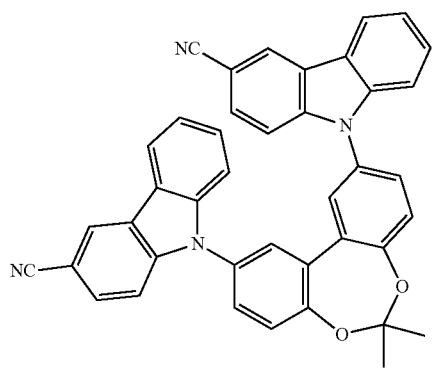
601
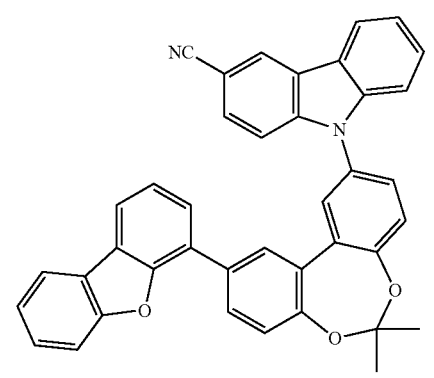
602
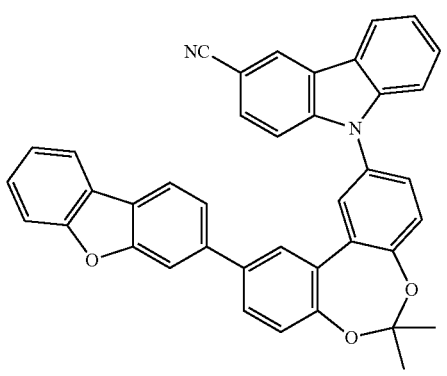
603
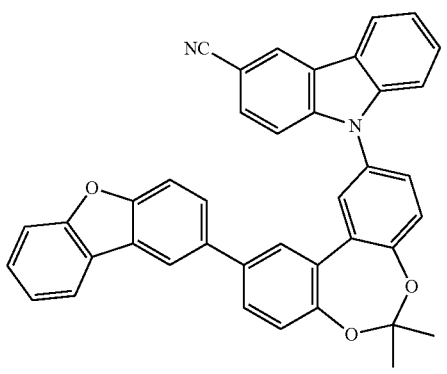
604
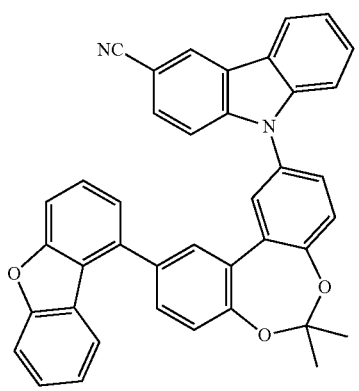
605
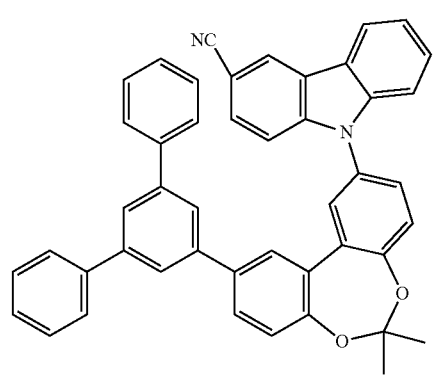
606
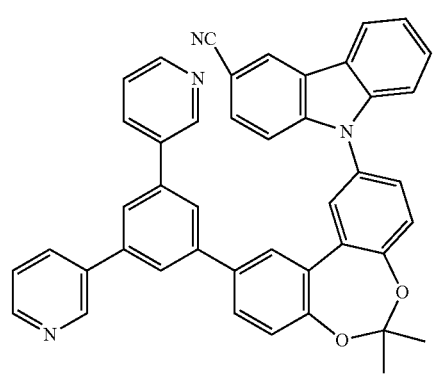
607
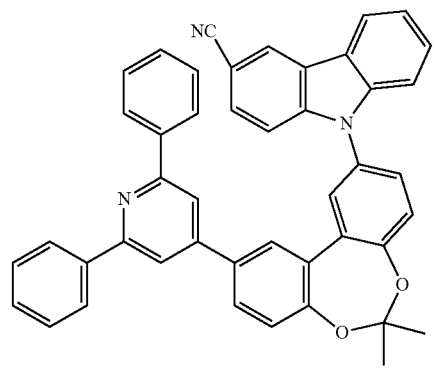

608
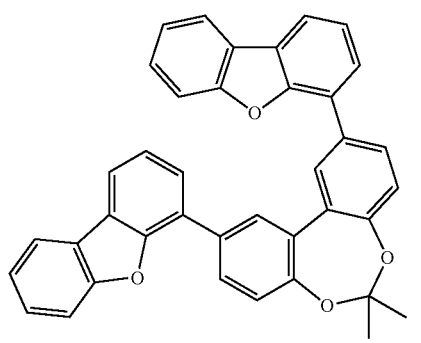
609
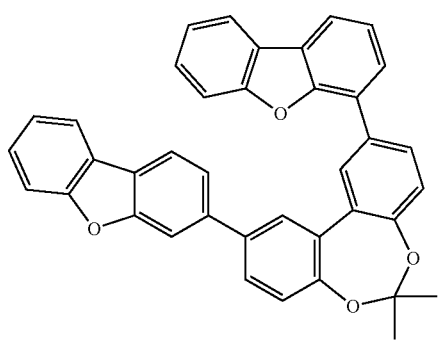
610
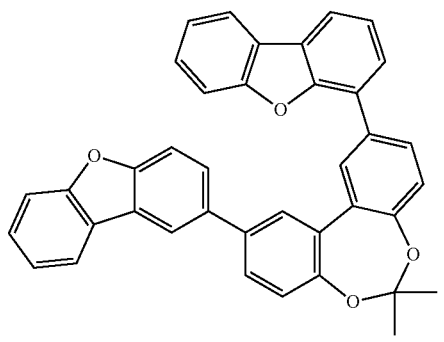
611
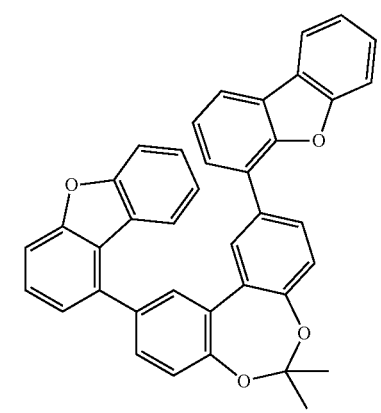
612
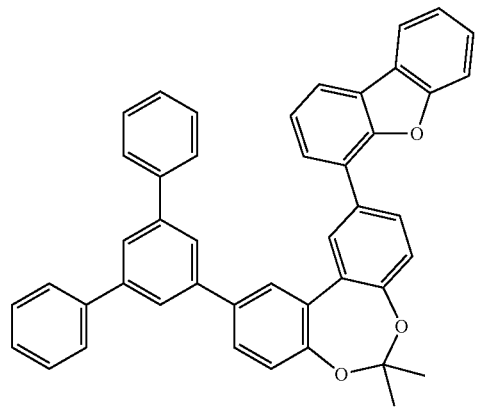
613
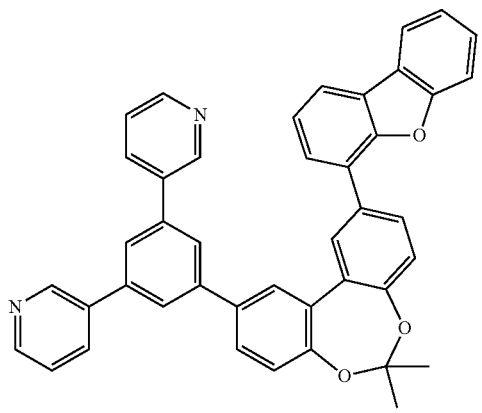
614
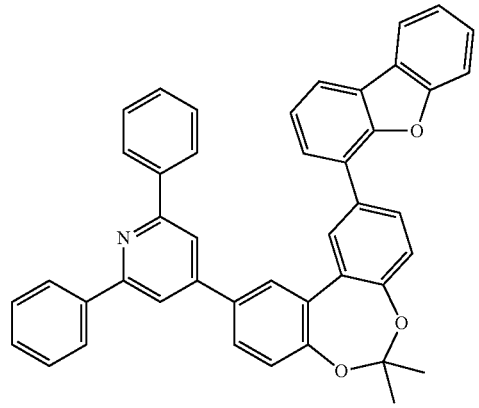

197
-continued
198
-continued
615
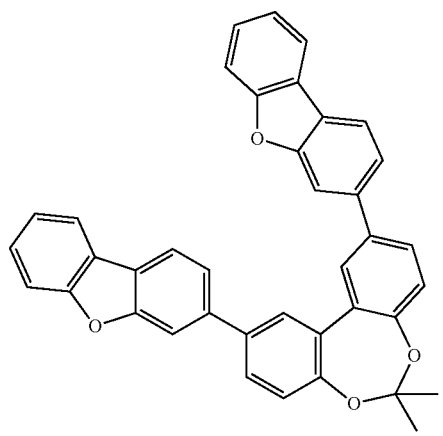
618
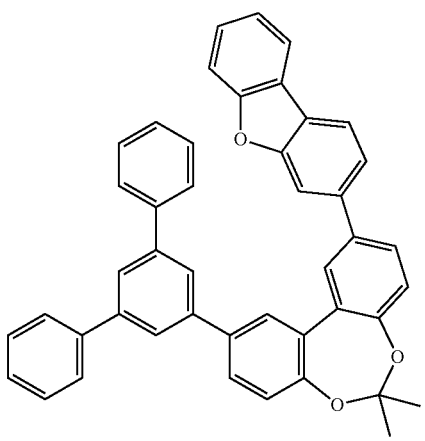
616
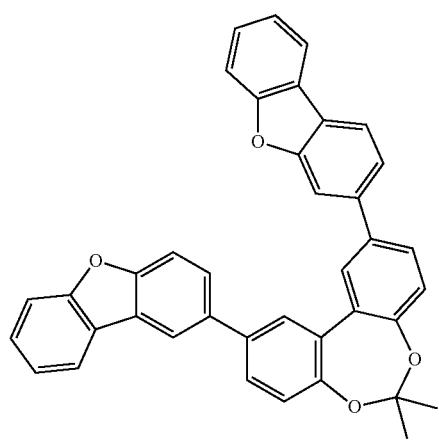
619
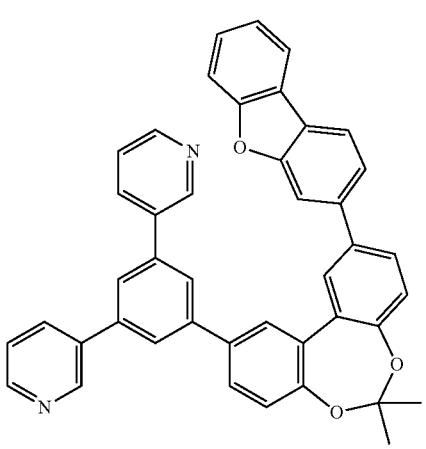
617
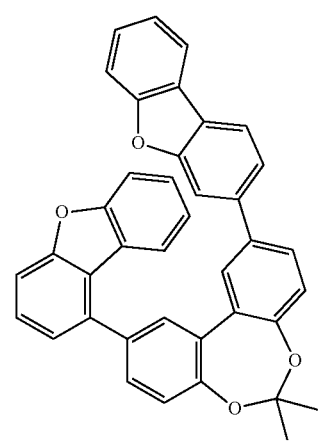
620
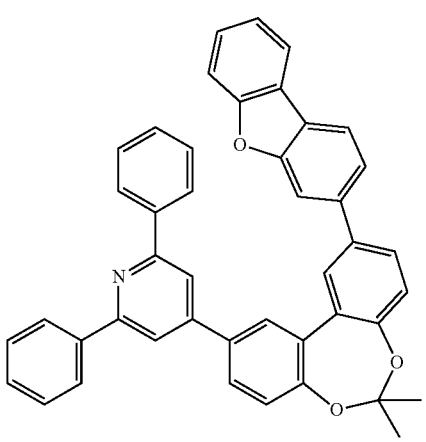

199
-continued
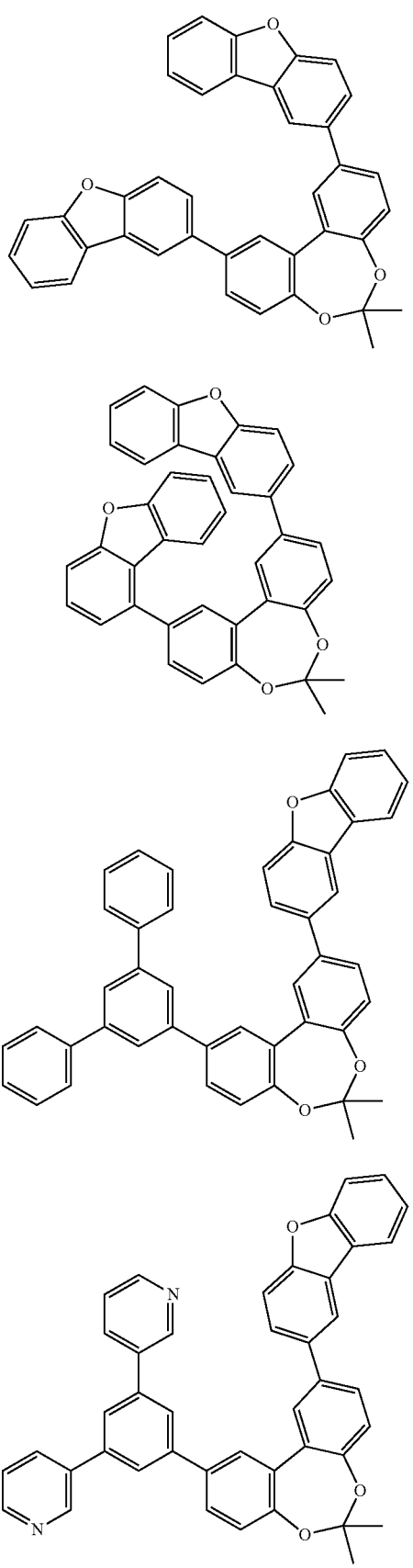
200
-continued
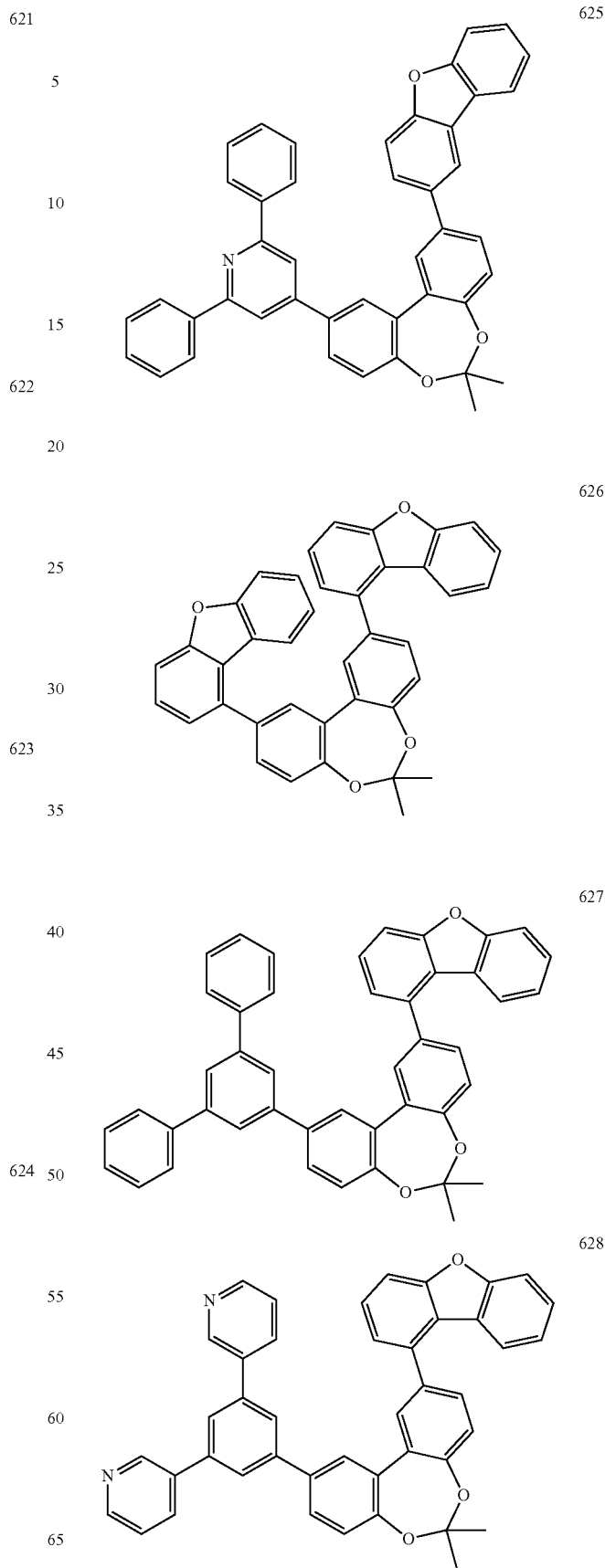

201
-continued
629
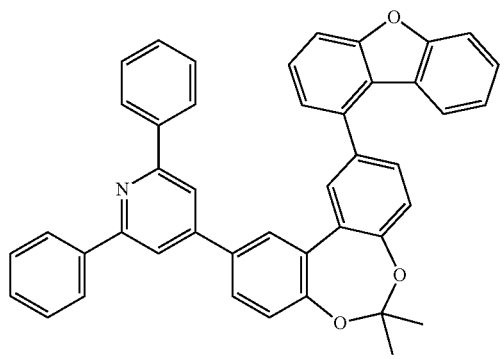
630
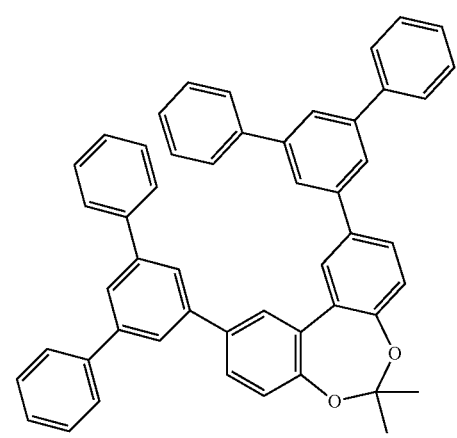
631
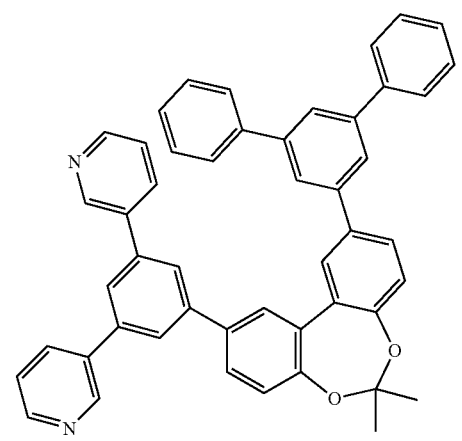
632
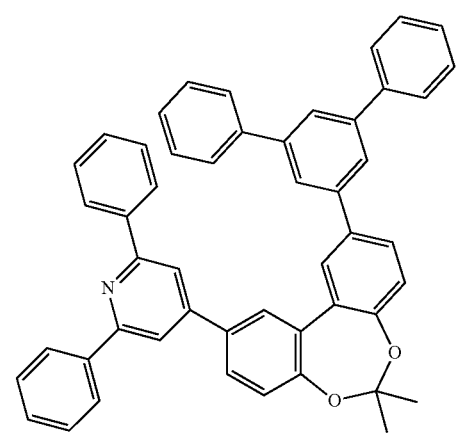
202
-continued
633
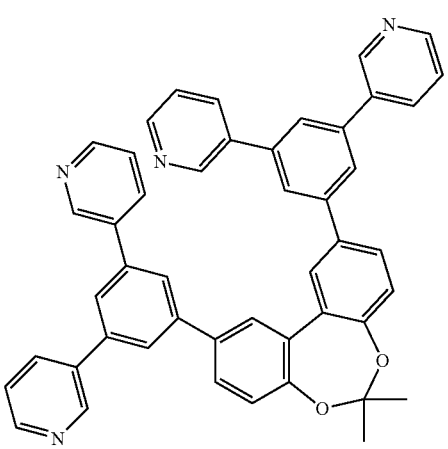
634
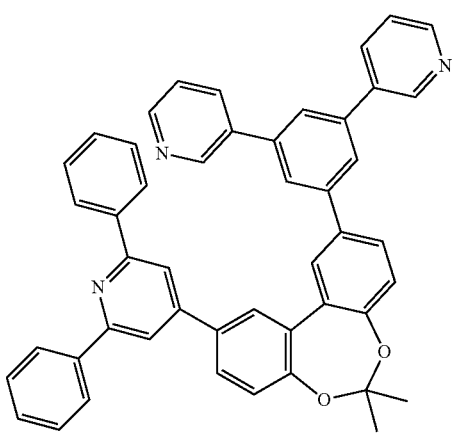
635
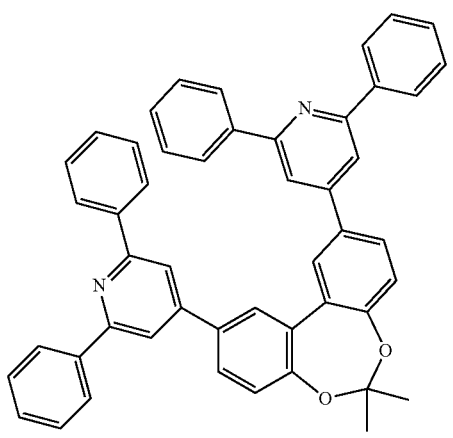

203
-continued
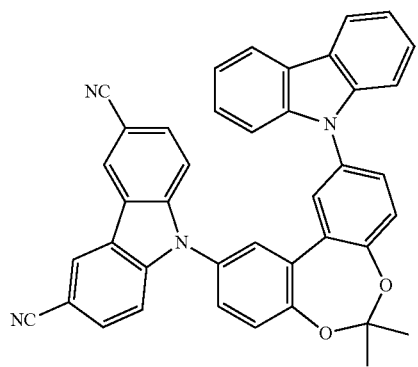
636
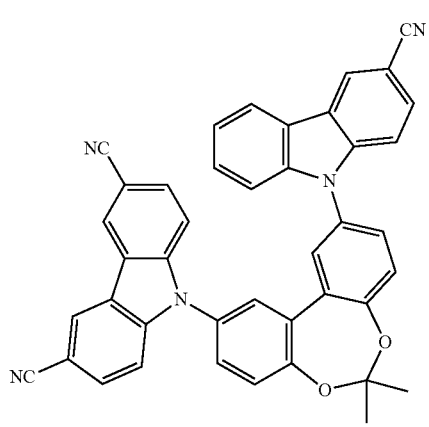
637
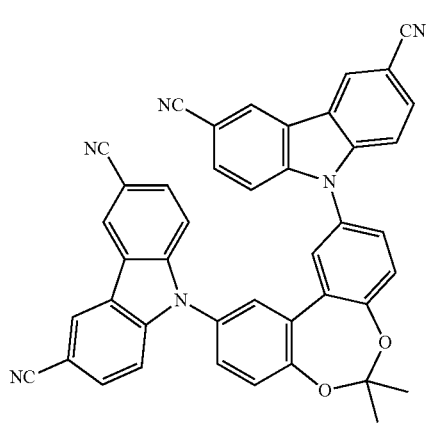
638
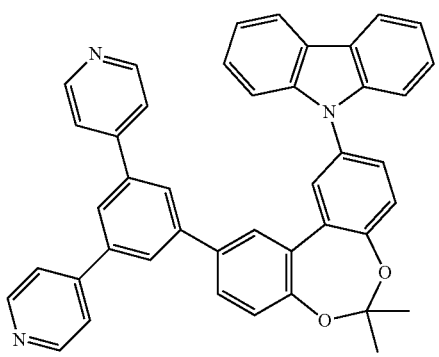
639
204
-continued
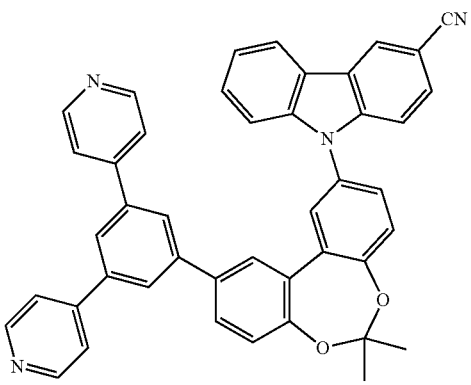
640
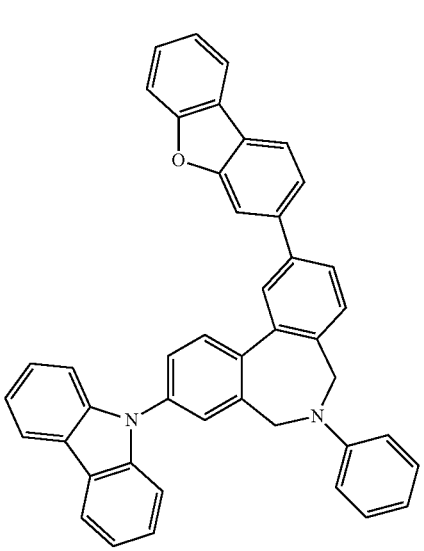
641
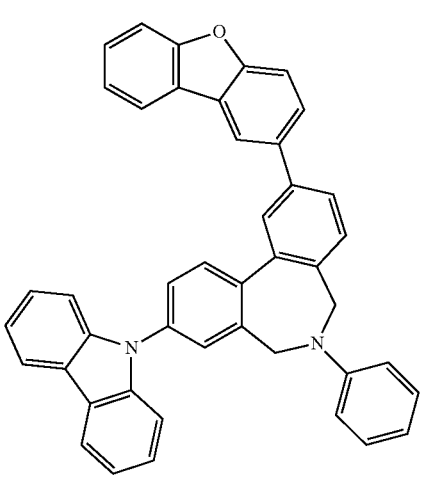
642

205
-continued
643
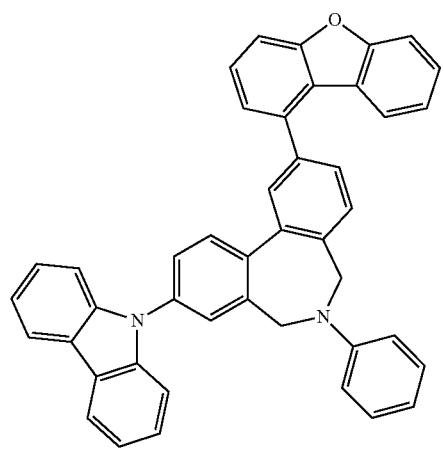
644
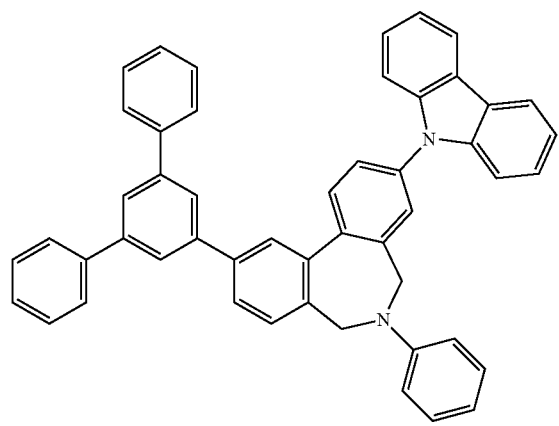
645
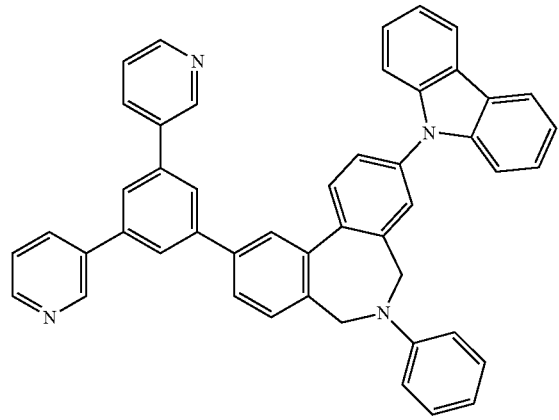
206
-continued
646
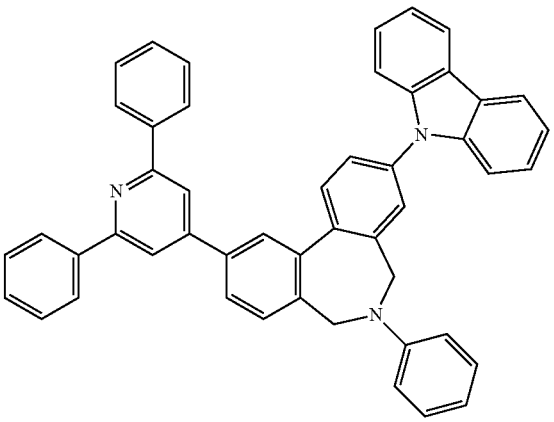
647
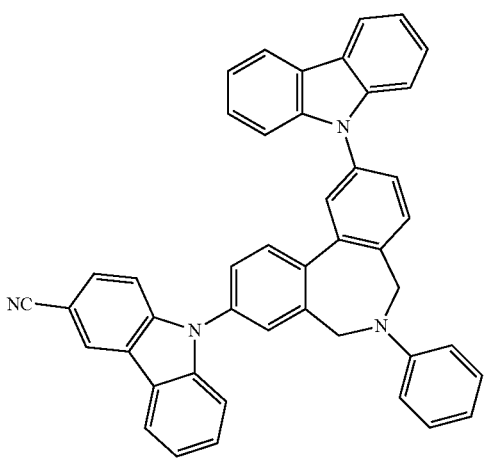
648
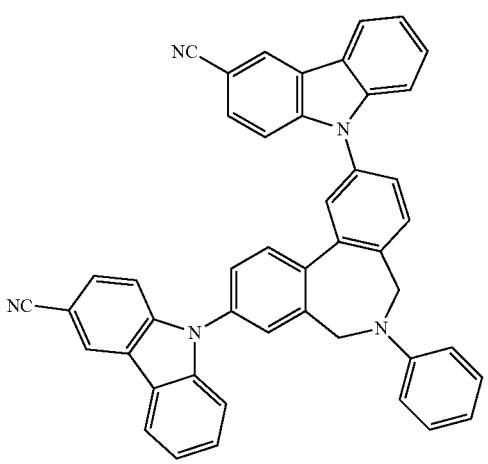

207
-continued
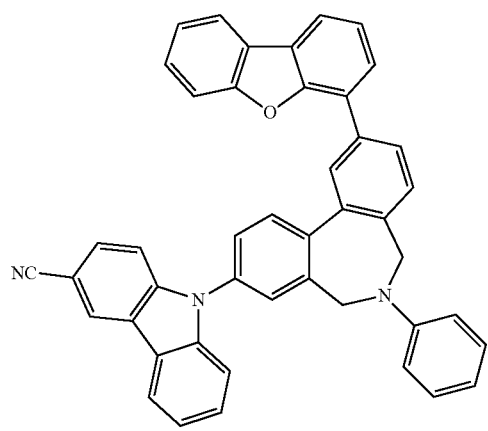
649
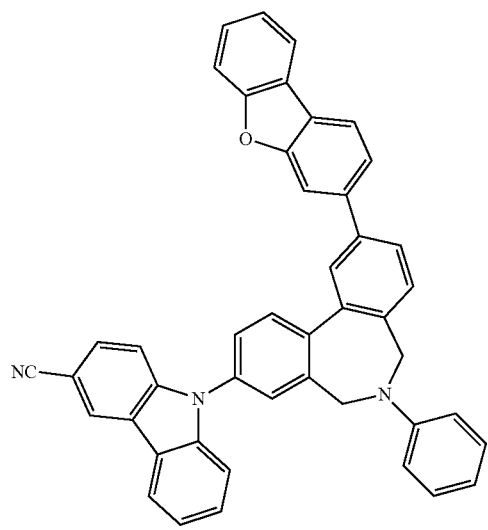
650
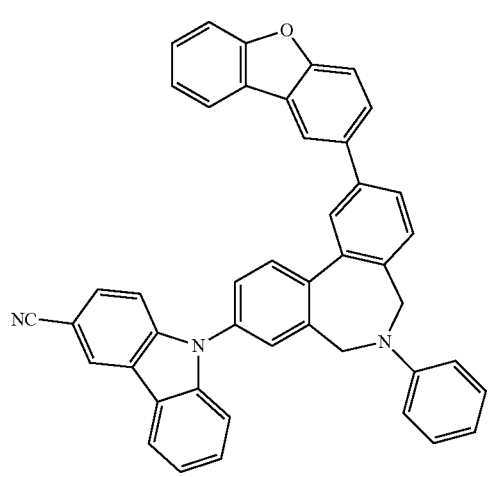
651
208
-continued
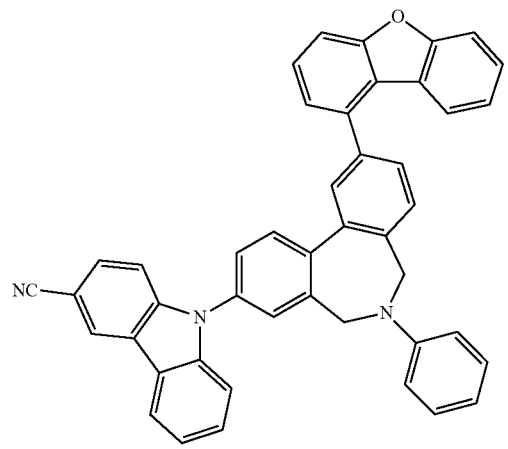
652
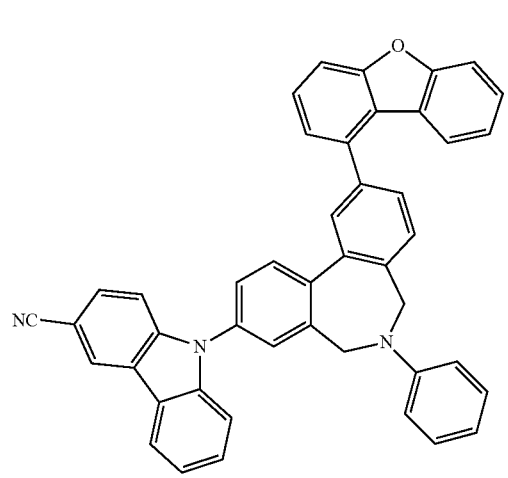
653
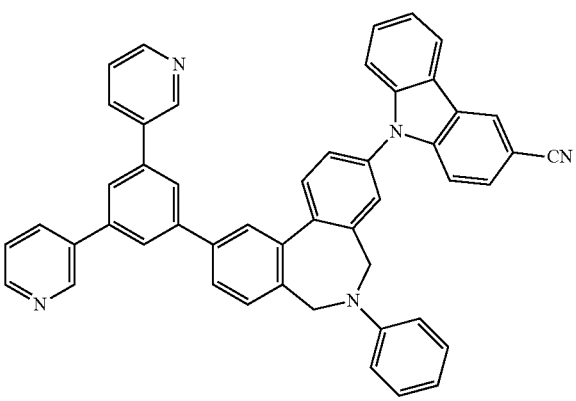
654

| 209 -continued | 210 -continued |
|---|---|
| 655 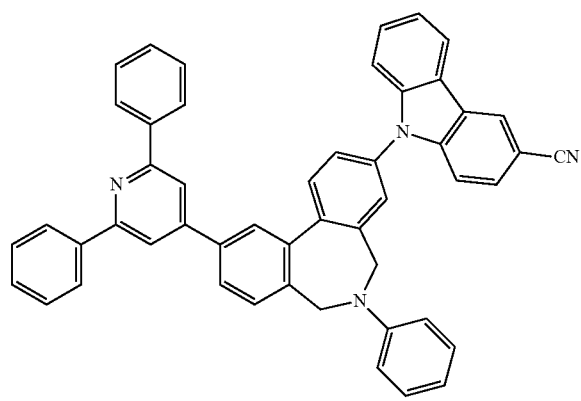 | 658 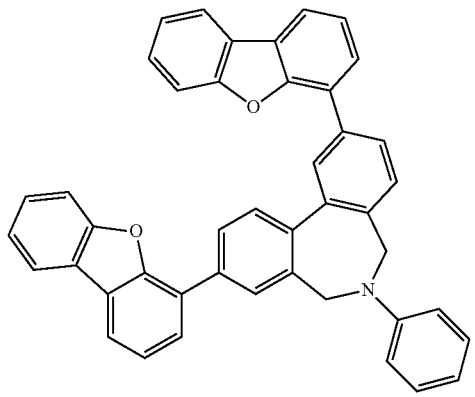 |
| 656 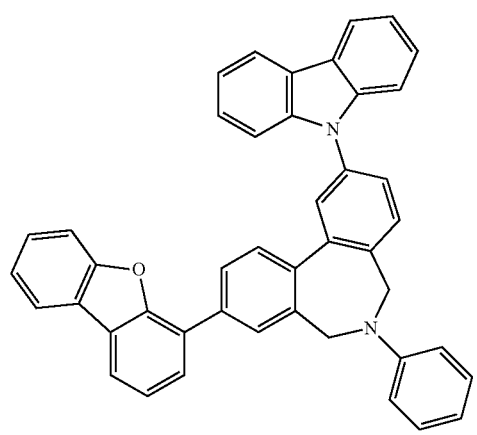 | 659 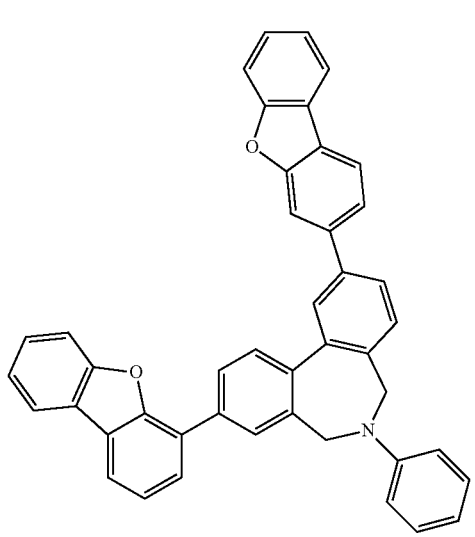 |
| 657 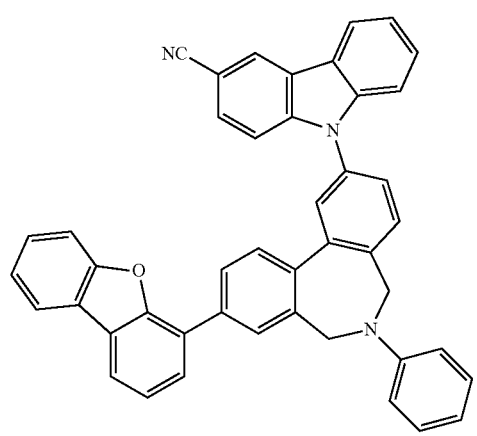 | 660 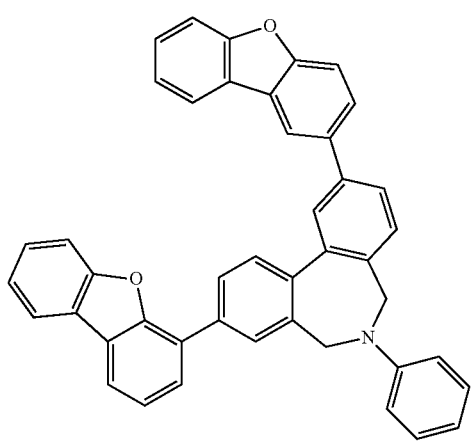 |

211
-continued
661
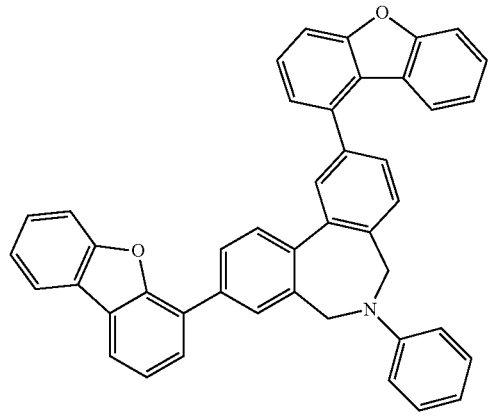
662
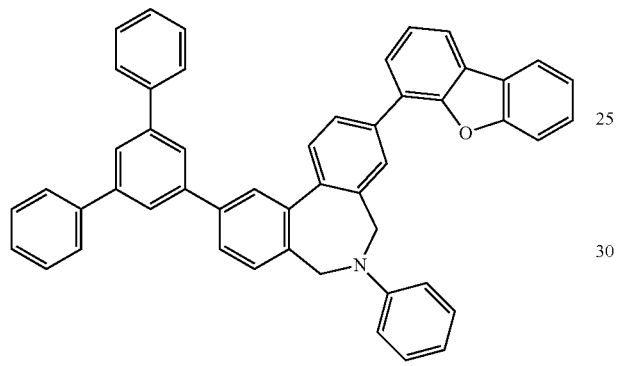
663
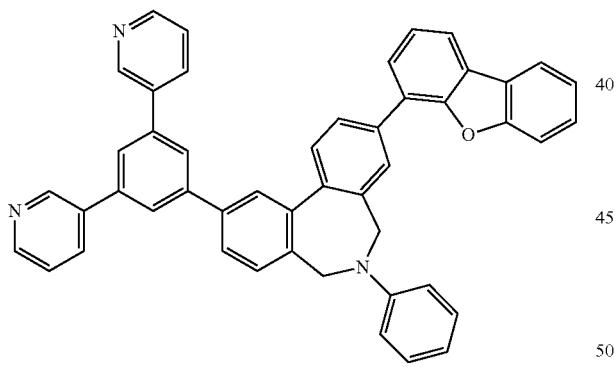
664
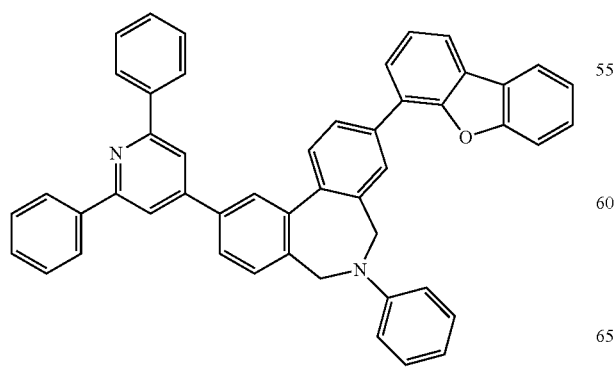
212
-continued
665
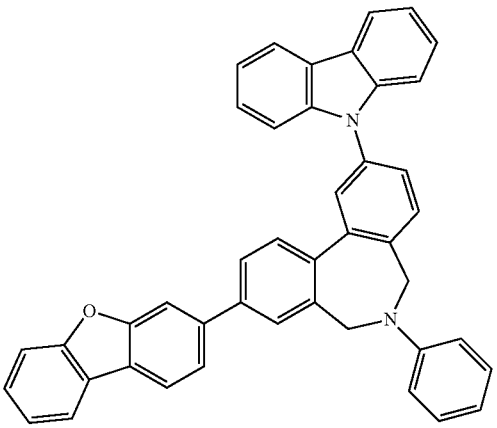
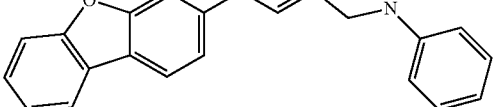
666
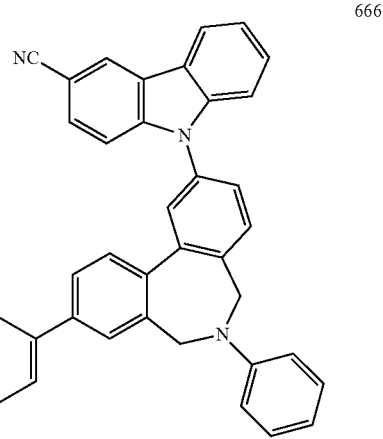
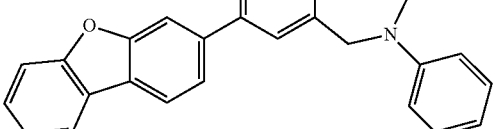
667
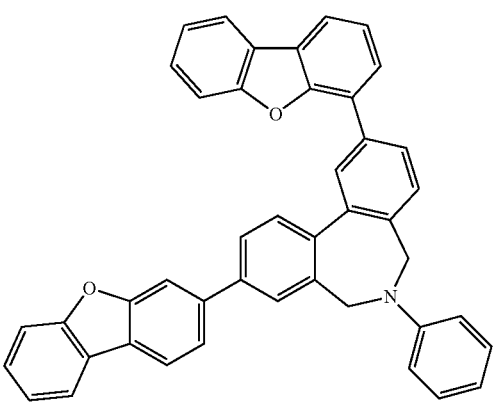

| 213 | 214 |
|---|---|
| 668 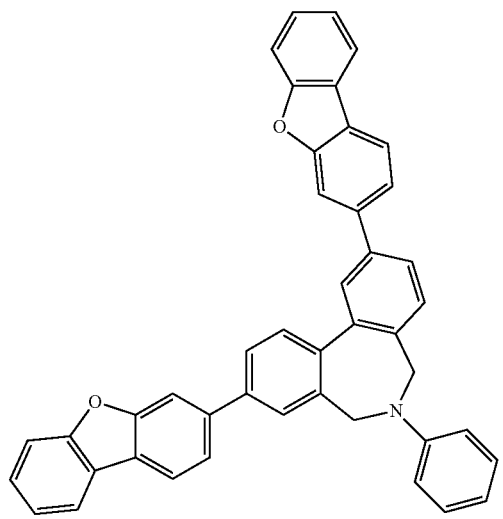 | 671 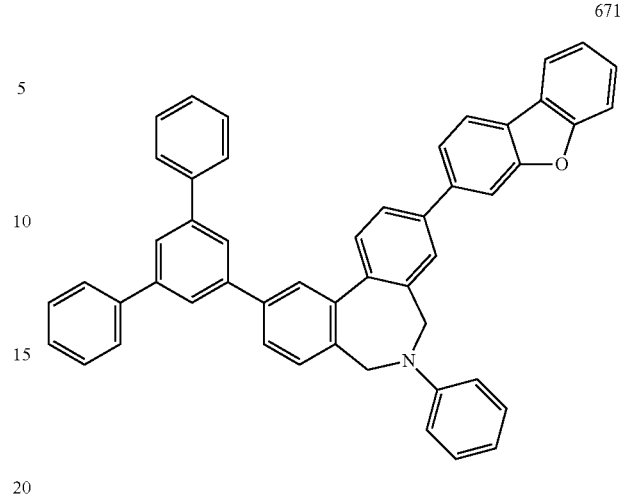 |
| 669 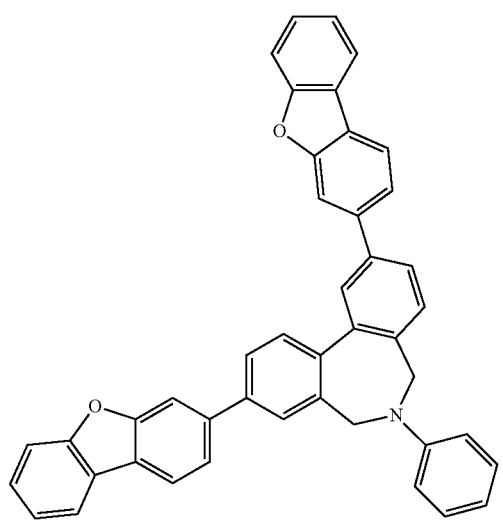 | 672 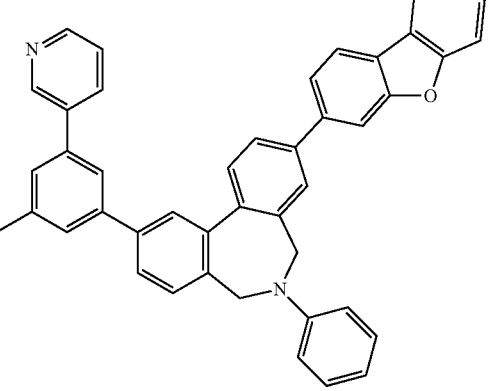 |
| 670 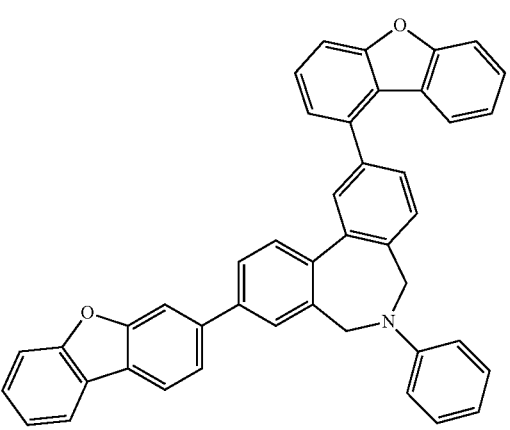 | 673 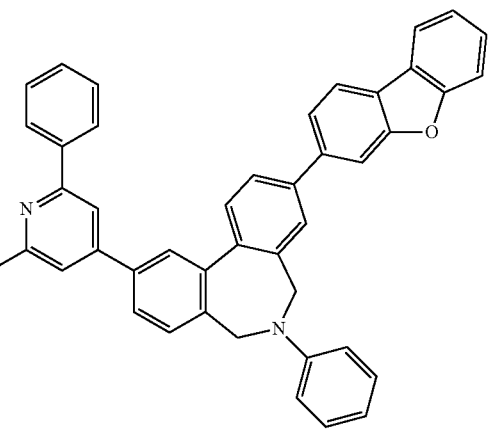 |

215
-continued
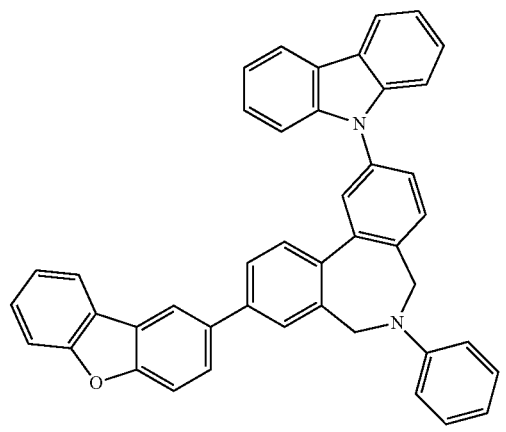
674
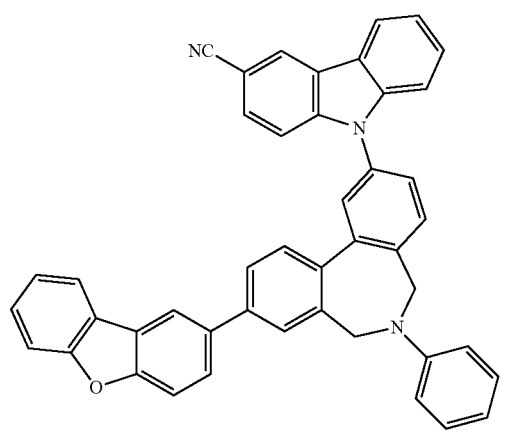
675
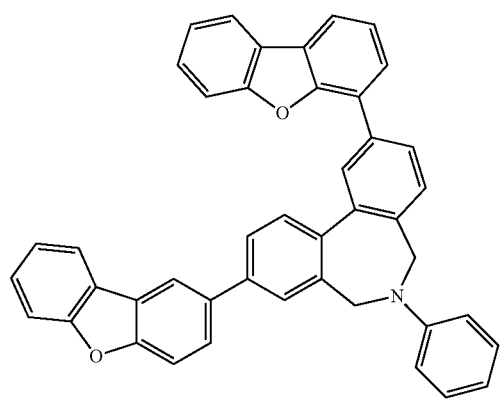
676
216
-continued
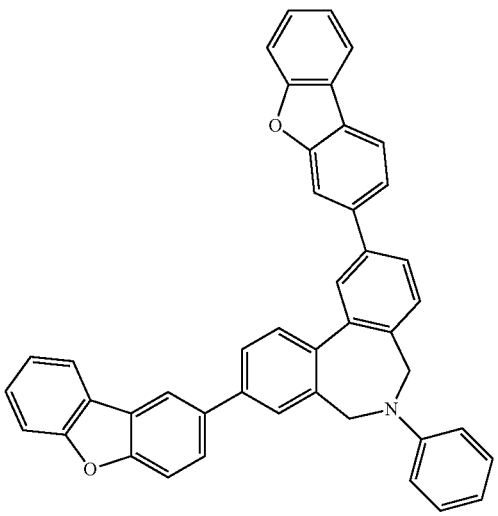
677
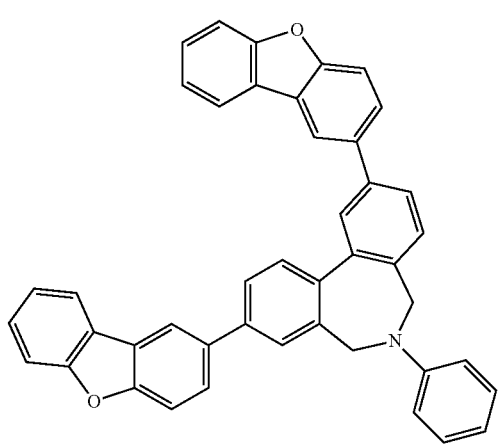
678
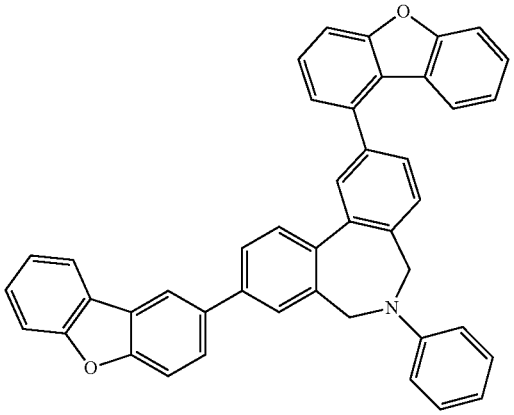
679

217
-continued
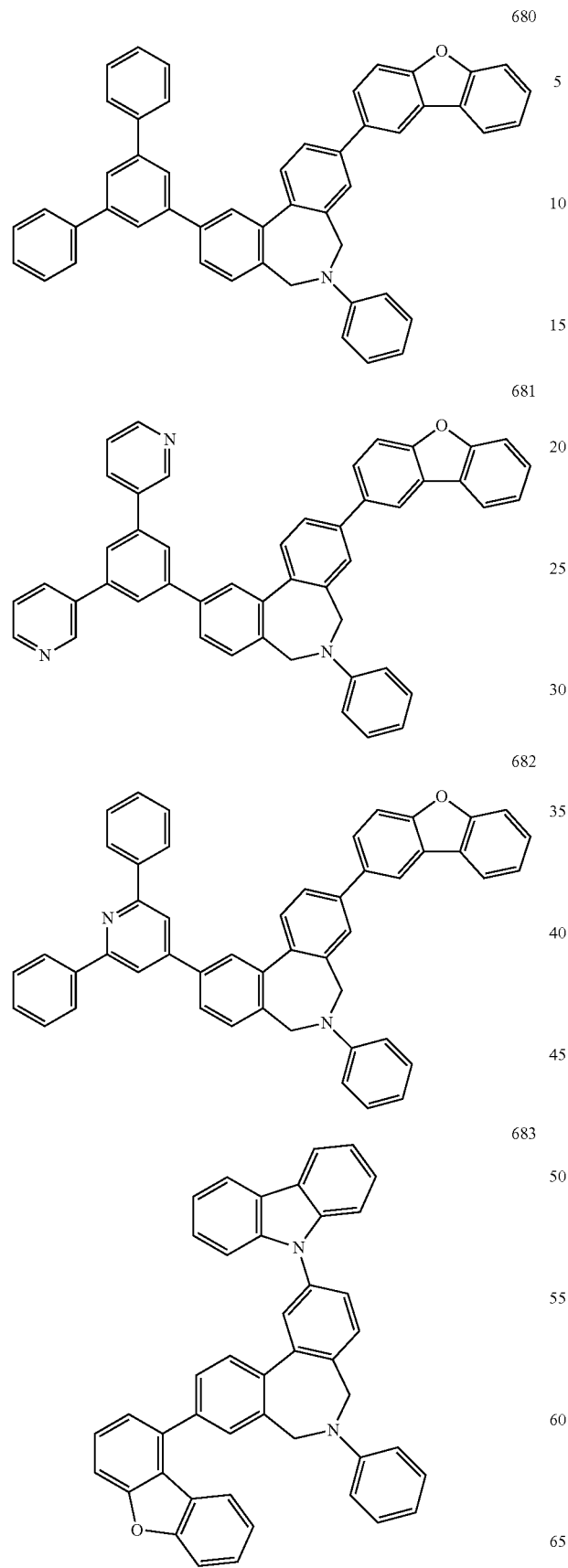
218
-continued
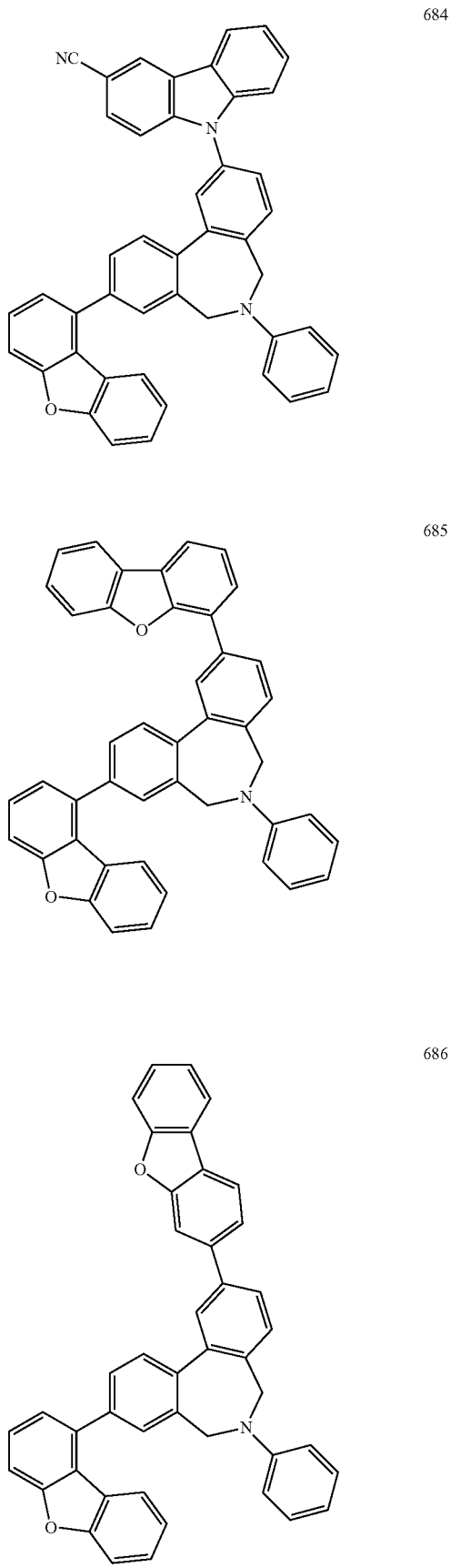

219
-continued
220
-continued
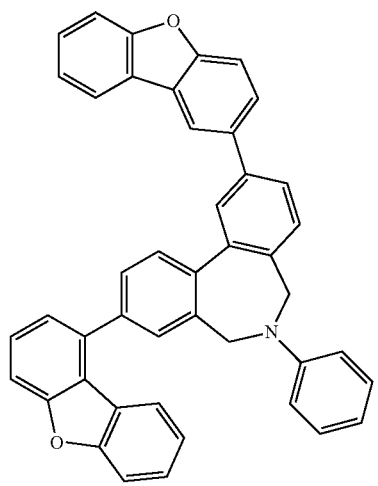
687
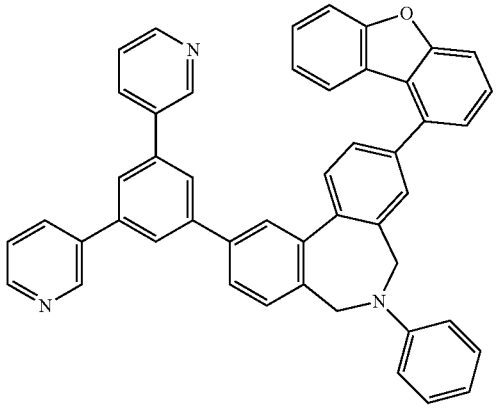
690
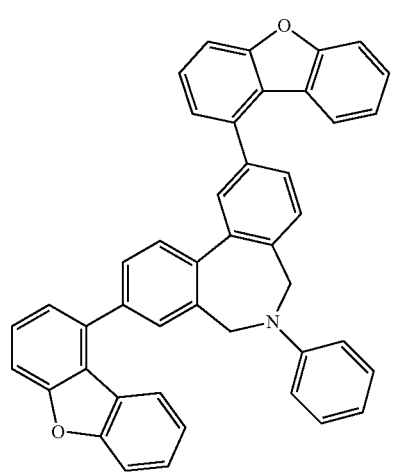
688
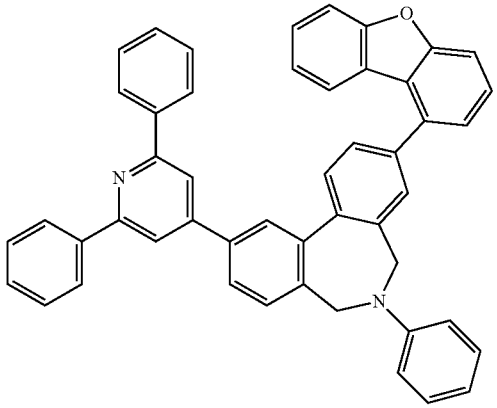
691
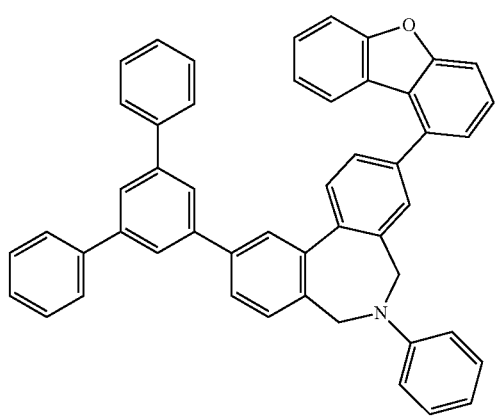
689
692

221
-continued
693
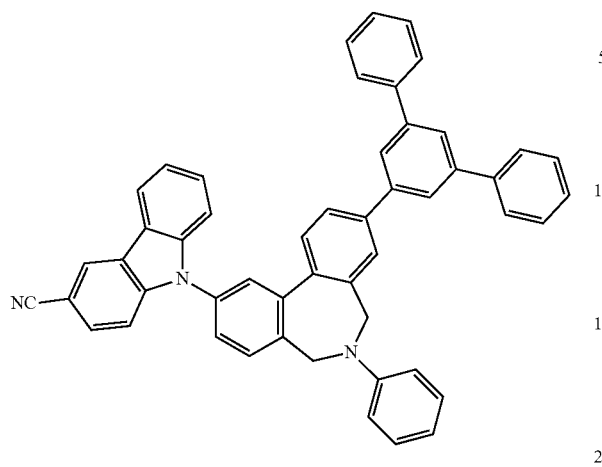
694
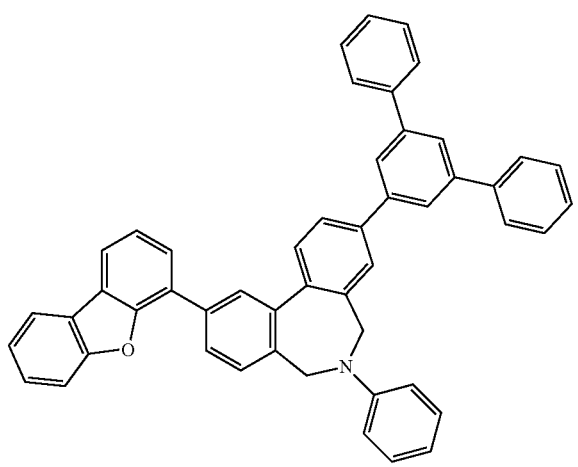
695
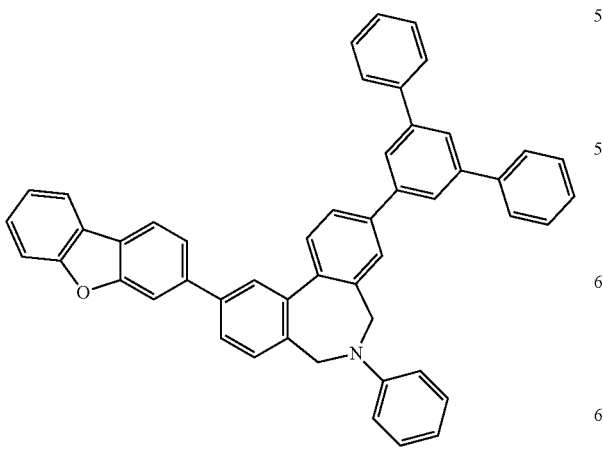
222
-continued
696
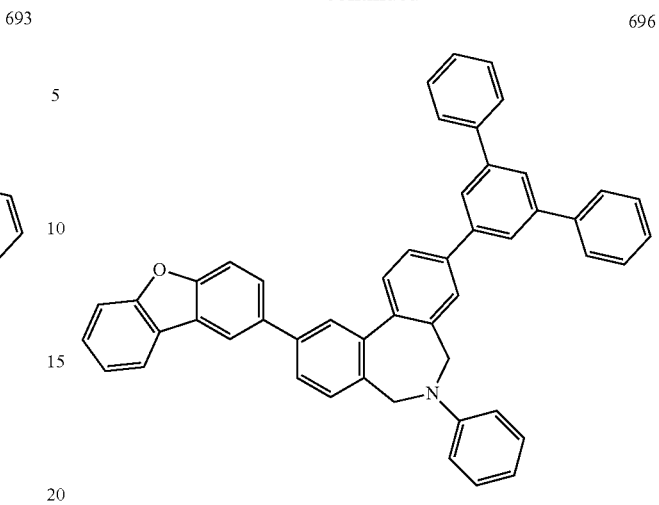
697
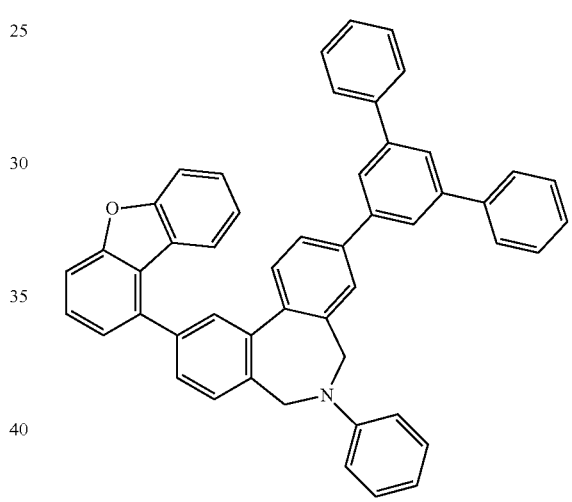
698
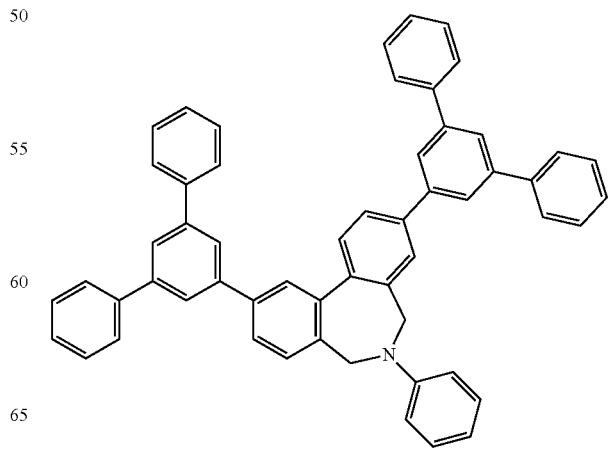

699
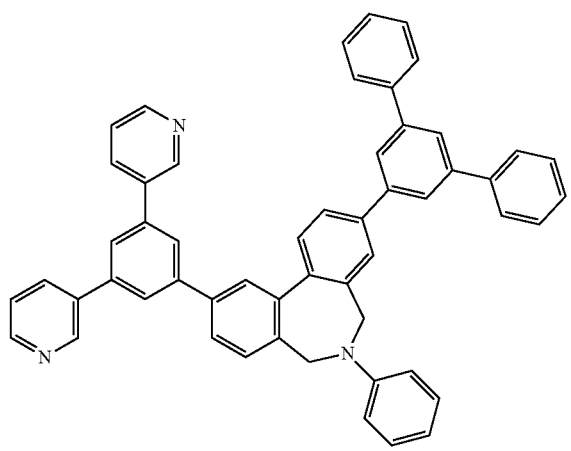
700
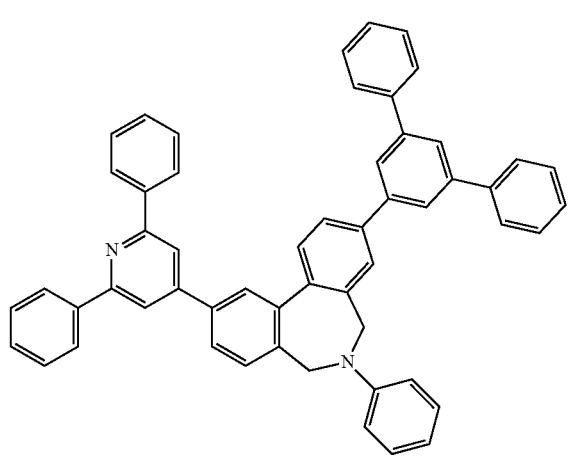
701
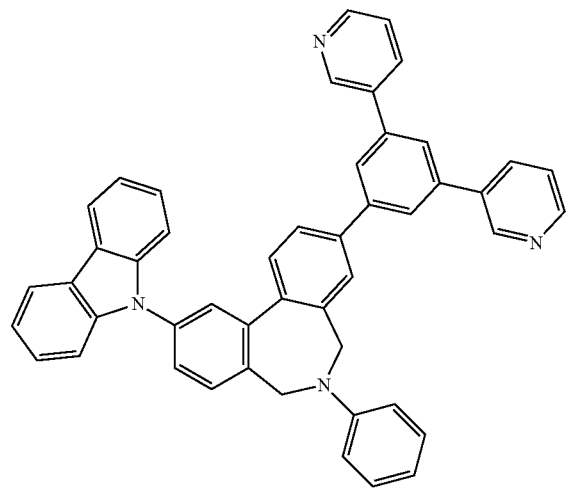
702
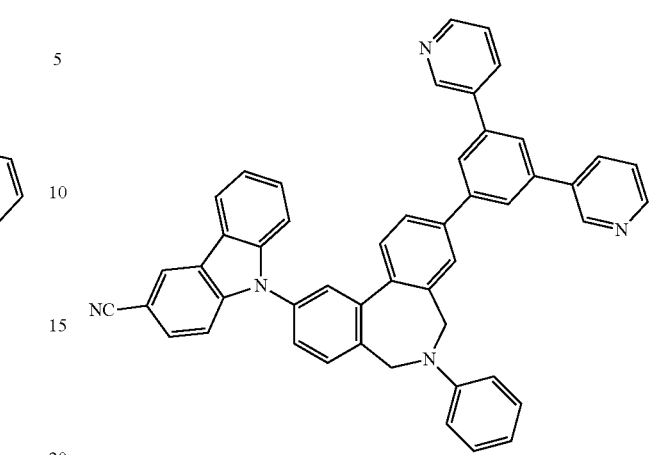
703
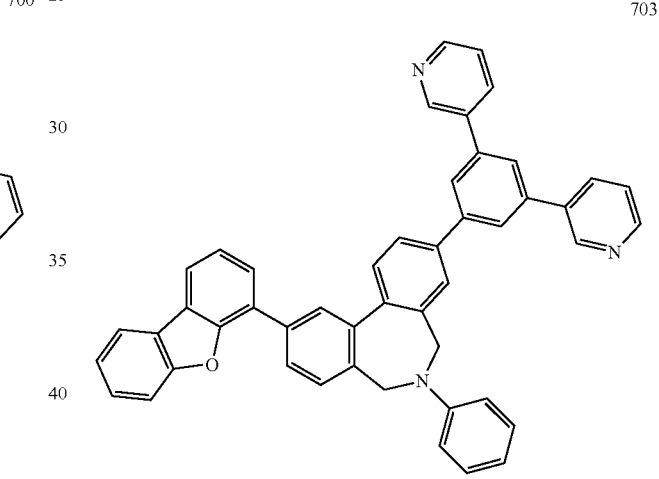
704
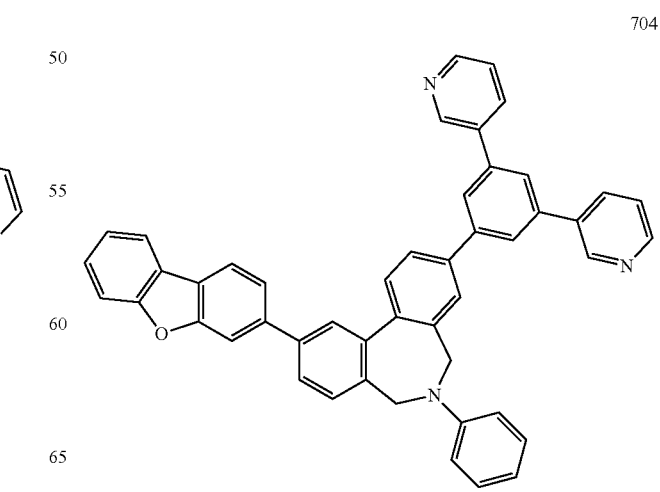

705
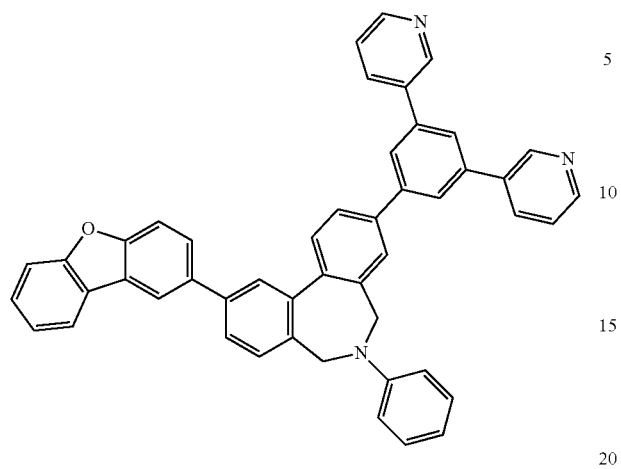
706
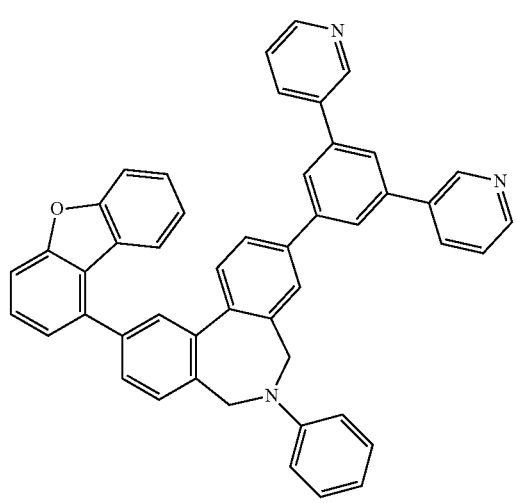
707
708
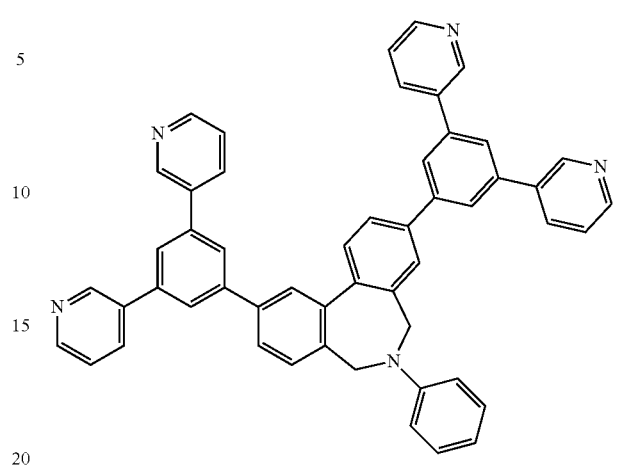
709
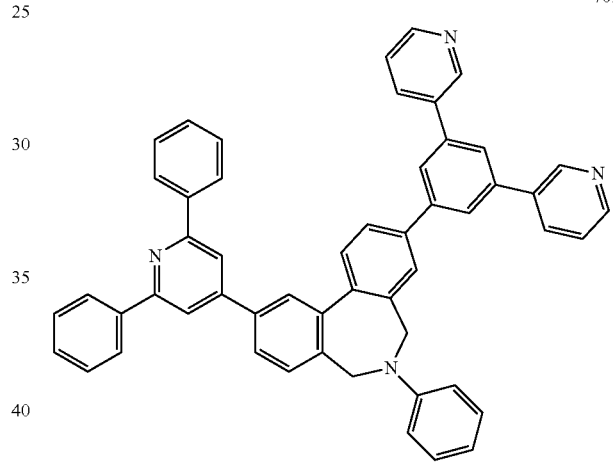
710
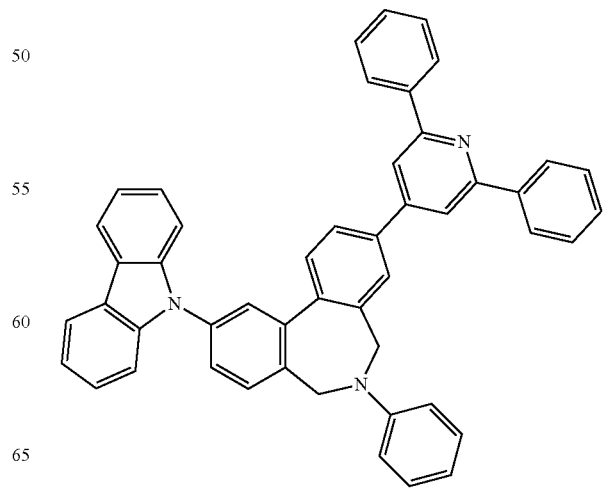

227
-continued
228
-continued
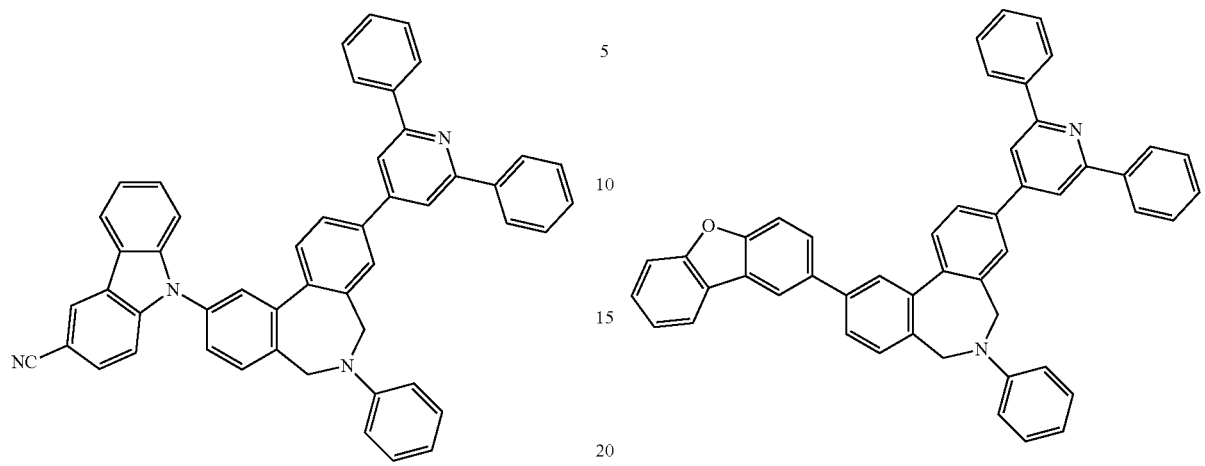
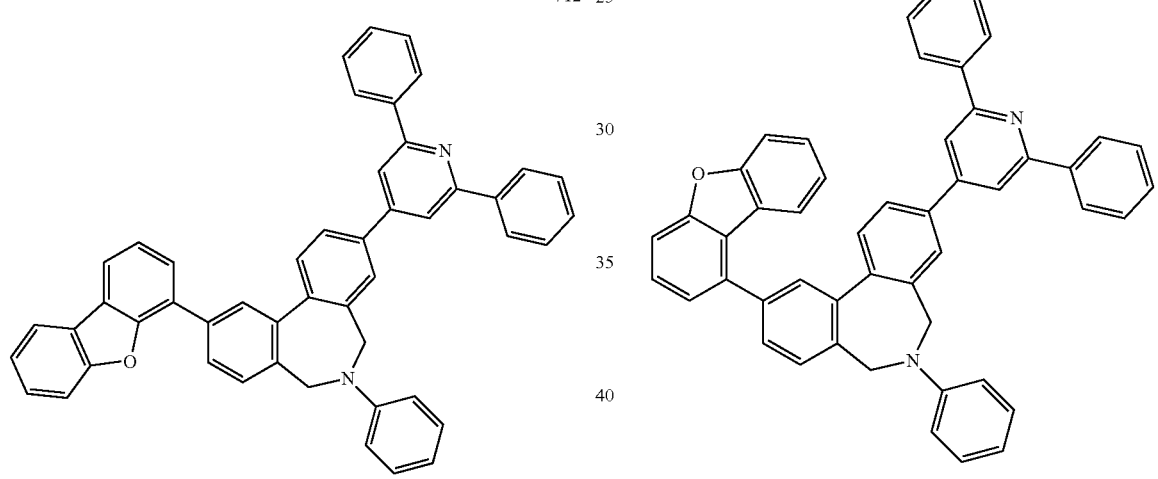
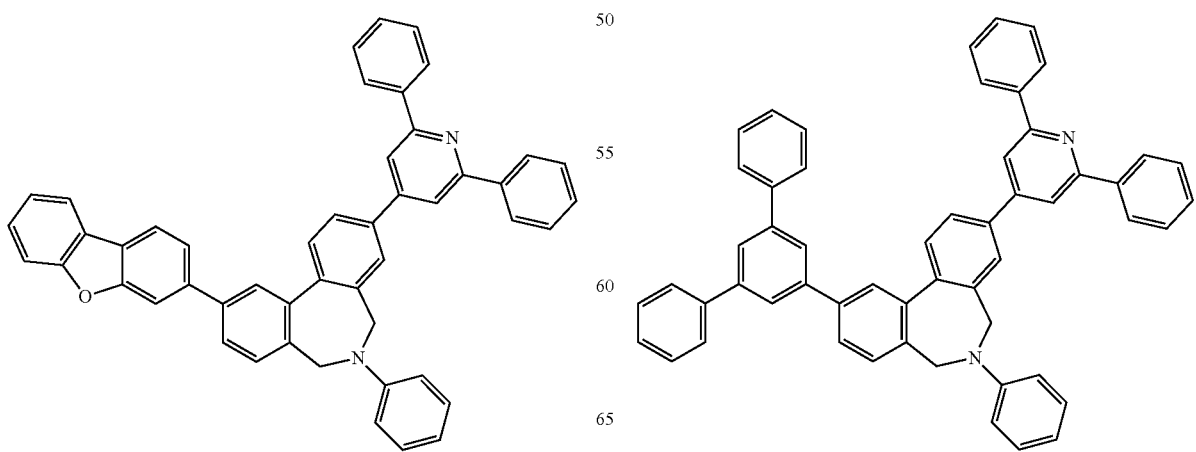

-continued
717
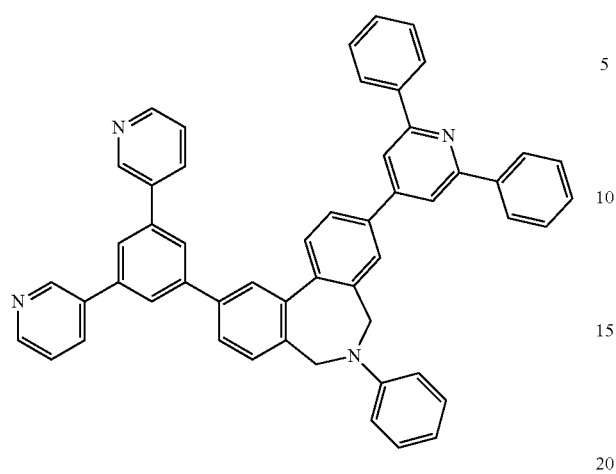
718
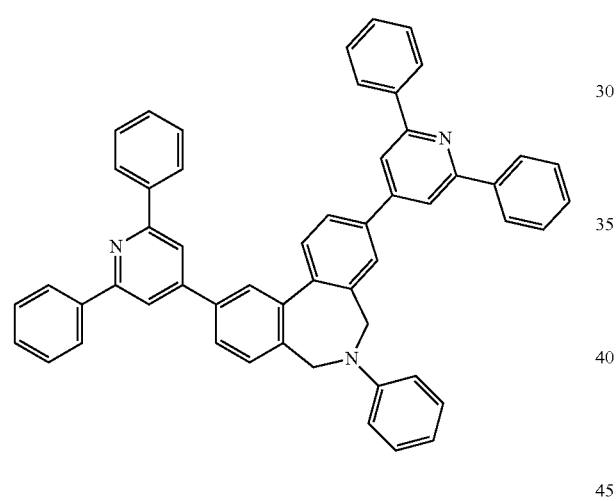
719
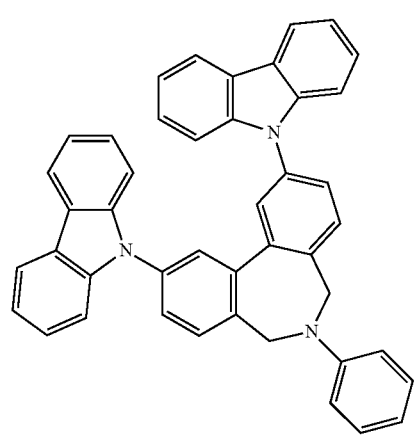
-continued
720
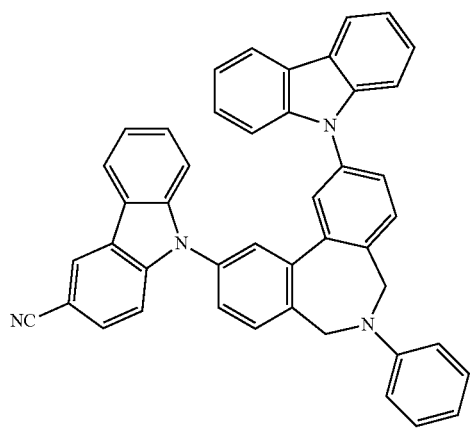
721
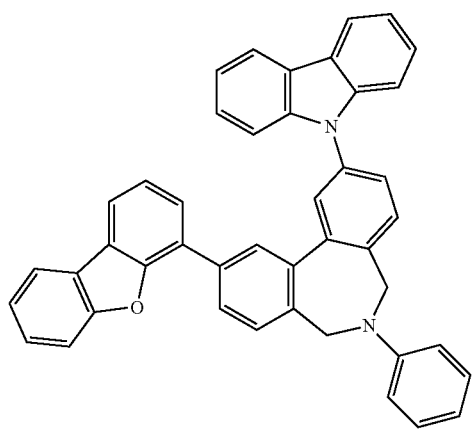
722
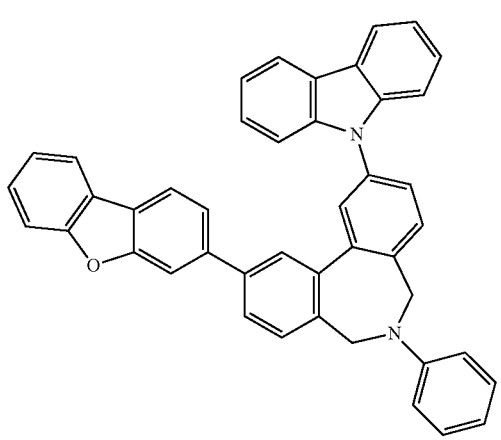

231
-continued
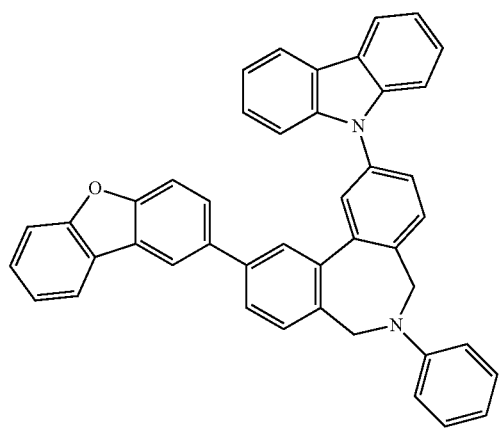
723
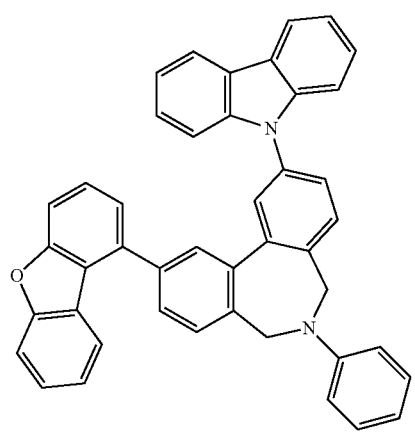
724
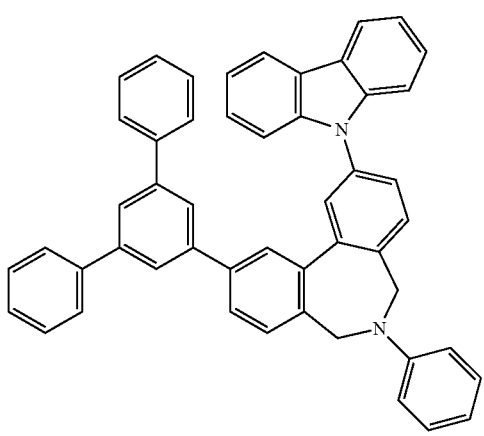
725
232
-continued
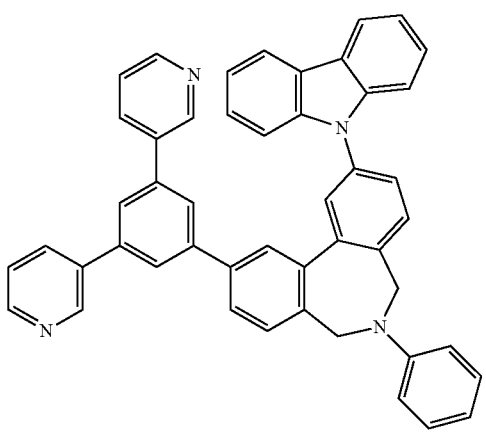
726
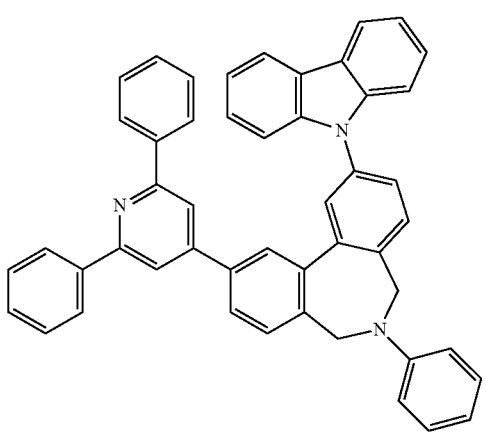
727
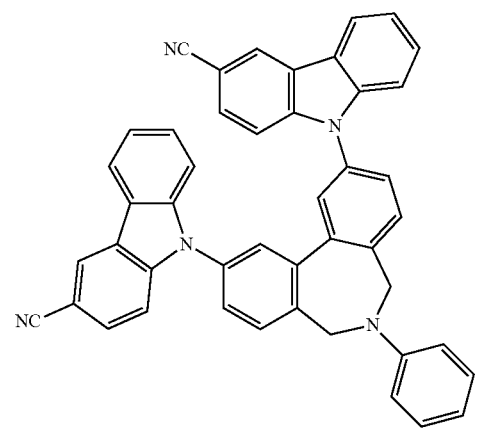
728

233
-continued
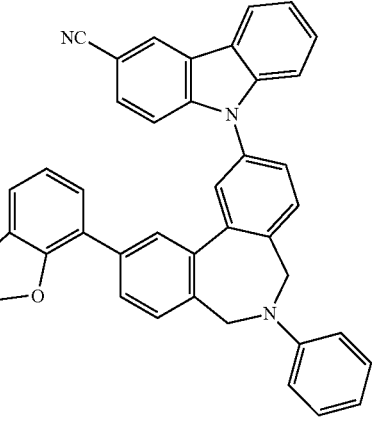
729

730

731
234
-continued
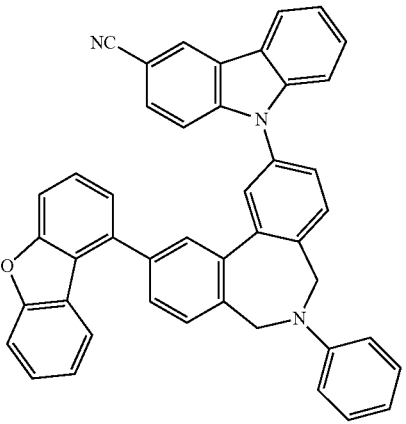
732
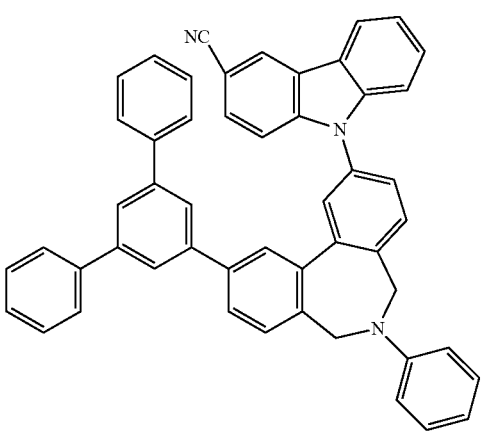
733
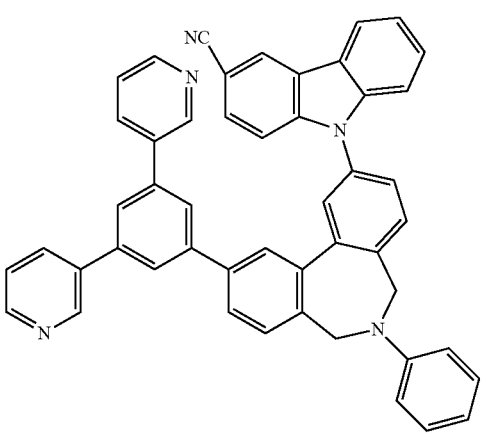
734

-continued
735
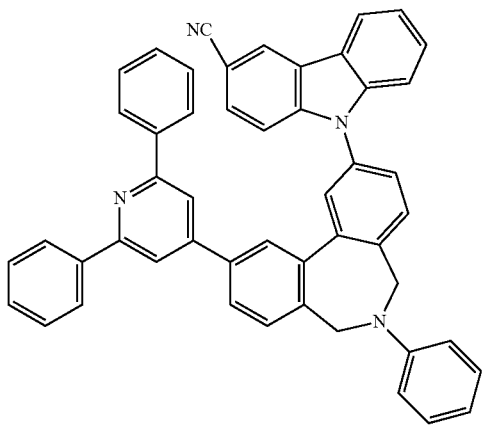
736
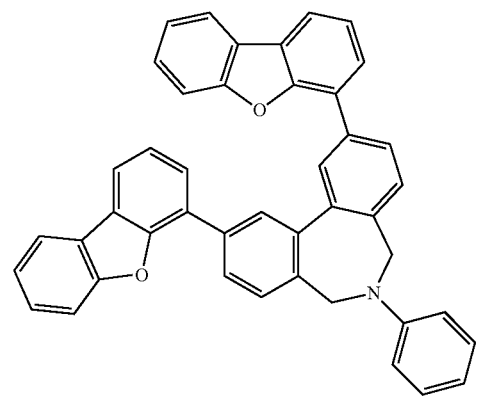
737

738

-continued
739
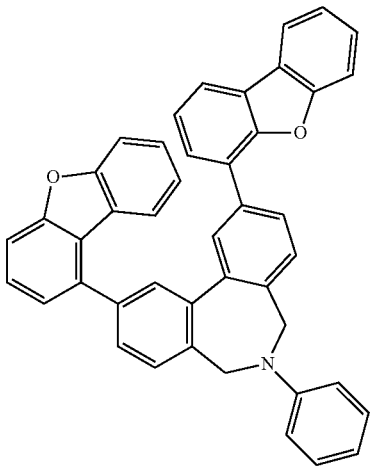
740
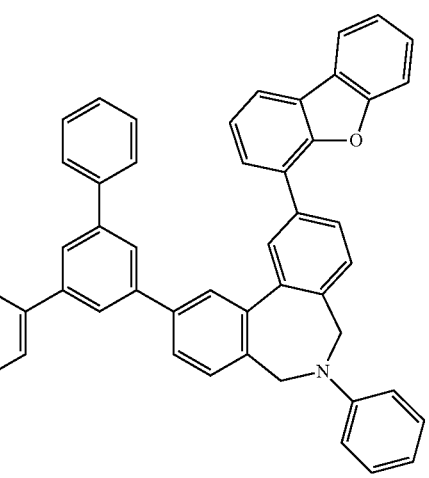
741
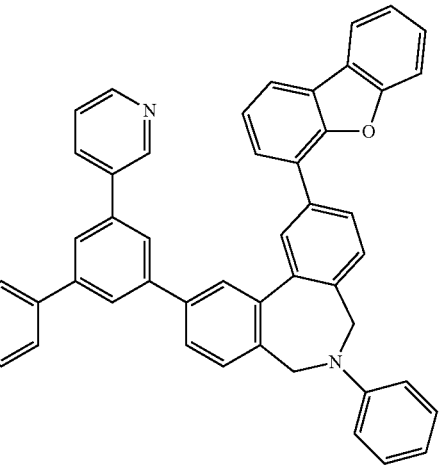

-continued
742
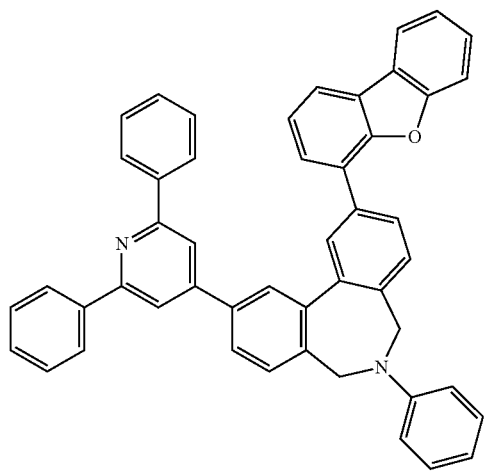
743
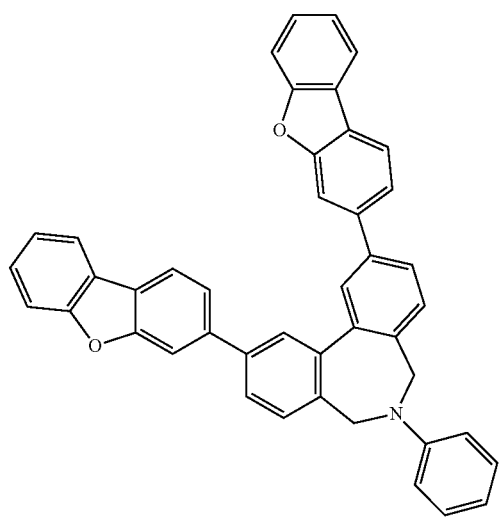
744
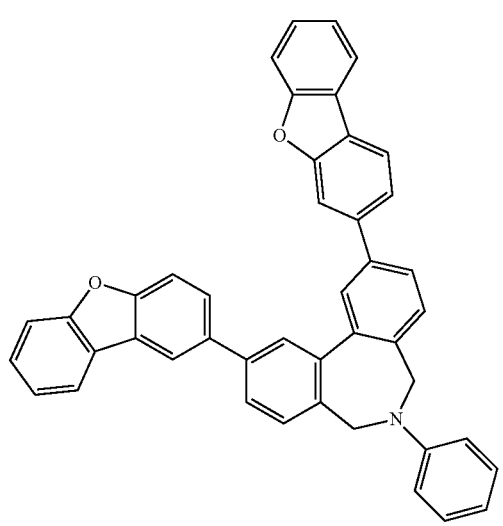
-continued
745
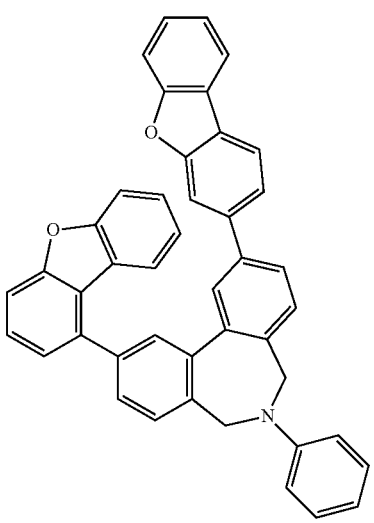
746
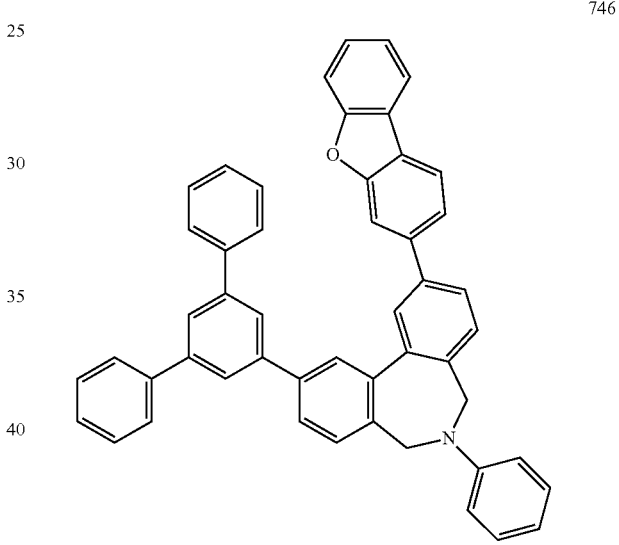
747
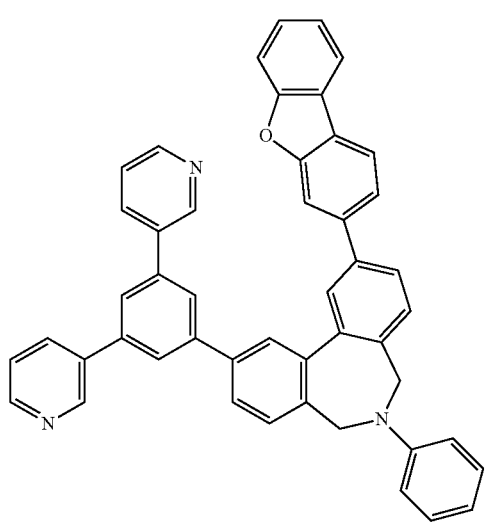

-continued
748
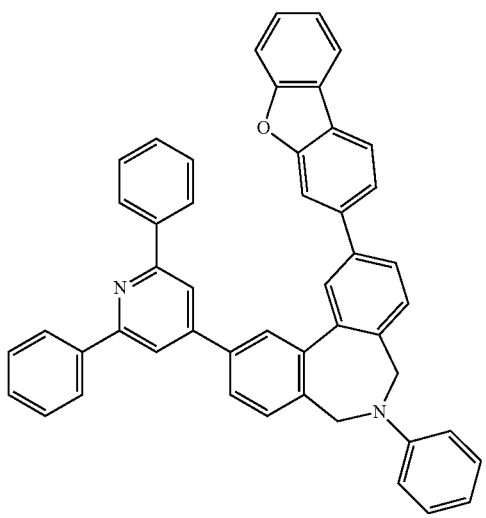
749
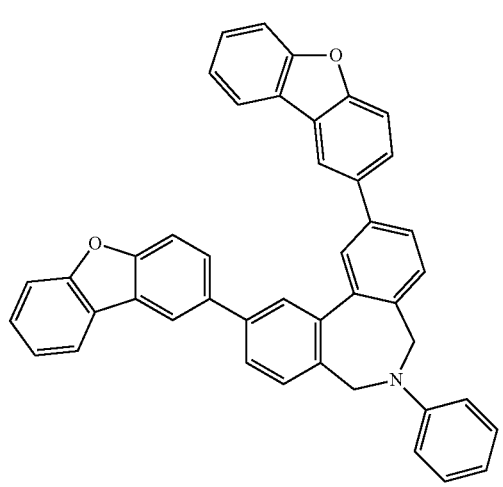
750
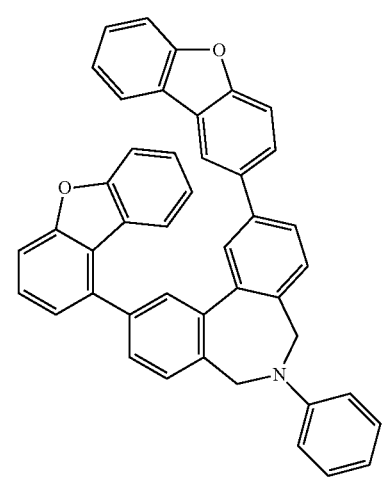
-continued
751
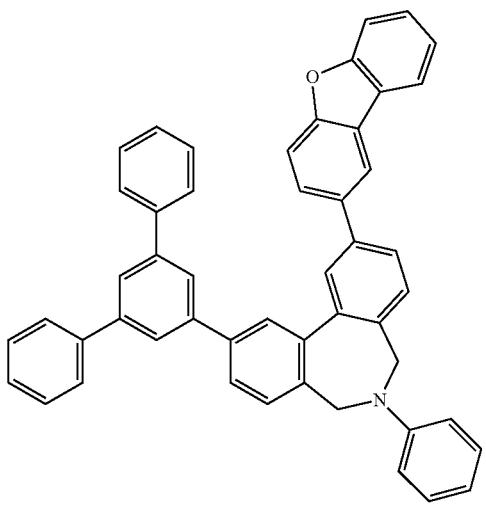
752
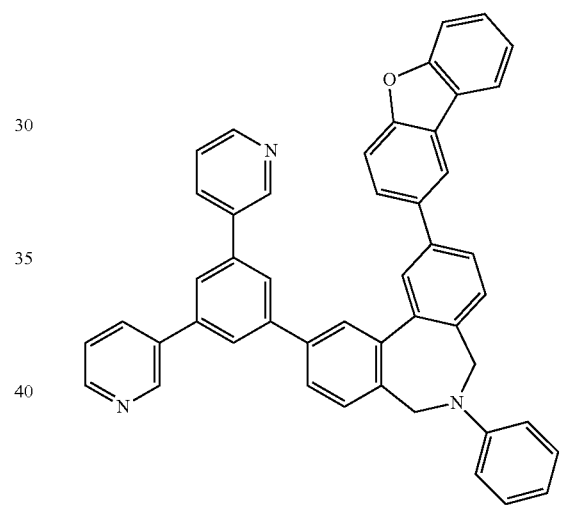
753
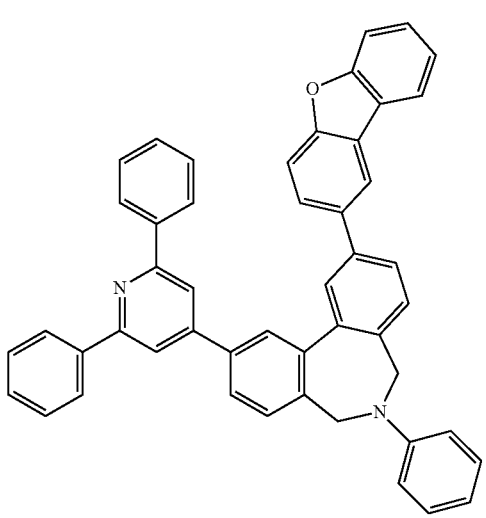

241
-continued
754
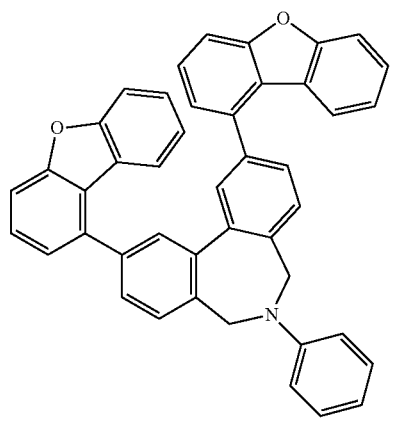
755
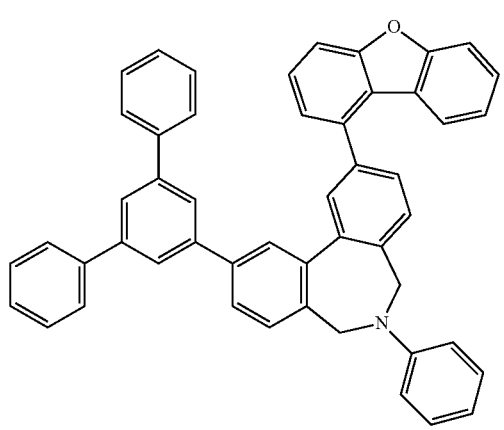
756
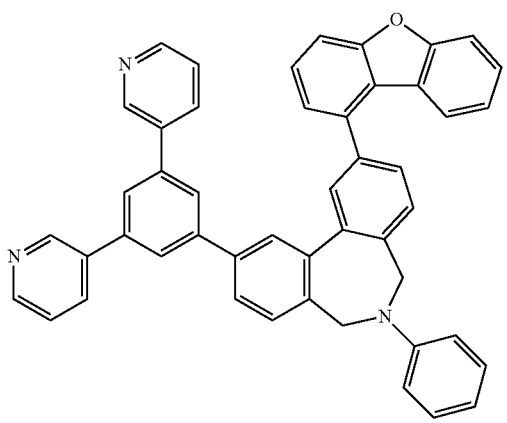
242
-continued
757
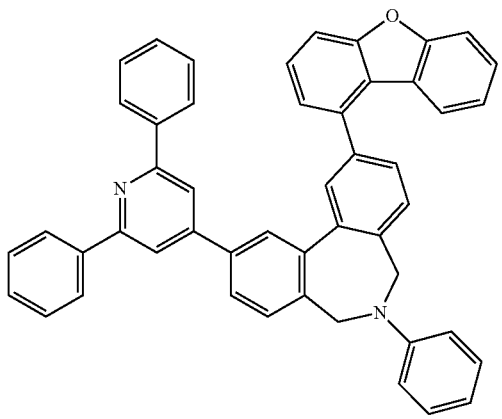
758
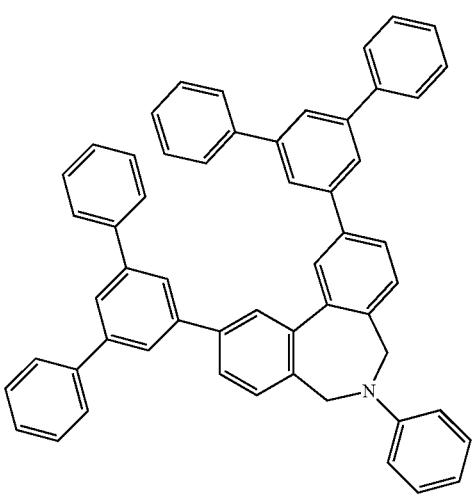
759
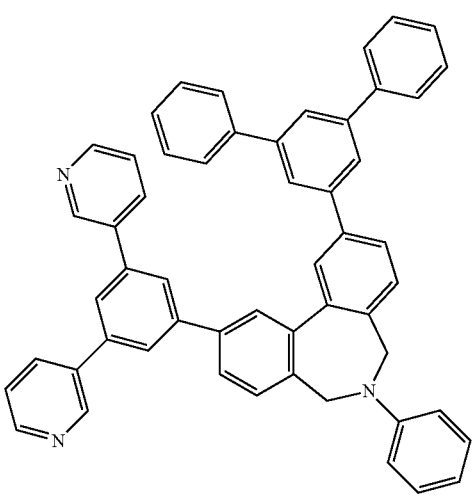

-continued
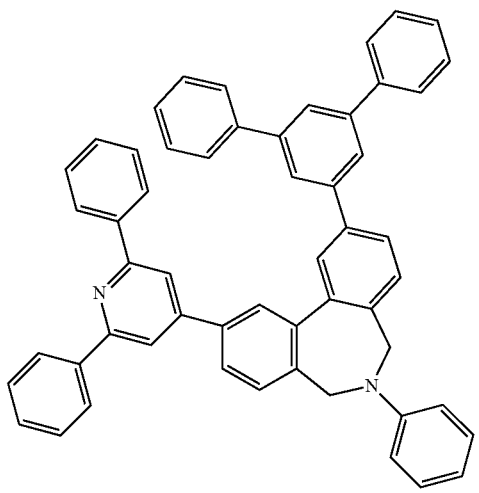
760
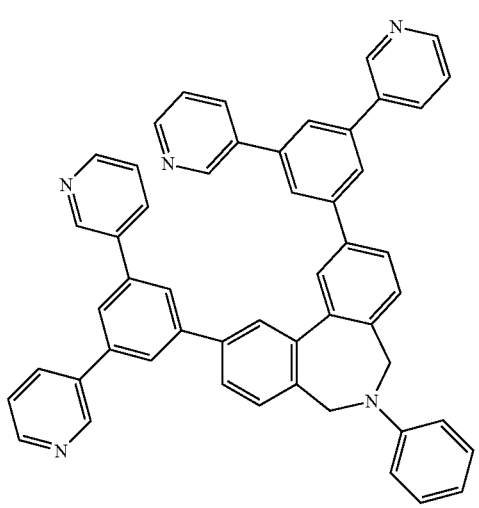
761
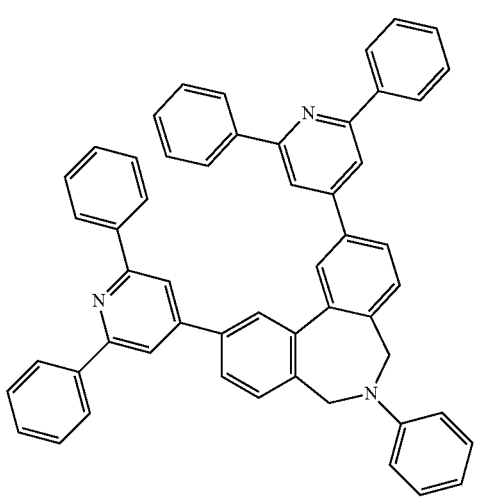
762
-continued
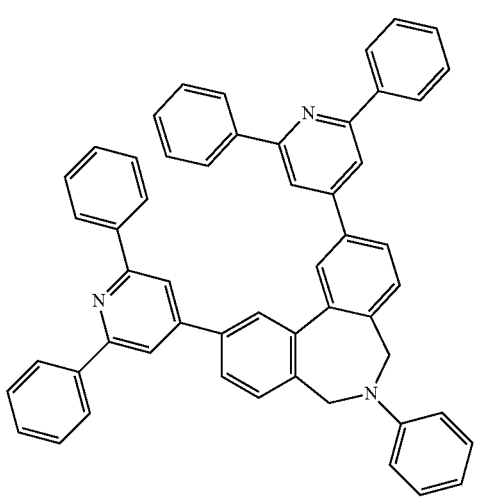
763
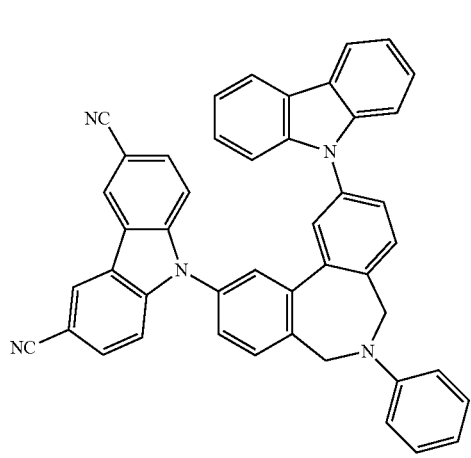
764
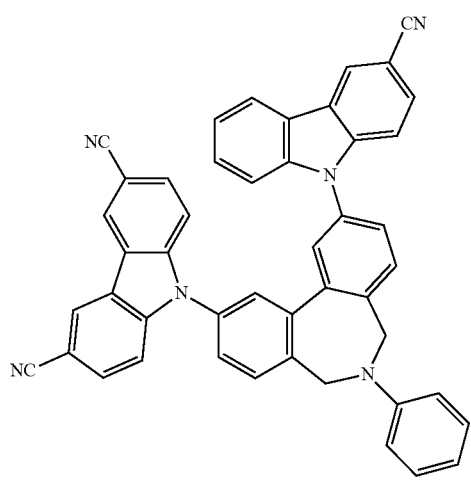
765

-continued

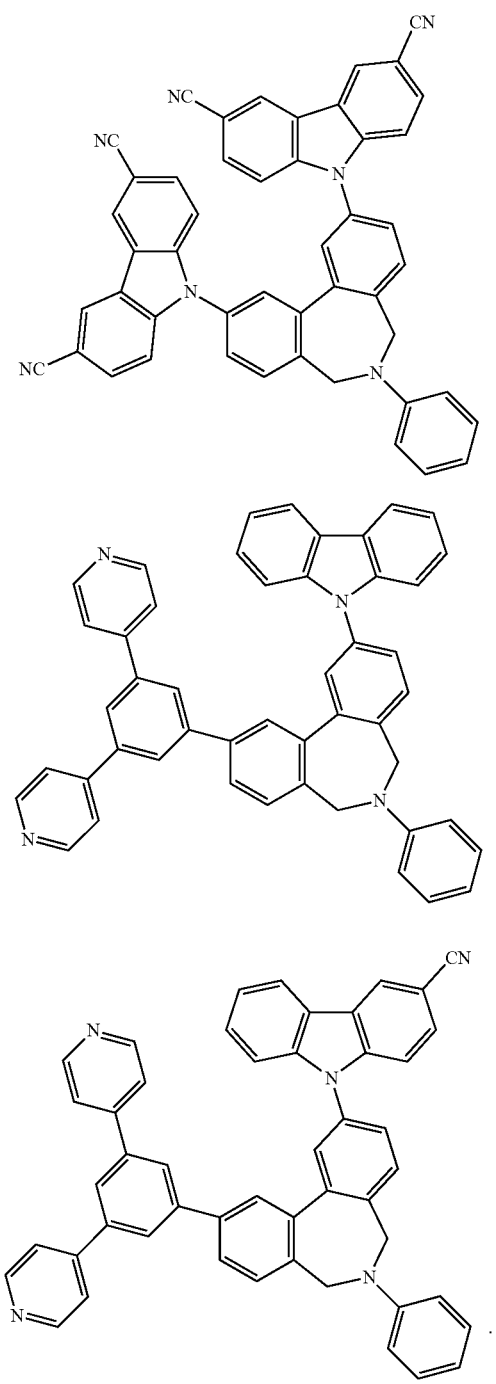

In regard to Formula 1, i) $X_{11}$ to $X_{18}$ are not all N, ii) $X_{11}$ to $X_{18}$ are not all CH, iii) at least one selected from $X_{17}$ and $X_{18}$ is CH, and iv) at least one selected from $X_{11}$ to $X_{18}$ is neither N nor CH. That is, at least one selected from $X_{11}$ to $X_{16}$ in Formula 1 is "carbon having a substituent that is not a hydrogen". That is, the condensed cyclic compound represented by Formula 1 has a substituent that is not a hydrogen at a position where a conjugation length in its molecular structure is reduced. Accordingly, the condensed cyclic compound has high triplet energy.

For example, the highest occupied molecular orbital (HOMO), lowest unoccupied molecular orbital (LUMO),
$T_1$, and $S_1$ energy levels of Compounds 1 to 123 and Compounds A and B were simulated by using the Gaussian method. Simulation evaluation results are shown in Table 1:

TABLE 1

| Compound No. | HOMO | LUMO | $T_1$ | $S_1$ |
|---|---|---|---|---|
| 1 | −5.379 | −1.405 | 2.902 | 3.36 |
| 2 | −5.372 | −1.167 | 3.07 | 3.408 |
| 3 | −5.389 | −1.34 | 3.04 | 3.36 |
| 4 | −5.364 | −1.214 | 3.022 | 3.46 |
| 5 | −5.427 | −1.408 | 3.031 | 3.364 |
| 6 | −5.427 | −1.526 | 2.957 | 3.359 |
| 7 | −5.556 | −1.505 | 3.109 | 3.329 |
| 8 | −5.963 | −1.703 | 3.107 | 3.337 |
| 9 | −5.801 | −1.459 | 2.969 | 3.338 |
| 10 | −5.819 | −1.543 | 2.9 | 3.348 |
| 11 | −5.814 | −1.384 | 3.08 | 3.338 |
| 12 | −5.833 | −1.497 | 3.052 | 3.345 |
| 13 | −5.807 | −1.408 | 3.027 | 3.342 |
| 14 | −5.869 | −1.568 | 3.04 | 3.349 |
| 15 | −5.869 | −1.659 | 2.957 | 3.281 |
| 16 | −5.364 | −1.388 | 2.934 | 3.35 |
| 17 | −5.806 | −1.541 | 2.937 | 3.335 |
| 18 | −5.751 | −1.304 | 2.917 | 3.35 |
| 19 | −5.728 | −1.364 | 2.885 | 3.505 |
| 20 | −5.758 | −1.295 | 2.938 | 3.404 |
| 21 | −5.812 | −1.347 | 2.936 | 3.45 |
| 22 | −5.78 | −1.298 | 2.932 | 3.442 |
| 23 | −5.876 | −1.406 | 2.932 | 3.453 |
| 24 | −5.879 | −1.467 | 2.92 | 3.298 |
| 25 | −5.384 | −1.461 | 2.876 | 3.358 |
| 26 | −5.821 | −1.61 | 2.871 | 3.346 |
| 27 | −5.708 | −1.372 | 2.869 | 3.476 |
| 28 | −5.715 | −1.424 | 2.855 | 3.712 |
| 29 | −5.721 | −1.374 | 2.876 | 3.494 |
| 30 | −5.753 | −1.416 | 2.873 | 3.505 |
| 31 | −5.721 | −1.377 | 2.87 | 3.519 |
| 32 | −5.798 | −1.473 | 2.87 | 3.575 |
| 33 | −5.805 | −1.512 | 2.873 | 3.293 |
| 34 | −5.384 | −1.233 | 3.04 | 3.41 |
| 35 | −5.826 | −1.431 | 3.04 | 3.33 |
| 36 | −5.748 | −1.248 | 2.964 | 3.412 |
| 37 | −5.74 | −1.339 | 2.898 | 3.522 |
| 38 | −5.76 | −1.129 | 3.034 | 3.422 |
| 39 | −5.807 | −1.267 | 3.026 | 3.465 |
| 40 | −5.771 | −1.164 | 3.004 | 3.457 |
| 41 | −5.856 | −1.347 | 3.007 | 3.47 |
| 42 | −5.864 | −1.459 | 2.953 | 3.299 |
| 43 | −5.407 | −1.401 | 3.022 | 3.357 |
| 44 | −5.851 | −1.569 | 3.019 | 3.341 |
| 45 | −5.819 | −1.33 | 2.956 | 3.431 |
| 46 | −5.786 | −1.398 | 2.898 | 3.522 |
| 47 | −5.819 | −1.314 | 3.007 | 3.438 |
| 48 | −5.875 | −1.369 | 3.01 | 3.472 |
| 49 | −5.846 | −1.313 | 2.997 | 3.471 |
| 50 | −5.929 | −1.433 | 3 | 3.483 |
| 51 | −5.934 | −1.509 | 2.95 | 3.294 |
| 52 | −5.383 | −1.299 | 2.991 | 3.354 |
| 53 | −5.828 | −1.482 | 2.995 | 3.339 |
| 54 | −5.818 | −1.264 | 2.95 | 3.424 |
| 55 | −5.762 | −1.351 | 2.892 | 3.53 |
| 56 | −5.81 | −1.196 | 2.985 | 3.437 |
| 57 | −5.879 | −1.293 | 2.991 | 3.468 |
| 58 | −5.864 | −1.216 | 2.974 | 3.482 |
| 59 | −5.973 | −1.372 | 2.976 | 3.495 |
| 60 | −5.988 | −1.465 | 2.95 | 3.3 |
| 61 | −5.405 | −1.458 | 2.995 | 3.359 |
| 62 | −5.85 | −1.627 | 3.001 | 3.344 |
| 63 | −5.874 | −1.365 | 2.95 | 3.432 |
| 64 | −5.795 | −1.427 | 2.89 | 3.569 |
| 65 | −5.855 | −1.365 | 2.987 | 3.447 |
| 66 | −5.922 | −1.407 | 2.994 | 3.472 |
| 67 | −5.935 | −1.365 | 2.976 | 3.49 |
| 68 | −6.061 | −1.475 | 2.979 | 3.504 |
| 69 | −6.025 | −1.518 | 2.951 | 3.296 |
| 70 | −5.445 | −1.602 | 2.945 | 3.28 |
| 71 | −5.89 | −1.752 | 2.946 | 3.263 |
| 72 | −5.925 | −1.498 | 2.933 | 3.29 |
| 73 | −5.838 | −1.541 | 2.889 | 3.289 |

TABLE 1-continued

| Compound No. | HOMO | LUMO | $T_1$ | $S_1$ |
|---|---|---|---|---|
| 74 | −5.905 | −1.51 | 2.945 | 3.288 |
| 75 | −5.966 | −1.54 | 2.95 | 3.289 |
| 76 | −5.987 | −1.508 | 2.938 | 3.284 |
| 77 | −6.033 | −1.601 | 2.939 | 3.277 |
| 78 | −6.036 | −1.613 | 2.937 | 3.295 |
| 79 | −5.42 | −1.246 | 3.177 | 3.369 |
| 80 | −5.562 | −1.47 | 3.118 | 3.327 |
| 81 | −5.364 | −1.304 | 2.974 | 3.35 |
| 82 | −5.383 | −1.39 | 2.905 | 3.361 |
| 83 | −5.378 | −1.153 | 3.086 | 3.389 |
| 84 | −5.387 | −1.322 | 3.05 | 3.36 |
| 85 | −5.364 | −1.196 | 3.034 | 3.426 |
| 86 | −5.422 | −1.391 | 3.044 | 3.365 |
| 87 | −5.445 | −1.509 | 2.957 | 3.285 |
| 88 | −5.975 | −1.684 | 3.116 | 3.336 |
| 89 | −5.814 | −1.444 | 2.97 | 3.336 |
| 90 | −5.833 | −1.525 | 2.902 | 3.353 |
| 91 | −5.828 | −1.358 | 3.085 | 3.335 |
| 92 | −5.836 | −1.477 | 3.048 | 3.346 |
| 93 | −5.814 | −1.38 | 3.037 | 3.343 |
| 94 | −5.868 | −1.545 | 3.047 | 3.35 |
| 95 | −5.891 | −1.645 | 2.958 | 3.276 |
| 96 | −5.819 | −1.238 | 2.956 | 3.502 |
| 97 | −5.753 | −1.316 | 2.897 | 3.476 |
| 98 | −5.808 | −1.233 | 2.973 | 3.397 |
| 99 | −5.861 | −1.265 | 2.971 | 3.427 |
| 100 | −5.835 | −1.227 | 2.967 | 3.42 |
| 101 | −5.914 | −1.328 | 2.966 | 3.428 |
| 102 | −5.93 | −1.435 | 2.951 | 3.297 |
| 103 | −5.771 | −1.358 | 2.888 | 3.561 |
| 104 | −5.769 | −1.324 | 2.902 | 3.49 |
| 105 | −5.783 | −1.347 | 2.902 | 3.499 |
| 106 | −5.756 | −1.318 | 2.897 | 3.538 |
| 107 | −5.818 | −1.398 | 2.896 | 3.548 |
| 108 | −5.843 | −1.462 | 2.901 | 3.295 |
| 109 | −5.819 | −1.07 | 3.068 | 3.401 |
| 110 | −5.846 | −1.243 | 3.047 | 3.439 |
| 111 | −5.814 | −1.115 | 3.022 | 3.431 |
| 112 | −5.885 | −1.323 | 3.029 | 3.441 |
| 113 | −5.906 | −1.447 | 2.959 | 3.296 |
| 114 | −5.906 | −1.293 | 3.042 | 3.565 |
| 115 | −5.88 | −1.235 | 3.022 | 3.458 |
| 116 | −5.954 | −1.36 | 3.029 | 3.464 |
| 117 | −5.97 | −1.461 | 2.959 | 3.293 |
| 118 | −4.676 | −2.391 | −0.745 | 1.291 |
| 119 | −5.987 | −1.316 | 3.012 | 3.47 |
| 120 | −5.986 | −1.435 | 2.958 | 3.296 |
| 121 | −6.089 | −1.405 | 3.021 | 3.483 |
| 122 | −6.032 | −1.502 | 2.958 | 3.292 |
| 123 | −6.018 | −1.512 | 2.955 | 3.288 |
| A | −4.767 | −1.177 | 2.494 | 3.073 |
| B | −5.543 | −1.357 | 2.724 | 3.773 |

Compound A

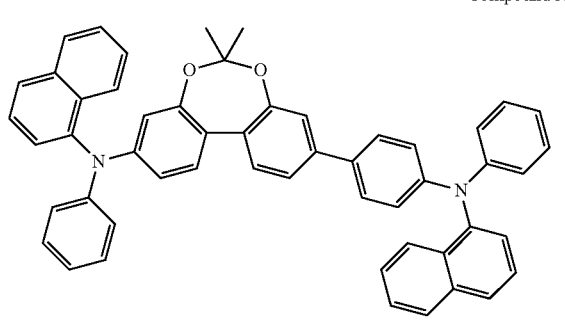

Compound B

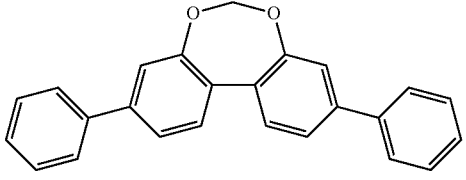

From Table 1, it may be seen that the condensed cyclic compound represented by Formula 1 has a HOMO energy level and a LUMO energy level which are suitable for use as a material for an organic light-emitting device and retains a high $T_1$ energy level.

A method of synthesizing the condensed cyclic compound represented by Formula 1 may be understood by one of ordinary skill in the art by referring to Synthesis Examples described below.

Accordingly, the condensed cyclic compound represented by Formula 1 is suitable for use in an organic layer of an organic light-emitting device, for example, for use as a host included in an emission layer constituting the organic layer. Accordingly, another aspect provides an organic light-emitting device including:

a first electrode;
a second electrode; and
an organic layer disposed between the first electrode and the second electrode,
wherein the organic layer includes an emission layer and at least one of the condensed cyclic compounds represented by Formula 1.

As described above, due to the inclusion of the organic layer including the condensed cyclic compound represented by Formula 1, the organic light-emitting device may have low driving voltage, high efficiency, high luminance, high quantum luminance efficiency, and a long lifespan.

The condensed cyclic compound represented by Formula 1 may be included in between a pair of electrodes of the organic light-emitting device. In some embodiments, the condensed cyclic compound may be included in at least one selected from the emission layer, a hole transport region (for example, including at least one selected from a hole injection layer, a hole transport layer, and an electron blocking layer) disposed between the first electrode and the emission layer, and an electron transport region (for example, including at least one selected from a hole blocking layer, an electron transport layer, and an electron injection layer) disposed between the emission layer and the second electrode. In some embodiments, the condensed cyclic compound represented by Formula 1 may be included in the emission layer. Here, the emission layer may further include a dopant, and the condensed cyclic compound included in the emission layer may serve as a host. The emission layer may be a green emission layer that emits green light or a blue emission layer that emits blue light, and the dopant may be a phosphorescent dopant.

As used herein, the expression the "(organic layer) includes at least one condensed-cyclic compound" may be construed as meaning the "(organic layer) may include one condensed-cyclic compound represented by Formula 1 or two different condensed-cyclic compounds represented by Formula 1".

For example, the organic layer may include only Compound 1 as the condensed-cyclic compound. In this regard, Compound 1 may be included in the emission layer of the organic light-emitting device. In some embodiments, the organic layer may include Compound 1 and Compound 2 as the condensed-cyclic compounds. In this regard, Compound 1 and Compound 2 may be included in the same layer (for example, both Compound 1 and Compound 2 may be included in the emission layer) or in different layers, respectively.

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole-transport region disposed between the first electrode and the emission layer, wherein the hole-transport region may include at least one selected from a hole injection layer, a hole-transport layer, and an electron blocking layer; and ii) an electron-transport region disposed between the emission layer and the second electrode, wherein the electron-transport region may include at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, a structure and a method of manufacturing the organic light-emitting device according to an embodiment will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum-depositing or sputtering a material for forming the first electrode on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). In some embodiments, the material for the first electrode 11 may be selected from a metal such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer (HIL), the HIL may be formed on the first electrode 11 by using a suitable method, such as vacuum-deposition, spin coating, casting, and Langmuir-Blodgett (LB) method.

When a HIL is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0 Angstroms per second (Å/sec) to about 100 Å/sec, though the conditions may vary depending on a compound that is used as a hole injection material and a structure and thermal properties of a desired HIL, but conditions for the vacuum-deposition is not limited thereto.

When a HIL is formed by spin coating, the spin-coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired HIL, but conditions for the spin-coating are not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

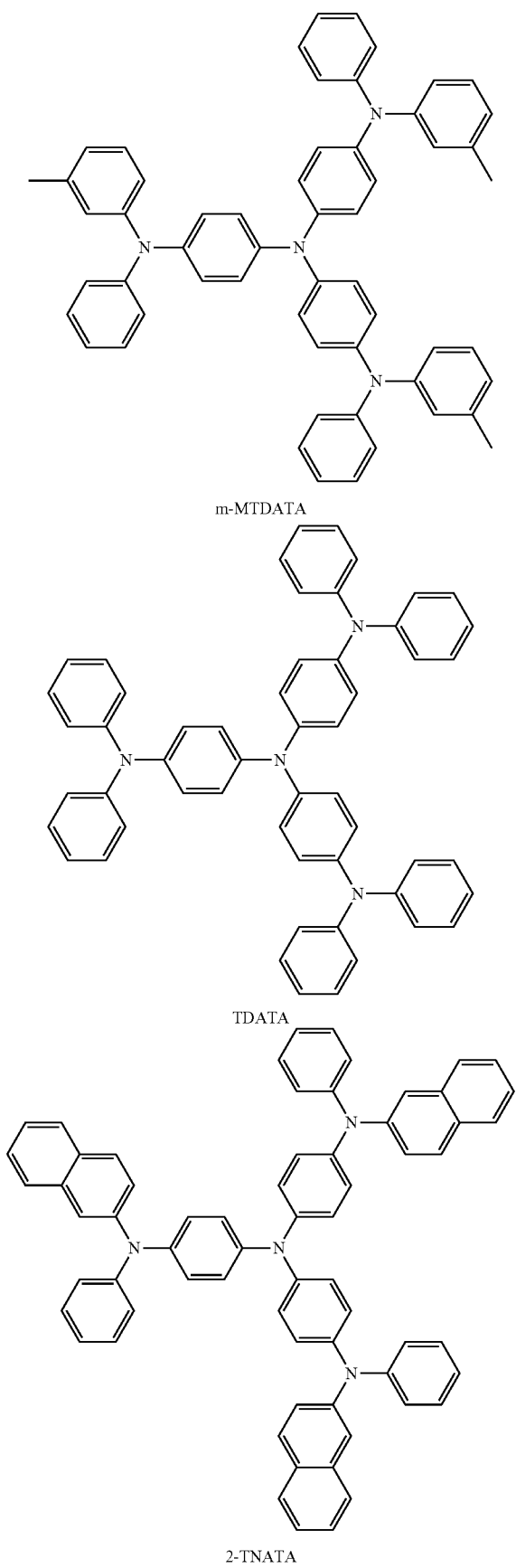
m-MTDATA
TDATA
2-TNATA
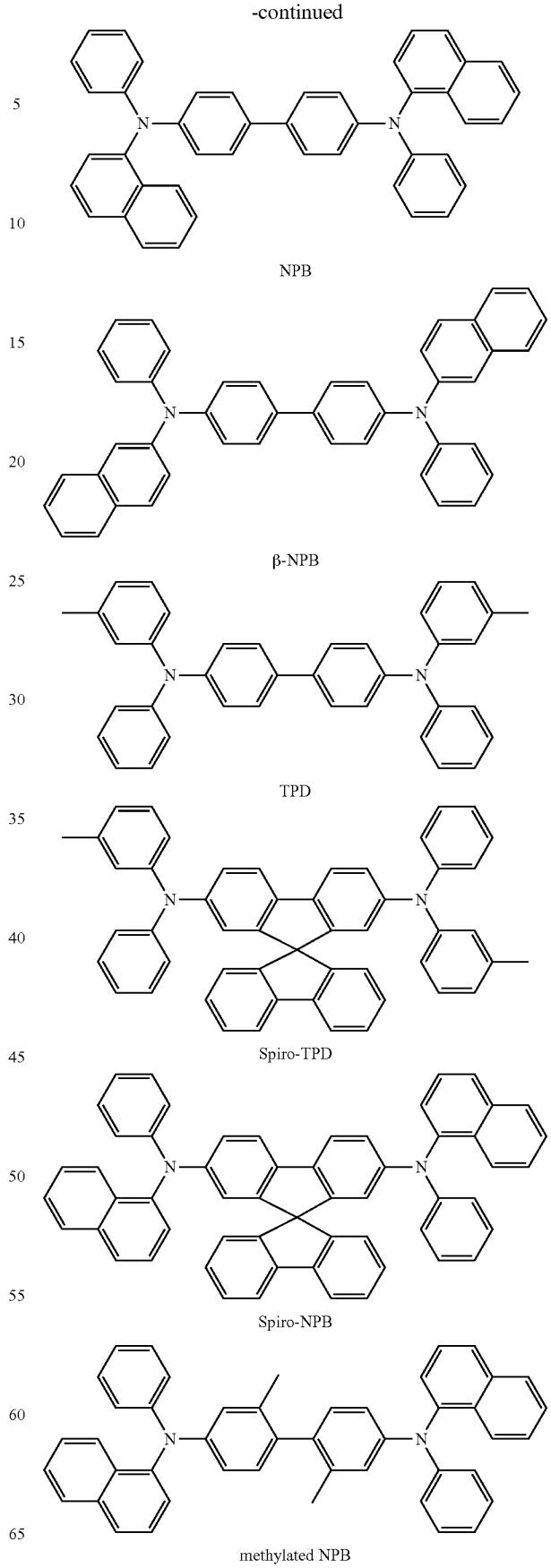
NPB
β-NPB
TPD
Spiro-TPD
Spiro-NPB
methylated NPB -continued

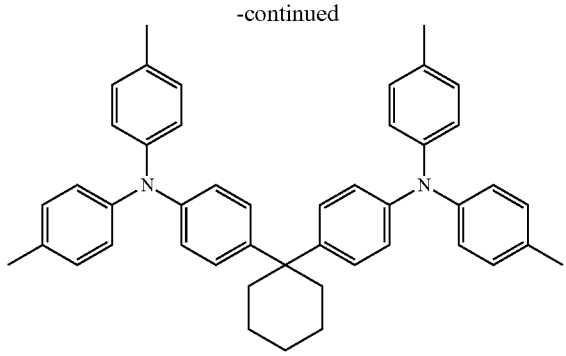

TAPC

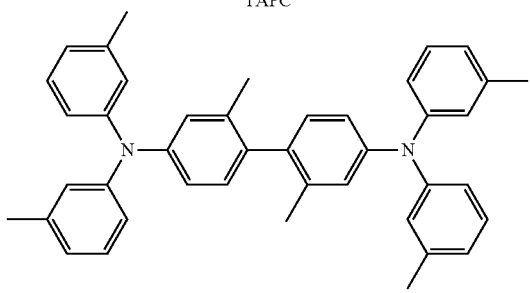

HMTPD

Formula 201

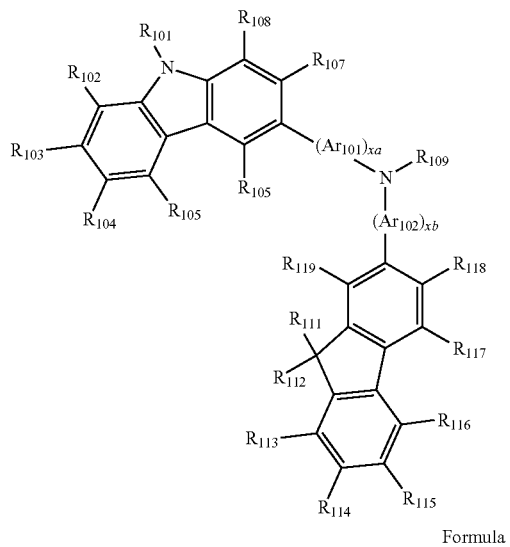

Formula 202

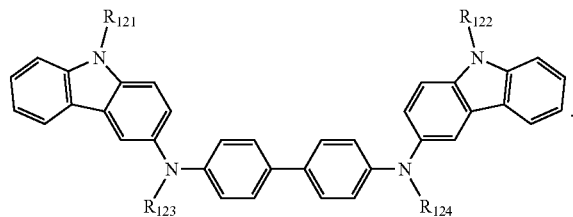

Ar$_{101}$ and Ar$_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

xa and xb in Formula 201 may be each independently an integer selected from 0 to 5, or may be 0, 1 or 2. For example, xa may be 1 and xb may be 0, but they are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, or the like) and a $C_1$-$C_{10}$ alkoxy group (for example, a methoxy group, an ethoxy group, a propoxy group, butoxy group, a pentoxy group, or the like);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In an embodiment, the compound represented by Formula 201 may be represented by Formula 201A, but the chemical structure thereof is not limited thereto:

Formula 201A
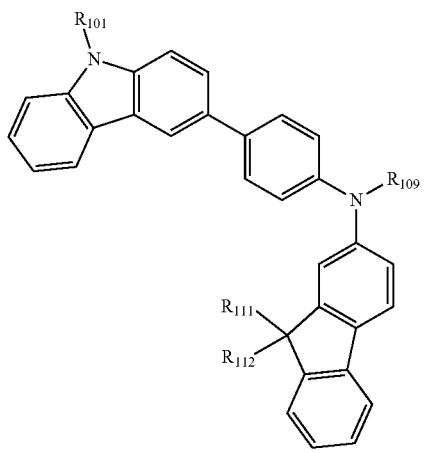
$R_{101}$, $R_{111}$, $R_{112}$, and $R_{109}$ in Formula 201A are the same as described above.
For example, the compound represented by Formula 201 and the compound represented by Formula 202 may include Compounds HT1 to HT20, but they are not limited thereto:
HT1
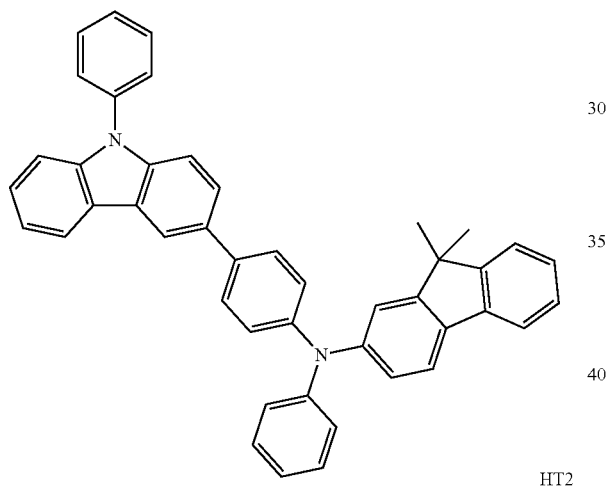
HT2
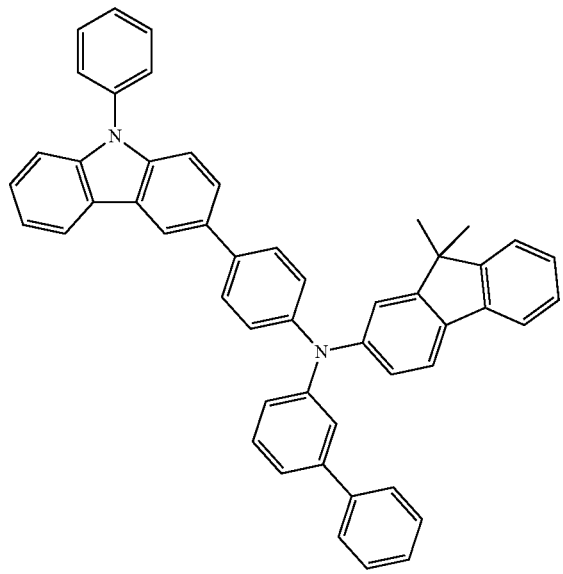
HT3
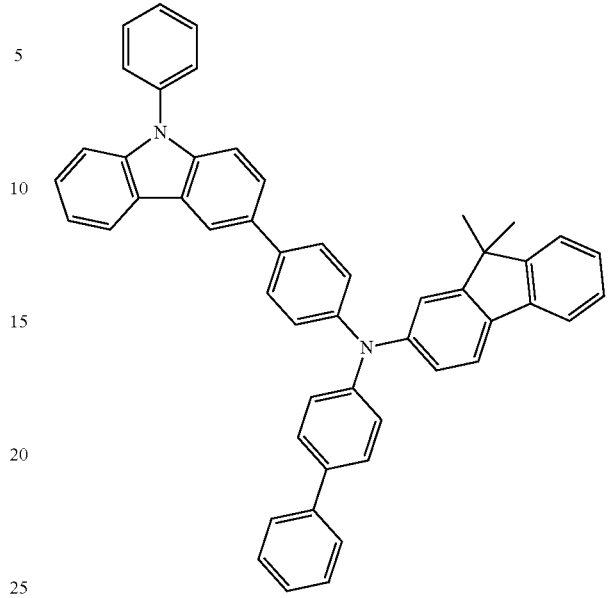
HT4
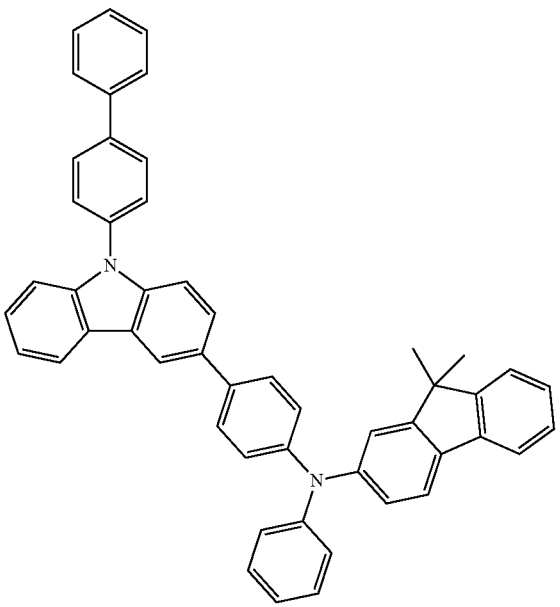

HT5
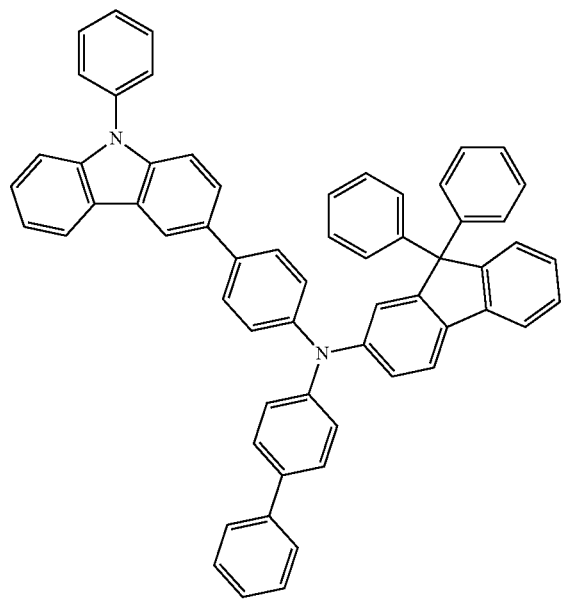
HT6
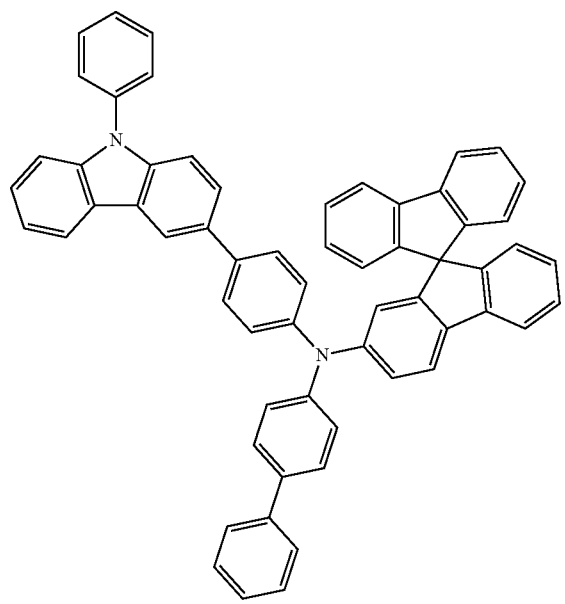
HT7
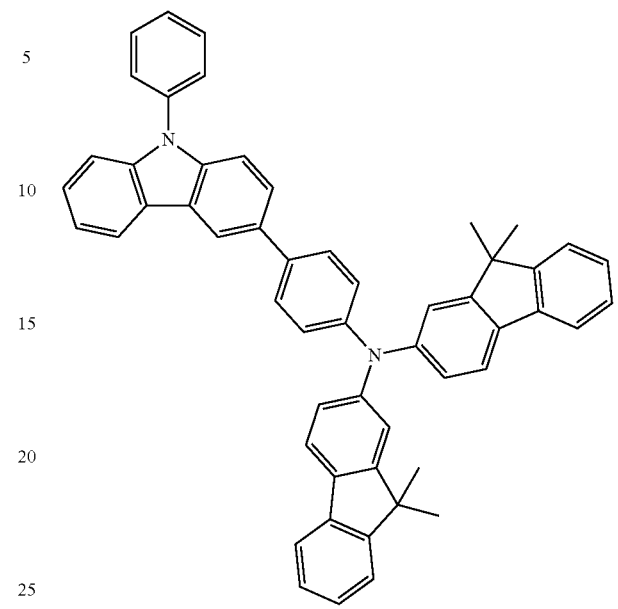
HT8
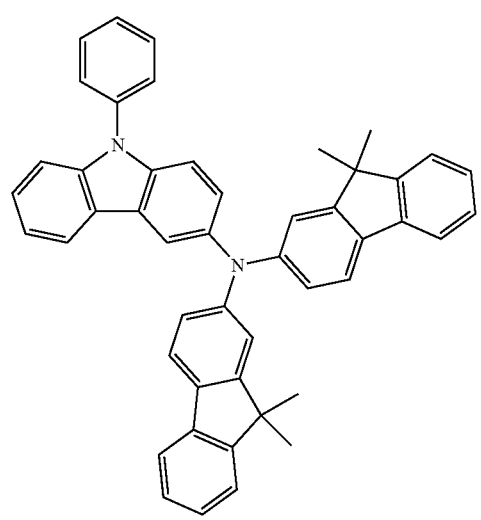
HT9

HT10
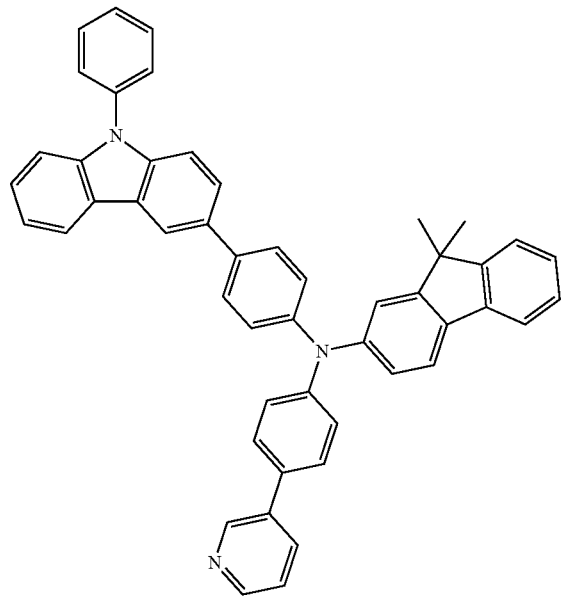
HT11
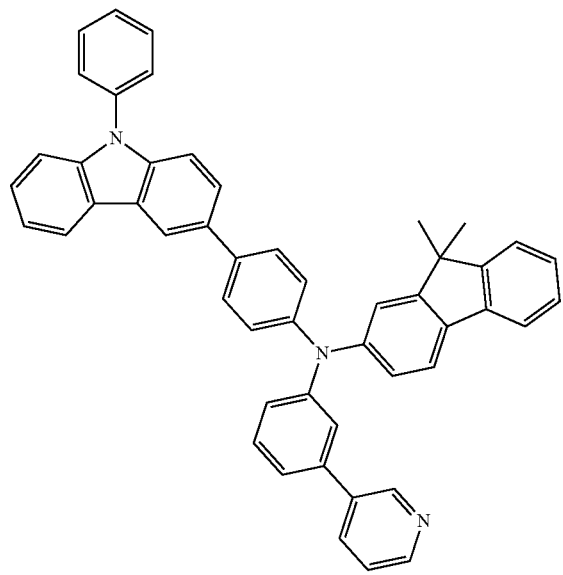
HT12
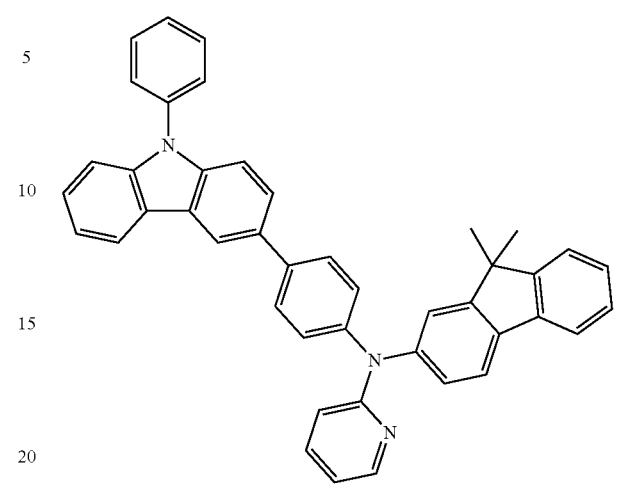
HT13
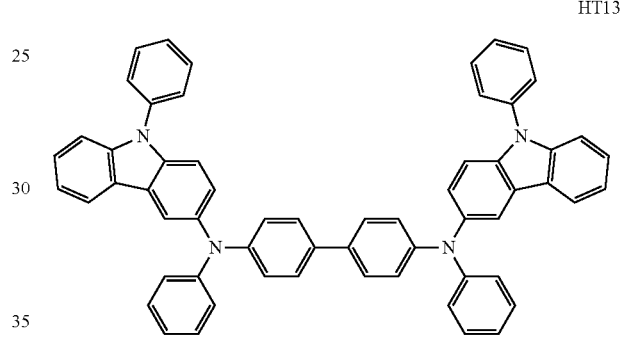
HT14
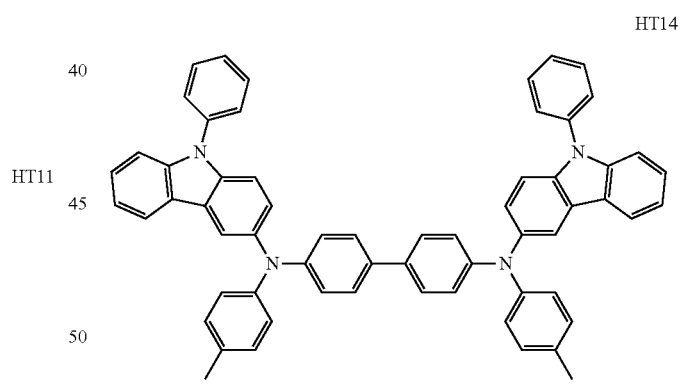
HT15
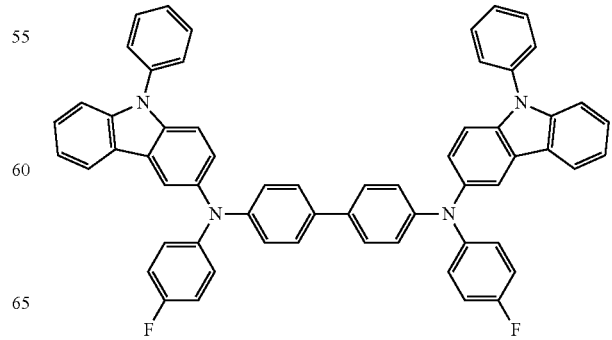

HT16
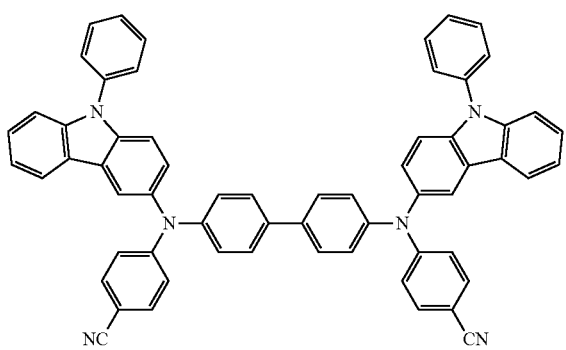

HT17
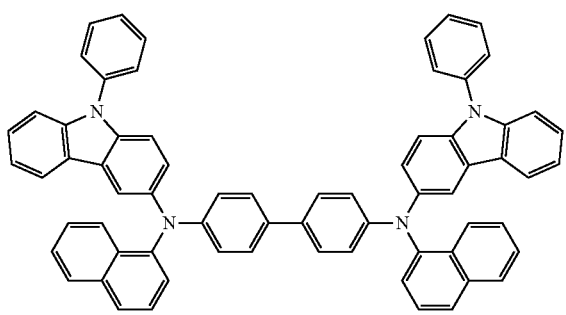

HT18
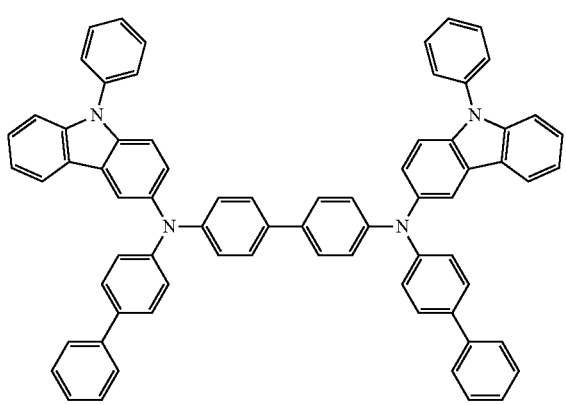

HT19
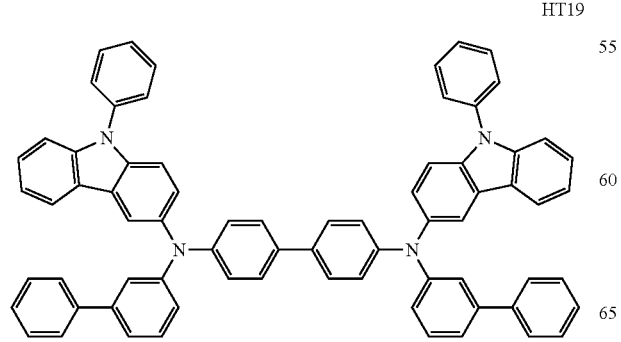

HT20
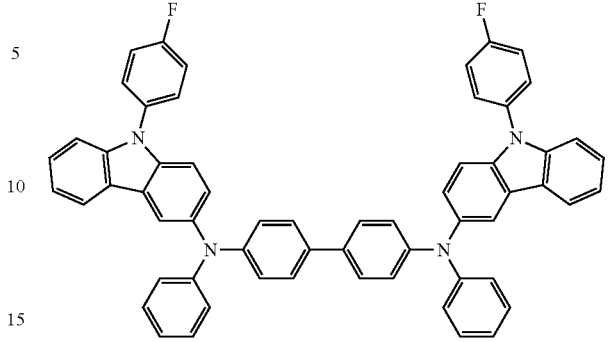

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 illustrated below, but they are not limited thereto.

Compound HT-D1
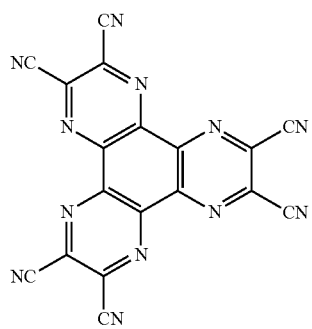

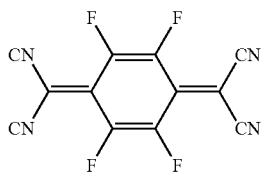

F4-TCNQ

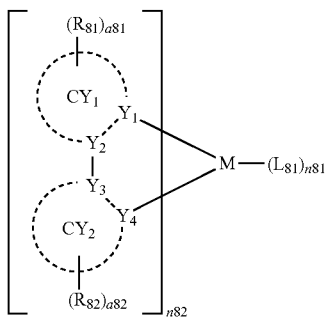

Formula 81

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using a suitable method, such as vacuum-deposition, spin coating, casting, or an LB method. When the emission layer is formed by vacuum-deposition or spin coating, vacuum-deposition and coating conditions for the emission layer may be generally similar to the conditions for forming a hole injection layer, though the conditions may vary depending on the compound used.

The hole transport region may further include an electron blocking layer. The electron blocking layer may include a known material, for example, mCP, but they are not limited thereto.

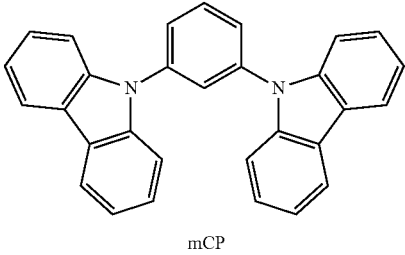 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. In some embodiments, the emission layer may include at least one layer selected from a red emission layer, a green emission layer, and a blue emission layer, which are stacked, to emit white light.

The emission layer may include the condensed cyclic compound represented by Formula 1. The emission layer may further include a dopant. The dopant may include at least one selected from a fluorescent dopant and a phosphorescent dopant.

For example, a host in the emission layer may include the condensed cyclic compound represented by Formula 1.

The dopant in the emission layer may include a fluorescent dopant which emits light according to a fluorescent emission mechanism or a phosphorescent dopant which emits light according to a phosphorescent emission mechanism.

According to an embodiment, the dopant in the emission layer may be a phosphorescent dopant, and the phosphorescent dopant may include an organometallic compound represented by Formula 81:

wherein in Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ may be each independently carbon (C) or nitrogen (N);

$Y_1$ and $Y_2$ may be linked to each other through a single bond or a double bond, and $Y_3$ and $Y_4$ may be linked to each other through a single bond or a double bond;

$CY_1$ and $CY_2$ may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran or a dibenzothiophene, and $CY_1$ and $CY_2$ are optionally linked to each other through a single bond or an linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

a81 and a82 may be each independently an integer selected from 1 to 5;

n81 may be an integer selected from 0 to 4;

n82 may be an integer selected from 1, 2, and 3; and $L_{81}$ is a monovalent organic ligand, a divalent organic ligand, or a trivalent organic ligand.

$R_{81}$ and $R_{82}$ are the same as described in connection with $R_{11}$ in the specification.

The phosphorescent dopant may include at least one selected from Compounds PD1 to PD78 and FIr$_6$, but embodiments are not limited thereto:
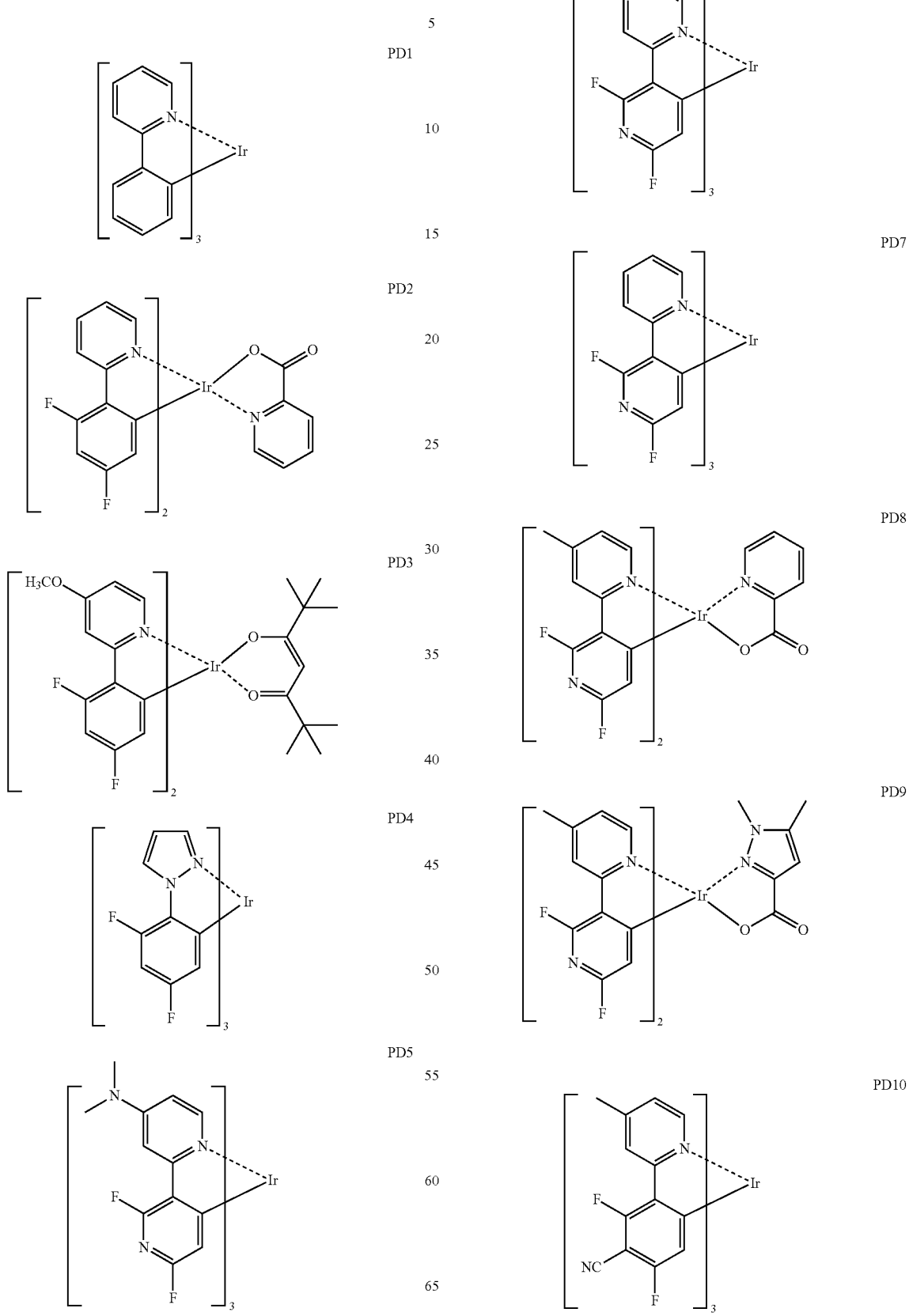

PD11 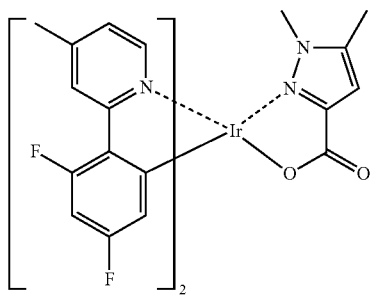
PD12 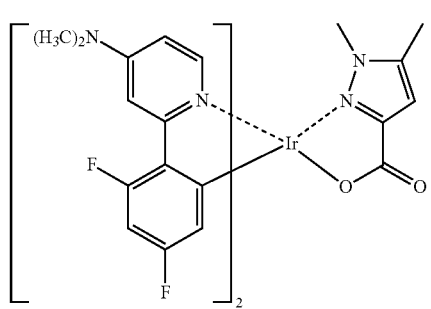
PD13 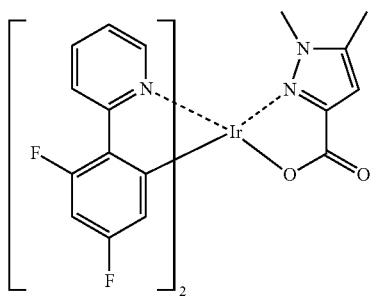
PD14 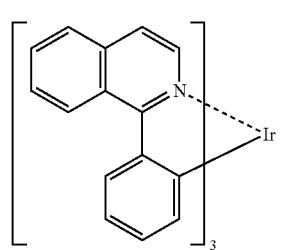
PD15 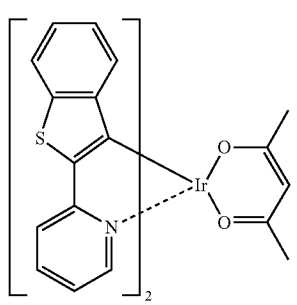
PD16 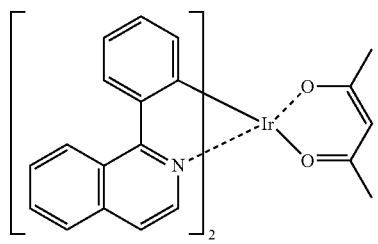
PD17 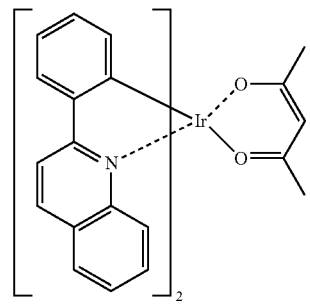
PD18 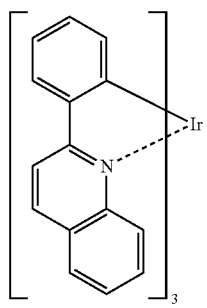
PD19 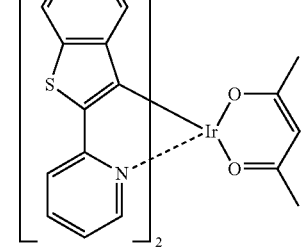
PD20 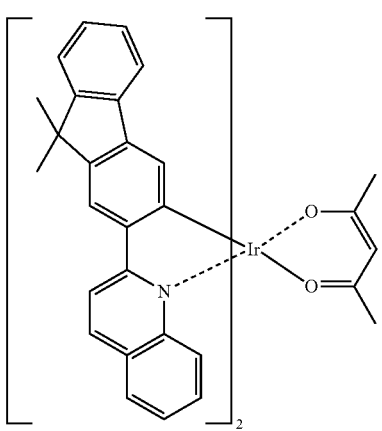

PD21 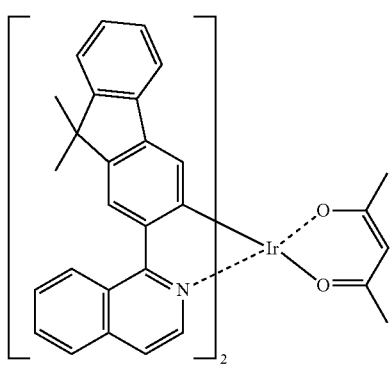
PD22 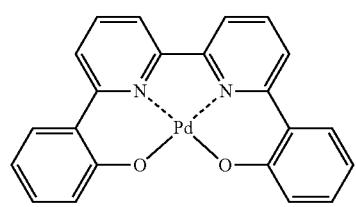
PD23 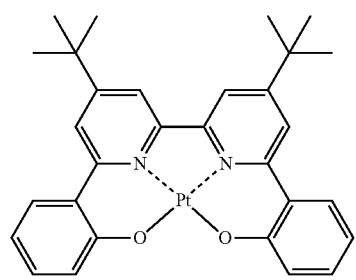
PD24 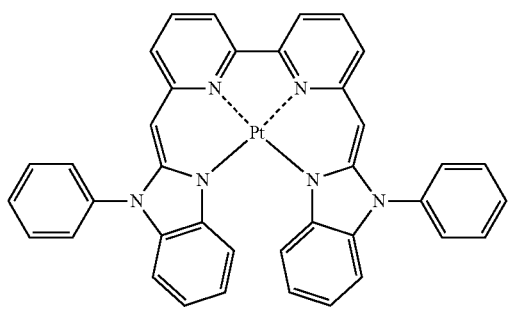
PD25 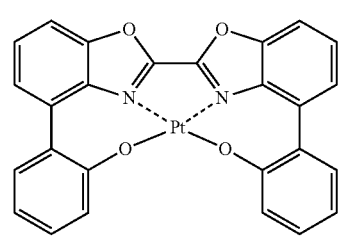
PD26 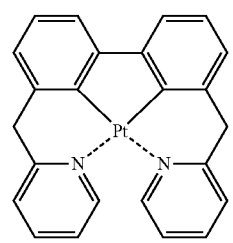
PD27 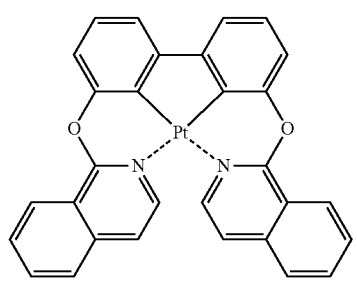
PD28 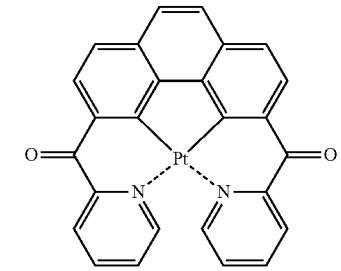
PD29 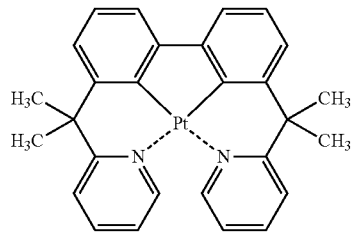
PD30 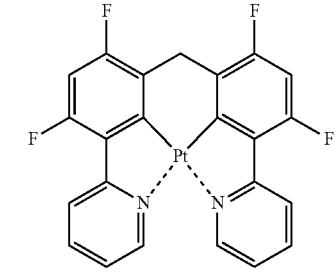
PD31 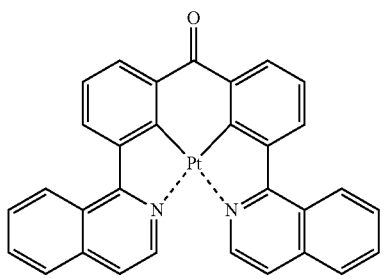
PD32 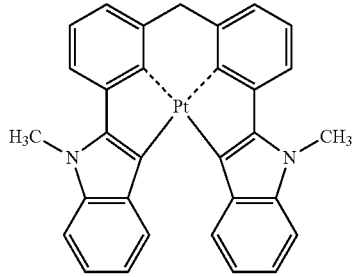

PD33
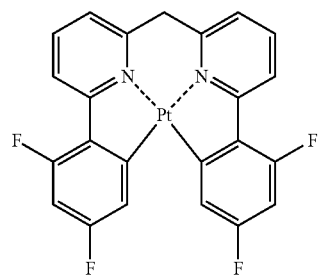
PD34
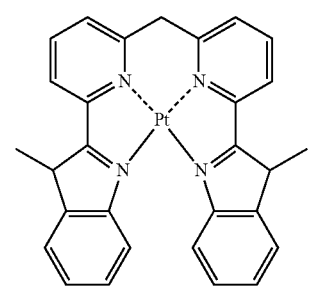
PD35
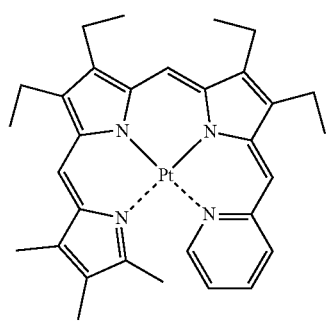
PD36
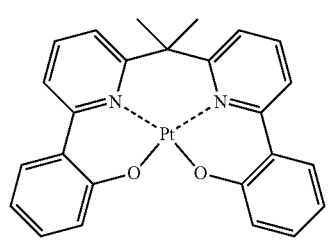
PD37
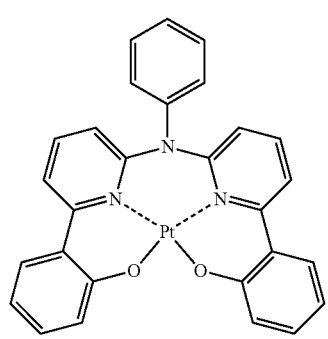
P38
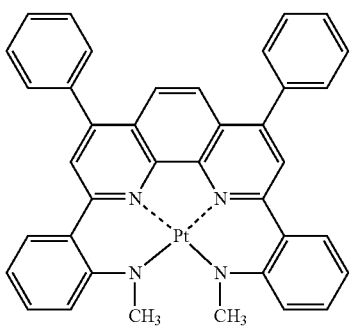
P39
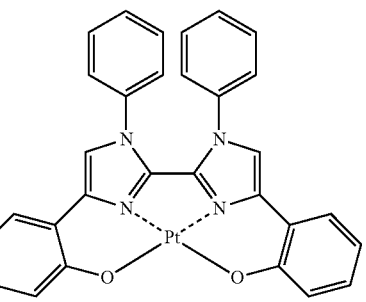
P40
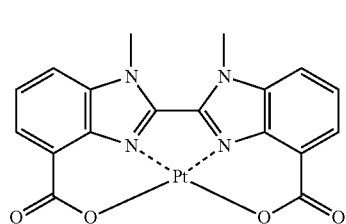
PD41
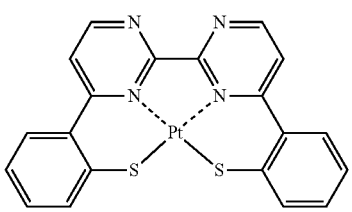
PD42
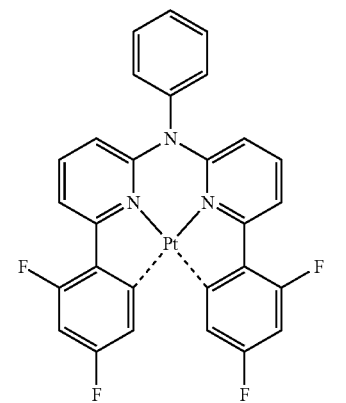

-continued
PD43
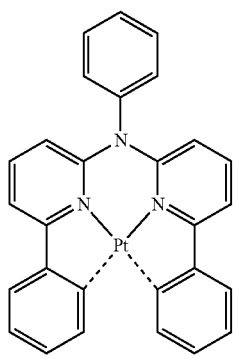
PD44
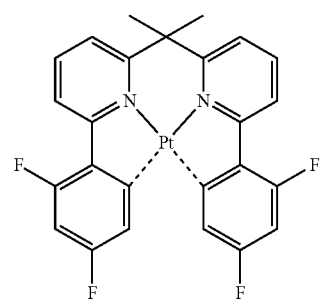
PD45
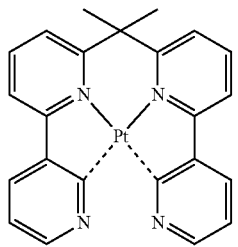
PD46
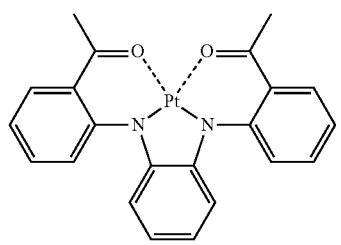
PD47
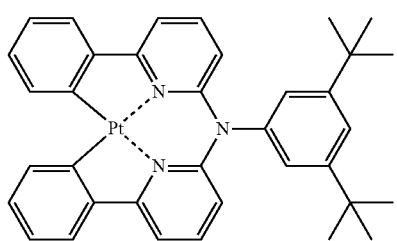
-continued
PD48
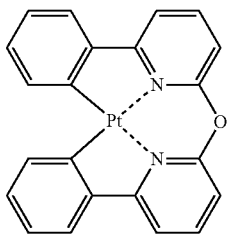
PD49
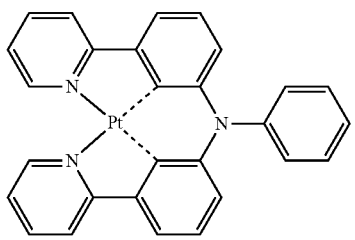
PD50
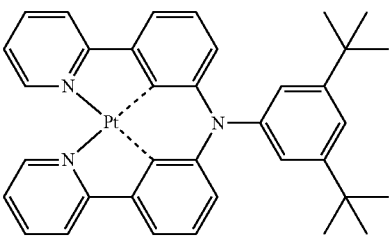
PD51
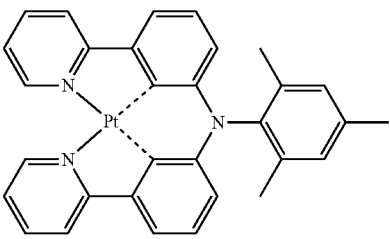
PD52
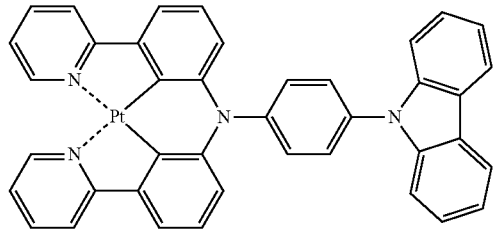
PD53

PD54
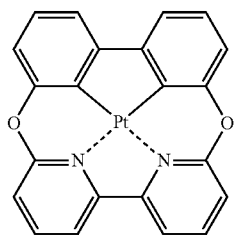
PD55
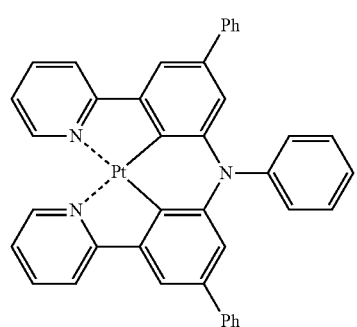
PD56
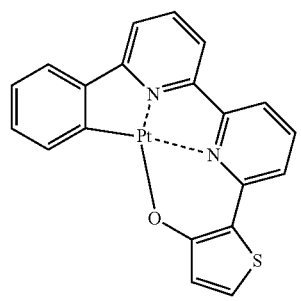
PD57
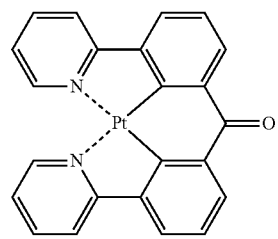
PD58
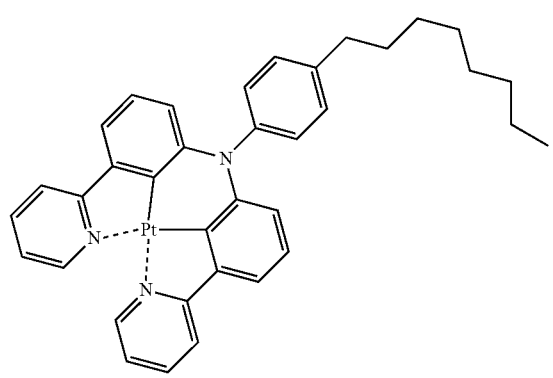
PD59
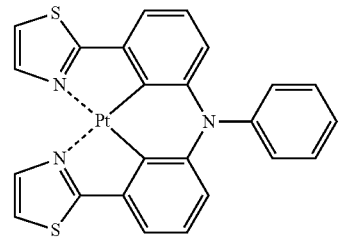
PD60
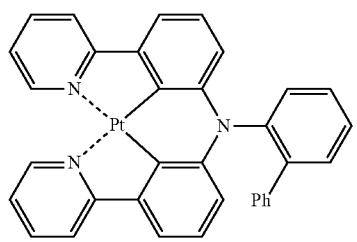
PD61
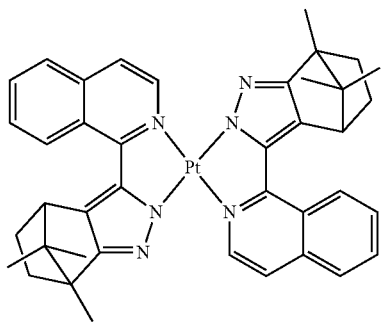
PD62
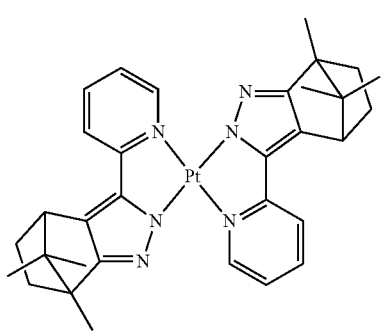
PD63
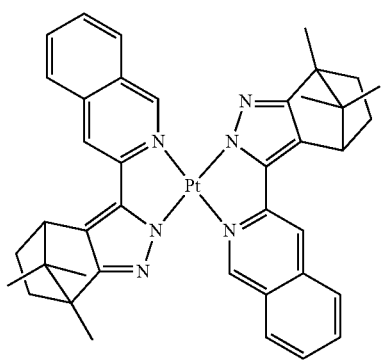

-continued
PD64 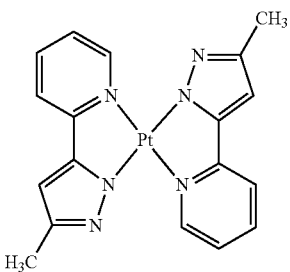
PD65 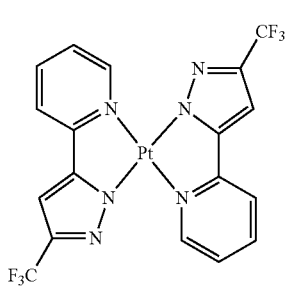
PD66 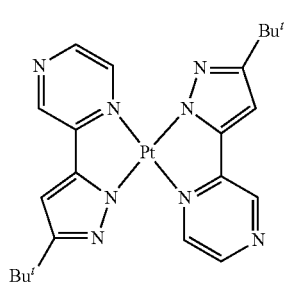
PD67 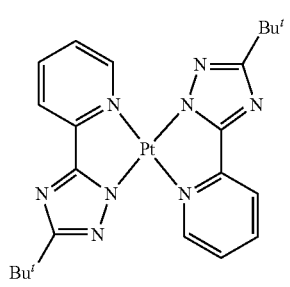
PD68 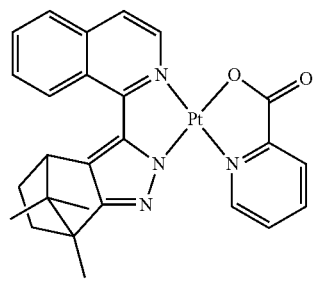
-continued
PD69 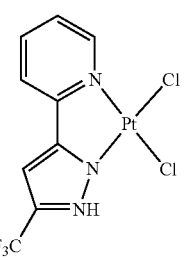
PD70 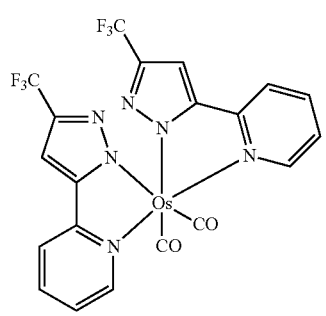
PD71 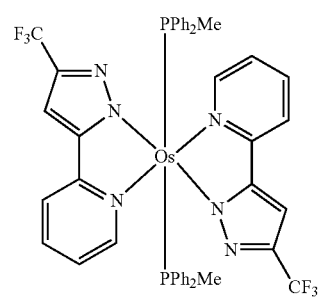
PD72 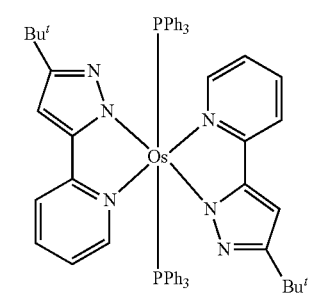
PD73 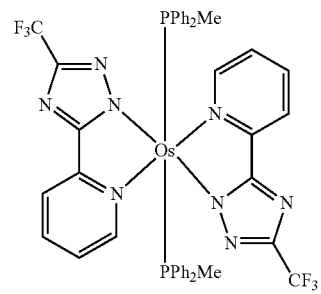

PD74

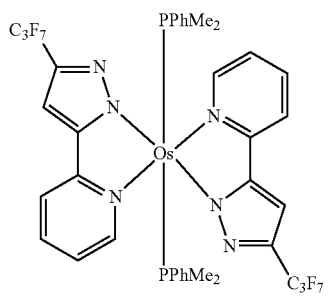

PD75

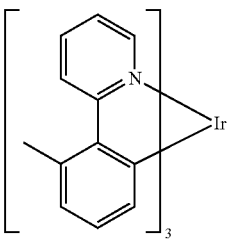

PD76

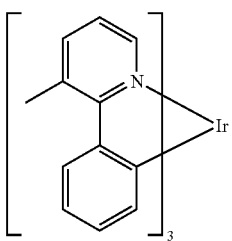

PD77

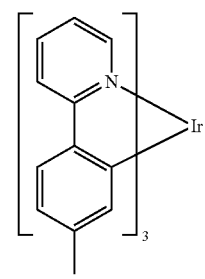

PD78

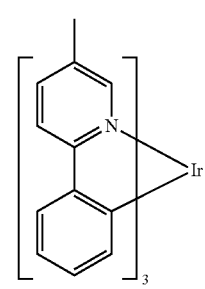

Flr6

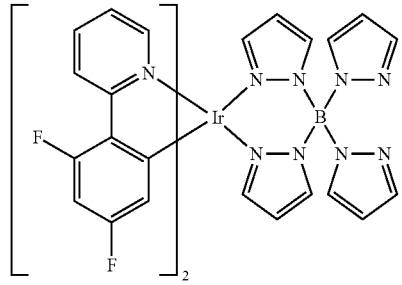

In some embodiments, the phosphorescent dopant may include PtOEP below:

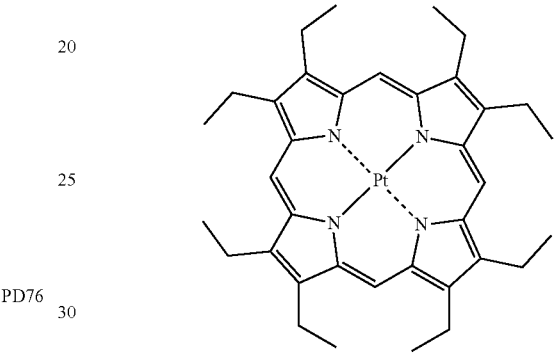

PtOEP

When the emission layer includes the host and the dopant, an amount of the dopant may be selected from in a range of about 0.01 to about 20 parts by weight based on about 100 parts by weight of the host, but the amount is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

For example, the electron transport region may have a structure of a hole blocking layer/an electron transport layer/an electron injection layer or a structure of an electron transport layer/an electron injection layer, but the structure thereof is not limited thereto.

The electron transport layer may have a single-layer structure or a multi-layer structure including two or more different materials.

Conditions for forming a hole blocking layer, an electron transport layer, and an electron injection layer may be understood by referring to the conditions for forming the hole injection layer.

When the electron transport region includes a hole blocking layer, the hole blocking layer may include, for example, at least one selected from BCP, Bphen, and TmPyPB, but it is not limited thereto.

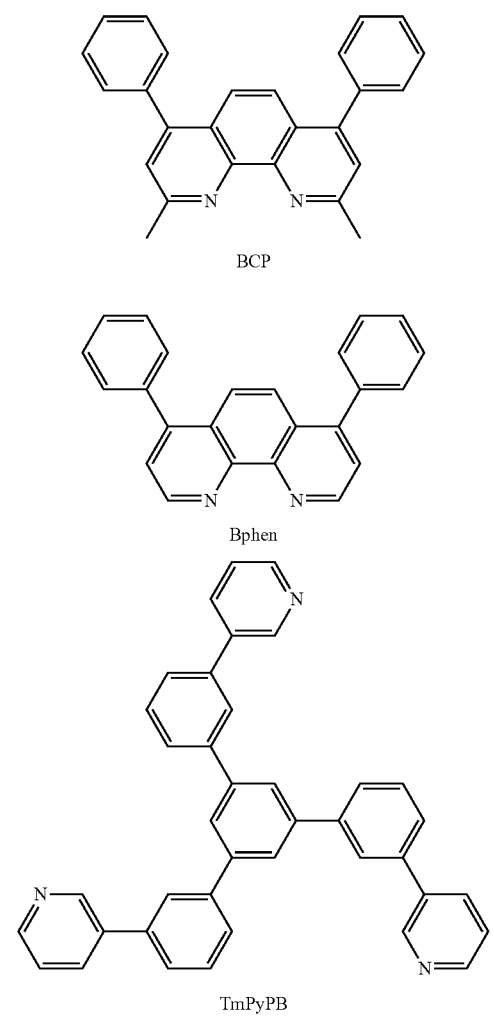

BCP

Bphen

TmPyPB

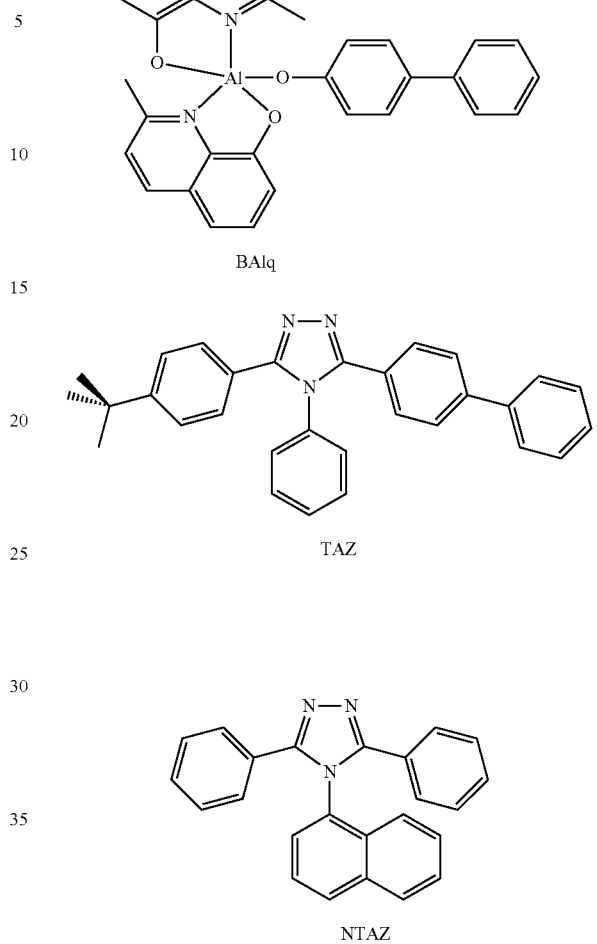

BAlq

TAZ

NTAZ

A thickness of the hole blocking layer may be in a range of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport layer may further include at least one selected from BCP, BPhen, Alq3, BAlq, TAZ, and NTAZ.

Alternatively, the electron transport layer may include at least one selected from Compounds ET1 and ET2, but it is not limited thereto.

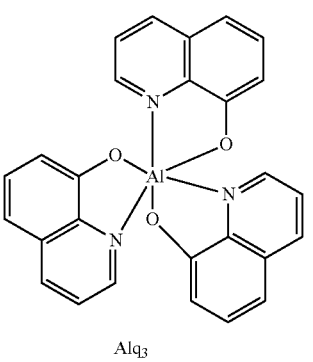

Alq3

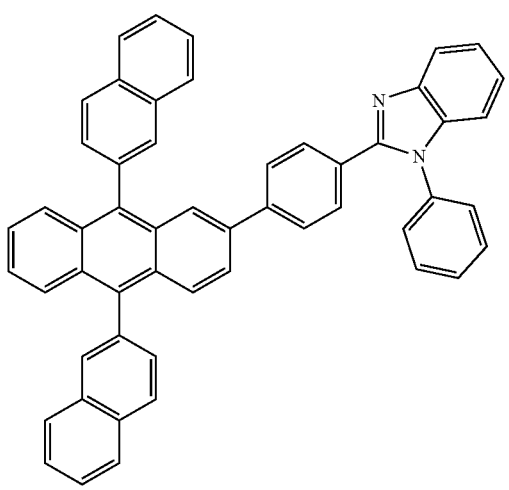

ET1

ET2

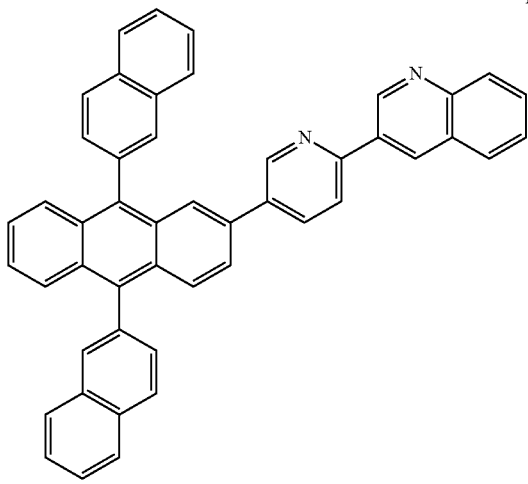

A thickness of the electron transport layer may be in a range of about 100 Å to about 1,000 Å, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET-D1

ET-D2

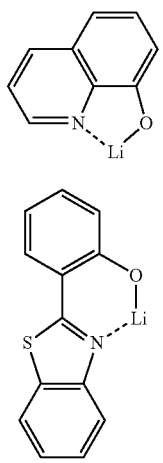

The electron transport region may include an electron injection layer (EIL) that facilitates electron injection from the second electrode 19.

The electron injection layer may include at least one selected from, LiF, NaCl, CsF, $Li_2O$, and BaO.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a metal, an alloy, an electrically conductive compound, and a mixture thereof, each of which has a relatively low work function. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, the organic light-emitting device has been described with reference to FIG. 1, but embodiments are not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as a $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by substituting at least one carbon triple bond in the middle or at the terminal of the $C_2$-$C_{60}$ alkyl group. Detailed examples thereof are an ethenyl group and a propenyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one hetero atom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in its ring, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_{60}$-$C_{60}$ aryl group as used herein refers to a monovalent group having a carbocyclic aromatic system having 6 to 60 carbon atoms, and a $C_{60}$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system including at least one hetero atom selected from N, O, P, and S as a ring-forming atom and 1 to 60 carbon atoms. A $C_1$-$C_{60}$ heteroarylene group as used herein refers to a divalent group having a carbocyclic aromatic system including at least one hetero atom selected from N, O, P, and S as a ring-forming atom and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as ring forming atoms, wherein the molecular structure as a whole is non-aromatic in the entire molecular structure. An example of the non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has a plurality of rings condensed with each other, has a hetero atom selected from N, O P, and S, other than carbon atoms (for example, the number of carbon atoms may be in a range of 1 to 60), as ring-forming atoms, wherein the molecular structure as a whole is non-aromatic in the entire molecular structure. The monovalent non-aromatic condensed heteropolycyclic group includes a carbazolyl group. A divalent non-aromatic condensed hetero-polycyclic group as used herein refers to a divalent group having the same structure as the monovalent non-aromatic condensed hetero-polycyclic group.

At least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, but they are not limited thereto.

The term "a biphenyl group" as used herein indicates "a phenyl group substituted with a phenyl group".

The term "a terphenyl group" as used herein indicates a monovalent substituent having three phenyl groups that are linked through a single bond.

Hereinafter, a compound and an organic light-emitting device according to embodiments are described in detail with reference to Synthesis Example and Examples. However, the compound and the organic light-emitting device are not limited thereto. The wording "B was used instead of A" used in describing Synthesis Examples means that an amount of A used was identical to an amount of B used, in terms of a molar equivalent.

EXAMPLE

Synthesis Example 1

Synthesis of Compound 79

Synthesis of 2,10-dibromo-5,7-dihydrobenzo[c,e]thiepine

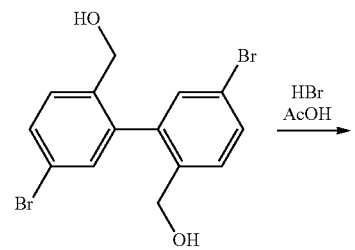

Chemical Formula: $C_{14}H_{12}Br_2O_2$
Molecular Weight: 372.06

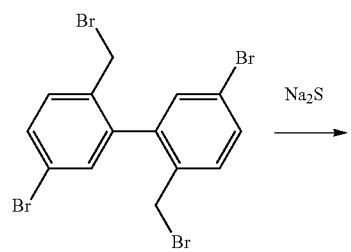

Chemical Formula: $C_{14}H_{10}Br_4$
Molecular Weight: 497.85

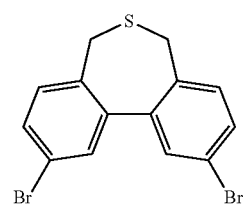

Chemical Formula: $C_{14}H_{10}Br_2S$
Molecular Weight: 370.10

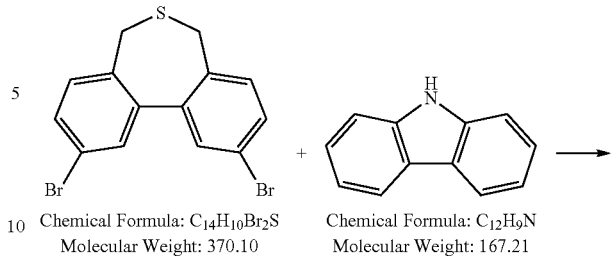

Chemical Formula: $C_{14}H_{10}Br_2S$  Chemical Formula: $C_{12}H_9N$
Molecular Weight: 370.10  Molecular Weight: 167.21

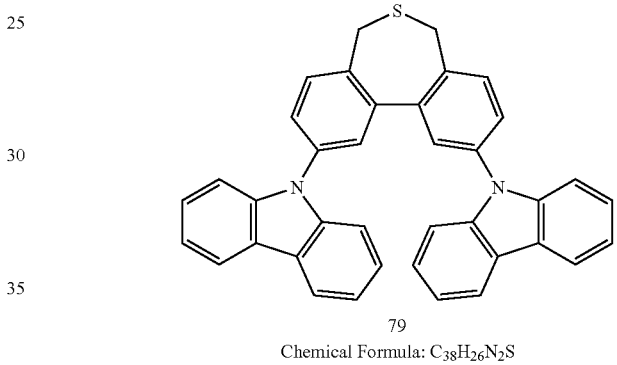

79
Chemical Formula: $C_{38}H_{26}N_2S$
Molecular Weight: 542.70

(5,5'-dibromo-[1,1'-biphenyl]-2,2'-diyl)dimethanol (2 grams (g), 5 millimoles (mmol)) and bromic acid (1.29 g, 16 mmol) were mixed, and 50 milliliters (mL) of acetic acid was added thereto. The resulting mixture was stirred under reflux. Once the reaction was complete, the reaction product was cooled and neutralized by adding water thereto, followed by extraction using methylene chloride. A solvent was removed from the obtained reaction product, which was purified by silica gel column chromatography to obtain crude 5,5'-dibromo-2,2'-bis(bromomethyl)-1,1'-biphenyl in a yield of about 70%. Immediately thereafter, a subsequent reaction was carried out as follows. 20 mL of ethanol was added to 5,5'-dibromo-2,2'-bis(bromomethyl)-1,1'-biphenyl (10 g, 20 mmol), and sodium sulfide (5.46 g, 70 mmol) and sodium hydroxide were reacted at room temperature for 24 hours. Once the reaction was complete, the reaction product was subjected to an extraction process using 2 molar (M) sodium hydroxide and methylene chloride. Magnesium sulfide was added to an organic layer to remove the remaining water, and the solution was then filtered. A solid obtained therefrom was purified by silica gel column chromatography to obtain 2,10-dibromo-5,7-dihydrobenzo[c,e]thiepine (light yellow, the yield of 57%). The obtained compound was identified by LC-MS.

LC-Mass (calc.: 370 g/mol. found: M+H=371 g/mol).

Synthesis of Compound 79

2,10-dibromo-5,7-dihydrobenzo[c,e]thiepine (10 g, 1 eq.) and 9H-carbazole (10.8 g, 2.4 equivalents (eq.)) were loaded into a flask, and a palladium catalyst (1.55 g, 0.1 eq.), sodium butoxide (5.194 g, 2 eq.), tri-tert-butylphosphine (1.093 g, 0.2 eq.) and xylene were added thereto. The resulting mixture was stirred under reflux at a temperature of 150° C. Once the reaction was complete, the reaction product was filtered to remove the catalyst therefrom. The residual solvent was removed, and the crude product was purified by silica gel column chromatography by using methylene chloride and hexane as an eluent to obtain Compound 79 (6.87 g, the yield of 47%). The obtained compound was identified by LC-MS.

LC-Mass (calc.: 542.7 g/mol. found: M+H=543 g/mol).

Synthesis Example 2

Synthesis of Compound 88

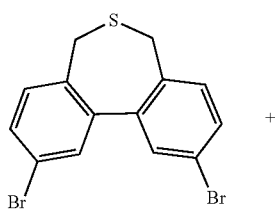

Chemical Formula: $C_{14}H_{10}Br_2S$
Molecular Weight: 370.10

+

-continued

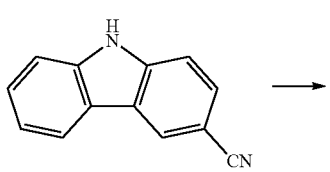

Chemical Formula: $C_{13}H_8N_2$
Molecular Weight: 192.22

-continued

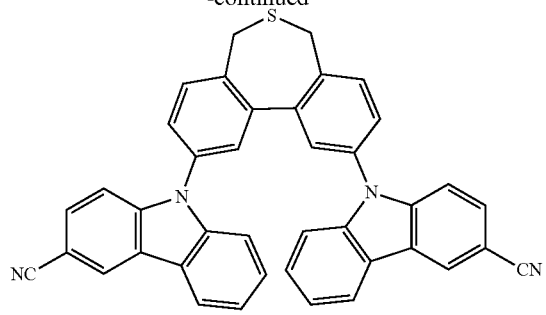

88
Chemical Formula: $C_{40}H_{24}N_4S$
Molecular Weight: 592.72

Compound 88 (1.2 g, the yield of 23%) was synthesized in the same manner as in Synthesis Example 1, except that 9H-carbazole-3-carbonitrile was used instead of 9H-carbazole. The obtained compound was identified by LC-MS.

LC-Mass (calculated.: 592.7 g/mol. found: M+H=593 g/mol).

Evaluation Example 1

Evaluation on HOMO, LUMO, and Triplet ($T_1$) Energy Levels

HOMO, LUMO and $T_1$ energy levels of Compounds 79 and 88 were evaluated according to the method shown in Table 2. Results thereof are shown in Table 3.

TABLE 2

| | |
|---|---|
| HOMO energy level evaluation method | A potential (Volts, V)-current (Amperes, A) graph of each compound was obtained by using cyclic voltammetry (CV) (electrolyte: 0.1M $Bu_4NPF_6$/solvent: $CH_2Cl_2$/electrode: 3-electrode system (working electrode: Pt disc (in a diameter of 1 mm), reference electrode: Pt wire, auxiliary electrode: Pt wire)), and then, from oxidation onset of the graph, a HOMO energy level of the compound was calculated. |
| LUMO energy level evaluation method | Each compound was diluted at a concentration of $1 \times 10^{-5}$ M in $CHCl_3$, and an UV absorption spectrum thereof was measured at room temperature by using a Shimadzu UV-350 spectrometer, and a LUMO energy level thereof was calculated by using an optical band gap (Eg) and HOMO energy levels from an edge of the absorption spectrum. |
| $T_1$ energy level evaluation method | A mixture (each compound was dissolved in an amount of 1 milligrams (mg) in 3 cubic centimeters (cc) of toluene) of toluene and each compound was loaded into a quartz cell, and the resultant quartz cell was loaded into liquid nitrogen (77 Kelvins (K)). A photoluminescence spectrum thereof was measured by using a device for measuring photoluminescence, and the obtained spectrum was compared with a photoluminescence spectrum measured at room temperature, and peaks observed only at low temperature were analyzed to calculate $T_1$ energy levels. |

TABLE 3

| Compound No. | HOMO (eV) (found) | LUMO (eV) (found) | $T_1$ energy level (eV) |
|---|---|---|---|
| 79 | −5.63 | −2.07 | 3.03 |
| 88 | −5.74 | −2.21 | 3.02 |

From Table 3, it is confirmed that the compounds above have electric characteristics that are suitable for use as a material for forming an organic light-emitting device.

Evaluation Example 2

Luminance Spectrum Evaluation

The ultraviolet (UV) absorption spectra and photoluminescence (PL) spectra of Compounds 79 and 88 were evaluated to identify luminescent characteristics of compounds. In addition, low temperature PL spectra (LTPL) of Compounds 79 and 88 were evaluated.

First, Compound 79 was diluted at a concentration of 0.2 millimolar (mM) in toluene, and then, the UV absorption spectrum thereof was measured by using a Shimadzu UV-350 spectrometer. The same experiment was performed on Compound 88.

Compound 79 was diluted at a concentration of 10 mM in toluene, and then, the PL spectrum (@298K) thereof was measured by using a xenon-equipped ISC PC1 spectrofluorometer. The same experiment was performed with Compound 88.

Finally, Compound 79 was diluted at a concentration of $10^{-4}$ M in 2-methyltetrahydrofuran, and the result was placed into a quartz cell. Liquid nitrogen (@77K) was added thereto, and a LTPL spectrum thereof was measured. This experiment was performed with Compound 88 in the same manner as described herein.

Figure 2:
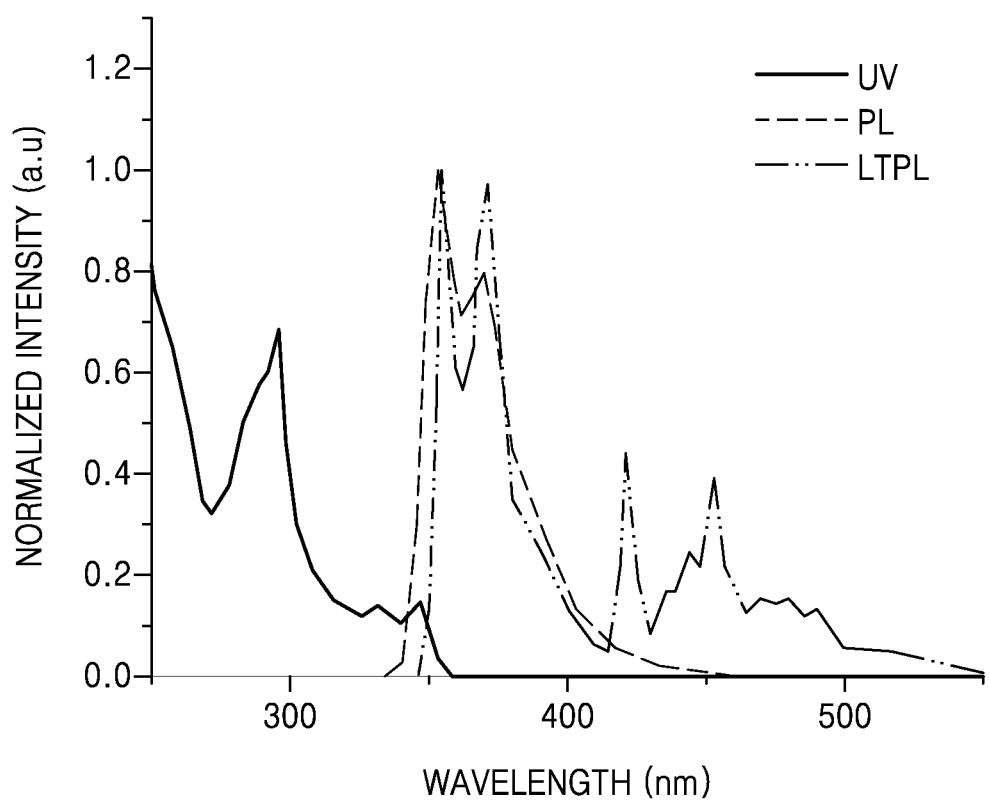
FIG. 2 is a graph of normalized intensity (arbitrary units, a. u.) versus wavelength (nanometers, nm) illustrating an ultraviolet (UV) absorption spectrum, photoluminescence (PL) spectrum, and low-temperature PL spectrum of Compound 79.
Figure 3:
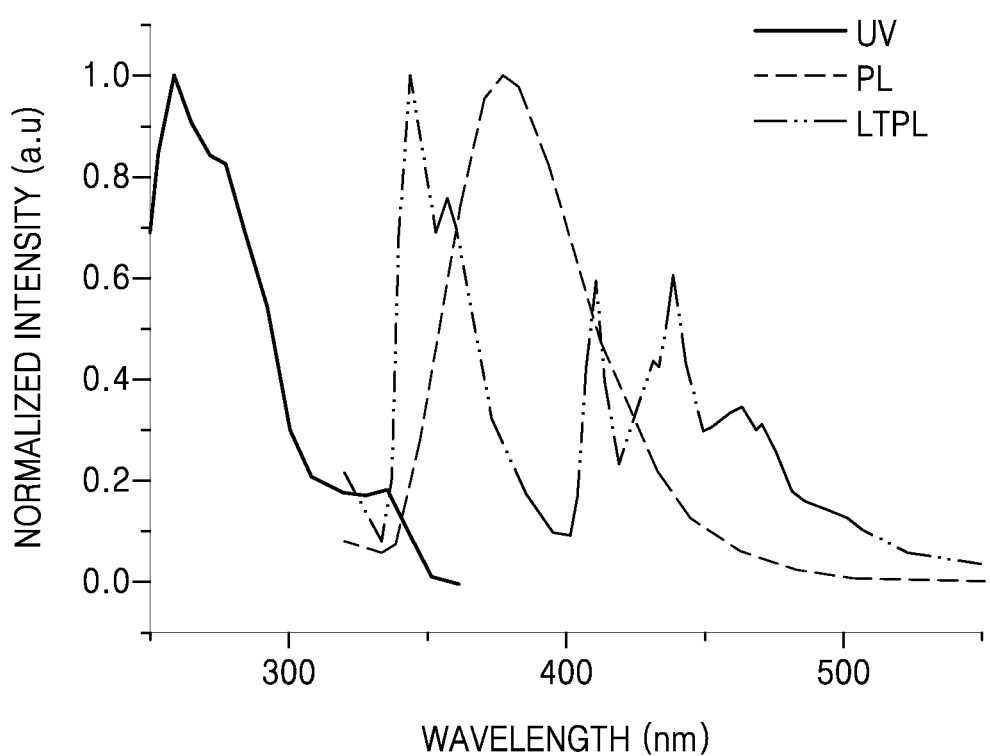
FIG. 3 is a graph of normalized intensity (arbitrary units, a. u.) versus wavelength (nanometers, nm) illustrating a UV absorption spectrum, PL spectrum, and low-temperature PL spectrum of Compound 88.

FIG. 2 illustrates the UV absorption spectrum, PL spectrum, and LTPL spectrum of Compound 79, and FIG. 3 illustrates the UV absorption spectrum, PL spectrum, and LTPL spectrum of Compound 88.

Referring to FIGS. 2 and 3, it may be seen that Compounds 79 and 88 have excellent luminescent characteristics.

Example 1

ITO glass substrate (ITO layer acts as an anode) having a surface resistance of 15 ohms per square centimeter ($Ω/cm^2$) was cut to a size of 50 millimeters (mm)×50 mm×0.7 mm and sonicated with acetone, isopropyl alcohol, and pure water, in each solvent for 15 minutes, and cleaned with UV ozone for 30 minutes.

On the ITO anode, NPB was deposited at a vacuum degree of $650×10^{-7}$ Pascals (Pa) and at a deposition speed of 0.1 to 0.3 nanometers per second (nm/s) to form a hole transport layer having a thickness of 700 Angstroms (Å), and mCP was deposited on the hole transport layer to form an electron blocking layer having a thickness of 50 Å to form a hole transport region.

Compound 79 (host) and Compound $FLr_6$ (dopant, 10 percent by weight (wt %)) were co-deposited on the hole transport region to form an emission layer having a thickness of 300 Å.

TmPyPB was vacuum deposited on the emission layer to form a hole blocking layer having a thickness of 300 Å, $Alq_3$ was vacuum deposited on the hole blocking layer to form an electron transport layer having a thickness of 100 Å. Then, LiF was deposited on the electron transport layer to form an electron injection layer having a thickness of 5 Å, and Al second electrode(cathode) having a thickness of 1,200 Å was formed on the electron injection layer, thereby completing the manufacture of an organic light-emitting device.

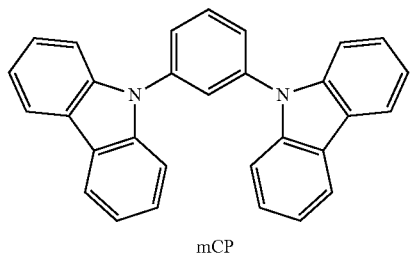

mCP

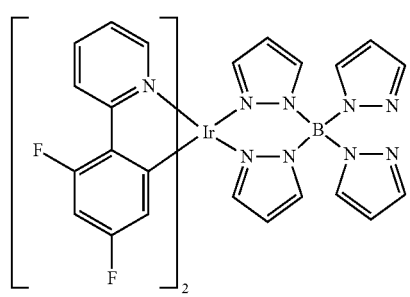

FIr6

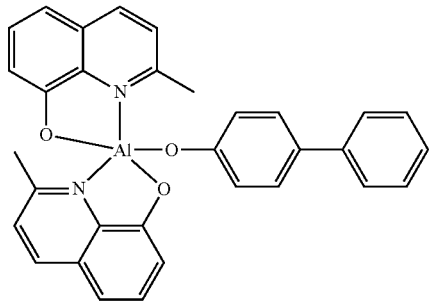

BAlq

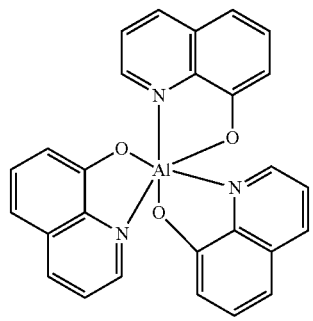

Alq$_3$

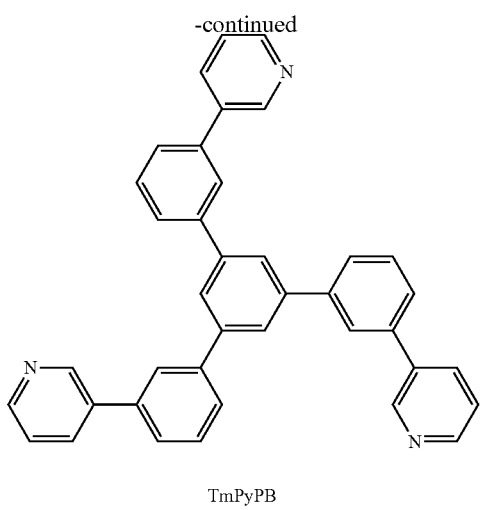

TmPyPB

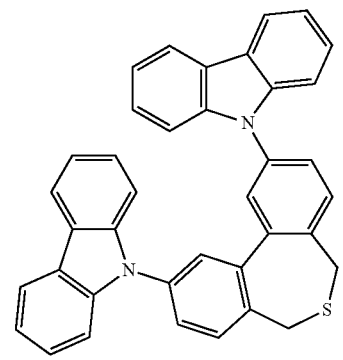

79

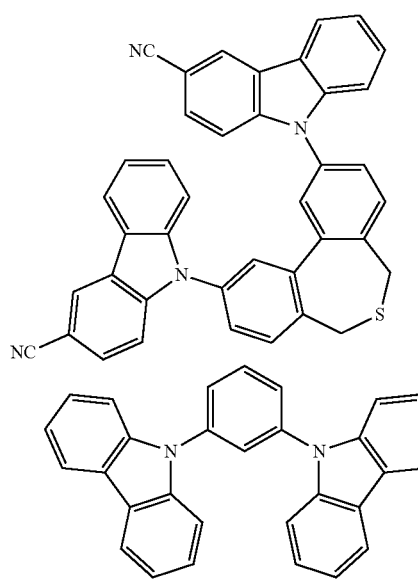

88 mCP

Example 2 and Comparative Example 1

Organic light-emitting devices were manufactured in the same manner as in Example 1, except that in forming an emission layer, for use as a host, corresponding compounds shown in Table 4 were used instead of Compound 79.

Evaluation Example 3

Evaluation on Characteristics of Organic Light-emitting Devices

The driving voltage, current density, quantum efficiency, and lifespan of the organic light-emitting devices manufactured according to Examples 1 and 2, and Comparative Example 1 were measured by using a current-voltage meter (Keithley 2400) and a brightness meter (Minolta Cs-1000A). Results thereof are shown in Table 4.

$T_{95}$ (at 500 candelas per square meter ($cd/m^2$)) in Table 4 indicates an amount of time that lapsed when 100% of the initial luminance was decreased to 95%.

In Table 4, the driving voltage, current density, quantum efficiency, and lifespan ($T_{95}$) of the organic light-emitting devices of Examples 1 and 2 were evaluated as relative values with respect to the driving voltage, current density, quantum efficiency, and lifespan ($T_{95}$) of the organic light-emitting device of Comparative Example 1. The driving voltage, current density, quantum efficiency, and lifespan ($T_{95}$) of the organic light-emitting device of Comparative Example 1 were regarded as "100."

From Table 4, it was confirmed that the organic light-emitting devices of Examples 1 to 2 have a lower driving voltage, a higher efficiency, a higher power, a higher quantum luminescent efficiency, and a longer lifespan than the organic light-emitting device of Comparative Example 1.

The condensed cyclic compound according to embodiments has excellent electric characteristics and thermal stability. Accordingly, an organic light-emitting device including the condensed cyclic compound may have low driving voltage, high efficiency, high luminance, and a long lifespan.

It should be understood that exemplary embodiments described herein should be considered in a descriptive sense only and not for purposes of limitation. Descriptions of features or aspects within each exemplary embodiment

TABLE 4

| | Host | Driving voltage (relative value) | Current density (relative value) | Quantum efficiency (relative value) | Lifespan (T95) (relative value) | Emission color |
|---|---|---|---|---|---|---|
| Example 1 | Compound 79 | 88 | 175 | 124 | 161 | Blue |
| Example 2 | Compound 88 | 96 | 148 | 101 | 108 | Blue |
| Comparative Example 1 | mCP | 100 | 100 | 100 | 100 | Blue | should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the instant inventive concept as defined by the following claims.

What is claimed is:

1. A condensed cyclic compound represented by Formula 1:

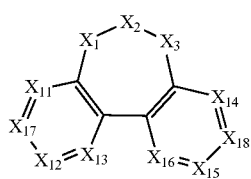

Formula 1 wherein in Formula 1, $X_1$ is selected from O, S, S(=O)$_2$, N-(L$_1$)$_{a1}$-(R$_1$), C(R$_4$)(R$_5$), and Si(R$_4$)(R$_5$), $X_2$ is selected from O, S, S(=O)$_2$, N-(L$_2$)$_{a2}$-(R$_2$), C(R$_6$)(R$_7$), and Si(R$_6$)(R$_7$), $X_3$ is selected from O, S, S(=O)$_2$, N-(L$_3$)$_{a3}$-(R$_3$), C(R$_8$)(R$_9$), and Si(R$_8$)(R$_9$), $X_{11}$ is N or C-(L$_{11}$)$_{a11}$-(R$_{11}$), $X_{12}$ is N or C-(L$_{12}$)$_{a12}$-(R$_{12}$), $X_{13}$ is N or C-(L$_{13}$)$_{a13}$-(R$_{13}$), $X_{14}$ is N or C-(L$_{14}$)$_{a14}$-(R$_{14}$), $X_{15}$ is N or C-(L$_{15}$)$_{a15}$-(R$_{15}$), $X_{16}$ is N or C-(L$_{16}$)$_{a16}$-(R$_{16}$), $X_{17}$ is N or C-(L$_{17}$)$_{a17}$-(R$_{17}$), and $X_{18}$ is N or C-(L$_{18}$)$_{a18}$-(R$_{18}$), provided that i) $X_{11}$ to $X_{18}$ are not all N, ii) $X_{11}$ to $X_{18}$ are not all CH, iii) at least one selected from $X_{17}$ and $X_{18}$ is CH, and iv) at least one selected from $X_{11}$ to $X_{16}$ is neither N nor CH, and provided that at least one selected from $R_{12}$ and $R_{17}$ or at least one selected from $R_{15}$ and $R_{18}$ is independently selected from a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, and a naphthyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a phenyl group substituted with a C$_1$-C$_{20}$ alkyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, $L_1$ to $L_3$ and $L_{11}$ to $L_{18}$ are each independently selected from —O—, —S—, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a3 and a11 to a18 are each independently an integer selected from 0 to 3, and $R_1$ to $R_9$ and $R_{11}$ to $R_{18}$ are each independently selected from a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, provided that -$(L_{12})_{a12}$-$(R_{12})$ and -$(L_{15})_{a15}$-$(R_{15})$ are not both —$OCH_3$ when $X_{12}$ is C-$(L_{12})_{a12}$-$(R_{12})$ and $X_{15}$ is C-$(L_{15})_{a15}$-$(R_{15})$, provided that when $X_2$ is $C(R_6)(R_7)$, at least one of $R_{11}$ to $R_{18}$ is selected from a substituted or unsubstituted $C_1$-$C_{10}$ heterocycloalkyl group, a substituted or unsubstituted $C_1$-$C_{10}$ heterocycloalkenyl group, a substituted or unsubstituted $C_1$-$C_{60}$ heteroaryl group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$.

2. The condensed cyclic compound of claim 1, wherein $X_1$ is $C(R_4)(R_5)$;

$X_2$ is $C(R_6)(R_7)$; or $X_3$ is $C(R_8)(R_9)$.

3. The condensed cyclic compound of claim 1, wherein $X_1$ and $X_3$ are identical to each other.

4. The condensed cyclic compound of claim 1, wherein $X_1$ is $C(R_4)(R_5)$, $X_2$ is selected from O, S, S(=O)$_2$, and N-$(L_2)_{a2}$-$(R_2)$, and $X_3$ is $C(R_8)(R_9)$; or $X_1$ is O or S, $X_2$ is $C(R_6)(R_7)$, and $X_3$ is O or S.

5. The condensed cyclic compound of claim 1, wherein $L_1$ to $L_3$ and $L_{11}$ to $L_{18}$ are each independently selected from a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group; and a phenylene group, a naphthylene group, a fluorenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a furanylene group, a benzofuranylene group, a thiophenylene group, a benzothiophenylene group, a thiazolylene group, an isothiazolylene group, an isoxazolylene group, an oxazolylene group, an oxadiazolylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a carbazolyl group, and —$Si(Q_{33})(Q_{34})(Q_{35})$, wherein $Q_{33}$ to $Q_{35}$ are each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group.

6. The condensed cyclic compound of claim 1, wherein a1 to a3 and a11 to a18 are each independently 0 or 1.

7. The condensed cyclic compound of claim 1, wherein $R_1$ to $R_3$ are each independently selected from a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —$Si(Q_{33})(Q_{34})(Q_{35})$, wherein $Q_{33}$ to $Q_{35}$ are each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group.

8. The condensed cyclic compound of claim 1, wherein $R_4$ to $R_9$ are each independently selected from a hydrogen, a deuterium, a $C_1$-$C_{10}$ alkyl group, a $C_1$-$C_{10}$ alkoxy group, a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group; and a phenyl group, a naphthyl group, a fluorenyl group, a phenanthrenyl group, a pyrenyl group, a triphenylenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a furanyl group, a benzofuranyl group, a thiophenyl group, a benzothiophenyl group, a thiazolyl group, an isothiazolyl group, an isoxazolyl group, an oxazolyl group, an oxadiazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —Si($Q_{33}$)($Q_{34}$)($Q_{35}$), wherein $Q_{33}$ to $Q_{35}$ are each independently selected from a hydrogen, a $C_1$-$C_{10}$ alkyl group, a $C_1$-$C_{10}$ alkoxy group, a phenyl group, a naphthyl group, a phenanthrenyl group, a pyrenyl group, a triphenylenyl group, a pyridinyl group, a pyrimidinyl group, and a triazinyl group.

9. The condensed cyclic compound of claim 1, wherein $R_{11}$ to $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, and a naphthyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a phenyl group substituted with a $C_1$-$C_{20}$ alkyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$); and
—Si($Q_3$)($Q_4$)($Q_5$),
wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group,
wherein selection of $R_{11}$ to $R_{18}$ is subject to limitations of claim 1.

10. The condensed cyclic compound of claim 1, wherein $R_1$ to $R_3$ are each independently selected from groups represented by Formulae 4-1 to 4-51, 5-1 to 5-6, and 6-1 to 6-10,
$R_{11}$ to $R_{18}$ are each independently selected from
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;
groups represented by Formulae 4-1 to 4-51, 5-1 to 5-6, and 6-1 to 6-10; and
—Si($Q_3$)($Q_4$)($Q_5$),
wherein $Q_3$ to $Q_5$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

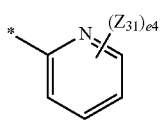

Formula 4-1

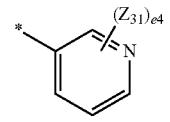

Formula 4-2

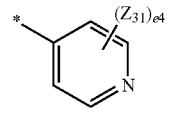

Formula 4-3

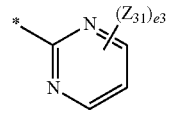

Formula 4-4

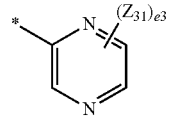

Formula 4-5

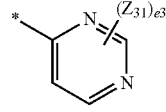

Formula 4-6

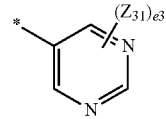

Formula 4-7

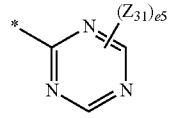

Formula 4-8

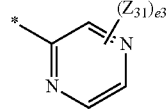

Formula 4-9

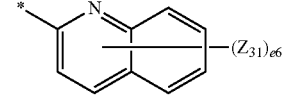

Formula 4-10

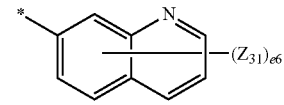

Formula 4-11

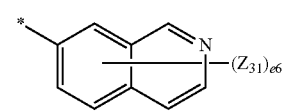

Formula 4-12

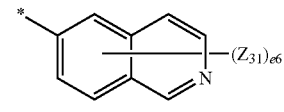

Formula 4-13

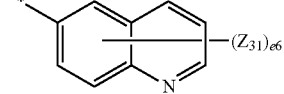

Formula 4-14

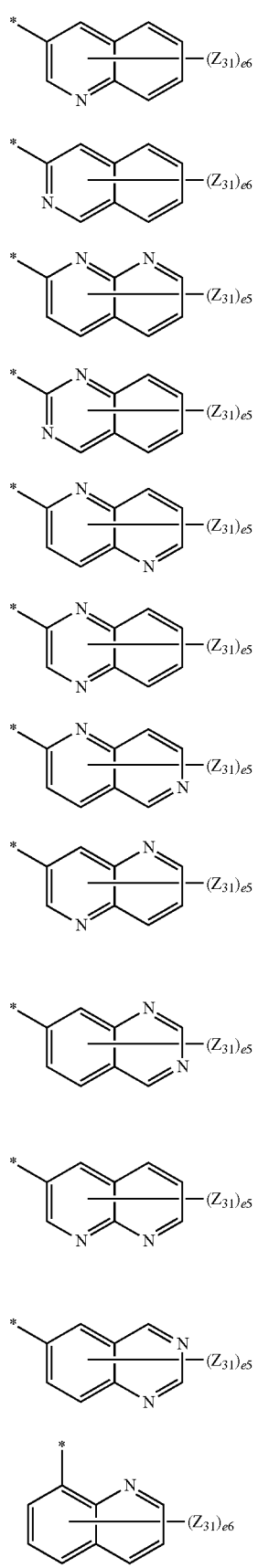
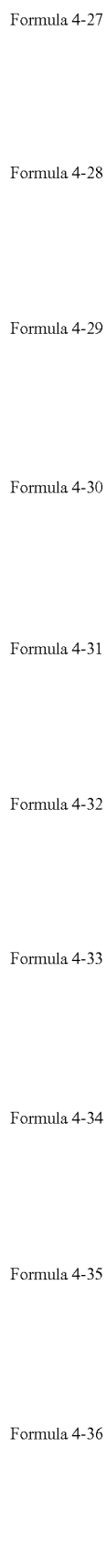
Formula 4-15
Formula 4-16
Formula 4-17
Formula 4-18
Formula 4-19
Formula 4-20
Formula 4-21
Formula 4-22
Formula 4-23
Formula 4-24
Formula 4-25
Formula 4-26
Formula 4-27
Formula 4-28
Formula 4-29
Formula 4-30
Formula 4-31
Formula 4-32
Formula 4-33
Formula 4-34
Formula 4-35
Formula 4-36

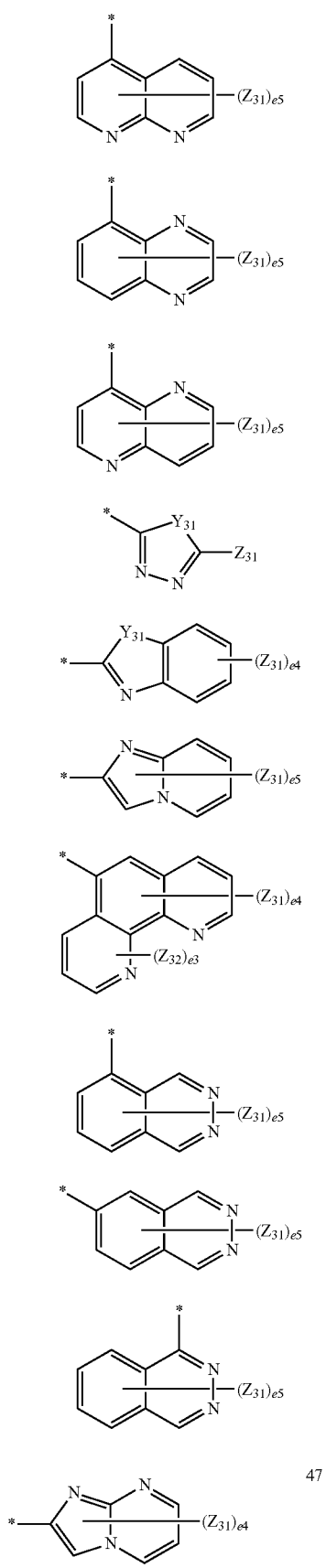
Formula 4-37
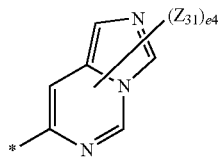
Formula 4-38
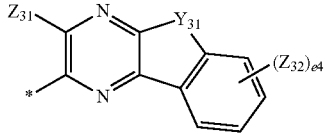
Formula 4-39
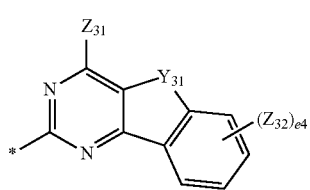
Formula 4-40
Formula 4-41
Formula 4-42
Formula 4-43
Formula 4-44
Formula 4-45
Formula 4-46
Formula 4-47
Formula 4-48
Formula 4-49
Formula 4-50
Formula 4-51
Formula 5-1
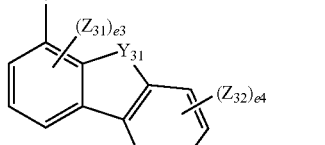
Formula 5-2
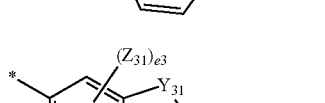
Formula 5-3
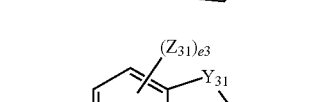
Formula 5-4
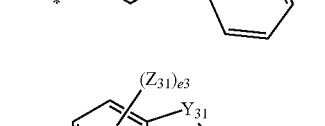
Formula 5-5
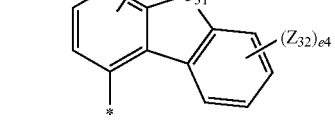
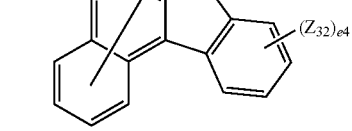

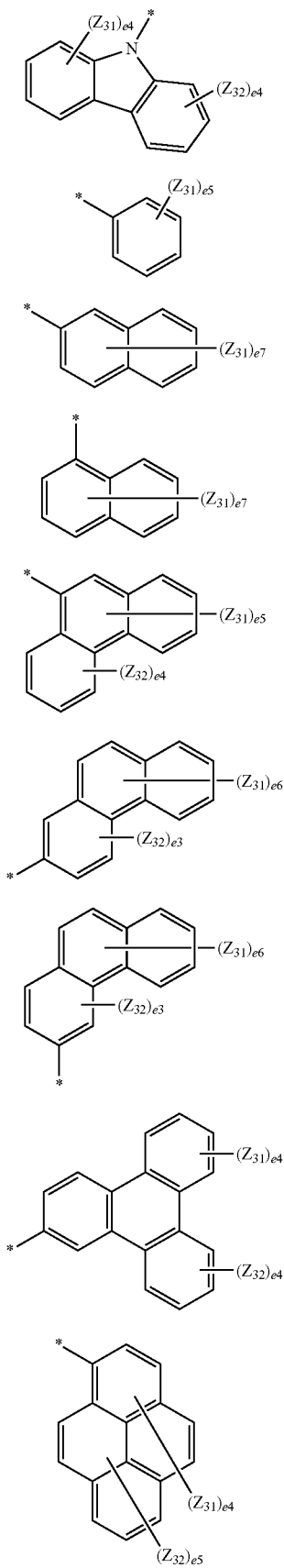

wherein in Formulae 4-1 to 4-51, 5-1 to 5-6, and 6-1 to 6-10, $Y_{31}$ is selected from O, S, $C(Z_{33})(Z_{34})$, $N(Z_{35})$, and $Si(Z_{36})(Z_{37})$, and $Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group substituted with a $C_1$-$C_{20}$ alkyl group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —$Si(Q_{33})(Q_{34})(Q_{35})$, wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, e2 is 1 or 2,
e3 is an integer selected from 1 to 3,
e4 is an integer selected from 1 to 4,
e5 is an integer selected from 1 to 5,
e6 is an integer selected from 1 to 6,
e7 is an integer selected from 1 to 7, and
* indicates a binding site to a neighboring atom,
wherein selection of $R_{11}$ to $R_{18}$ is subject to limitations of claim 1.

11. The condensed cyclic compound of claim 1, wherein $R_{11}$ to $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

groups represented by Formulae 4-1(1) to 4-8(1), 4-1(2) to 4-8(2), 4-1(3) to 4-8(3), 5-1(1) to 5-4(1), 5-1(2) to 5-4(2), 5-1(3) to 5-4(3), 5-1(4) to 5-4(4), 5-6(1) to 5-6(3), and 6-1(1) to 6-1(8); and —Si($Q_3$)($Q_4$)($Q_5$), wherein $Q_3$ to $Q_5$ are each independently selected from a hydrogen, a $C_1$-$C_{20}$ alkyl group, a $C_1$-$C_{20}$ alkoxy group, a phenyl group, and a naphthyl group:

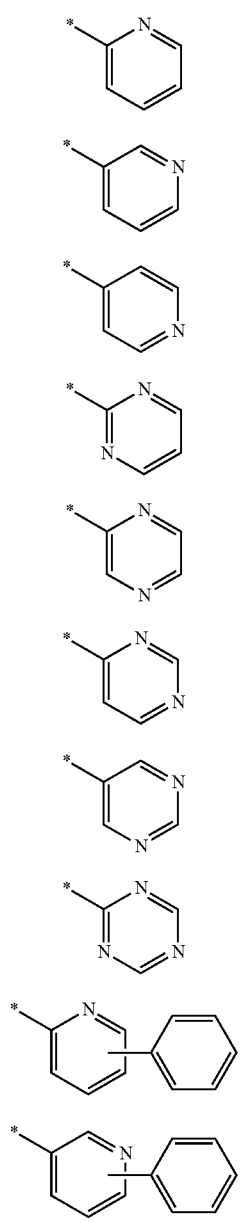

Formula 4-1(1)

Formula 4-2(1)

Formula 4-3(1)

Formula 4-4(1)

Formula 4-5(1)

Formula 4-6(1)

Formula 4-7(1)

Formula 4-8(1)

Formula 4-1(2)

Formula 4-2(2)

-continued

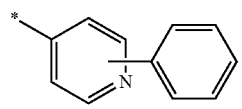

Formula 4-3(2)

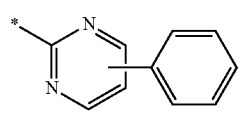

Formula 4-4(2)

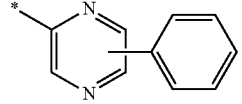

Formula 4-5(2)

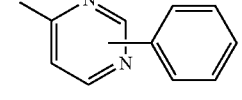

Formula 4-6(2)

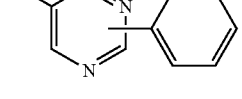

Formula 4-7(2)

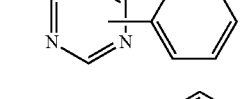

Formula 4-8(2)

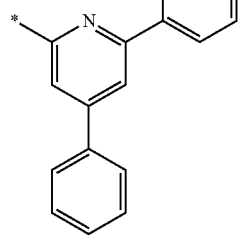

Formula 4-1(3)

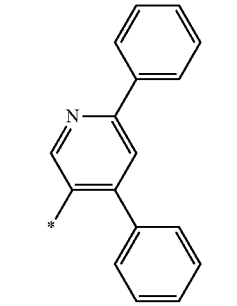

Formula 4-2(3)

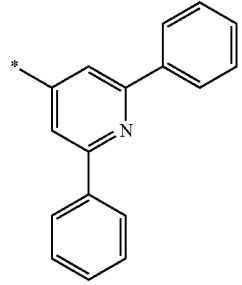

Formula 4-3(3)

-continued
Formula 4-4(3)
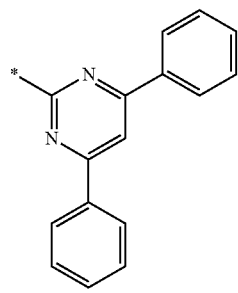
Formula 4-5(3)
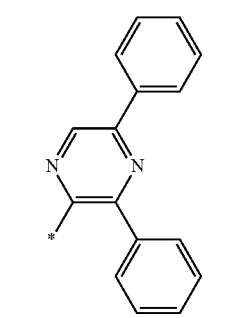
Formula 4-6(3)
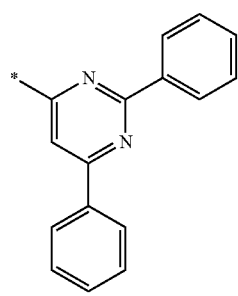
Formula 4-7(3)
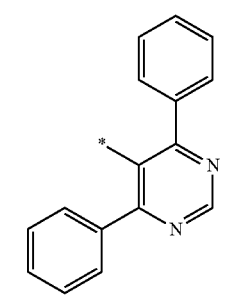
Formula 4-8(3)
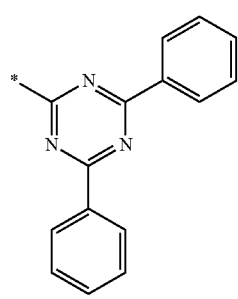
-continued
Formula 5-1(1)
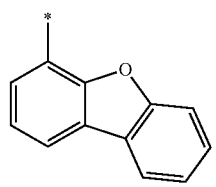
Formula 5-2(1)
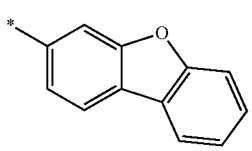
Formula 5-3(1)
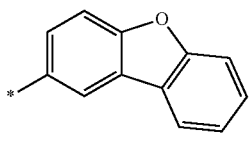
Formula 5-4(1)
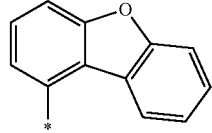
Formula 5-1(2)
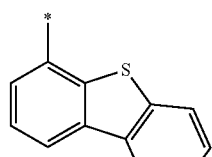
Formula 5-2(2)
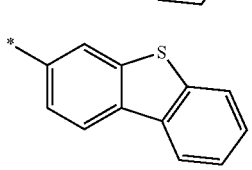
Formula 5-3(2)
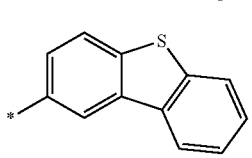
Formula 5-4(2)
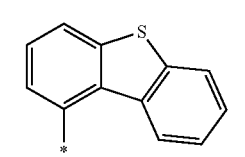
Formula 5-1(3)
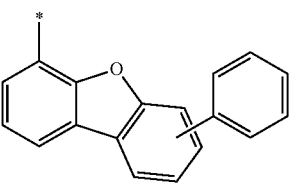
Formula 5-2(3)
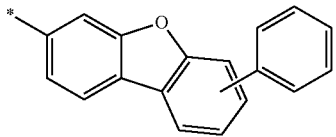

Formula 5-3(3)
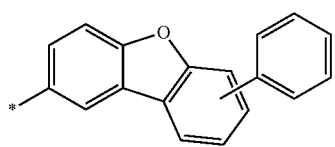
Formula 5-4(3)
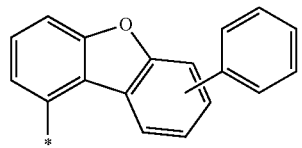
Formula 5-1(4)
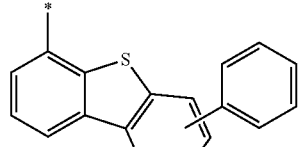
Formula 5-2(4)
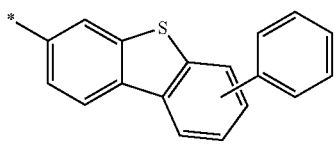
Formula 5-3(4)
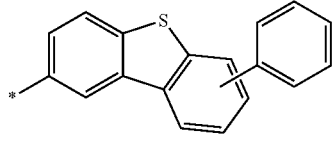
Formula 5-4(4)
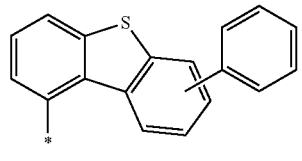
Formula 5-6(1)
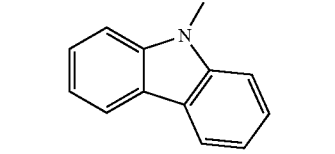
Formula 5-6(2)
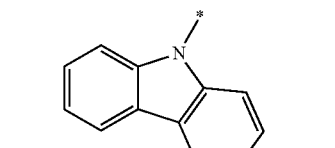
Formula 5-6(3)
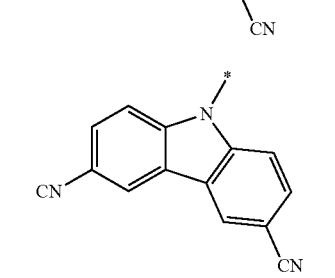
Formula 6-1(1)
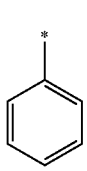
Formula 6-1(2)
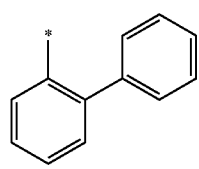
Formula 6-1(3)
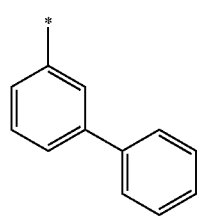
Formula 6-1(4)
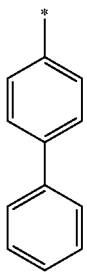
Formula 6-1(5)
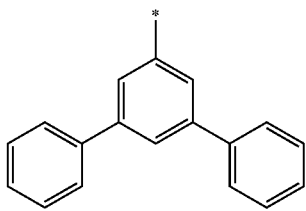
Formula 6-1(6)
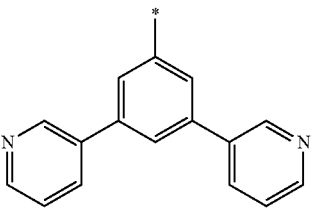
Formula 6-1(7)
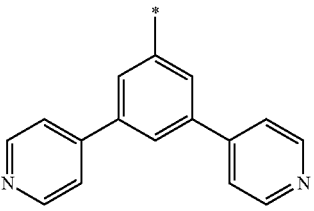

-continued

Formula 6-1(8)

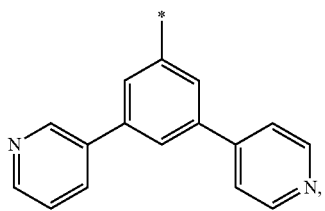

wherein selection of $R_{11}$ to $R_{18}$ is subject to limitations of claim 1.

12. The condensed cyclic compound of claim 1, wherein
$X_{11}$ is $C$-$(L_{11})_{a11}$-$(R_{11})$,
$X_{12}$ is $C$-$(L_{12})_{a12}$-$(R_{12})$,
$X_{13}$ is $C$-$(L_{13})_{a13}$-$(R_{13})$,
$X_{14}$ is $C$-$(L_{14})_{a14}$-$(R_{14})$,
$X_{15}$ is $C$-$(L_{15})_{a15}$-$(R_{15})$,
$X_{16}$ is $C$-$(L_{16})_{a16}$-$(R_{16})$,
$X_{17}$ is $CH$,
$X_{18}$ is $C$-$(L_{18})_{a18}$-$(R_{18})$, and
$R_{18}$ and at least one selected from $R_{11}$ to $R_{16}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a $C_6$-$C_{20}$ aryl group substituted with a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group,
wherein selection of $R_{11}$ to $R_{16}$ is subject to limitations of claim 1.

13. The condensed cyclic compound of claim 1, wherein
$X_{11}$ is $C$-$(L_{11})_{a11}$-$(R_{11})$,
$X_{12}$ is $C$-$(L_{12})_{a12}$-$(R_{12})$,
$X_{13}$ is $C$-$(L_{13})_{a13}$-$(R_{13})$,
$X_{14}$ is $C$-$(L_{14})_{a14}$-$(R_{14})$,
$X_{15}$ is $C$-$(L_{15})_{a15}$-$(R_{15})$,
$X_{16}$ is $C$-$(L_{16})_{a16}$-$(R_{16})$, and
$X_{17}$ and $X_{18}$ are $CH$, and
at least one selected from $R_{11}$ to $R_{16}$ is each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a $C_6$-$C_{20}$ aryl group substituted with a $C_6$-$C_{60}$ aryl group, a $C_6$-$C_{60}$ aryloxy group, a $C_6$-$C_{20}$ arylthio group, a $C_1$-$C_{60}$ heteroaryl group, a monovalent non-aromatic condensed polycyclic group, or a monovalent non-aromatic condensed heteropolycyclic group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group,
wherein selection of $R_{11}$ to $R_{16}$ is subject to limitations of claim 1.

14. The condensed cyclic compound of claim 1, wherein
$X_{11}$ is $C$-$(L_{11})_{a11}$-$(R_{11})$,
$X_{12}$ is $C$-$(L_{12})_{a12}$-$(R_{12})$,
$X_{13}$ is $C$-$(L_{13})_{a13}$-$(R_{13})$,
$X_{14}$ is $C$-$(L_{14})_{a14}$-$(R_{14})$,
$X_{15}$ is $C$-$(L_{15})_{a15}$-$(R_{15})$,
$X_{16}$ is $C$-$(L_{16})_{a16}$-$(R_{16})$,
$X_{17}$ is $CH$, and
$X_{18}$ is $C$-$(L_{18})_{a18}$-$(R_{18})$,
$R_{12}$ and $R_{18}$ are selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a $C_6$-$C_{20}$ aryl group substituted with a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, wherein selection of $R_{11}$ and $R_{13}$ to $R_{16}$ is subject to limitations of claim 1; or $X_{11}$ is $C$-$(L_{11})_{a11}$-$(R_{11})$,
$X_{12}$ is $C$-$(L_{12})_{a12}$-$(R_{12})$,
$X_{13}$ is $C$-$(L_{13})_{a13}$-$(R_{13})$,
$X_{14}$ is $C$-$(L_{14})_{a14}$-$(R_{14})$,
$X_{15}$ is $C$-$(L_{15})_{a15}$-$(R_{15})$,
$X_{16}$ is $C$-$(L_{16})_{a16}$-$(R_{16})$, and
$X_{17}$ and $X_{18}$ are $CH$, and
$R_{12}$ and $R_{15}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a $C_6$-$C_{20}$ aryl group substituted with a $C_6$-$C_{60}$ aryl group, a $C_6$-$C_{60}$ aryloxy group, a $C_1$-$C_{60}$ arylthio group, a $C_1$-$C_{60}$ heteroaryl group, a monovalent non-aromatic condensed polycyclic group, or a monovalent non-aromatic condensed heteropolycyclic group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, wherein selection of $R_{11}$, $R_{13}$, $R_{14}$, and $R_{16}$ is subject to limitations of claim 1.

15. The condensed cyclic compound of claim 1, wherein the condensed cyclic compound is represented by Formula 1A or 1B:

Formula 1A

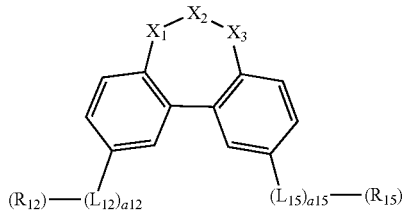

Formula 1B

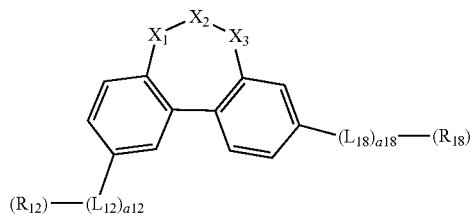

$X_1$, $X_2$, $X_3$, $L_{12}$, $L_{15}$, $L_{18}$, a12, a15, a18, $R_{12}$, $R_{15}$, and $R_{18}$ in Formulae 1A and 1B are the same as define in claim 1, provided that each of $R_{12}$, $R_{15}$, and $R_{18}$ is not a hydrogen.

16. The condensed cyclic compound of claim 1, wherein the condensed cyclic compound is represented by one of Formulae 1A(1) to 1A(3) and 1B(1) to 1B(3):

Formula 1A(1)

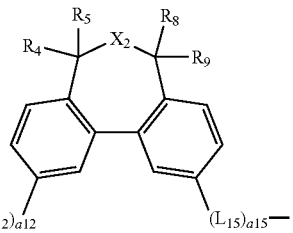

Formula 1A(2)

Formula 1A(3)

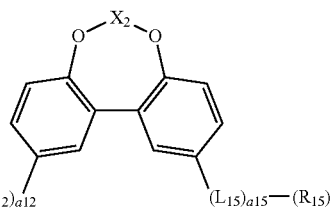

Formula 1B(1)

Formula 1B(2)

Formula 1B(3)

wherein $X_2$, $L_{12}$, $L_{15}$, $L_{18}$, a12, a15, a18, $R_4$, $R_5$, $R_8$, $R_9$, $R_{12}$, $R_{15}$, and $R_{18}$ in Formulae 1A(1) to 1A(3) and 1B(1) to 1B(3) are the same as defined in claim 1, provided that each of $R_{12}$, $R_{15}$, and $R_{18}$ is not a hydrogen.

17. A condensed cyclic compound, which is one of Compounds 1 to 768:

1

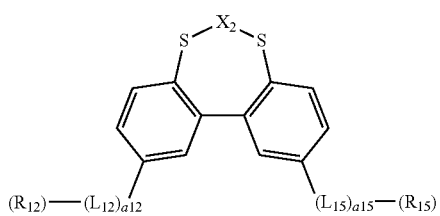

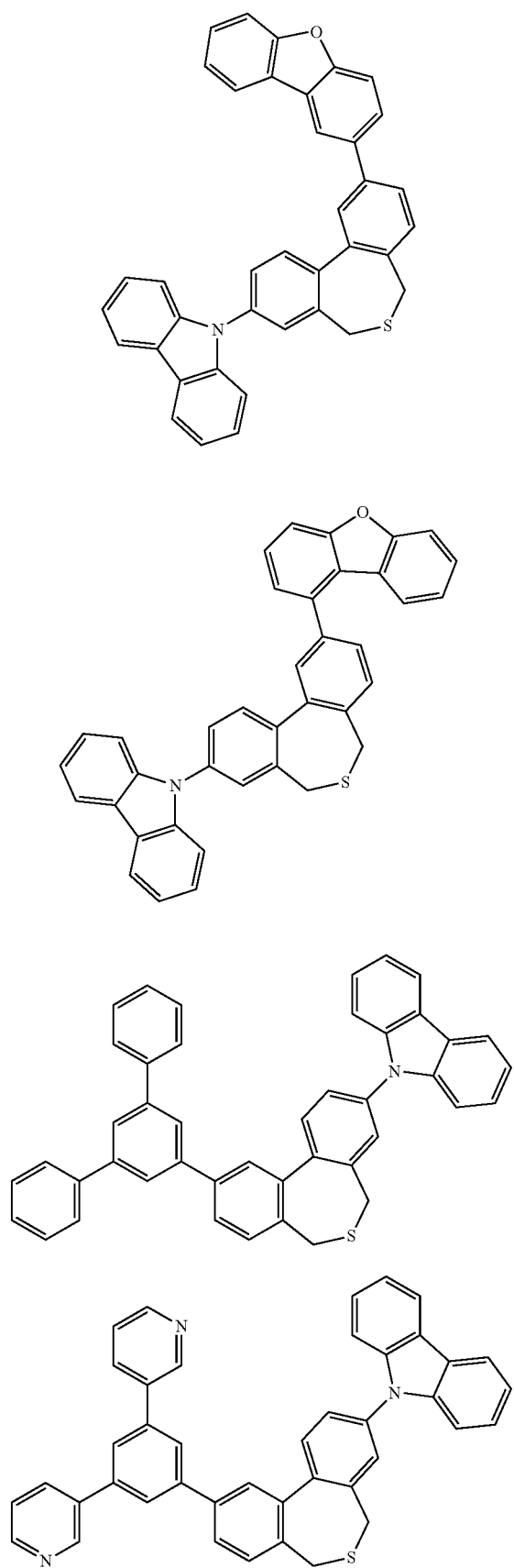
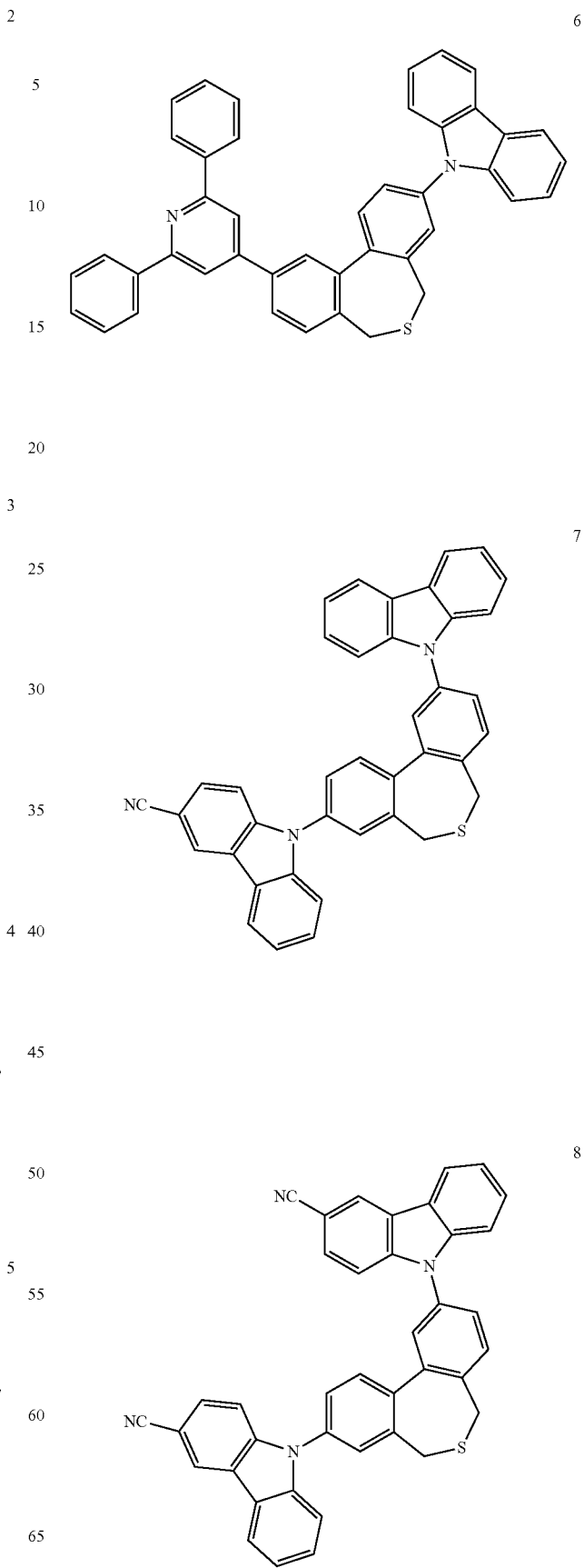

9
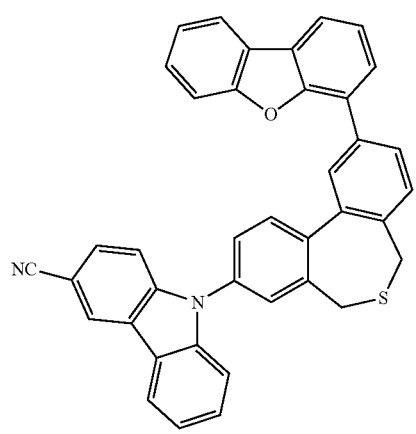
12
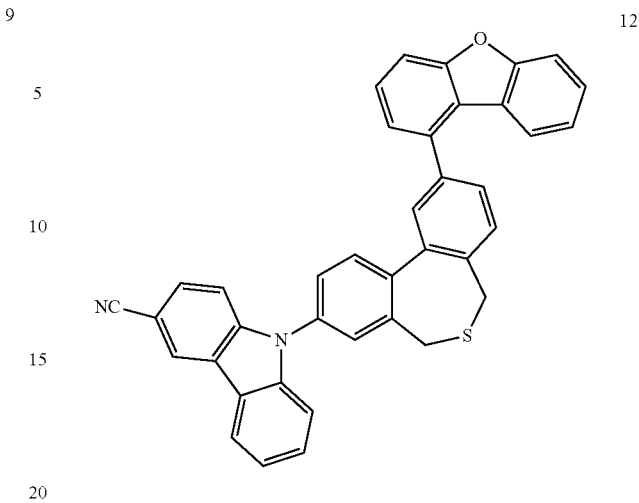
10
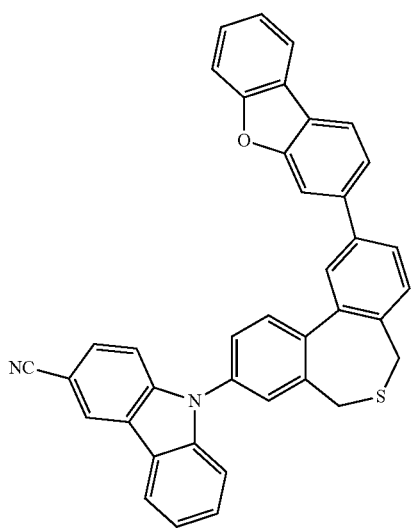
13
11
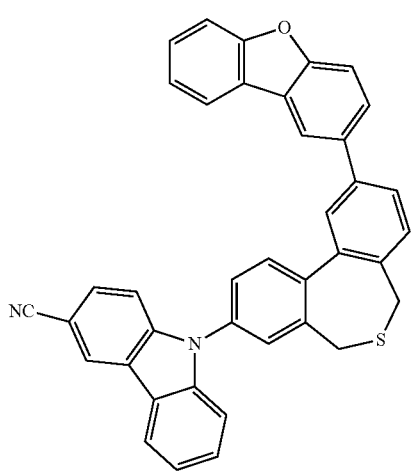
14
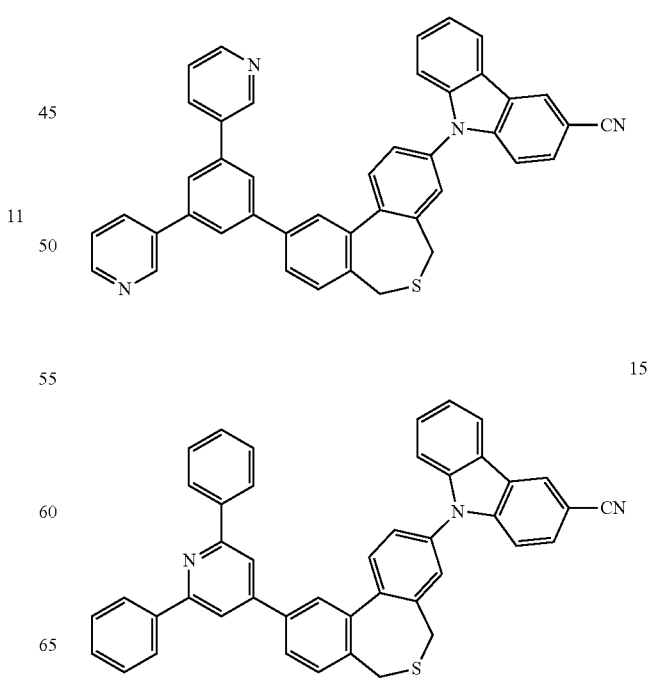
15

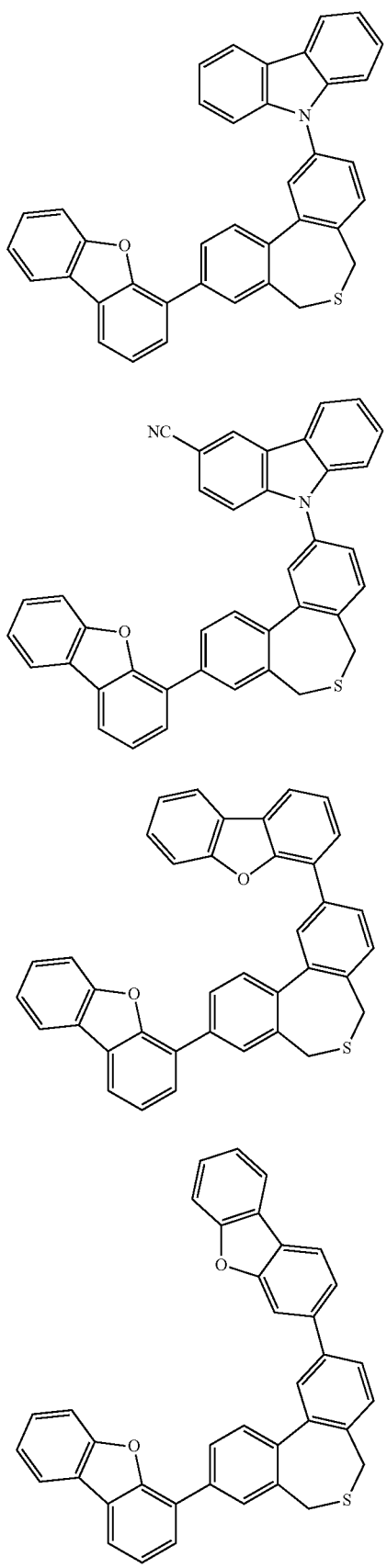
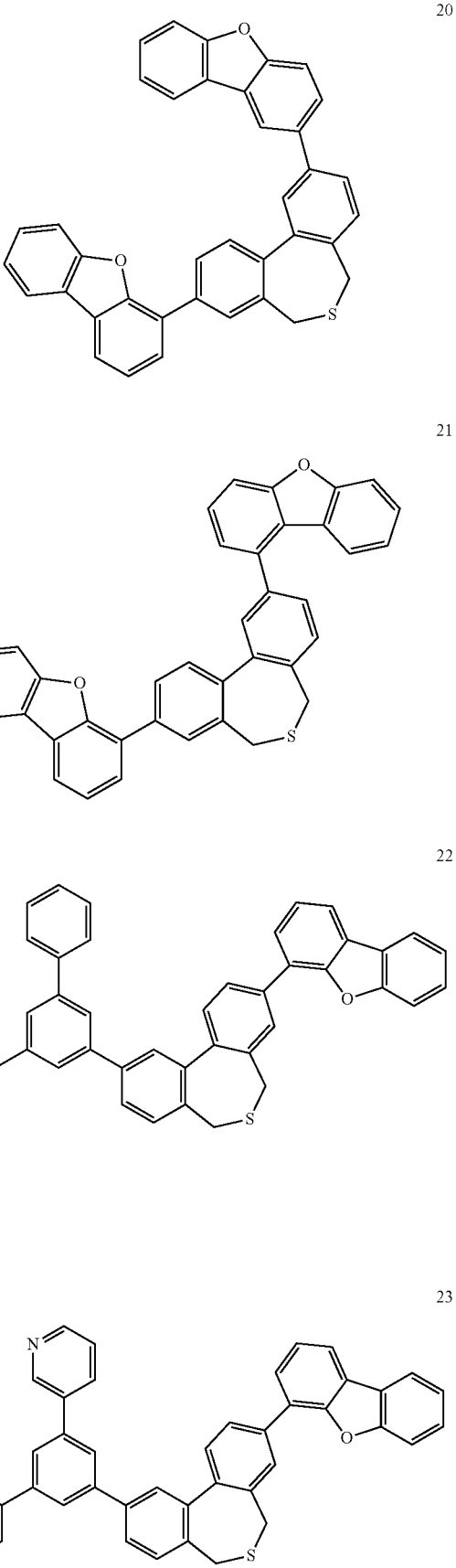

24
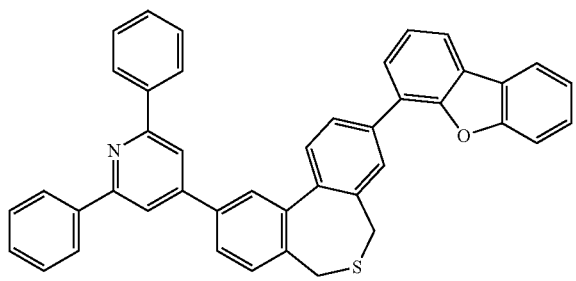
25
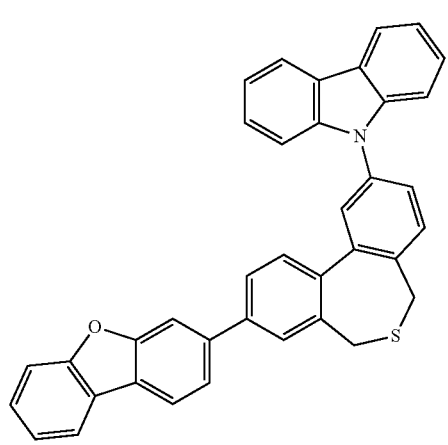
26
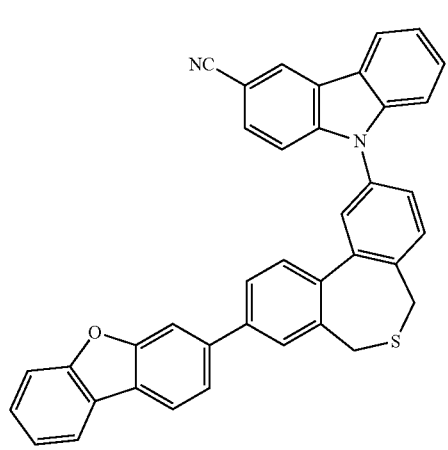
27
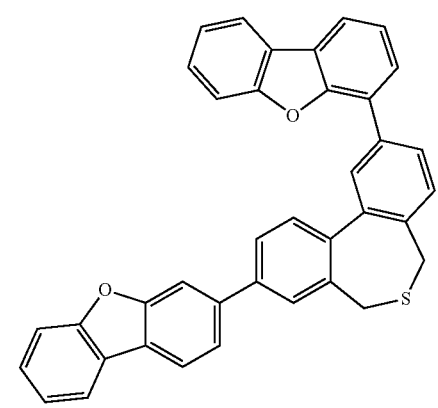
28
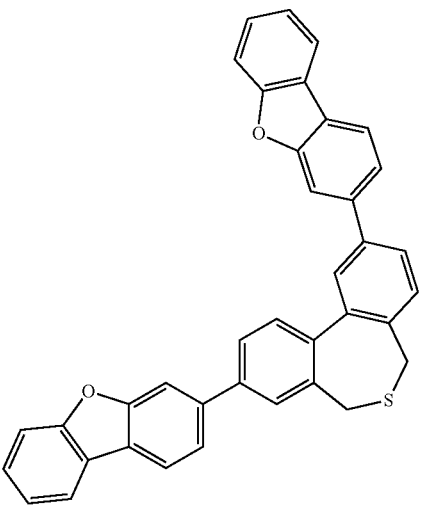
29
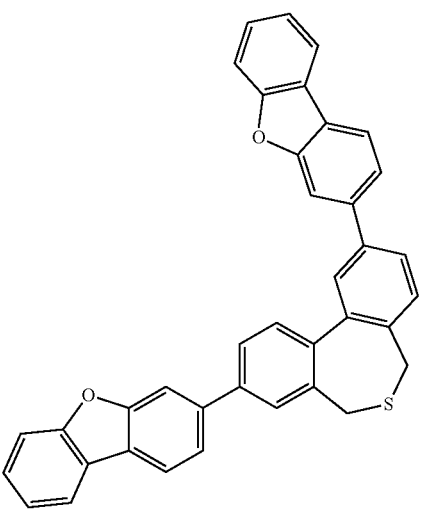
30
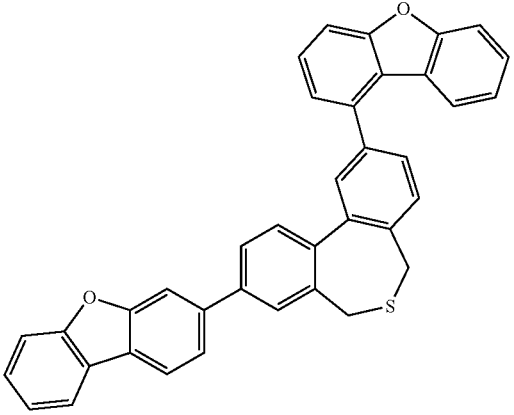

-continued
31
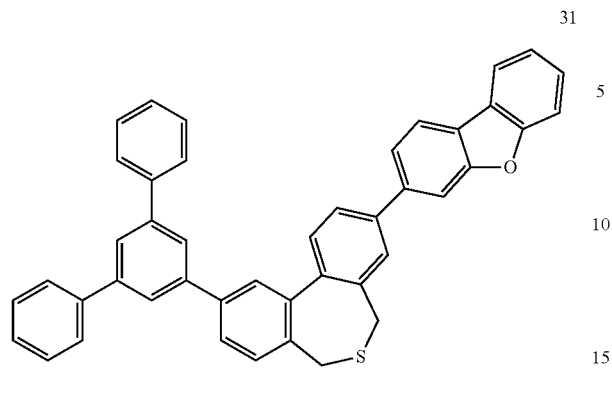
32
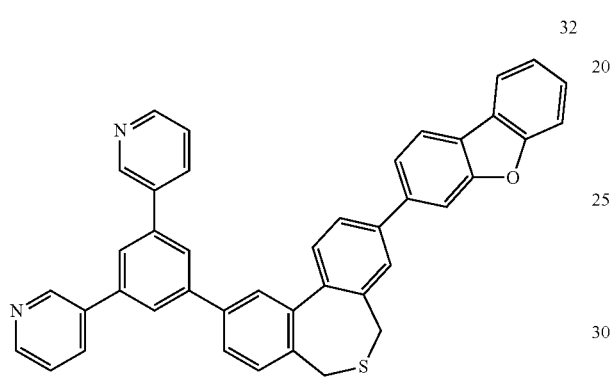
33
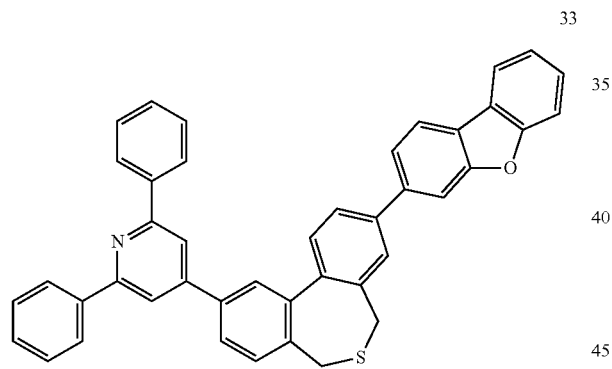
34
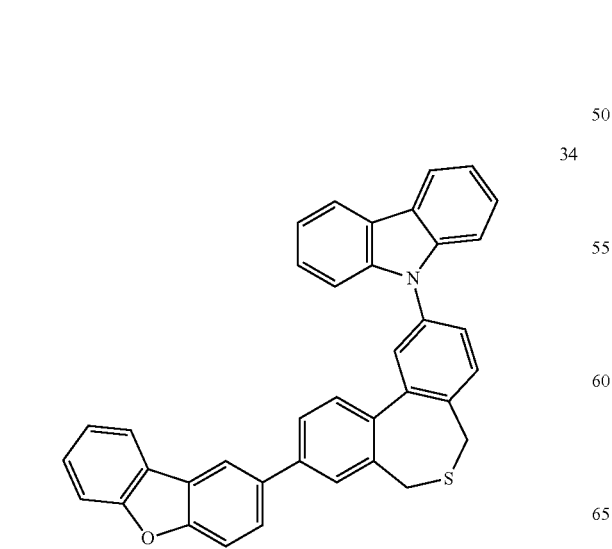
-continued
35
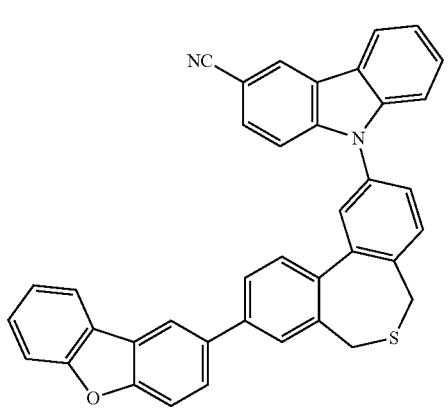
36
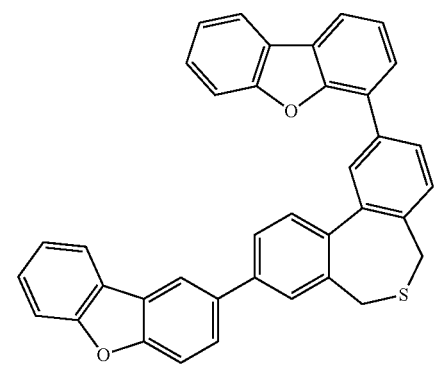
37
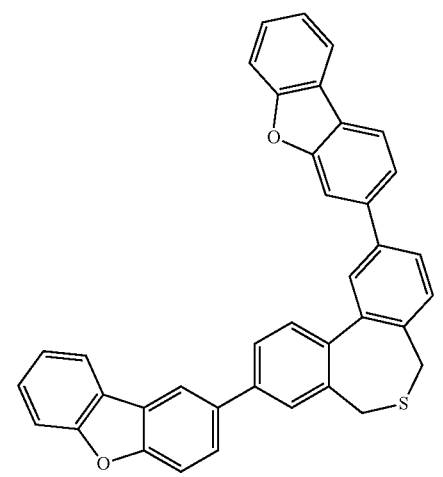
38
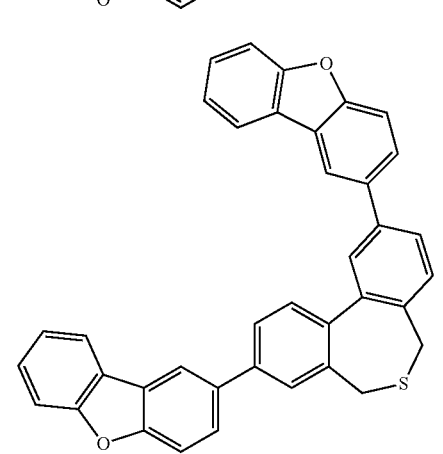

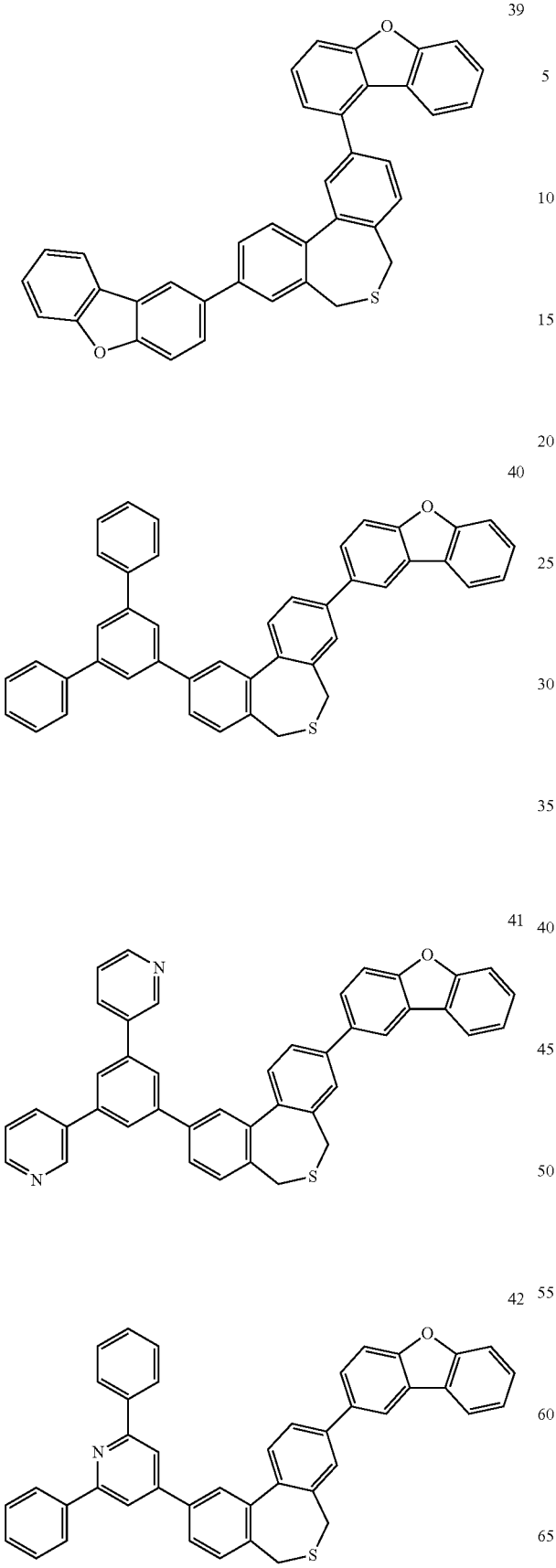
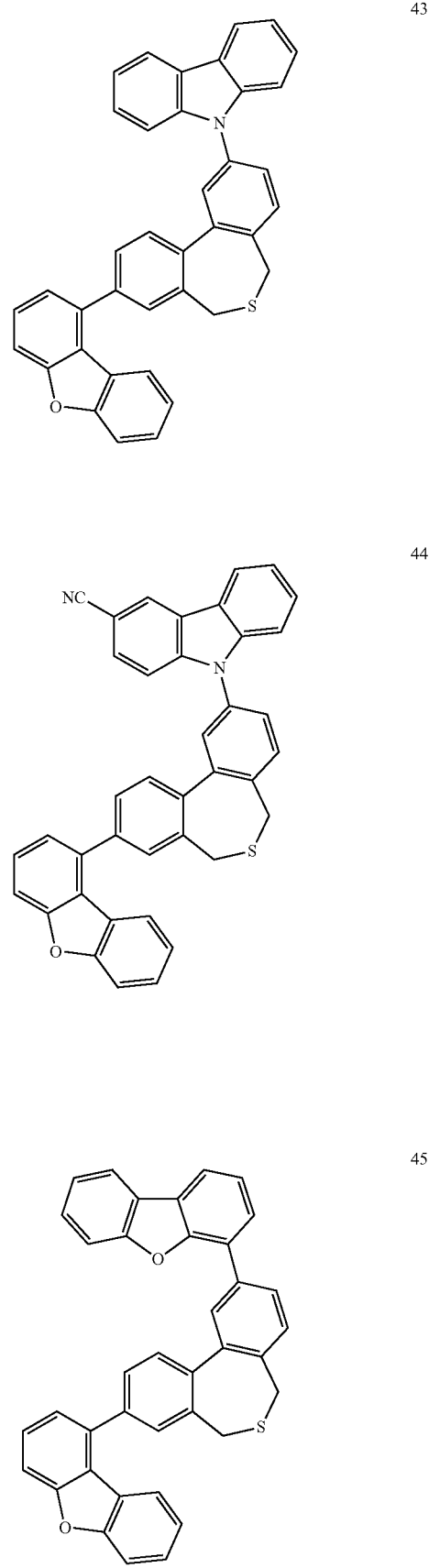

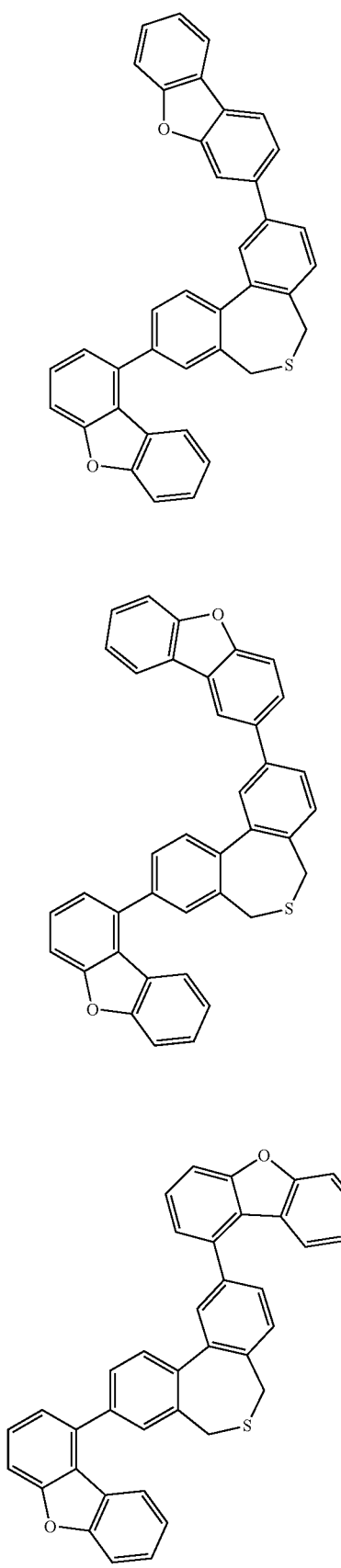
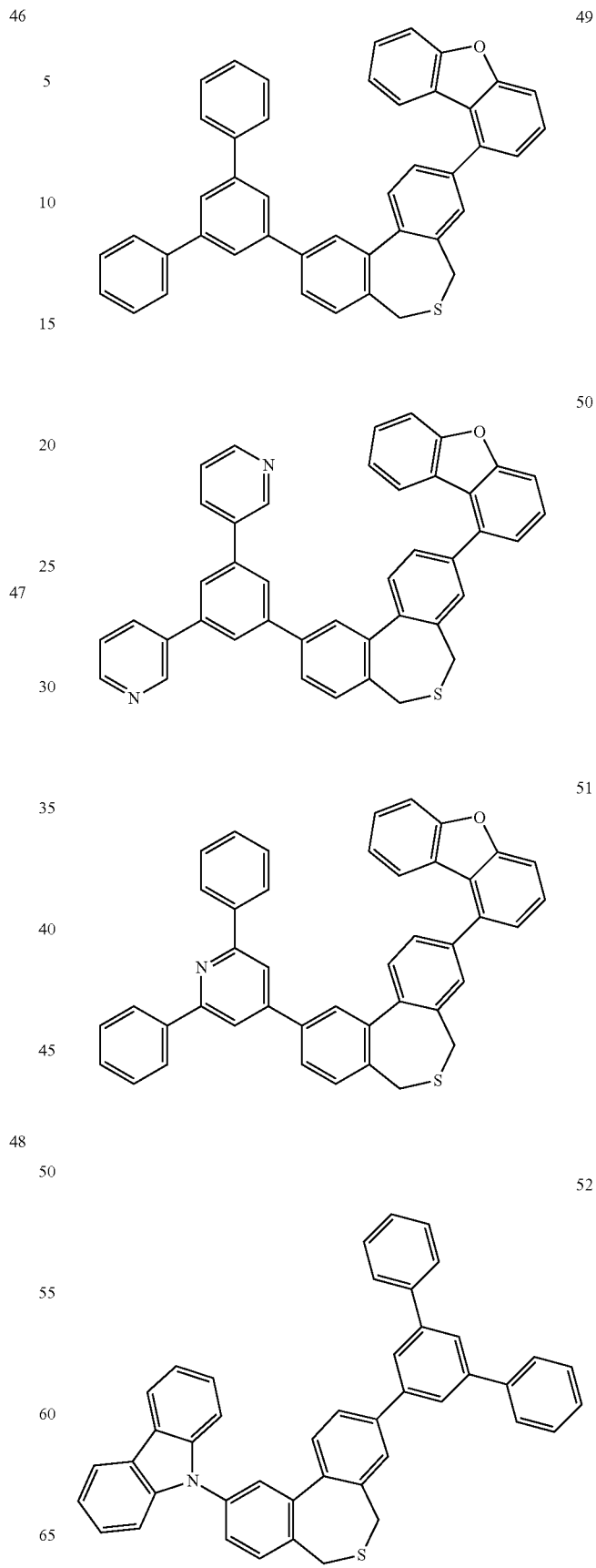

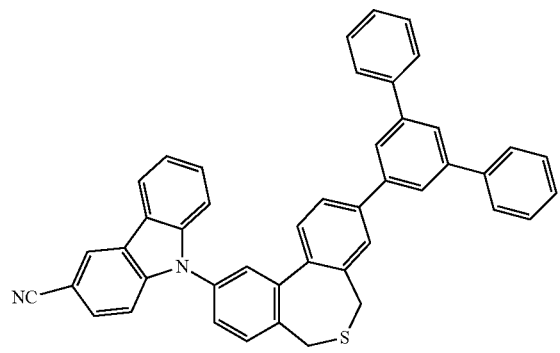
53
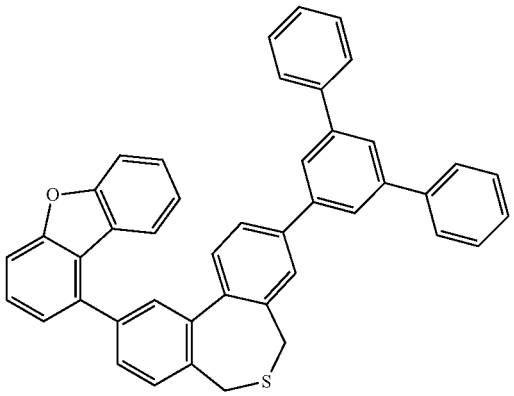
57
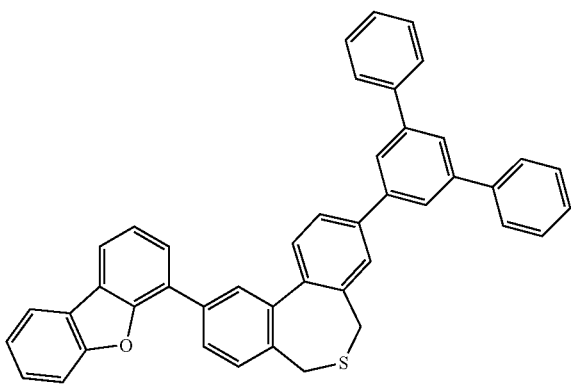
54
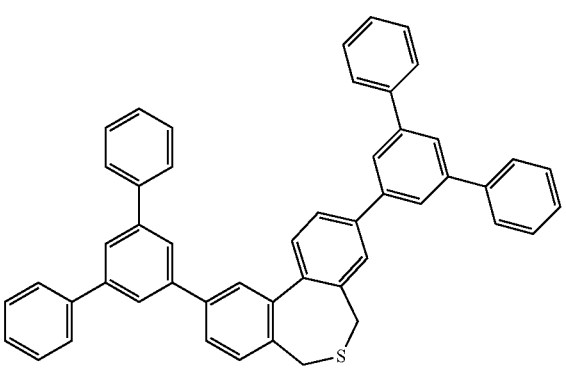
58
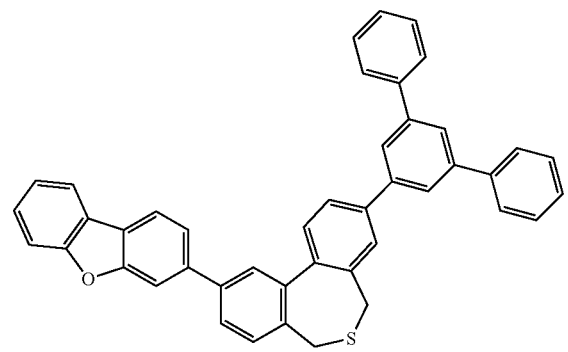
55
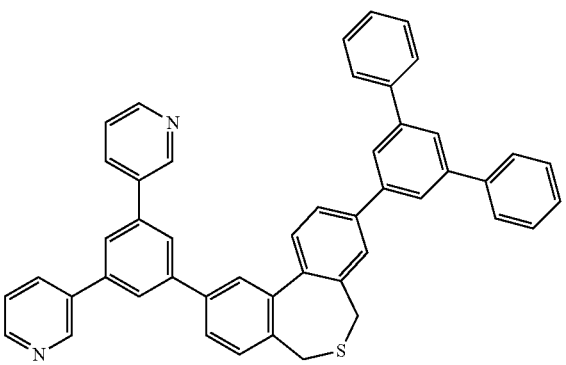
59
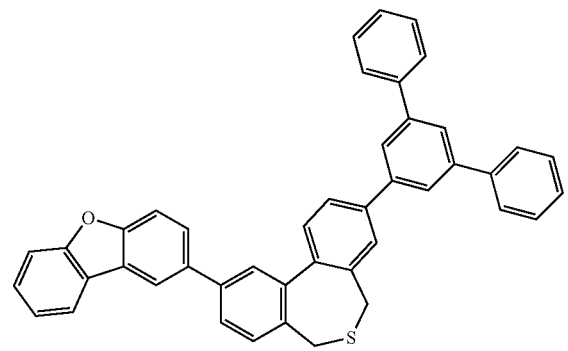
56
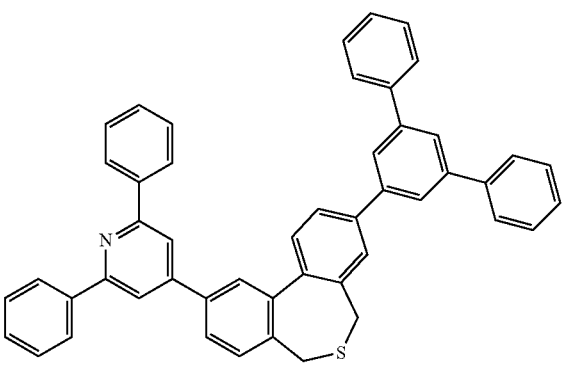
60

-continued
61
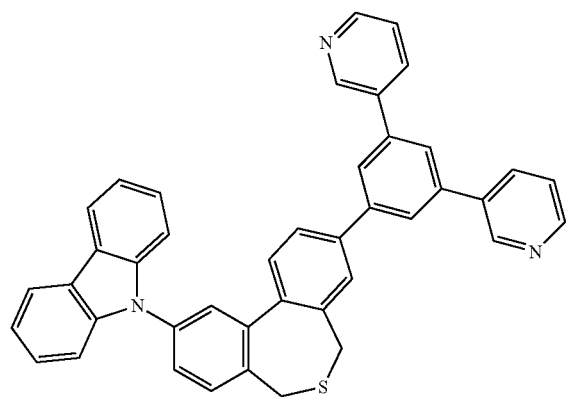
62
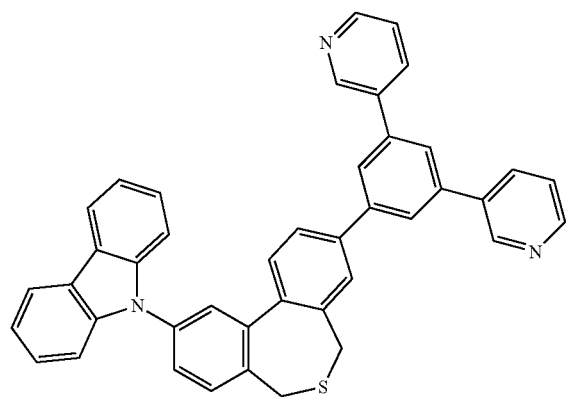
63
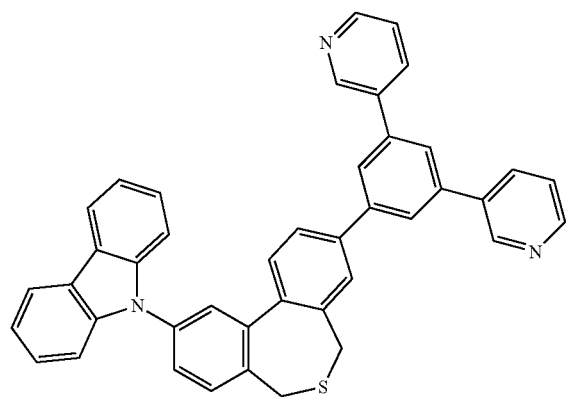
64
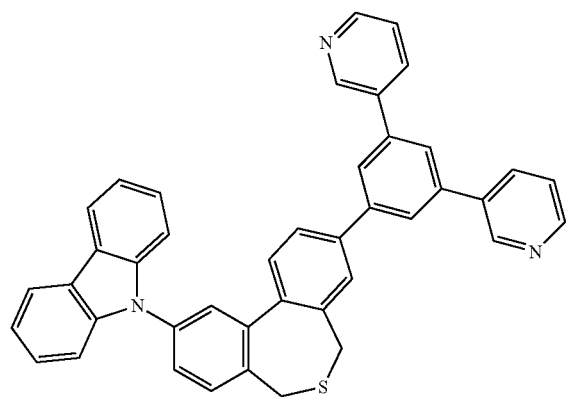
-continued
65
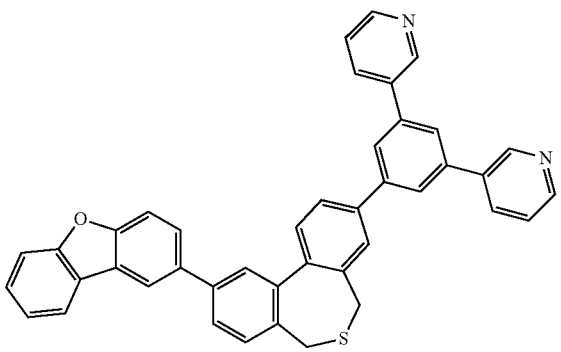
66
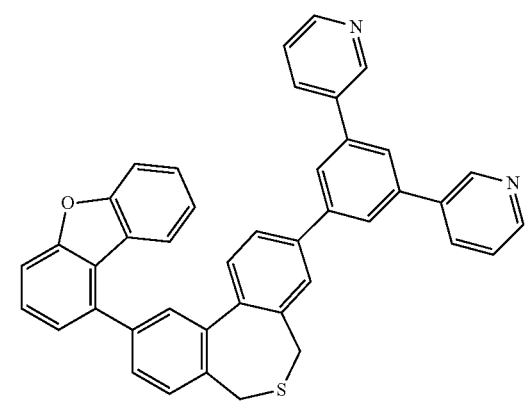
67
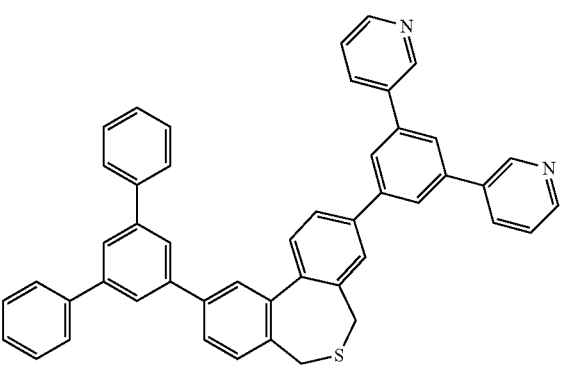
68
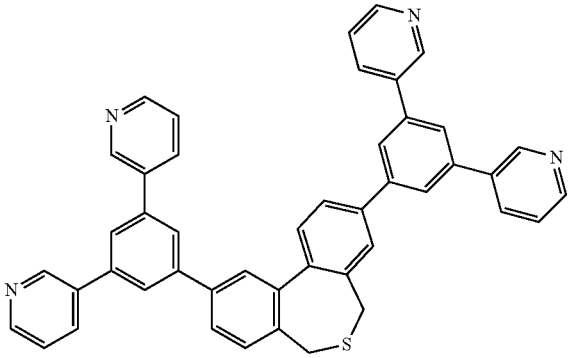

-continued
69
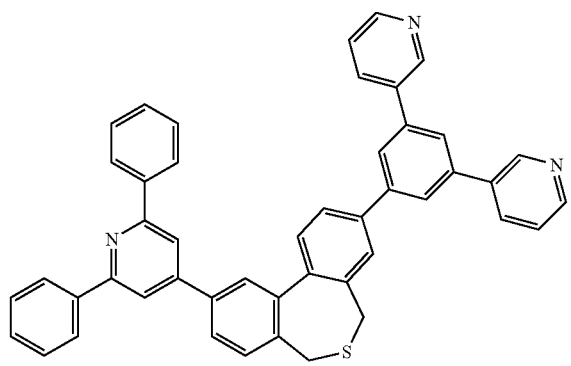
70
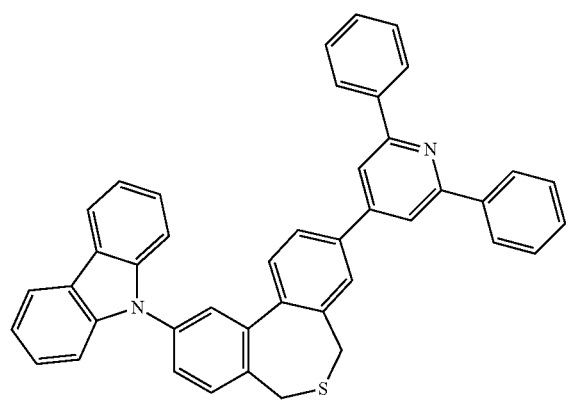
71
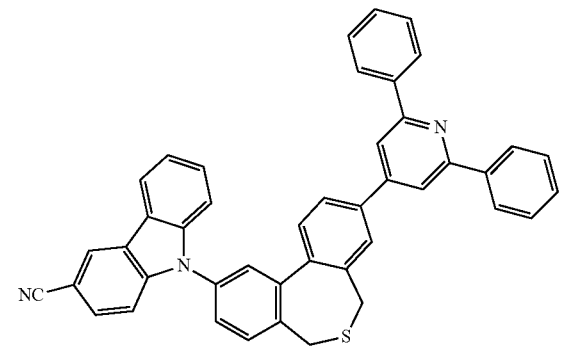
72
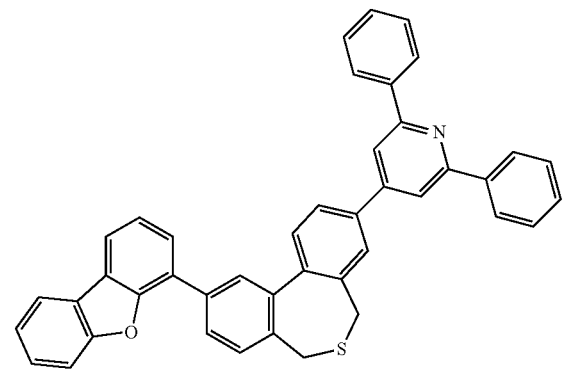
-continued
73
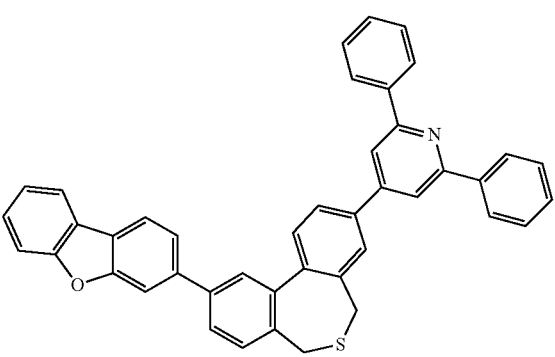
74
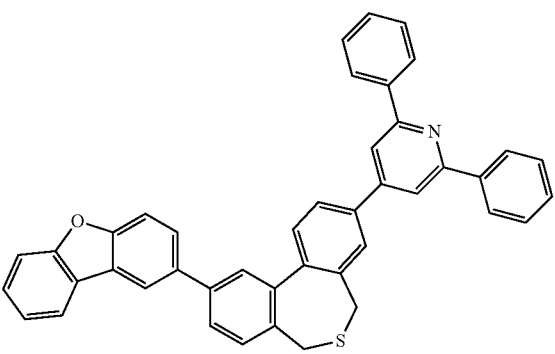
75
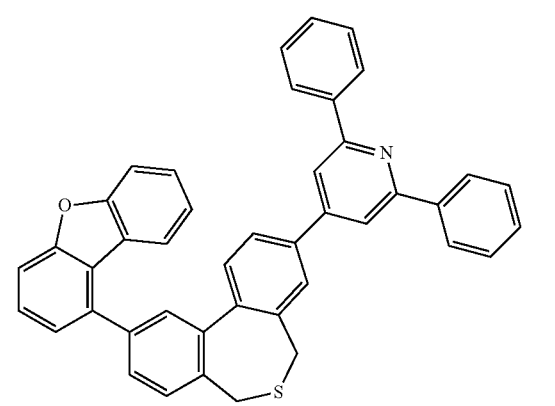
76
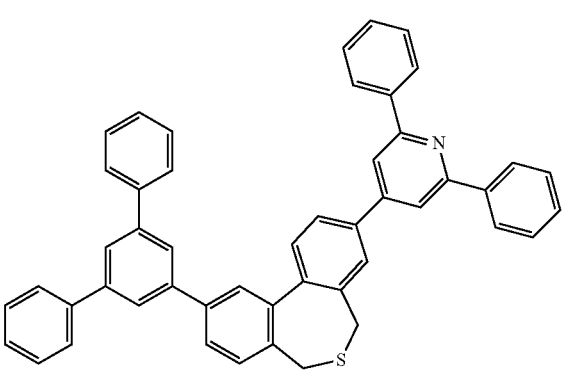

77
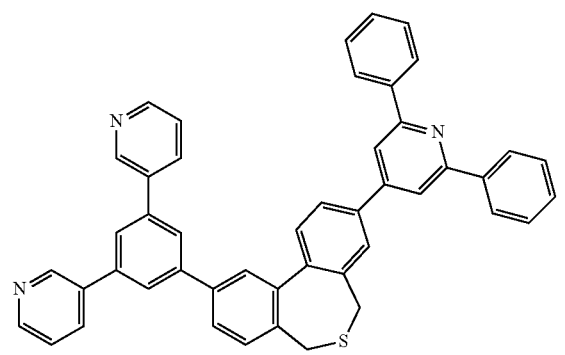
78
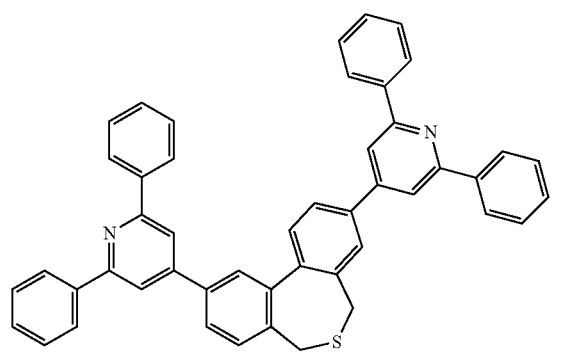
79
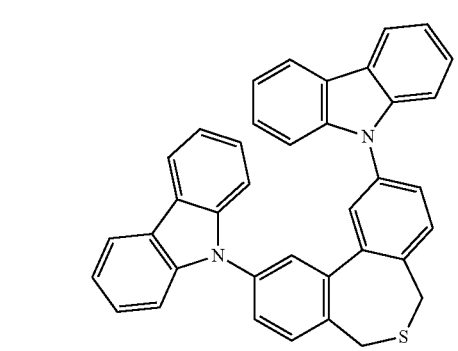
80
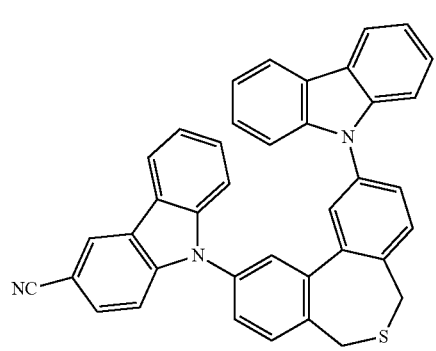
81
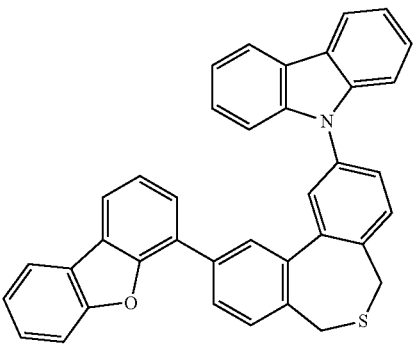
82
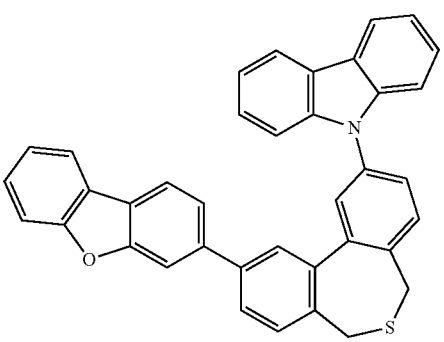
83
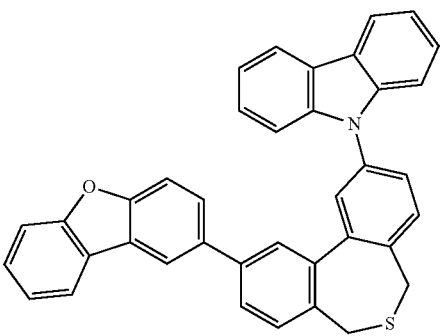
84
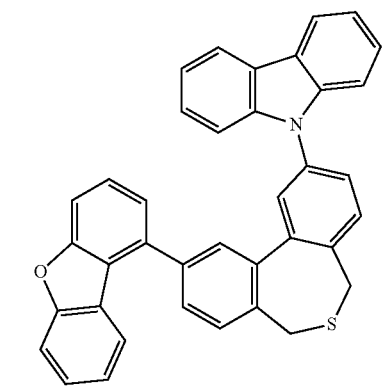

343
-continued
85
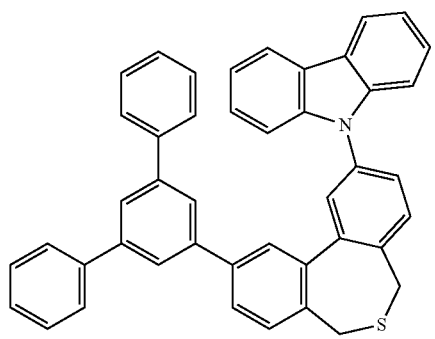
86
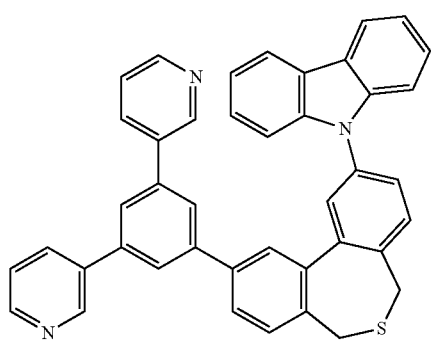
87
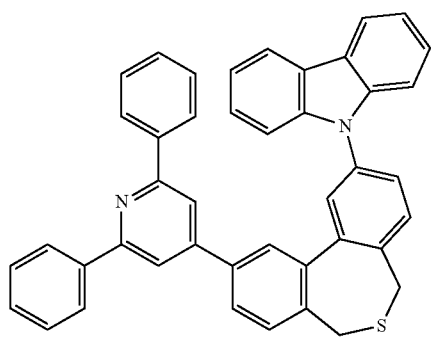
88
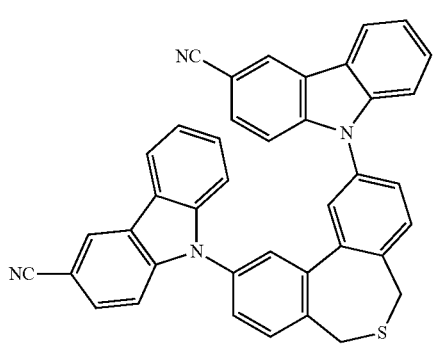
344
-continued
89
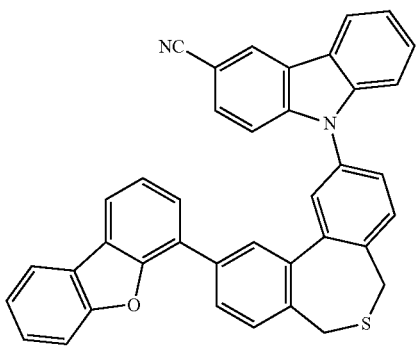
90
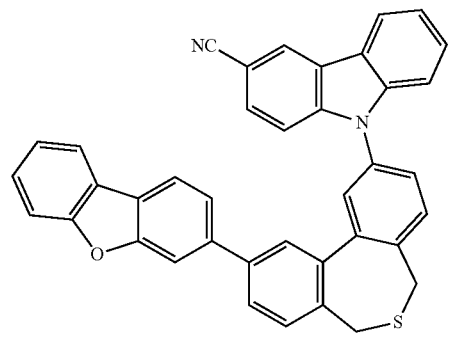
91
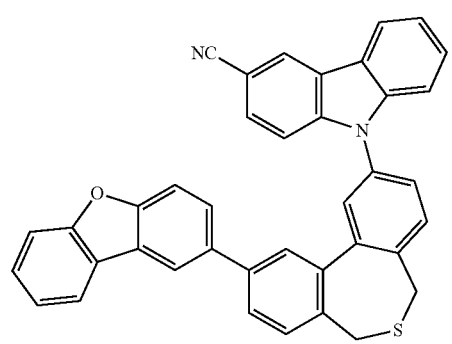
92
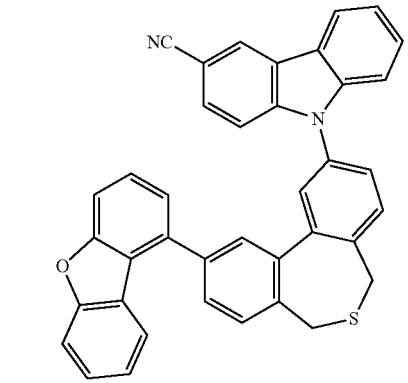

93
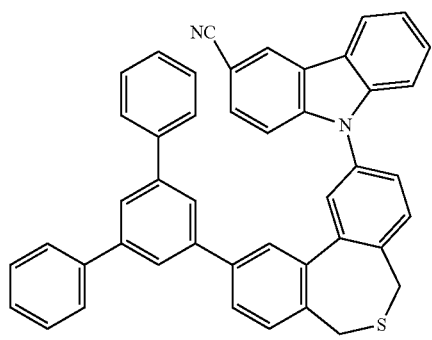
94
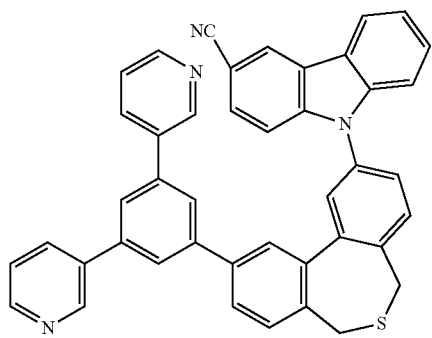
95
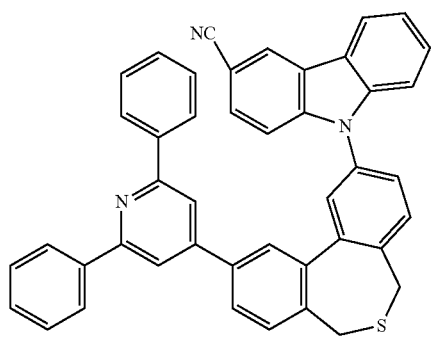
96
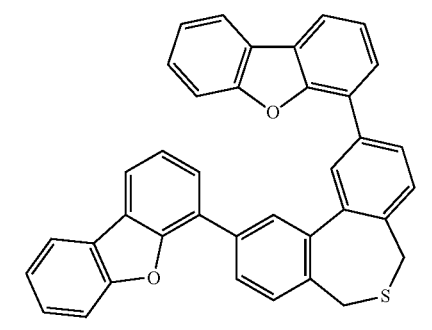
97
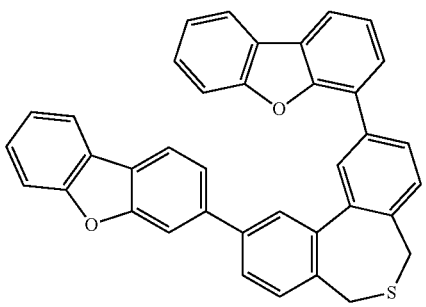
98
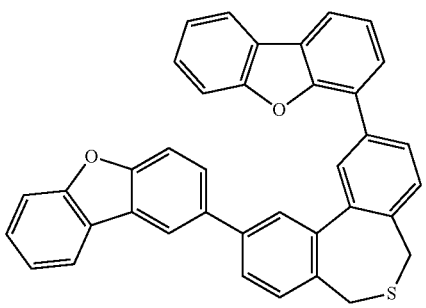
99
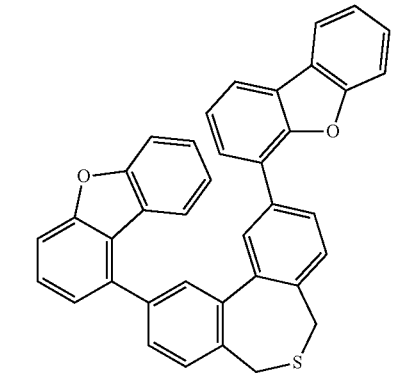
100
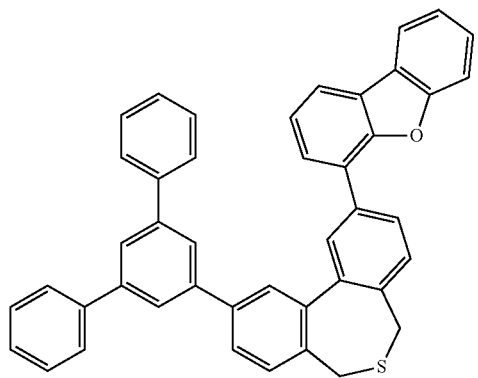

101
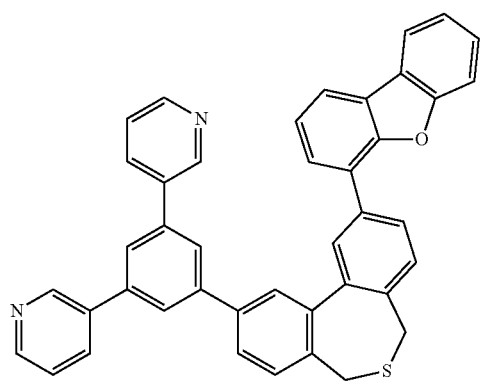
102
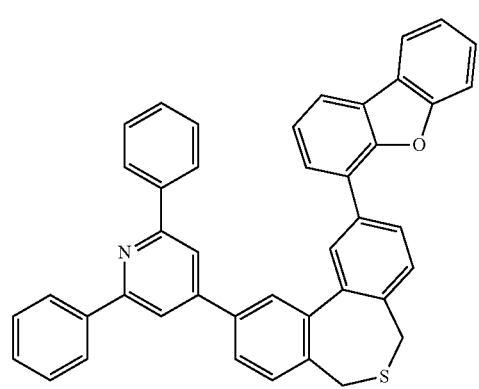
103
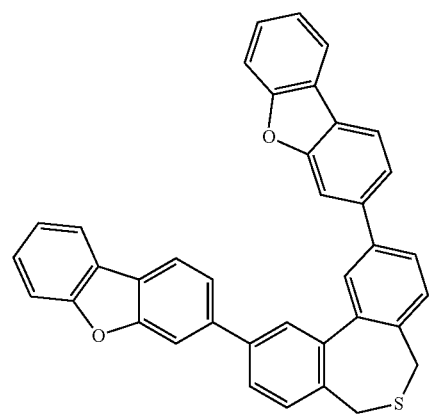
104
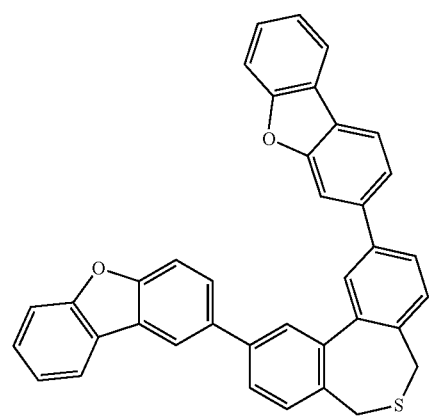
105
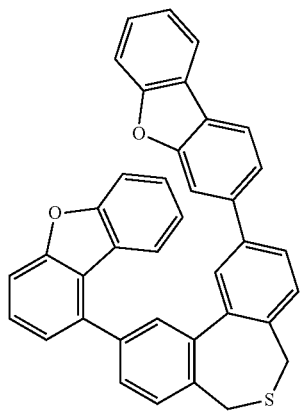
106
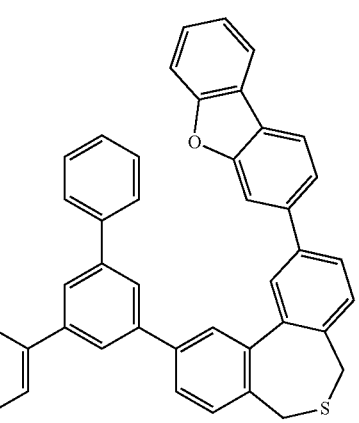
107
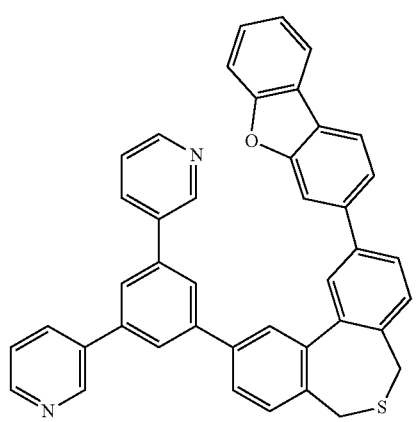

US 10,581,000 B2
349
-continued
108
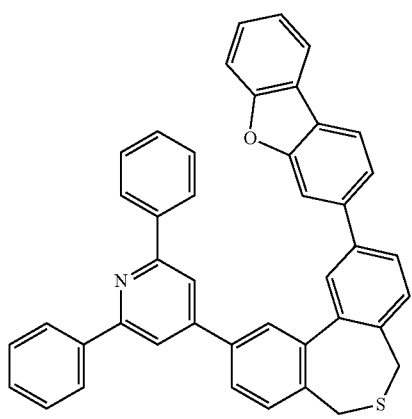
109
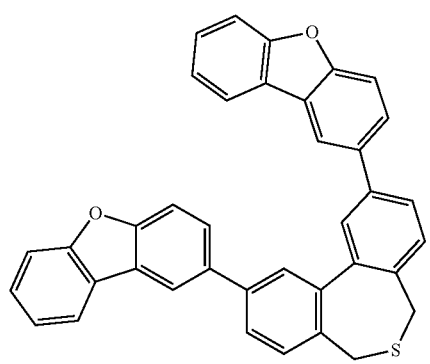
110
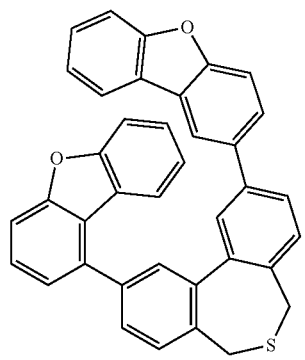
111
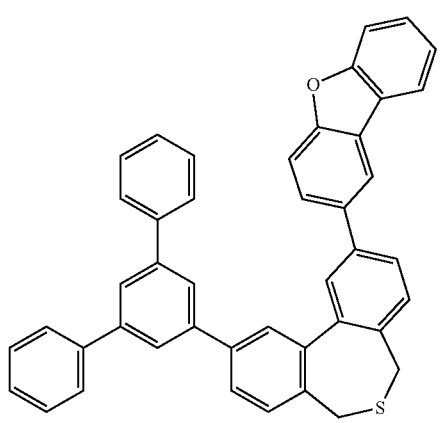
350
-continued
112
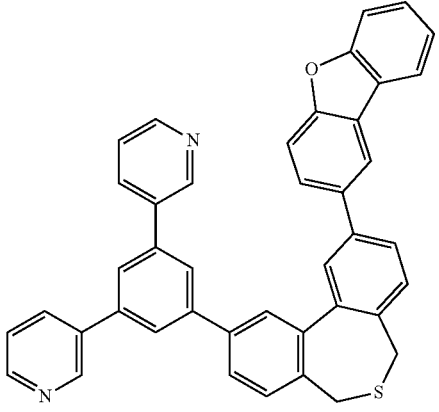
113
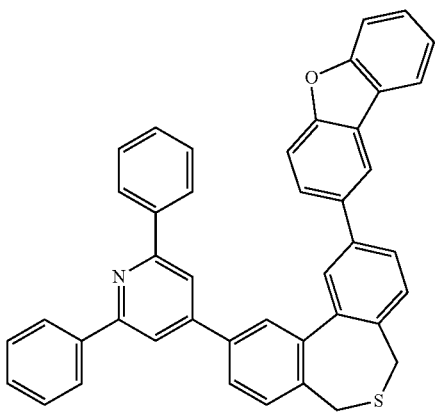
114
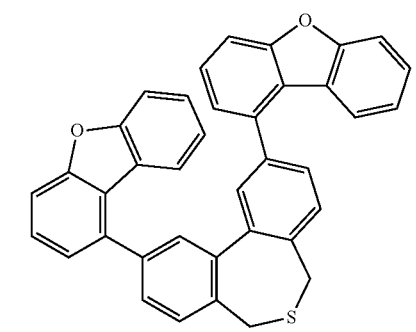
115
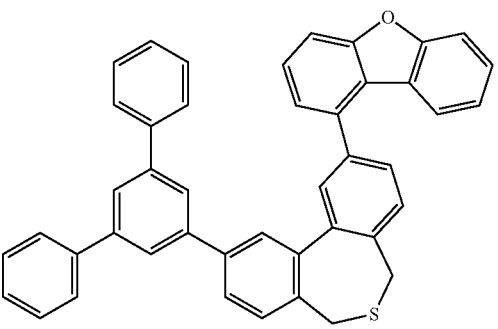

351
-continued
116
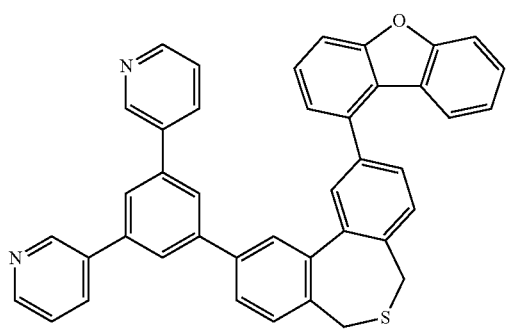
117
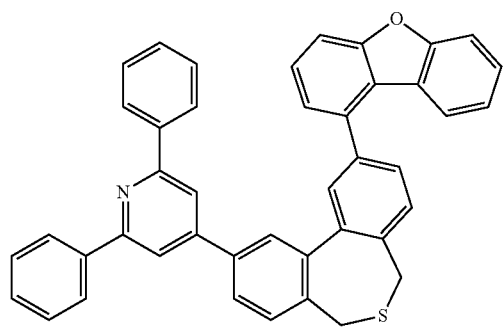
118
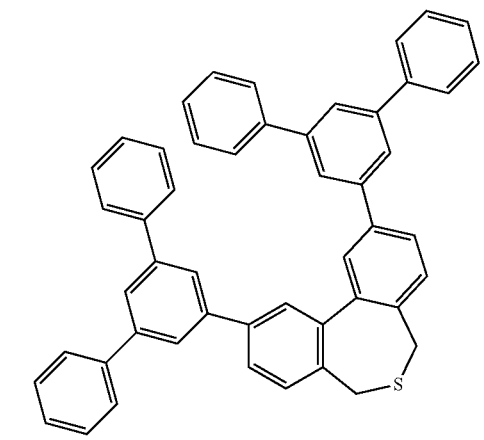
119
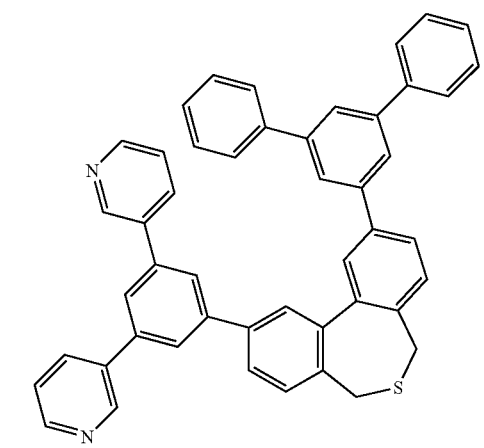
352
-continued
120
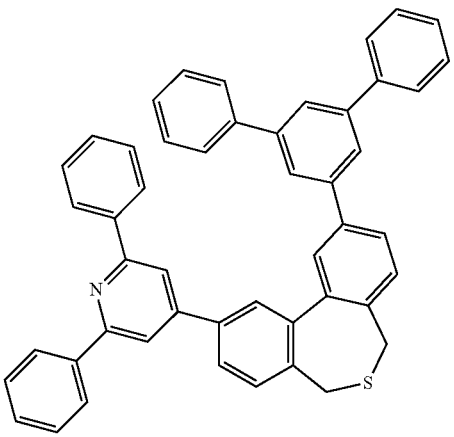
121
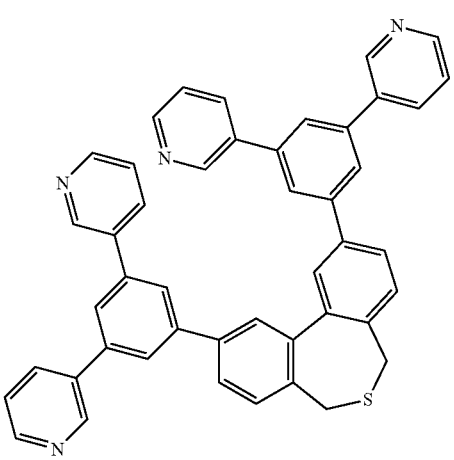
122
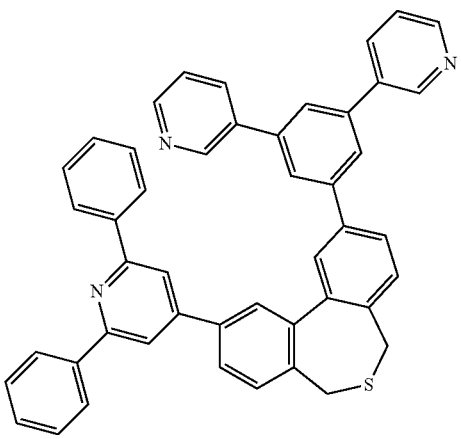

-continued
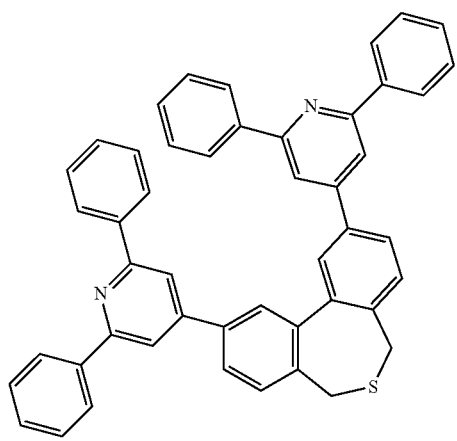
123
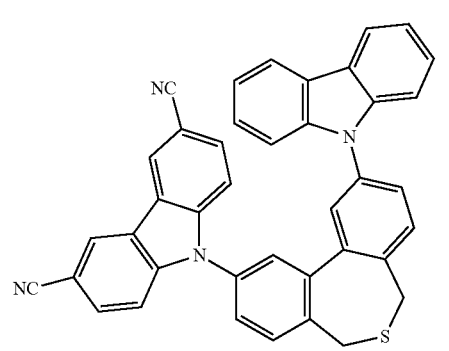
124
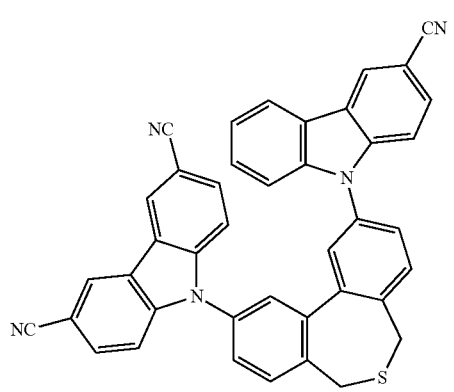
125
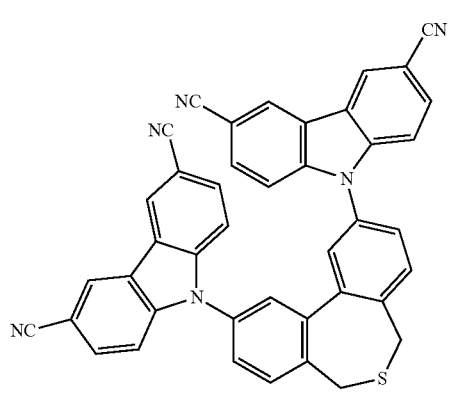
126
-continued
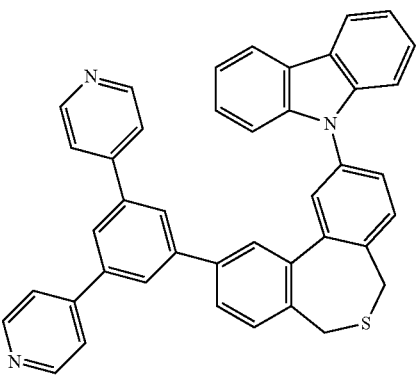
127
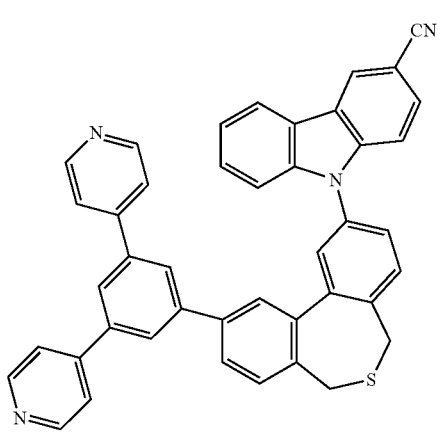
128
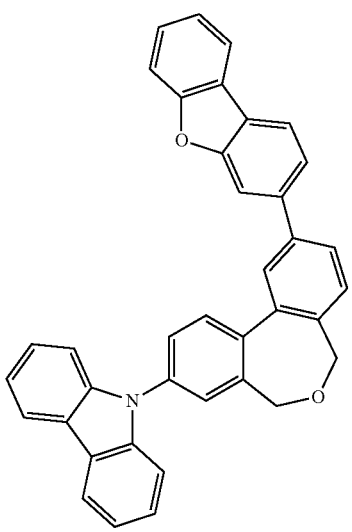
129

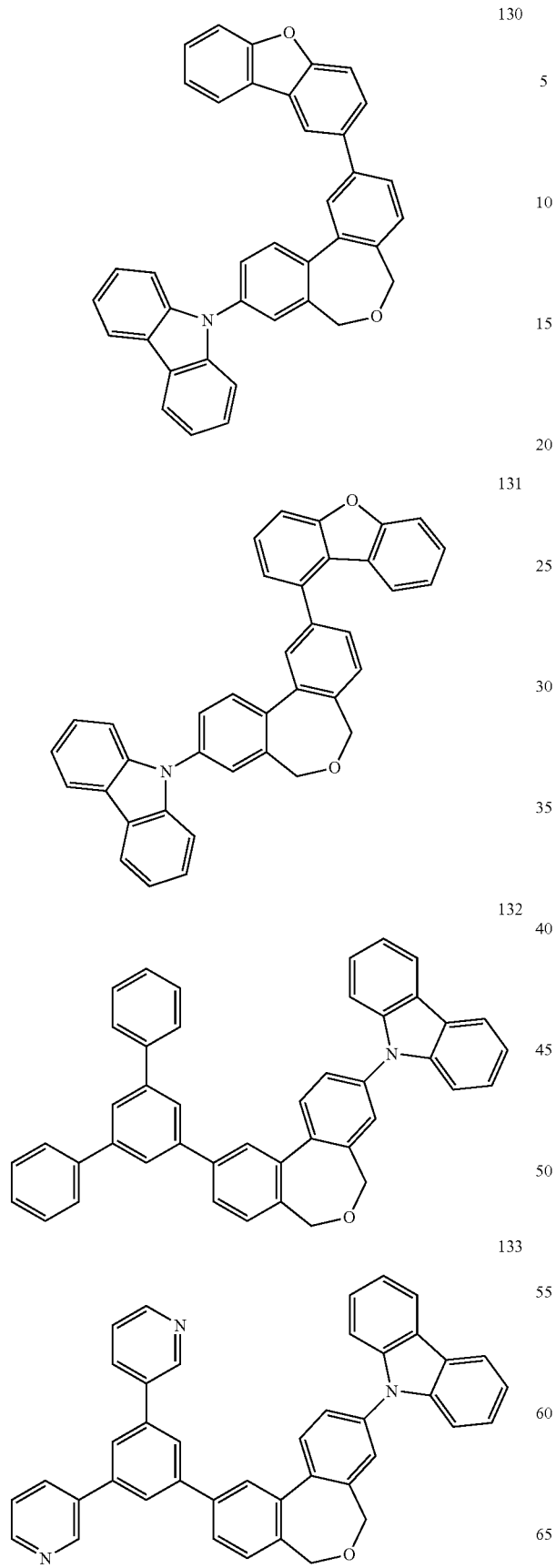

357
-continued
138
137
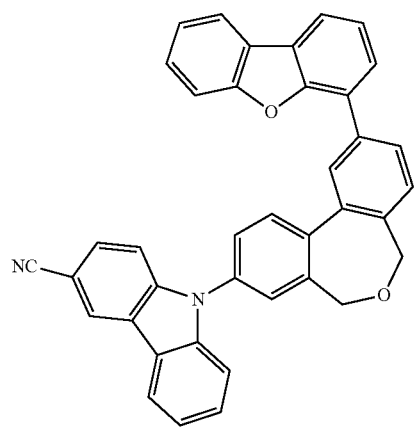
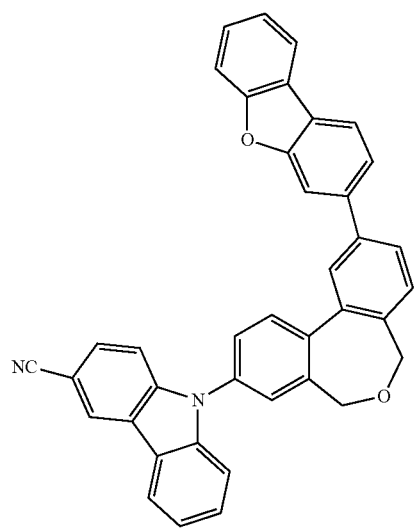
139
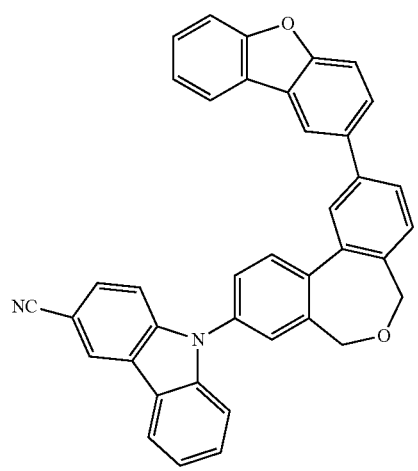
358
-continued
140
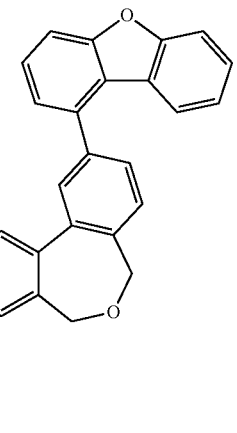
141
142
143
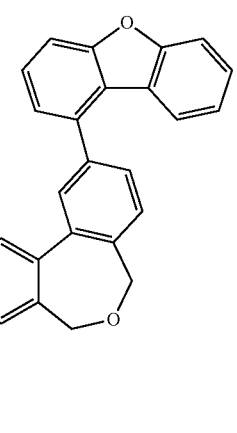

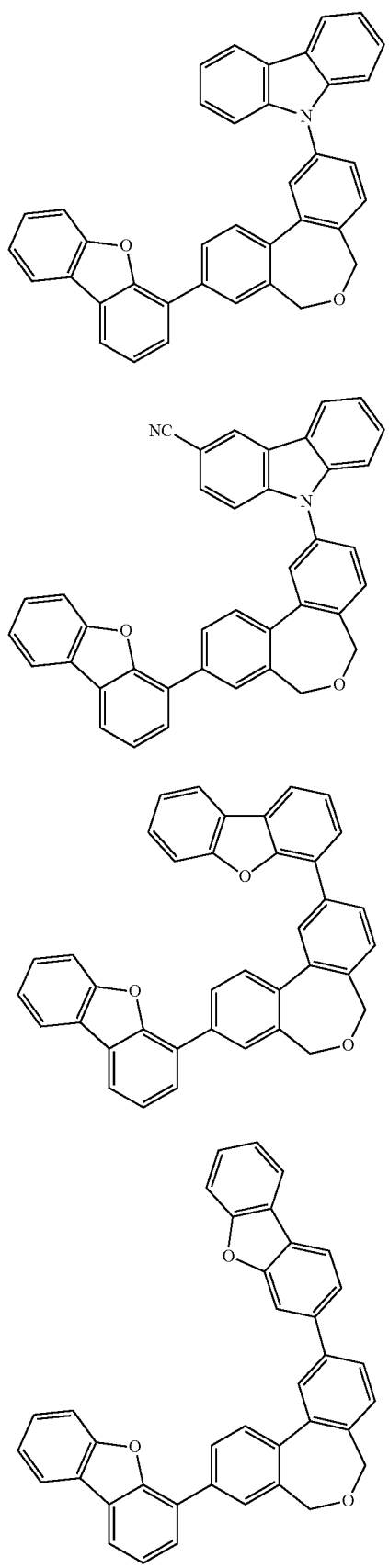
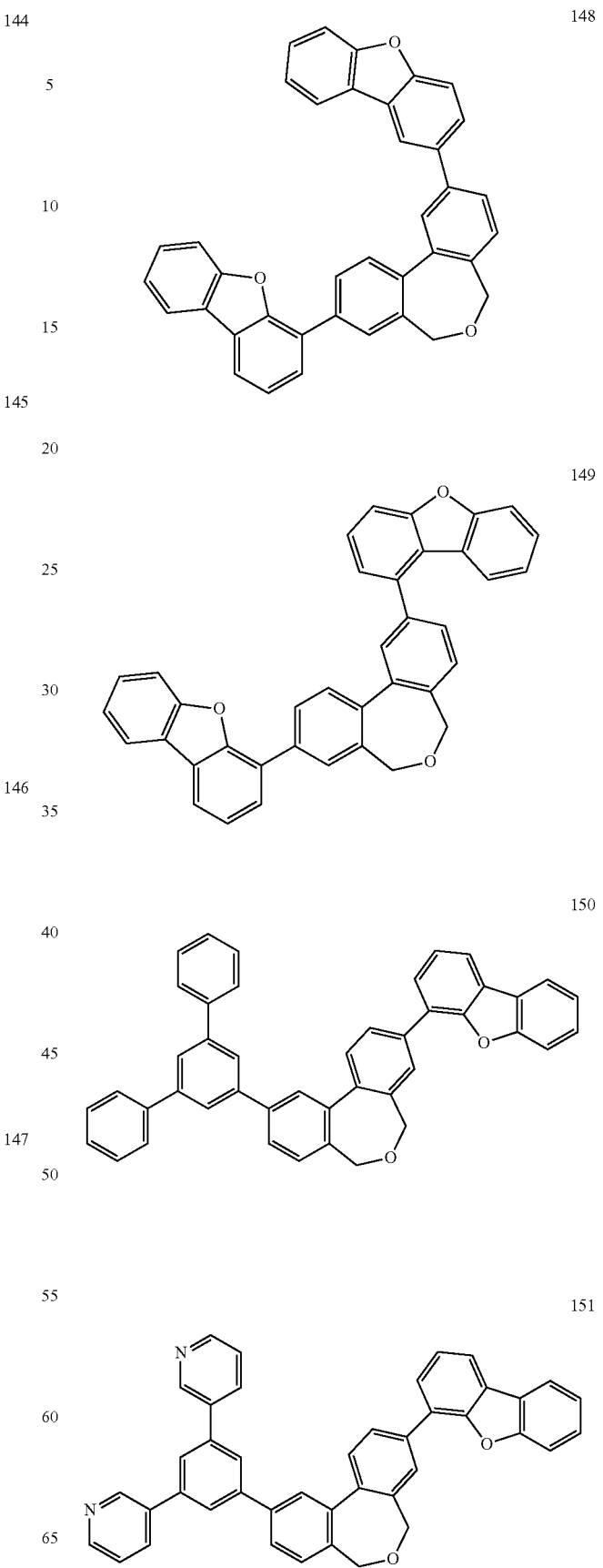

361
-continued
152
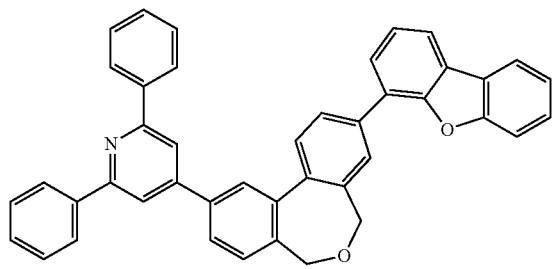
153
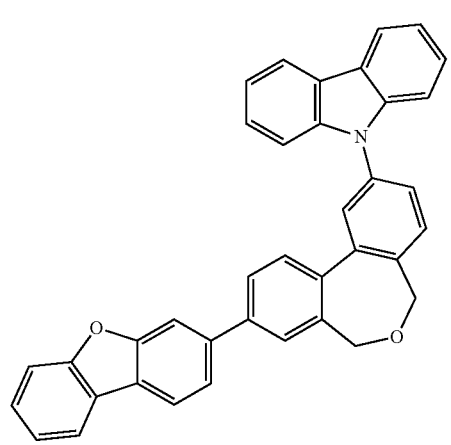
154
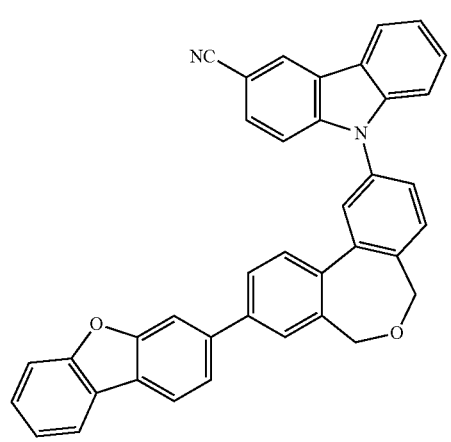
155
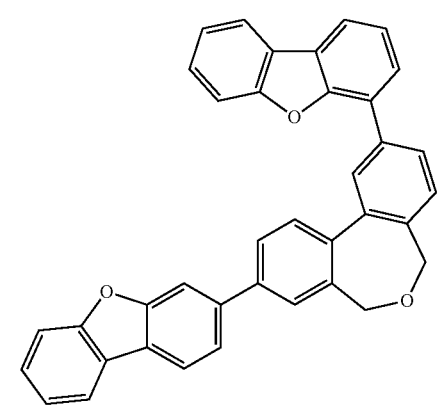
362
-continued
156
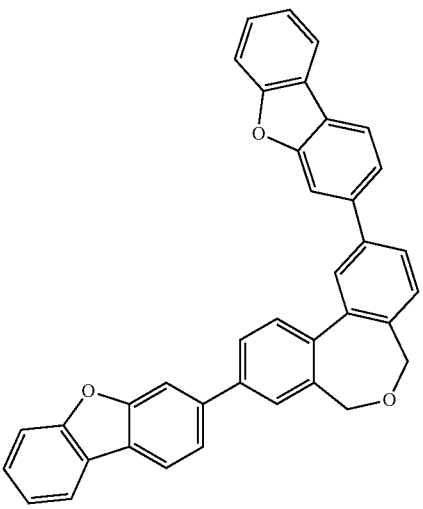
157
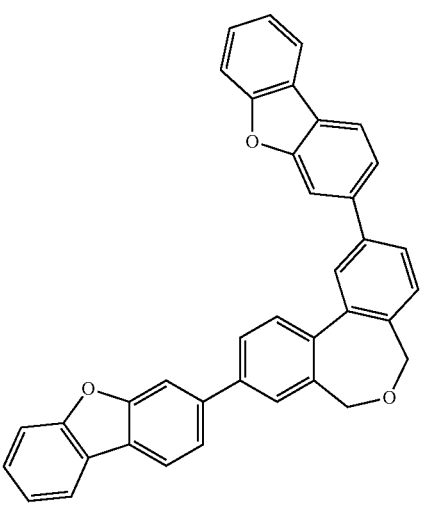
158
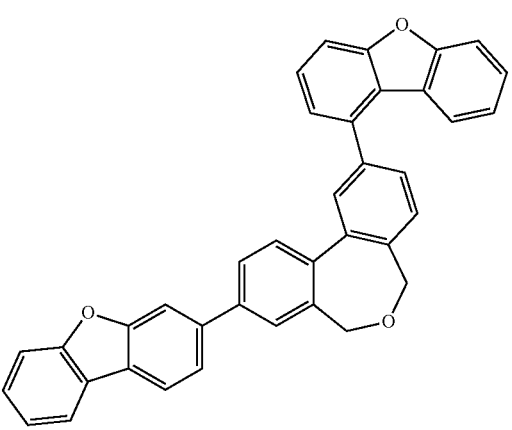

159
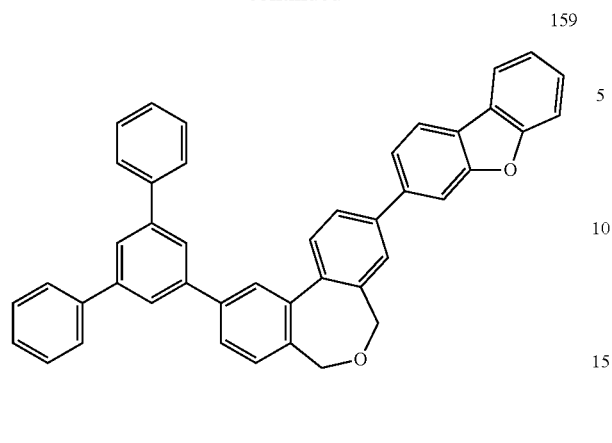
160
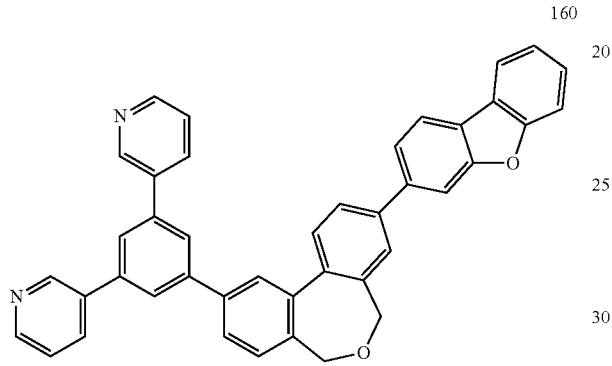
161
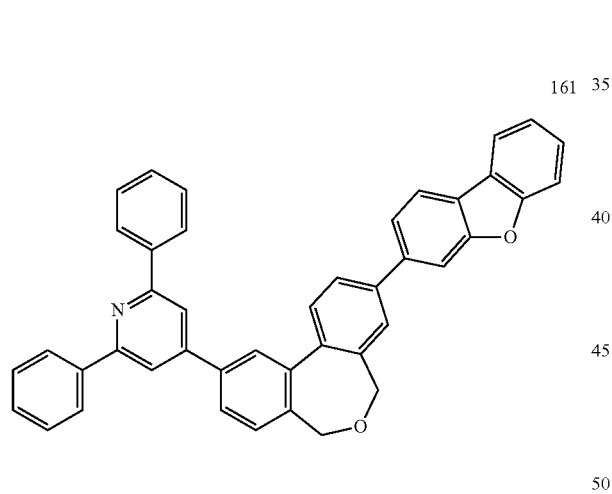
162
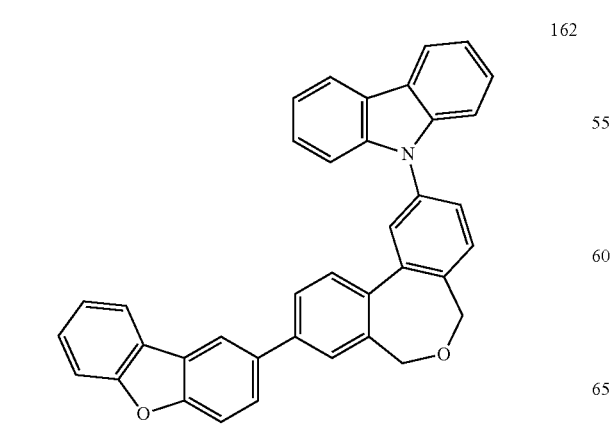
163
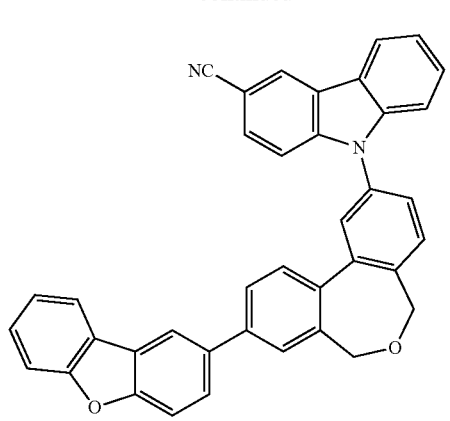
164
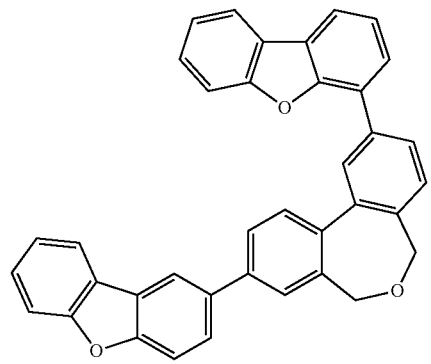
165
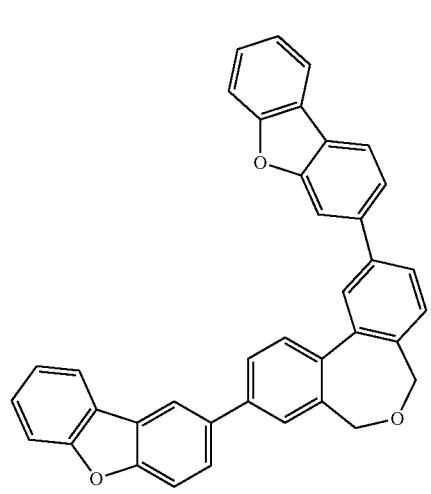
166
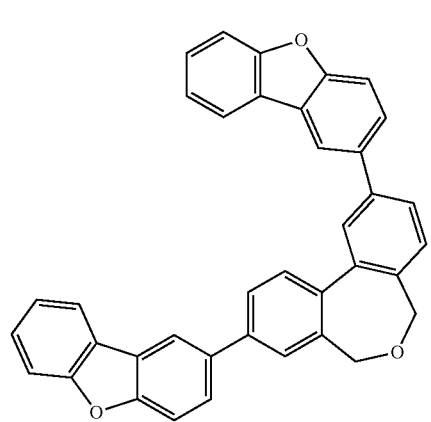

167
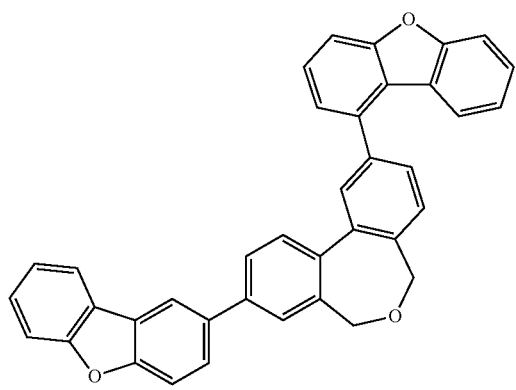
168
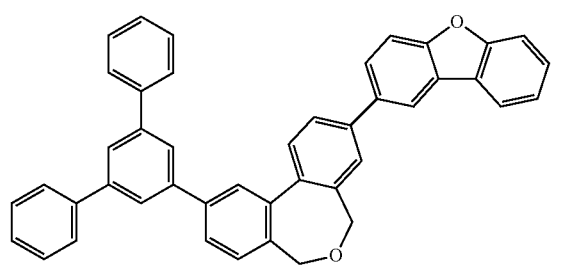
169
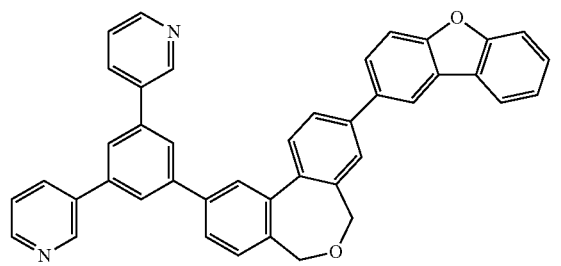
170
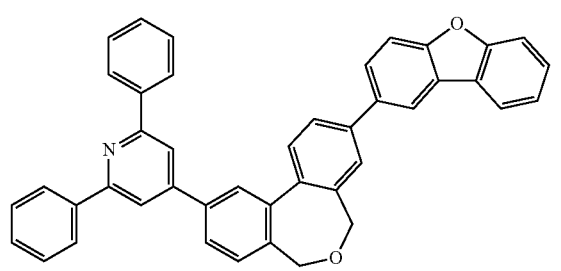
171
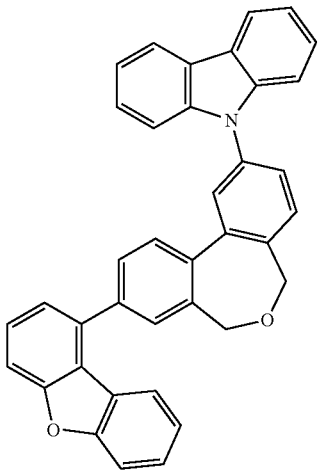
172
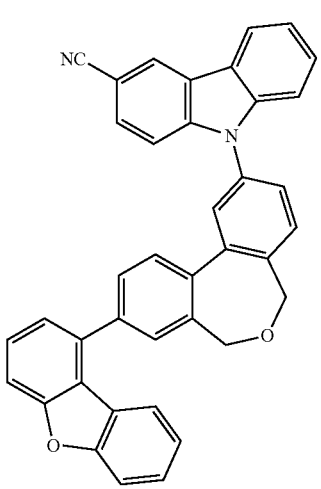
173
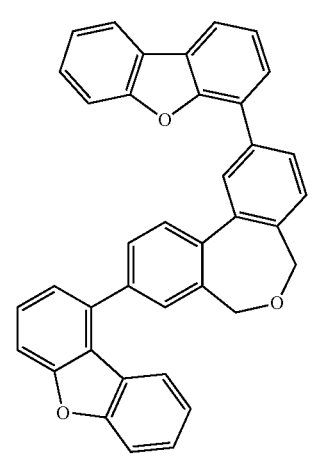

367
-continued
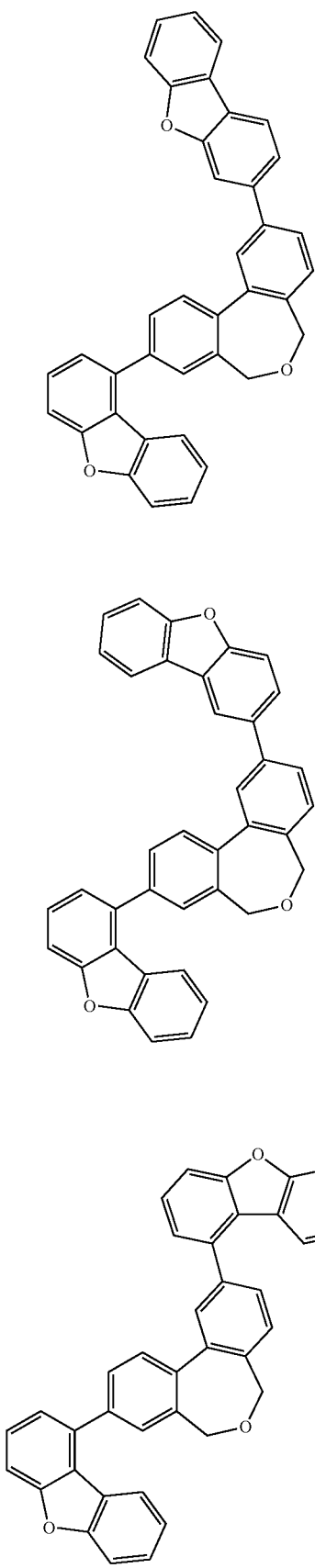
368
-continued
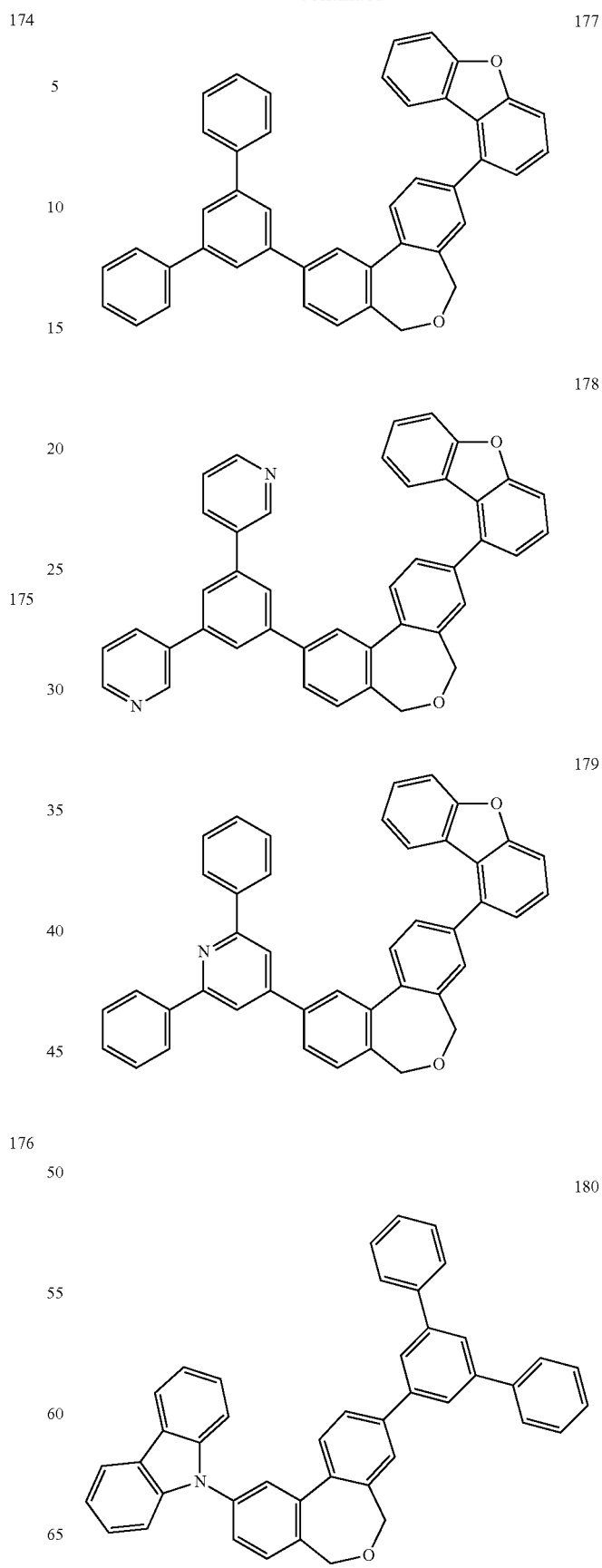

369
-continued
181
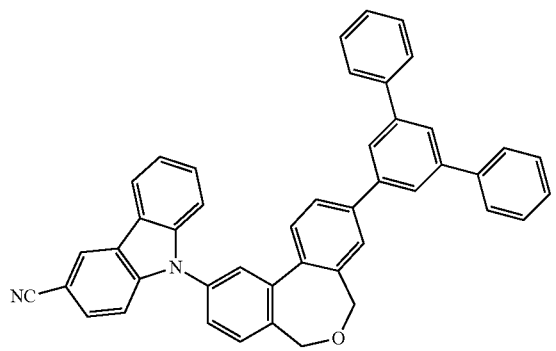
182
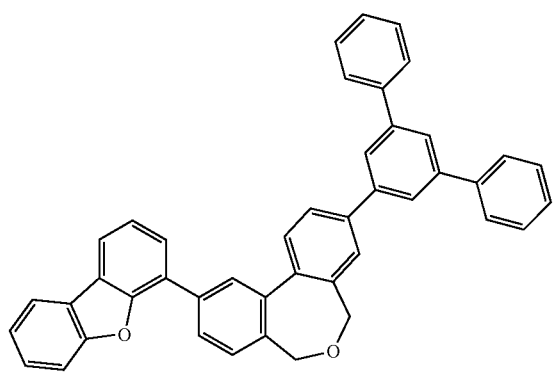
183
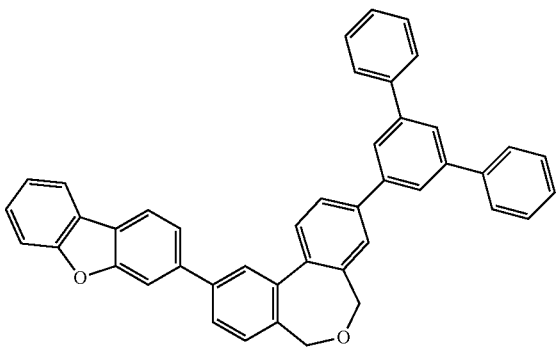
184
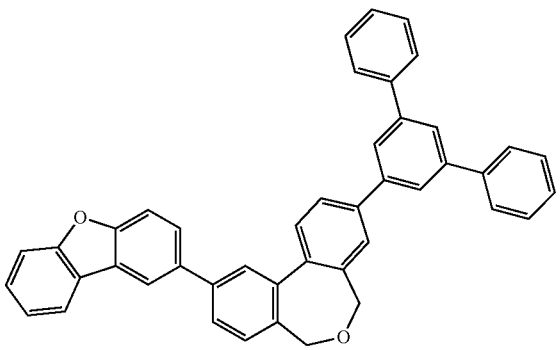
370
-continued
185
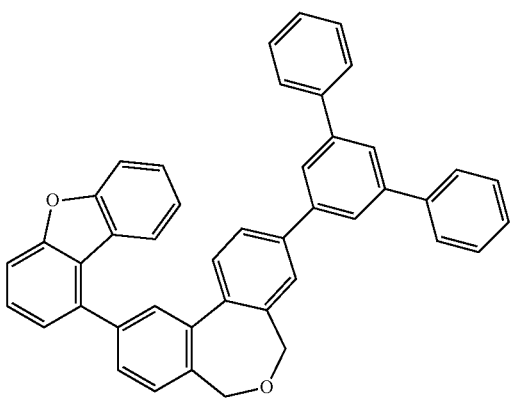
186
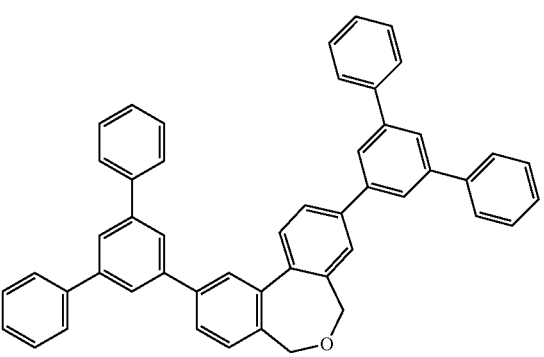
187
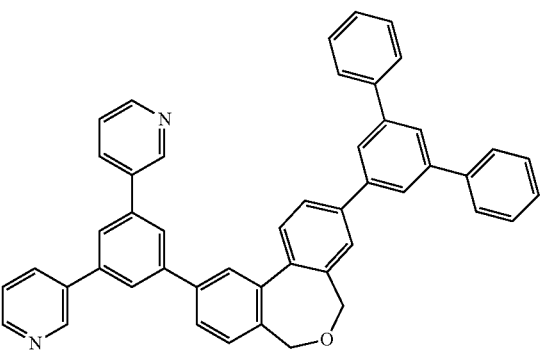
188
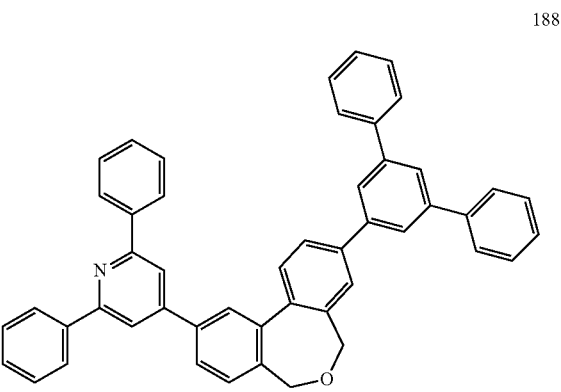

371
-continued
189
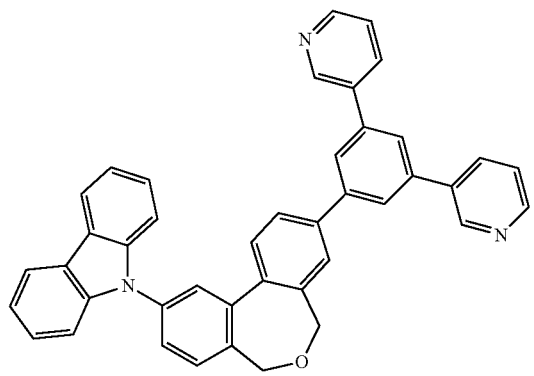
190
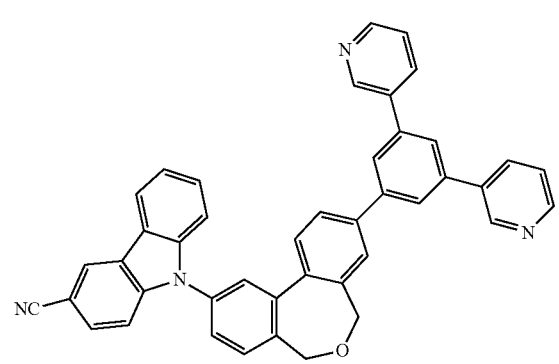
191
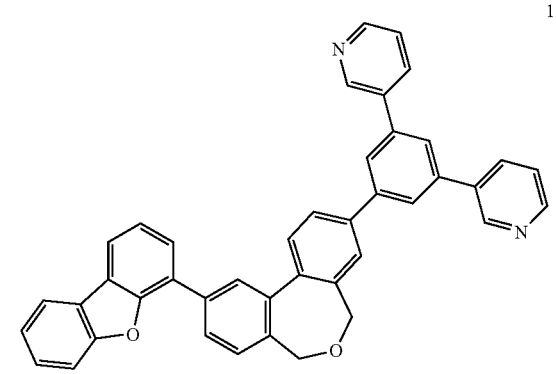
192
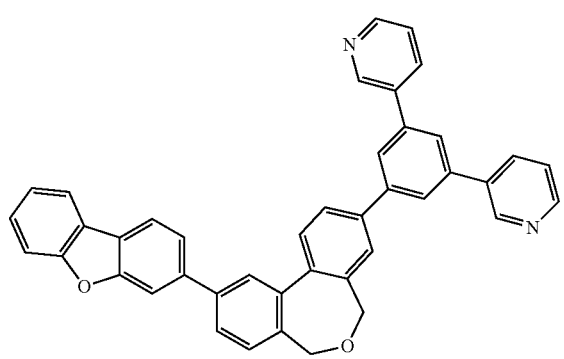
372
-continued
193
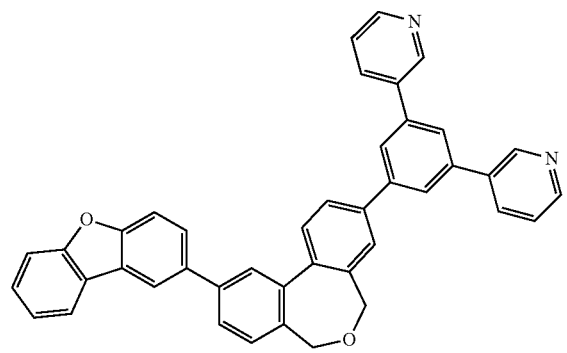
194
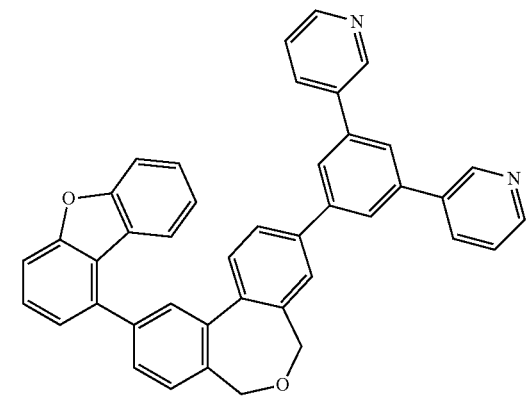
195
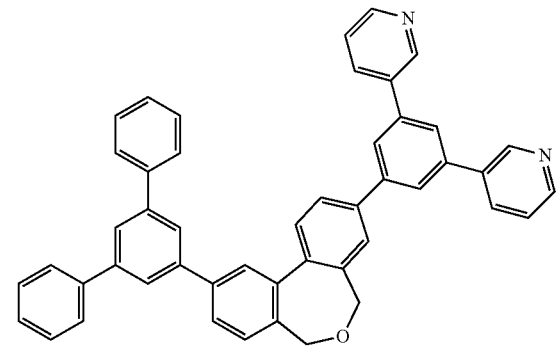
196
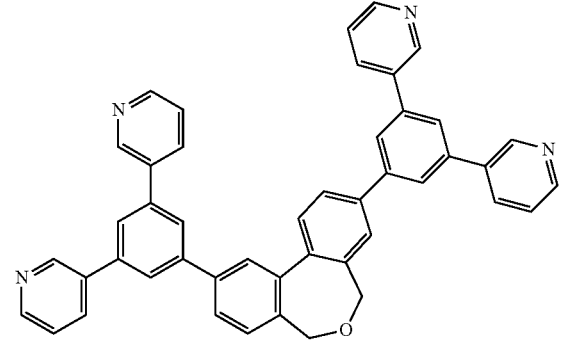

197
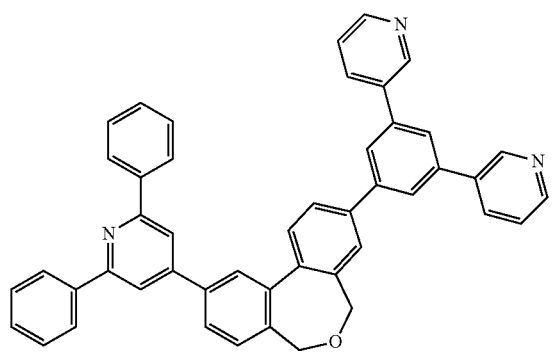
198
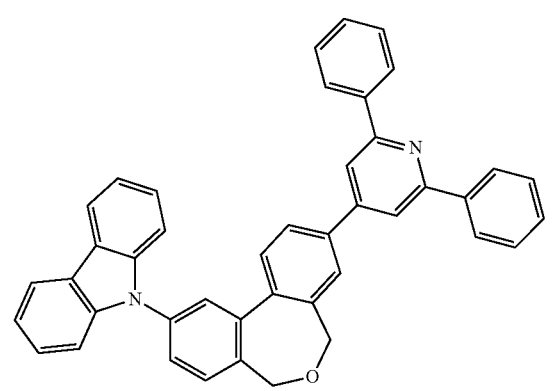
199
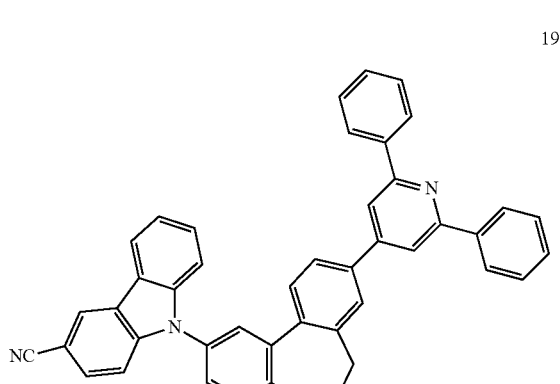
200
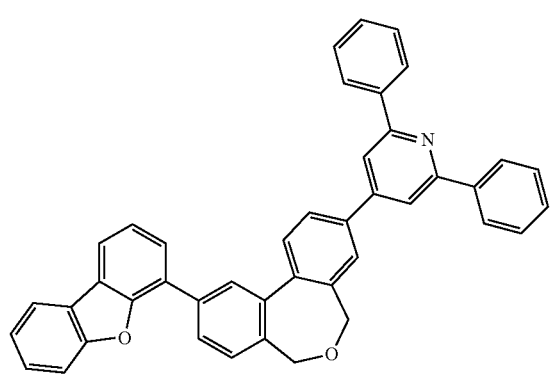
201
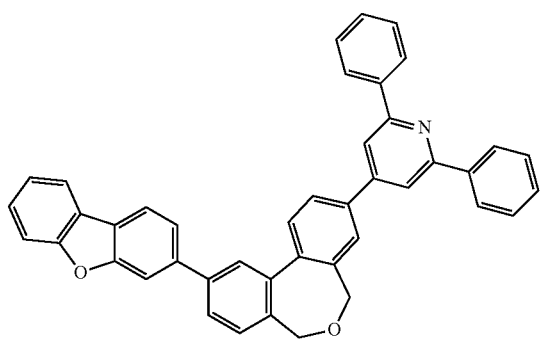

205 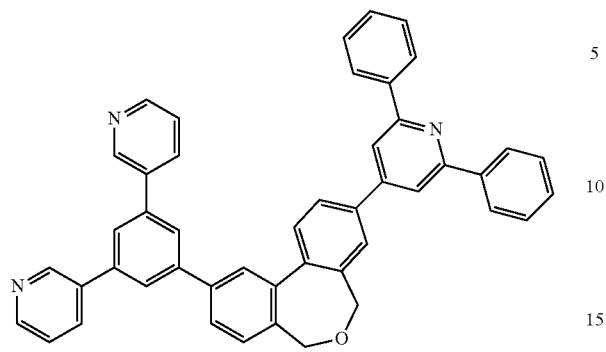
206 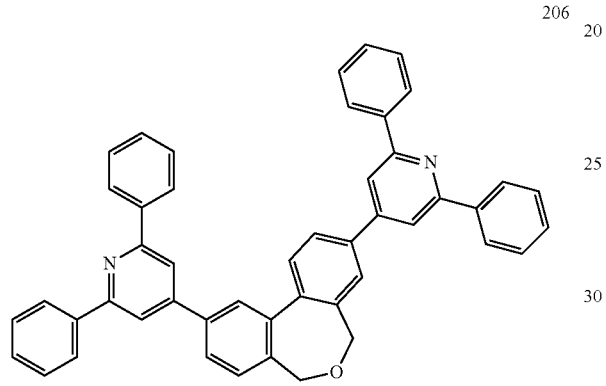
207 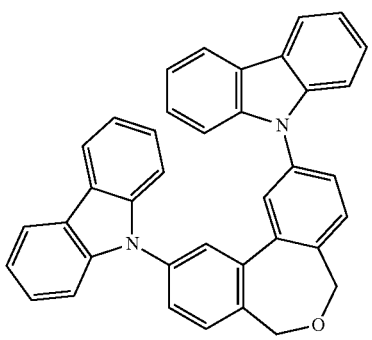
208 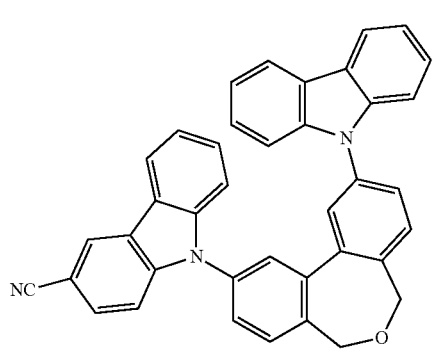
209 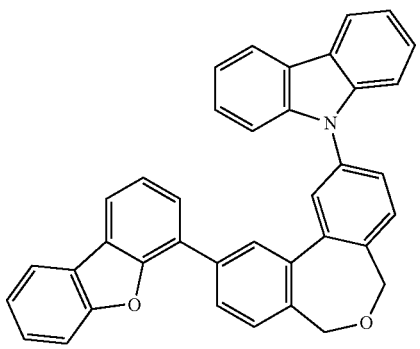
210 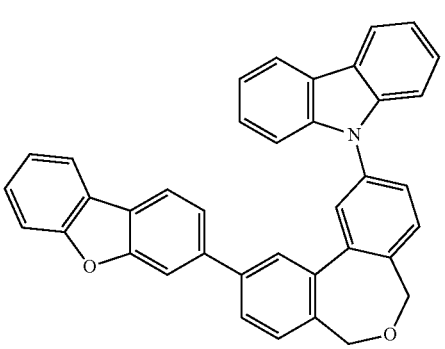
211 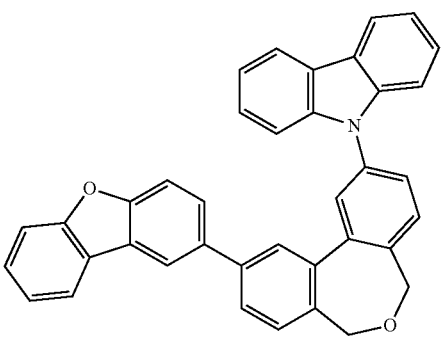
212 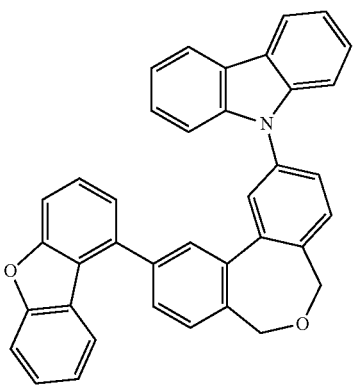

213
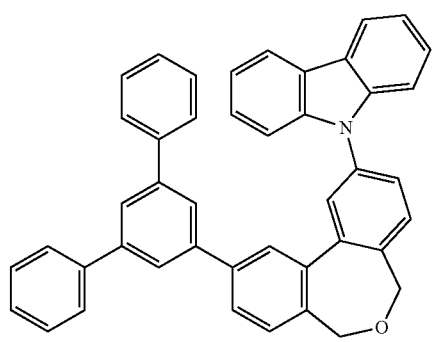
214
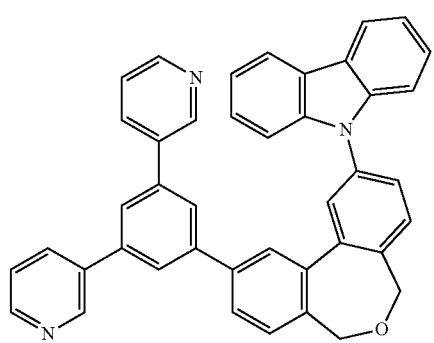
215
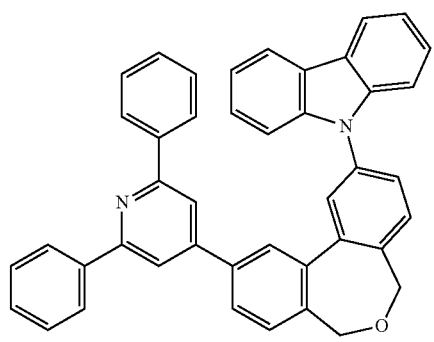
216
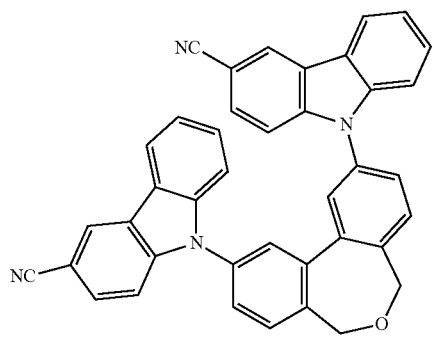
217
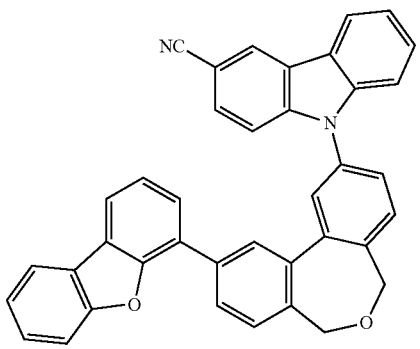
218
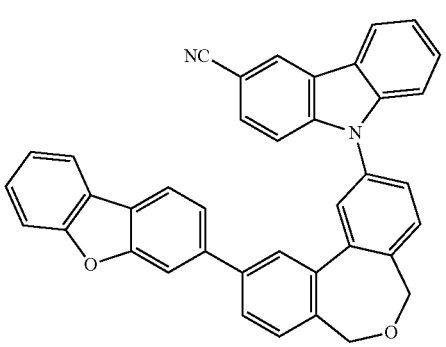
219
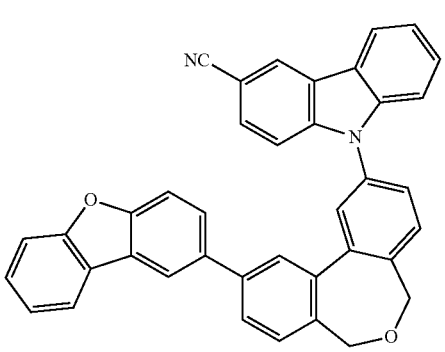
220
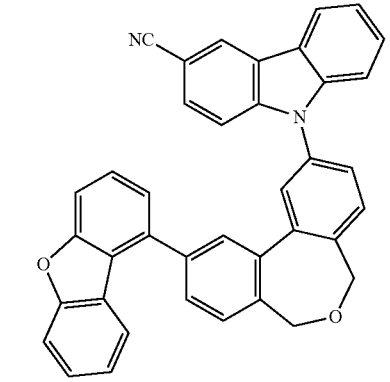

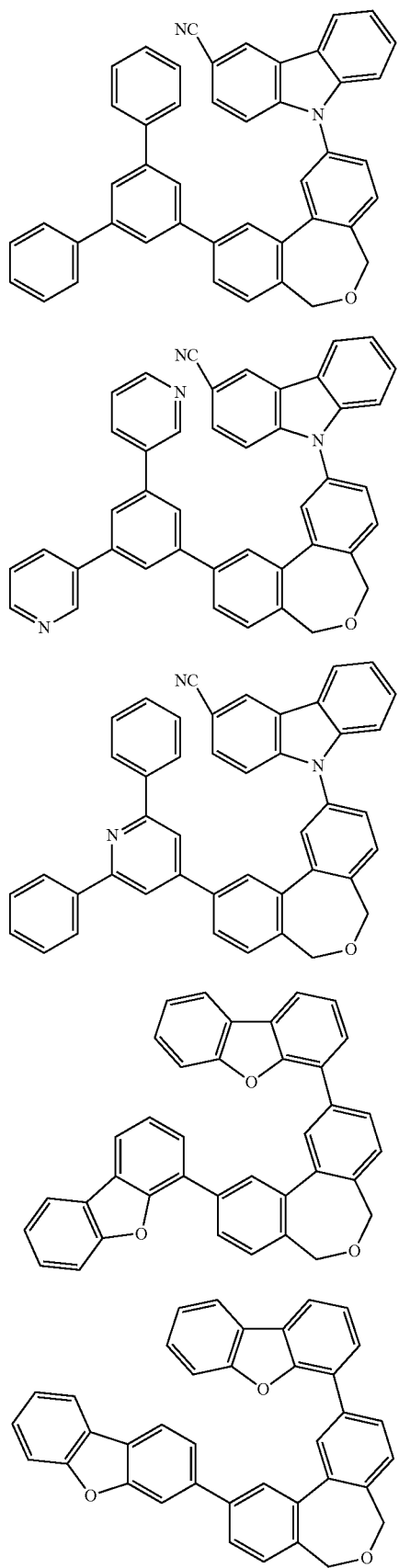

381
-continued
230
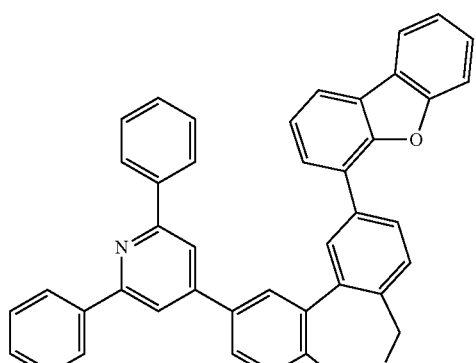
231
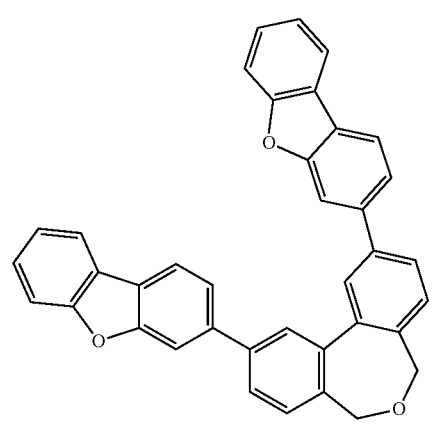
232
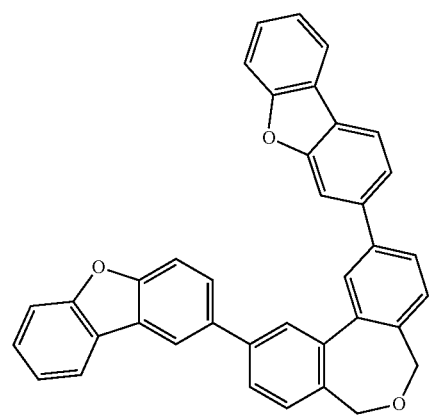
233
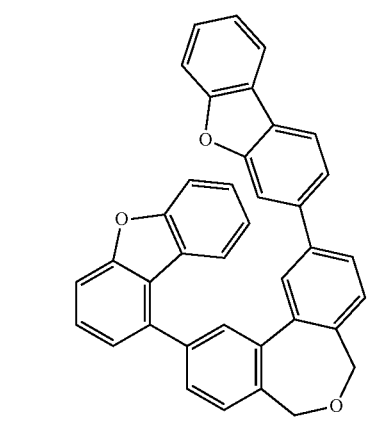
382
-continued
234
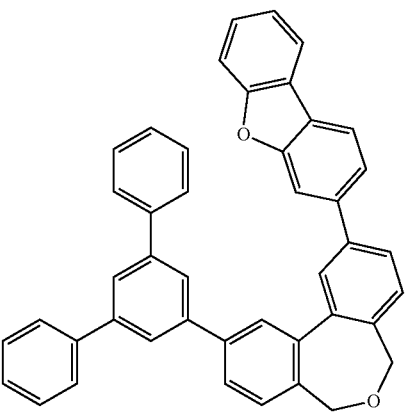
235
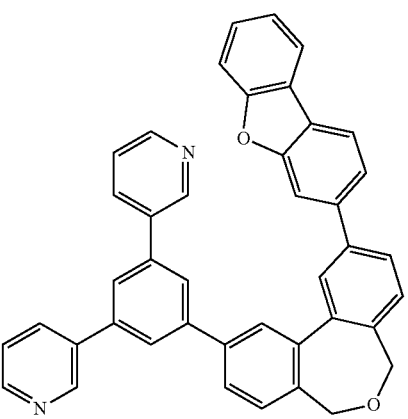
236
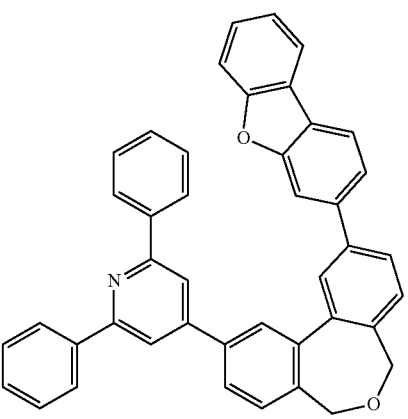
237
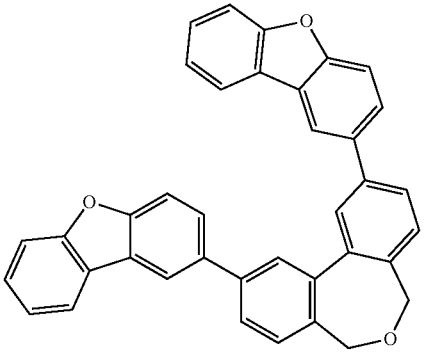

383
-continued
238
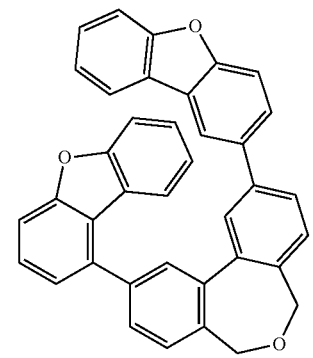
239
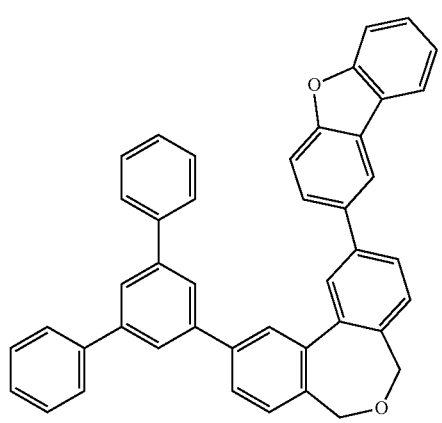
240
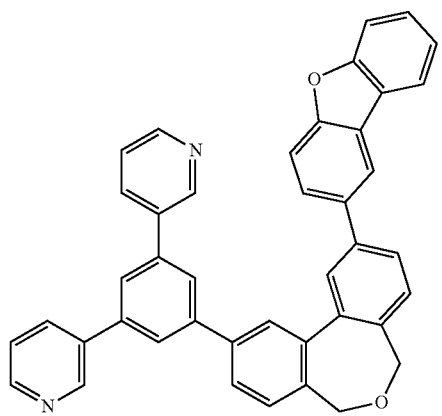
241
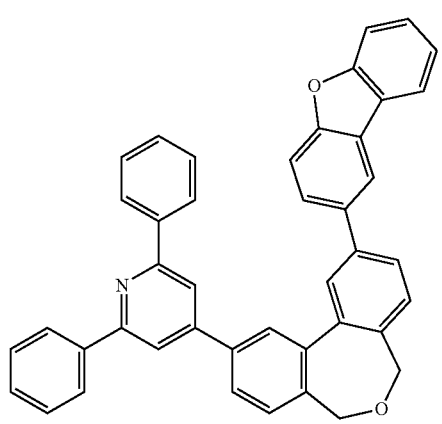
384
-continued
242
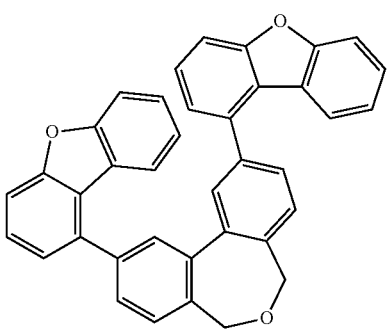
243
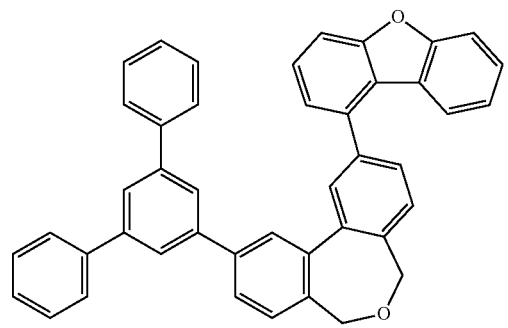
244
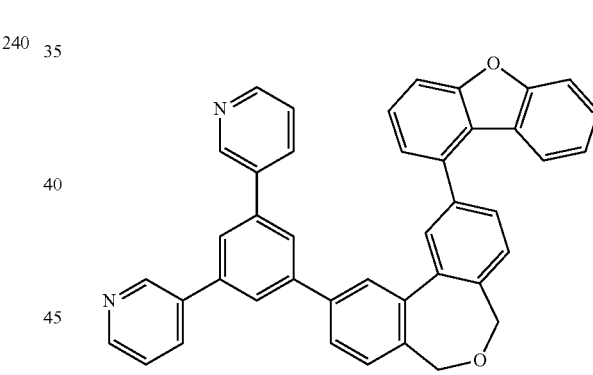
245
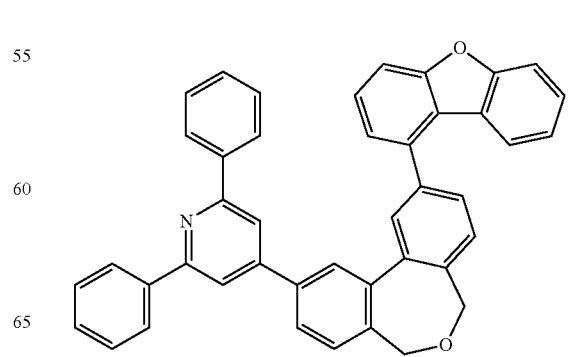

-continued
246
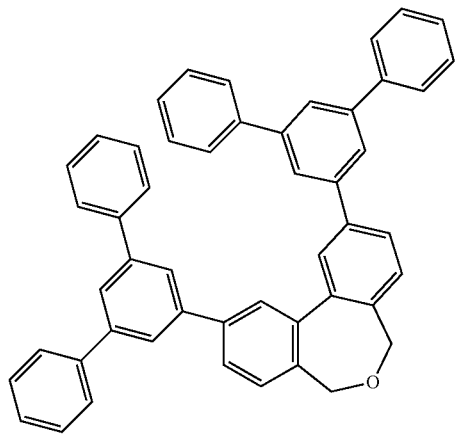
247
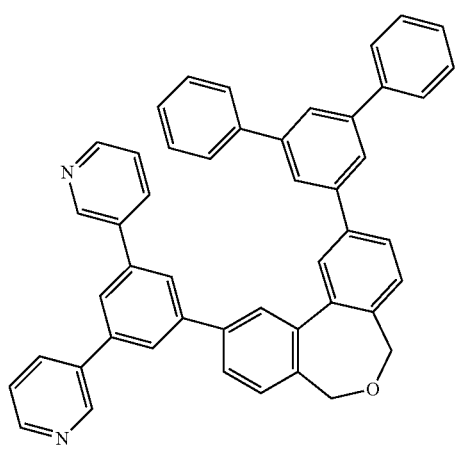
248
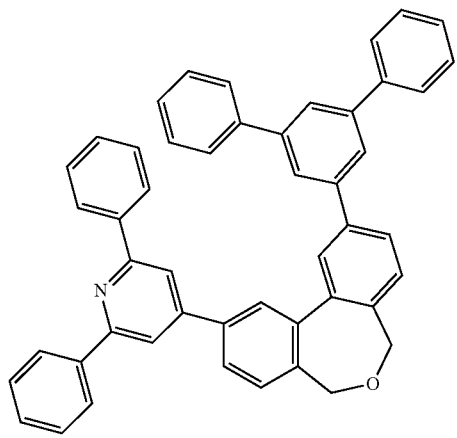
-continued
249
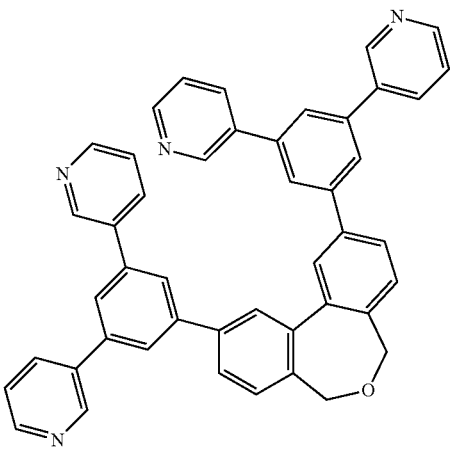
250
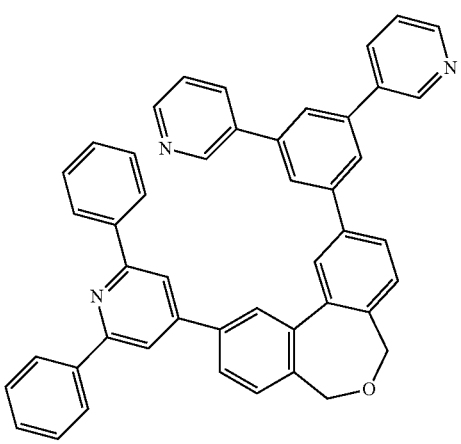
251
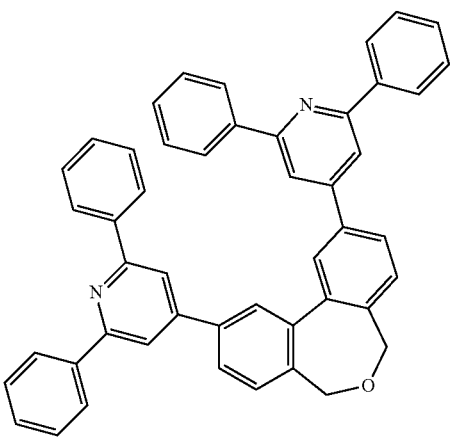
252
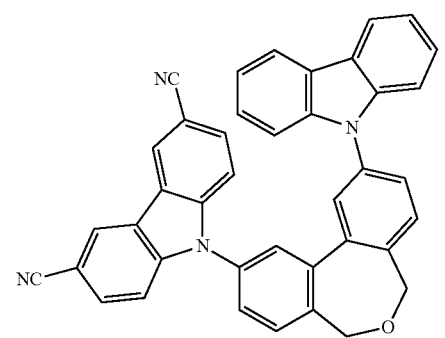

253 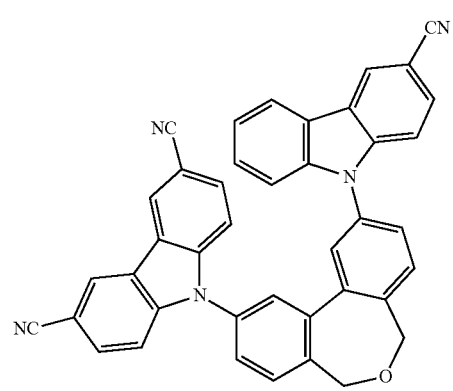
254 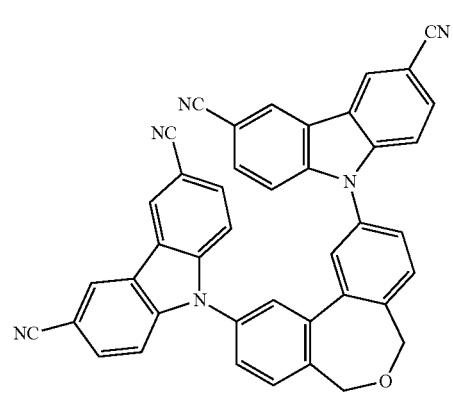
255 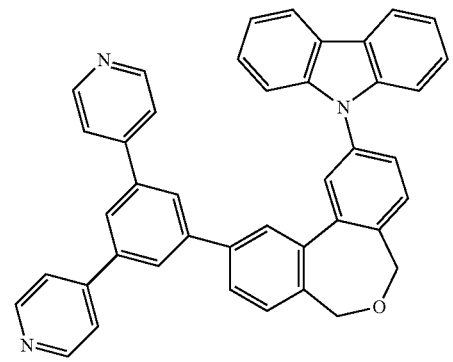
256 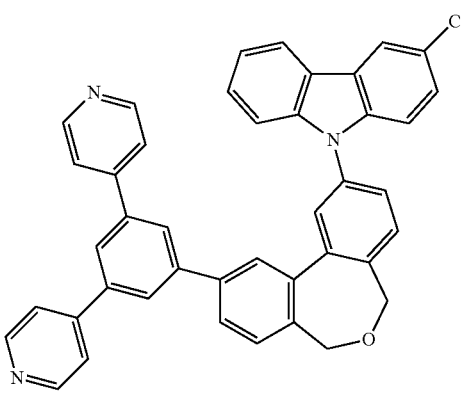
257 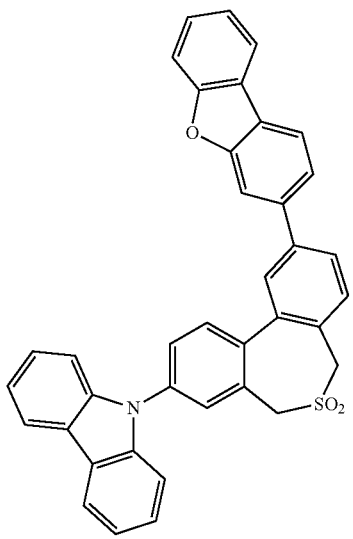
258 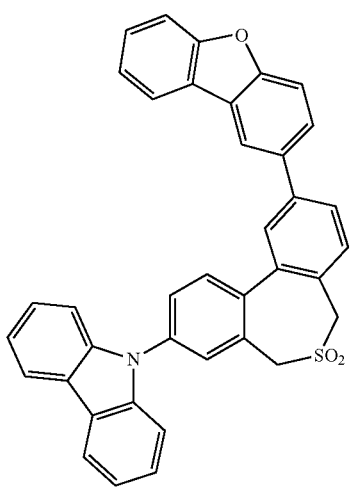
259 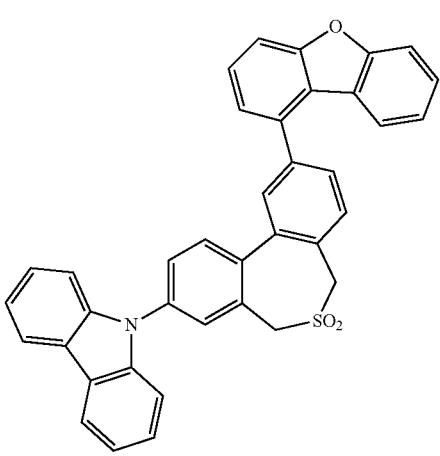

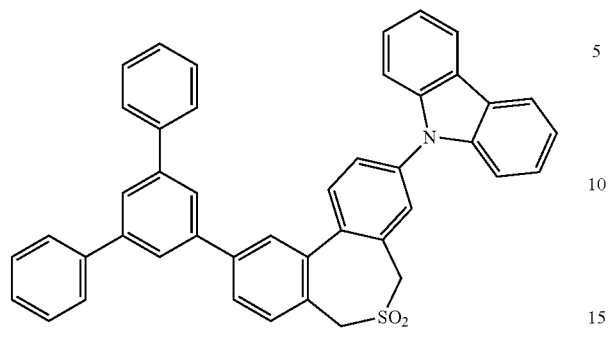
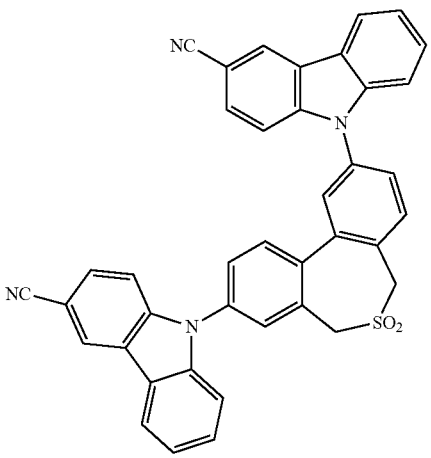
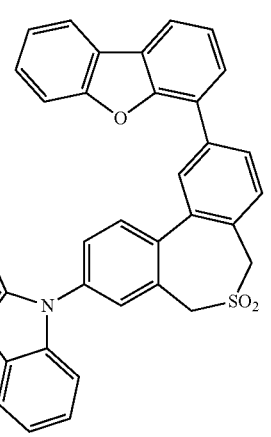
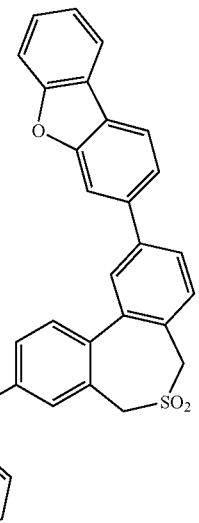

391
-continued
267
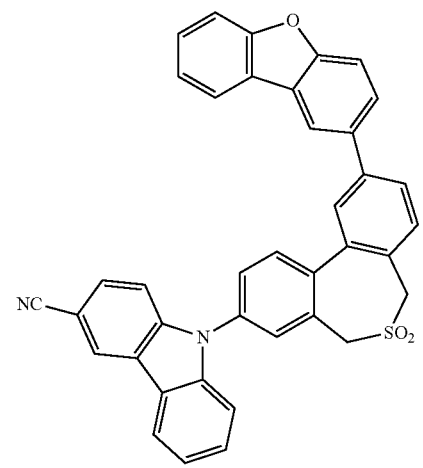
268
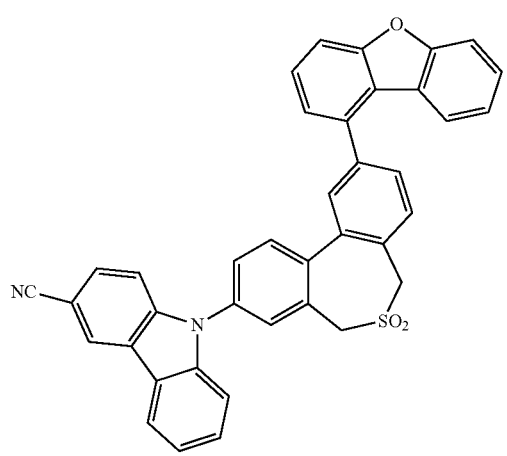
269
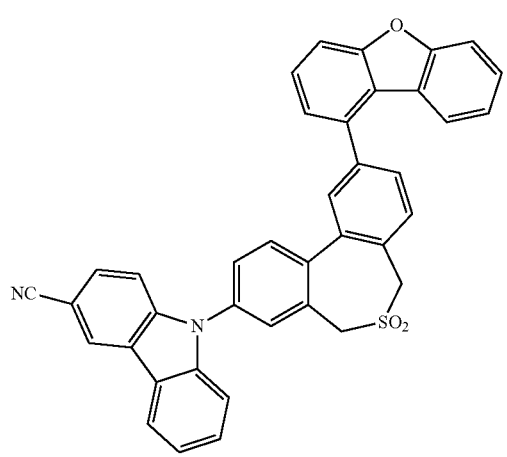
392
-continued
270
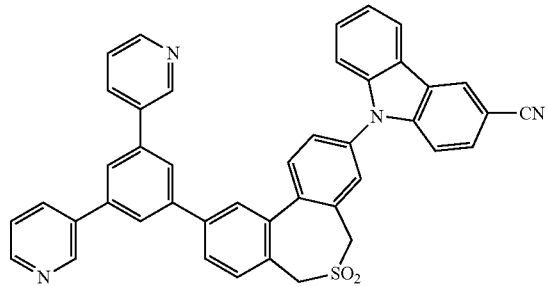
371
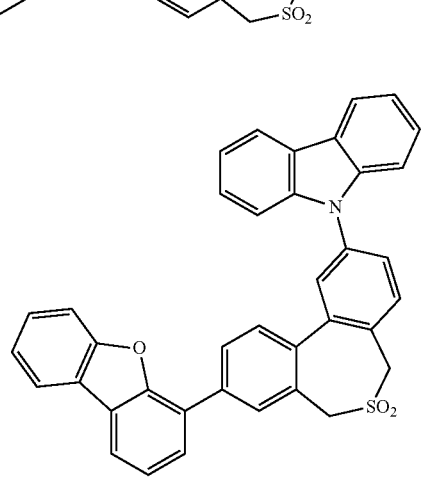
272
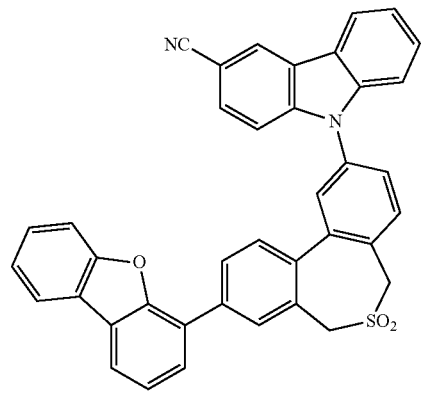
273

274
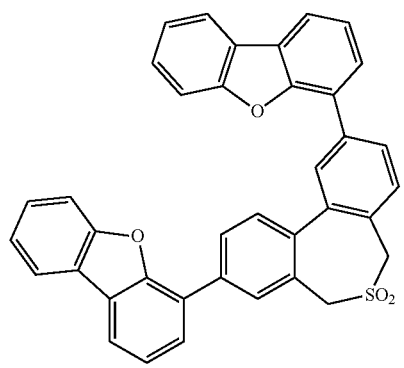
275
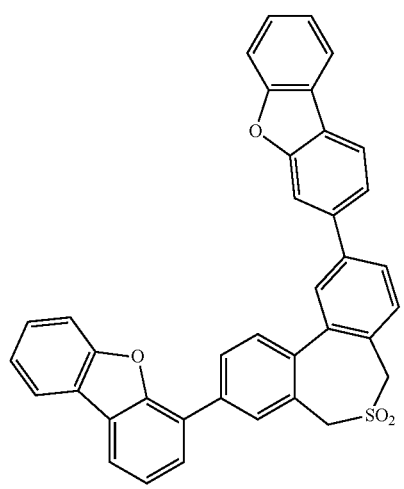
276
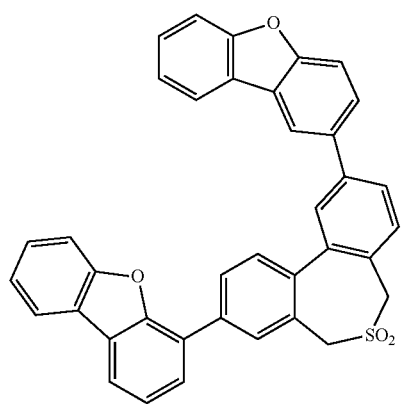
277
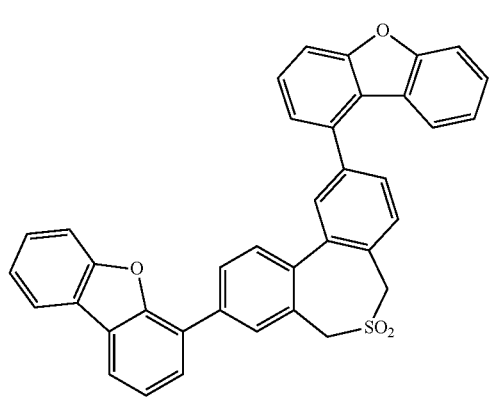
278
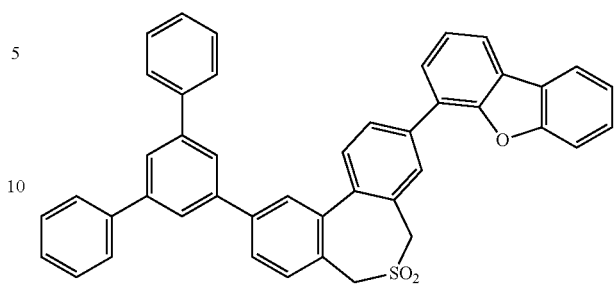
279
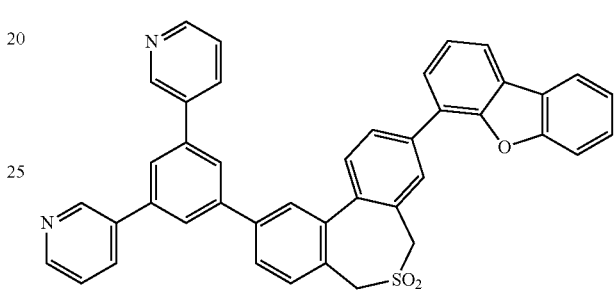
280
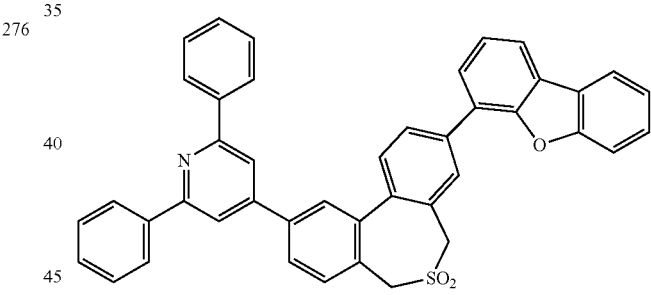
281
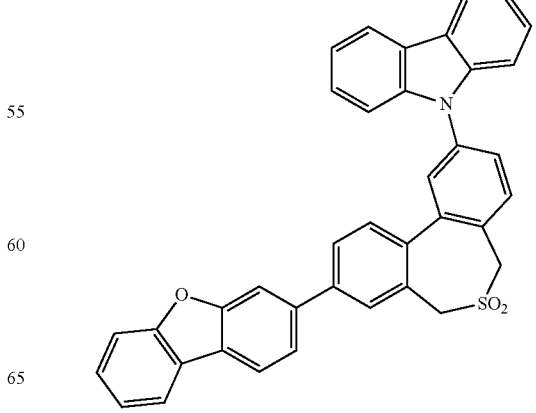

-continued
282
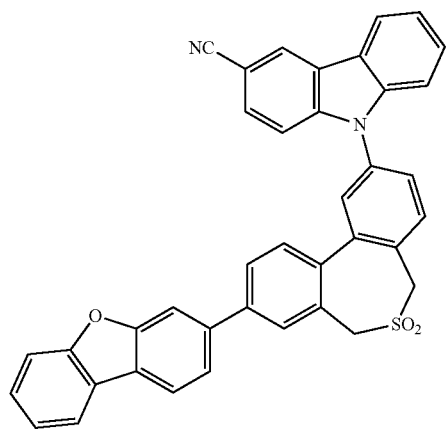
283
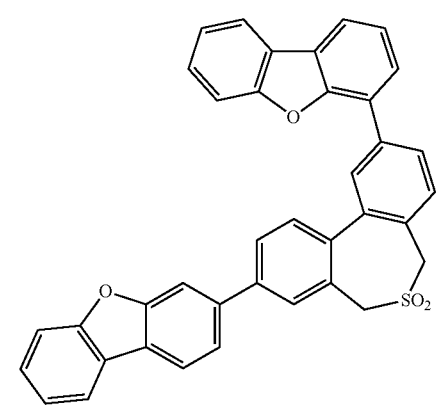
284
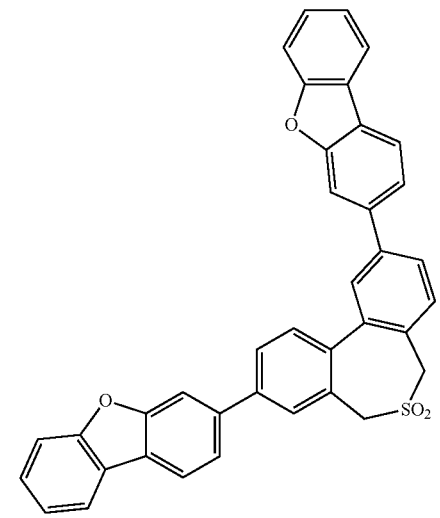
-continued
285
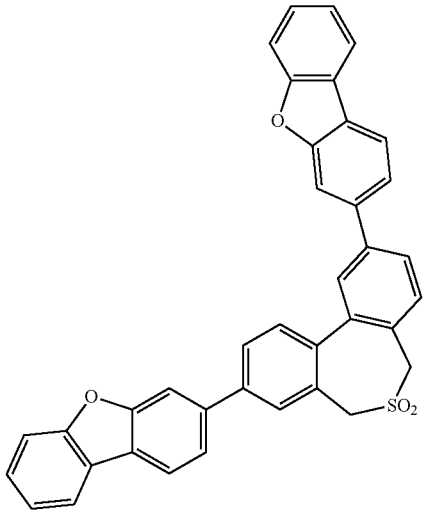
286
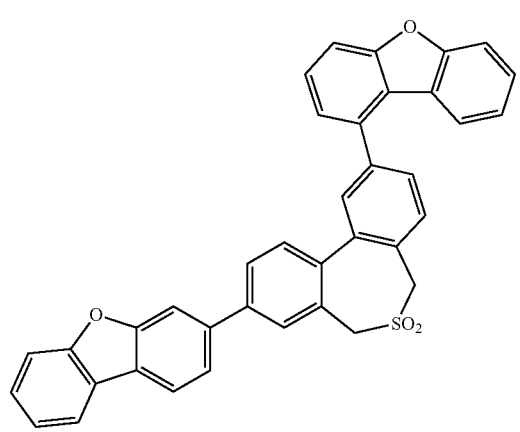
287
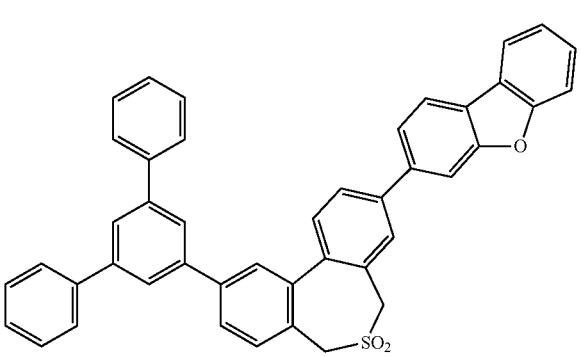
288
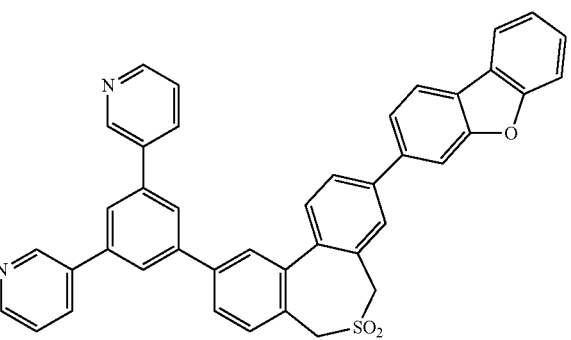

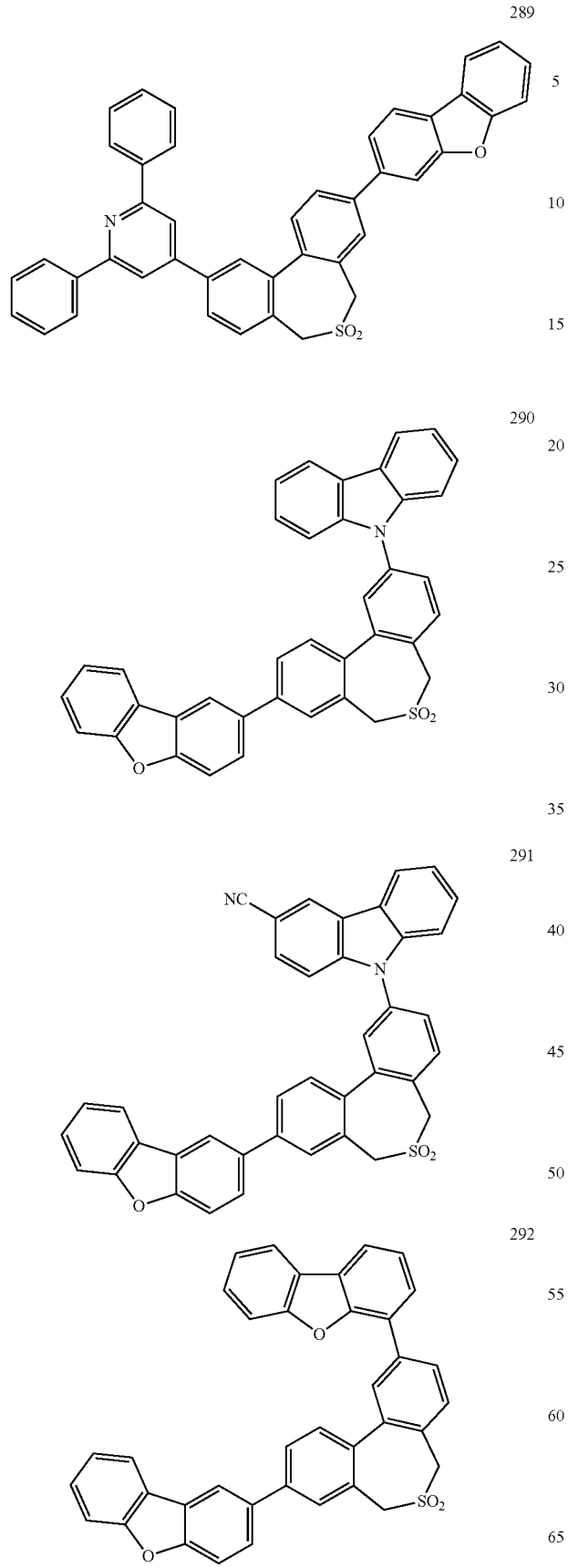
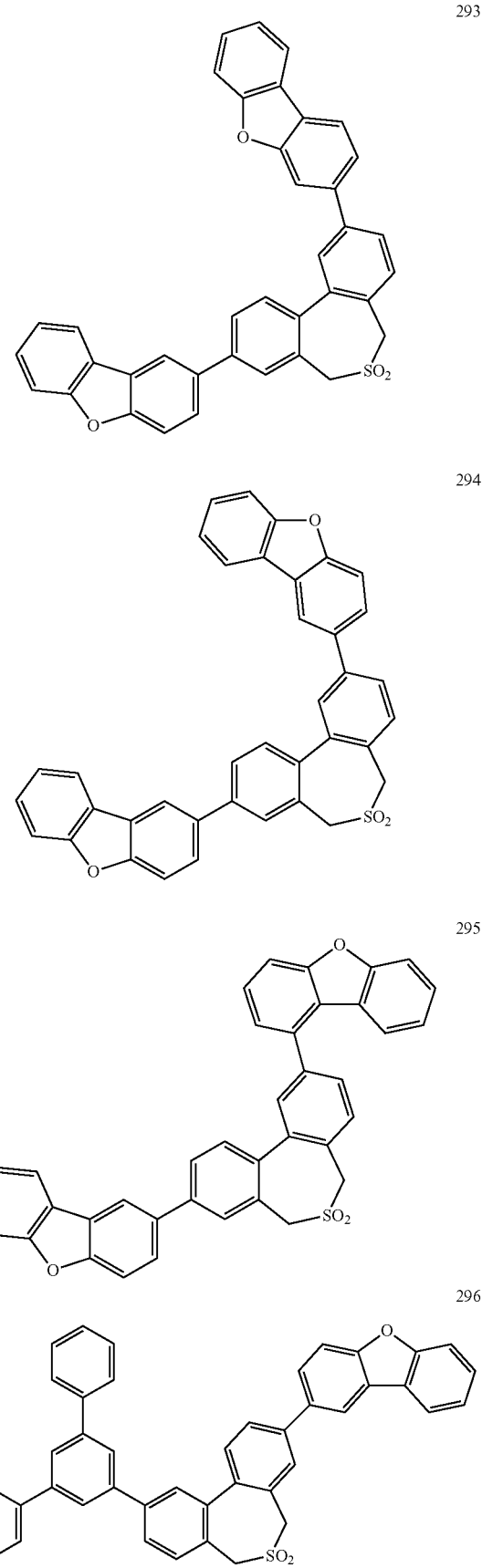

297
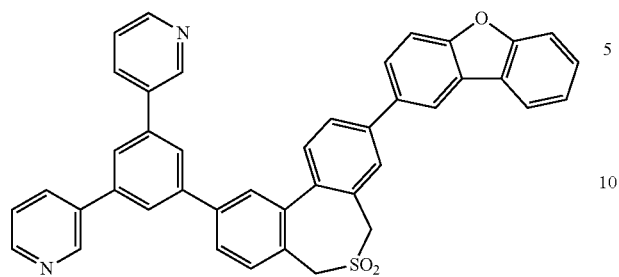
298
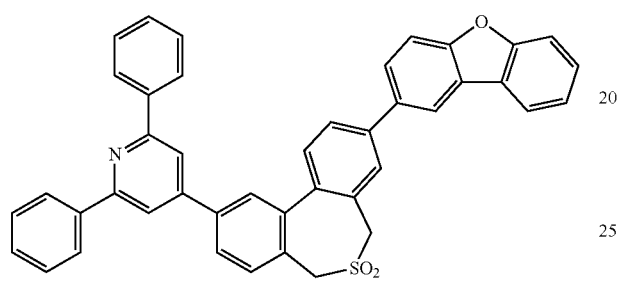
299
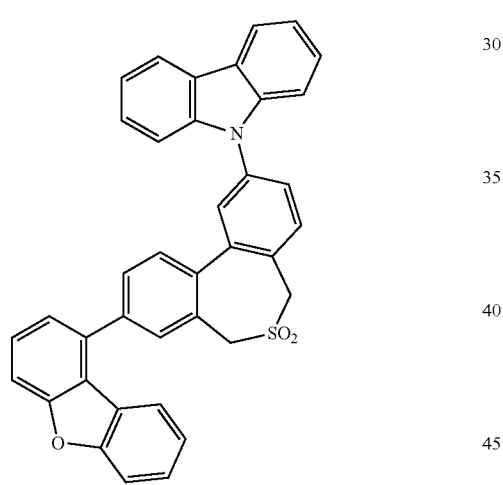
300
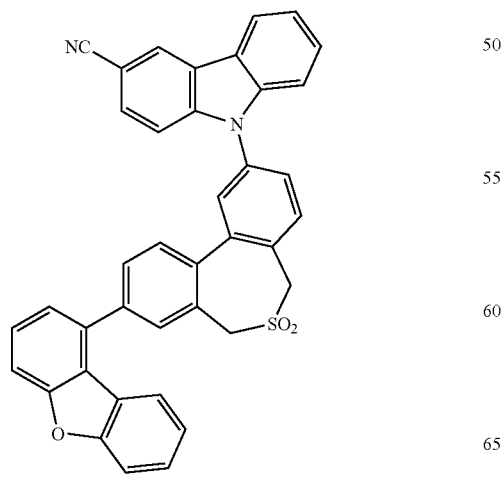
301
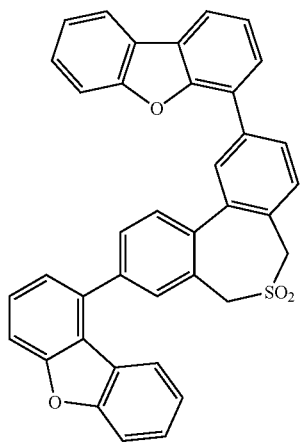
302
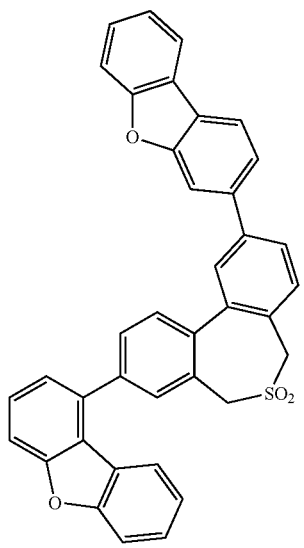
303
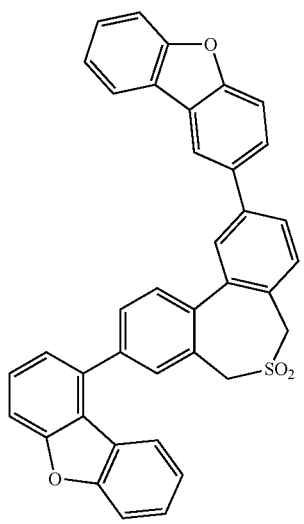

-continued
304
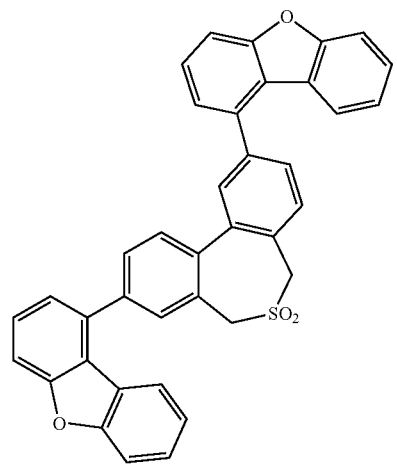
308
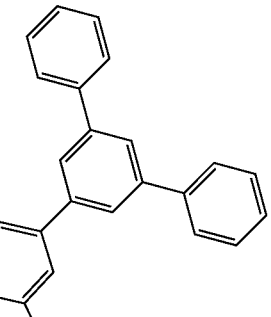
305
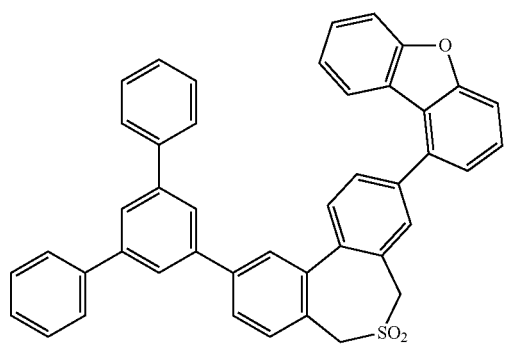
309
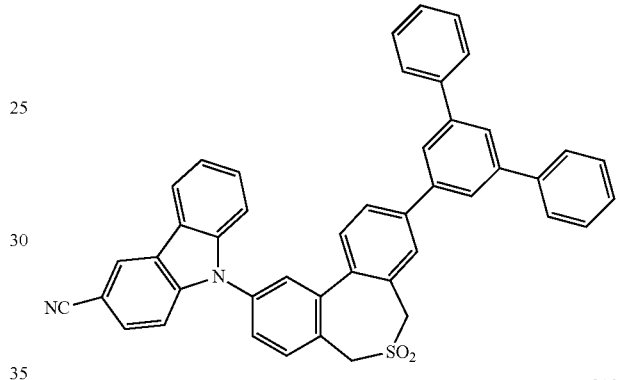
306
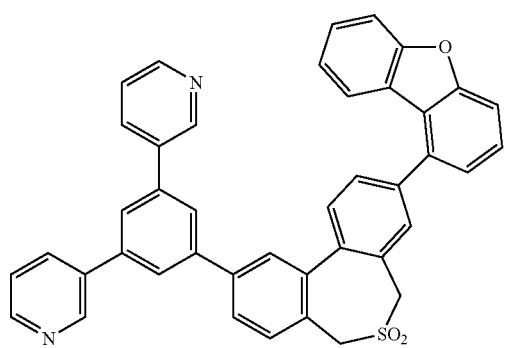
310
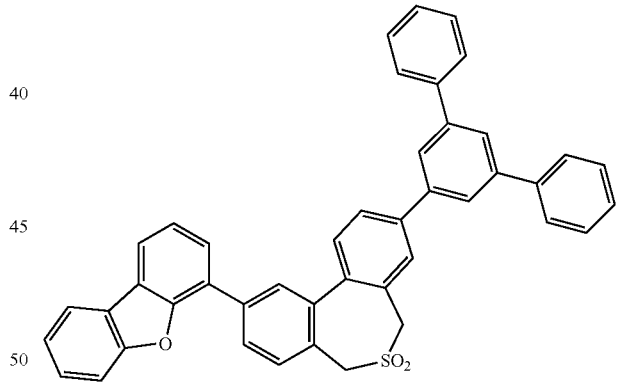
307
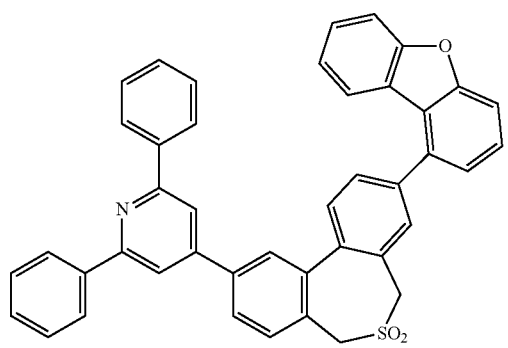
311
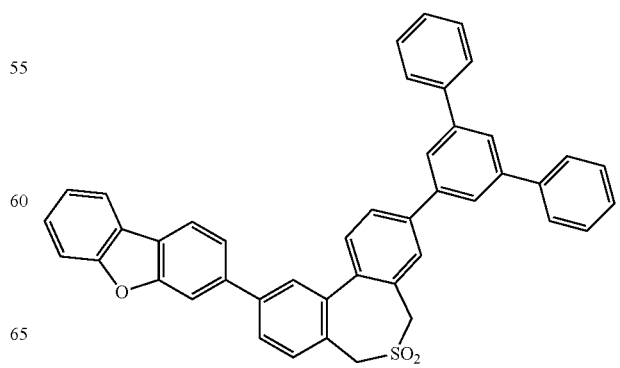

403
-continued
312
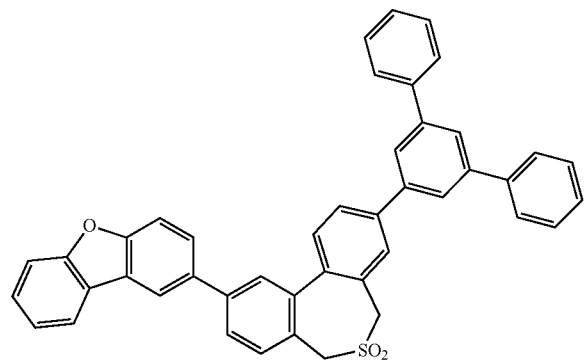
313
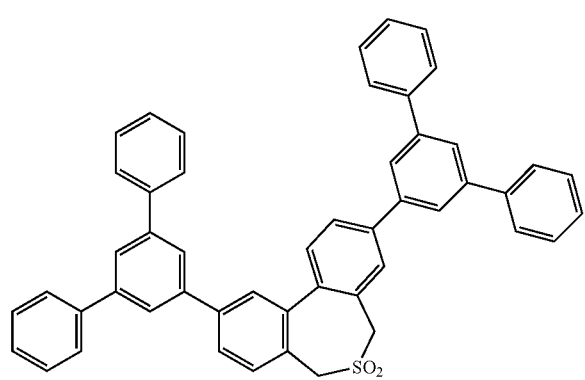
314
315
404
-continued
316
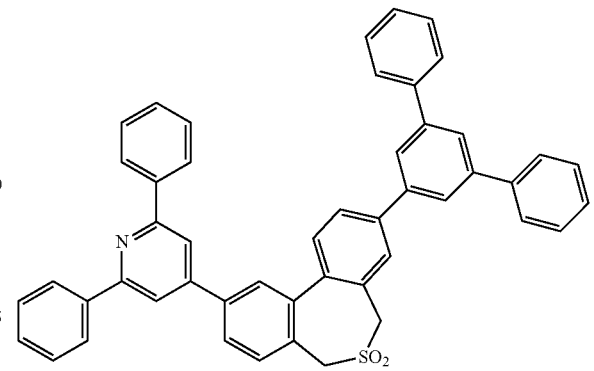
317
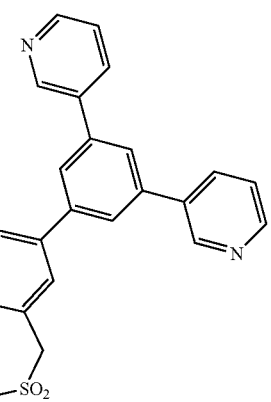
318
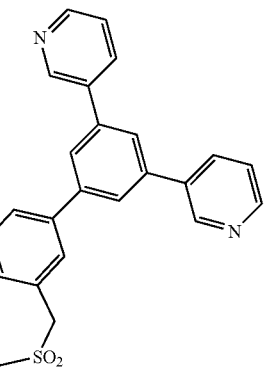
319
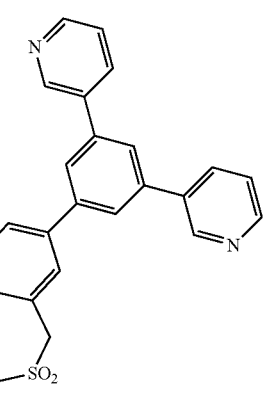

320
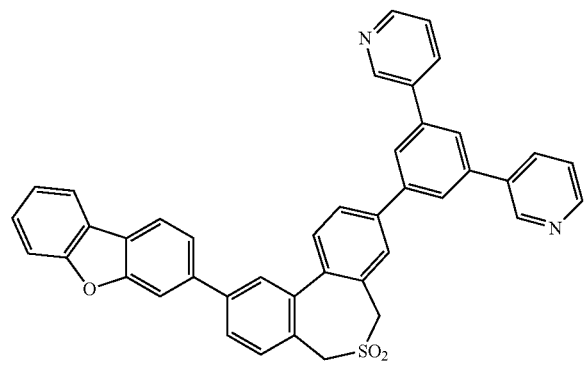
321
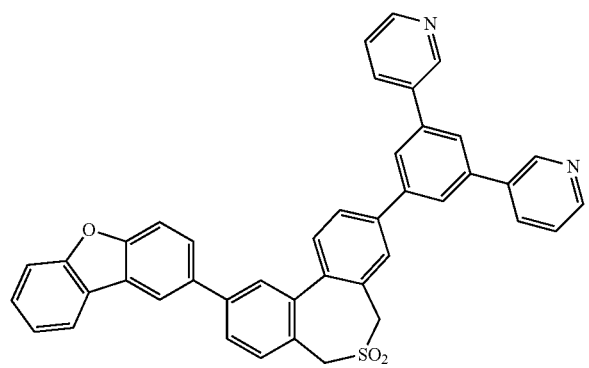
322
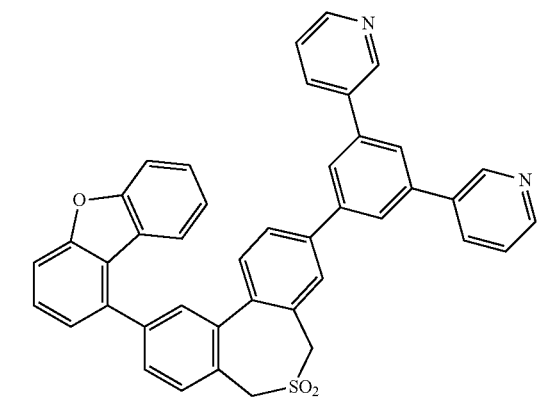
323
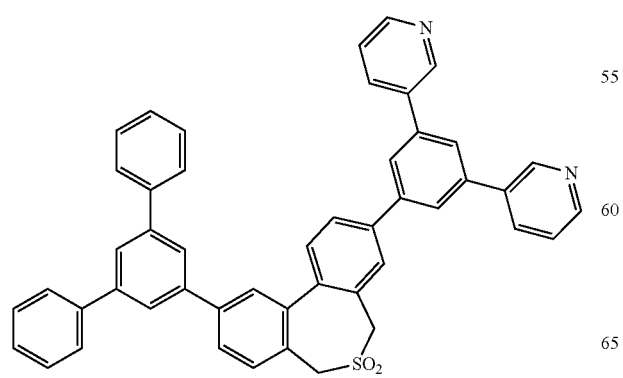
324
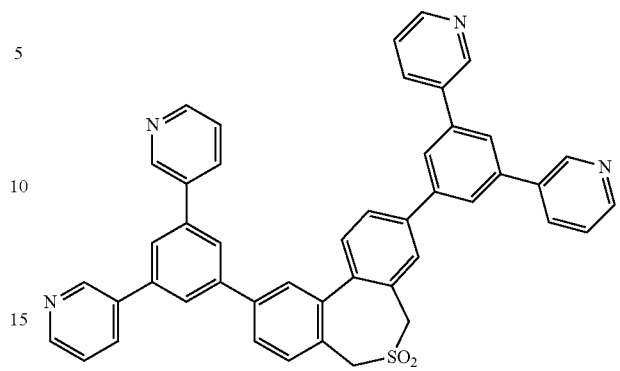
325
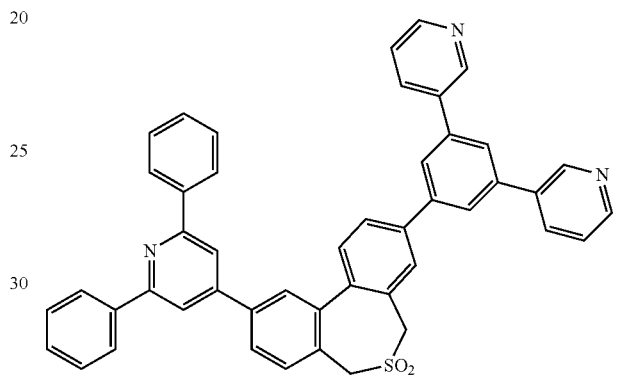
326
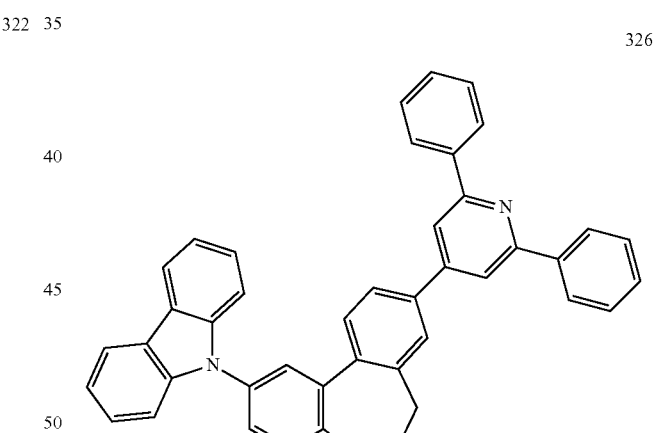
327
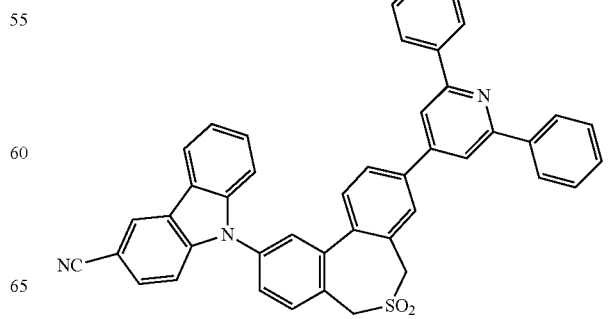

328
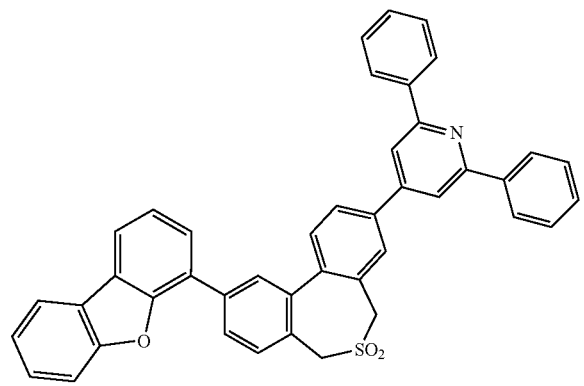
329
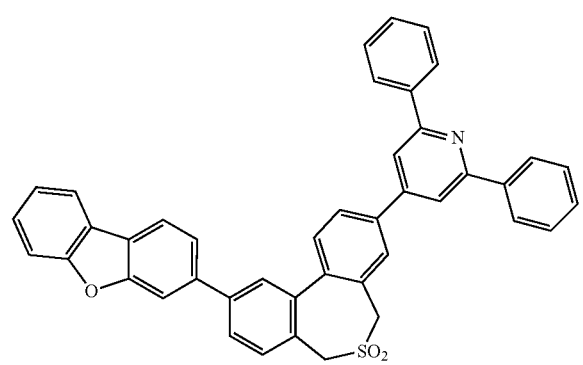
330
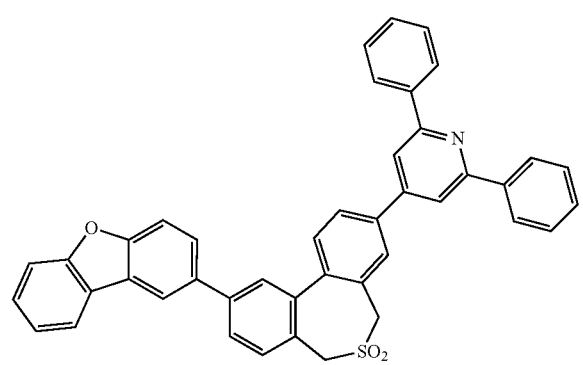
331
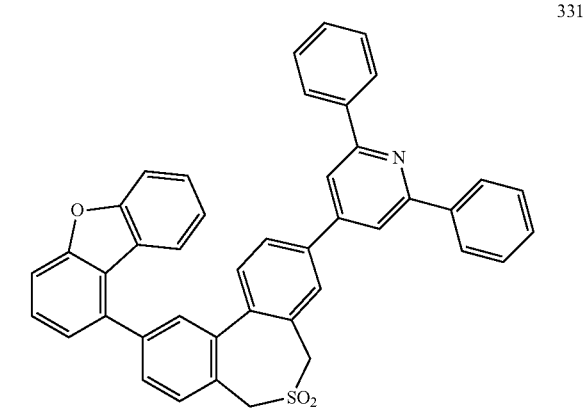
332
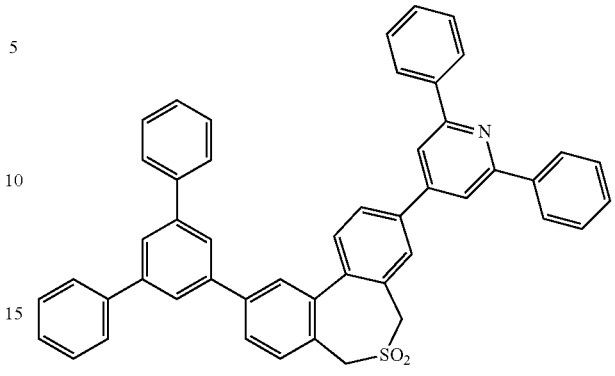
333
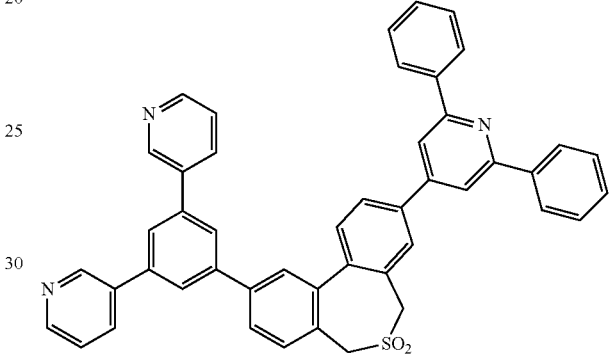
334
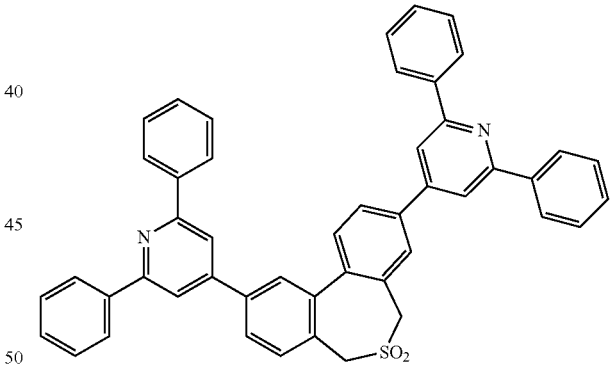
335
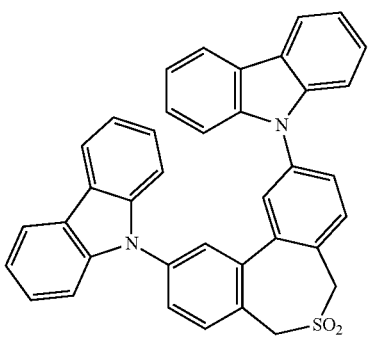

336 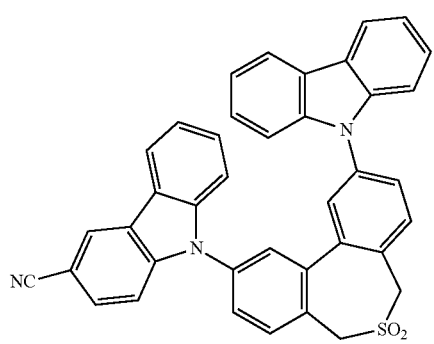
337 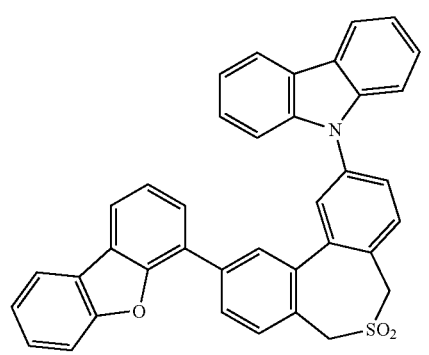
338 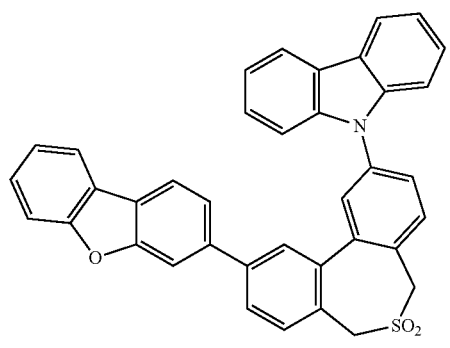
339 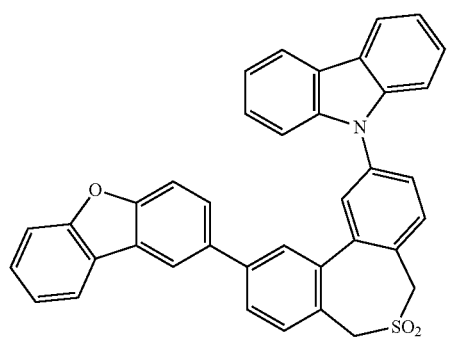
340 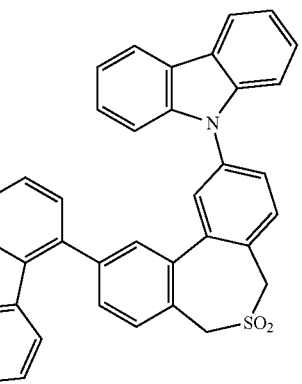
341 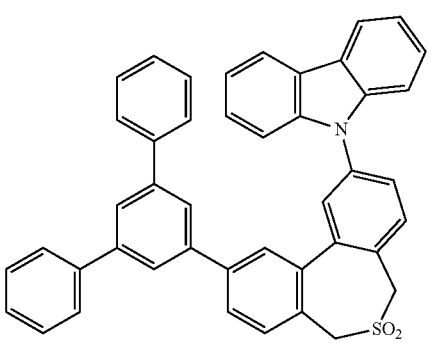
342 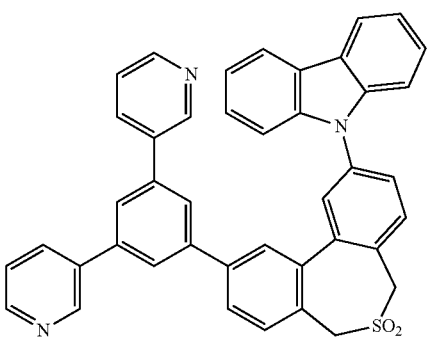
343 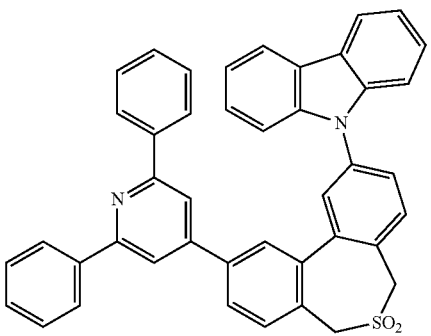

411
-continued
344
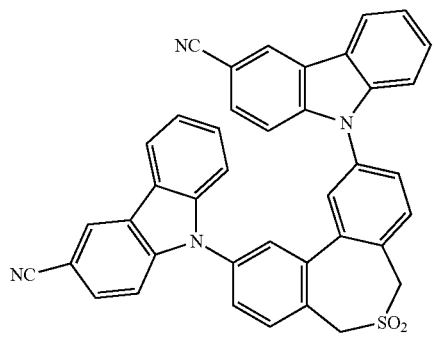
345
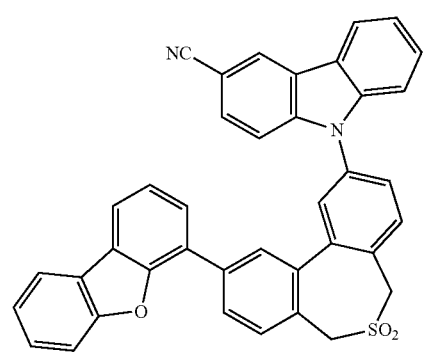
346
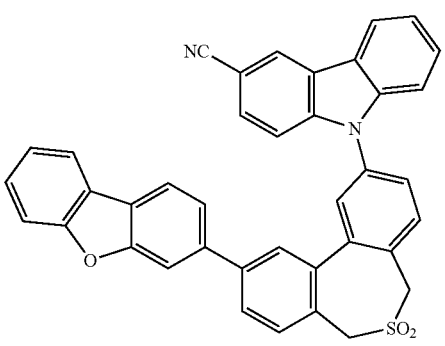
347
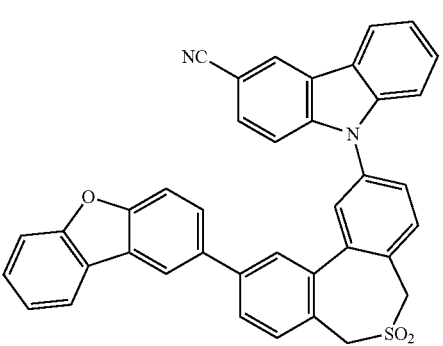
412
-continued
348
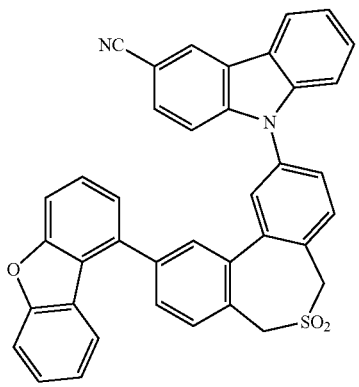
349
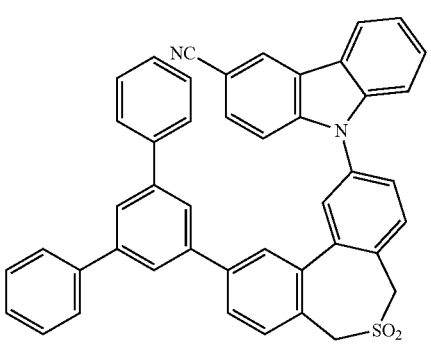
350
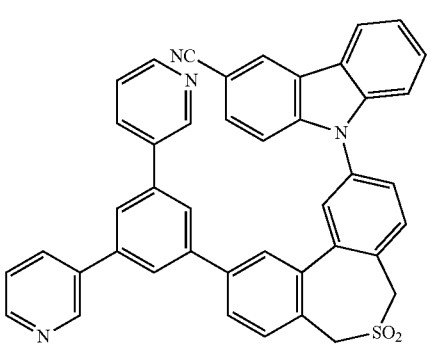
351
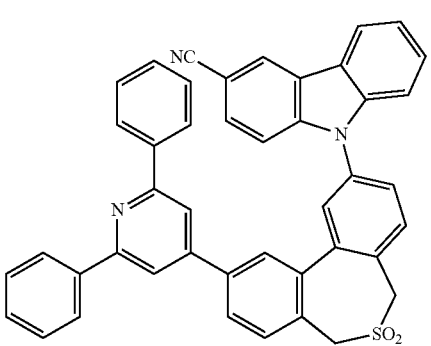

| 413 | 414 |
|---|---|
| -continued | -continued |
| 352 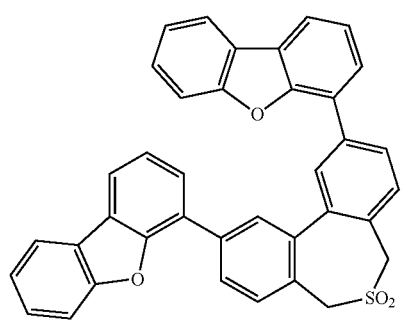 | 356 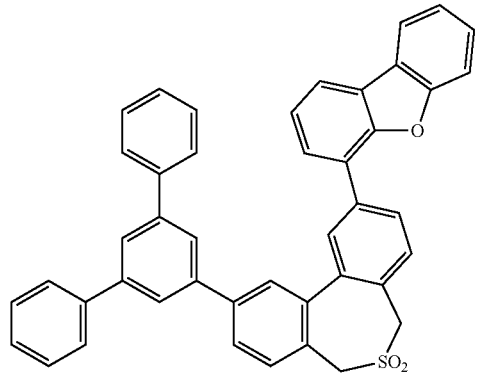 |
| 353 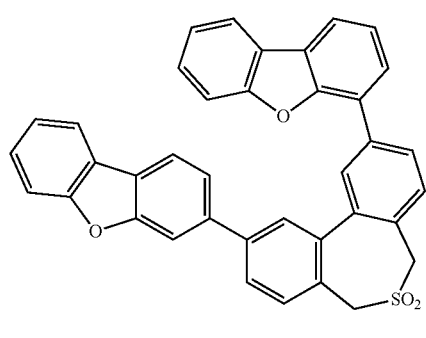 | 357 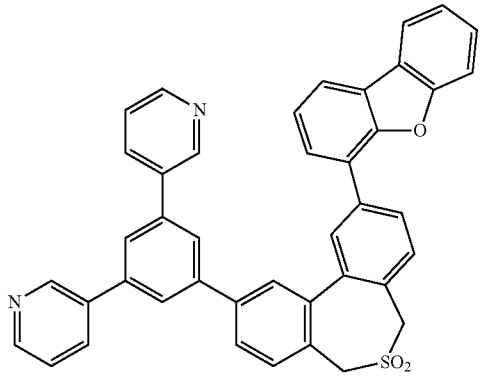 |
| 354 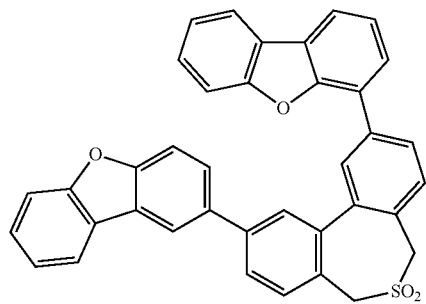 | 358 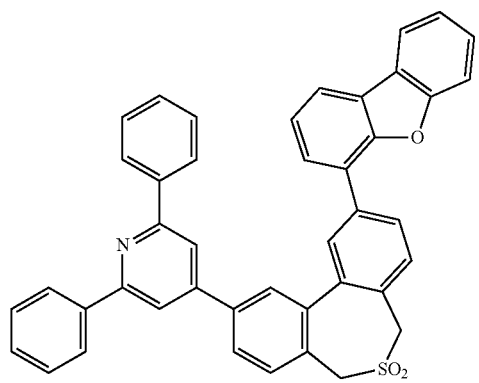 |
| 355 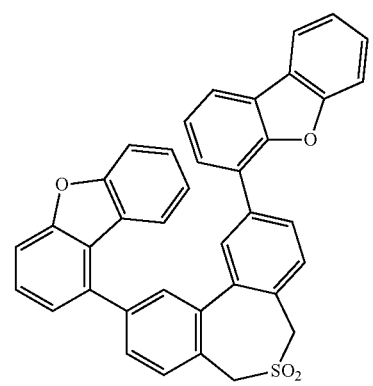 | 359 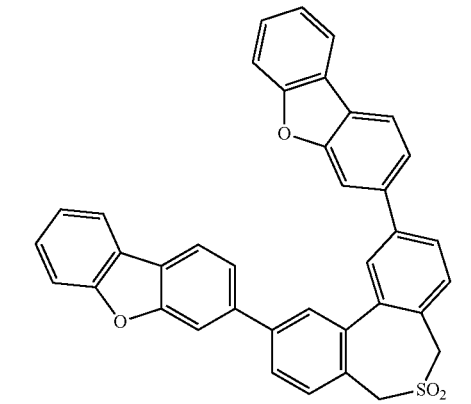 |

360
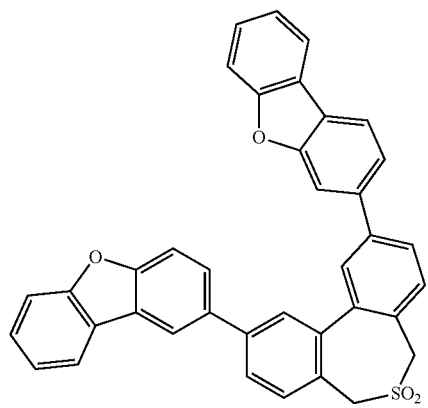
361
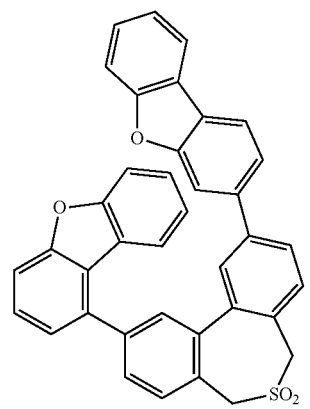
362
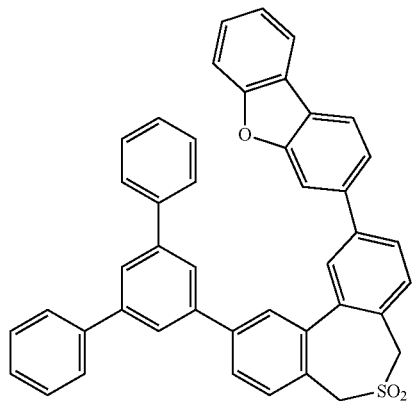
363
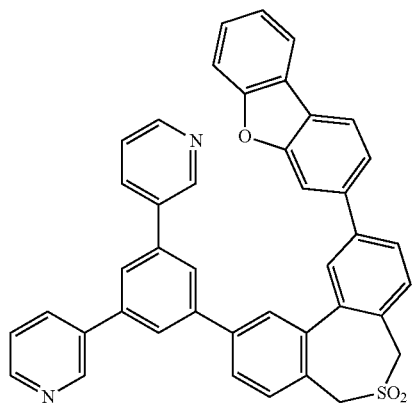
364
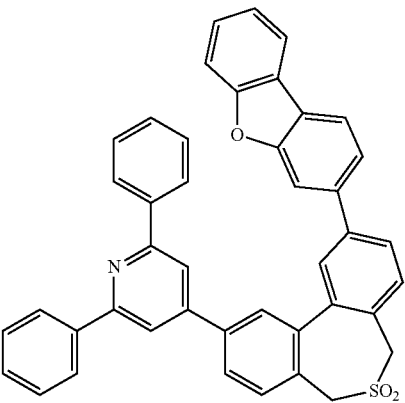
365
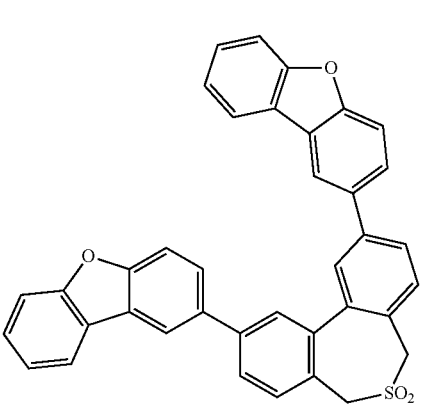
366
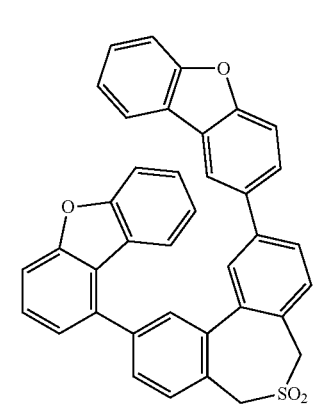
367
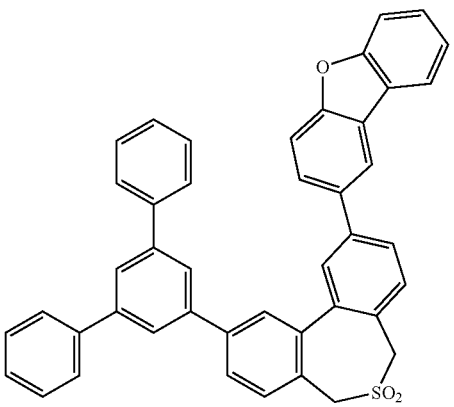

368
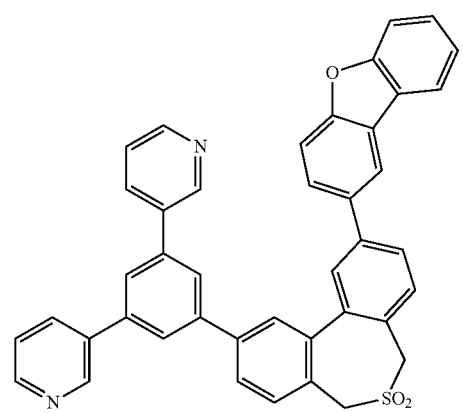
369
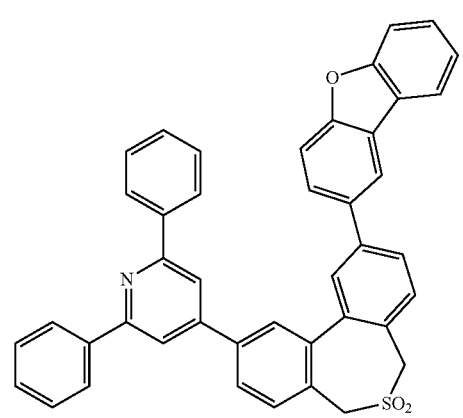
370
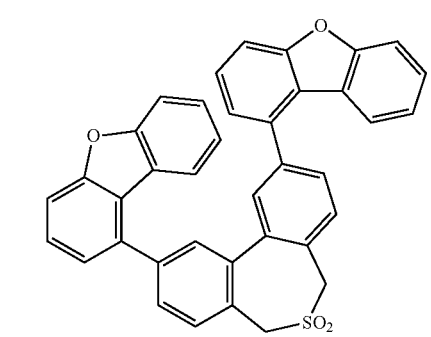
371
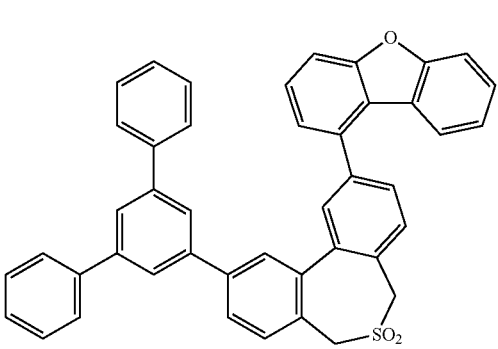
372
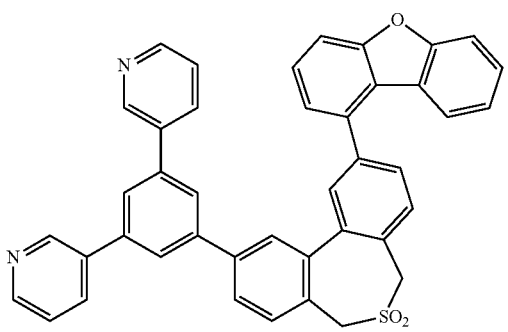
373
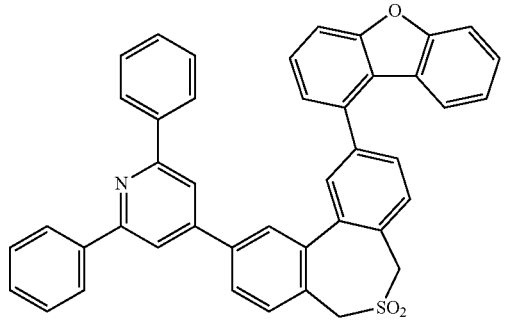
374
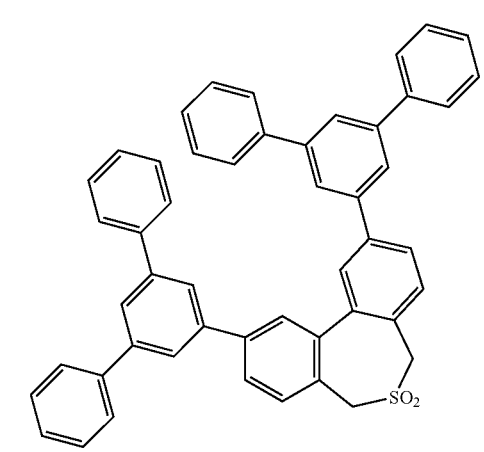
375
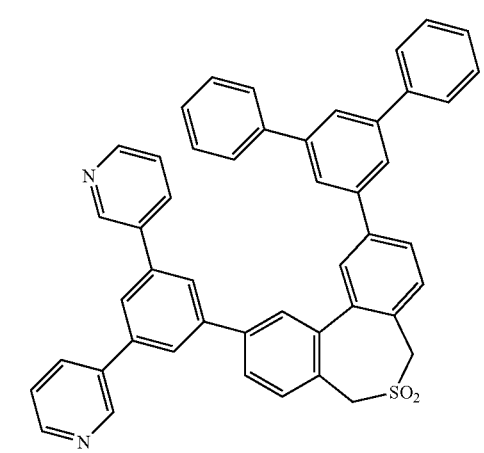

-continued
376
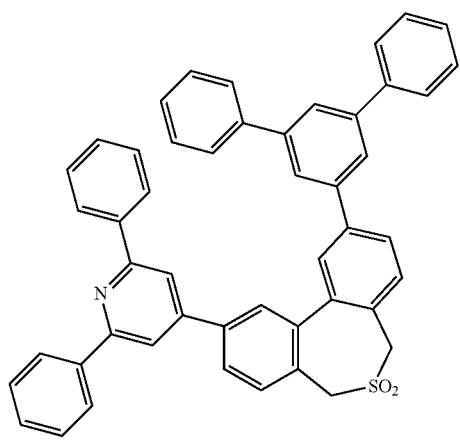
377
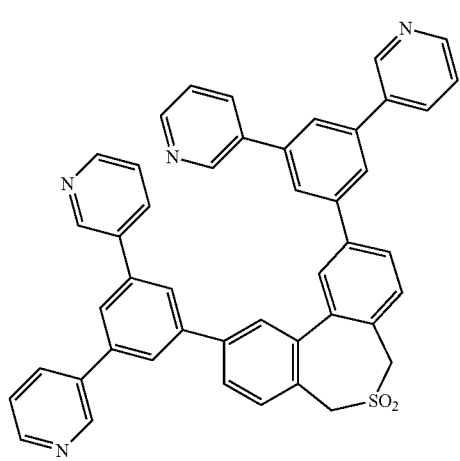
378
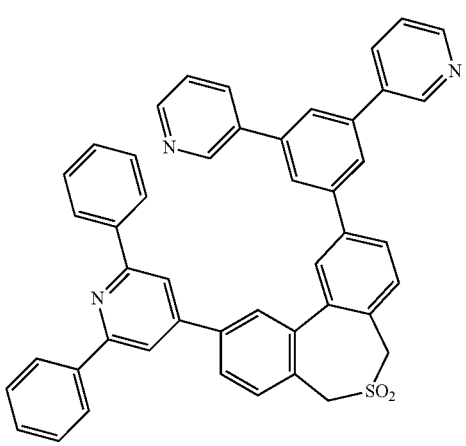
-continued
379
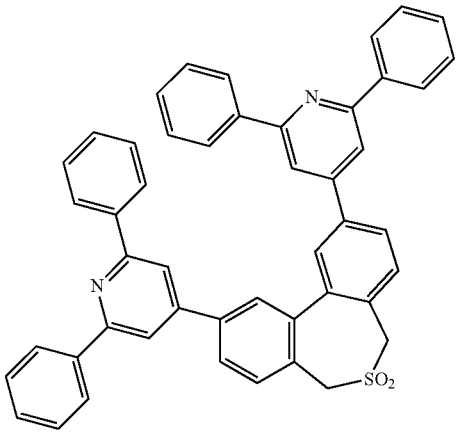
380
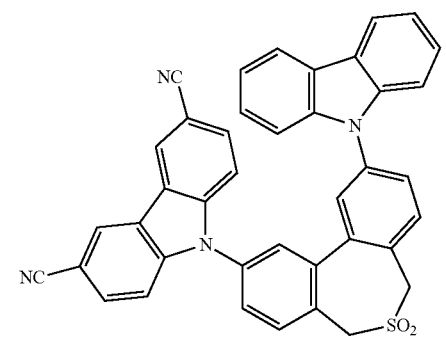
381
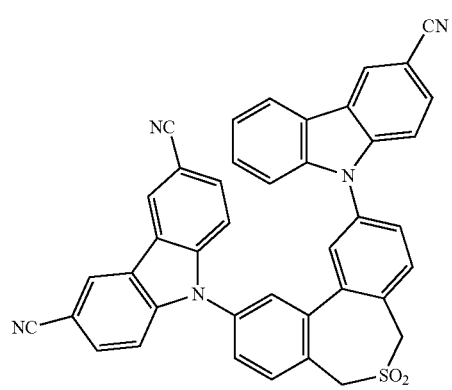
382
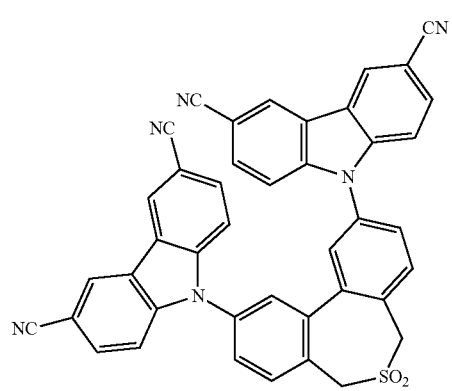

383 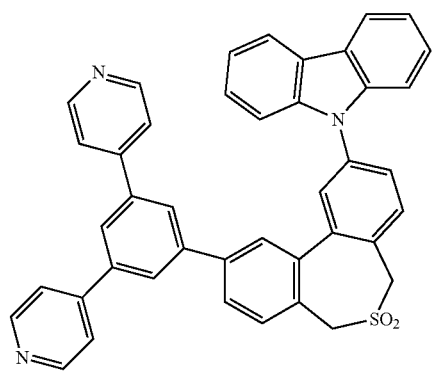
384 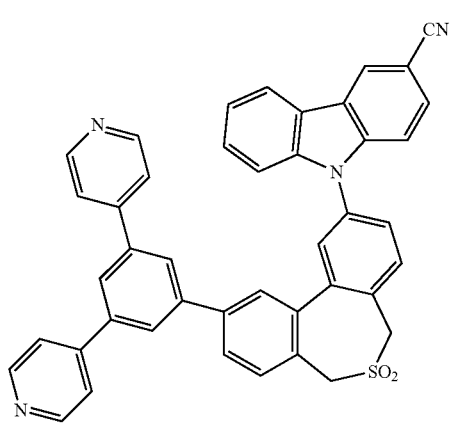
385 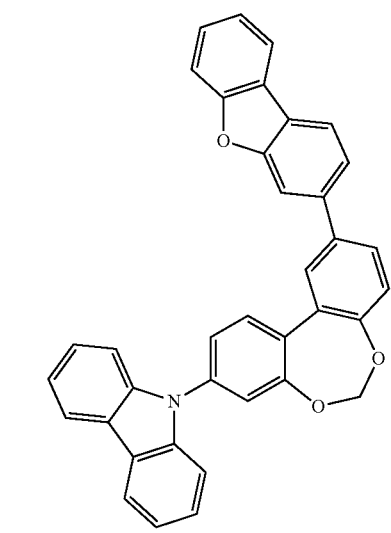
386 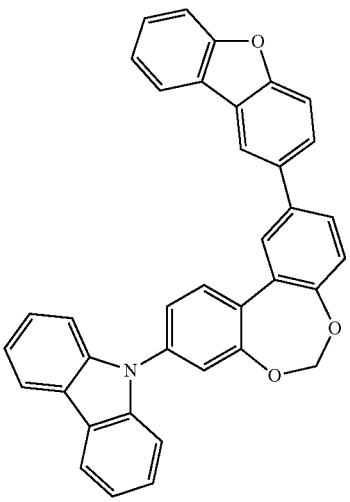
387 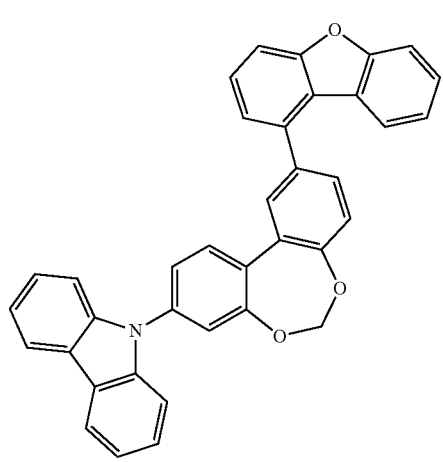
388 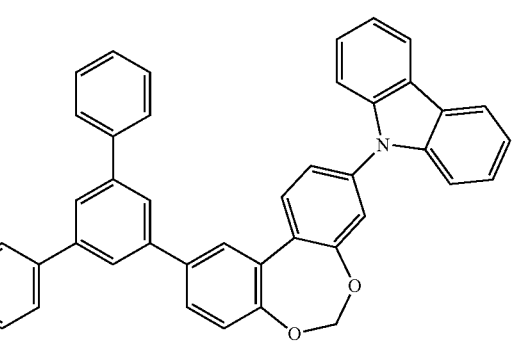
389 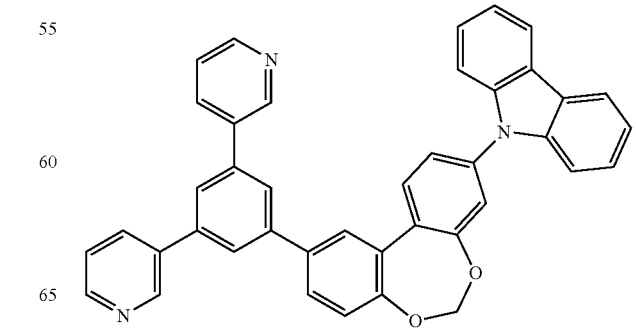

-continued
390
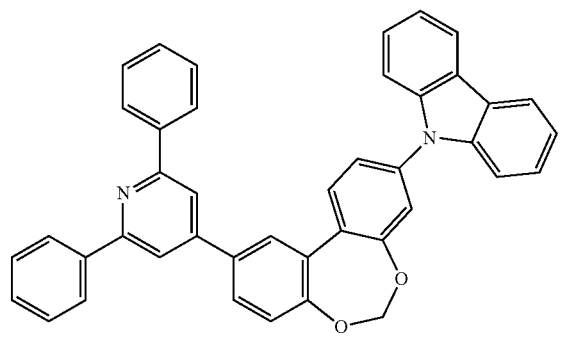
391
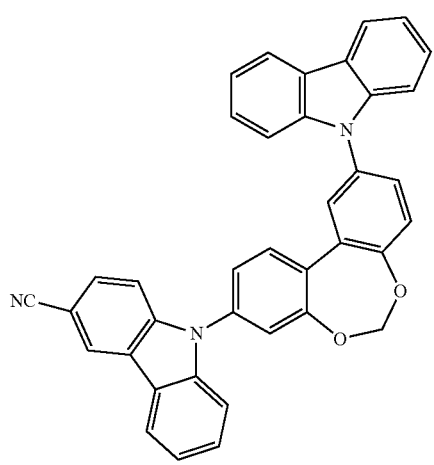
392
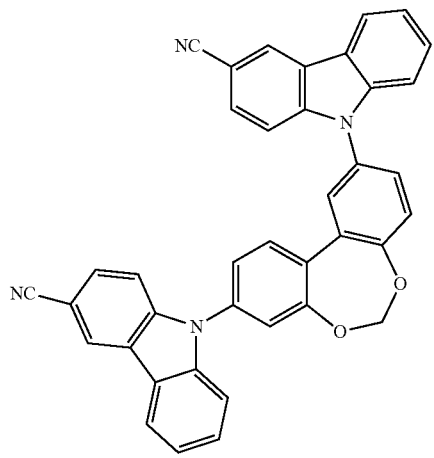
-continued
393
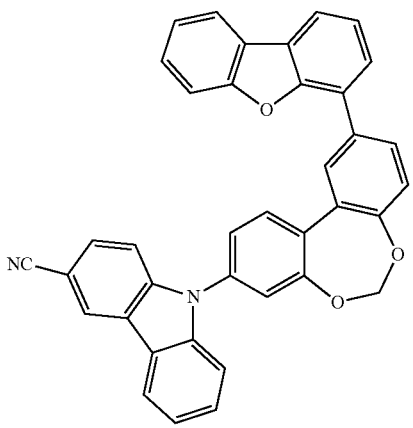
394
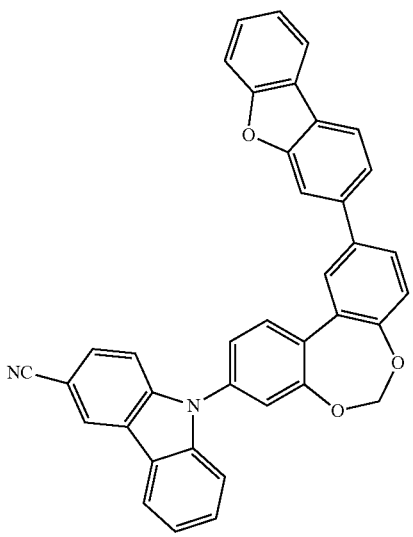
395
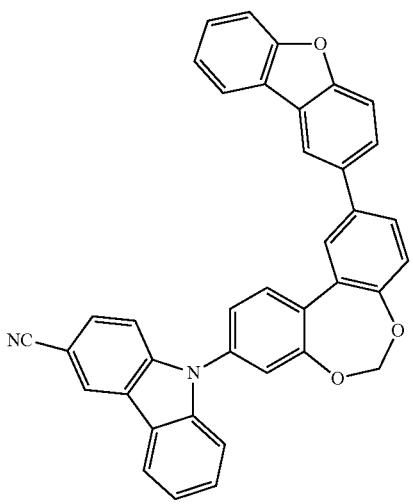

-continued
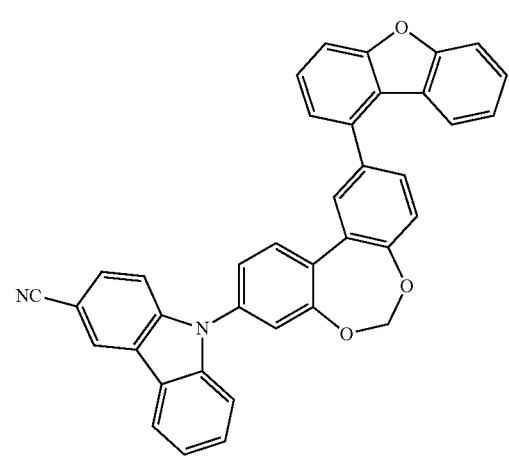
396
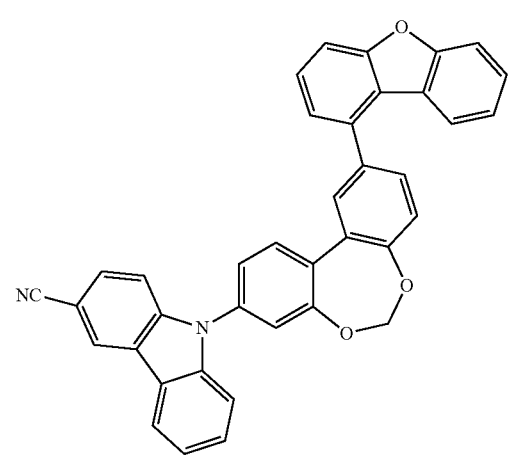
397
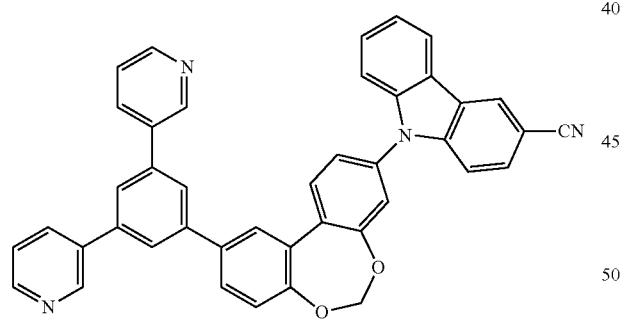
398
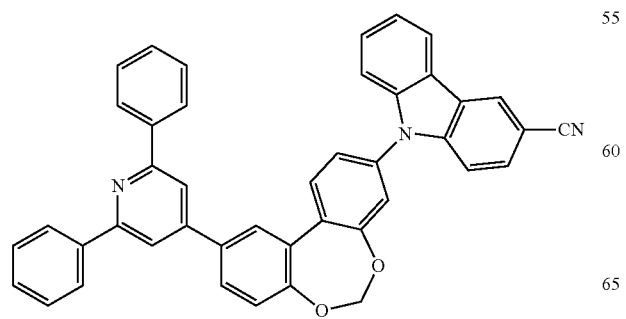
399
-continued
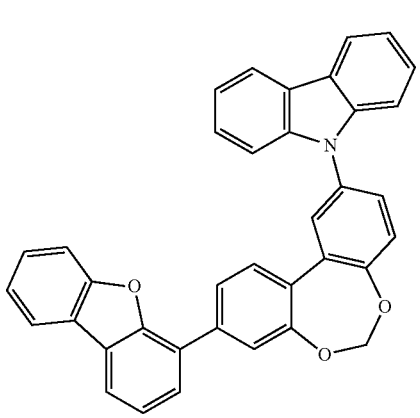
400
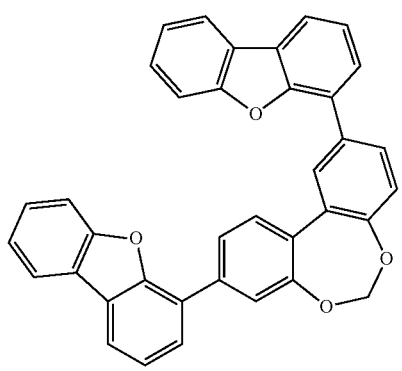
401
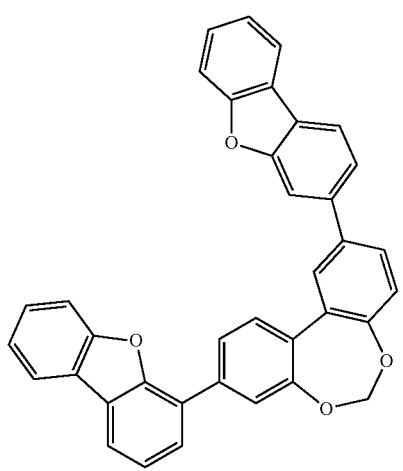
402
403

427
-continued
404
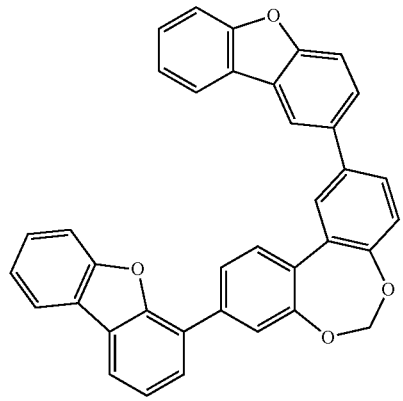
405
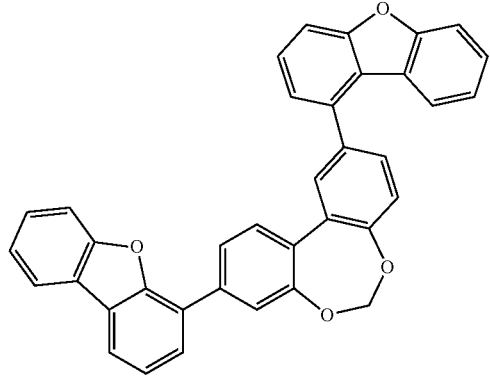
406
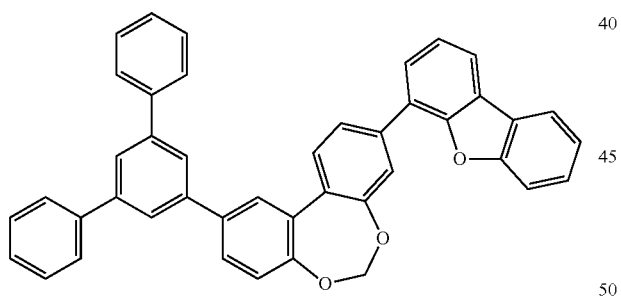
407
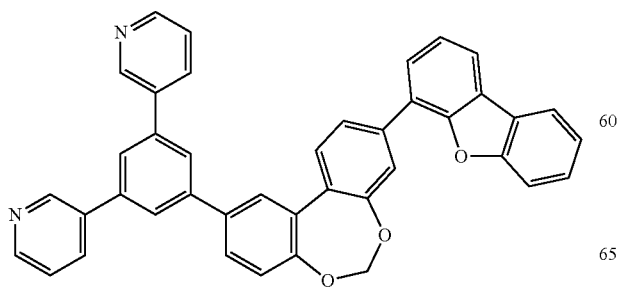
428
-continued
408
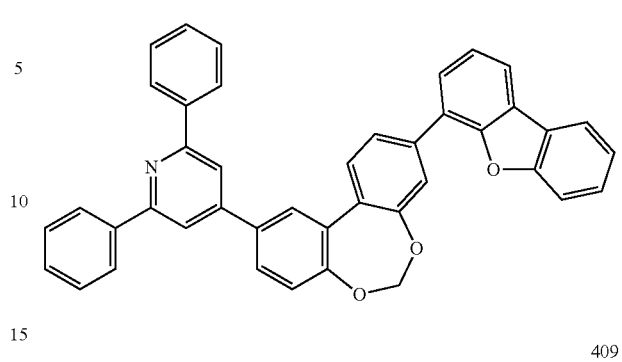
409
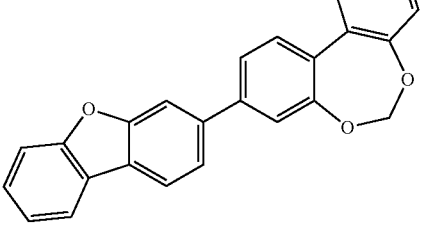
410
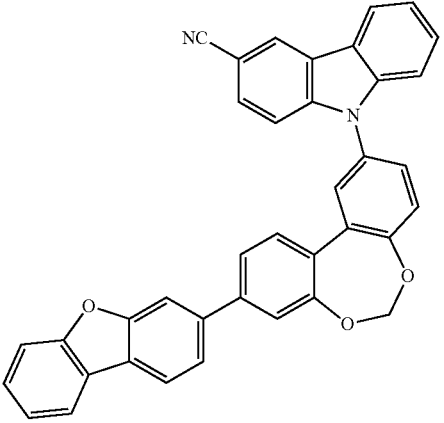
411
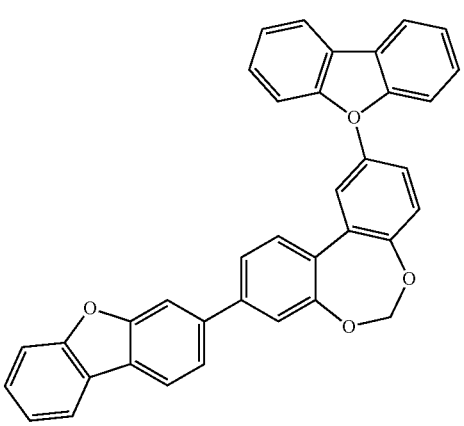

412
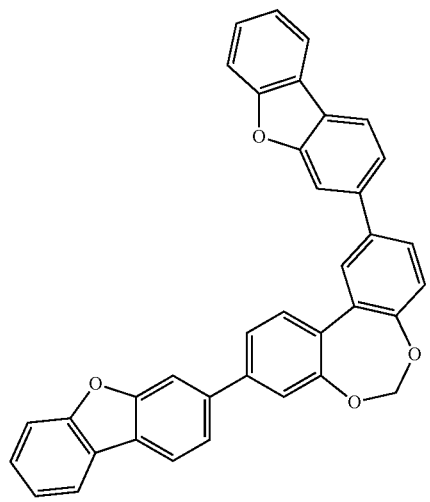
413
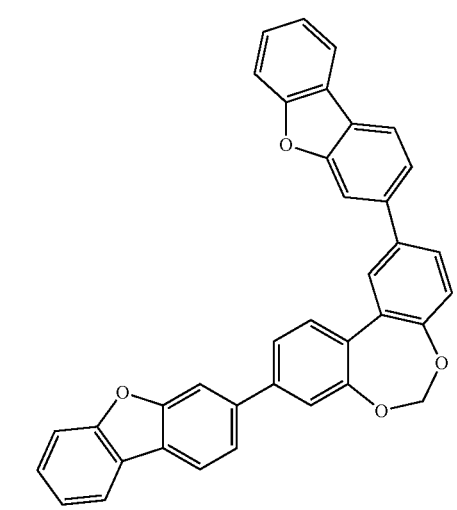
414
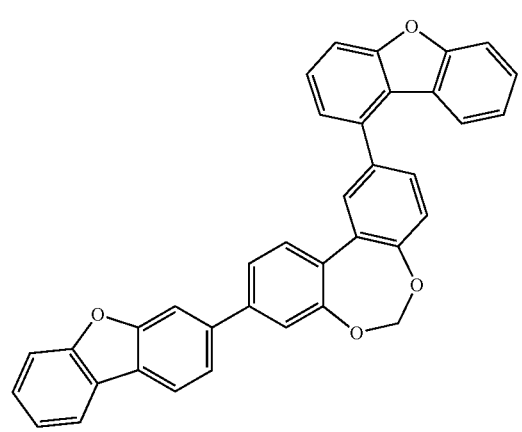
415
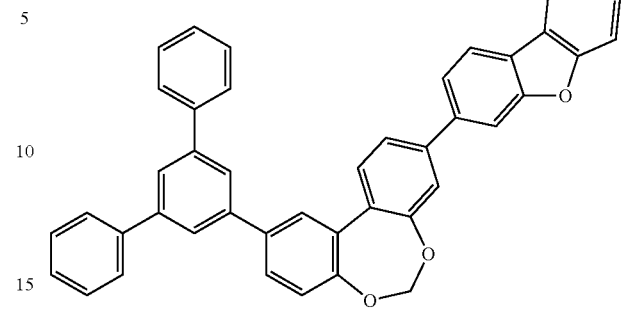
416
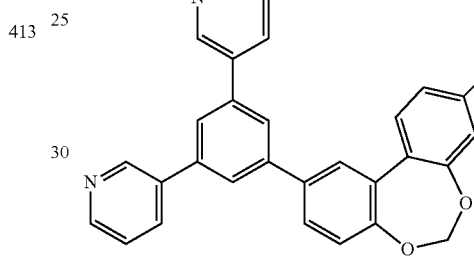
417
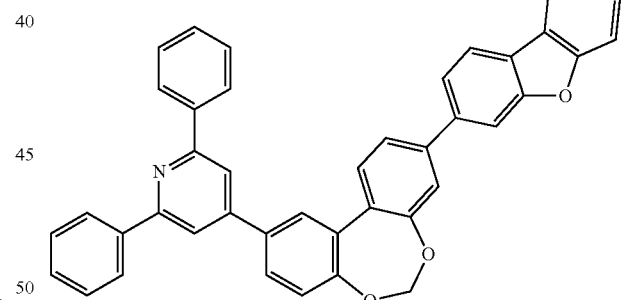
418
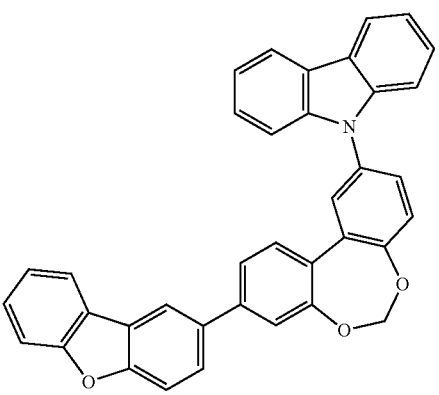

431
-continued
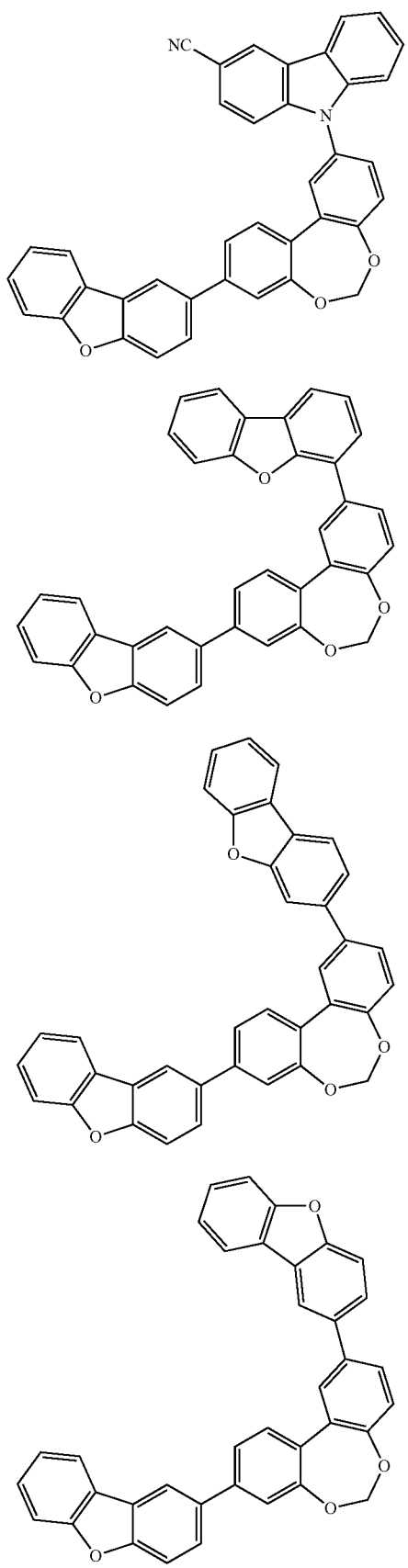
432
-continued
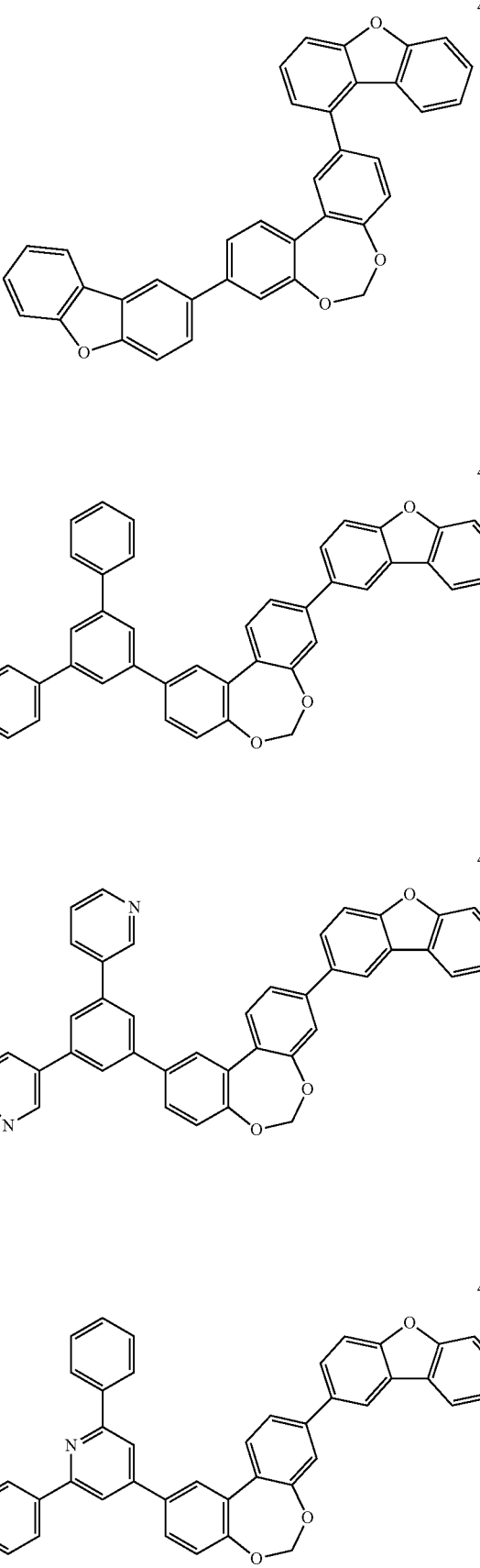

433
-continued
427
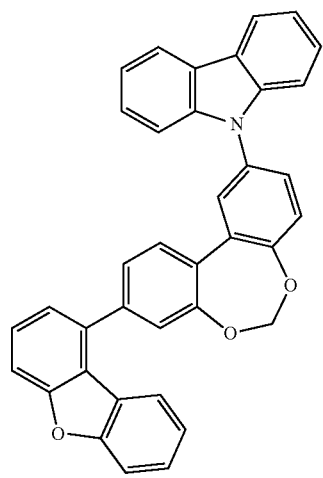
428
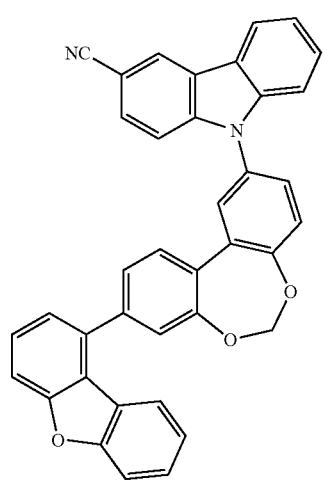
429
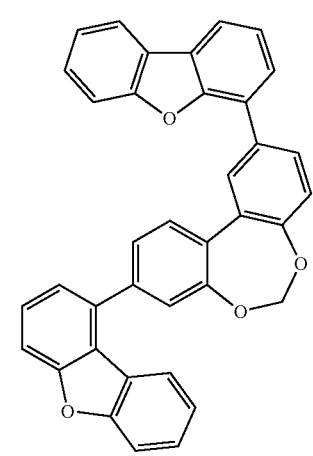
434
-continued
430
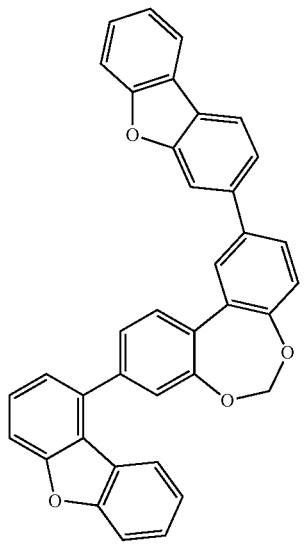
431
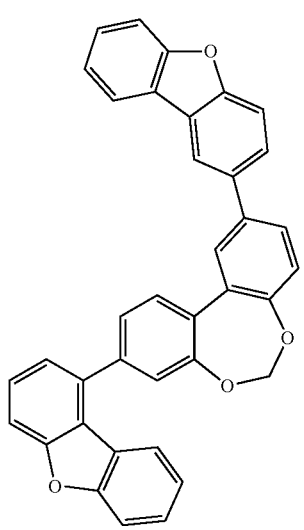
432
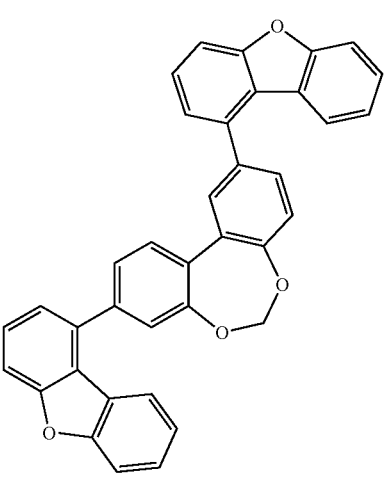

435
-continued
433
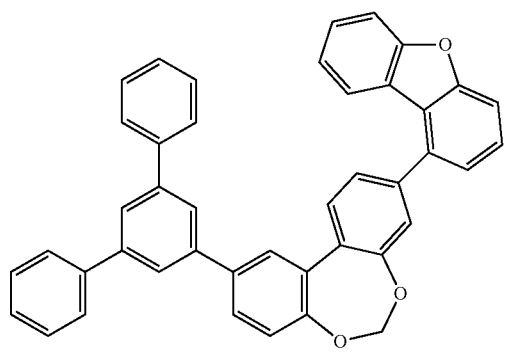
434
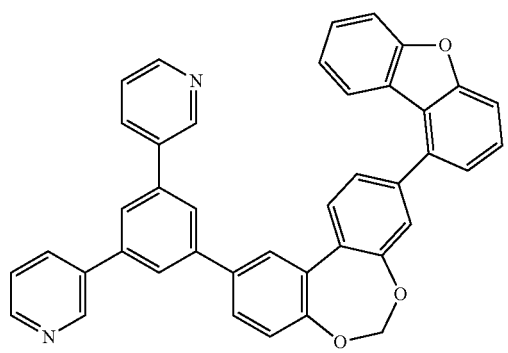
435
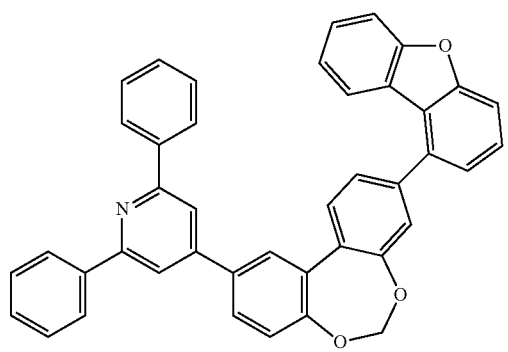
436
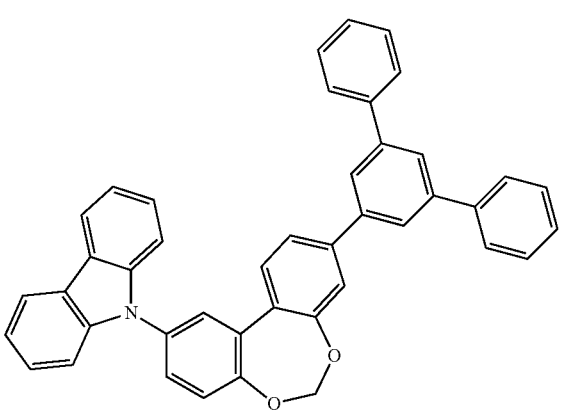
436
-continued
437
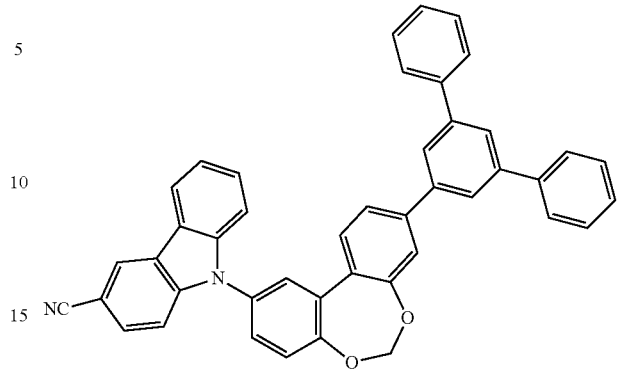
438
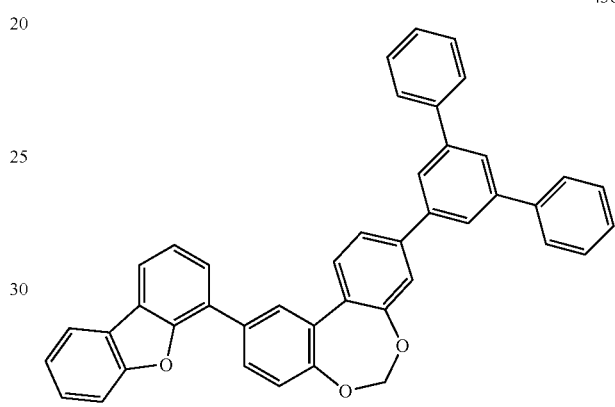
439
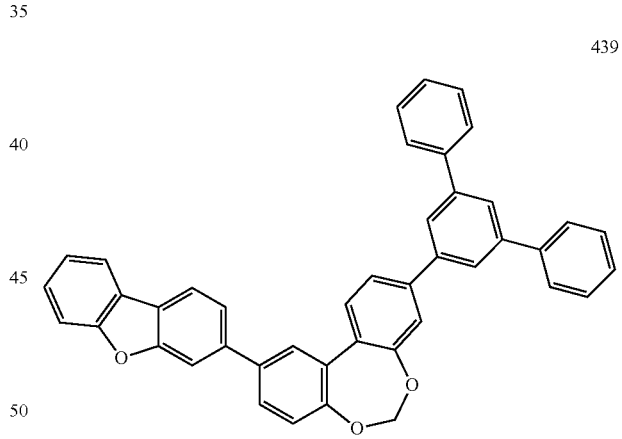
440
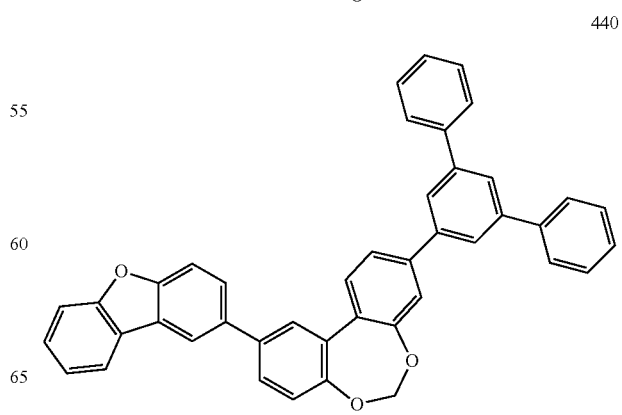

437
-continued
441
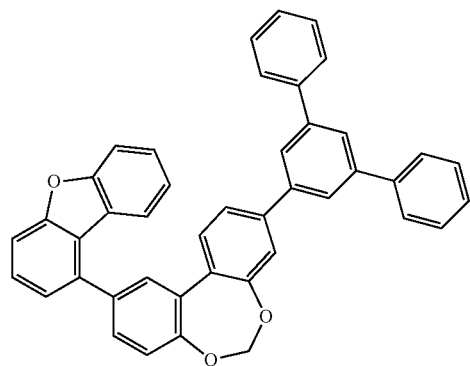
442
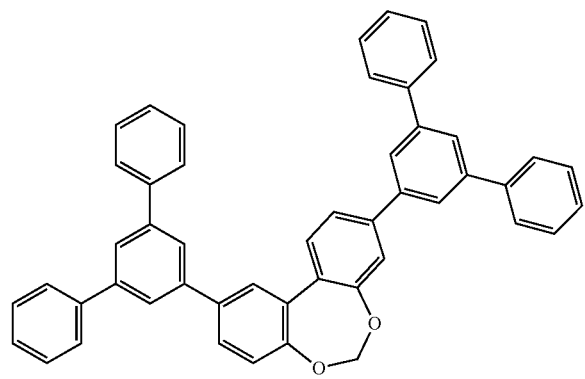
443
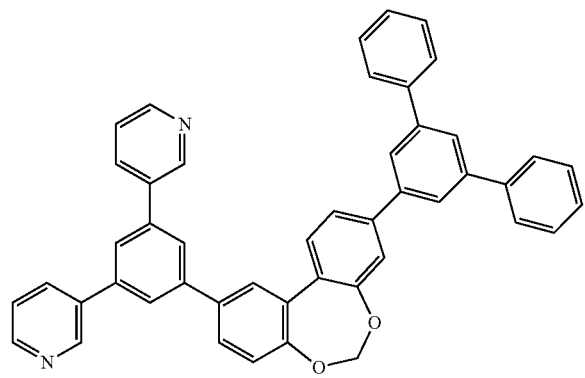
444
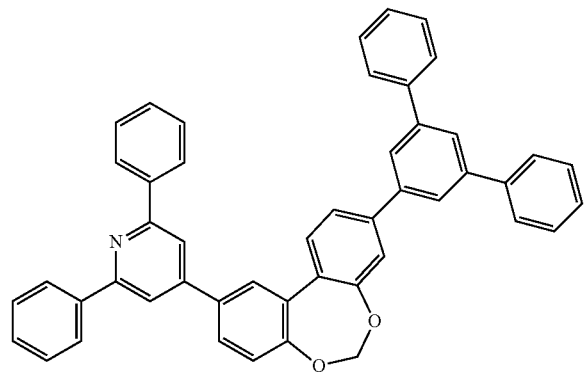
438
-continued
445
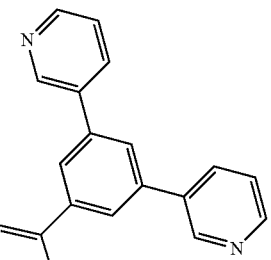
446
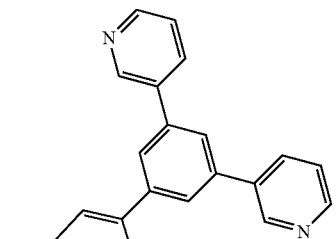
447
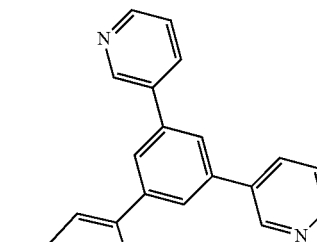
448
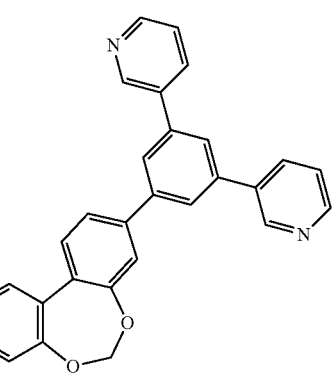

439
-continued
449
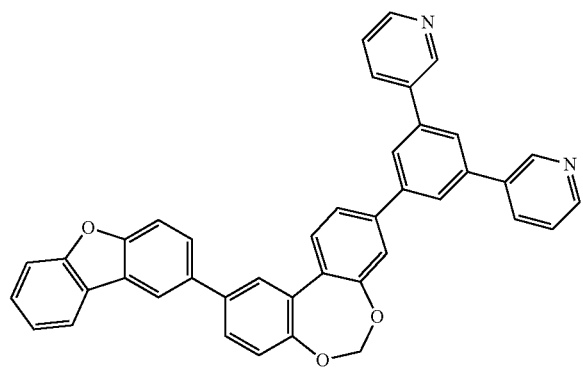
450
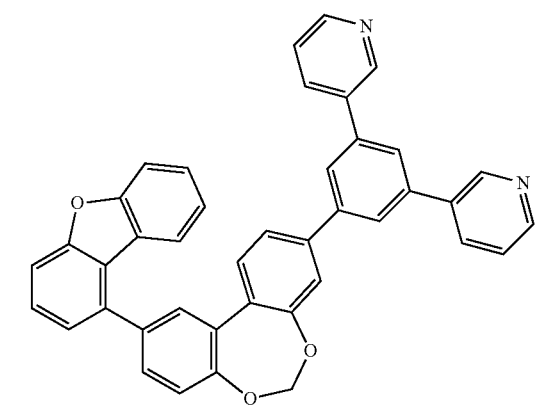
451
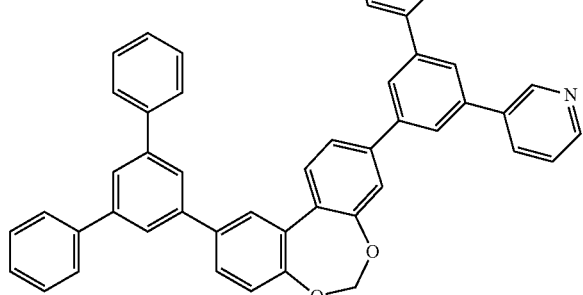
452
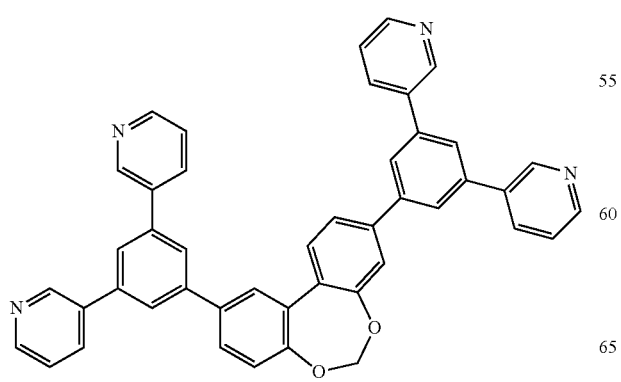
440
-continued
453
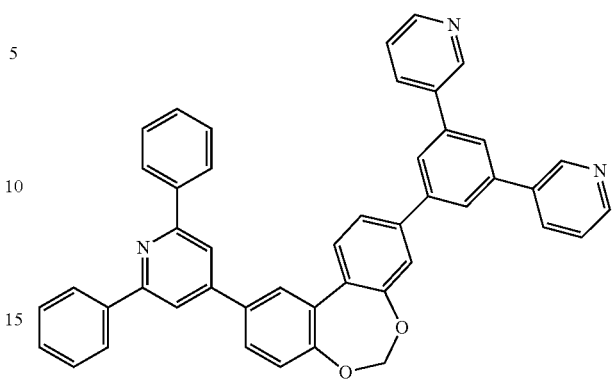
454
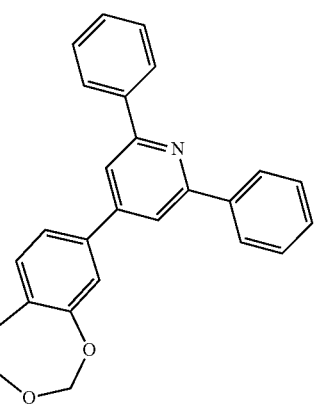
455
456
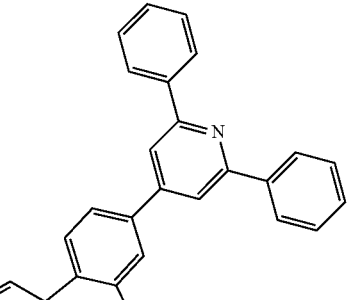

441
-continued
457
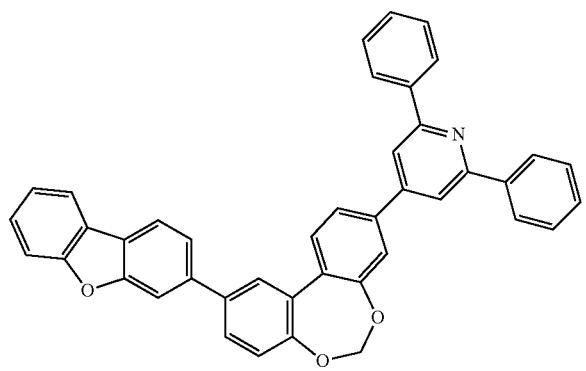
458
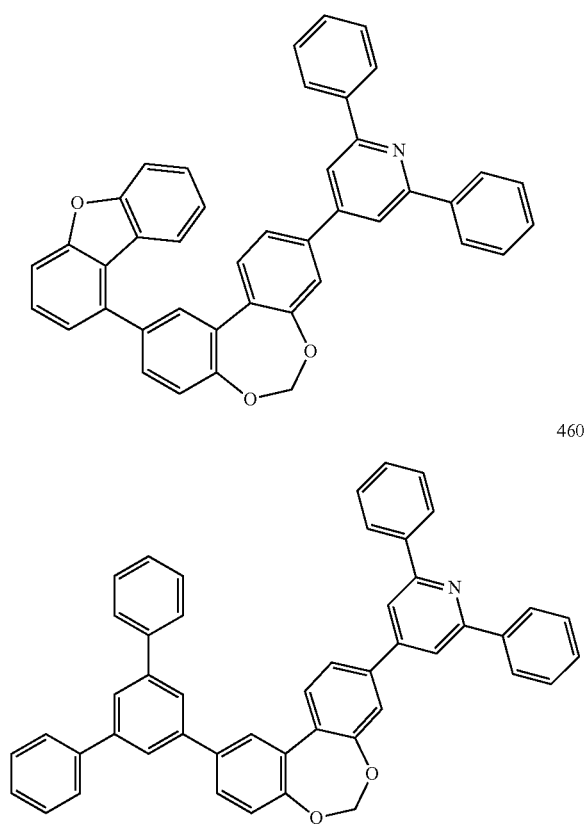
459
460
442
-continued
461
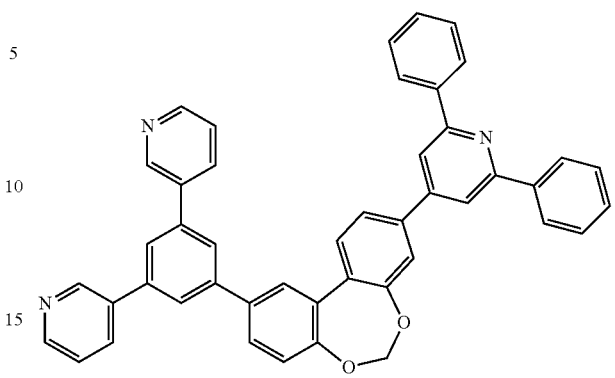
462
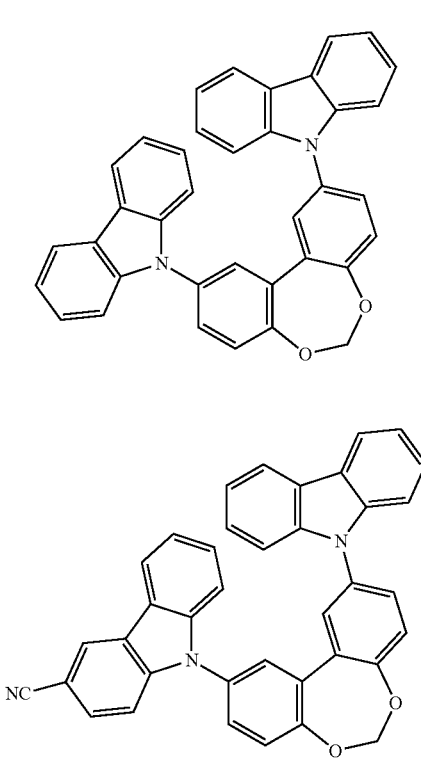
463
464

465
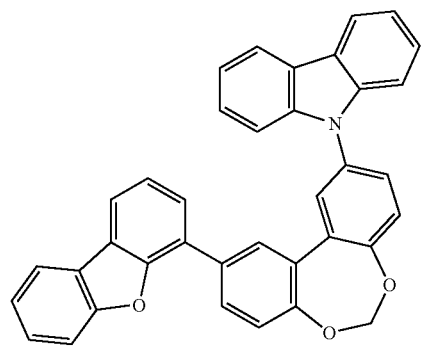
466
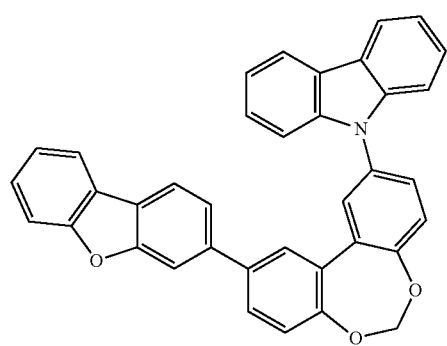
467
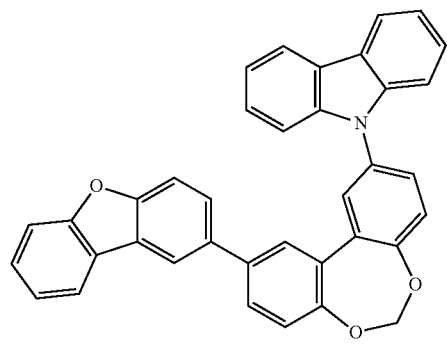
468
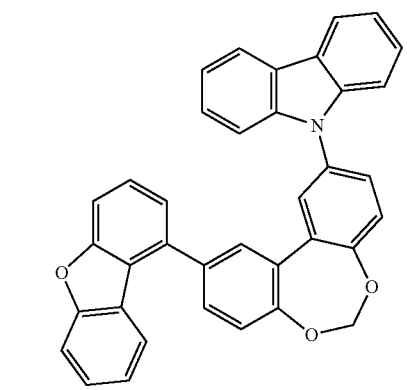
469
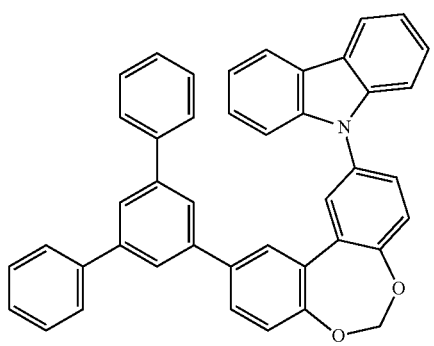
470
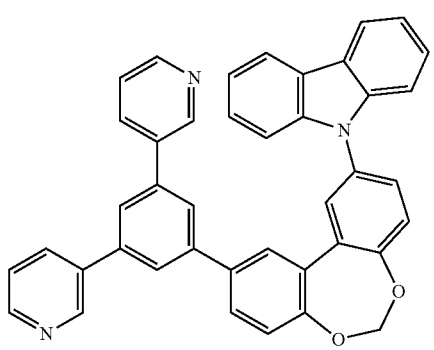
471
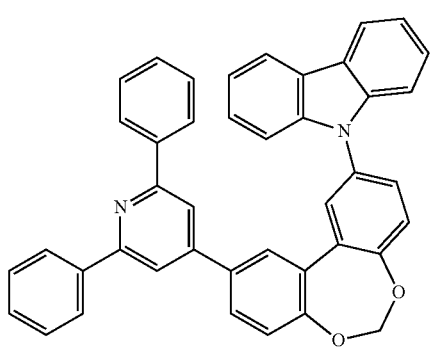
472
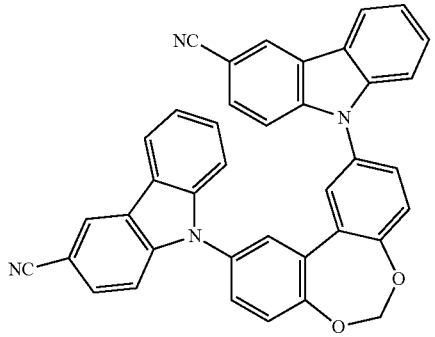

445
-continued
473
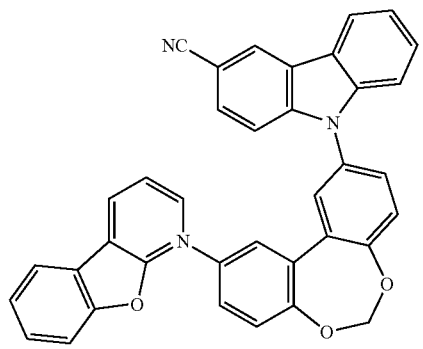
474
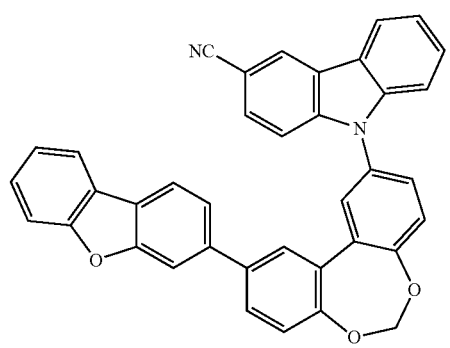
475
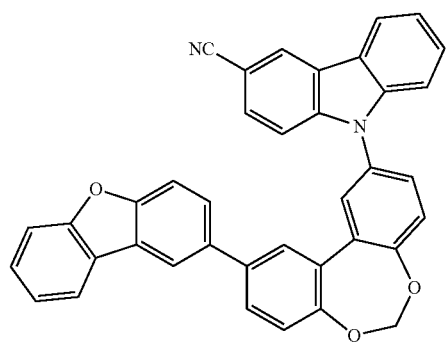
476
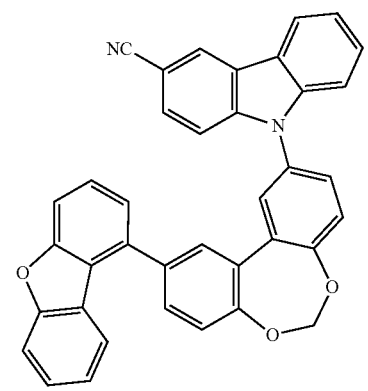
446
-continued
477
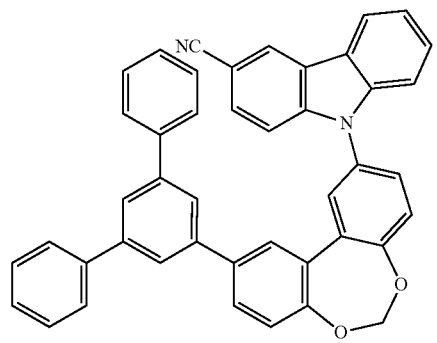
478
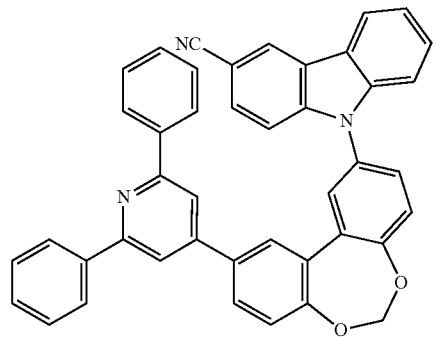
479
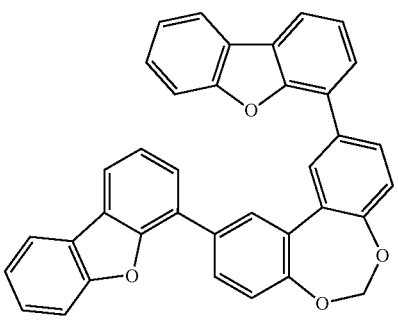
480

447
-continued
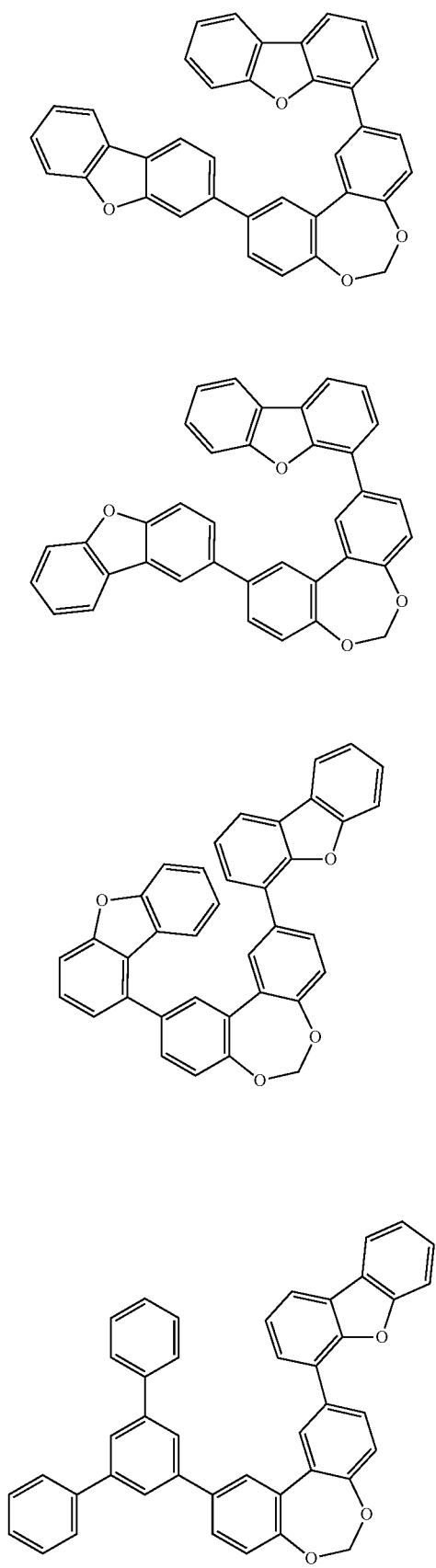
481
482
483
484
448
-continued
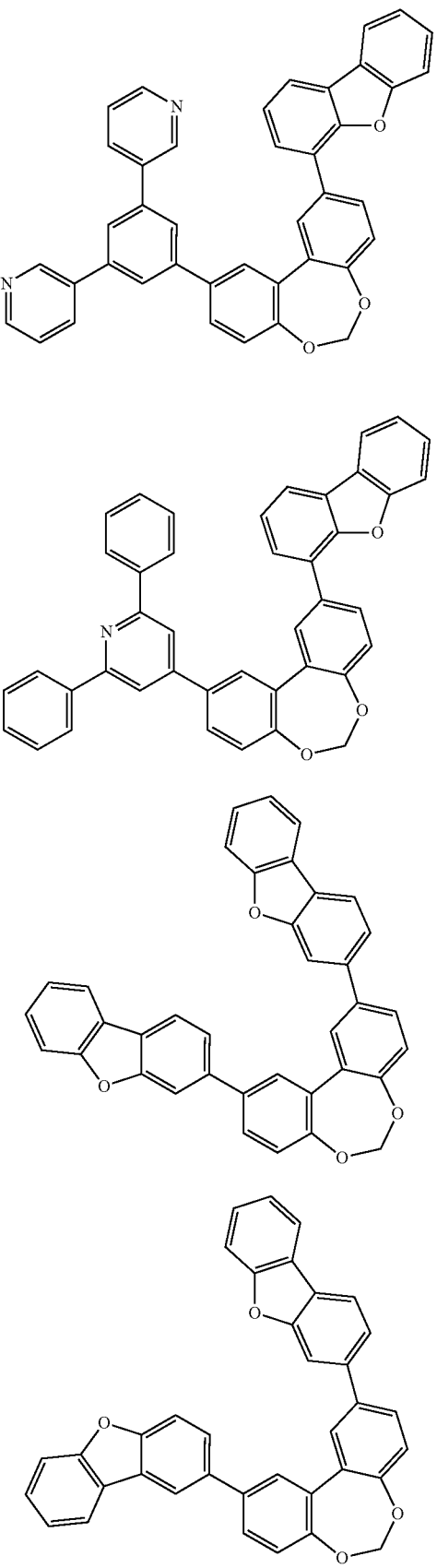
485
486
487
488

449
-continued
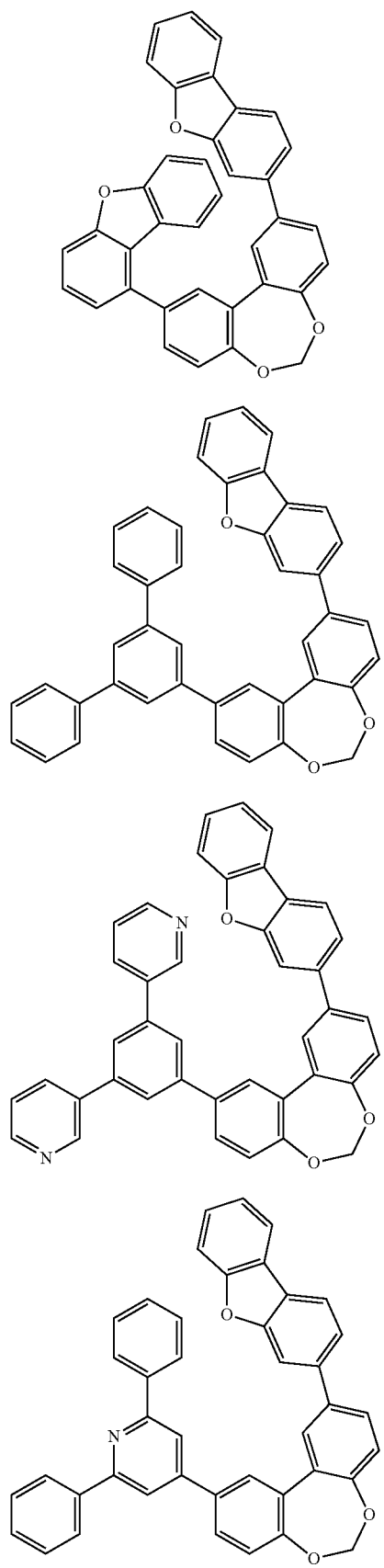
450
-continued
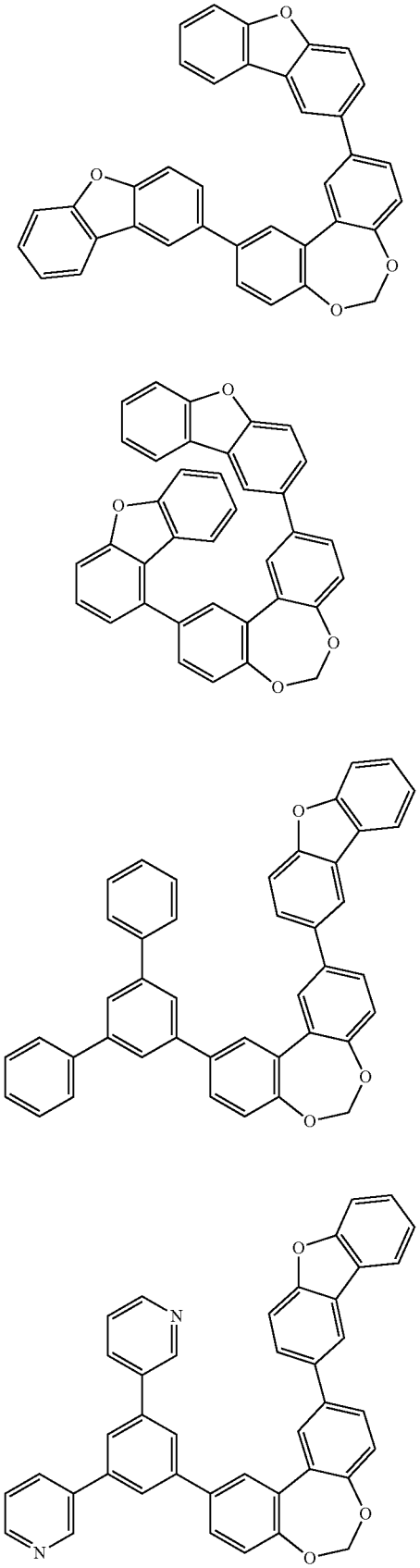

451
-continued
497
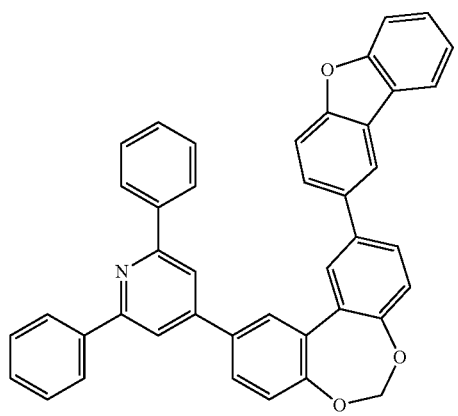
498
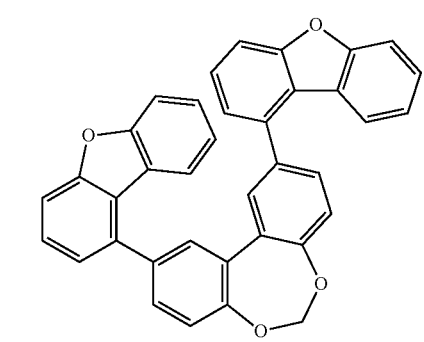
499
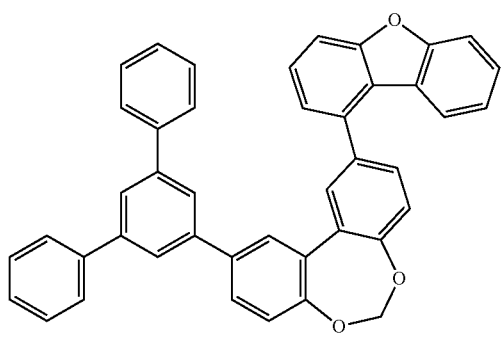
500
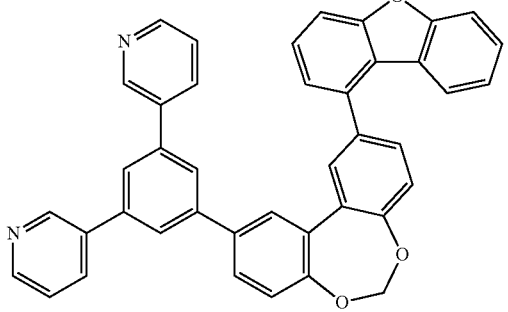
452
-continued
501
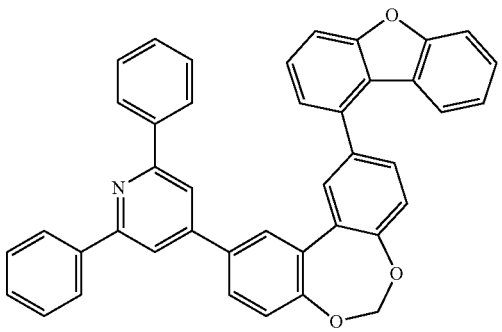
502
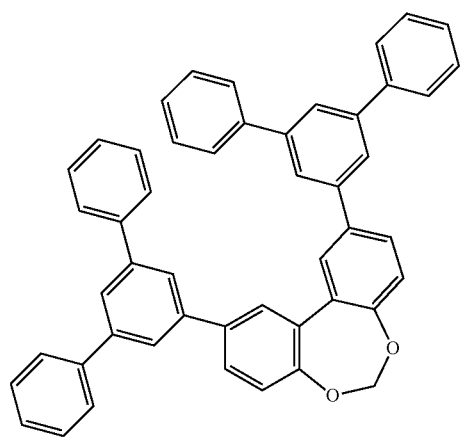
503
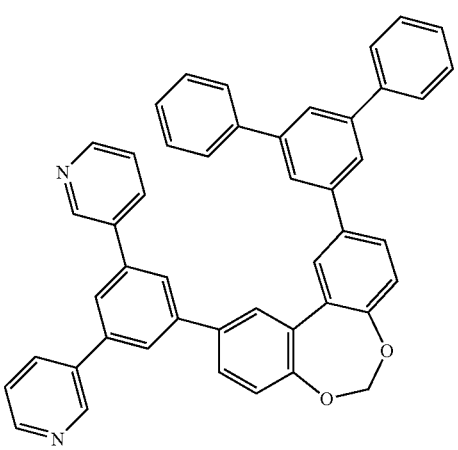
504
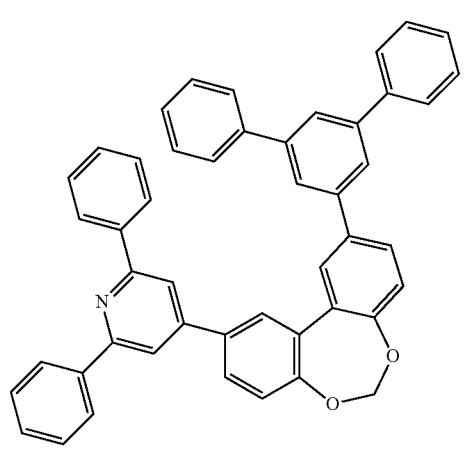

505 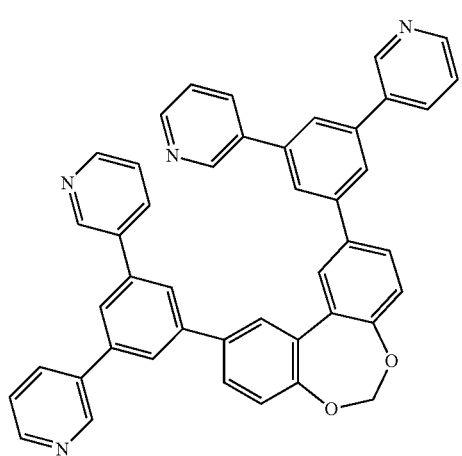
506 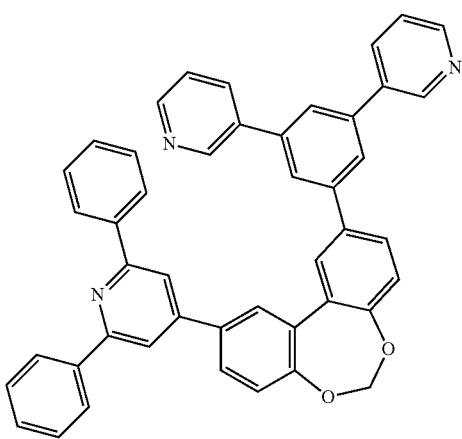
507 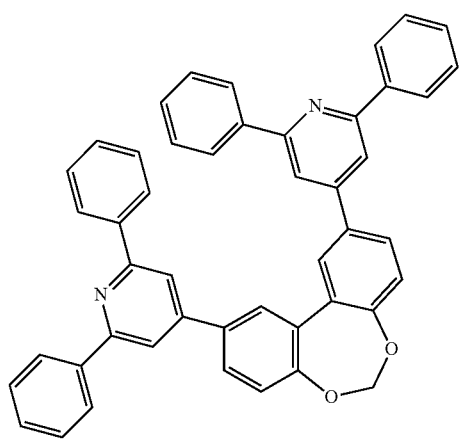
508 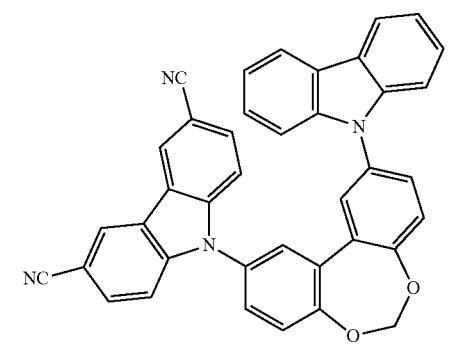
509 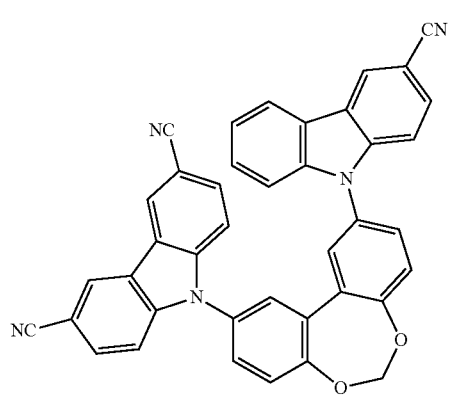
510 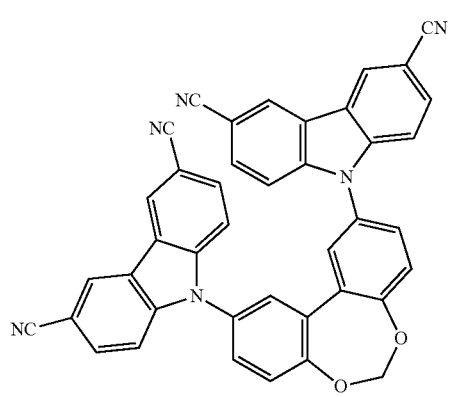
511 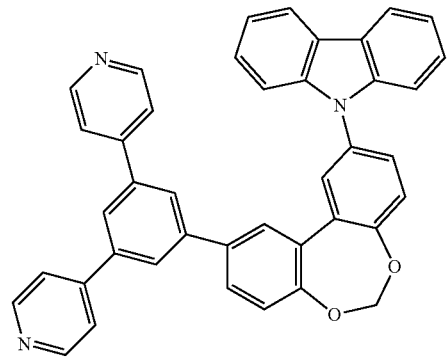
512 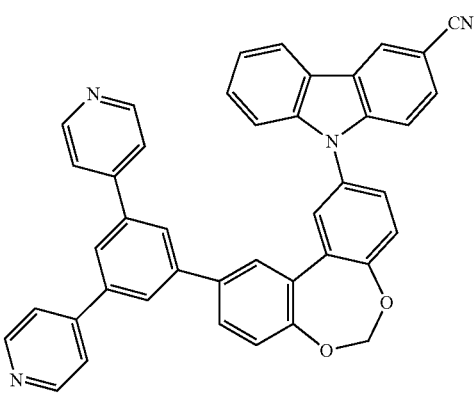

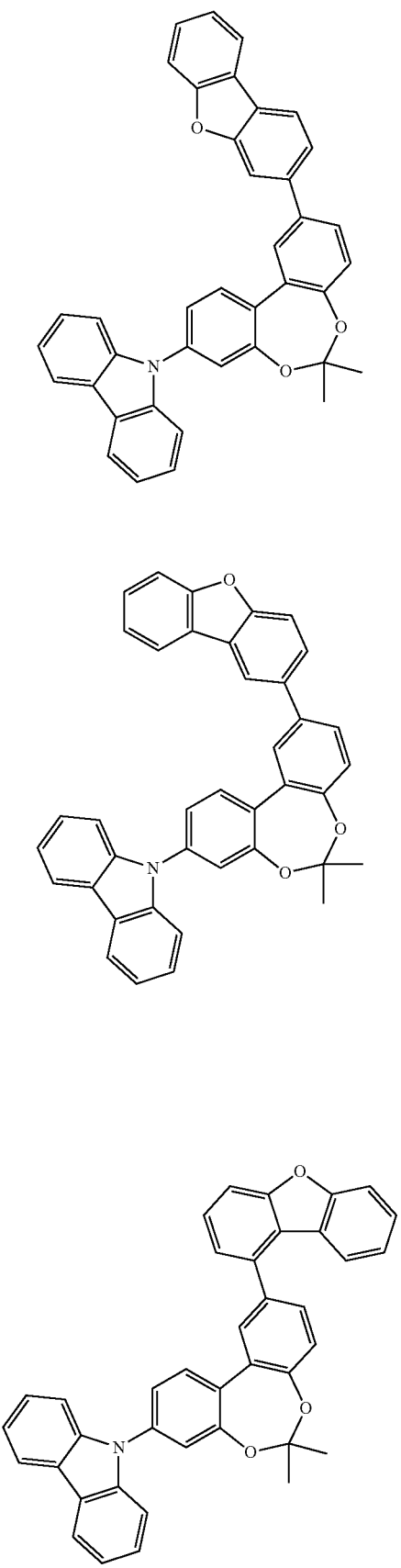
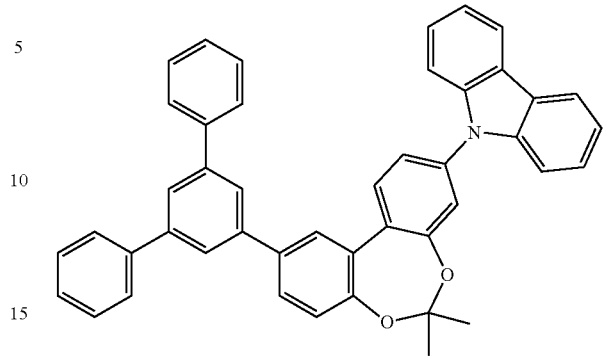
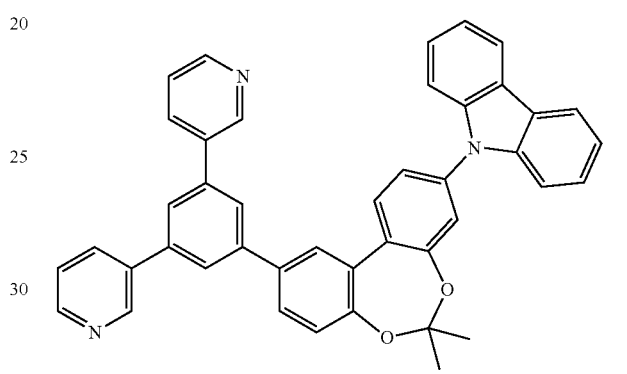
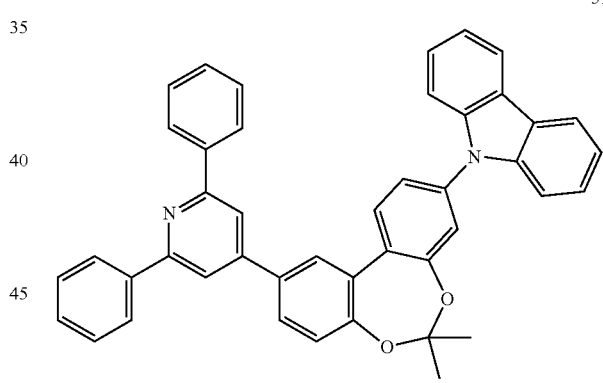
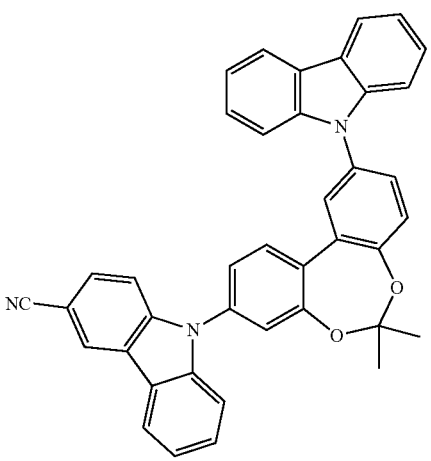

-continued
520
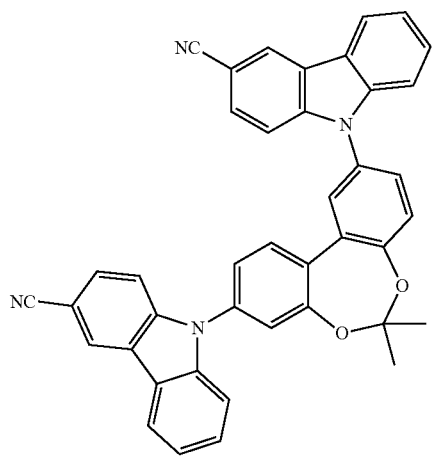
521
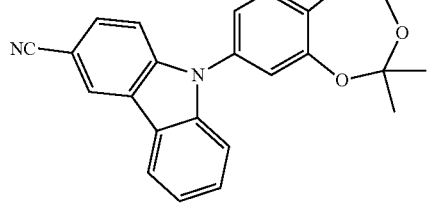
522
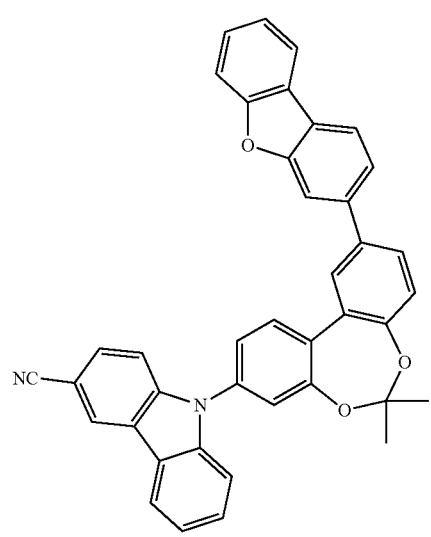
-continued
523
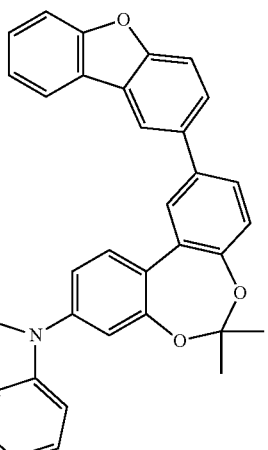
524
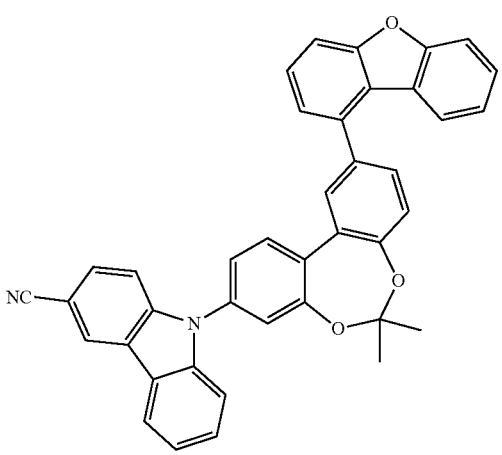
525
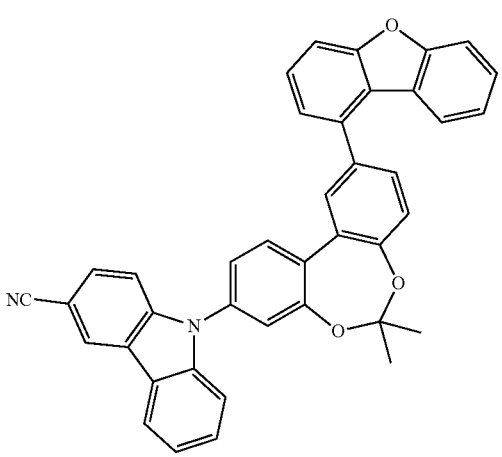

459
-continued
526
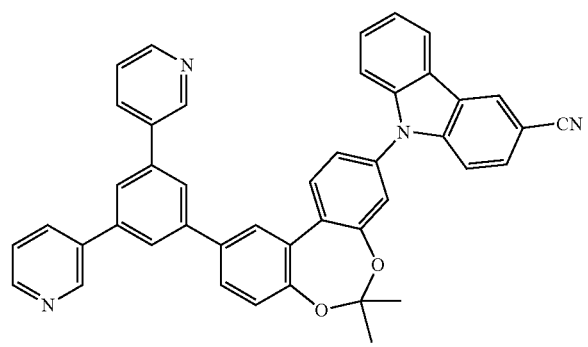
527
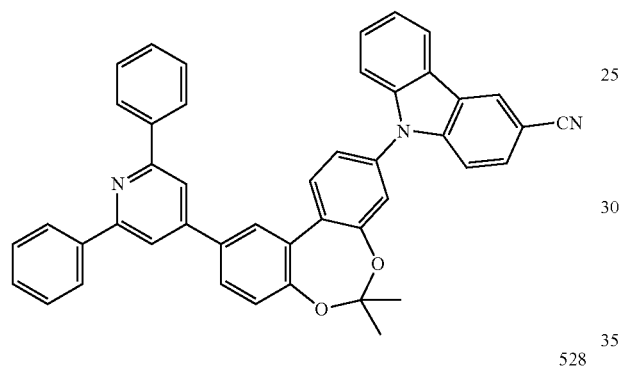
528
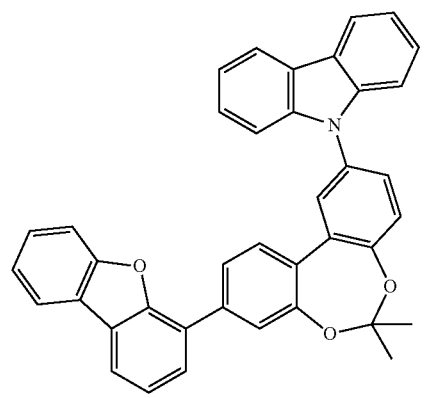
529
460
-continued
530
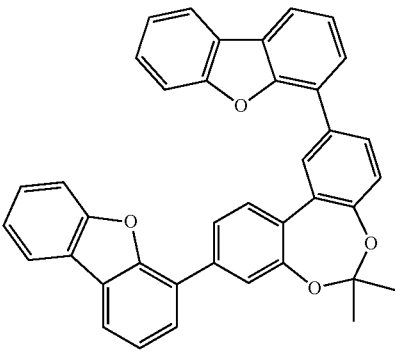
531
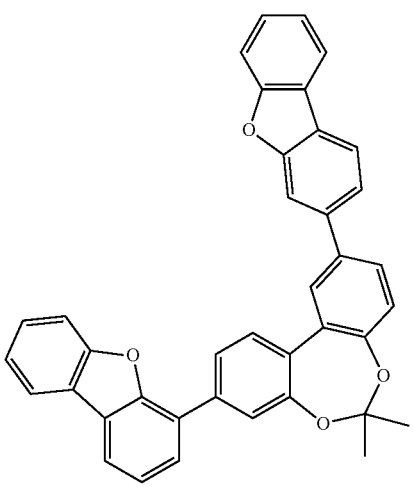
532
533
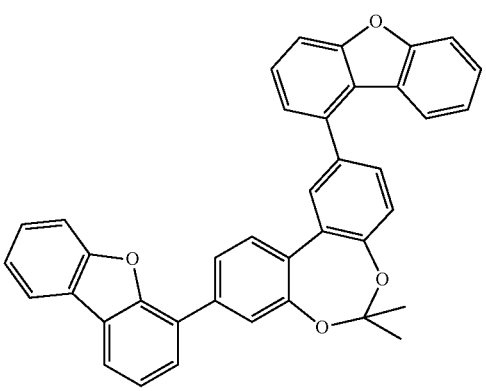

461
-continued
534
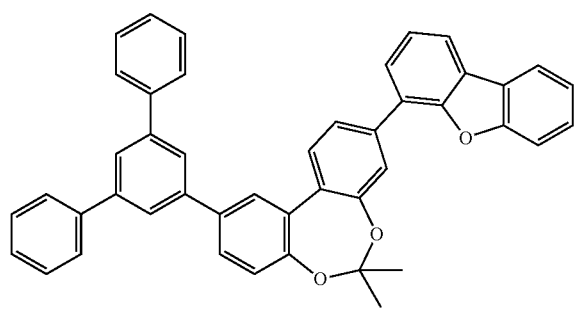
535
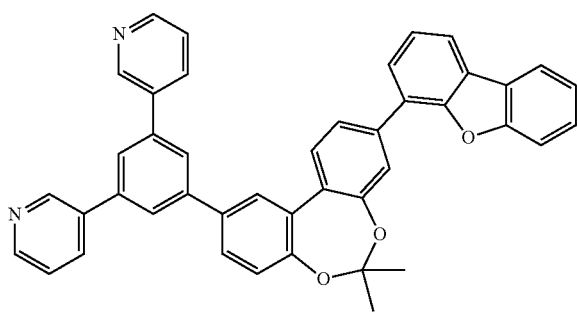
536
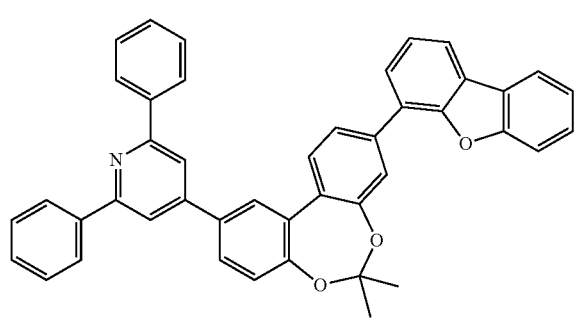
537
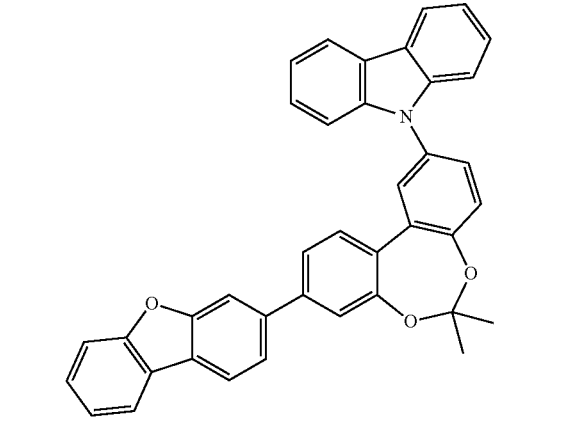
462
-continued
538
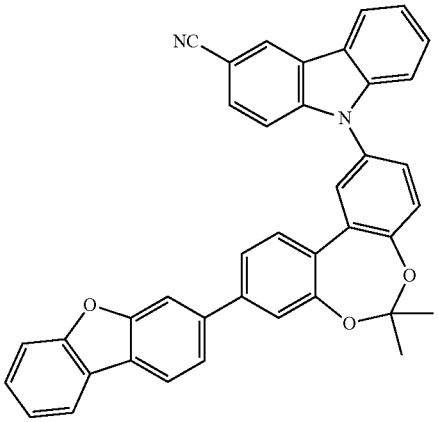
539
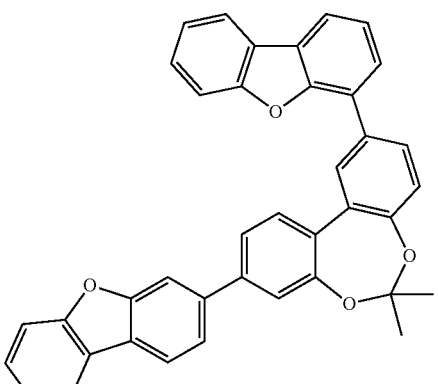
540
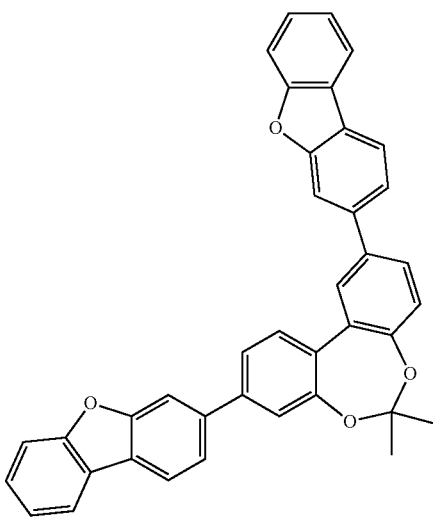

-continued
541
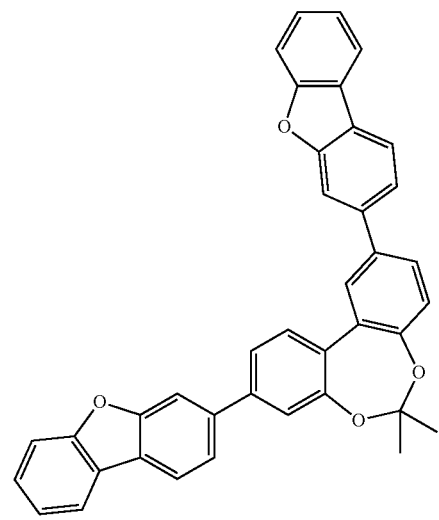
542
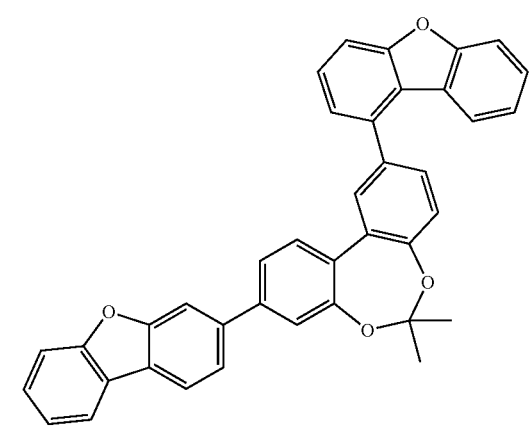
543
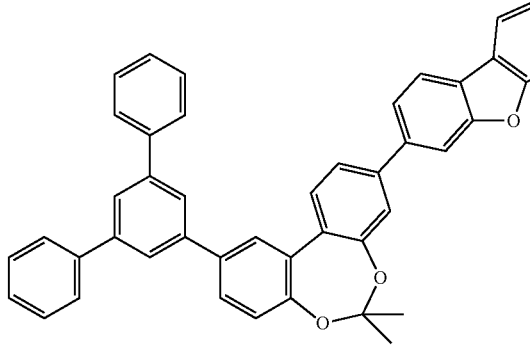
-continued
544
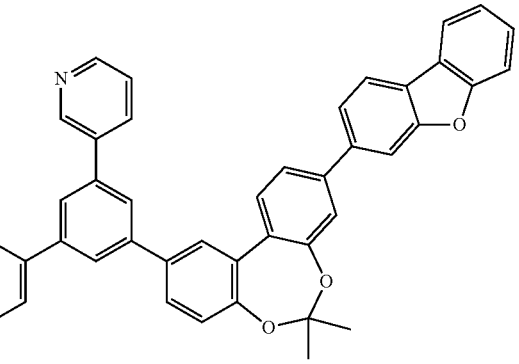
545
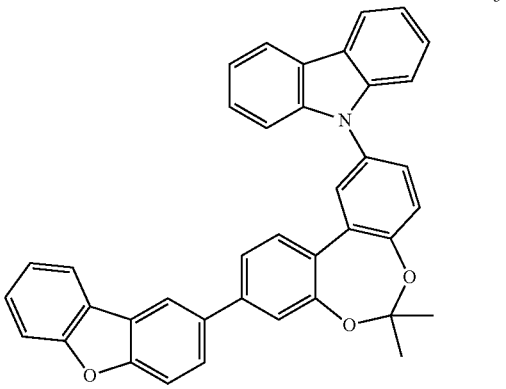
546
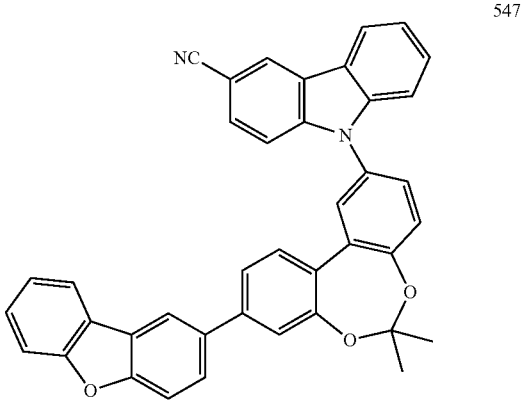
547

465
-continued
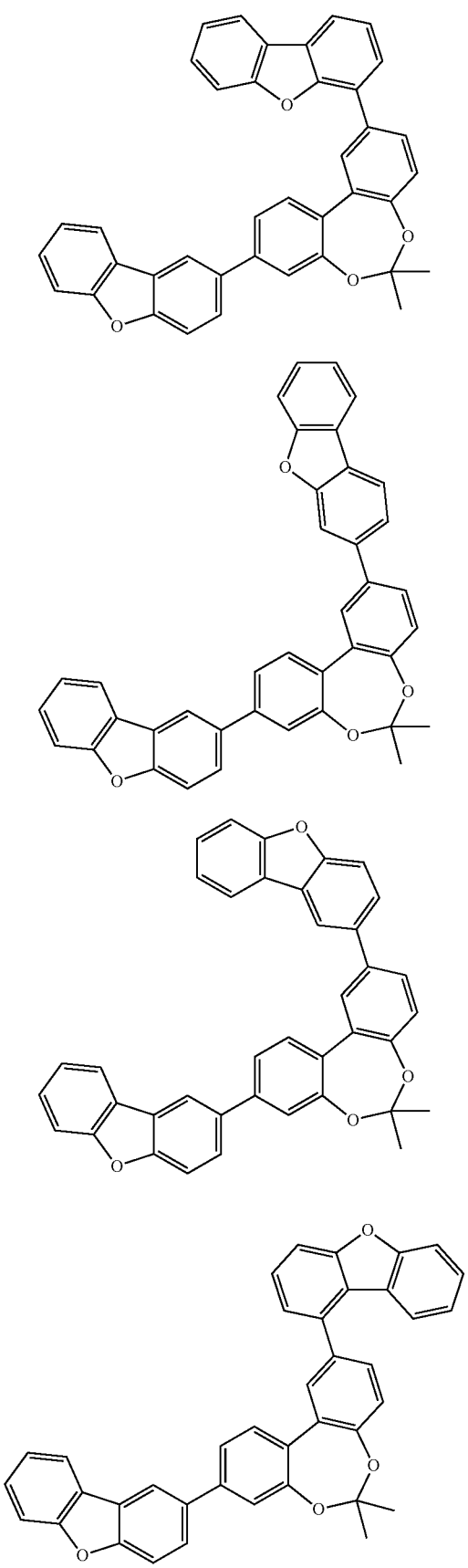
466
-continued
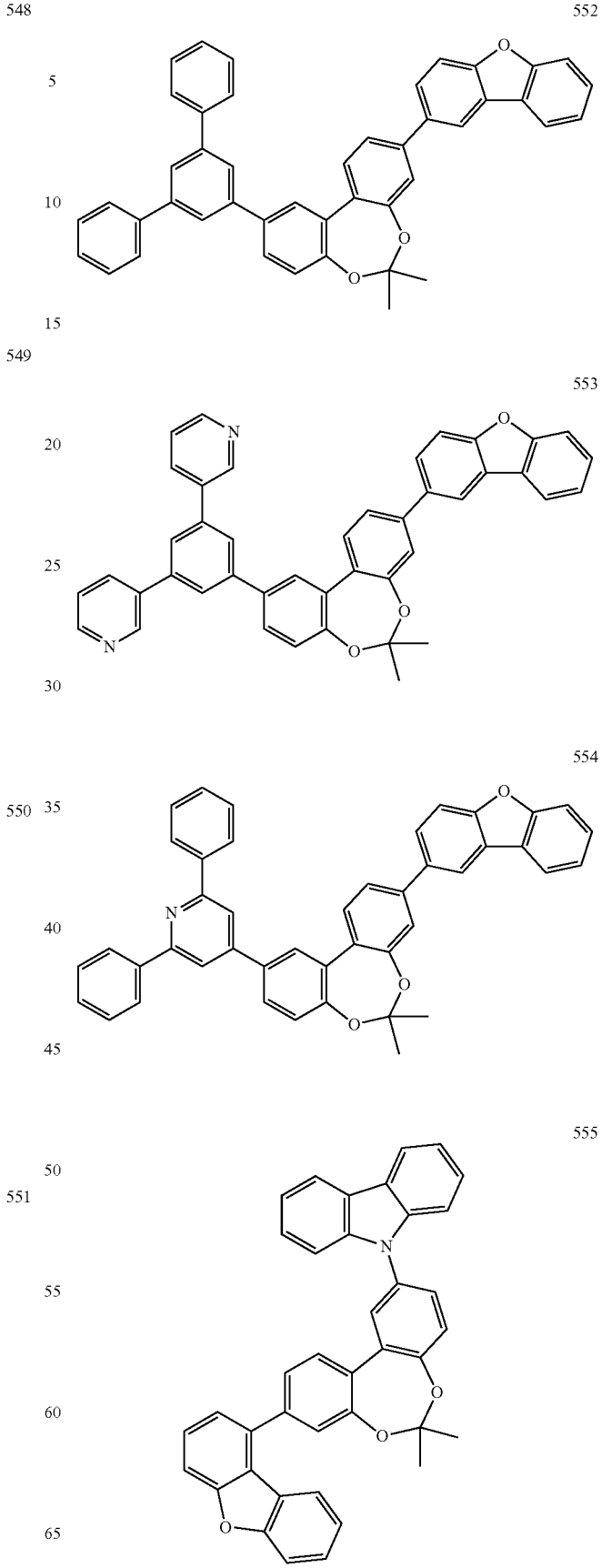

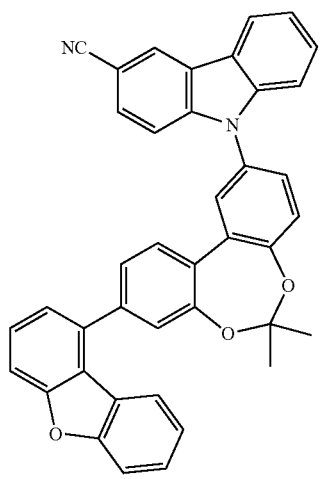
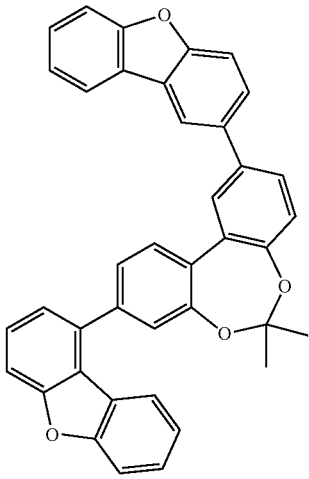

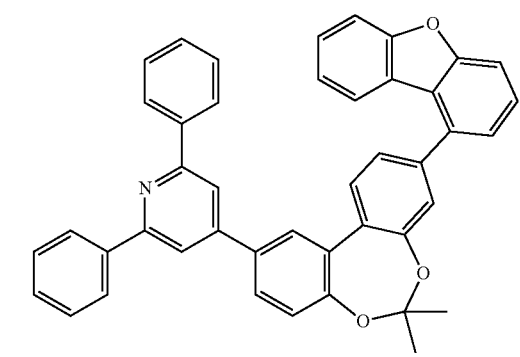
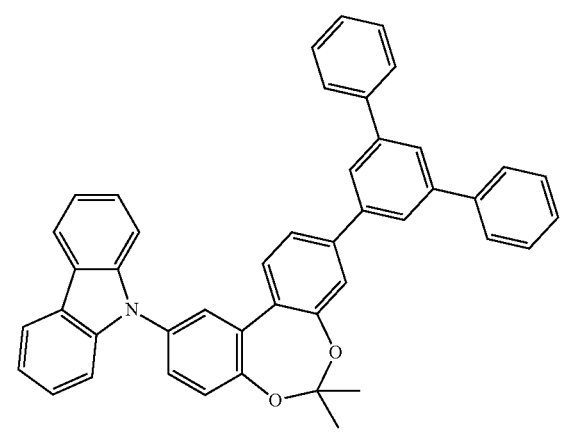
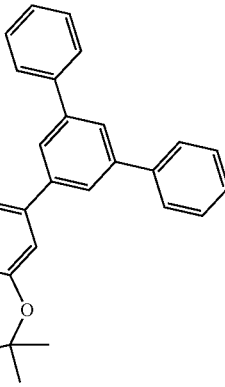
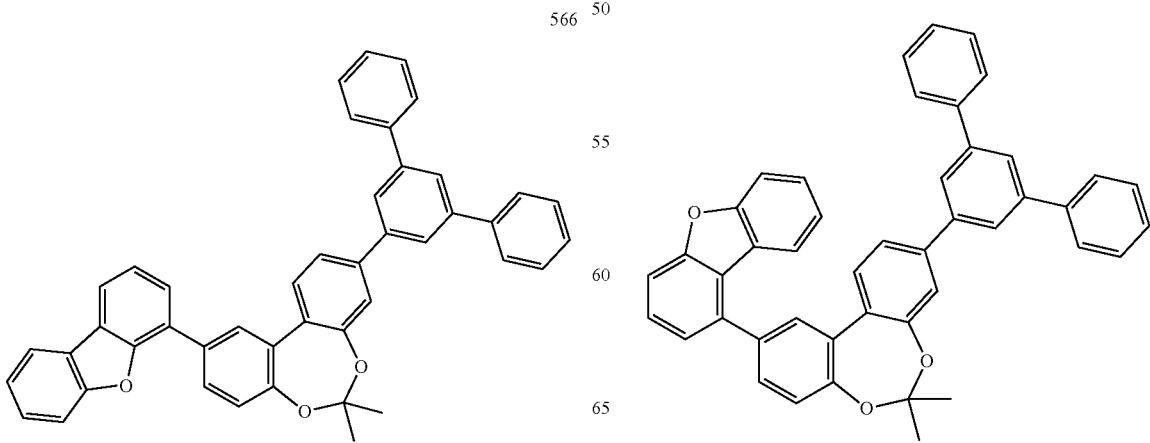

-continued
570
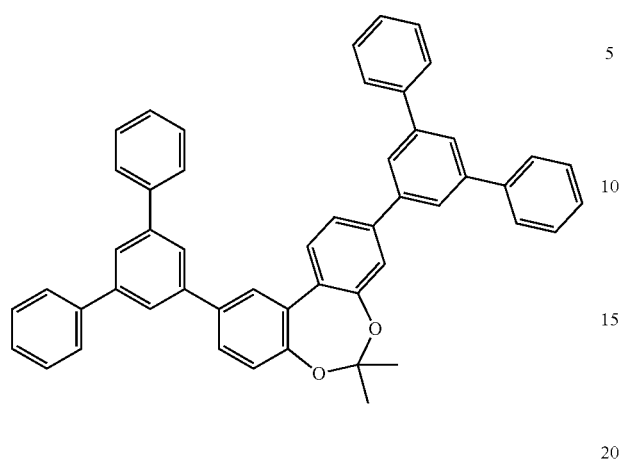
571
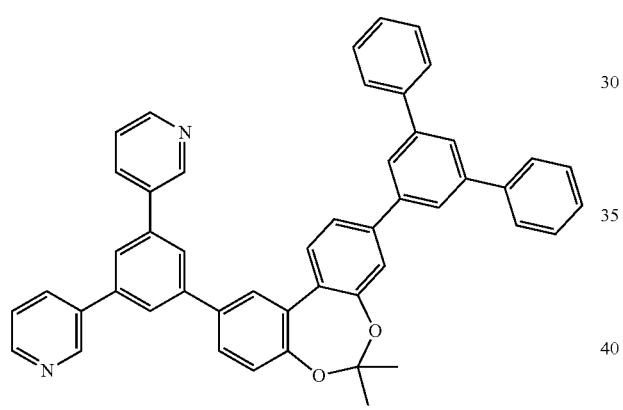
572
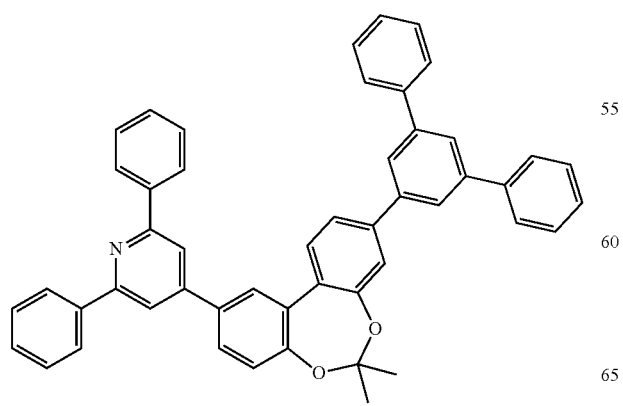
-continued
573
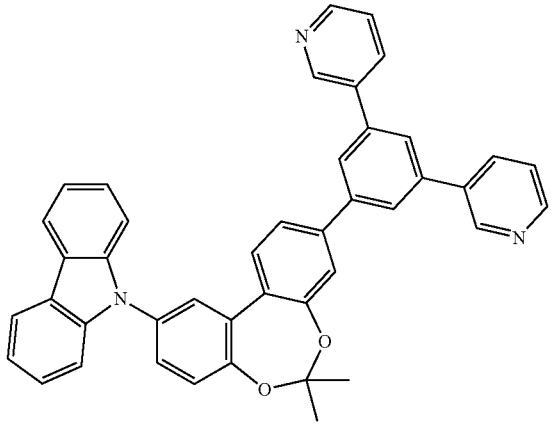
574
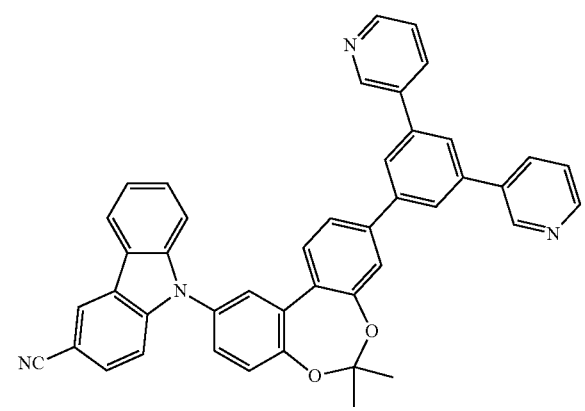
575
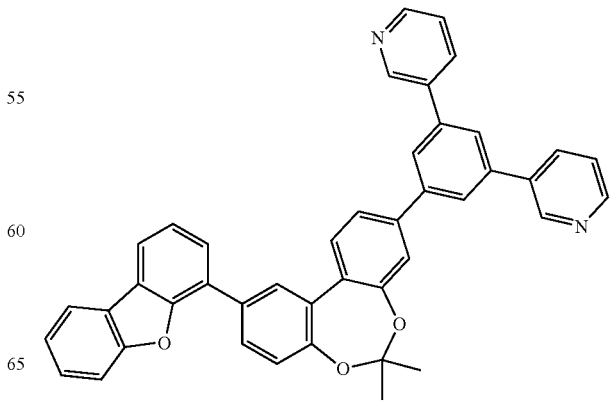

473
-continued
576
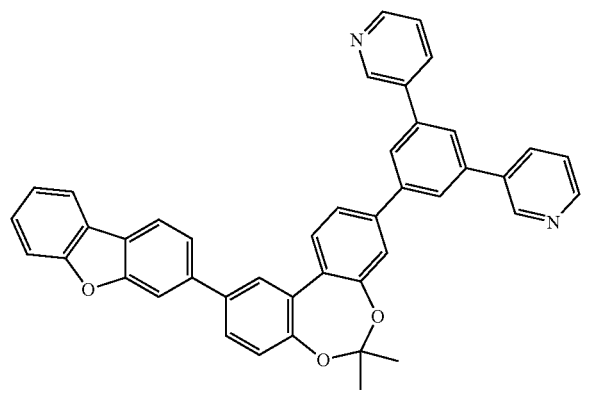
577
578
474
-continued
579
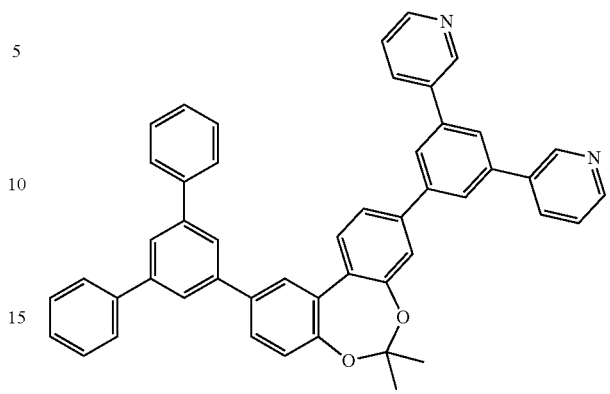
580
581

475
-continued
582
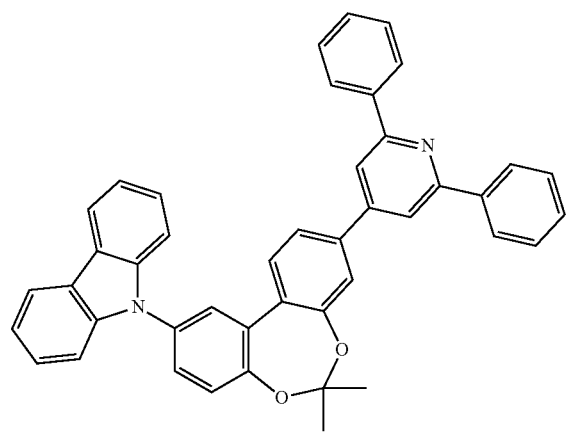
583
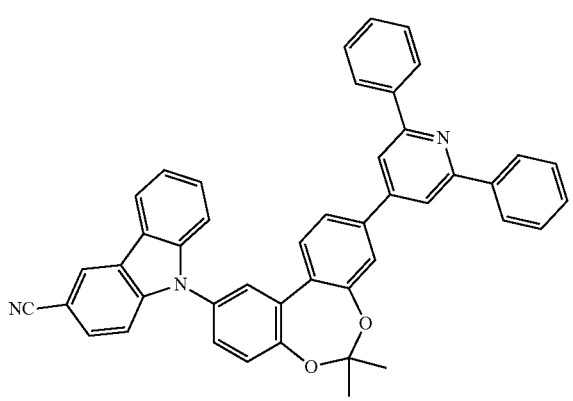
584
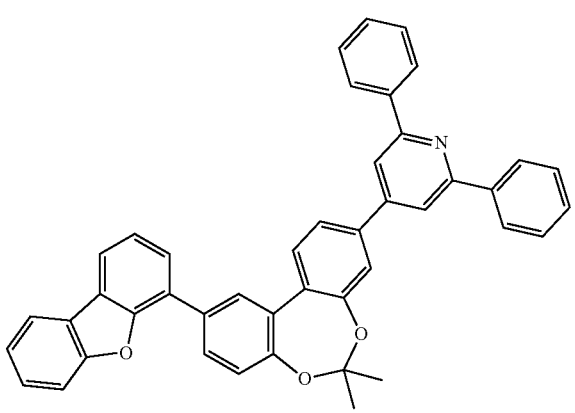
476
-continued
585
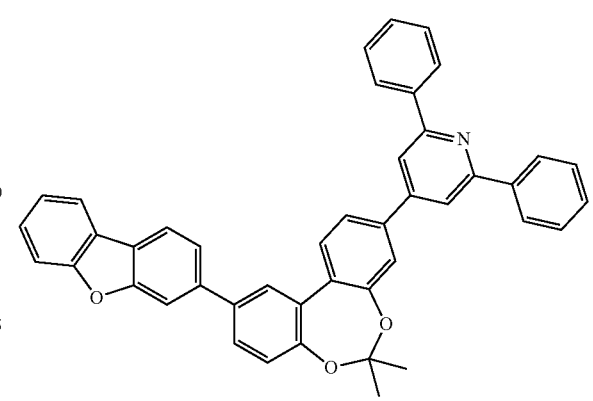
586
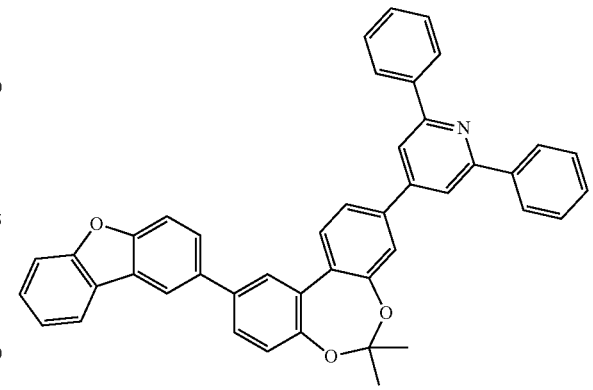
587
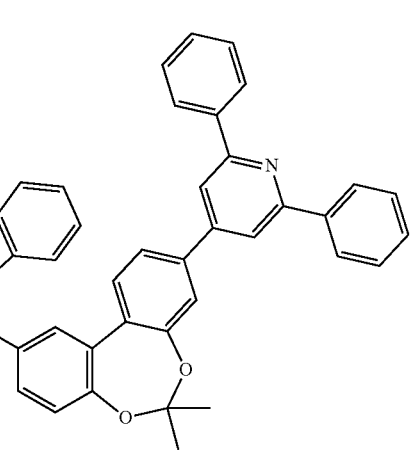

588
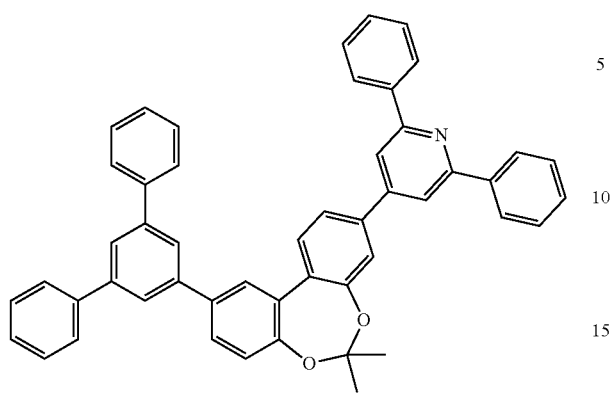
589
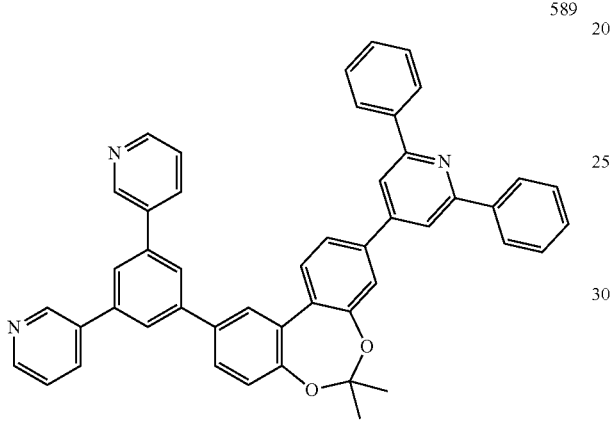
590
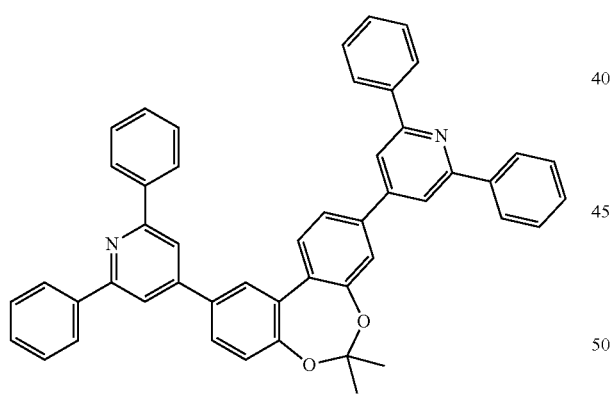
591
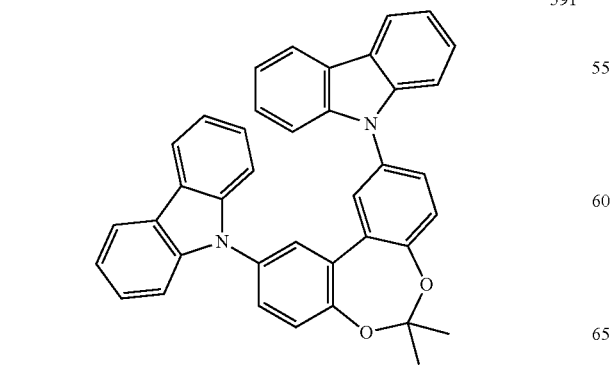
592
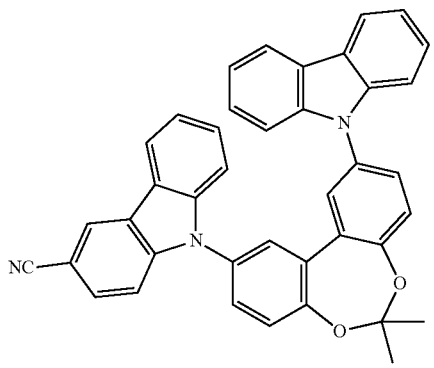
593
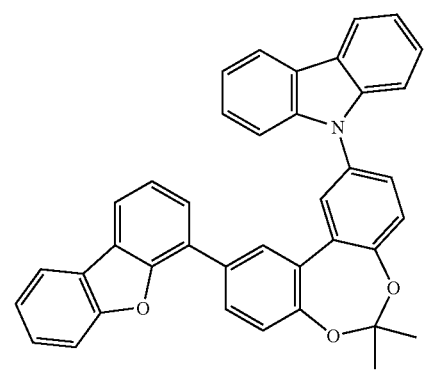
594
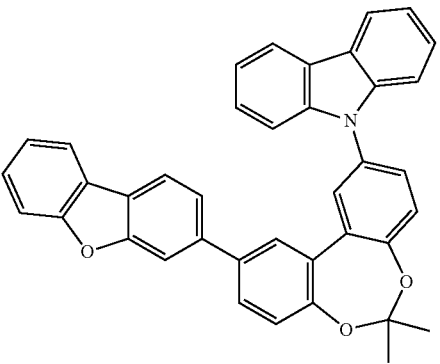
595
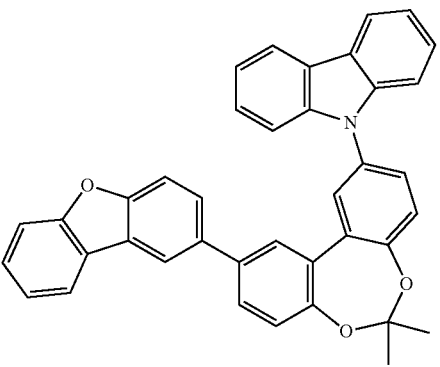

596
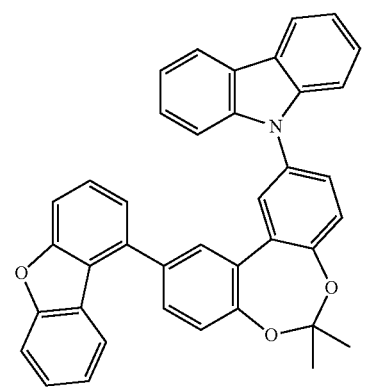
597
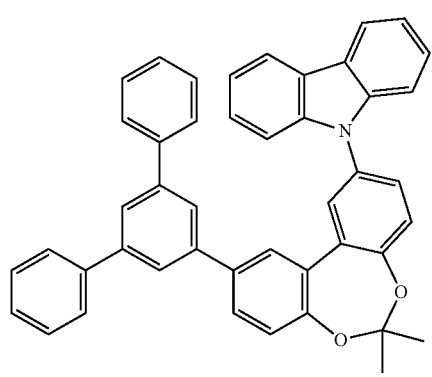
598
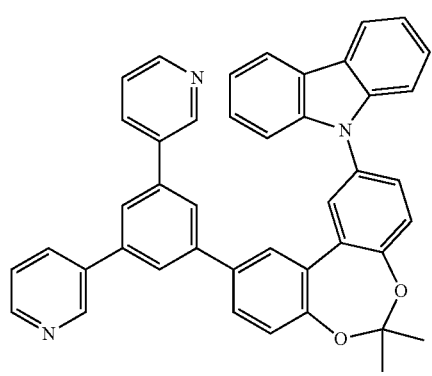
599
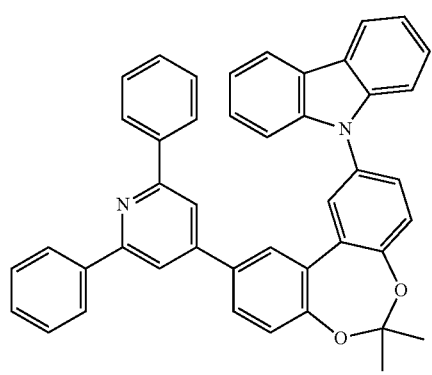
600
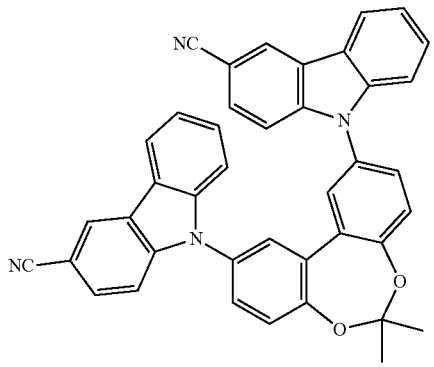
601
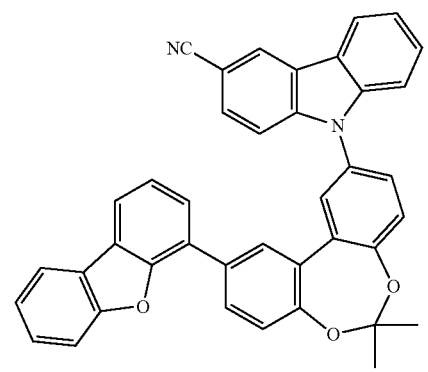
602
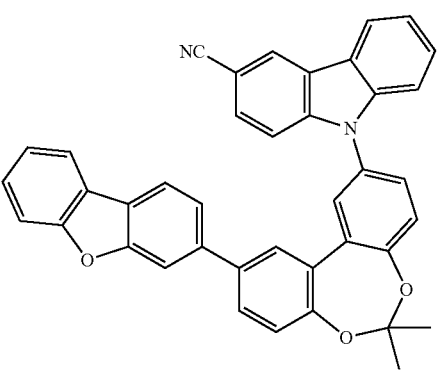
603
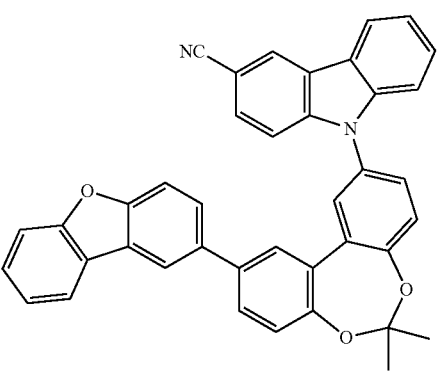

481
-continued
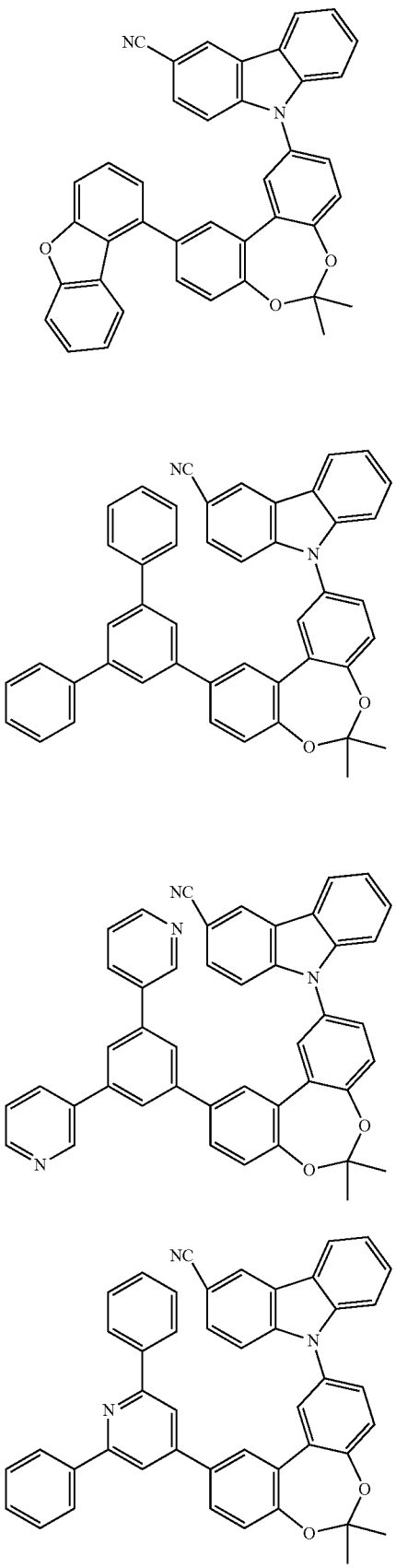
482
-continued
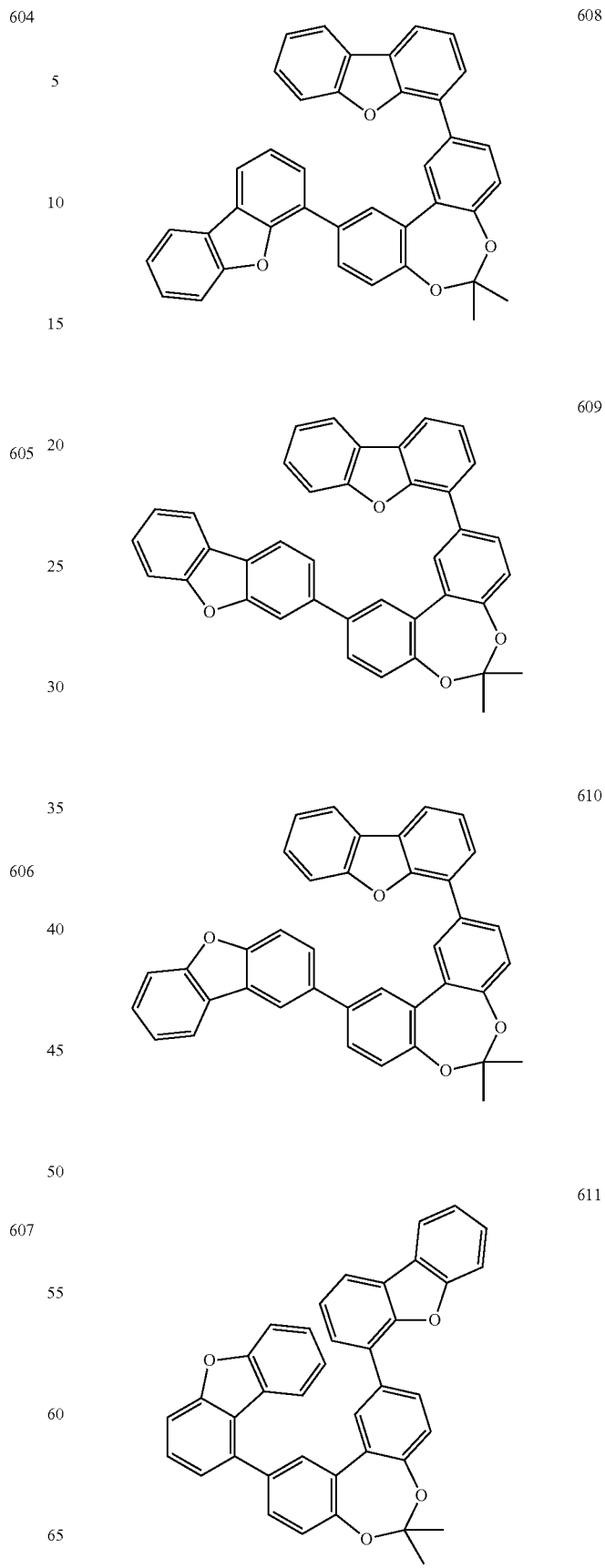

-continued
612
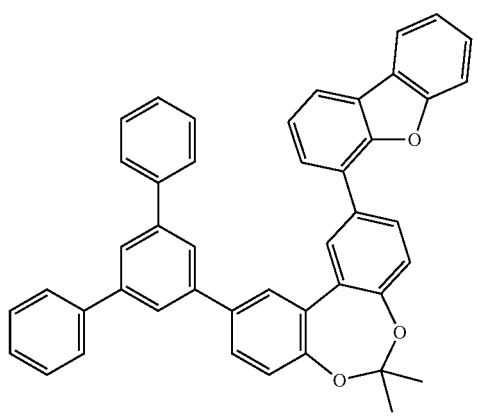
613
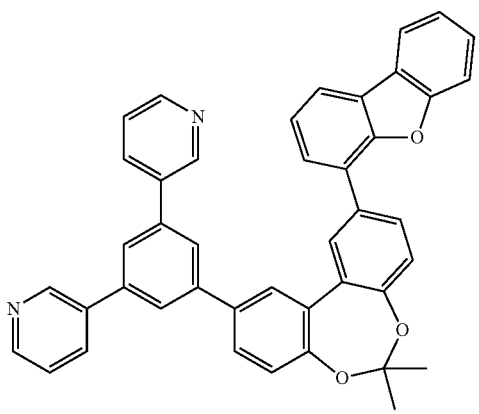
614
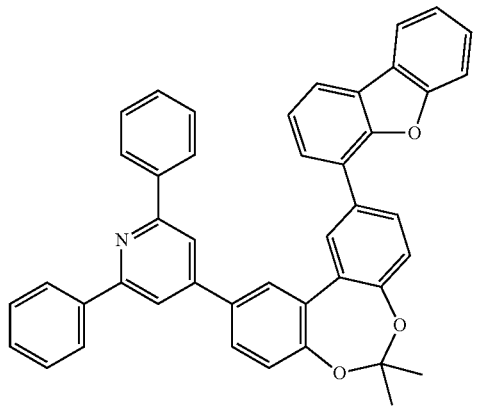
-continued
615
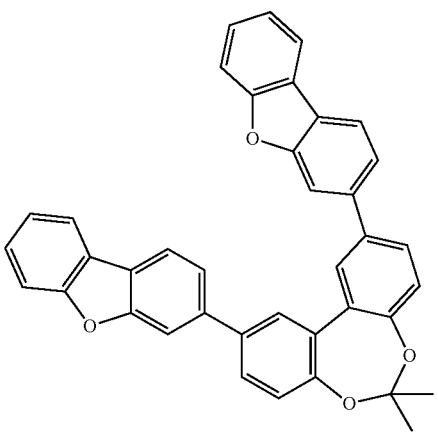
616
617
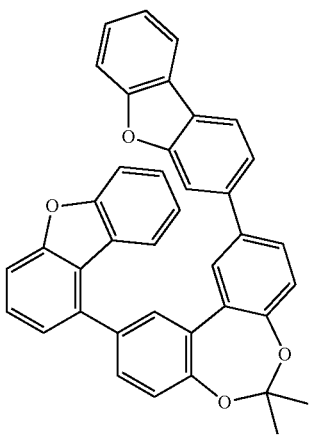

618
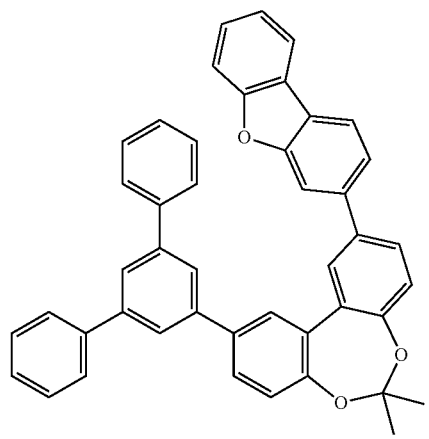
619
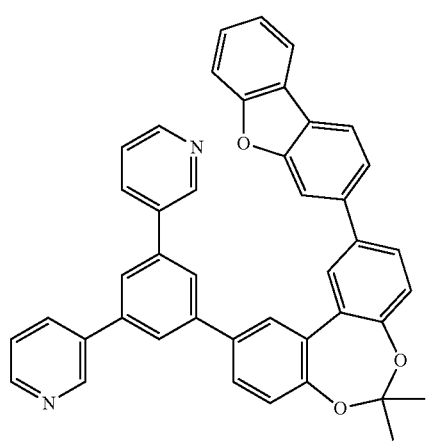
620
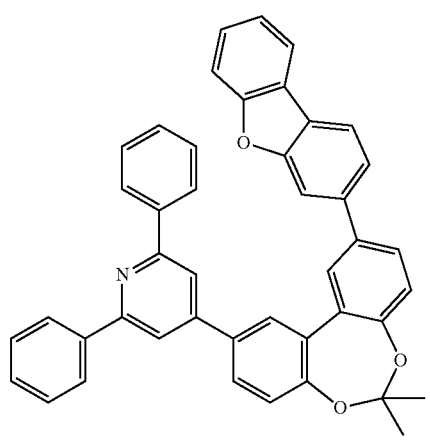
621
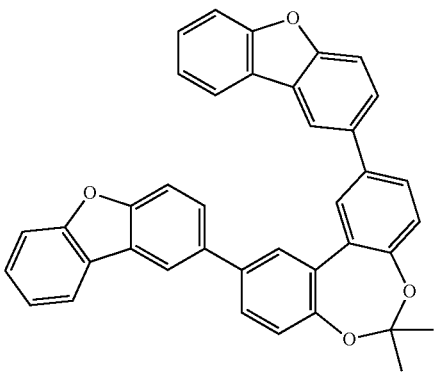
622
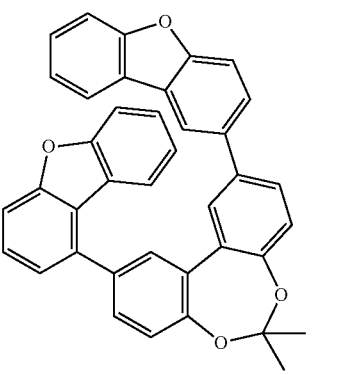
623
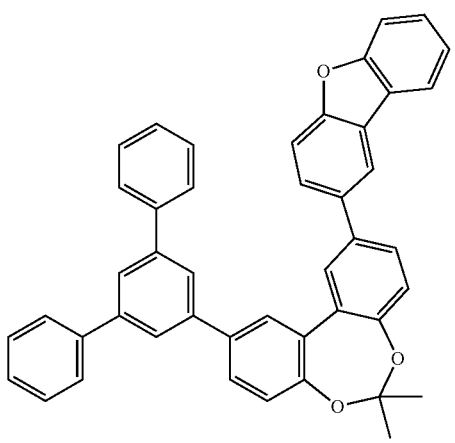
624
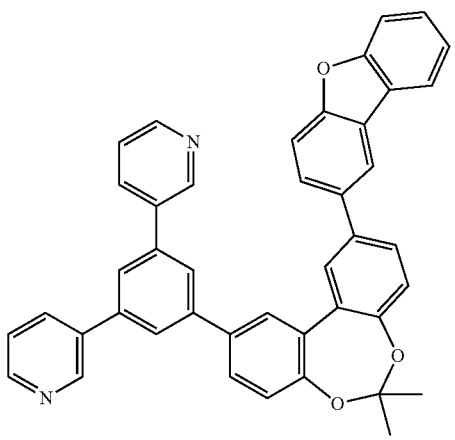

625 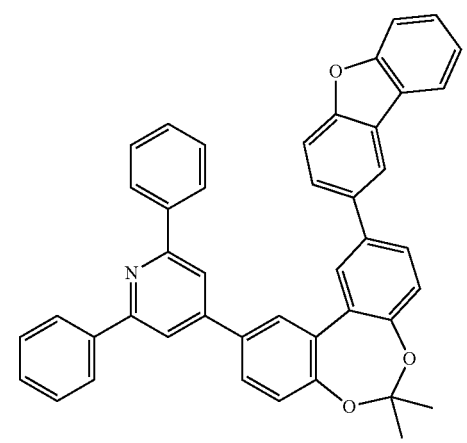
626 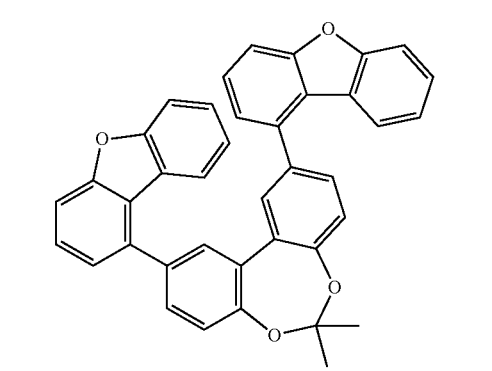
627 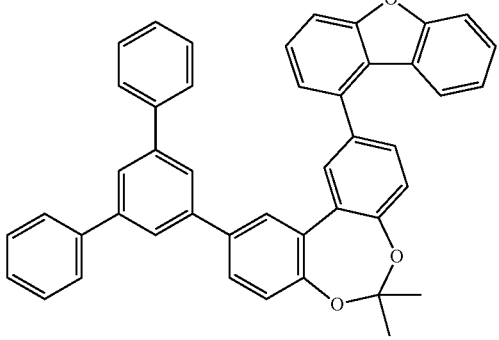
628 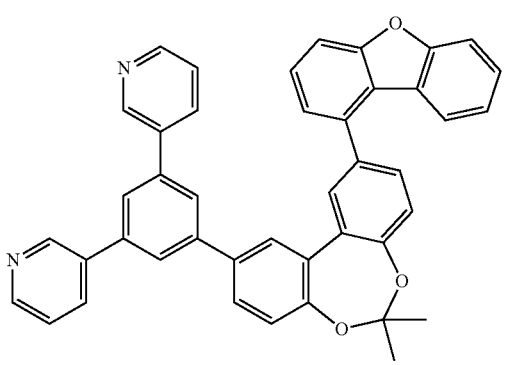
629 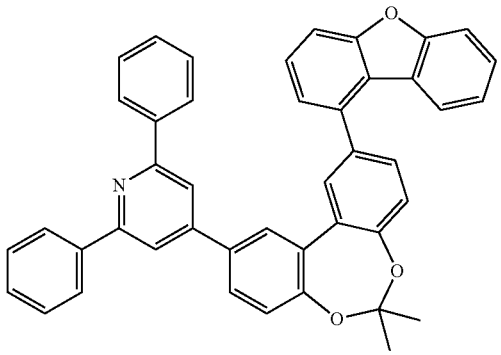
630 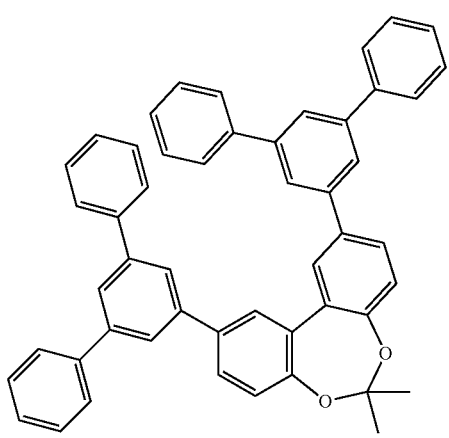
631 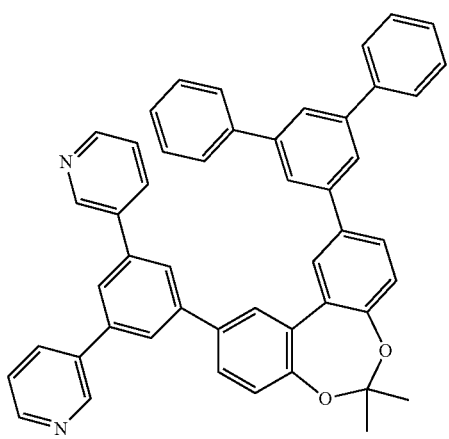
632 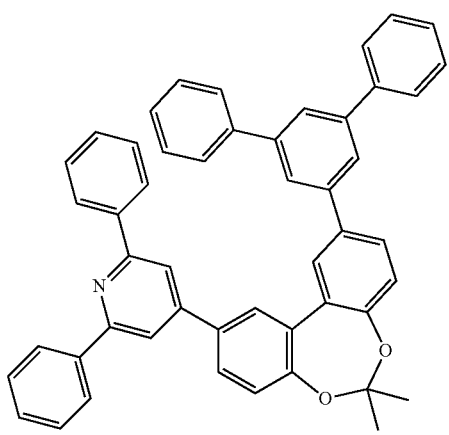

633
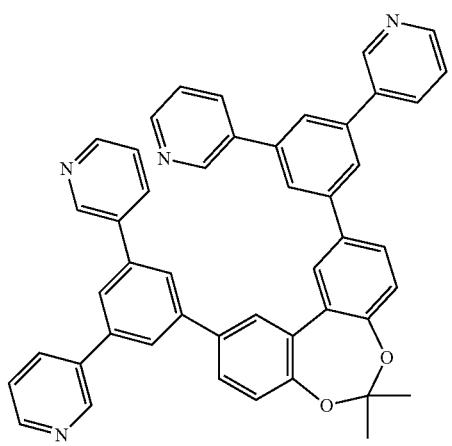
634
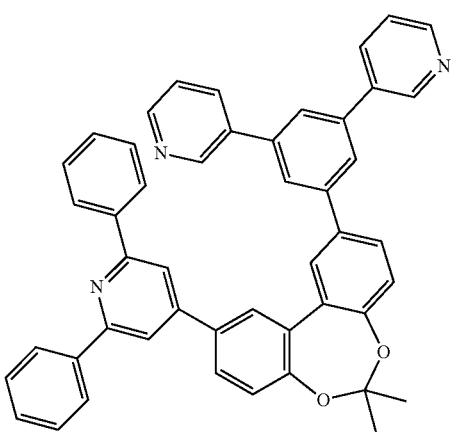
635
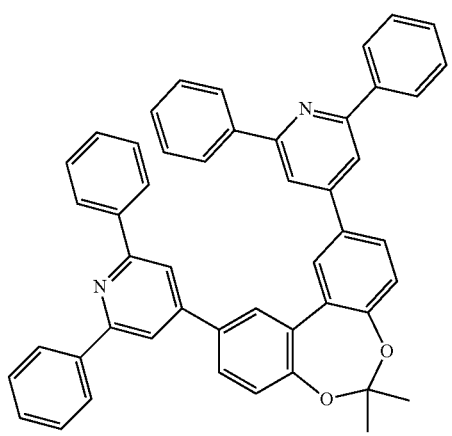
636
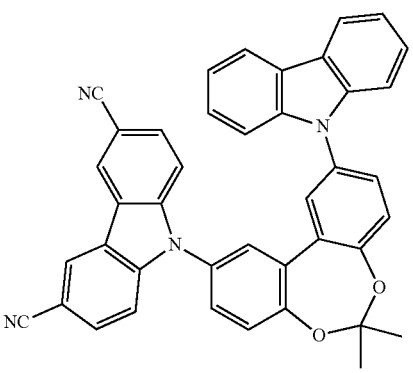
637
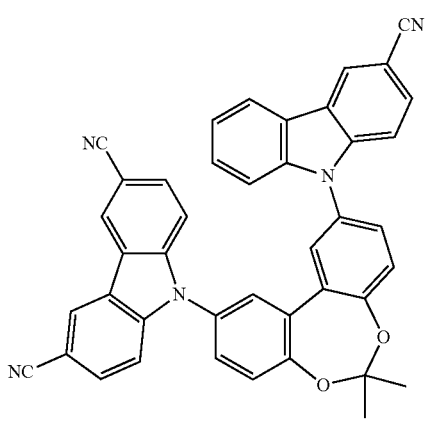
638
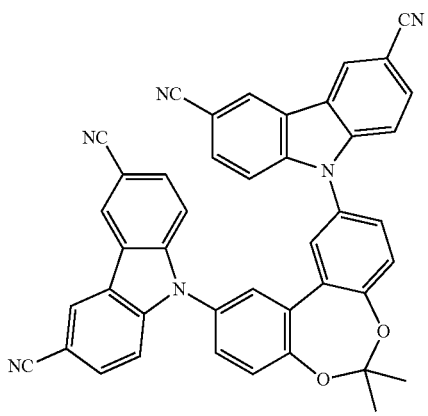
639
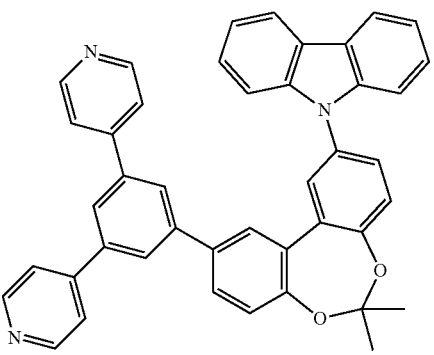

491
-continued
640
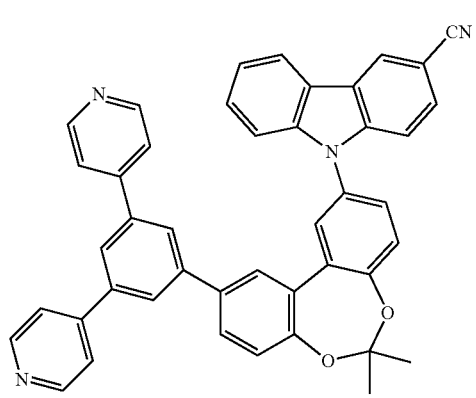
641
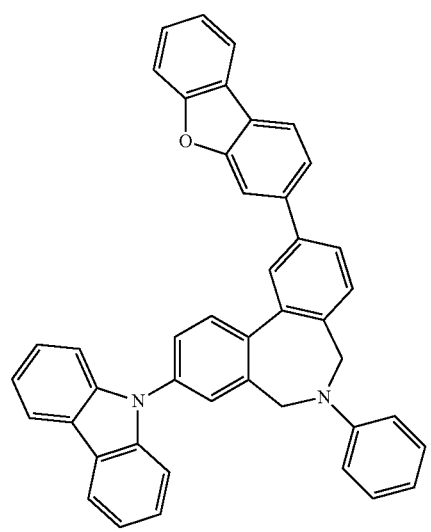
642
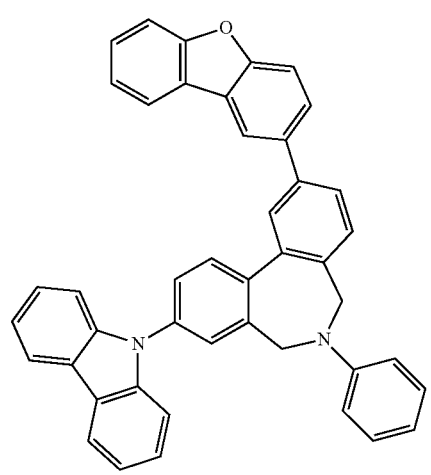
492
-continued
643
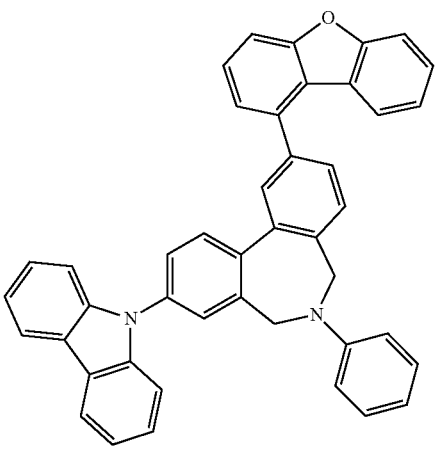
644
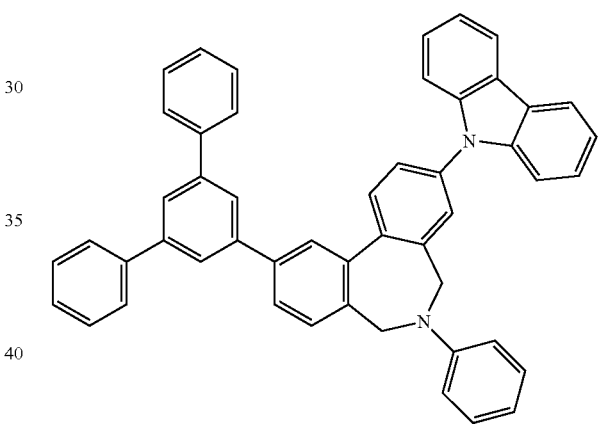
645
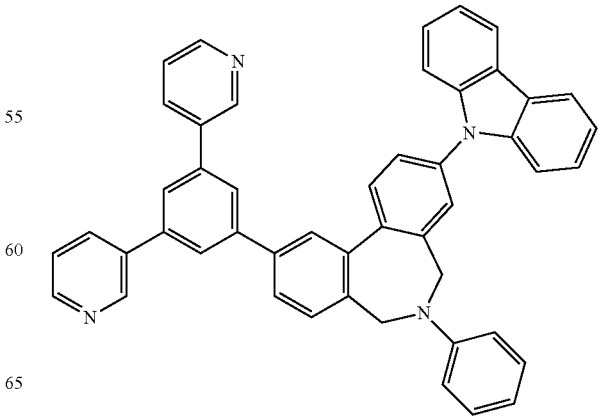

493
-continued
646
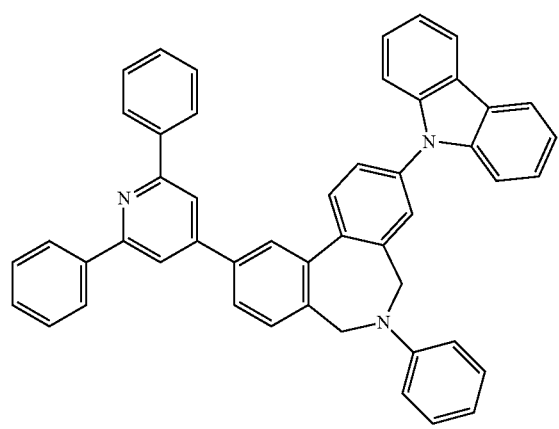
647
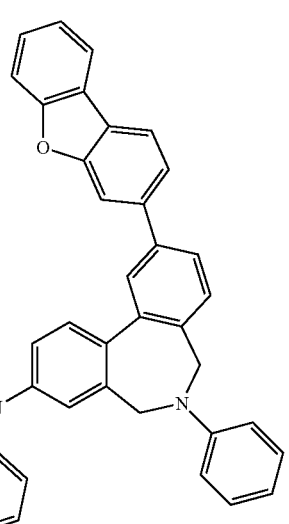
648
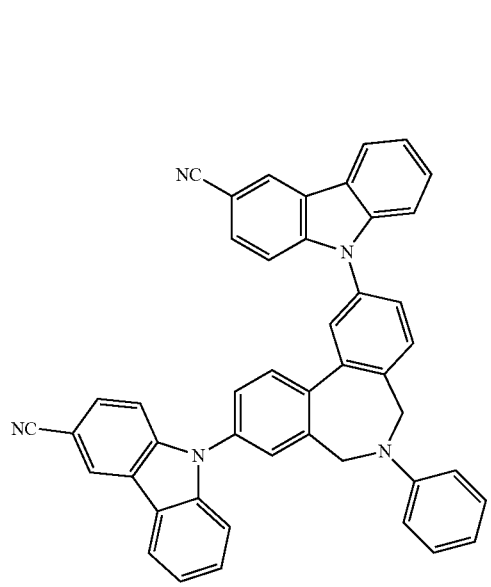
494
-continued
649
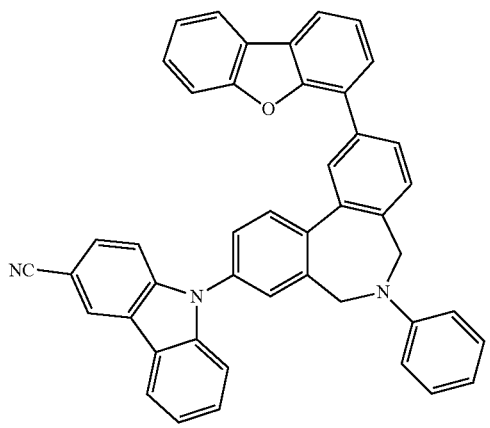
650
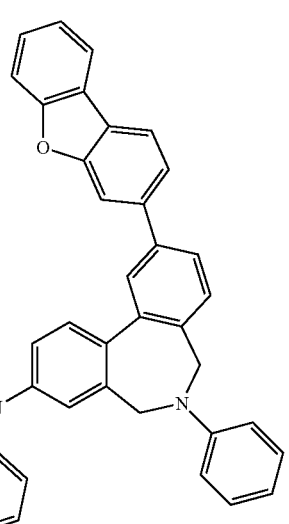
651
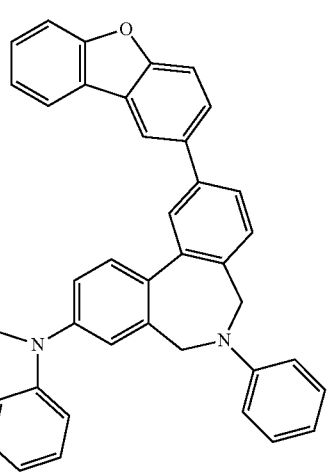

652 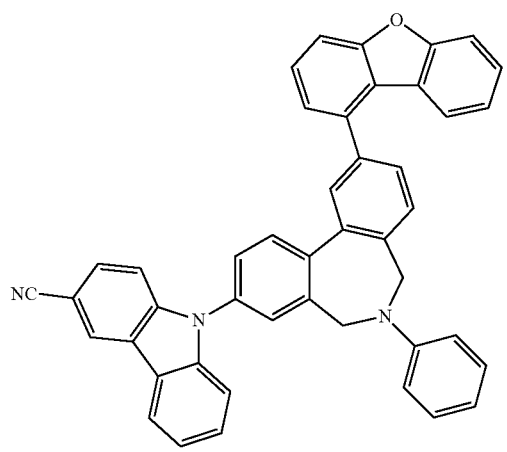
653 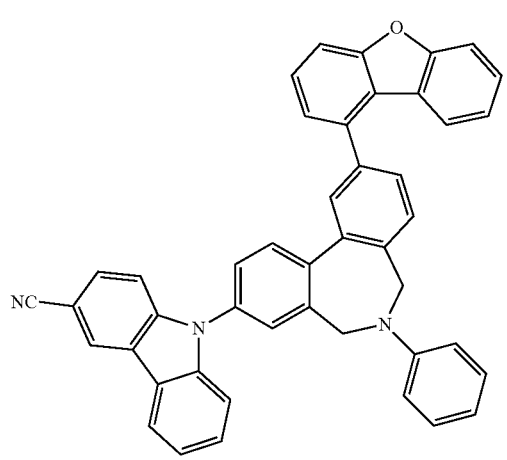
654 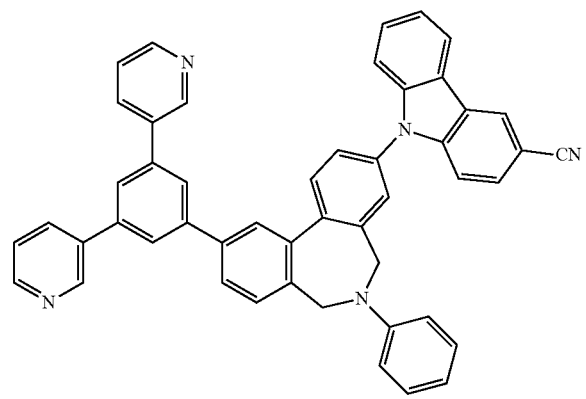
655 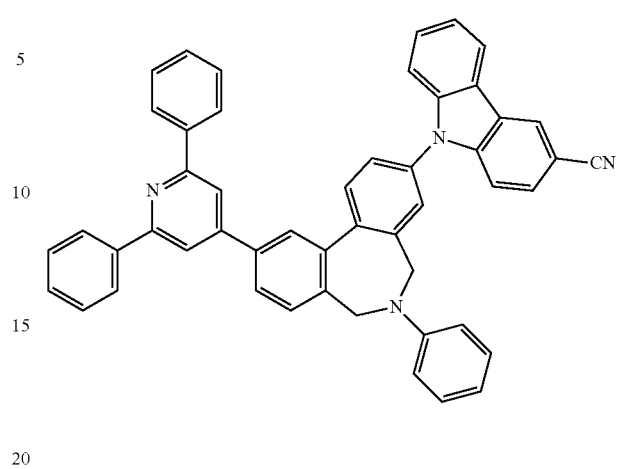
656 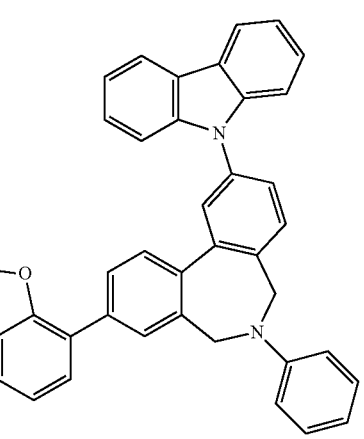
657 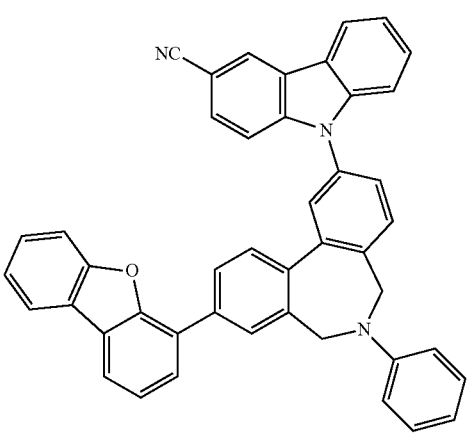

497
-continued
498
-continued
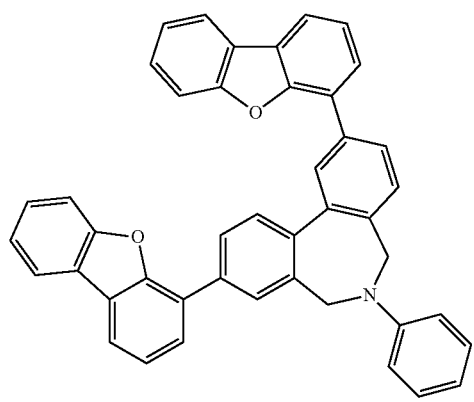
658
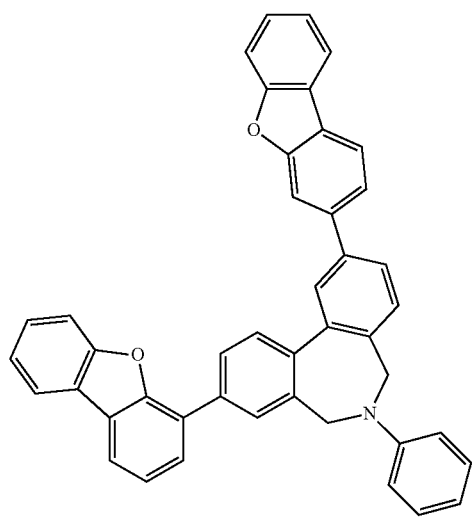
659
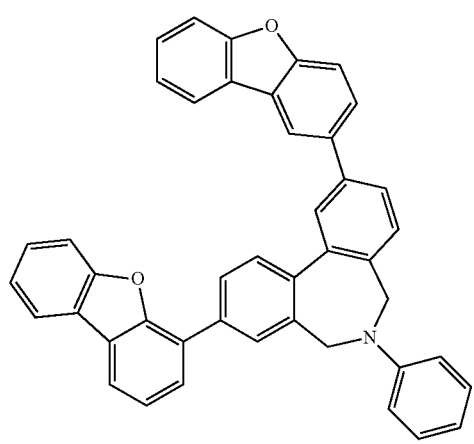
660
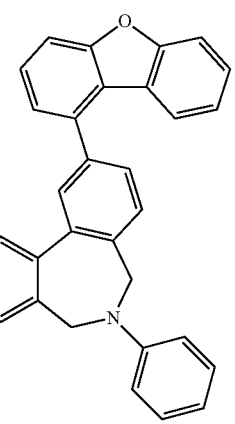
661
662
663
664

499
-continued
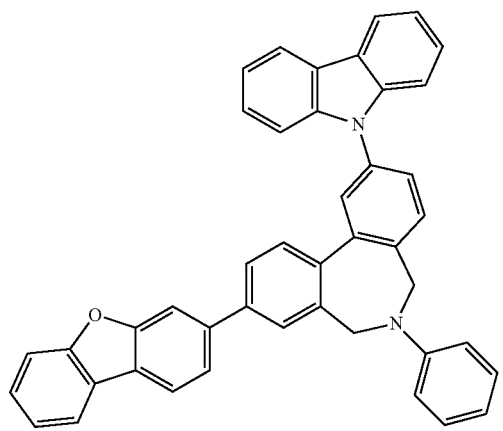
665
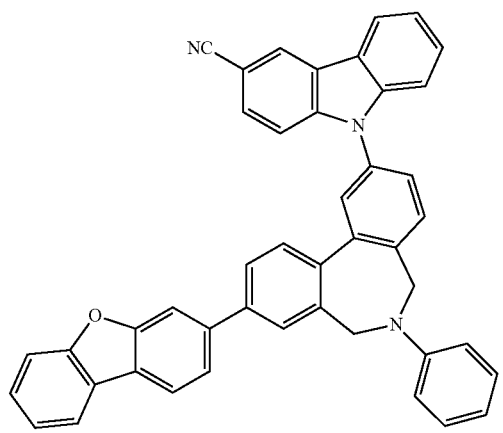
666
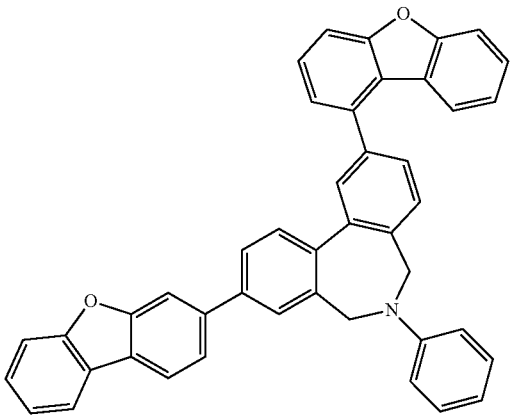
667
500
-continued
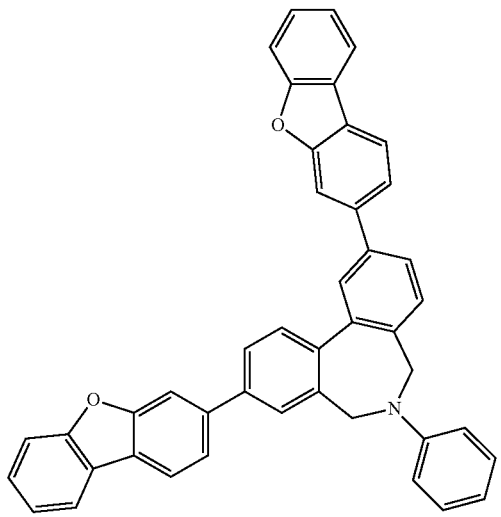
668
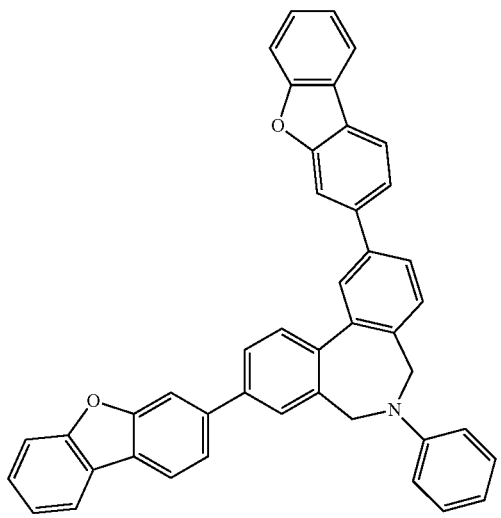
669
670

-continued
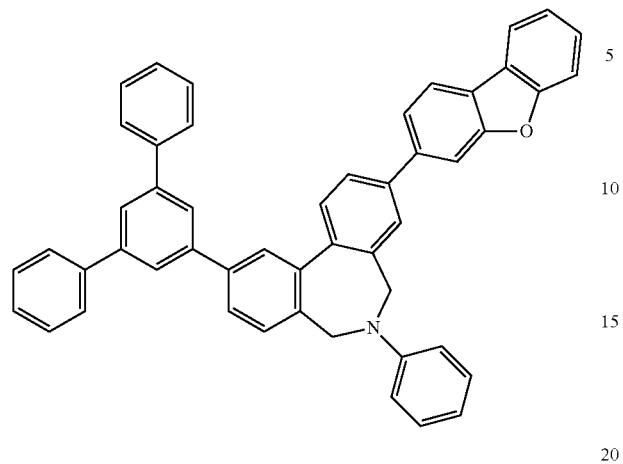
671
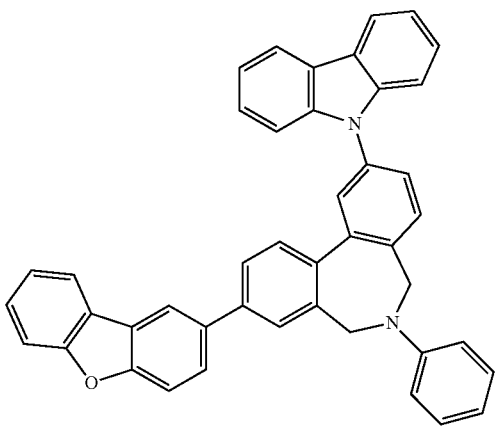
674
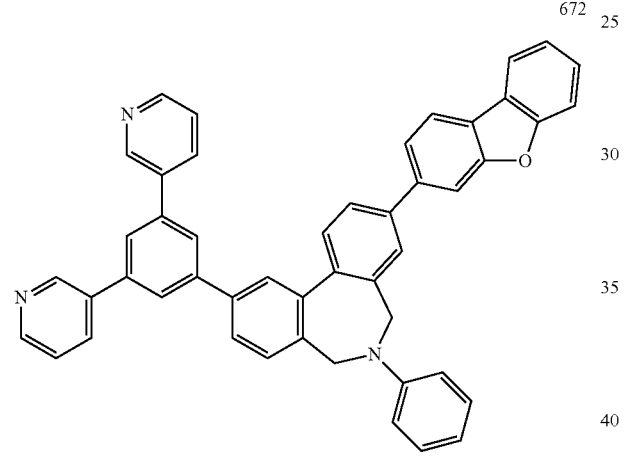
672
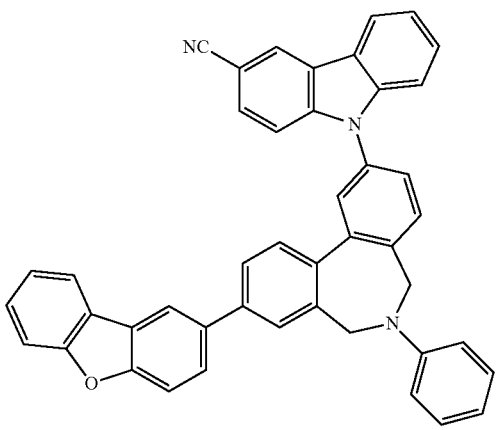
675
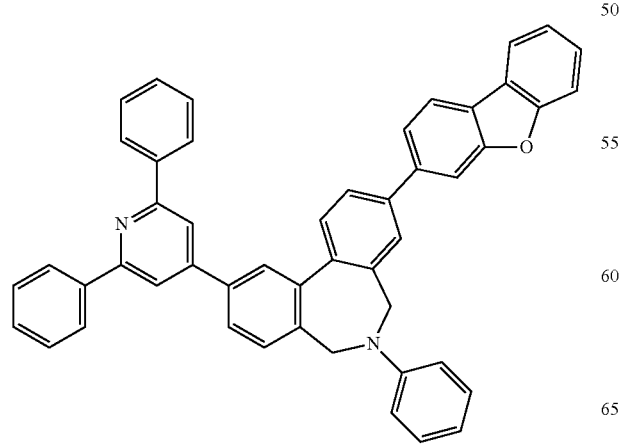
673
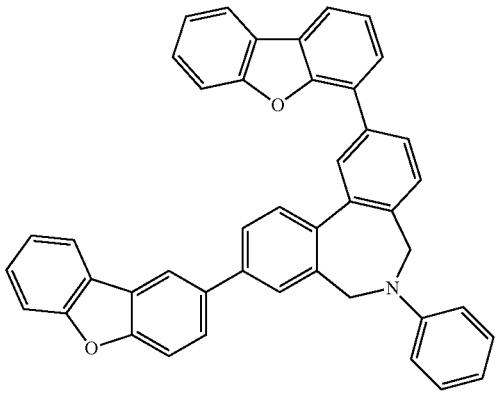
676

503
-continued
677
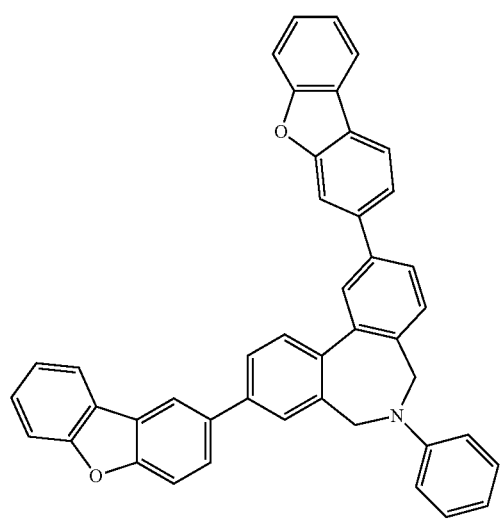
678
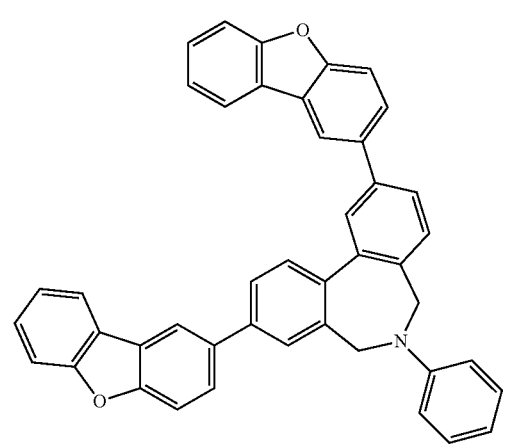
679
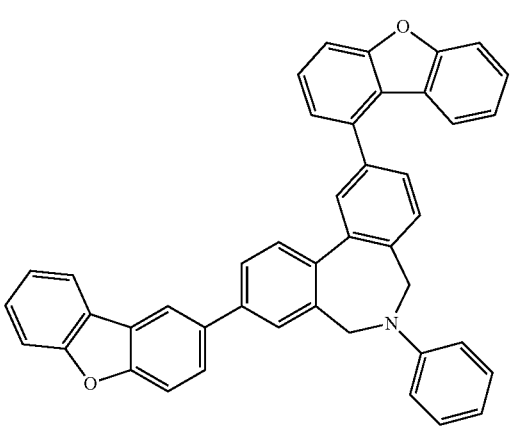
504
-continued
680
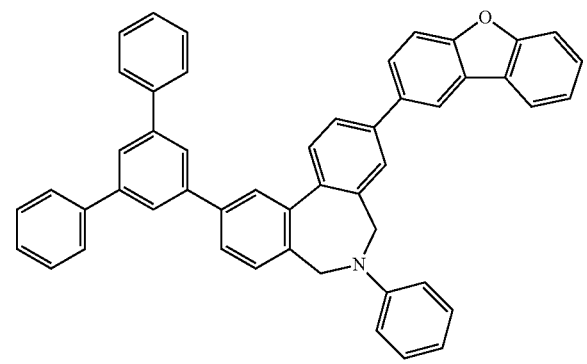
681
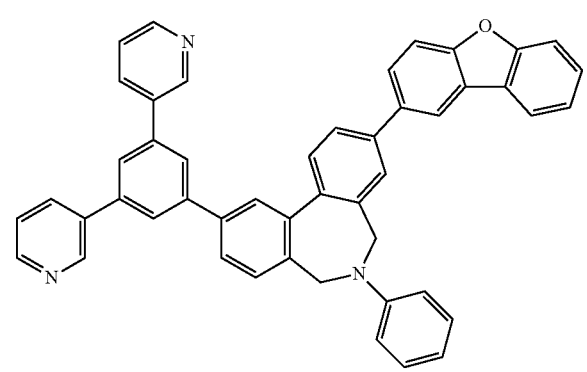
682
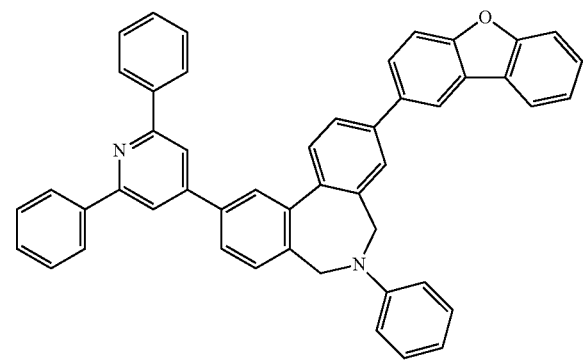
683
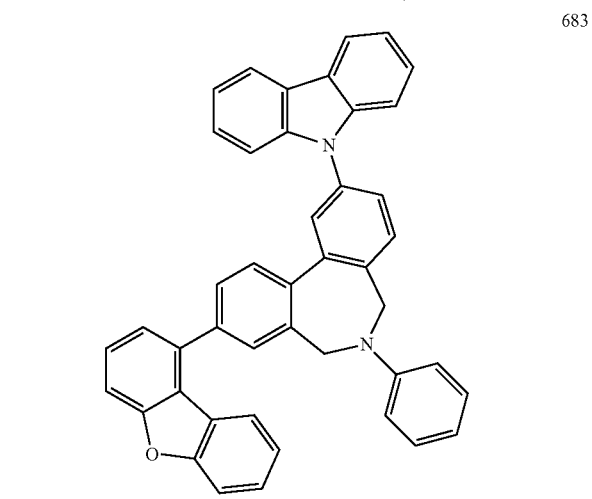

505
-continued
684
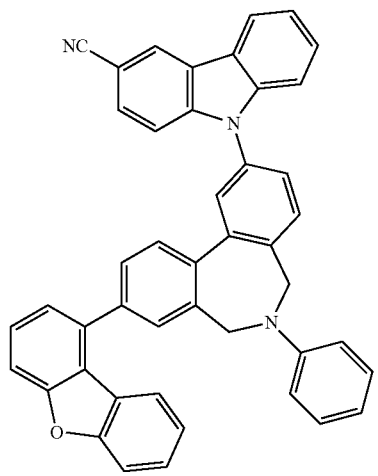
685
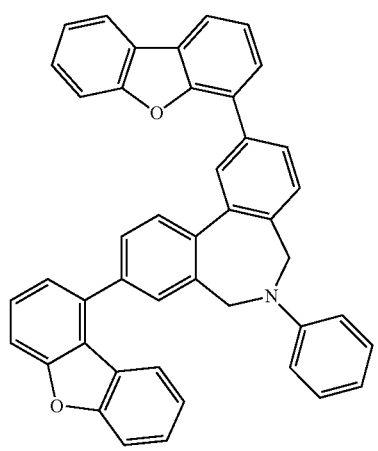
686
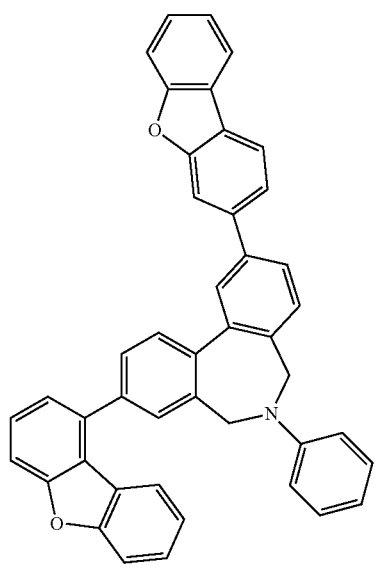
506
-continued
687
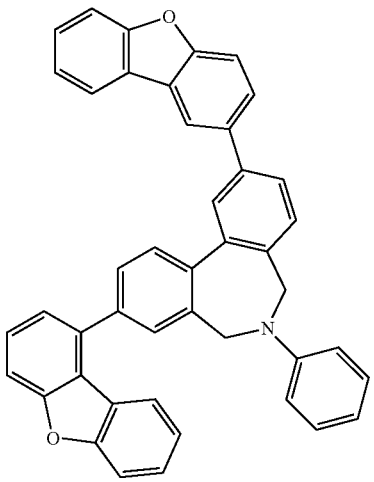
688
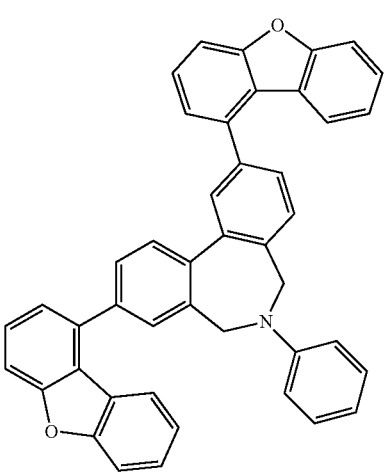
689
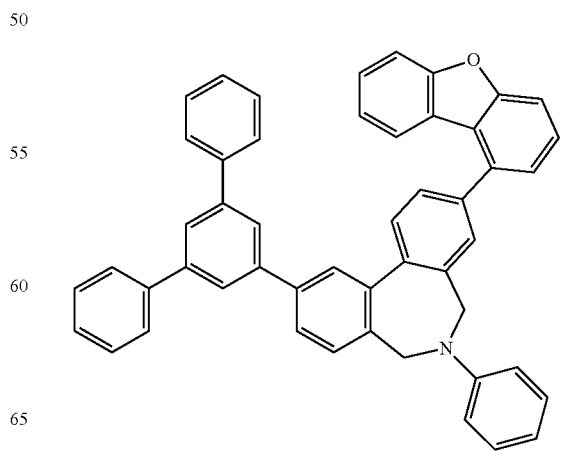

507
-continued
690
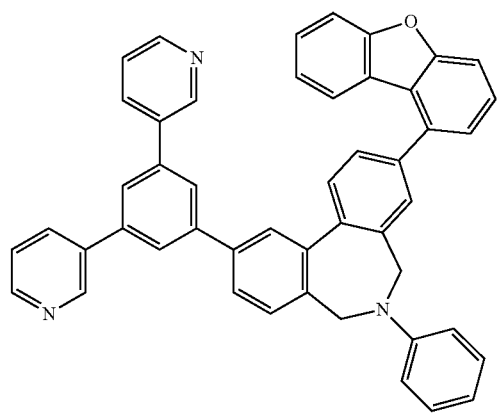
691
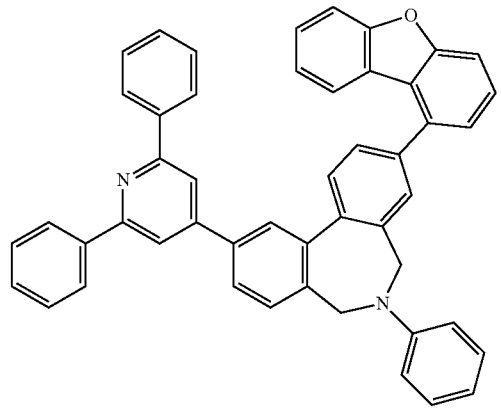
692
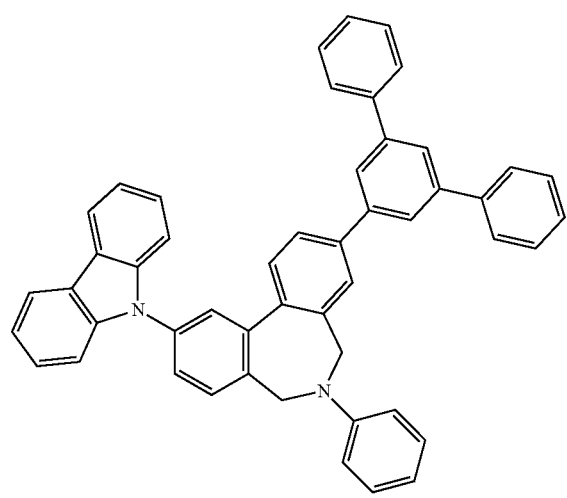
508
-continued
693
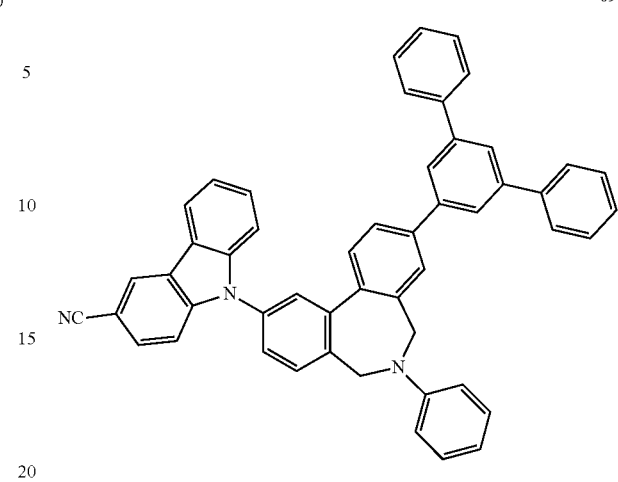
694
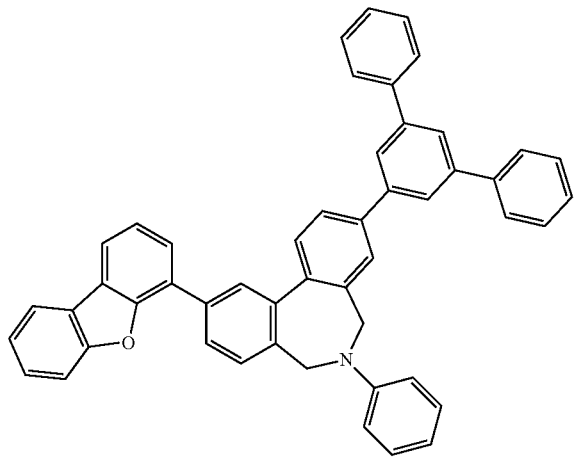
695
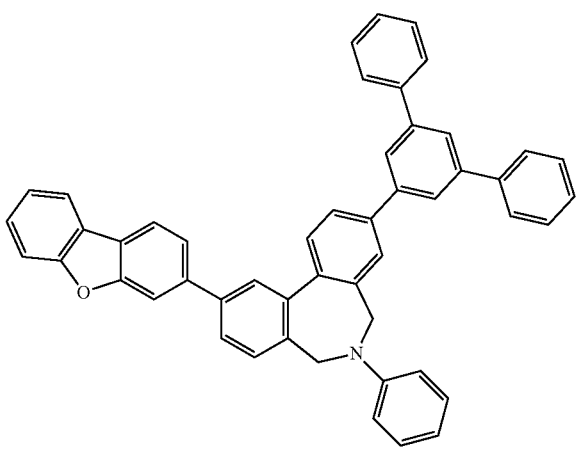

509
-continued
696
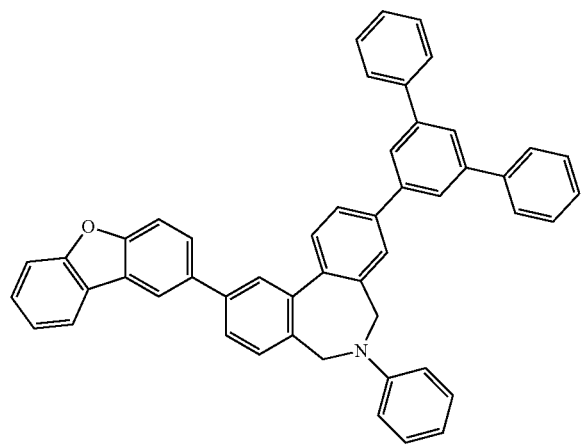
697
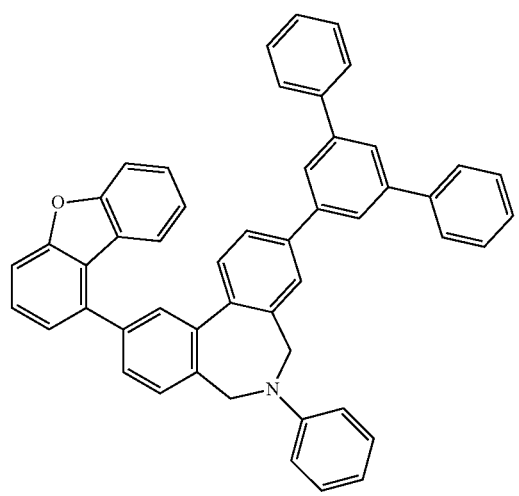
698
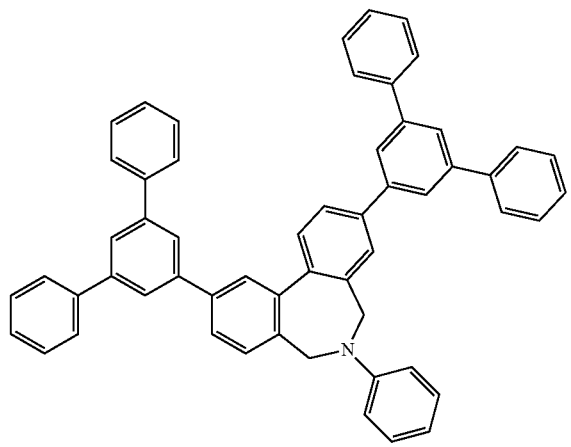
510
-continued
699
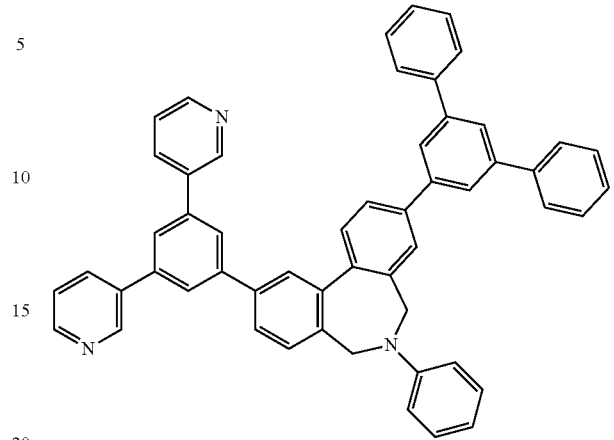
700
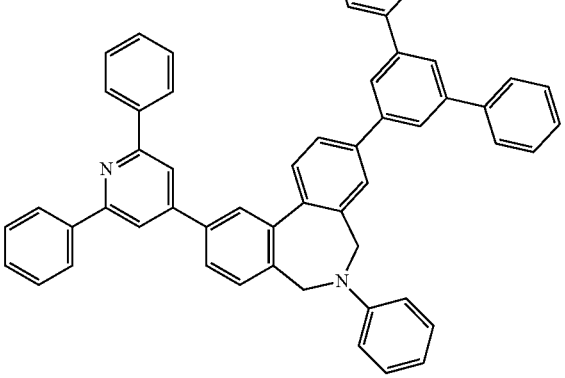
701
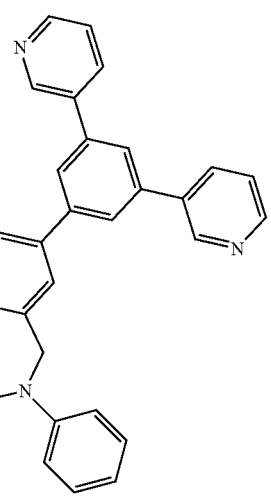

702
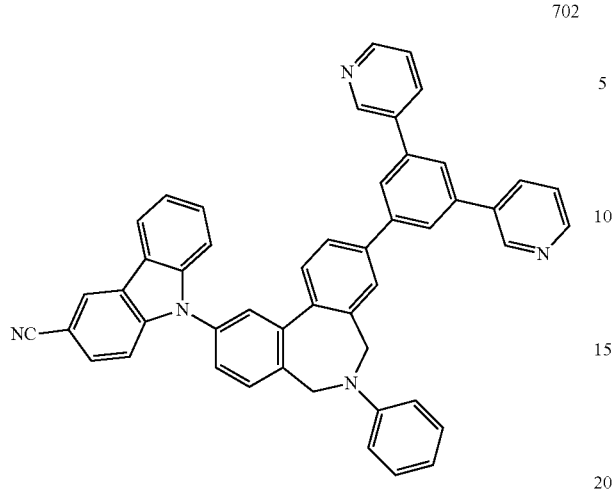
705
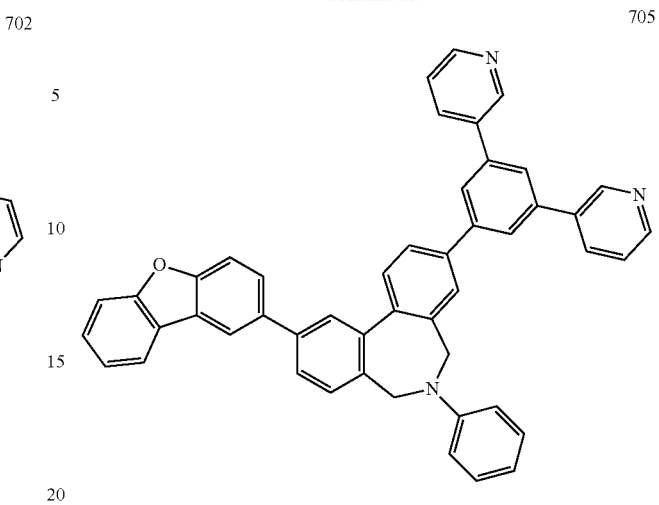
703
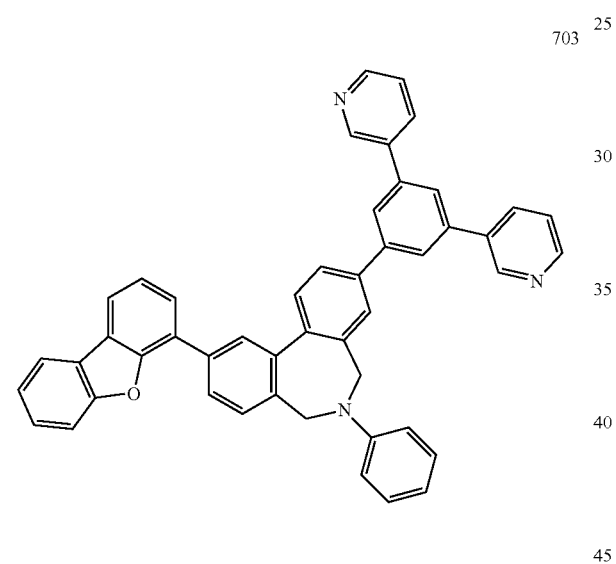
706
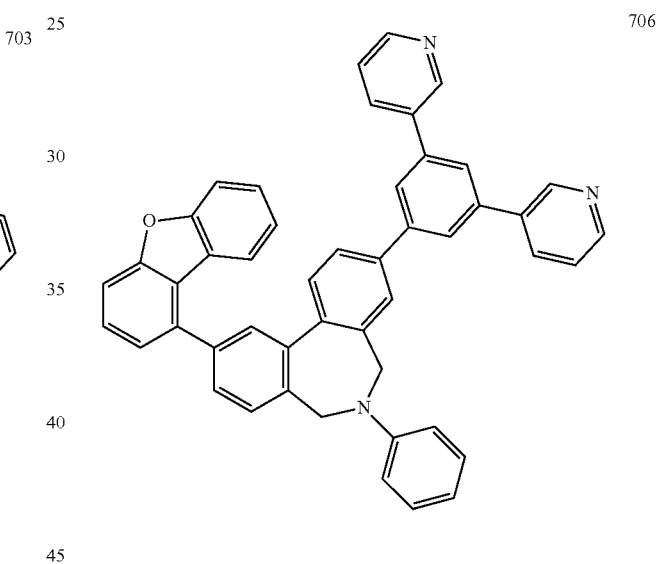
704
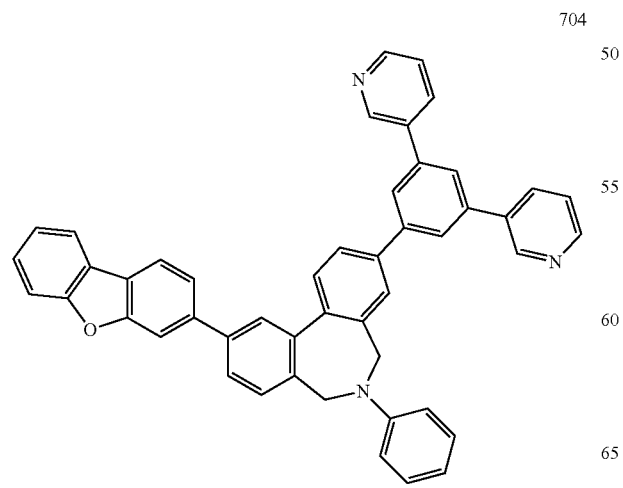
707
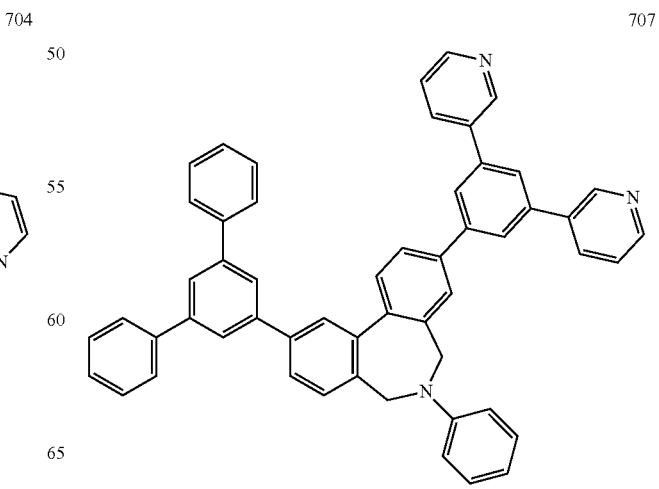

513
-continued
514
-continued
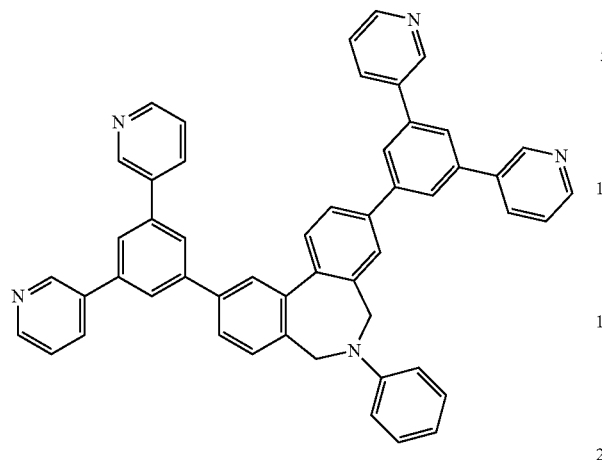
708
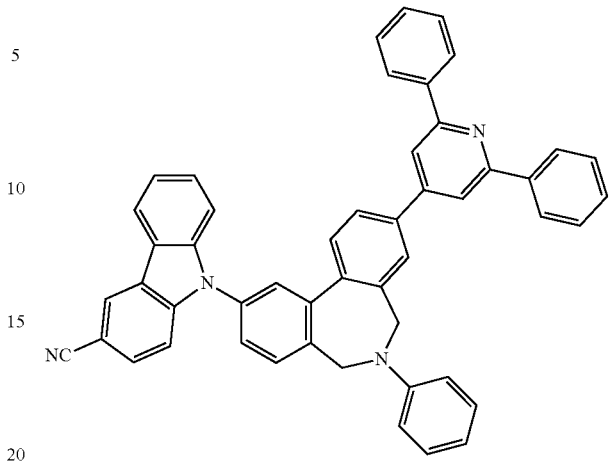
711
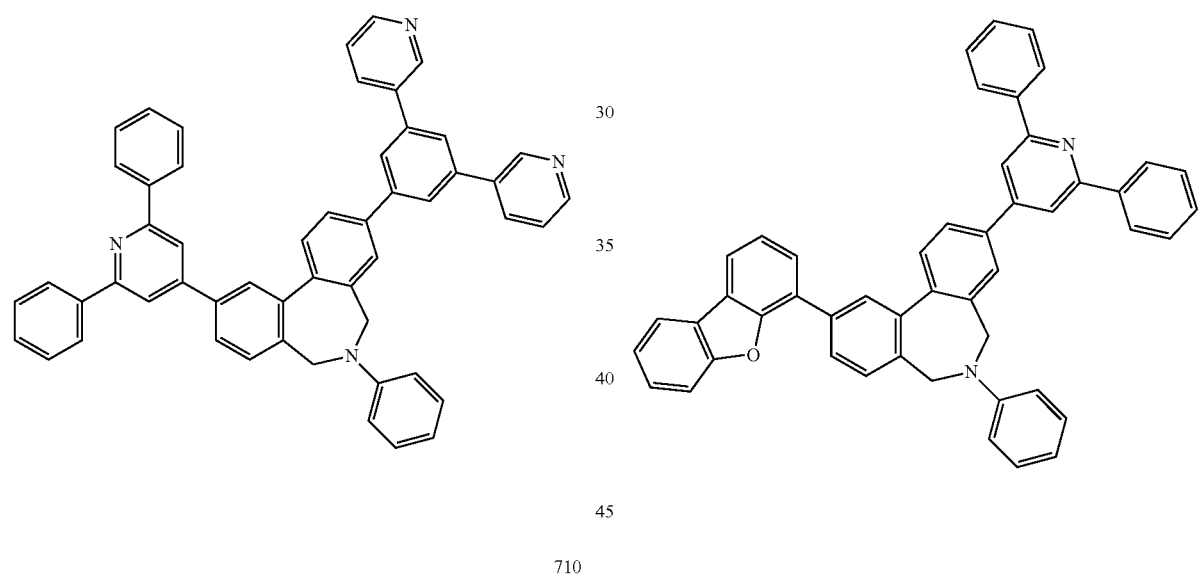
709
710
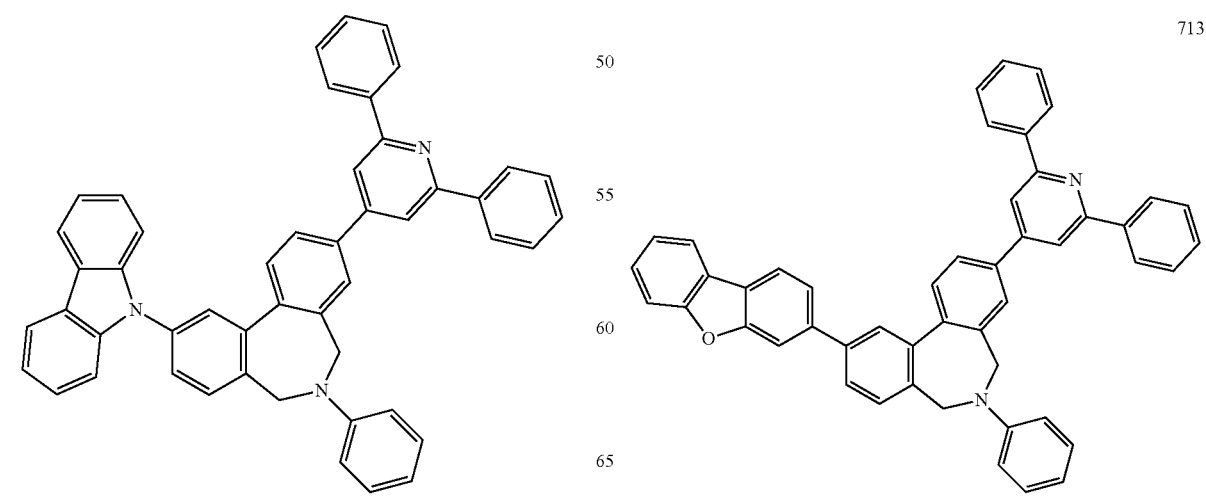
712
713

714
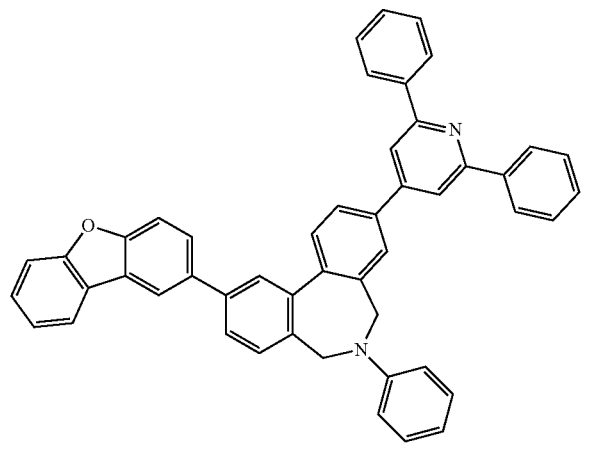
715
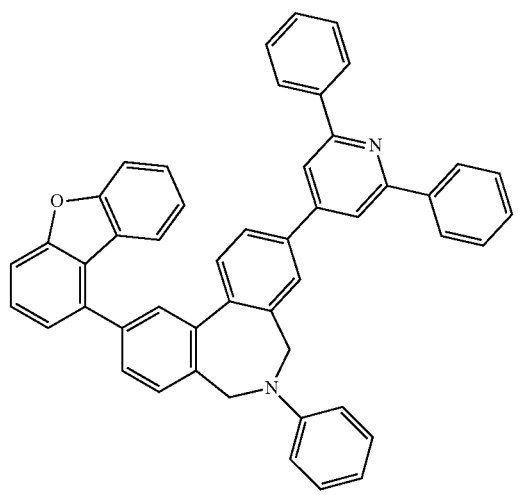
716
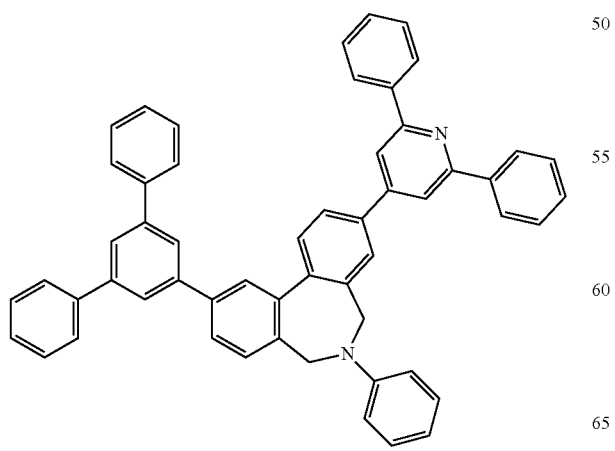
717
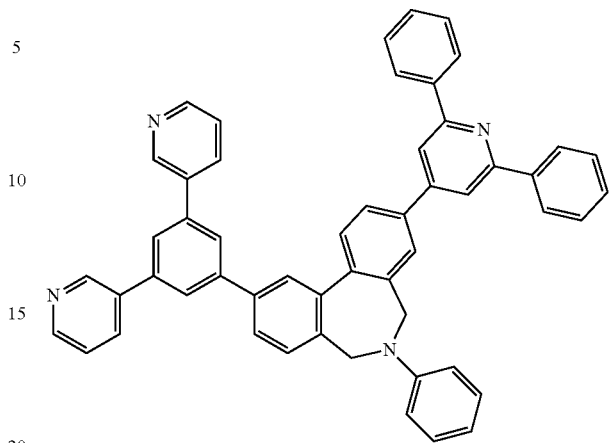
718
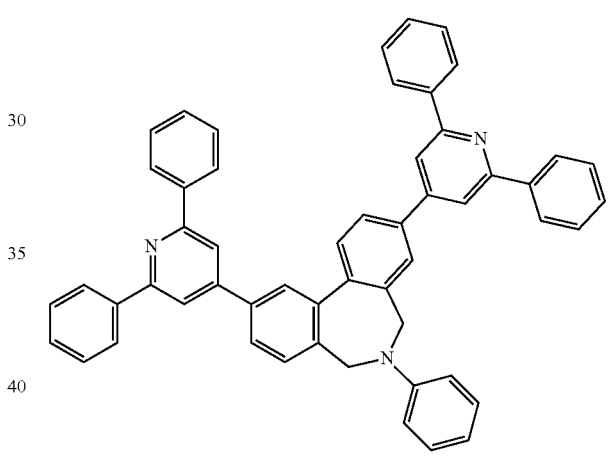
719
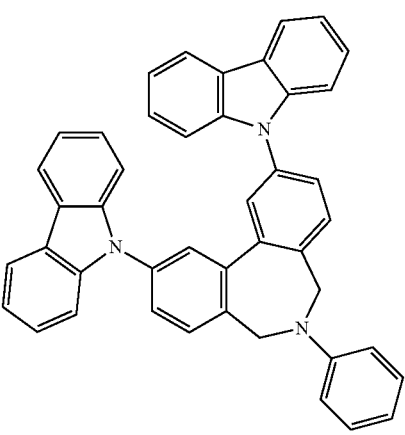

517
-continued
720
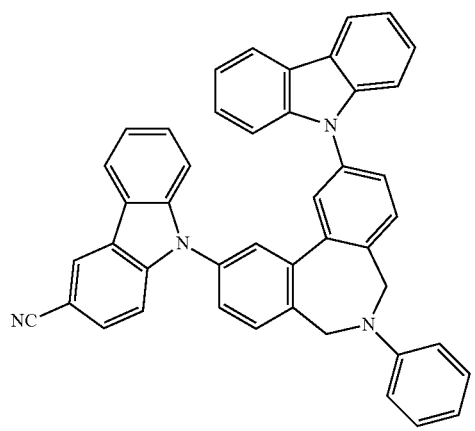
721
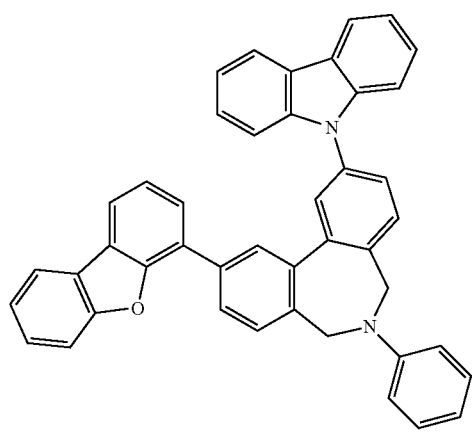
722
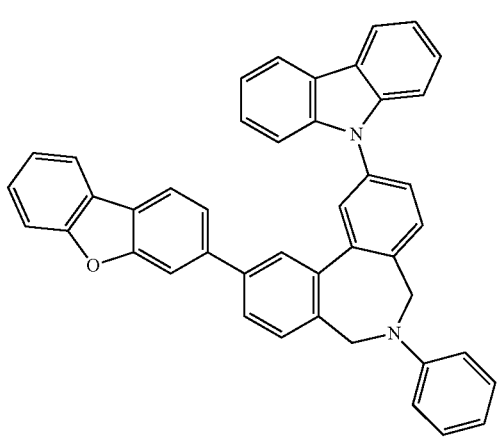
518
-continued
723
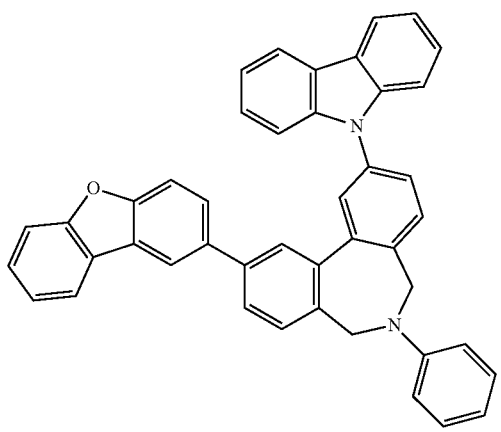
724
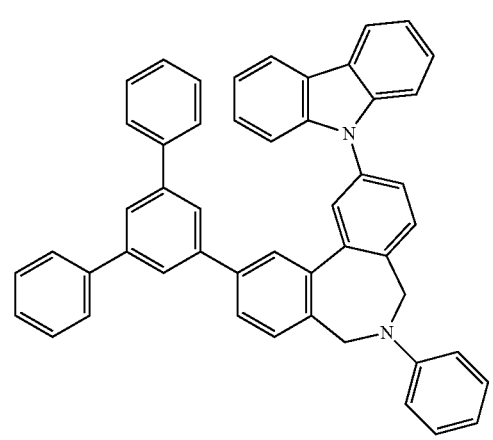
725

-continued
726
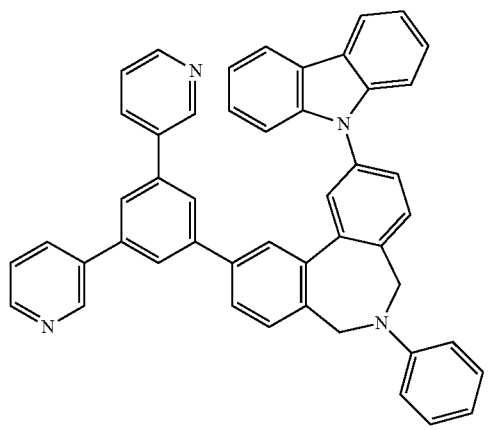
727
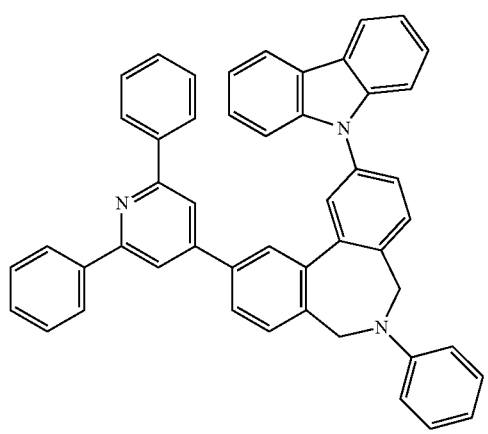
728
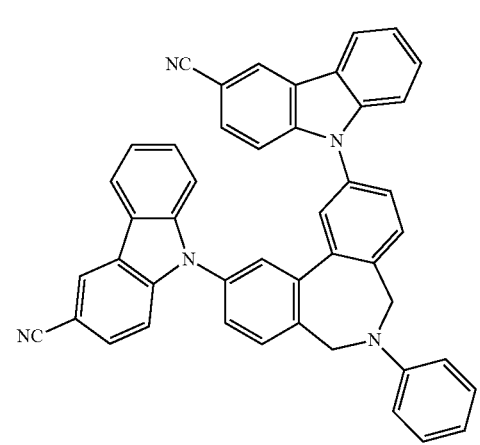
-continued
729
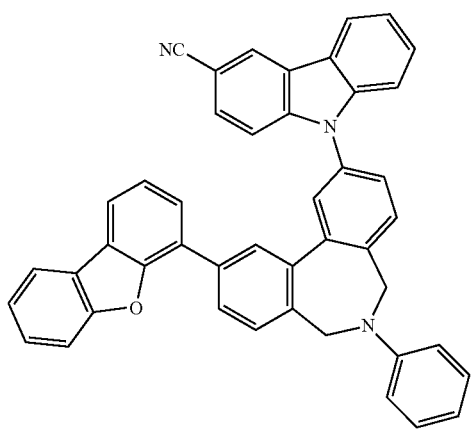
730
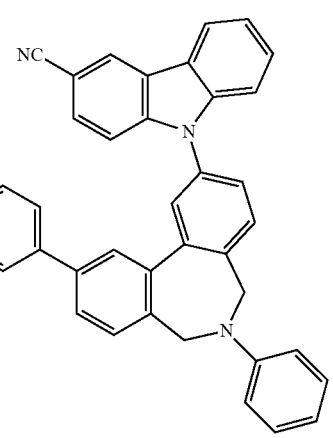
731
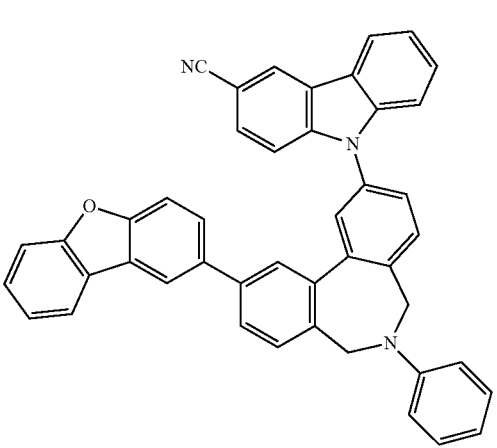

US 10,581,000 B2
521
-continued
522
-continued
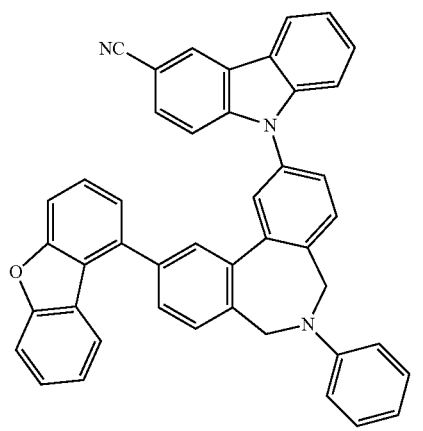
732
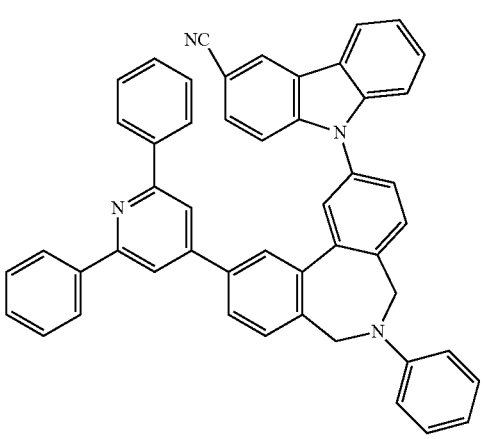
735
733
736
737
734
738

523
-continued
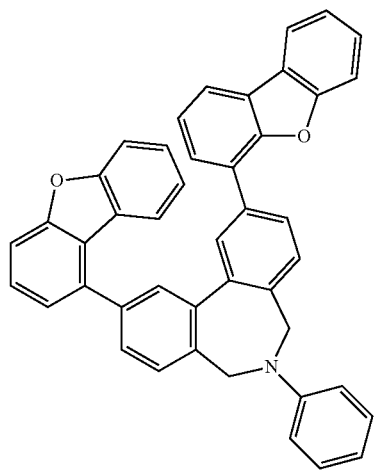
739
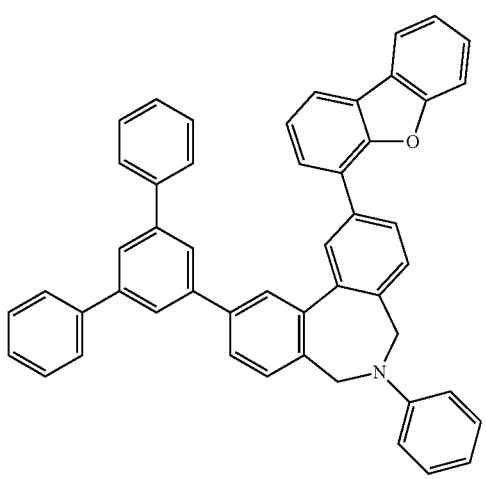
740
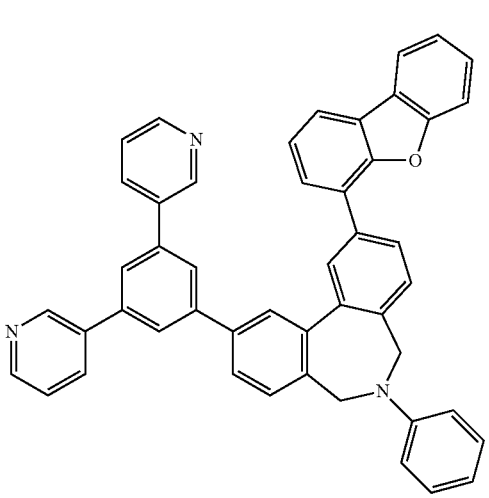
741
524
-continued
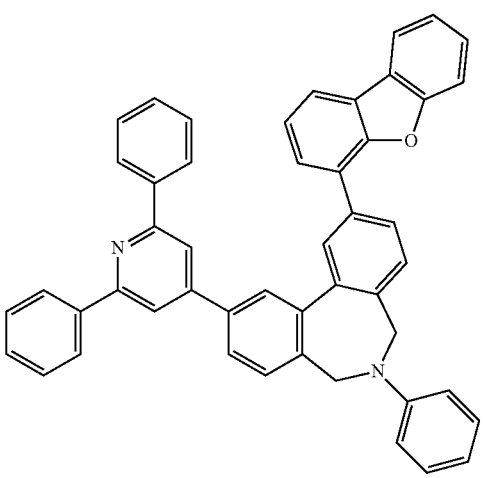
742
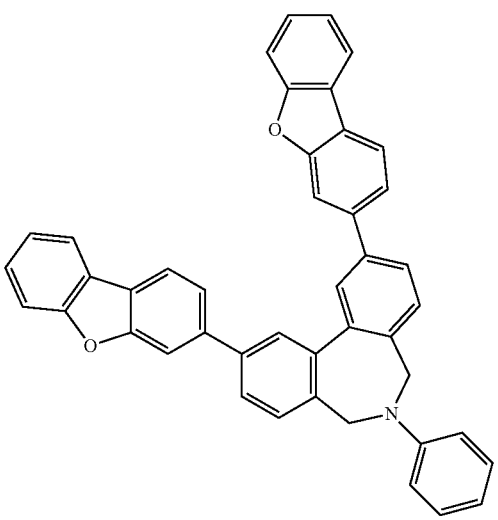
743
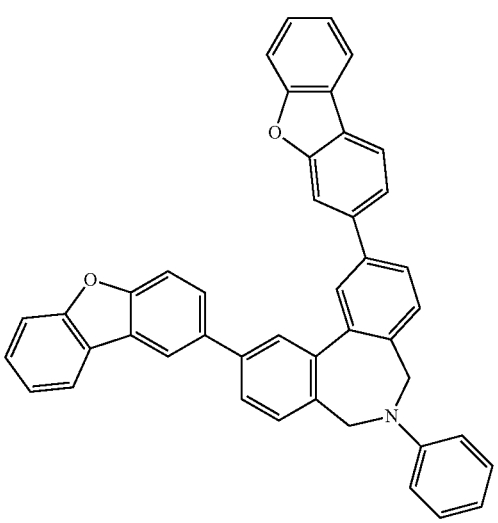
744

525
-continued
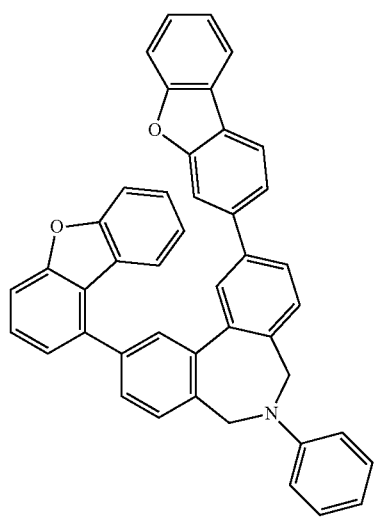
745
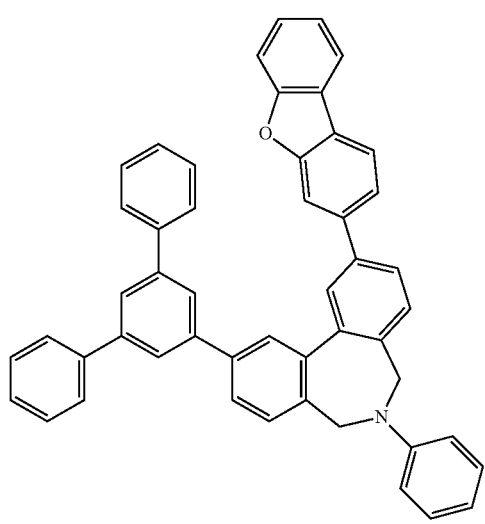
746
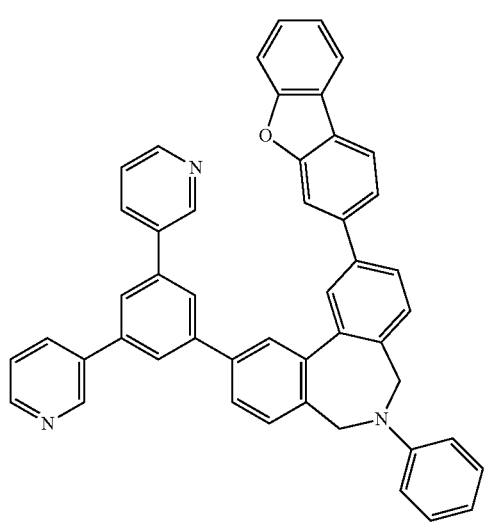
747
526
-continued
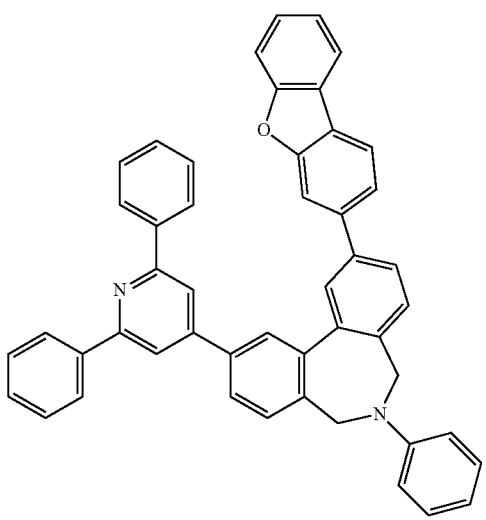
748
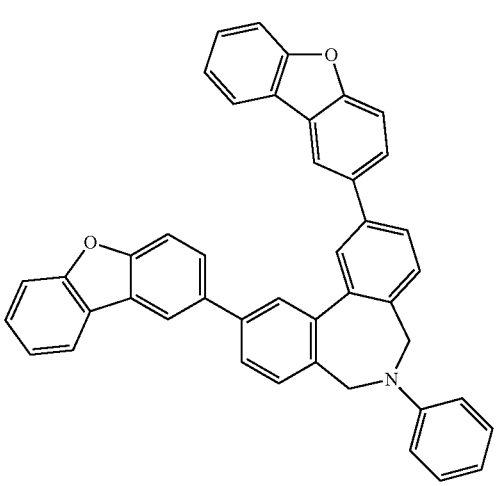
749
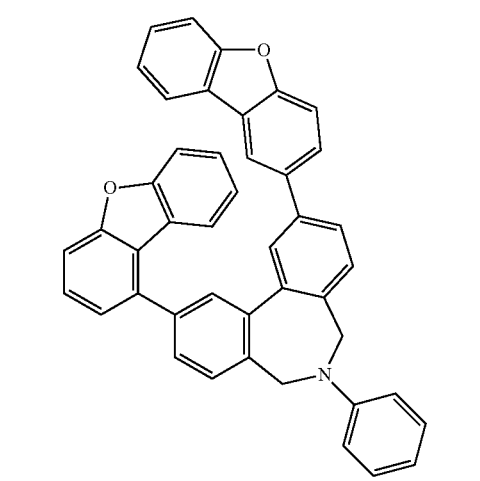
750

527
-continued
751
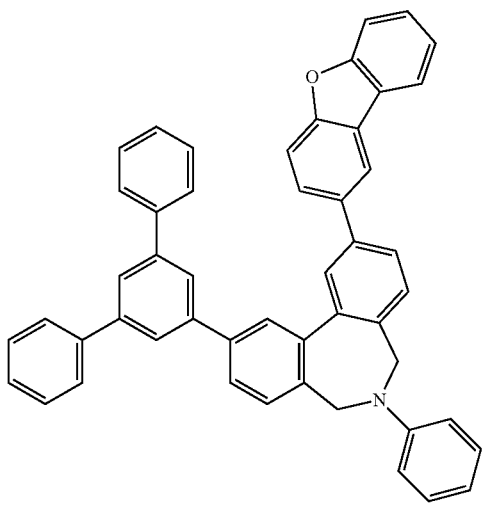
752
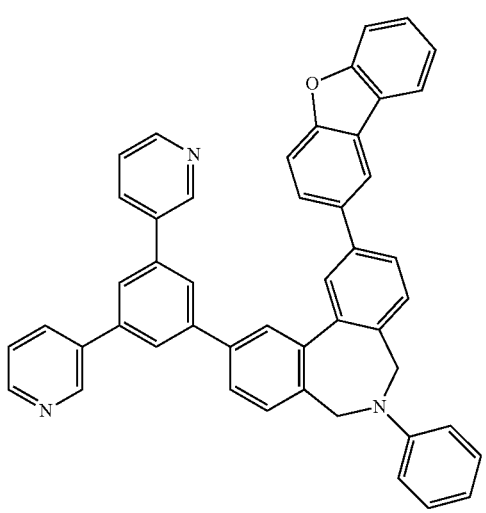
753
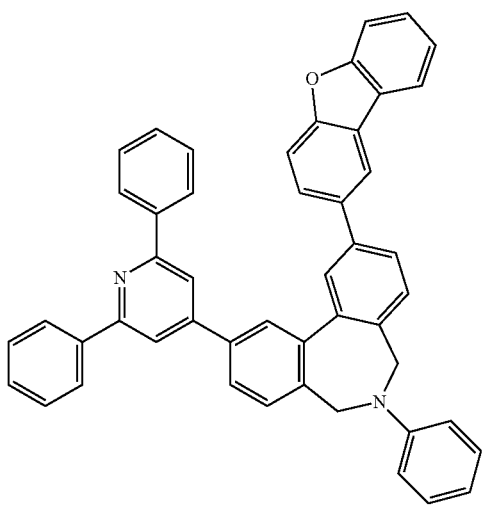
528
-continued
754
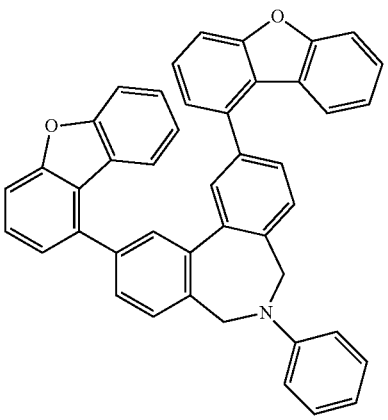
755
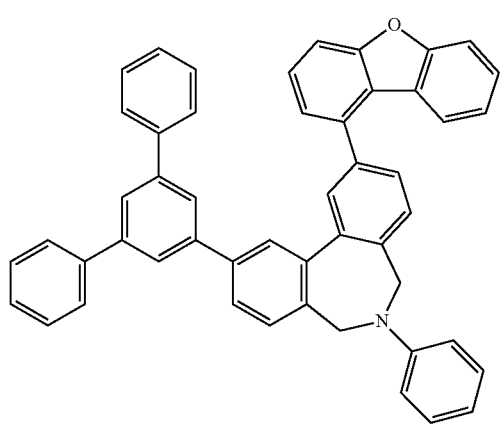
756
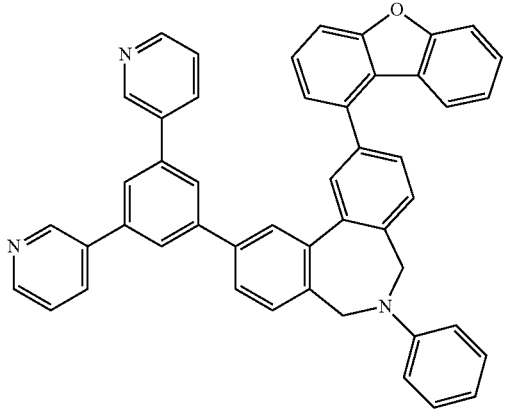

529
-continued
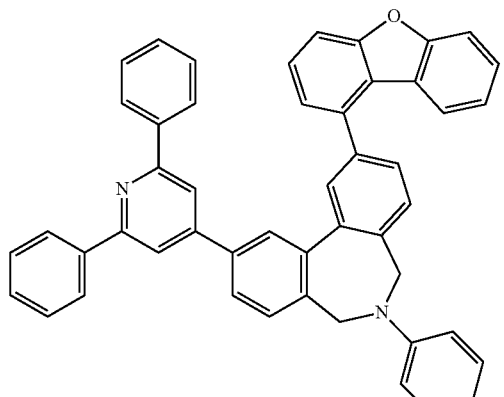
757
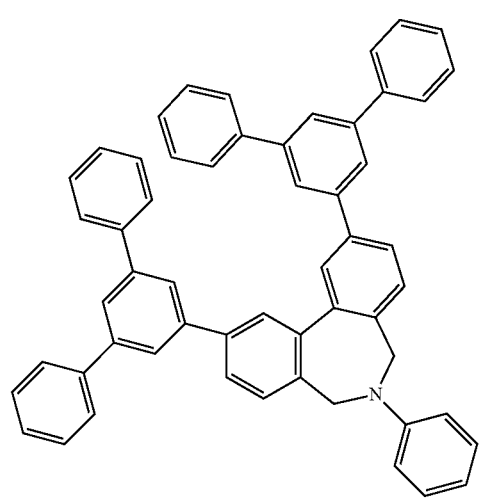
758
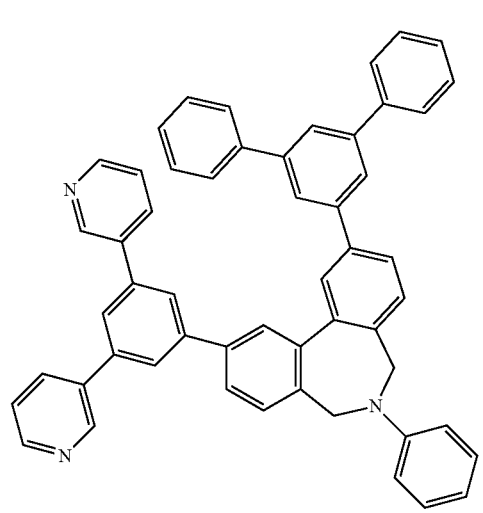
759
530
-continued
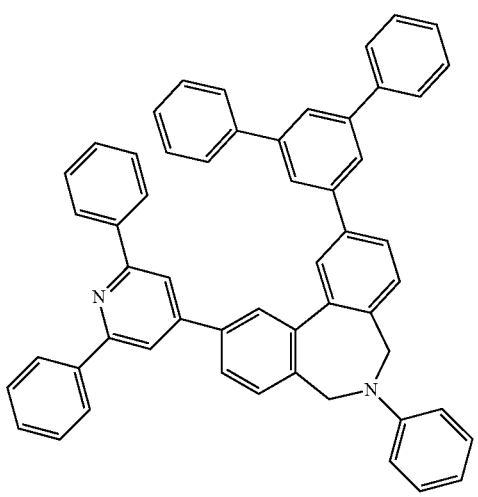
760
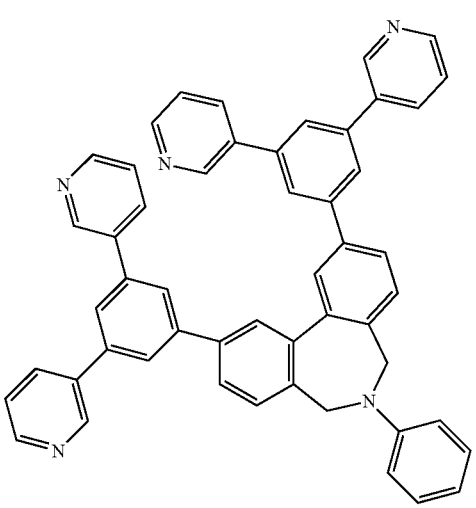
761
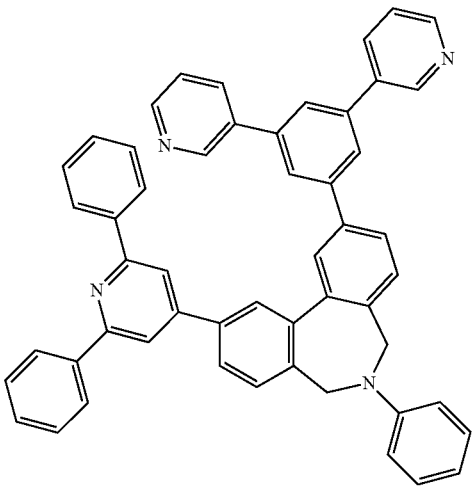
762

531
-continued

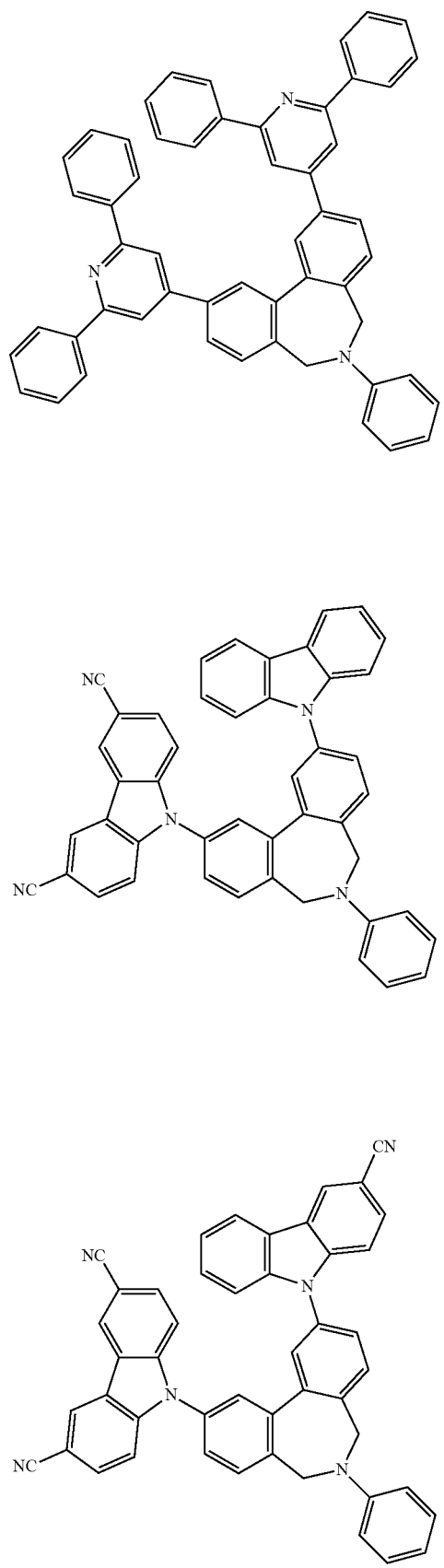

532
-continued

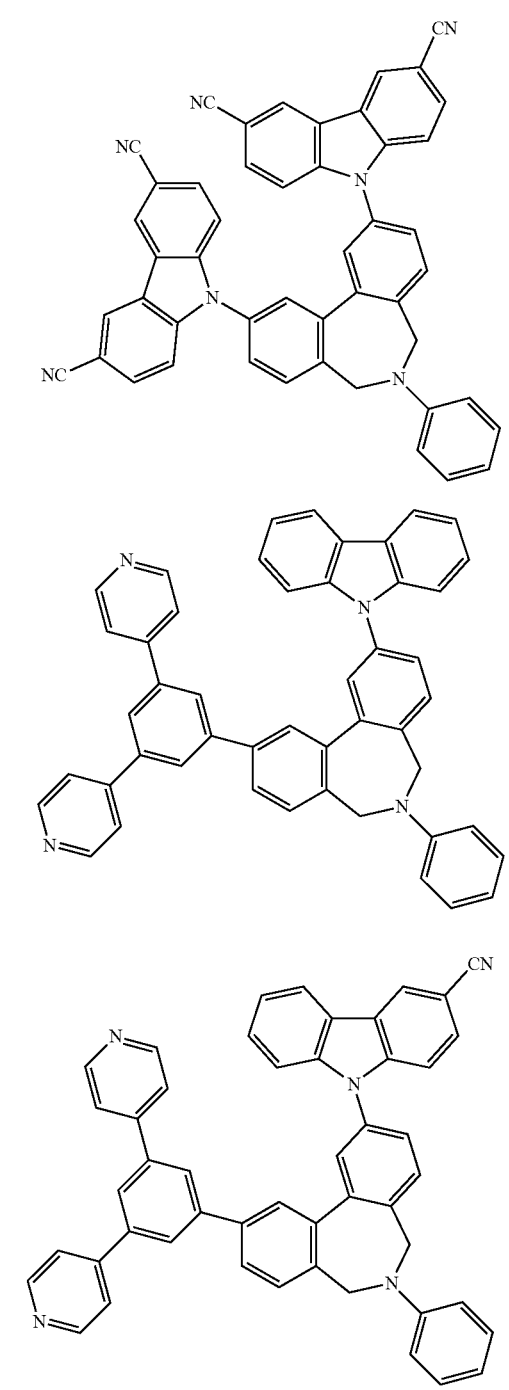

18. An organic light-emitting device comprising:
   a first electrode;
   a second electrode; and
   an organic layer disposed between the first electrode and the second electrode,
   wherein the organic layer comprises an emission layer and at least one of the condensed cyclic compounds represented by Formula 1 of claim 1.

19. The organic light-emitting device of claim 18, wherein the emission layer comprises the condensed cyclic compound represented by Formula 1.

20. An organic light-emitting device comprising:
a first electrode;
a second electrode; and
an organic layer disposed between the first electrode and the second electrode,
wherein the organic layer comprises an emission layer, and
wherein the emission layer comprises a phosphorescent dopant and a condensed cyclic compound represented by Formula 1:

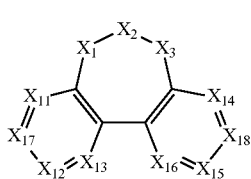

Formula 1 wherein in Formula 1,
$X_1$ is selected from O, S, S(=O)$_2$, N-(L$_1$)$_{a1}$-(R$_1$), C(R$_4$)(R$_5$), and Si(R$_4$)(R$_5$),
$X_2$ is selected from O, S, S(=O)$_2$, N-(L$_2$)$_{a2}$-(R$_2$), C(R$_6$)(R$_7$), and Si(R$_6$)(R$_7$),
$X_3$ is selected from O, S, S(=O)$_2$, N-(L$_3$)$_{a3}$-(R$_3$), C(R$_8$)(R$_9$), and Si(R$_8$)(R$_9$),
$X_{11}$ is N or C-(L$_{11}$)$_{a11}$-(R$_{11}$),
$X_{12}$ is N or C-(L$_{12}$)$_{a12}$-(R$_{12}$),
$X_{13}$ is N or C-(L$_{13}$)$_{a13}$-(R$_{13}$),
$X_{14}$ is N or C-(L$_{14}$)$_{a14}$-(R$_{14}$),
$X_{15}$ is N or C-(L$_{15}$)$_{a15}$-(R$_{15}$),
$X_{16}$ is N or C-(L$_{16}$)$_{a16}$-(R$_{16}$),
$X_{17}$ is N or C-(L$_{17}$)$_{a17}$-(R$_{17}$), and
$X_{18}$ is N or C-(L$_{18}$)$_{a18}$-(R$_{18}$),
provided that i) $X_{11}$ to $X_{18}$ are not all N, ii) $X_{11}$ to $X_{11}$ are not all CH, iii) at least one selected from $X_{17}$ and $X_{18}$ is CH, and iv) at least one selected from $X_{11}$ to $X_{16}$ is neither N nor CH, and
provided that at least one selected from $R_{12}$ and $R_{17}$ or at least one selected from $R_{15}$ and $R_{18}$ is independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a $C_6$-$C_{20}$ aryl group substituted with a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group,
$L_1$ to $L_3$ and $L_{11}$ to $L_{18}$ are each independently selected from —O—, —S—, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
a1 to a3 and a11 to a18 are each independently an integer selected from 0 to 3, and
$R_1$ to $R_9$ and $R_{11}$ to $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$),
at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

* * * * *